US009670480B2

(12) United States Patent
Hoe et al.

(10) Patent No.: US 9,670,480 B2
(45) Date of Patent: Jun. 6, 2017

(54) **GENOME-WIDE CONSTRUCTION OF *SCHIZOSACCHAROMYCES POMBE* HETEROZYGOUS DELETION MUTANTS CONTAINING GENE-SPECIFIC BARCODES BY THE METHODS OF 4-ROUND SERIAL OR BLOCK PCR, OR TOTAL GENE SYNTHESIS THEREOF**

(75) Inventors: Kwang Lae Hoe, Daejeon (KR); Dong Uk Kim, Daejeon (KR); Mi Sun Won, Daejeon (KR); Hyang Sook Yoo, Daejeon (KR); Dong Sup Kim, Daejeon (KR); Han Oh Park, Daejeon (KR); Kyung Sook Chung, Daejeon (KR); Young Joo Jang, Seoul (KR); Mi Young Nam, Daejeon (KR); Sang Jo Han, Daejeon (KR); Shin Jung Choi, Daejeon (KR); Seung Tae Baek, Daejeon (KR); Hyong Bai Kim, Seoul (KR); Kyung Sun Heo, Daejeon (KR); Hye Mi Lee, Daejeon (KR); Min Ho Lee, Daejeon (KR); Jo Young Park, Chungcheongnam-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1397 days.

(21) Appl. No.: 12/989,192

(22) PCT Filed: Aug. 27, 2008

(86) PCT No.: PCT/KR2008/005031
§ 371 (c)(1),
(2), (4) Date: Feb. 17, 2011

(87) PCT Pub. No.: WO2009/131279
PCT Pub. Date: Oct. 29, 2009

(65) Prior Publication Data
US 2011/0190163 A1 Aug. 4, 2011

(30) Foreign Application Priority Data

Apr. 22, 2008 (KR) .................. 10-2008-0037420

(51) Int. Cl.
| | | |
|---|---|---|
| *C40B 50/00* | (2006.01) | |
| *C40B 40/02* | (2006.01) | |
| *C40B 30/06* | (2006.01) | |
| *C12N 1/00* | (2006.01) | |
| *C12N 15/10* | (2006.01) | |
| *C40B 30/00* | (2006.01) | |

(52) U.S. Cl.
CPC .......... *C12N 15/1034* (2013.01); *C40B 30/00* (2013.01); *C40B 40/02* (2013.01); *C40B 50/00* (2013.01); *C12N 1/00* (2013.01)

(58) Field of Classification Search
None
See application file for complete search history.

(56) References Cited

FOREIGN PATENT DOCUMENTS

| KR | 10-2006-0086990 A | 8/2006 |
|---|---|---|
| WO | WO 02/053728 A2 | 7/2002 |

OTHER PUBLICATIONS

Krawchuk et al. High-Efficiency Gene Targeting in Schizoaccharomyces pombe Using a Modular PCR-Based Approach with Long Tracts of Flanking Homology. Sep. 30, 1999. Yeast. vol. 15, No. 13, pp. 1419-1427.*
Shoemaker et al. Quantitative phenotypic analysis of yeast deletion mutants using a highly parallel molecular bar-coding strategy. Dec. 1996. Nature Genetics. vol. 14, pp. 450-456.*
Pasrija et al. Squalene epoxidase encoded by ERG1 affects morphogenesis and drug susceptibilities of Candida albicans. Journal of Antimicrobial Chemotherapy. vol. 55, pp. 905-913.*
Sequence Alignment of Seq Id No. 7922 with EG672566. Search conducted on Mar. 4, 2014. 1 page.*
Sequence Alignment of Seq Id No. 7923 with EK826663. Search conducted on Mar. 4, 2014. 1 page.*
Baek, S.T., et al., "Genome-wide Drug-induced Haploinsufficiency Screening of Fission Yeast for Identification of Hydrazinocurcumin Targets," *J. Microbiol. Biotechnol.* 18(2):263-269, The Korean Society for Microbiology and Biotechnology, Korea (2008).
Park, J-Y., et al., "Drug-Induced Haploinsufficiency of Fission Yeast Provides a Powerful Tool for Identification of Drug Targets," *J. Micriobiol. Biotechnol.* 13(2):317-320, The Korean Society for Microbiology and Biotechnology, Korea (2003).
English language abstract of Korean Patent Publication No. KR 10-2006-0086990 A (listed as FP1 on the accompanying form PTO/SB/08a), 2 pages.
International Search Report for International Application No. PCT/KR2008/005031, Korean Intellectual Property Office, Daejeon, Republic of Korea, mailed on Mar. 11, 2009, 3 pages.
NPL5 International Preliminary Report on Patentability, including the Written Opinion of the International Searching Authority, for International Application No. PCT/KR2008/005031, The International Bureau of WIPO, Geneva, Switzerland, issued Oct. 26, 2010, 6 pages.

(Continued)

*Primary Examiner* — Channing S Mahatan
(74) *Attorney, Agent, or Firm* — Rubin and Rudman LLP; Judith U. Kim

(57) ABSTRACT

A method comprising transforming *Schizosaccharomyces pombe* with a deletion cassette, constructed by four-round serial PCR, block PCR or total gene synthesis, containing a homologous recombination site is provided for preparing gene-targeted heterozygous deletion *Schizosaccharomyces pombe*. Also provided are gene-targeted hetero2ygous deletion *Schizosaccharomyces pombe* mutants prepared by the method, and a library of gene-targeted heterozygous deletion *Schizosaccharomyces pombe* mutants. Further, the library is useful in constructing a method and a kit for screening a drug's modes of action.

11 Claims, 60 Drawing Sheets

(56) References Cited

OTHER PUBLICATIONS

Chung, K-S., et al., "Identification of small molecules inducing apoptosis by cell-based assay using fission yeast deletion mutants," *Investigational New Drugs* 26:299-307, Springer, United States (2008).

Giaever, G., et al., "Genomic profiling of drug sensitivities via induced haploinsufficiency," *Nature Genetics* 21:278-283, Nature Publishing Group, United States (1999).

Extended European Search Report, which includes the supplementary European Search Report and the European Search Opinion, for European Patent Application No. EP 08 79 3534, European Patent Office, Munich, Germany, mailed on Aug. 18, 2011, 7 pages.

Office Action for Korean Patent Application No. 10-2008-0037420, dated Feb. 25, 2011, Korean Intellectual Property Office, Republic of Korea, 6 pages.

English language translation of Office Action for Korean Patent Application No. 10-2008-0037420, dated Feb. 25, 2011, Korea Research Institute of Bioscience and Biotechnology, Republic of Korea, 4 pages.

Huh, et al., "HCS Drug Target Screening Technology Using Haploinsufficiency," *Studies on Chemical Genomics*, 1-56, Korea Research Institute of Bioscience and Biotechnology, Repulic of Korea (Feb. 26, 2008), 58 pages. Summary only in English.

Kaur, R., et al., "PCR-mediated direct gene disruption in *Schizosaccharomyces pombe*," *Nucleic Acids Research* 25(5):1080-81, Oxford University Press, England (1997).

Tatebayashi, K., et al., "Structural analyses of DNA fragments integrated by illegitimate recombination in *Schizosaccharomyces pombe*," *Mol. Gen. Genet.* 244:111-19, Springer-Verlag, Germany (1994).

Office Action for European Application No. 08793534.2, dated Jul. 11, 2014, European Patent Office, Munich, Germany, 6 pages.

* cited by examiner

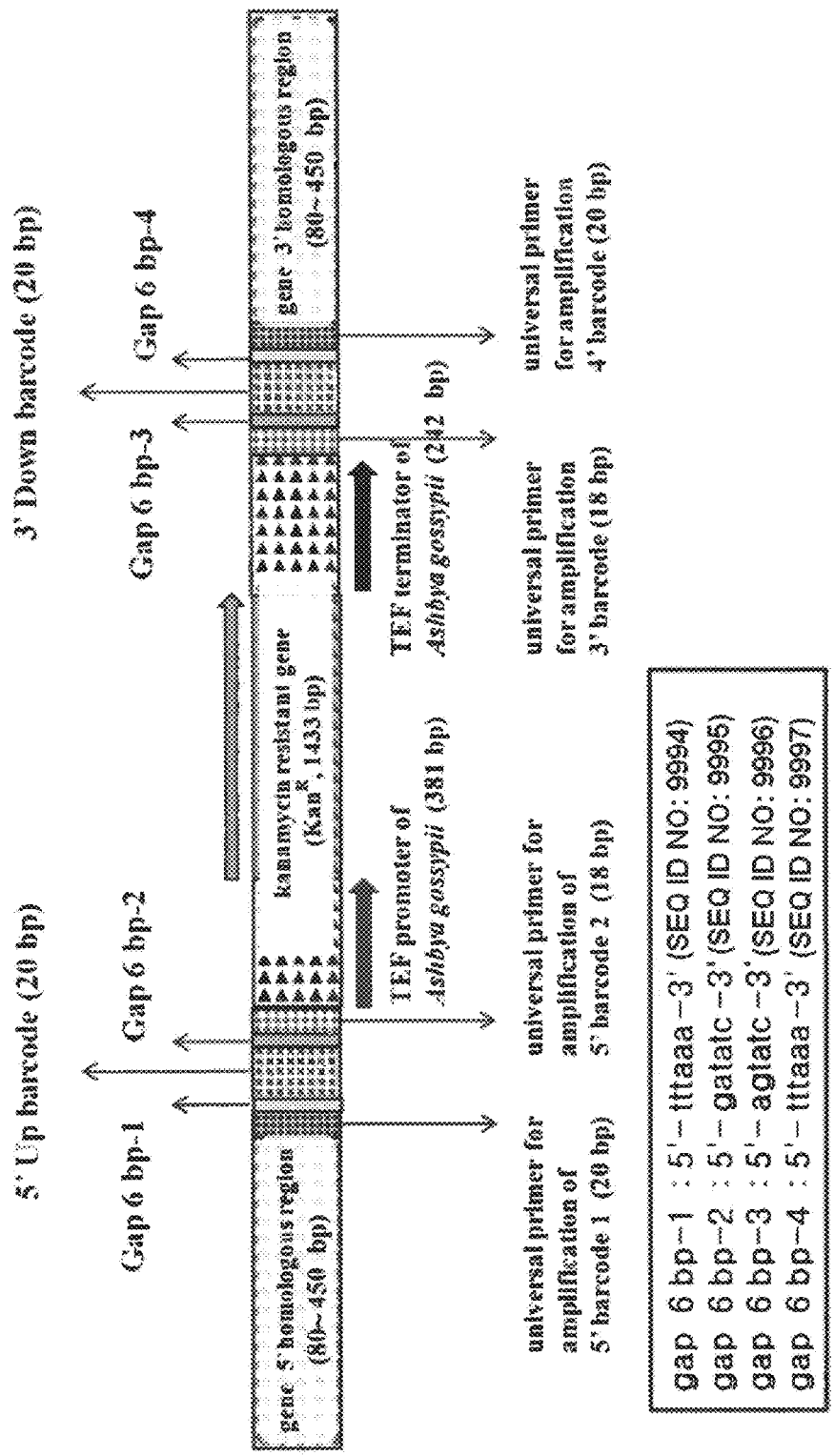

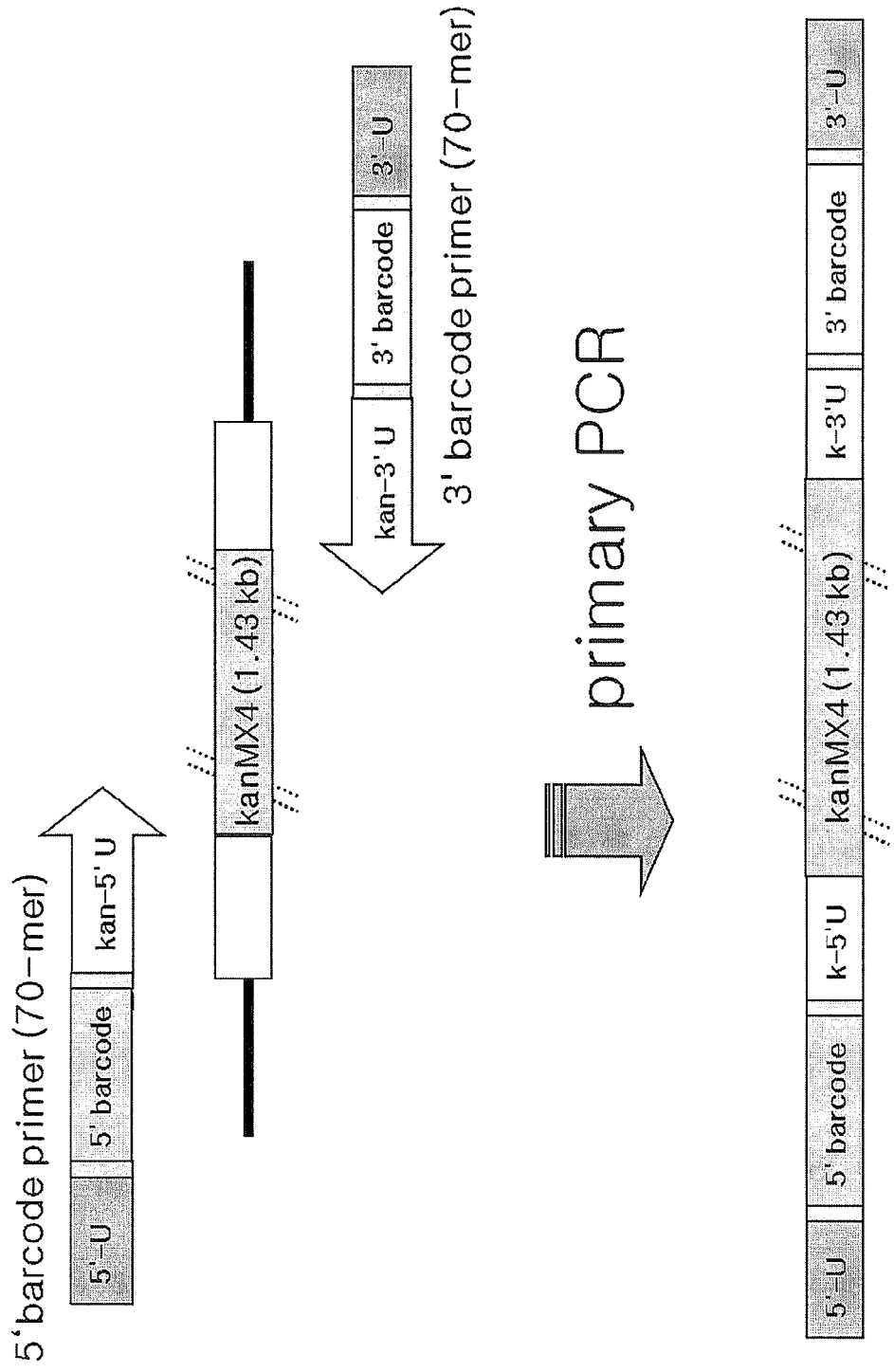
FIG. 2 Process of Constructing KanR-Barcode Module of Deletion Cassette

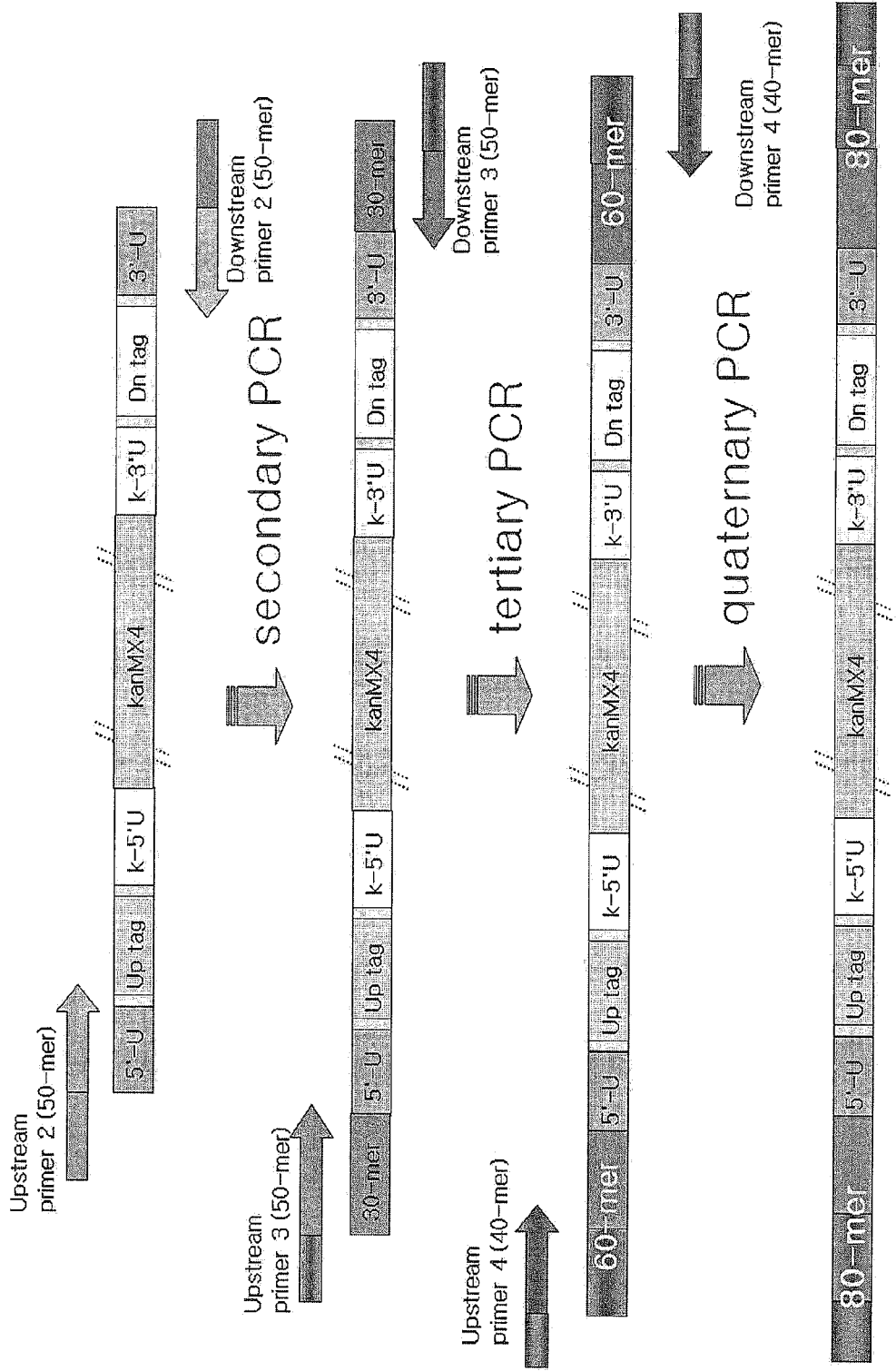
FIG. 3 construction of deletion cassette by 4-roudn serial PCR

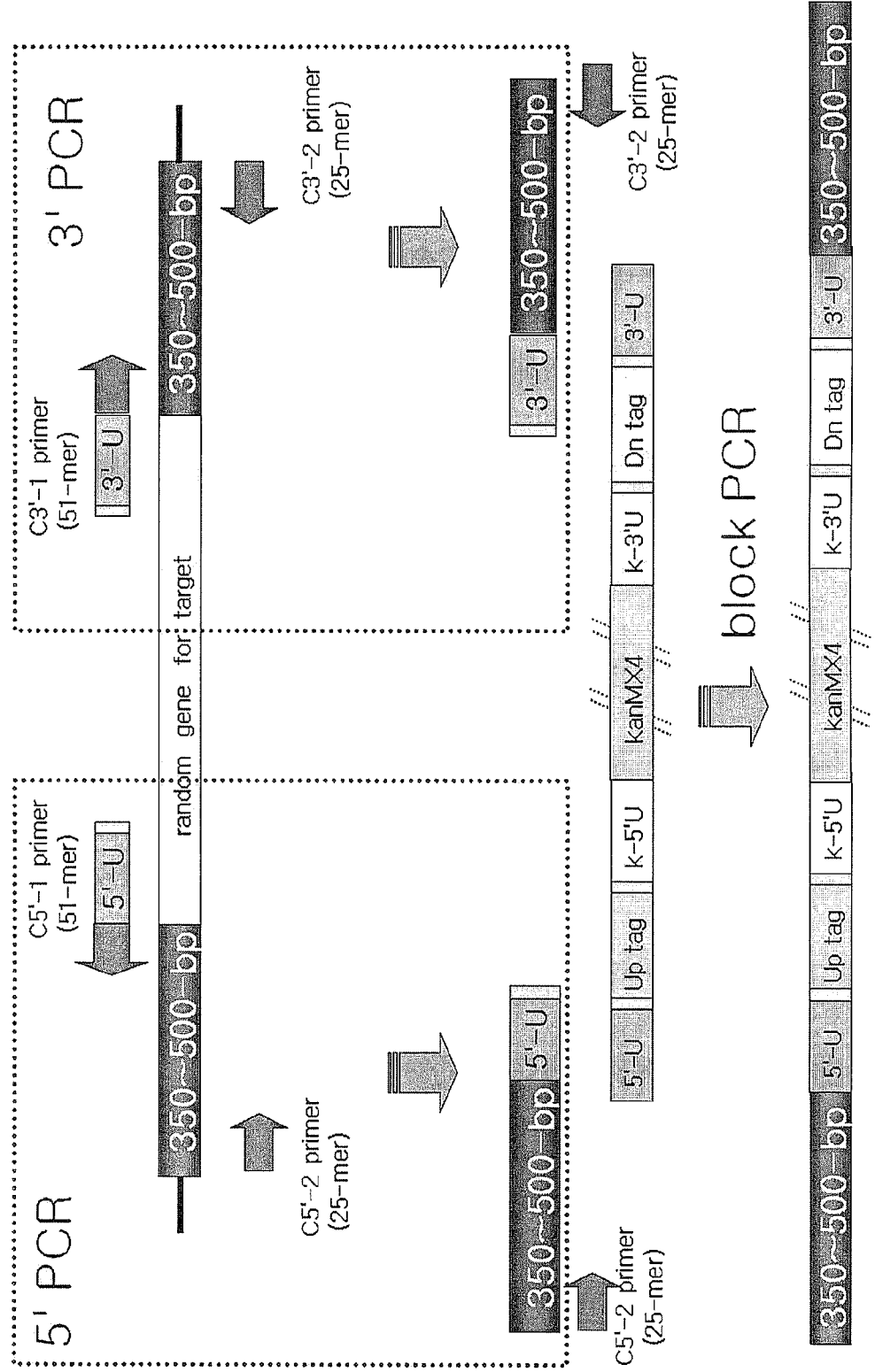
FIG. 4 construction of deletion cassette by quadruple block PCR

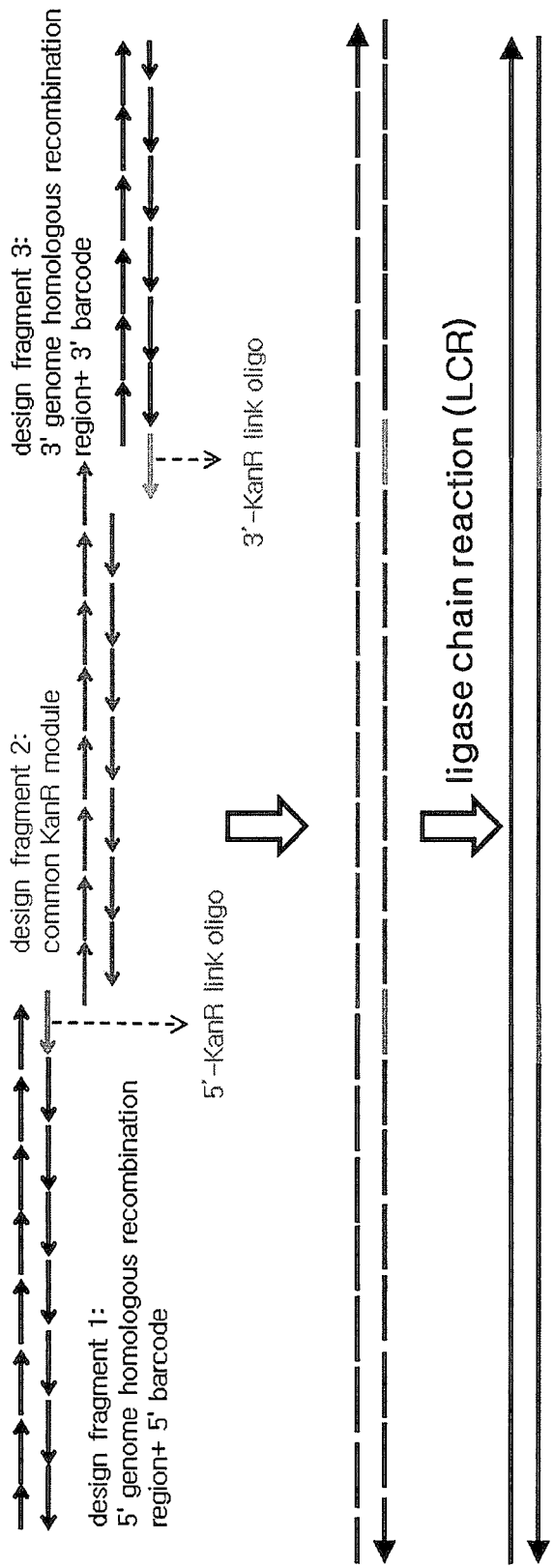
FIG. 5 construction of deletion cassette by gene synthesis

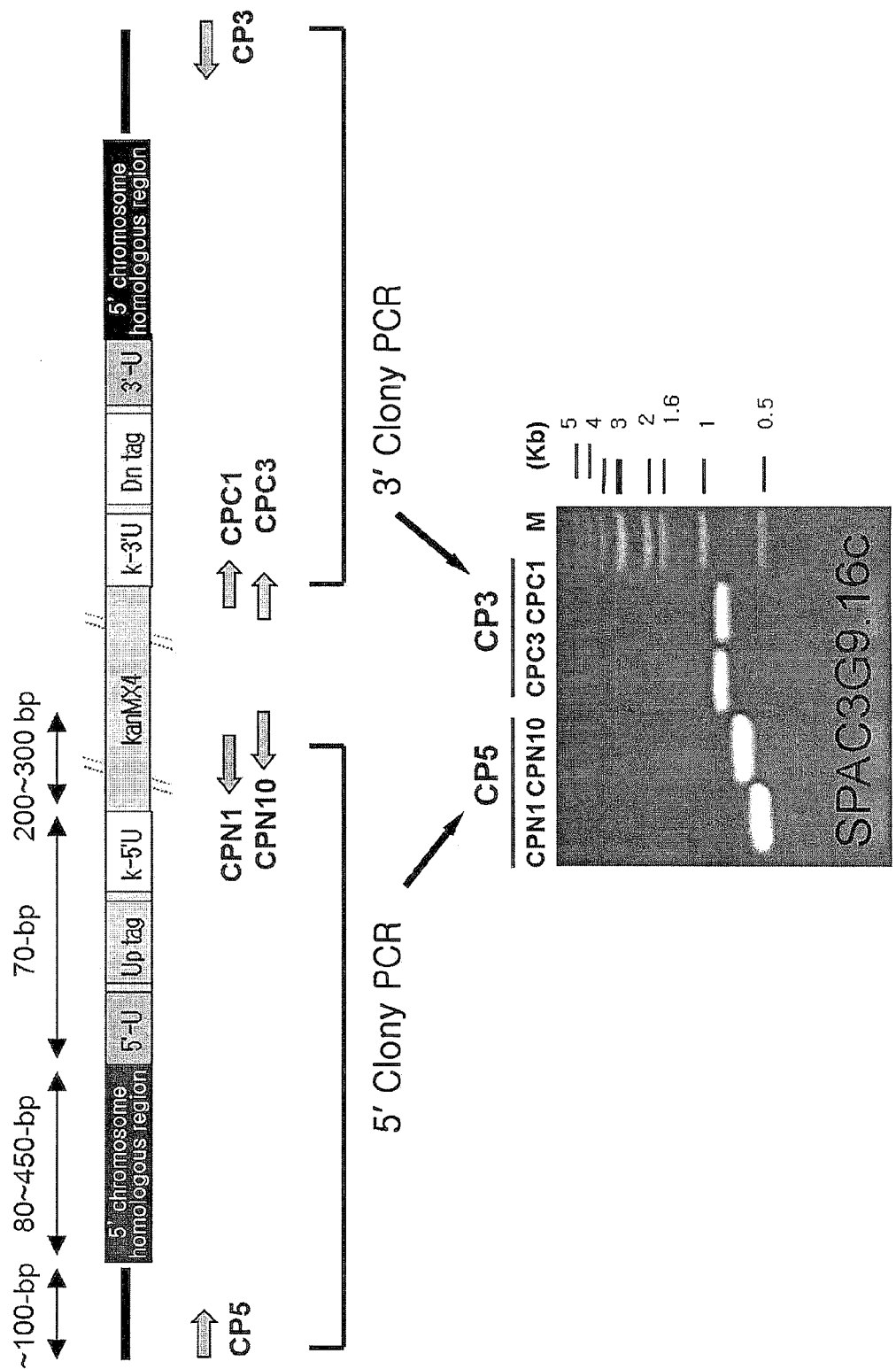
FIG. 6 colony PCR of prepared strain

FIG. 7

| Sequence number | Name | Base sequence |
|---|---|---|
| 1 | CPN1 | CGTCTGTCAGGGGAGCGTTT |
| 2 | CPN10 | GATGTGAGAACTGTATCCTAGCAAG |
| 3 | CPC1 | TGATTTTGATGACGAGCGTAAT |
| 4 | CPC3 | GGCTGGCCTGTTGAACAAGTCTGGA |
| 5 | U1 | GCTCCCGCCTTACTTCGCAT |
| 6 | U2 | CGGGGACGAGGCAAGCTAA |
| 7 | D1 | GCCGCCATCCAGTGTCG |
| 8 | D2 | TTGCGTTGCGTAGGGGGG |
| 9 | at_KRIBB_SP1 | GTCGTCAAGATGCTACCGTTCAGGA |
| 10 | 5U-Block | CGCTCCCGCCTTACTTCGCATTTAAA |
| 11 | K5U-Block | GGGGACGAGGCAAGCTAAGATATC |
| 12 | 3U-Block | TTGCGTTGCGTAGGGGGGATTTTAAA |
| 13 | K3U-Block | CGCCATCCAGTGTCGAAAAGTATC |
| 14 | 5U-Block (rev comp) | TTTAAATGCGAAGTAAGGCGGGAGCG |
| 15 | K5U-Block (rev comp) | GATATCTTAGCTTGCCTCGTCCCC |
| 16 | 3U-Block (rev comp) | TTTAAAATCCCCCCTACGCAACGCAA |
| 17 | K3U-Block (rev comp) | GATACTTTTCGACACTGGATGGCG |
| 18 | SPAC1002.09c_UP | AACGGCTCAGACCACTGTCG |
| 19 | SPAC1002.09c_DN | GAAAATGGGAGGGAGCGCGC |
| 20 | SPAC1006.08_UP | CTCCGTGGTCACAACCCGAA |
| 21 | SPAC1006.08_DN | GTCCGAGAGTCGGCACGAAT |
| 22 | SPAC1039.11c_UP | TGGAGGTTGAAAGGGGGGCT |
| 23 | SPAC1039.11c_DN | CAAGATGCTGCCGGGAAACG |
| 24 | SPAC1071.01c_UP | ACGGATAGTGCCCTGAGCTG |
| 25 | SPAC1071.01c_DN | GCGTGTAGTGCAGCTGTGTC |
| 26 | SPAC1093.01_UP | TCAGGCTTGGGATCGCGGAA |
| 27 | SPAC1093.01_DN | GATGGGCGGCAGCAGATAA |
| 28 | SPAC10F6.01c_UP | GCACGGGGGGAAACTCACAGC |
| 29 | SPAC10F6.01c_DN | TGTATGTCGGGTGGCGGGTA |
| 30 | SPAC10F6.03c_UP | CTCTTTCGTCCGCCGCTTCC |
| 31 | SPAC10F6.03c_DN | CAGGGCGTGAGTGGGGCAAG |
| 32 | SPAC10F6.17c_UP | AGATCCGAGGGGAACCCAGC |
| 33 | SPAC10F6.17c_DN | CCAATGCTGTAGGCGGGGTC |
| 34 | SPAC110.04c_UP | GCTGGTCCACAAAACGCCCT |
| 35 | SPAC110.04c_DN | CGTTGCGGTTTATTGCTCGC |
| 36 | SPAC1142.02c_UP | GTTCGTGCCCGTCTTTCCCC |
| 37 | SPAC1142.02c_DN | TTCTGAGCTTGACGGGGCGC |
| 38 | SPAC1142.08_UP | TATCTGCGCTAGGGGTCGCC |
| 39 | SPAC1142.08_DN | TGCCCCGCGCTTCCTTACC |
| 40 | SPAC11E3.01c_UP | GTCTGTCGTCGTGTGCGCGGG |
| 41 | SPAC11E3.01c_DN | TCTCTCGGCAPTGGGGGGGT |
| 42 | SPAC11E3.03_UP | CGTACACCGCCGCAAACAAG |
| 43 | SPAC11E3.03_DN | CCCACAAACAACGGCACGGA |
| 44 | SPAC11E3.07_UP | GCTCGGGGGTAGGGTGGACA |
| 45 | SPAC11E3.07_DN | CACCCTTCGCTGCCCATTGA |
| 46 | SPAC11E3.15_UP | CGTTCGATGTGGGGGTTTTT |
| 47 | SPAC11E3.15_DN | CGAGCCCAATGCATAGCCCC |
| 48 | SPAC11H11.06_UP | GGTGGCATTGGGGCTTTCGA |
| 49 | SPAC11H11.06_DN | TCCATCGCGAAACACAGCCT |
| 50 | SPAC1296.01c_UP | CCGAAAACCGACCGAACACC |
| 51 | SPAC1296.01c_DN | CGGAGGGTACGCCAATGGAA |
| 52 | SPAC12B10.01c_UP | CCCGTCTGCTCGCCACTTTG |
| 53 | SPAC12B10.01c_DN | GAGCGGGTCGGGAGAGGTTT |
| 54 | SPAC12G12.02_UP | CCCCAAGACAACGCGCCAAC |
| 55 | SPAC12G12.02_DN | TTGGCGCGACGGCTAGCATCT |
| 56 | SPAC12G12.14c_UP | ACGGCTCGATGAAACCCGTG |
| 57 | SPAC12G12.14c_DN | GCTCTCCATCGACGTCCGC |
| 58 | SPAC12G12.16c_UP | GGTTGTGCAGCGAGGGCGTT |
| 59 | SPAC12G12.16c_DN | ACCCCGACCCGAAAGCCATC |
| 60 | SPAC139.01c_UP | TCCCCCGTGGCTCTTCGTTT |
| 61 | SPAC139.01c_DN | GTTTCAGTCAAGTCGGGGGC |
| 62 | SPAC13A11.06_UP | ATACCAGACCGTTTCGCCG |
| 63 | SPAC13A11.06_DN | AGTCGCGTAGGGGCGGGTC |
| 64 | SPAC13C5.02_UP | AGGAGGATAACGGCACGGGA |
| 65 | SPAC13C5.02_DN | ACTGGGGGTGGTTAATGGCG |
| 66 | SPAC13F5.01c_UP | TCGGAACCCCAASGCAAACA |
| 67 | SPAC13F5.01c_DN | GCCGGCCTAACGCTATCCCA |
| 68 | SPAC13G6.12c_UP | CCACCGCCCATATGTTCCC |
| 69 | SPAC13G6.12c_DN | GCCTCCCGACCATGCACTTT |
| 70 | SPAC13G6.14_UP | ACCAGTGAAACGAAGCCGCG |
| 71 | SPAC13G6.14_DN | CACAACTCGACCGCCCGCTT |
| 72 | SPAC13G7.01c_UP | AAGTTGCGGCCTAGTGGCCT |
| 73 | SPAC13G7.01c_DN | GACGGTGTGGGGGCGAAGGT |
| 74 | SPAC13G7.03_UP | GGGGGCGGGCATCGATTATA |
| 75 | SPAC13G7.03_DN | TTGCGGGGCTGTCGGTGATA |
| 76 | SPAC13G7.07_UP | ATGCAGGTGGAGGGAACGGG |
| 77 | SPAC13G7.07_DN | CGTAACTTTGTGCCCGCGTG |
| 78 | SPAC13G7.11_UP | GAATGGCAGTGGCGGGAAGC |
| 79 | SPAC13G7.11_DN | CGGGACGACAAGGGAGGAGA |
| 80 | SPAC13G7.13_UP | CGTCCCTGCGCAATAAGCTG |
| 81 | SPAC13G7.13_DN | CCAGGTCCCGCTCACTTCCC |
| 82 | SPAC144.08_UP | CTTCCACCGACGGACCAACA |
| 83 | SPAC144.08_DN | TTTTTATGGCCGGGATCGCG |
| 84 | SPAC144.12_UP | CGCGTGGTCTTGTCGGTGAA |
| 85 | SPAC144.12_DN | CGATCCCCTACCAGCCCCGT |
| 86 | SPAC14B6.06_UP | CCTCACGGCATGTGCGTGTT |
| 87 | SPAC14B6.06_DN | GCCCACGTAGCGGATAACCT |
| 88 | SPAC14B6.10_UP | TCCCCGACGCACACGAAGAT |
| 89 | SPAC14B6.10_DN | CCGCAAACAGAAGGCAATCG |
| 90 | SPAC1527.02_UP | TGTCGACGGACTCCTCACGA |
| 91 | SPAC1527.02_DN | CTCCGTAATCGGCGCGAATG |
| 92 | SPAC1556.01c_UP | TGTCGAGTGGGCGCGTTATC |
| 93 | SPAC1556.01c_DN | TCTGTCATAACCGCCGCCGA |
| 94 | SPAC1556.07_UP | ACGACGCGGTAGTAACCGCT |
| 95 | SPAC1556.07_DN | TGAGTCCGGTCGATAGGGGT |
| 96 | SPAC15A10.01_UP | AGCGGAAGGAAGAGGGAGCC |
| 97 | SPAC15A10.01_DN | GGGTGTTTGTCGGGGGCAC |
| 98 | SPAC15A10.16_UP | TCCGCCTCTGCCCACCTGAC |
| 99 | SPAC15A10.16_DN | GACGGTTGCAAGGTGGCTGG |
| 100 | SPAC15E1.07c_UP | AGGGGATCCAGTGCGGCTTT |
| 101 | SPAC15E1.07c_DN | CATCCCCGTACCCACCCCTG |
| 102 | SPAC15F9.03c_UP | GGGATTTCGACGTGGTTGCA |
| 103 | SPAC15F9.03c_DN | GCCCTACCAGATTGCCAGCG |
| 104 | SPAC16.02c_UP | CGACGTCACGCCGATCCTTA |
| 105 | SPAC16.02c_DN | GACGAGTGTGACCGTGCAGA |
| 106 | SPAC1610.01_UP | TGACATAATCGAGGGGCGCG |
| 107 | SPAC1610.01_DN | AAACTGCCGATGCCTGACCG |
| 108 | SPAC1639.02c_UP | TGCGGCGGAATCAGTTAGGG |
| 109 | SPAC1639.02c_DN | CGTATGCGAGCCTCGGAAGGT |
| 110 | SPAC167.02_UP | CACGGGGCAATGGGAGAGACG |
| 111 | SPAC167.02_DN | TGAGCGCGGAGGGAAGAAGG |
| 112 | SPAC167.06c_UP | GTGTTGTTCATGGGCGCGGA |
| 113 | SPAC167.06c_DN | GCTGTGTGAGCTGACGCCAT |
| 114 | SPAC167.08_UP | ACGCGAGGGTTCAAGGCAGA |
| 115 | SPAC167.08_DN | GAACGAAACCGATCGCGCTC |
| 116 | SPAC1687.22c_UP | AGTACCGAGGGAGGCCGGAA |
| 117 | SPAC1687.22c_DN | GGGGGGGAGTGGTGAACGCAG |
| 118 | SPAC16A10.05c_UP | TGCGAGAGTGCCGACGTGAT |
| 119 | SPAC16A10.05c_DN | AATGCGCTGACAGGTCTCGC |
| 120 | SPAC16C9.01c_UP | TGGTGAGCAGGCAGCGATTT |
| 121 | SPAC16C9.01c_DN | TGCGTGAACACGGGCCAGAT |
| 122 | SPAC16C9.07_UP | CGGATTGTTGAACGGTGGGG |
| 123 | SPAC16C9.07_DN | TGCGTGTCTCGCTCGGTTCT |
| 124 | SPAC16E8.02_UP | CACCCAAGCTTCGCCACACC |
| 125 | SPAC16E8.02_DN | CCTCTCCTTCCGCGCGTCTT |
| 126 | SPAC16E8.08_UP | GGGAACCAGCGGGGCGATAG |
| 127 | SPAC16E8.08_DN | ACTTGCTTCCGGGTTCGATG |
| 128 | SPAC1705.03c_UP | CCGTGTGCGAAGCCAGAAAA |
| 129 | SPAC1705.03c_DN | GCGCCTCTGCCACTCCCAAC |
| 130 | SPAC1782.04_UP | GGGCAAAAGGACGTGGGTGG |
| 131 | SPAC1782.04_DN | GCTATCGGTTTTGGGCGGGA |
| 132 | SPAC1783.04c_UP | GGGCGAGTCGAACCTCATCT |
| 133 | SPAC1783.04c_DN | TGCGGCTCACTGGGGATTA |
| 134 | SPAC17A2.14_UP | TACTCCGTTCCCCACCCGCT |
| 135 | SPAC17A2.14_DN | TTAGGGTCGGGGGGTCGGAG |
| 136 | SPAC17A5.08_UP | ATGTGGGCGGGCGTGAACGC |
| 137 | SPAC17A5.08_DN | ACTCCCCACACTCCGCCCTA |
| 138 | SPAC17C9.01c_UP | TGGGATGGAAATTGCAGGGC |
| 139 | SPAC17C9.01c_DN | TATTGCGGGCCTTGCGGTGT |
| 140 | SPAC17C9.03_UP | TGGAGGCAGGTAGGGGTGGA |
| 141 | SPAC17C9.03_DN | ACTTGTTGTTGGCAGCGCGG |
| 142 | SPAC17C9.06_UP | TCCGGATCTGTGCAGCCAGT |
| 143 | SPAC17C9.06_DN | TGGCTAGAGTACGCCGGAAC |
| 144 | SPAC17D4.04_UP | TCTACCGCCACGCTCCCCAT |
| 145 | SPAC17D4.04_DN | GCCGCCTCTTGACTCGCTTG |
| 146 | SPAC17G6.09_UP | GGGGGGGATGCCGCTTAAGA |
| 147 | SPAC17G6.09_DN | CCGCGGGTTCTTCTGGCTTG |
| 148 | SPAC17G6.11c_UP | GGGGTAGCGTTTGGGGATCG |
| 149 | SPAC17G6.11c_DN | CGACATACCACGGCGAATCG |
| 150 | SPAC17G8.06c_UP | TTTTTCTATCACGGCCGCCC |
| 151 | SPAC17G8.06c_DN | CAGCAACATTCACGCCCGC |
| 152 | SPAC17G8.10c_UP | TGACACGCTTAGTCCGCGCC |
| 153 | SPAC17G8.10c_DN | ATCCGCGTAAGGCGTCACCC |
| 154 | SPAC17G8.14c_UP | TCGCATTGTTCGCCTCCCTT |
| 155 | SPAC17G8.14c_DN | ACAAAAGGTGGCGAACGGGGC |
| 156 | SPAC1805.01c_UP | TTGGGCGTTTGGGCGGTACG |
| 157 | SPAC1805.01c_DN | GGGCGCAGTCGGAAATAACC |
| 158 | SPAC1805.03c_UP | TCGGGCGTGCGGACAAAGAG |
| 159 | SPAC1805.03c_DN | CCCCCCCGTACCGCTGAAAA |
| 160 | SPAC1805.13_UP | TCGACAGCAGGACAAGCACGG |
| 161 | SPAC1805.13_DN | CGGTTTGCCGAGGTTTTGGG |
| 162 | SPAC1805.17_UP | TCACGACTACCCCGCCAATG |
| 163 | SPAC1805.17_DN | ATACACTCCGCCCCCCTCGT |
| 164 | SPAC1934.02_UP | TCTCCCCCATACCCCCGCAA |
| 165 | SPAC1934.02_DN | CATCGGGGGATACGCTTAGG |
| 166 | SPAC18B11.05_UP | TGTAACTCCGTCGCGCTGGC |
| 167 | SPAC18B11.05_DN | TTGTGCGGCGTGTTCGTGAT |
| 168 | SPAC18B11.09c_UP | TGGGTGATATGGCGTCCGAT |
| 169 | SPAC18B11.09c_DN | CCAGGCACGCGCAATTATGA |
| 170 | SPAC18B11.11_UP | TTATTCCCCTGAGCGCCACC |
| 171 | SPAC18B11.11_DN | GAGGAAGGGAAGGCGGGGTC |
| 172 | SPAC18G6.06_UP | TAGAAGCATGACCACCGCGC |
| 173 | SPAC18G6.06_DN | TCCTAATCCCCTCACGCTCT |
| 174 | SPAC18G6.09c_UP | CTCCCTCATCCCCAGCCACG |
| 175 | SPAC18G6.09c_DN | TGGAAAAGCCGAGGGACGCC |
| 176 | SPAC18G6.11c_UP | TGGGTTGCGCCTGGTATGCC |
| 177 | SPAC18G6.11c_DN | GGGGGACGCTTATTCGCAAG |
| 178 | SPAC1952.02_UP | ACTCCCGCCTTCGCCACTTG |
| 179 | SPAC1952.02_DN | CAATAGGCACCCGCAGACGC |
| 180 | SPAC1952.17c_UP | GGTGTCCAAGGGCGCAAGTG |
| 181 | SPAC1952.17c_DN | TTCCCCGGCACACCAGGCTAC |
| 182 | SPAC19A8.06_UP | AATTGTCCCGCCCAGCTCT |
| 183 | SPAC19A8.06_DN | TCGGCCAACGGATAAACGCA |
| 184 | SPAC19B12.01_UP | AGGAAGCCAAGCCCGCGTAC |
| 185 | SPAC19B12.01_DN | GTACGCTTAATCTGTCGCCC |
| 186 | SPAC19B12.03_UP | GTCGTACTCGGCCTTTGCGC |
| 187 | SPAC19B12.03_DN | AAAGGCGGGCGGTGAAAAGA |
| 188 | SPAC19G12.07_UP | ATTGCGACGGGACGGAGGTA |
| 189 | SPAC19G12.07c_DN | TCGCGCCGGGTGAATAAGCT |
| 190 | SPAC1A6.01c_UP | GCTGCGGGCGTGTGTTTGTCA |
| 191 | SPAC1A6.01c_DN | GTACACGCTTCACCATCGCA |
| 192 | SPAC1A6.03c_UP | CCGCCCCTGCTTACCTTCCA |
| 193 | SPAC1A6.03c_DN | GGGTCATAGCGATCGGCGGT |
| 194 | SPAC1B3.13_UP | GGACTAAGCGGGGCGGATTT |
| 195 | SPAC1B3.13_DN | GTCCGTTGCTTGTGGGTGCG |
| 196 | SPAC1B9.03c_UP | ACTGTTCGTTCGCTGCCCCC |
| 197 | SPAC1B9.03c_DN | AAGGGTGGAAACGGTGGGGA |
| 198 | SPAC1D4.10_UP | CCTCGGACCCCTAACCCCCT |
| 199 | SPAC1D4.10_DN | GAGGGAACGCCGGTGAGGAT |
| 200 | SPAC1D4.14_UP | GCGGGAACTTGGTGGGGTGA |
| 201 | SPAC1D4.14_DN | CGCGGAAGGGAACACCCATT |
| 202 | SPAC1F7.04_UP | GACCCTCGAAACCTGCTCGC |
| 203 | SPAC1F7.04_DN | ACCGAGGCGTCATTCCCAGC |
| 204 | SPAC1F7.12_UP | ATAAGCATCGAGCGGGCGGA |

| Sequence number | Name | Base sequence |
|---|---|---|
| 409 | SPAC823.12_DN | CGGGAGTCTTGGCGCAATTG |
| 410 | SPAC824.07_UP | AAGCAGGGAGGAGGCCAAGC |
| 411 | SPAC824.07_DN | ATGCTATTGGTCGGGCTGGG |
| 412 | SPAC8E11.01c_UP | CTCCTCGTCGTTGGCGTGCA |
| 413 | SPAC8E11.01c_DN | GCGCAGGGACCGAGATACG |
| 414 | SPAC8F11.06_UP | ATGGACGAGGTGCGAGAGAC |
| 415 | SPAC8F11.06_DN | TCGCCCCACCCCTCGTTATC |
| 416 | SPAC8F11.10c_UP | ACATGCCGTCCTCCGCCTCC |
| 417 | SPAC8F11.10c_DN | GCATTAACCAGGCGCGCAGC |
| 418 | SPAC9E9.09c_UP | GGGGGAAAAGTGGGGCTTCG |
| 419 | SPAC9E9.09c_DN | CACAAGCTCCCCCCACGGCT |
| 420 | SPAC977.05c_UP | TCCCCCCGTCTCGTCATTTC |
| 421 | SPAC977.05c_DN | CGGCCCAATCAGCAGCAAAG |
| 422 | SPAC977.07c_UP | TGCCGACTCAGGCGGAAAAC |
| 423 | SPAC977.07c_DN | TTAACCGGGTCGCACACTCG |
| 424 | SPAC9E9.07c_UP | TCGCGCGGACTCAAATGGAC |
| 425 | SPAC9E9.07c_DN | GCCAACGCCAATCCCGAACTC |
| 426 | SPAC9E9.11_UP | AGATGGGGGGGCTAACCGAA |
| 427 | SPAC9E9.11_DN | TACTGGCCCTTCTTCACCGAC |
| 428 | SPACUNK4.07c_UP | TCTTGTGGCGTTTGCCTCGG |
| 429 | SPACUNK4.07c_DN | CCCACCATCTCGTTCCCTGG |
| 430 | SPAP11E10.01_UP | TGCGGACTAGCCTACGTCAS |
| 431 | SPAP11E10.01_DN | AACCCGTTGATCTCCGGACC |
| 432 | SPAP27G11.03_UP | TCTGAGGGGATGCGTGACAG |
| 433 | SPAP27G11.03_DN | CGACTTTCAGCCCCGACAT |
| 434 | SPAP27G11.05c_UP | CCGAAGCGCCAACCCACAGT |
| 435 | SPAP27G11.05c_DN | ACATTAGGAGCCACGGGGCG |
| 436 | SPAP27G11.07c_UP | TTTCTTTGCCGGTGCGTCGT |
| 437 | SPAP27G11.07c_DN | ATAGTAGCGCGCGCATGAGT |
| 438 | SPAP27G11.09c_UP | CGTCAAGCGAAAGGCCCCAC |
| 439 | SPAP27G11.09c_DN | CCGTCTTAATGGGCGCCGAC |
| 440 | SPAP7G5.02c_UP | CTTGGTGAGCGCGATGTGTC |
| 441 | SPAP7G5.02c_DN | CAGACCCCGACTAGCACGCA |
| 442 | SPAPB3A3.06_UP | CACCCGCCTTCCGTTGTCAG |
| 443 | SPAPB3A3.06_DN | TTCGTCCCCTCCGCTTGTTC |
| 444 | SPAPB21F2.03_UP | TGCGCCCATGCCTCGTAGTC |
| 445 | SPAPB21F2.03_DN | CGCCTACTCTTCGGCTGCCC |
| 446 | SPAPB2B4.02_UP | GCGGGTTCGGATTTTAGGG |
| 447 | SPAPB2B4.02_DN | TCGGGTTGCTGTGAGGGGAG |
| 448 | SPAPB2B4.06_UP | GACACGGCCTAACGCCTCCG |
| 449 | SPAPB2B4.06_DN | CGGTCAGGGAGAAAGAGGCG |
| 450 | SPAPB8E5.09_UP | CTGCACGCCCATACGAACCG |
| 451 | SPAPB8E5.09_DN | CCGTTGCCTTGCTGTACCCC |
| 452 | SPAPYUG7.05_UP | GCCCCCAACAGGAGCAGGAC |
| 453 | SPAPYUG7.05_DN | CTTGGCGGTGCTCTGTGGGG |
| 454 | SPBC106.18_UP | GACCGCGGTGTCCCCTTTG |
| 455 | SPBC106.18_DN | TCTGGGCAACTGGCGGAAGT |
| 456 | SPBC106.20_UP | CCCCGCTTTCATGCACGACC |
| 457 | SPBC106.20_DN | TTTCAACGGCGAGGACGAGA |
| 458 | SPBC119.09c_UP | GTTGTAGGACGGGGCTGGGG |
| 459 | SPBC119.09c_DN | ATACTTGGTTGAGCGGGGGA |
| 460 | SPBC1198.04c_UP | CGCCCGACCTTCATTTACGC |
| 461 | SPBC1198.04c_DN | TTCGCGCCGCCTGATAACCT |
| 462 | SPBC1198.12_UP | AAAGTAGTTCCTGCGCCCGC |
| 463 | SPBC1198.12_DN | CCACCCATGCATCGCCACTT |
| 464 | SPBC1198.14c_UP | ATCGGGTGCCGTCGCTGTCG |
| 465 | SPBC1198.14c_DN | TATGCAGGCGCACAGGCAA |
| 466 | SPBC11C11.04c_UP | AAATGCGGGGTGTGGGACTC |
| 467 | SPBC11C11.04c_DN | GCTACGGTCTGGAGGTCCGG |
| 468 | SPBC11C11.10_UP | AAACCTACGCCGTGTACCGCC |
| 469 | SPBC11C11.10_DN | CTTAAGGGAGGGCGCGAGAA |
| 470 | SPBC11G11.04_UP | CCCCCCACTTCCAGCACTCG |
| 471 | SPBC11G11.04_DN | TTAGTCGCCAGGCCGTCCTC |
| 472 | SPBC11G11.06c_UP | GCGGCCCGGCGTTAGGGACTA |
| 473 | SPBC11G11.06c_DN | GGTACGTCCGGTTGCTCTTC |
| 474 | SPBC1271.13_UP | CGCAACAAACCTGCACGCGA |
| 475 | SPBC1271.13_DN | GTACCGGCCAAGTCAGCGGT |
| 476 | SPBC1289.14_UP | GGGGGCCGTGGGAATAAGAGG |
| 477 | SPBC1289.14_DN | ATGCGGCCGTGTTGATTTGC |
| 478 | SPBC1289.16c_UP | GTTACCGCGGGCTTCTGTGG |
| 479 | SPBC1289.16c_DN | AATGATGGCGGTGGAGGACG |
| 480 | SPBC12C2.06_UP | AGGTCGACAGGAGGGGAGGC |
| 481 | SPBC12C2.06_DN | AAACAATGTCGCACGTCGGG |
| 482 | SPBC12C2.10c_UP | GCCTCAGGCACAACAGACCG |
| 483 | SPBC12C2.10c_DN | CACGTGCGCCCCTCTCCCTT |
| 484 | SPBC12C2.12c_UP | ATCGTAAGGGTTTTTGGGCT |
| 485 | SPBC12C2.12c_DN | CGGTCCAGCCATCCACAAGG |
| 486 | SPBC12D12.01_UP | GGGGCTTAGTGCTGGTGGGA |
| 487 | SPBC12D12.01_DN | GGGTCTGGGGGCGATTACAA |
| 488 | SPBC1306.01c_UP | CGCCGAGAAAAACAGCCAGC |
| 489 | SPBC1306.01c_DN | TGTGGGTTGACGAGCTGGCG |
| 490 | SPBC1347.01c_UP | ACGAATGTGAGTGCCTCCGG |
| 491 | SPBC1347.01c_DN | GCTTGGTGATTGTGGCGGAG |
| 492 | SPBC1347.05c_UP | CTCACGCCCGTTATTTCGCC |
| 493 | SPBC1347.05c_DN | GGGCGGAGGACCGGTACAGA |
| 494 | SPBC1347.07_UP | AACGTGGCGGCGTCGCACCTTA |
| 495 | SPBC1347.07_DN | CCGGATTAACGACCACGCCT |
| 496 | SPBC1348.14c_UP | CGCACAGGTCCCCAGCCAAC |
| 497 | SPBC1348.14c_DN | TCTGCCGCTTCCCAATACCG |
| 498 | SPBC13E7.10c_UP | GCAACCTGGCCTCGACAACG |
| 499 | SPBC13E7.10c_DN | ACGGTCCTGCGAAACTGCCC |
| 500 | SPBC13G1.01c_UP | TTACGGGAGGACGGCAATG |
| 501 | SPBC13G1.01c_DN | AAAGTGGGTCGTGGGGCGAT |
| 502 | SPBC13G1.07_UP | GAGGGGCAACCGAAAGCGAG |
| 503 | SPBC13G1.07_DN | GGTCGAGTGGGGGGCCTTTG |
| 504 | SPBC13G1.11_UP | GATGGGGGTTTAGACGGGGG |
| 505 | SPBC13G1.11_DN | TGTTGGGCGAAGAATGCTGG |
| 506 | SPBC13G1.13_UP | ACATCGATTACCGACCGCC |
| 507 | SPBC13G1.13_DN | GGCGGGGTGAGTTGGTGCTT |
| 508 | SPBC146.01_UP | TAGGGAGCGGGGGGTGAACGA |
| 509 | SPBC146.01_DN | ATATCAGAAGGACCGGCGCG |
| 510 | SPBC146.13c_UP | AAACGCCACCGCATACCCAG |
| 511 | SPBC146.13c_DN | GGTGGCTGGGAGAGA3CGGA |
| 512 | SPBC14C8.01c_UP | GTGACAAATGCTGGGCGCCT |
| 513 | SPBC14C8.01c_DN | TCGTAGATTGACCGCCGCCT |
| 514 | SPBC14C8.07c_UP | ACCGCCCGAAGTGTGCTCAC |
| 515 | SPBC14C8.07c_DN | ACCCCATTTCGCCGGTTCCT |
| 516 | SPBC1539.01c_UP | AGCGAGGGTTGCGGGTGAAA |
| 517 | SPBC1539.01c_DN | TCCCGATTCAACCGGCTCTT |
| 518 | SPBC1539.09c_UP | TCGCCGCACAGCCGTAGACC |
| 519 | SPBC1539.09c_DN | GGGTGAAGGGGTGCCAGCTCG |
| 520 | SPBC15C4.01c_UP | TCGGGGGACCTTGGTTTTAG |
| 521 | SPBC15C4.01c_DN | TAACCAGGCCGGAGCGACAG |
| 522 | SPBC15C4.03_UP | CCGCTCCAACACCCCGACAG |
| 523 | SPBC15C4.03_DN | CTACAACCCTGCACTCCCGC |
| 524 | SPBC15D4.01c_UP | AGCGAGTTAGCCGGGTGGCC |
| 525 | SPBC15D4.01c_DN | TACATCCCGCCACCACCCAC |
| 526 | SPBC15D4.11c_UP | TTTTTGCGCGGCACTGCTCT |
| 527 | SPBC15D4.11c_DN | TCGACAGGCCGGAACAAAGC |
| 528 | SPBC1604.06c_UP | CCGTCGTCGCCATAGTCTGG |
| 529 | SPBC1604.06c_DN | GCTGGCTAACTGCGGTGACG |
| 530 | SPBC1604.09c_UP | CACACGAAAATCTGCCGCTCG |
| 531 | SPBC1604.09c_DN | TCGGACTAGGTGCATTGCCG |
| 532 | SPBC1685.10_UP | CGCCCTGACGAGCAACCACT |
| 533 | SPBC1685.10_DN | ACCGGCGCCCCCATACTCAAG |
| 534 | SPBC18A3.02c_UP | GGAGTTCCCGGTCAGACGTT |
| 535 | SPBC16A3.02c_DN | CGGGTCGTTGCCTGGTCTGG |
| 536 | SPBC16C5.13c_UP | TCCGCAGCTGGGGATCATAC |
| 537 | SPBC16C5.13c_DN | TCAAAACGGACGGCCCAACA |
| 538 | SPBC16E9.01c_UP | AAGGAAGAGGCTGGGGCACG |
| 539 | SPBC16E9.01c_DN | ACGGTCGGCTAGCAGGTTGG |
| 540 | SPBC16E9.16c_UP | TTCCGCCTCGATCCCTTCCA |
| 541 | SPBC16E9.16c_DN | CATCGCTCGCTACGCGATCT |
| 542 | SPBC16E9.18_UP | CGACACTCCAAGCTCCCGGG |
| 543 | SPBC16E9.19_DN | GCCGGTGCCCTCAATTGGAT |
| 544 | SPBC16G5.01_UP | TCGGGCTCAGTGCGTACAAC |
| 545 | SPBC16G5.01_DN | TGCGCTTAGGTCGCAACAT |
| 546 | SPBC16H5.10c_UP | AGGGCTTGAGATTCGGCGGG |
| 547 | SPBC16H5.10c_DN | AGGTGCGCTGTGGGGGAAG |
| 548 | SPBC16H5.12c_UP | GCGGGTGTGGAGTAGCGAGC |
| 549 | SPBC16H5.12c_DN | CCGCGGCACCAAGTAGGAAT |
| 550 | SPBC1703.11_UP | CCGACATAGAGCCGCACCTG |
| 551 | SPBC1703.11_DN | GAAACTCGCTCCGCACCCC |
| 552 | SPBC1703.15c_UP | GGAAAGCTAAAGGGCACGCC |
| 553 | SPBC1703.15c_DN | CTGCGCGGTGTCTTTTGCCT |
| 554 | SPBC1709.C1_UP | TCCTCTGCGGTGGTCGTGTC |
| 555 | SPBC1709.01_DN | CTCAGGGGTAGTGCAGGCGA |
| 556 | SPBC1709.17_UP | GGCGATTCGAAGGGCGAGTT |
| 557 | SPBC1709.17_DN | CTCTGCGCATTAAGCGCCAT |
| 558 | SPBC1709.19c_UP | TTCGGCCCACCACCTATCGA |
| 559 | SPBC1709.19c_DN | GAGGGCGCGCTTGTCACTTT |
| 560 | SPBC1711.14_UP | ACCACCATTCGGACCCATCC |
| 561 | SPBC1711.14_DN | TCAGGCATGGCGTGGGTTTG |
| 562 | SPBC1711.16_UP | AAGTGGGCAGCCGATCATC |
| 563 | SPBC1711.16_DN | CGTCAGGCGAGCACCGGTTA |
| 564 | SPBC1718.05_UP | GCTCCCGCTGATGGTTGCTT |
| 565 | SPBC1718.05_DN | CAGACGAACACCGCCGACCG |
| 566 | SPBC1734.07c_UP | GGGCCGGTCATCTTCTCCT |
| 567 | SPBC1734.02c_DN | AGGCCCGTCCCTCGTAAGGAT |
| 568 | SPBC1734.04_UP | ACGGCCGTCACAGCTGCTTT |
| 569 | SPBC1734.04_DN | CATCCGGGTCGGTAGACGCG |
| 570 | SPBC1734.10c_UP | CTGCCCAACCCTCATCGCGT |
| 571 | SPBC1734.10c_DN | GGATAGGCTCGCAAAACGGG |
| 572 | SPBC1734.16c_UP | CTGATCGCTCGGCGCAAATGA |
| 573 | SPBC1734.16c_DN | CCGGCAGGGGAATGATGAAG |
| 574 | SPBC1778.01c_UP | TCATTACCGTCGTGCCCCCG |
| 575 | SPBC1778.01c_DN | GTCATGGTGTGCGGGGCTGT |
| 576 | SPBC17A3.01c_UP | ACCGTGCGAACGGAACAGTC |
| 577 | SPBC17A3.01c_DN | AAAATCAAGGCACGGGGACG |
| 578 | SPBC17A3.05c_UP | CGCTTCACAACCCCCAGTCC |
| 579 | SPBC17A3.05c_DN | GTTGTTTGCATGCCTCCGGA |
| 580 | SPBC17A3.09c_UP | CTGCCTCGTTCGTCGCCTTG |
| 581 | SPBC17A3.09c_DN | TTGTTACTCGTCCGGCCCTG |
| 582 | SPBC1701.01_UP | CGCACAAGTATCGCCCCGAT |
| 583 | SPBC17D1.01_DN | CCTTGCTCCATCGCCCTTCG |
| 584 | SPBC1815.01_UP | CGCGGCCGTGGTCATGTTTA |
| 585 | SPBC1815.01_DN | GCGATGGGTTGGTGGCCTTG |
| 586 | SPBC1861.01c_UP | AGAGTGGGGGGAAAGTGGCG |
| 587 | SPBC1861.01c_DN | TCGAATAGGGAAGCAGCGCA |
| 588 | SPBC18E5.02c_UP | TGCGGCGTGGCTTGCTTACA |
| 589 | SPBC18E5.02c_DN | ACGAAACCGGTATGGGGCAG |
| 590 | SPBC18E5.12c_UP | GGCTCCCGCACTCATAACCG |
| 591 | SPBC18E5.12c_DN | ACCCCCCCCAAGTTTAGTCGG |
| 592 | SPBC18H10.17c_UP | GCGCACCGTTCCCATGTTTG |
| 593 | SPBC18H10.17c_DN | GCCCCGCAAAAAAAAGCACA |
| 594 | SPBC1921.02_UP | ACGGCACGCGGAGAGAGAGA |
| 595 | SPBC1921.02_DN | GGACTAATGCACCCGGCCTC |
| 596 | SPBC19C2.01_UP | CCGGACGCCTTCGCACCCTTA |
| 597 | SPBC19C2.01_DN | CTTGCCGGTGTTCTCGGACG |
| 598 | SPBC19C2.07_UP | CCCCACACCGACTTGCACCA |
| 599 | SPBC19C2.07_DN | CCCCCCTGCGGAAGTACGTC |
| 600 | SPBC19C2.11c_UP | CAGTGGGGCTTTAGGCGTCG |
| 601 | SPBC19C2.11c_DN | TGCTTTCTCTCCGGGGCGTC |
| 602 | SPBC19C2.15c_UP | TGGCGGGTTGGTGCATTTTG |
| 603 | SPBC19C2.15c_DN | AGCGGAGCGGACACATAGGG |
| 604 | SPBC19C7.02_UP | GGCTTAGCCGCTTCCAGCCCG |
| 605 | SPBC19C7.02_DN | GCTGGATCGGAGGGGACTTG |
| 606 | SPBC19F8.01c_UP | AGGTCGGACTGGTCCTGACT |
| 607 | SPBC19F8.01c_DN | TGCTGCACCCTTAACGAGGT |
| 608 | SPBC19F8.05_UP | AACTTTGAACCACCCGCGCA |
| 609 | SPBC19F8.05_DN | CGTTAGGGCGGGATTCGAGG |
| 610 | SPBC19G7.01c_UP | GTGTCTTCGATTTGCGCGGG |
| 611 | SPBC19G7.01c_DN | AACAGTAGCAGCGCAGCCCA |
| 612 | SPBC1A4.01_UP | ACCGCCAAGCTGCACGAAAC |

FIG. 10

| Sequence number | Name | Base sequence |
|---|---|---|
| 613 | SPBC1A4.01_DN | CTGCGCATTTCCGTCCTTCA |
| 614 | SPBC1A4.10c_UP | CACTCGACCACACCGCTCCC |
| 615 | SPBC1A4.10c_DN | GGGGCTGGAACGTGATGGAA |
| 616 | SPBC2CF10.04c_UP | GTGTTTCGACGGGCCTCCAC |
| 617 | SPBC2CF10.04c_DN | TTCGTTCTCAGCTTCCCGCC |
| 618 | SPBC211.01_UP | CCGTGGTGTTCGGCCTCTCG |
| 619 | SPBC211.01_DN | AACTTGCCCCCACCAACTCG |
| 620 | SPBC215.12_UP | CGGGGCGGACATTTGAGTGG |
| 621 | SPBC215.12_DN | GATTAAACCGGCTCCGCCCG |
| 622 | SPBC21B10.08c_UP | GCCGCTTCCGATTACCCCAC |
| 623 | SPBC21B10.08c_DN | ACAAATCACCCCAGCGCCCA |
| 624 | SPBC21C3.01c_UP | AGGGCCAGCAGGTACCGCAA |
| 625 | SPBC21C3.01c_DN | CAAACGTGGGGCAAAACGGG |
| 626 | SPBC21C3.05_UP | ATACCACATCGCACGGCTCGG |
| 627 | SPBC21C3.05_DN | CATCCCGCCACAAATCGCTC |
| 628 | SPBC21D10.08c_UP | CTCCCGAGCTTAAGCGGTCT |
| 629 | SPBC21D10.08c_DN | GGAGGACACGGGGATGGGGT |
| 630 | SPBC23E6.06c_UP | CCGGTCGCGCGATGCTAGAAT |
| 631 | SPBC23E6.06c_DN | TTGCTTACGGTCGGGCTTGC |
| 632 | SPBC23G7.05_UP | GGACGCTCACACGTCCTTGT |
| 633 | SPBC23G7.05_DN | TGTAACGTACCGTCGCGAGC |
| 634 | SPBC23G7.12c_UP | AGGTCGGTGGGGGCAGTGTG |
| 635 | SPBC23G7.12c_DN | GCAGGGTAGGGCGGGGATTC |
| 636 | SPBC23G7.16_UP | TGTTGGGTGCGTGTGGTCA |
| 637 | SPBC23G7.16_DN | CACCACCCCATTCGCCGTTC |
| 638 | SPBC244.02c_UP | AACCCCCAGACACCGCCGAC |
| 639 | SPBC244.02c_DN | CCGTTGGATTGTTTGCAGGA |
| 640 | SPBC24C6.05_UP | GCAAGAAGCGCGGGGTACAT |
| 641 | SPBC24C6.05_DN | TGAGGATGAGGTACGGAGCA |
| 642 | SPBC25B2.02c_UP | CCGCCGTAACGACGAATGGC |
| 643 | SPBC25B2.02c_DN | GACGGCTTACGGGGTCCTGG |
| 644 | SPBC25D12.04_UP | TTTCCTCCTATACGCGCGCC |
| 645 | SPBC25D12.04_DN | CACCTAGACCCTGCCTCGCG |
| 646 | SPBC27.08c_UP | ACGAGCAAAATGGGCCGACC |
| 647 | SPBC27.08c_DN | GCCCGCGCCGTAGTTGTGAC |
| 648 | SPBC27B12.02_UP | AATGGCCTCGGGCTGGGAAC |
| 649 | SPBC27B12.02_DN | TAGGGGCGGGGATCAGCGTC |
| 650 | SPBC27B12.04c_UP | CGCGACTCTCAGAGGGACT |
| 651 | SPBC27B12.04c_DN | TCGACTGGTCAGGGACTGGA |
| 652 | SPBC27B12.12c_UP | AGCGGAAAGAGAAGAACCGG |
| 653 | SPBC27B12.12c_DN | GCGTTCTGCCTCTGGTCTCCC |
| 654 | SPBC28E12.02_UP | TCTGGGTATGGTGTTCCGGGG |
| 655 | SPBC28E12.02_DN | TCAGGGGGACGTTGTGGCTC |
| 656 | SPBC28E12.06c_UP | ACACCGCACCATCTCACCGC |
| 657 | SPBC28E12.06c_DN | AATTCCTTTTCGCGGCTGGC |
| 658 | SPBC29F2.09_UP | TCGCTGGGCCGTTGTTCTGT |
| 659 | SPBC28K2.09_DN | GGCAAAGGATGCAGGGCCTA |
| 660 | SPBC29A10.01_UP | TGGGCCGTCGGGTTCCAATAA |
| 661 | SPBC29A10.01_DN | AATGGCAATCGCACGGTGGT |
| 662 | SPBC29A10.03c_UP | GGAAGGCATGGCTGGAAGGA |
| 663 | SPBC29A10.03c_DN | GGTCGTCGTCTCGGGCTCTT |
| 664 | SPBC2A9.09_UP | CCGAACCCCTTATGCCACCC |
| 665 | SPBC2A9.09_DN | TACAACTGCCTCCCCCACCC |
| 666 | SPBC2A9.11c_UP | CTGACCGCGGCCTAACTCCT |
| 667 | SPBC2A9.11c_DN | CAGATTGGCAGTGGGACCGA |
| 668 | SPBC2D10.16_UP | CTTCTCCTTTTCCGCGCCCA |
| 669 | SPBC2D10.16_DN | GCATCATCGAAAGCAGGGGG |
| 670 | SPBC2D10.20_UP | AATTGTTTAGCGCCGGCCGA |
| 671 | SPBC2D10.20_DN | CCGAACCGCACTGCACGTGA |
| 672 | SPBC2G2.01c_UP | CGCAACGGACTGGGGATCAT |
| 673 | SPBC2G2.01c_DN | TCCCCCCGCCGGTGTGCTTAAC |
| 674 | SPBC2G2.05_UP | GACTCCGGCTTCGCTTGCGG |
| 675 | SPBC2G2.05_DN | CCCAAGCCCTGATTCGCCTG |
| 676 | SPBC30B4.01c_UP | TGTTTCCCTGGCGCTTCGTC |
| 677 | SPBC30B4.01c_DN | GAAGCCGATGGGGAGACCGA |
| 678 | SPBC30D10.06_UP | CGTCTCACTCCGGCCTTGCG |
| 679 | SPBC30D10.06_DN | TCCCATCACCACGTCCAGCG |
| 680 | SPBC31A8.01c_UP | TTTTGATTCGCGGACGCTGG |
| 681 | SPBC31A8.01c_DN | CCTGGCCCTGCTTCGTAACG |
| 682 | SPBC31E1.04_UP | GCCCCTCGCTGTTACTCGT |
| 683 | SPBC31E1.04_DN | CGGGTGGGCGCAATGAAGAG |
| 684 | SPBC31E1.06_UP | GCGGAAGATAGCGGCGATGC |
| 685 | SPBC31E1.06_DN | TCTGGTTGCGTGGCGTGATT |
| 686 | SPBC31F10.05_UP | GGTTTTCGACGCCTGCCTTG |
| 687 | SPBC31F10.05_DN | TCGGCGAGCATTAAGGGGT |
| 688 | SPBC31F10.11c_UP | CTCCGCACGCAACACCAACG |
| 689 | SPBC31F10.11c_DN | ACAGGCAACCAACCAAGCGC |
| 690 | SPBC32F12.10_UP | TTACGTAGGAGTCGGCGCG |
| 691 | SPBC32F12.10_DN | CGAACTGCGCACCCACCACT |
| 692 | SPBC336.09c_UP | TGCAGTGGGTCCTTTCGTGG |
| 693 | SPBC336.09c_DN | GCACGGCAATAACGACCCC |
| 694 | SPBC336.11_UP | CAAAAAGCAACCAGTCGGCG |
| 695 | SPBC336.11_DN | CGAATTCCCCGCGCGATAACT |
| 696 | SPBC336.15_UP | AGGATGGGGGATTTTCGAG |
| 697 | SPBC336.15_DN | ACCCGCGGCCTGCTACAAAT |
| 698 | SPBC337.09_UP | ACCCATGACGGACTCCCCTA |
| 699 | SPBC337.09_DN | ATGGGTCCCGTCACGCTTCA |
| 700 | SPBC337.13c_UP | AAACATTACTAGGCGCCGGG |
| 701 | SPBC337.13c_DN | CATCGTTACTAGGCGCCGGG |
| 702 | SPBC342.01c_UP | CGCCTGCCGCTCTCCGACTA |
| 703 | SPBC342.01c_DN | CGCCCTCCTACCCCACGCTA |
| 704 | SPBC354.01_UP | TCAGCGGCCCAACCCTAGTCC |
| 705 | SPBC354.01_DN | GGGAATCAGGCGCGCGGACA |
| 706 | SPBC36.08c_UP | TTGGGGTTCTCCTTGGCCTG |
| 707 | SPBC36.08c_DN | TGGCGCGGGGGATCTGTAGT |
| 708 | SPBC36.12c_UP | CGCTCCCTCACACATCCACG |
| 709 | SPBC36.12c_DN | TGGCCGTGTGTCTTTCCTCG |
| 710 | SPBC365.13c_UP | CTGCGGCGCAACAGAGGTGGT |
| 711 | SPBC365.13c_DN | CGCCACGCGAGGTAACCAC |
| 712 | SPBC365.15_UP | AGCCCTCTGACCTGCACCTT |
| 713 | SPBC365.15_DN | ATTGTACGTGTGCTGCGGCG |
| 714 | SPBC3637.07_UP | CGCACGCCTACCAACGCT |
| 715 | SPBC36B7.07_DN | GAACAGACCGGTGGGCGAGG |
| 716 | SPBC36B7.09_UP | TGTTTCGGGATCTGCTGGCA |
| 717 | SPBC36B7.09_DN | CGCCGCGCAAITATGTTACG |
| 718 | SPBC3B9.03_UP | AAACGGTGCCAGGCCAGGAA |
| 719 | SPBC3B9.03_DN | TACGTGCGAGCTGCCACTA |
| 720 | SPBC3B9.13c_UP | ACAAAAGACGGCGGAGGGA |
| 721 | SPBC3B9.13c_DN | AGCCCCCCACCGAACCATTG |
| 722 | SPBC3D6.15_UP | ACTGTGATTTCGGGGGCGT |
| 723 | SPBC3D6.15_DN | TGTTATCCGAGGGTGCCGCC |
| 724 | SPBC3E7.13c_UP | ATGGGGGCTGCTTACCGTGT |
| 725 | SPBC3E7.13c_DN | CCTGTTTCTCGCGTGGTCGG |
| 726 | SPBC3E7.15c_UP | CCCCCGTAAGCATGGGGCAA |
| 727 | SPBC3E7.15c_DN | GCGGTCGAAATGGTCAGGGC |
| 728 | SPBC3H7.11_UP | ACGGGGTCACTGGGGGCTGT |
| 729 | SPBC3H7.11_DN | ACAGCAASGGTGGGTCAGCG |
| 730 | SPBC405.01_UP | TCGCAGCTGGGGAACACTAG |
| 731 | SPBC405.01_DN | CCCGCCCGTAAAGTTGCAGC |
| 732 | SPBC409.04c_UP | GCCCAACGCAGAGCCCATCA |
| 733 | SPBC409.04c_DN | CACCCATACGCAACGGCCAA |
| 734 | SPBC409.12c_UP | GTGTTTTCATCCCCCCCCAT |
| 735 | SPBC409.12c_DN | AAATGCGATGAGGCGACGA |
| 736 | SPBC418.01c_UP | AAATTATCGGGCGGGGGTCC |
| 737 | SPBC418.01c_DN | GCGGGGGACAAAATCAGCTC |
| 738 | SPBC428.01c_UP | TGCACGCCTCTGATTTCCCG |
| 739 | SPBC428.01c_DN | GGAATGGTGGCAGGAAGGGG |
| 740 | SPBC428.15c_UP | GAGTTGTTCCCGTGCGCTTG |
| 741 | SPBC428.16c_DN | CGAATGGGGGTGCTGTTGG |
| 742 | SPBC428.20c_UP | CACTTTTCCGGCGACTTGGC |
| 743 | SPBC428.20c_DN | GCACCGCAGAACCCAACCAG |
| 744 | SPBC4C3.10c_UP | AAAATCCGCCCCCCATCAAA |
| 745 | SPBC4C3.10c_DN | GCACACTGACGAACCGCCGA |
| 746 | SPBC530.12c_UP | TCATAAGCCGGAAGCGGCCA |
| 747 | SPBC530.12c_DN | GCTCCAGCCGCACTTTTCGA |
| 748 | SPBC557.03c_UP | CCAACCCGCCATCAGCAAAA |
| 749 | SPBC557.03c_DN | CGTCCCTCCTGACAGGCCAT |
| 750 | SPBC577.02_UP | CGGTGAAGGGGAATGCGAAC |
| 751 | SPBC577.02_DN | TGTGGCGGCATGGTCGATAT |
| 752 | SPBC577.04_UP | CGACCTGCCTACCCGCTCCC |
| 753 | SPBC577.04_DN | GCTTTGGCCTCGGTTGCTGT |
| 754 | SPBC582.07c_UP | CGTTACCCGCATCCAGCAAA |
| 755 | SPBC5E2.07c_DN | GCGCCAATTAGACGCACCCC |
| 756 | SPBC646.05c_UP | GACGGTGTGGGGCGAAGGTG |
| 757 | SPBC646.05c_DN | ACAGCTTCGCACAGGGCAGT |
| 758 | SPBC646.07c_UP | GTCGGTTAAGCGGCGGTGTG |
| 759 | SPBC646.07c_DN | CGACACGCCTCACGAACGAC |
| 760 | SPBC646.11_UP | GCGCGGCCCCTCAACCTTAT |
| 761 | SPBC646.11_DN | ACCGGGTCACCTACCCTCAA |
| 762 | SPBC646.17c_UP | GGACACCCAGCCGTCGACCAA |
| 763 | SPBC646.17c_DN | TTCGACCGGCAGCCTTGTTT |
| 764 | SPBC660.16_UP | GCCAGCCAACCCATCACCCT |
| 765 | SPBC660.16_DN | AGGGTGGCGCATAACGGAGT |
| 766 | SPBC691.04_UP | TAGCCGCGCCCATTGAGAAC |
| 767 | SPBC691.04_DN | ATCCCACCCCGCTAGTTGCA |
| 768 | SPBC725.09c_UP | GGCGCAGCTCAAACCACCGA |
| 769 | SPBC725.09c_DN | TCGACAGGGGCCAGAAGACG |
| 770 | SPBC725.13c_UP | AGCGTTAGTGCGTTGGCGAA |
| 771 | SPBC725.13c_DN | TGGCGCGAAAGGGATGGTTG |
| 772 | SPBC725.17c_UP | GTGCTTGGGGGATGCGCTTA |
| 773 | SPBC725.17c_DN | CTCCCGTGCGCCTTGACCTC |
| 774 | SPBC776.10c_UP | TCACGTGTTTGGGGCAGAGG |
| 775 | SPBC776.10c_DN | CCCGGCGCCTTCGTTCGTAATC |
| 776 | SPBC776.12c_UP | GAAACAAGGTGCCCGGATCA |
| 777 | SPBC776.12c_DN | TTCCCGGCAAAAACACCCAR |
| 778 | SPBC83.04_UP | CGCTTTGGTCGCCCTCTCAG |
| 779 | SPBC83.04_DN | ATTCTATCGATCGCGCCGGG |
| 780 | SPBC83.14c_UP | GATGGGTGGCGGGTGATTCT |
| 781 | SPBC83.14c_DN | GGGTATGGGGGTGTCTCGGG |
| 782 | SPBC839.10_UP | GCGGGGAGGGGAGACAAGAC |
| 783 | SPBC839.10_DN | CAAACGCCGGAATCAAGCCC |
| 784 | SPBC839.12_UP | GGCCTTCATGCTACCLCTGG |
| 785 | SPBC839.12_DN | TGTGATTGGTTGTCGGGGCG |
| 786 | SPBC839.14c_UP | CGAGGCCGACTAAGTGCTGA |
| 787 | SPBC839.14c_DN | TCTCTCACGGGTGGCCAGAA |
| 788 | SPBC887.03c_UP | TAGGCCCCAATCAAACCCC |
| 789 | SPBC887.03c_DN | ACATCATCATCCGCCCGCTCA |
| 790 | SPBC887.09c_UP | AGACTTCCCCCTTCCGCCCC |
| 791 | SPBC887.09c_DN | TTAGCCCAACCCGCCCGATT |
| 792 | SPBC887.13c_UP | TGGAAGGGGACTAACGCGGG |
| 793 | SPBC887.13c_DN | ACACACGCCGAGAACCACGA |
| 794 | SPBC8D2.02c_UP | CGGGCGATGAGGGGAAGTAC |
| 795 | SPBC8D2.02c_DN | GCTTGCGTTGCGCTGTCCTA |
| 796 | SPBC8D2.04_UP | CCGCGTTGTTTGGTTGCCGT |
| 797 | SPBC8D2.04_DN | CGTGGCAAGGGAACAGGGCA |
| 798 | SPBC8D2.06_UP | ATCGTGCCTTTCGCCTCCAA |
| 799 | SPBC8D2.06_DN | ATGCGAGACGGGGTTGGAAAG |
| 800 | SPBC8D2.11_UP | AATTACCTCCCCACCCAGA |
| 801 | SPBC8D2.11_DN | AAGTTGGTTCGCCGTCGGTCGG |
| 802 | SPBC8D2.13_UP | ACGGGACGGGGCGAGTTACG |
| 803 | SPBC8D2.13_DN | CGCTACGGGCTTGCAAACAG |
| 804 | SPBC8D2.15_UP | CCGCCGCACATCCAAAGCTA |
| 805 | SPBC8D2.15_DN | TTCCAAAATCCAACGTCGCC |
| 806 | SPBC8E4.01c_UP | GCTGGAAACTGCGGGAGGGT |
| 807 | SPBC8E4.01c_DN | GCGGCTGAGTGGGTCTCTCC |
| 808 | SPBC9B6.05c_UP | CCCCTTCCACGCCTACGTCCC |
| 809 | SPBC9B6.05c_DN | CGGAGACGAAACGCGCAACA |
| 810 | SPBP1SF5.02_UP | AGCTTCAGCCGGGAACGTAG |
| 811 | SPBP15F5.02_DN | GTGGGCGGAGATGAGTCGAA |
| 812 | SPBP19A11.07c_UP | CACCGCCCGTCCAAACACTT |
| 813 | SPBP19A11.07c_DN | GAGGGGTAAFCGCGCCAACG |
| 814 | SPBP22H7.03_UP | AGCTCTTCTGACGGGGCCAC |
| 815 | SPBP22H7.03_DN | CCCCGTCGCATGGAATTTGA |
| 816 | SPBP22H7.08_UP | TGGCGCAAGGAGCTGTATCG |

FIG.11

| Sequence number | Name | Base sequence |
|---|---|---|
| 817 | SPEB22H7.08_DN | CCGTCCCCGCAGCATACATA |
| 818 | SPEB23A10.04_UP | GGAAAATGGTGGCTGCTGCG |
| 819 | SPEB23A10.04_DN | CCCTCTGCGCCCTTCATCCA |
| 820 | SPEB4H10.06a_UP | TCGTTGAGCACCCCAGCCTT |
| 821 | SPEB4H10.06a_DN | ATGCTTAGGGTCCGGTGCGG |
| 822 | SPEB4H10.08_UP | CGCGCATACACGGACAAGGT |
| 823 | SPEB4H10.08_DN | CCTGCAGCGGCCTATCCACCC |
| 824 | SPEB4H10.12_UP | TTCGTGCCGTGCTGTATGGG |
| 825 | SPEB4H10.12_DN | ATTGCAACTGGGTGGGGGCT |
| 826 | SPEB9B7.01c_UP | AAGGCCGTGGGGGAATGTTT |
| 827 | SPEB9B7.01c_DN | CAACCACACCCAAGCCCCCA |
| 828 | SPEB9B7.03c_UP | ACCTTGCCGCGTTACAGCGCC |
| 829 | SPEB9B7.03c_DN | TATCTCACCACGCCGCCAGC |
| 830 | SPEB9B7.29_UP | GTCCCGTCCCATTCGTCCCT |
| 831 | SPEB9B7.29_DN | GAGTTTCCTGTCCCGTGCGC |
| 832 | SPEB9B7.31_UP | AAATGGGGGGAGCGTCAGGTG |
| 833 | SPEB9B7.31_DN | GCTGTTTCGCTTGCCGCCAT |
| 834 | SPCC1020.01c_UP | CGCCTCACCTCTCCACCACC |
| 835 | SPCC1320.01c_DN | AGCAAGCAGTCGGGGAGGCAC |
| 836 | SPCC1320.13c_UP | CGCACCGAGAGCACGACAGT |
| 837 | SPCC1320.13c_DN | GGGGTCCGGCTGTTGATGTG |
| 838 | SPCC10H11.01_UP | CTGCGCAAACGACCCCACATG |
| 839 | SPCC10H11.01_DN | GAGGGGCGTGCATAGCCATTG |
| 840 | SPCC1183.01_UP | CCACGGCTCTCCCTCCACCAA |
| 841 | SPCC1183.01_DN | AGCTACTGGCCGAGCGAAGT |
| 842 | SPCC1183.03c_UP | ACCACCCGCCARAACAGTCC |
| 843 | SPCC1183.03c_DN | AGGGTCAGCGGAAGCAAGGG |
| 844 | SPCC1183.05c_UP | CGCCGCCTGGGTCATGTATT |
| 845 | SPCC1183.05c_DN | CAACAGTGCGTCGAAACCGA |
| 846 | SPCC1183.11_UP | CGCCGAGCGTAGCCCGAAGTT |
| 847 | SPCC1183.11_DN | TGGGGTCGAAGAGCGAGGCA |
| 848 | SPCC11E10.02c_UP | AATCGGACACCAGGCACCCA |
| 849 | SPCC11E10.02c_DN | GGGCATGGGTGGAGAGCAGT |
| 850 | SPCC1223.01_UP | CCGACTCCCCAAAGCCCTGC |
| 851 | SPCC1223.01_DN | TGCTCGTTCGTCTGTGCCTG |
| 852 | SPCC1235.02_UP | CCAGCTCGCCTCCCCCTTCTT |
| 853 | SPCC1235.02_DN | ATACTTCTCGCCGGCGCCCTG |
| 854 | SPCC1235.08c_UP | TTGGTTTGCTCCCTCCTCGA |
| 855 | SPCC1235.08c_DN | GGAGCATTCCCGTTGCACAA |
| 856 | SPCC1259.01c_UP | AGTCGCCATGAGCCCTTCGGT |
| 857 | SPCC1259.01c_DN | AGCGCCCGAAAACTGCACGT |
| 858 | SPCC126.14_UP | TGGACGAAGCGAAAGGGGAG |
| 859 | SPCC126.14_DN | TTGTCGCGCGCGTTATCTCCA |
| 860 | SPCC1281.01_UP | ATGACACTCGCGATAGGCCC |
| 861 | SPCC1281.01_DN | GAGGGGGGCGATTTTCTTCC |
| 862 | SPCC132.01c_UP | GGCCTCCTGCAGTTATCCCG |
| 863 | SPCC132.01c_DN | TGGTATTCTTCTCCGTGCCCG |
| 864 | SPCC1393.04_UP | AGGGACGGAGGCCAGGATAG |
| 865 | SPCC1393.04_DN | AGACGGGCCAGCATTCACGG |
| 866 | SPCC1393.06c_UP | GTCAGGGATTGTCGGTGCGC |
| 867 | SPCC1393.06c_DN | AGAGTGGGCAAAAACGGGGC |
| 868 | SPCC1393.08_UP | GCCATTTCTCGGGGGCTACA |
| 869 | SPCC1393.08_DN | ACGCCAGCCTCTTGCGTCTG |
| 870 | SPCC1442.01_UP | ATTGCAGCTCCGCGGACTA |
| 871 | SPCC1442.01_DN | GCCTATGAGCCTACGGCGAA |
| 872 | SPCC1442.03_UP | CAGCAAACTCCAGGCGGTGG |
| 873 | SPCC1442.03_DN | GCAGCAGCCTTCACCXAGT |
| 874 | SPCC1442.17c_UP | TCCATAACGCAGAAAACGCC |
| 875 | SPCC1442.17c_DN | AGCCCAAACACCACCGCAA |
| 876 | SPCC1450.02_UP | TGTCGCGCCGATTCAAACGT |
| 877 | SPCC1450.02_DN | TTGTTCCGGCCCCTCGTTCA |
| 878 | SPCC1494.10_UP | TCCAGTCCGACACATACGGC |
| 879 | SPCC1494.10_DN | GAGCGCCGGGTATCCAATGC |
| 880 | SPCC14G10.01_UP | CCAGCTACTTTTCTTGCCCC |
| 881 | SPCC14G10.01_DN | ACCCGGCCACCTAGCCATCAA |
| 882 | SPCC14G10.03c_UP | GCGGCGAGCTCAGACCTAAT |
| 883 | SPCC14G10.03c_DN | AGTAAGGCCGACGGACAGTG |
| 884 | SPCC162.08c_UP | TCTGCCTTGGGCTGTCGGA |
| 885 | SPCC162.08c_DN | AAGGAGGCACAGGGAGCGGA |
| 886 | SPCC162.12_UP | CGAACACATCCCGACGCAAC |
| 887 | SPCC162.12_DN | TCCGCGTTGCCCTTTTTCTG |
| 888 | SPCC1620.14c_UP | ACACCAGCCCCCCCTCTCTG |
| 889 | SPCC1620.14c_DN | AGATTCGCACCGACCCCACG |
| 890 | SPCC1672.04c_UP | TCAACCCGTGTACTGAGCCC |
| 891 | SPCC1672.04c_DN | GTGTTCTACGCGAGTGCGGT |
| 892 | SPCC1682.07_UP | GGGTTCAGATGTTTGCGGGG |
| 893 | SPCC1682.07_DN | CCTCATCCCCGTTCTGCTG |
| 894 | SPCC1682.11c_UP | GCCGTTCATGCTTTGTGCCC |
| 895 | SPCC1682.11c_DN | CTGGGTGGACACCGTGTGAT |
| 896 | SPCC16A11.05c_UP | ACAAATGGTGCGGTGGTGG |
| 897 | SPCC16A11.05c_DN | GCTGGGGTTCGAGGTGCTTC |
| 898 | SPCC16A11.09c_UP | CTCTTCGCCACCACGGCACCCT |
| 899 | SPCC16A11.09c_DN | GGGGTTCGACTGATGCGCG |
| 900 | SPCC16A11.13_UP | CCTTAACGCGCTTTTGTCG |
| 901 | SPCC16A11.13_DN | GCCTCCAGGACGTCAACTCA |
| 902 | SPCC16A11.17_UP | TCTGCGGCATCCGGCTTGAC |
| 903 | SPCC16A11.17_DN | CGGAACGGGCTGCGGTCTTA |
| 904 | SPCC16C4.04_UP | ATGATGCXXXTTATCCCTGC |
| 905 | SPCC16C4.04_DN | TCACACATTCCCCTTCGCCA |
| 906 | SPCC1795.01c_UP | TCCCACCAAGCGATCCACCA |
| 907 | SPCC1795.01c_DN | AGCGGGACTAGGGTGGGCAT |
| 908 | SPCC18.01_UP | GCTTTCGACCGTGGTAGCCA |
| 909 | SPCC18.01_DN | TAGCGTGAGATCGCGGACAC |
| 910 | SPCC18.13_UP | GTGAATCGCGGAAACCCCGC |
| 911 | SPCC18.13_DN | GCGGTTTATGCTTTGTGCCC |
| 912 | SPCC18.15_UP | TGACCTCCCCTTTGCACCGG |
| 913 | SPCC18.15_DN | CTTAGACGTCGGCCGAGTGA |
| 914 | SPCC1827.01c_UP | CCCCGCTAGTCCCGTTCTC |
| 915 | SPCC1827.01c_DN | ATGACCGGAAGAGGCCCCAC |
| 916 | SPCC1827.07c_UP | TGTCCGGCAGGGTTTGGCT |
| 917 | SPCC1827.07c_DN | GTCCGTCTGTCCGCAAAGGGG |
| 918 | SPCC1840.01c_UP | GTGCAGCCTAGGGTGTTCCT |

| Sequence number | Name | Base sequence |
|---|---|---|
| 919 | SPCC1840.01c_DN | TCTACGGCATCCGTGGACCT |
| 920 | SPCC1840.03_UP | CACCTGGCCGATCGTTTCC |
| 921 | SPCC1840.03_DN | TGGCCACTACCCGGAAAACT |
| 922 | SPCC1840.11_UP | CCCAATACGCCTGCCATCGC |
| 923 | SPCC1840.11_DN | GTGGGGCGAGCGTGTTGAG |
| 924 | SPCC186.04c_UP | GATCTCGCCGCCTACAACCG |
| 925 | SPCC186.04c_DN | ACGATCCCAGCTGCACACCA |
| 926 | SPCC188.11_UP | GCAGGCTAGGTGCAGCCTTA |
| 927 | SPCC188.11_DN | CCGTCACCCTTGCTCCACC |
| 928 | SPCC188.13c_UP | GAAGCGCGGGATTGTATGT |
| 929 | SPCC188.13c_DN | CGGGTTTGGTTGGCGTCATT |
| 930 | SPCC1884.02_UP | GTGGGGCTTGGAACAAACG |
| 931 | SPCC1884.02_DN | CGCACAGCCCCACTAGAAAC |
| 932 | SPCC1902.01_UP | ATAAGGGGCAGAGGGGCAGG |
| 933 | SPCC1902.01_DN | TACGCCCGAGCGATGCAAA |
| 934 | SPCC191.11_UP | GCTCCATGCTACCCGAAAAC |
| 935 | SPCC191.11_DN | TGTGSTTTGTGGGCTCGGAT |
| 936 | SPCC23B6.01c_UP | GACGACAACCGGCACCACGAA |
| 937 | SPCC23B6.01c_DN | CTAATGGCGTACGGCGGGAT |
| 938 | SPCC24B10.11c_UP | CGGGGGTGGGTTTGAAGGGA |
| 939 | SPCC24B10.11c_DN | CGAAACCACCCACGAAGGCG |
| 940 | SPCC285.08_UP | CGACAATTCCCCAGCCCCAG |
| 941 | SPCC285.08_DN | TCCCACCCAGCGTCGTCGTTT |
| 942 | SPCC285.10c_UP | CGGGGAAACGCTCTGGAATGA |
| 943 | SPCC285.10c_DN | ATTGCCGTGAAGATGCCCGG |
| 944 | SPCC297.03_UP | CCAAAATGGCGTCCGGGCTA |
| 945 | SPCC297.03_DN | CAACCGCCCCAGACCATTTT |
| 946 | SPCC2H8.04_UP | CTTGAATCCTTCCGCACCGA |
| 947 | SPCC2H8.04_DN | ATCACTCCGCCCAGCATTCC |
| 948 | SPCC31H12.06_UP | CAAAAGCGAAAACCGGGCAG |
| 949 | SPCC31H12.06_DN | CTATTGGGTTCGCGGCAGGG |
| 950 | SPCC31K12.08c_UP | GTATGGGACGGCGGAAGTGG |
| 951 | SPCC31H12.08c_DN | CCCCCTCATTGCCCCTATCGT |
| 952 | SPCC320.12_UP | CGCCCGATTAGCCGAACGA |
| 953 | SPCC320.12_DN | GGCACTTTCGTGGCGGGGTT |
| 954 | SPCC320.14_UP | TCCCACGCAAGCCCATCAAA |
| 955 | SPCC320.14_DN | AAAAAAGGCAGCGCGAGACC |
| 956 | SPCC330.02_UP | ACCGAAATGACGACCCCCCC |
| 957 | SPCC330.02_DN | GGATTGGGCCCGTCTCTGAG |
| 958 | SPCC338.15_UP | CGGCCCCCTTACGCAATCAAG |
| 959 | SPCC338.15_DN | TATGGGGAGCACGACCGGGA |
| 960 | SPCC417.11c_UP | GCACCCCTCGGCACCATATT |
| 961 | SPCC417.11c_DN | GTCAAGGTCGGTTTGTGCA |
| 962 | SPCC4B3.03c_UP | CCCGGTGTATGCGCTTTTCC |
| 963 | SPCC4B3.03c_DN | GGGTCGGCCTGGAAGATGTG |
| 964 | SPCC459.01c_UP | TACGACAACGGGCCATGCAA |
| 965 | SPCC459.01c_DN | GGCCCGTCGCATCTGTCATT |
| 966 | SPCC569.08c_UP | CCACGTCCGCGCCCTCTAAT |
| 967 | SPCC569.08c_DN | GAGTACAGTGGGCTTGGGGG |
| 968 | SPCC576.06c_UP | TCCACCCGATCTCCAGCGTT |
| 969 | SPCC576.06c_DN | GGCAGGCATTTTACCGTCGG |
| 970 | SPCC584.05_UP | GCAGTGGGCGAGAGAGCCGA |
| 971 | SPCC584.05_DN | TCCCAACCCGGTCAAAGCGA |
| 972 | SPCC584.16c_UP | TGGAGGGAGGTGCGTGATGC |
| 973 | SPCC584.16c_DN | ATGGGGATCACAAGGGCTGC |
| 974 | SPCC613.04c_UP | ACATTAGCCAGACCCCCCGC |
| 975 | SPCC613.04c_DN | AGGTGCGTGGCGAGTTGGA |
| 976 | SPCC622.06c_UP | AGTCACGGGACGTCTTGGGC |
| 977 | SPCC622.06c_DN | GGGCCTGGGCATGAAAGGAG |
| 978 | SPCC645.06c_UP | AGTTGGTTCGTGCGGATGGG |
| 979 | SPCC645.06c_DN | AACCCCTACCCGCCGCCAAT |
| 980 | SPCC70.07c_UP | CCATCAGTACAGCCCGCCCG |
| 981 | SPCC70.07c_DN | CCGGCTCCCCATCCTTTGTC |
| 982 | SPCC70.09c_UP | GATTAGGGAGCGCGGGAGG |
| 983 | SPCC70.09c_DN | TTCCACCACCTGCCACCAAA |
| 984 | SPCC737.09c_UP | AAAGGGTCGGGGGGATATCG |
| 985 | SPCC737.09c_DN | GGGAAGGATGGGTGCGTTTC |
| 986 | SPCC757.06_UP | TGTCTGCATGGAAGCCGGGA |
| 987 | SPCC757.06_DN | CTAGCAAAGAACGGGGCGG |
| 988 | SPCC757.10_UP | ACCCGCCCCCAGACCAAAATA |
| 989 | SPCC757.10_DN | TGCCGTGGGCTTGAGTTCGT |
| 990 | SPCC825.03c_UP | TCCTTCTTCCGGCGCCTATG |
| 991 | SPCC825.03c_DN | CCGAGAAGGGGCCCAAATACG |
| 992 | SPCC962.01_UP | GCGCGAGGGAGAATGTGATG |
| 993 | SPCC962.01_DN | CCATAGACAGAAGGGCCGCG |
| 994 | SPCC965.03_UP | TATGCCGCCTCTCTTCCGCT |
| 995 | SPCC965.03_DN | TCCGATGTTGTGAGGAGGCG |
| 996 | SPBB22H7.07_UP | ACGGAAGTACGGGGGGCAG |
| 997 | SPBB22H7.07_DN | ATGACGTCGGCGGTGTTCCA |
| 998 | SPAC1002.10c_UP | CCCCGACCACCGAAAATGAG |
| 999 | SPAC1002.10c_DN | CGGCGAGCAAGGCATAGGGA |
| 1000 | SPAC1002.16c_UP | ATGACGGGTCGGCGTACTCGA |
| 1001 | SPAC1002.16c_DN | GAGCACGGGGCTCACGTAT |
| 1002 | SPAC1006.09_UP | CCACTCCTTCCGTATCCCGC |
| 1003 | SPAC1006.09_DN | GATAAAAGCGCGGGCCAACC |
| 1004 | SPAC1039.10_UP | GGCAATCATGGGGCGCAAAC |
| 1005 | SPAC1039.10_DN | ACGTAACACGACCGCTGGTG |
| 1006 | SPAC105.01c_UP | ACCACCCTCTCCCCCTCGTC |
| 1007 | SPAC105.01c_DN | AATGGCACGGAAGACCGCAA |
| 1008 | SPAC1071.10c_UP | ACGGGTCCTCACATCCGTCT |
| 1009 | SPAC1071.10c_DN | AAACAGTCTGGTCGCACGGA |
| 1010 | SPAC1071.12c_UP | GCTCCGGGGGTCTGCCATAA |
| 1011 | SPAC1071.12c_DN | CCGGGACGGTGGTTGAAGAT |
| 1012 | SPAC1093.06c_UP | ATCCGCCAGACATTCCCACG |
| 1013 | SPAC1093.06c_DN | AGTGGCGGGGTTGCGTTAGG |
| 1014 | SPAC110.01_UP | CGCTCGGGTGCGCTACAPTA |
| 1015 | SPAC110.01_DN | TCCCGCGCGGTCTAGTTACA |
| 1016 | SPAC1142.01_UP | AGGCCCCGTGTTGTTTGCGG |
| 1017 | SPAC1142.01_DN | CACCCCCGCCTGCTGATCTC |
| 1018 | SPAC1142.03c_UP | AAGTCGTGGCGGGGAGGCAAC |
| 1019 | SPAC1142.03c_DN | CCCCCGCTCTACCCCTTTCAC |
| 1020 | SPAC1142.05_UP | GCGTGTGTGTCCTGCTTGGG |

FIG.12

| Sequence number | Name | Base sequence |
|---|---|---|
| 1021 | SEAC1142.05_DN | CCGTCCGTCTTTGCCTGTCG |
| 1022 | SEAC11E3.10_UP | GGGCTATCCTGGTGTGGGC |
| 1023 | SEAC11E3.10_DN | AGAGGCGGGGCTAGGTCCAA |
| 1024 | SEAC1250.01_UP | CAGGCGCAAAGTACCACGG |
| 1025 | SEAC1250.01_DN | CGCCTATCCACGCCGATCCT |
| 1026 | SEAC1296.02_UP | CCGGCCATGAGGTGTCGTTT |
| 1027 | SEAC1296.02_DN | GGCCCGTGGAGGATTCATTG |
| 1028 | SEAC1296.04_UP | ATCTCACCCCGCAGGCCATT |
| 1029 | SEAC1296.04_DN | AAGCACGGCGGGAAATTGAT |
| 1030 | SEAC1296.06_UP | CCGTCACTCCCCCTCGAATC |
| 1031 | SEAC1296.06_DN | TTGGCCCCCGTGCTTCTCTT |
| 1032 | SEAC12B10.08c_UP | CGCAACGGCCGGTAGAATGT |
| 1033 | SEAC12B10.08c_DN | CAAGACTCGCTAACCGCCGC |
| 1034 | SEAC12G12.01c_UP | CGACAGGCCCAAGCCCCTAA |
| 1035 | SEAC12G12.01c_DN | GTTGACAGGGGTCGGTGGCG |
| 1036 | SEAC12G12.13c_UP | GCCAAAGCCCCCCGCAATGT |
| 1037 | SEAC12G12.13c_DN | GCCTGCCTCCTATTGCGCTCG |
| 1038 | SEAC1327.01c_UP | CGGGGCCCGTCTCGTGCTGT |
| 1039 | SEAC1327.01c_DN | GAGCACCCGTAAGGCCCATG |
| 1040 | SPAC139.06_UP | CGACCCCCCGTGAGCAACTA |
| 1041 | SPAC139.06_DN | ACATGACTTGCGCCGGTGAC |
| 1042 | SPAC13A11.01c_UP | GCGGCGTGGGGTGATTCTGT |
| 1043 | SPAC13A11.01c_DN | AGTGGATGTGGGGAGCGAC |
| 1044 | SPAC13C5.01c_UP | CGGATGGTGTCGAACTGGGG |
| 1045 | SPAC13C5.01c_DN | GTCCTCCGTGCGCTTGTTGC |
| 1046 | SPAC13D6.05_UP | TCCACGCGGCACTCACTCTT |
| 1047 | SPAC13D6.05_DN | CCGACTGGCCGAAGCAAACG |
| 1048 | SPAC13G6.01c_UP | TCCCGGGGTAGTTTGTGGCA |
| 1049 | SPAC13G6.01c_DN | ATGCGTGAGGGGGATGAACC |
| 1050 | SPAC13G6.05c_UP | TAGCTTGTGGGACCTGCGGA |
| 1051 | SPAC13G6.05c_DN | TGACCTGAGATACGCGGCGG |
| 1052 | SPAC13G6.11c_UP | CCCCCCACGGTCTTCATGTT |
| 1053 | SPAC13G6.11c_DN | CCCGTTGTTATGAGCGGCCT |
| 1054 | SPAC13G6.13_UP | CAGCTCTTCGTTGCGCGGTT |
| 1055 | SPAC13G6.13_DN | AGGGGCTCGCTCTTCTTCGCG |
| 1056 | SPAC13G6.15c_UP | CACTCACCTCCGCGGCAAGC |
| 1057 | SPAC13G8.15c_DN | AGGGTGAAGGTGGTCGGTCGG |
| 1058 | SPAC13G7.10_UP | TAAGGGTCAGGGCAGGGCGA |
| 1059 | SPAC13G7.10_DN | GGATCCGCCACCCTATTCG |
| 1060 | SPAC13G7.12c_UP | CCGGGGGTGGGGTTAGAGGA |
| 1061 | SPAC13G7.12c_DN | GGATCGGACTGGCGTAGGCG |
| 1062 | SPAC1420.01c_UP | GGGGCTAGGGATGGACCGGT |
| 1063 | SPAC1420.01c_DN | CCGCAACCGCAGATCCACAG |
| 1064 | SPAC144.07c_UP | TTTTTCCAAGCTGCCGGCT |
| 1065 | SPAC144.07c_DN | CGCATTGGTGTTGAGGGGGT |
| 1066 | SPAC144.15c_UP | GATCCGCACAGAACCTCGCC |
| 1067 | SPAC144.15c_DN | TCCATGACAAGGGCTGCCCG |
| 1068 | SPAC1486.01_UP | TGTAGCAATAACGCGCCCGG |
| 1069 | SPAC1486.01_DN | CACGTGCCGTAGTCAGGCTT |
| 1070 | SPAC1486.07c_UP | AGGGATGCGAGGACACAGG |
| 1071 | SPAC1486.07c_DN | GGACGGGTATGCTTGTTGGC |
| 1072 | SPAC1486.09_UP | GGGACGAAAGCCGAACAATG |
| 1073 | SPAC1486.09_DN | TACCTGTGTGGGCGTGGGAC |
| 1074 | SPAC14C4.15c_UP | GATGGGCGGAATTGAGGGGA |
| 1075 | SPAC14C4.15c_DN | GCAGATCAGGCGACCCGAAG |
| 1076 | SPAC1527.01_UP | CTGTGCTGTGCCCGGTATG |
| 1077 | SPAC1527.01_DN | AGTCCGCGGGTAGAAGGGG |
| 1078 | SPAC1556.06.1_UP | CGGECGGTGCAGGTGTTAGT |
| 1079 | SPAC1556.06.1_DN | TGGGTGATCTCGTGCCGCC |
| 1080 | SPAC1556.06.2_UP | CGGGCGTTGCAGGTGTTAGT |
| 1081 | SPAC1556.06.2_DN | TGGGTGATCTTCGTGCCGTC |
| 1082 | SPAC1556.08c_UP | GCCCCCCGTGCATGAAAGAT |
| 1083 | SPAC1556.08c_DN | TGCCACACCACCGCCATGAG |
| 1084 | SPAC1565.08_UP | ACCACGCCACCTCGCCCTTC |
| 1085 | SPAC1565.08_DN | AAAGGGCGGAGGGCGGAGAT |
| 1086 | SPAC15A10.12c_UP | TTTTTGTCTTCCCCGCACG |
| 1087 | SPAC15A10.12c_DN | TTAACGTCAGCCACCCCCGG |
| 1088 | SPAC15E1.06_UP | GTACGAAGGGGCCCGGAAA |
| 1089 | SPAC15E1.06_DN | GCGGGCGGATTTGTCTTGAA |
| 1090 | SPAC15E1.10_UP | CCCAAATACCCGACCGCAAC |
| 1091 | SPAC15E1.10_DN | CGTCTCCCCTTTCGCGCCTT |
| 1092 | SPAC1639.01c_UP | GATGGGCCGTTTCACGATT |
| 1093 | SPAC1639.01c_DN | AACTGATGATACCGCGGGGG |
| 1094 | SPAC167.03c_UP | GGGGTGACGTCGATTGGGGT |
| 1095 | SPAC167.03c_DN | TCCCGTCGTTTCTCCCACCCC |
| 1096 | SPAC167.05_UP | GCCGCACCCCCATGTACTG |
| 1097 | SPAC167.05_DN | GTGGGGCGCTGGAAAGGATG |
| 1098 | SPAC167.07c_UP | CTCCGCTCCTCCCGTCTCAG |
| 1099 | SPAC167.07c_DN | CGCAAAGACGCAAGGAGCAG |
| 1100 | SPAC1687.03c_UP | CTTGCGCTGCACGTTCTGGG |
| 1101 | SPAC1687.03c_DN | GCCTGCATGACGGCGAATAA |
| 1102 | SPAC1687.11_UP | TTCCCGTCCTGCGTTTGCGT |
| 1103 | SPAC1687.11_DN | AGGGGGAGGATCTTGGGCAT |
| 1104 | SPAC1687.21_UP | GGCCCTGTCGCGTAGTTTCG |
| 1105 | SPAC1687.21_DN | TGAAAAATGCGGGCGCTGGT |
| 1106 | SPAC1687.23c_UP | GATATGCGCGTCCGCAGTA |
| 1107 | SPAC1687.23c_DN | ATGGGACCCGTGTGAGAGCR |
| 1108 | SPAC16A10.08c_UP | GTCGCTCTTATCGCTGGCC |
| 1109 | SPAC16A10.06c_DN | AATTCTTGCCACCTGCGGGG |
| 1110 | SPAC16E8.03_UP | CCAAGGGCGCCAAGTTCAAC |
| 1111 | SPAC16E8.03_DN | TTGCGTACGTGCGCCATCGG |
| 1112 | SPAC16E8.07c_UP | TACGGTGGCAAGGGTGGATT |
| 1113 | SPAC16E8.07c_DN | TCAATCCGCCCAGACTCCA |
| 1114 | SPAC16E8.11c_UP | GAAATGCGTGATGGGGCAAA |
| 1115 | SPAC16E8.11c_DN | GGCTCGTGCTGGCGGTTTAG |
| 1116 | SPAC1751.03_UP | CCTCCGGTCGCTGTCCTCCT |
| 1117 | SPAC1751.03_DN | CTCTTTCCCTCCCCTGCCAT |
| 1118 | SPAC1782.01_UP | TCCCGGGCGTGCACACTTTG |
| 1119 | SPAC1782.01_DN | GAGCCGGCCTTTGGTATCCC |
| 1120 | SPAC1782.11_UP | AGCACGGATGGGGGTTTTTG |
| 1121 | SPAC1782.11_DN | GCGGGGGTGGGAGTGATGT |
| 1122 | SPAC1786.01c_UP | TTGCACATCTTTCCCGGCA |

| Sequence number | Name | Base sequence |
|---|---|---|
| 1123 | SPAC1786.01c_DN | AGGGAGGAAGATGCGCG |
| 1124 | SPAC1786.03_UP | TTTTGGTGGTTCGGTCGC |
| 1125 | SPAC1786.03_DN | ACAGCCCACAAACAGCCC |
| 1126 | SPAC17A5.07c_UP | ACCGCGCPGAGGCATTTG |
| 1127 | SPAC17A5.07c_DN | TGGGATGAGGACTGTGGG |
| 1128 | SPAC17A5.13_UP | GCGTGGCGGAGGAATTGC |
| 1129 | SPAC17A5.13_DN | GGGGAAGGGGAAAGGCCA |
| 1130 | SPAC17A5.15c_UP | AGCCAACAGCAGACGGAA |
| 1131 | SPAC17A5.15c_DN | CACACCCTTCACCGCGCA |
| 1132 | SPAC17D4.01_UP | GACAGGGCCATACCGTGG |
| 1133 | SPAC17D4.01_DN | ACCGTGTGTGACCTACGG |
| 1134 | SPAC17G6.04c_UP | AAACCGCGACAGCAAAC |
| 1135 | SPAC17G6.04c_DN | GCCCGCAACAACGAAACC |
| 1136 | SPAC17G8.01c_UP | AGATCCTGCTCCAACCCC |
| 1137 | SPAC17G8.01c_DN | GCATGGGAAAGTTGGGCG |
| 1138 | SPAC17G8.05_UP | GCTGGCTGGCGGTTGGAC |
| 1139 | SPAC17G8.05_DN | GTCCCCTATCCGCGGTCC |
| 1140 | SPAC17G8.09_UP | CTTTTGGGCTTGCGCGAG |
| 1141 | SPAC17G8.09_DN | GACCGGGATGGGGGCTGT |
| 1142 | SPAC17H9.05_UP | CGGGCTCCCCCCATAAGA |
| 1143 | SPAC17H9.05_DN | CGCTACGAGTCACTGCGT |
| 1144 | SPAC17H9.07_UP | TCCGTCGCCCCAACAACG |
| 1145 | SPAC17H9.07_DN | TTCCTCAGCCCCTCCTCG |
| 1146 | SPAC17H9.20_UP | CCGCACTCCCTTACCGCA |
| 1147 | SPAC17H9.20_DN | CCACGCACACAAAGGCAC |
| 1148 | SPAC1805.08_UP | TATTAAGCCCCGAAGCCG |
| 1149 | SPAC1805.08_DN | TTCCCGAGCAAAGTCACC |
| 1150 | SPAC1805.14_UP | ATCAGAATGGCAAAGGGC |
| 1151 | SPAC1805.14_DN | TTGGCCCGCTTTTACCCG |
| 1152 | SPAC1934.11c_UP | CCTGGGGAAGATGGGGTTT |
| 1153 | SPAC1834.11c_DN | ATCAAGACCCCGCGCAGA |
| 1154 | SPAC1951.02_UP | TCTCTCGCCTCCACTTGC |
| 1155 | SPAC1951.02_DN | AGGCGTAGGCGAGACAGG |
| 1156 | SPAC1951.04c_UP | CGGGGGGTTAATCAGCGT |
| 1157 | SPAC1951.04c_DN | TCTTTTTCATGGTGGCGG |
| 1158 | SPAC19B11.08c_UP | GATGGGGCCTTTCTCCGT |
| 1159 | SPAC19B11.08c_DN | CGTTGCGGCAATGCTGTT |
| 1160 | SPAC1952.01_UP | AAACCGGACCCTTCCATC |
| 1161 | SPAC1952.01_DN | TCCCGCCCCTTTTGAAGC |
| 1162 | SPAC19A8.01c_UP | TGTGAAGAAGTAGCCCGC |
| 1163 | SPAC19A8.01c_DN | GCGCGCACGATGGATAGA |
| 1164 | SPAC19A8.11c_UP | CTGATGTGGAGAGCGGCG |
| 1165 | SPAC19A8.11c_DN | ACCCCCTCCCGATTGCTT |
| 1166 | SPAC19A8.15_UP | TTTGTCATGGGGCGTTTT |
| 1167 | SPAC19A8.15_DN | ATTCCCCGCTTGCGTATG |
| 1168 | SPAC19E9.03_UP | ACCGATGCGCTCGCTGAG |
| 1169 | SPAC19E9.03_DN | TCTCCACCTCTTTCCGCC |
| 1170 | SPAC1A6.02_UP | GCGGGTTATGTGGTTGCC |
| 1171 | SPAC1A6.02_DN | CGCCCACCCTCTTGCCTC |
| 1172 | SPAC1A6.10_UP | CCCGTCTCGCCCCAACCT |
| 1173 | SPAC1A6.10_DN | CGTCCGTCGGCCCCATAA |
| 1174 | SPAC1B2.03c_UP | CAGAACGGGCGGACGAGA |
| 1175 | SPAC1B2.03c_DN | TGTTATTCCGAAGCGCCC |
| 1176 | SPAC1B2.05_UP | GCGCGGCACGTAATCCAT |
| 1177 | SPAC1B2.05_DN | TCACCTGTTGGCGGCATC |
| 1178 | SPAC1E3.14_UP | ACTGGCTCACTGCCCCCT |
| 1179 | SPAC1E3.14_DN | TTCCGGCACCACACGAGG |
| 1180 | SPAC1D4.01_UP | CCCACCCAATACCAGCCG |
| 1181 | SPAC1D4.01_DN | GGGACGACTGACACCATG |
| 1182 | SPAC1E5.06_UP | ATTCTGCGGGAGAGCTTG |
| 1183 | SPAC1E5.06_DN | CCATGCCATCTGAGCCCA |
| 1184 | SPAC1E7.01c_UP | CCGATACTCAAAGGGCCX |
| 1185 | SPAC1E7.01c_DN | CGGGGGTAGTGGTTGGCT |
| 1186 | SPAC1E7.05_UP | CAGAACGCATCCGCCCGA |
| 1187 | SPAC1E7.05_DN | GACTGCGGTGGGGGGCT |
| 1188 | SPAC1E7.13c_UP | CCACCGACAACGACCCTC |
| 1189 | SPAC1E7.13c_DN | CGTCCGCAACTCCCTTCT |
| 1190 | SPAC20G4.08_UP | AAGCACCTCCAACATCGC |
| 1191 | SPAC20G4.08_DN | CAGCCGCAAACAACGGGCA |
| 1192 | SPAC2068.02_UP | CACCAGCAAAATCGCCGC |
| 1193 | SPAC2068.02_DN | GCATGTAGGCGGGGGTCC |
| 1194 | SPAC20G8.10c_UP | TCGGTGAGAAGGGCGTGA |
| 1195 | SPAC20G8.10c_DN | GCGTACAGCGGGAATGGC |
| 1196 | SPAC222.03c_UP | CTGCGCGGTATCGAGGAA |
| 1197 | SPAC222.03c_DN | ACGACCGACGCCACTTTC |
| 1198 | SPAC222.11_UP | GCCAACATGCACCAACCC |
| 1199 | SPAC222.11_DN | TACATGTTGGGGTGCGH |
| 1200 | SPAC222.15_UP | TCTGCAACGCTCCCGACG |
| 1201 | SPAC222.15_DN | GCTCGGTAGGCGGGTTT |
| 1202 | SPAC227.01c_UP | CTACCCCCGCCAGCAAA |
| 1203 | SPAC227.01c_DN | TCGCATAGGCCACTGAG |
| 1204 | SPAC22A12.01c_UP | AAACGGAACTCTTCGCCC |
| 1205 | SPAC22A12.01c_DN | CTGCGCGACTCCCCTCGA |
| 1206 | SPAC22E12.08_UP | GGACCTTTCATGCCCTCT |
| 1207 | SPAC22E12.08_DN | CTCGCCTCATAGGCCAA |
| 1208 | SPAC22F8.05_UP | AGCGTACTCGCTGACAG |
| 1209 | SPAC22F8.05_DN | TTACCTAGGGCCCCGGA |
| 1210 | SPAC22F8.09_UP | GTCTCGGCCCGTTGTCG |
| 1211 | SPAC22F8.09_DN | GTAACACTATGCCCACC |
| 1212 | SPAC22F8.10c_UP | GCGGTTCTGGGGCTGCA |
| 1213 | SPAC22F8.10c_DN | GTGGGGGTGAGAGATG |
| 1214 | SPAC22F8.12c_UP | TGGGGATGCGGATGAAA |
| 1215 | SPAC22F8.12c_DN | GGCTTGCTGAATCTGGC |
| 1216 | SPAC22H10.02_UP | AGGGATAAGGCGGGGGT |
| 1217 | SPAC22H10.02_DN | TCGCCCGCCTCCCACTG |
| 1218 | SPAC22H10.12c_UP | AGCCTCGGAGATAGCCA |
| 1219 | SPAC22H10.12c_DN | GGCCCGCTCCCACAAAA |
| 1220 | SPAC22H12.01c_UP | ACGCATCTAACCCCCGC |
| 1221 | SPAC22H12.01c_DN | GCACGGTTTTTGATGGG |
| 1222 | SPAC23A1.03_UP | GTGCGGTCCCAATTACC |
| 1223 | SPAC23A1.03_DN | GAGCCACCGCCCGACAT |
| 1224 | SPAC23A1.05_UP | TATCTTCTCGCCCCTCC |

FIG.13

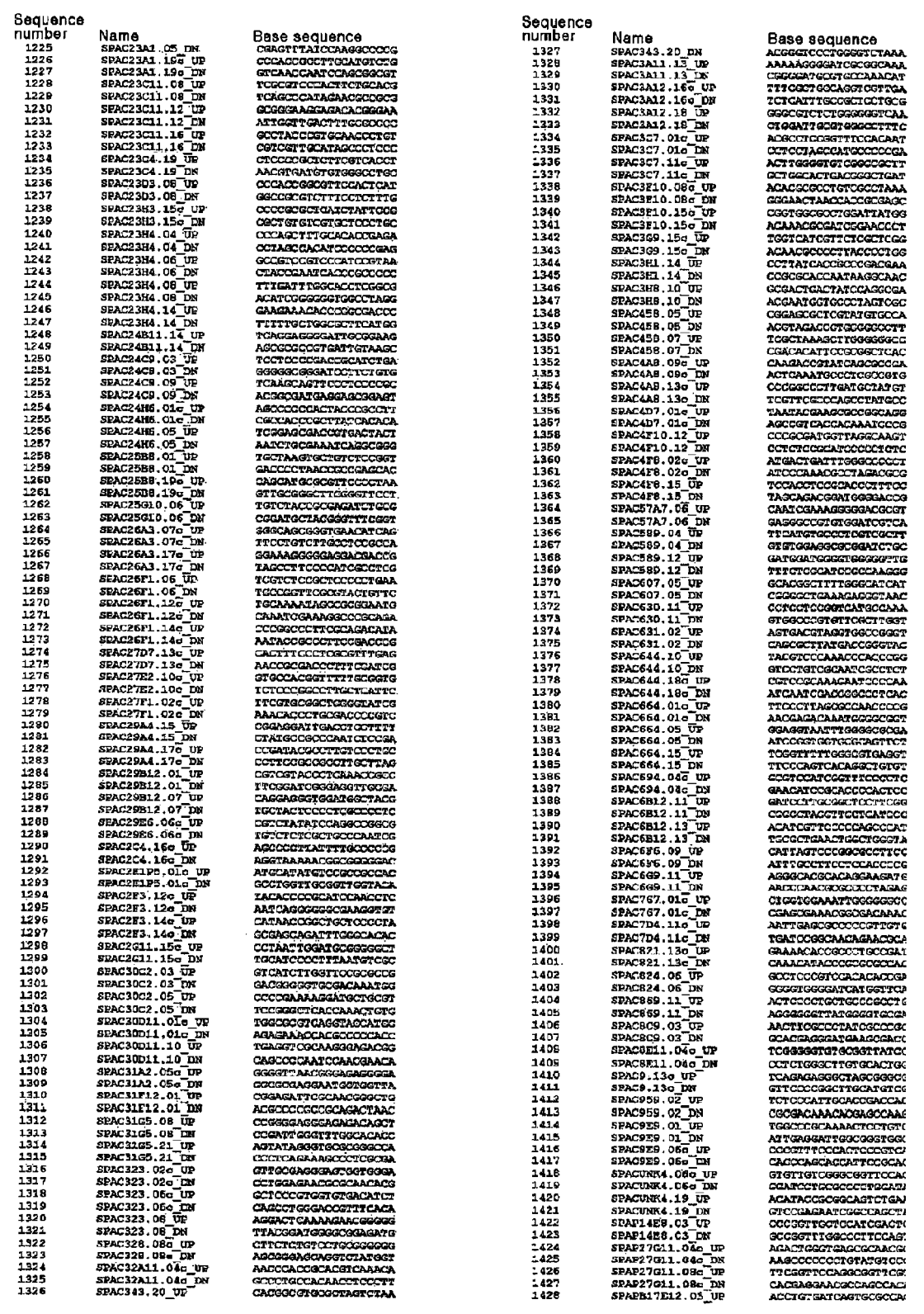

The figure shows a large table of DNA sequences with columns for Sequence number, Name, and Base sequence. Due to the extremely small text and dense tabular data containing hundreds of sequence entries that are largely illegible at this resolution, the full content cannot be reliably transcribed.

Figure 15:
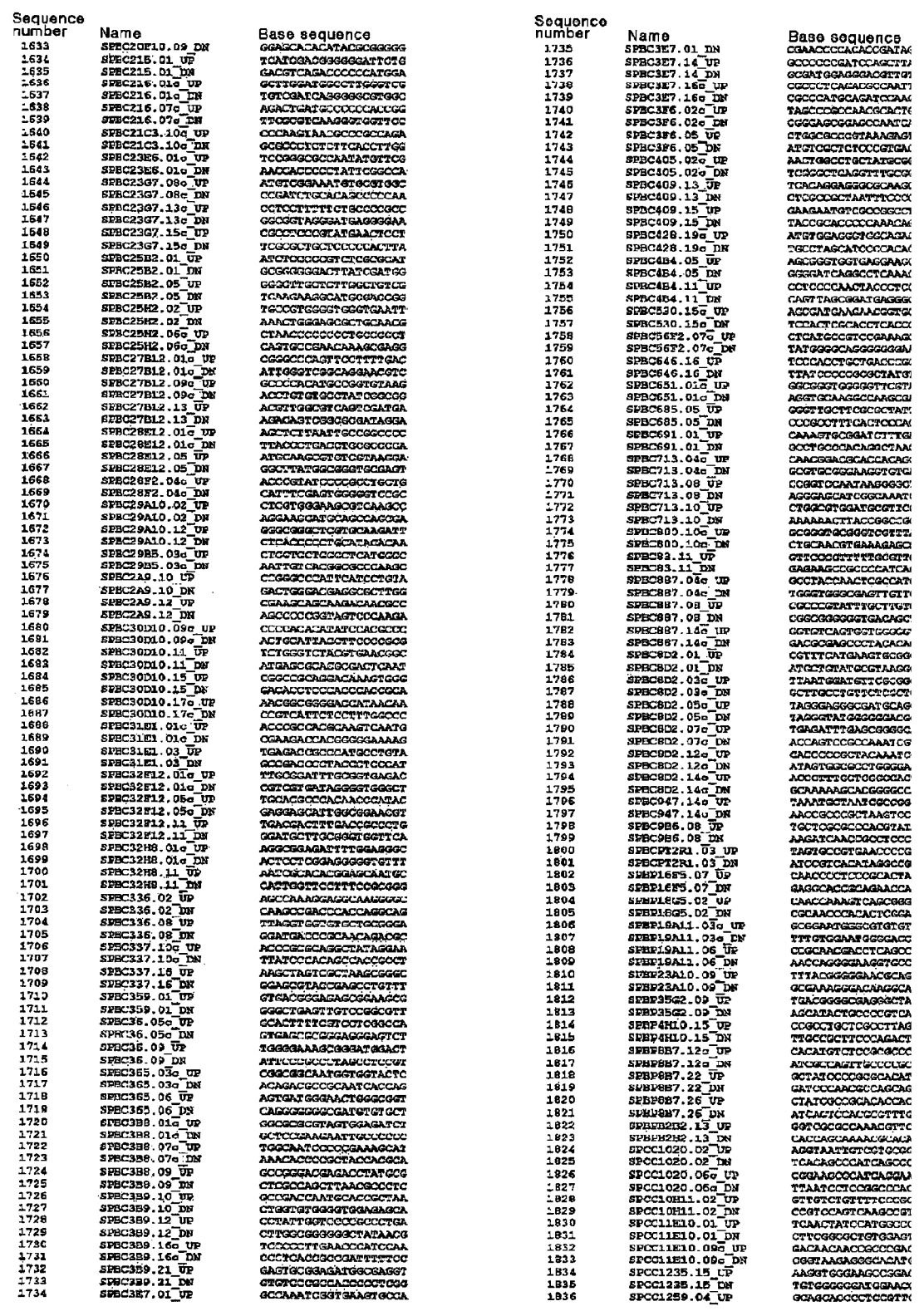

The image is too low-resolution to reliably transcribe the sequence table contents.

FIG.16

| Sequence number | Name | Base sequence | Sequence number | Name | Base sequence |
|---|---|---|---|---|---|
| 1837 | SPCC1259.04_DN | ACTTGAGGCATGGGGATCGG | 1939 | SPCC4B3.02c_DN | CGCGCCCATTGATACCGTGT |
| 1838 | SPCC126.01c_UP | CCTACCCACCGCGCCAAACA | 1940 | SPCC4B3.18_UP | GGGTGGTTGGACTGGGCGAT |
| 1839 | SPCC126.01c_DN | ATGGCCTCGGGTAACAAGCG | 1941 | SPCC4B3.18_DN | TGCTTGCTGGGTGGTTTCAT |
| 1840 | SPCC126.15c_UP | ATTCGGCTAGTCCCCGGCCTC | 1942 | SPCC4E9.02_UP | CGTTATATGCGCCGGCGAGA |
| 1841 | SPCC126.15c_DN | TTCCGCGCTTAATTGACCCC | 1943 | SPCC4E9.02_DN | TAGGCGTGAGCCCAGTAGGT |
| 1842 | SPCC1322.01_UP | GTTAGTGGCCCCCGCGGTA | 1944 | SPCC4G3.10c_UP | AACGGTCCGGGCCCTAATA |
| 1843 | SPCC1322.01_DN | CTGGTGCGATCGTGTGAGCG | 1945 | SPCC4G3.10c_DN | TAGTGCGCGACCTCTGGACT |
| 1844 | SPCC1322.11_UP | CCCCTATGCCCAACGCCACT | 1946 | SPCC4G3.12c_UP | ATCGGCGCGCTACGACAGAT |
| 1845 | SPCC1322.11_DN | CCCTTGCCCCGGTTAAGACA | 1947 | SPCC4G3.12c_DN | TCGCTCCGCGAAAGTACCGA |
| 1846 | SPCC1393.11_UP | TCGCTTCCAATTCGGCCGTG | 1948 | SPCC553.01c_UP | GCCCCCCGCCGTTTTGTAGAG |
| 1847 | SPCC1393.11_DN | CGCCTCTCGTGTGATCGTCC | 1949 | SPCC553.01c_DN | ATCGTACCGCAACCCCCGTG |
| 1848 | SPCC13B11.04c_UP | GATTAAGCCAAAAGCCGCCG | 1950 | SPCC553.12c_UP | AGGGCGACGGAGCAGGGATG |
| 1849 | SPCC13B11.04c_DN | CGAAACTGGACTGCCCCCTC | 1951 | SPCC553.12c_DN | ACTAAGCCCGTTCCCCGCCA |
| 1850 | SPCC1442.02_UP | GTCCCGTAACCCCTGCATGC | 1952 | SPCC576.01c_UP | TTGACCATCGCCTCGCCTTC |
| 1851 | SPCC1442.02_DN | CTCGAAGTCCCGTCCCGCCT | 1953 | SPCC576.01c_DN | ACCTCCCCCAACAGACCGCT |
| 1852 | SPCC1442.06_UP | GGACTACCCACGGCCGCAAC | 1954 | SPCC594.01_UP | TCGAAAAGCTACCGGGCACG |
| 1853 | SPCC1442.06_DN | AGCGCGCAATTAACGTGGAA | 1955 | SPCC594.01_DN | GTGGTCGCCCCGTCTTTCAG |
| 1854 | SPCC1442.16c_UP | TCTCGGATGGGACGGTGGTT | 1956 | SPCC5E4.04_UP | CCTAACGGGTTCGCTGTCCA |
| 1855 | SPCC1442.16c_DN | GACAAGTGAAGCGGGGAGCC | 1957 | SPCC5E4.04_DN | AGATGAGCGATGAGCCCCGA |
| 1856 | SPCC1450.13c_UP | TGTACGCTCTAGGTGCCACG | 1958 | SPCC61.04c_UP | TTGCGGGTTGGGGTAGCTTG |
| 1857 | SPCC1450.13c_DN | GAGACTGCGTAGGCCGACAT | 1959 | SPCC61.04c_DN | ACACCCCGAACCGCCGCTACT |
| 1858 | SPCC1450.15_UP | TCGCCGGAGCTCCCTTAACA | 1960 | SPCC613.01_UP | ATCGCCCGCTCCAGGCTAAC |
| 1859 | SPCC1450.15_DN | TTCGCTTTCGTTACCGGGCT | 1961 | SPCC613.01_DN | TAAGTGCGGGTGCTGGGCAG |
| 1860 | SPCC1494.01_UP | AGAGAGACCGAGCCTCGCAT | 1962 | SPCC622.19_UP | GCTTTCGAGTCATGGCGCGC |
| 1861 | SPCC1494.01_DN | CGCCCACCATTAAGCAACCG | 1963 | SPCC622.19_DN | CGTCTCGCGCTCCCTTCTCG |
| 1862 | SPCC14G10.02_UP | AGCCACATGGGGATCCGCTT | 1964 | SPCC645.03c_UP | TGTGCGTGGTGTGGAGTGCG |
| 1863 | SPCC14G10.02_DN | AACGGCTTACCTACGGCCTC | 1965 | SPCC645.03c_DN | TGCTAGTGTTGGGTCCGCTG |
| 1864 | SPCC14G10.04_UP | TCAAGCCGATCTGACGGGTG | 1966 | SPCC663.01c_UP | GCTGGATGCCCGGGACTGTTG |
| 1865 | SPCC14G10.04_DN | GGAACTGGGGCCGTAAAGCG | 1967 | SPCC663.01c_DN | TATTAGCTTGGCGCCGGTGG |
| 1866 | SPCC162.09c_UP | AGCACAGCGGATCTCCTGGGT | 1968 | SPCC663.13c_UP | CGGACTGGCGGACTGAGGG |
| 1867 | SPCC162.09c_DN | TCCTGTCCGTATGCTGTCGC | 1969 | SPCC663.13c_DN | AAAGGTGGGCGTTGGTCTCG |
| 1868 | SPCC162C.01c_UP | TATCTGCTAGCGCTATGGGCG | 1970 | SPCC70.06_UP | TAATACGGCTCCCGCCACCA |
| 1869 | SPCC162C.01c_DN | ATGGCGTGCAGCCTGACATA | 1971 | SPCC70.06_DN | CGACCCACTTTATCGCGCCG |
| 1870 | SPCC162C.05_UP | TCGTGCTCACACGGTCGATG | 1972 | SPCC74.05_UP | GATCTTGGGGGACGCTCCGG |
| 1871 | SPCC162C.05_DN | TGACTGGGGTGCGAGGAGA | 1973 | SPCC74.05_DN | CCATGGGGAGCGCAAGAAC |
| 1872 | SPCC16B2.01_UP | AGCGAGCGCAAGGCTTAGGA | 1974 | SPCC794.15_UP | CCCTTGCTAATGCCCGTTCG |
| 1873 | SPCC16B2.01_DN | AGAGCCGCGTAGATACGGGT | 1975 | SPCC794.15_DN | AGCCGCCCGTCATACCATCA |
| 1874 | SPCC16B2.10_UP | TCCAGGCACTCTCTCGCAT | 1976 | SPCC962.02c_UP | CCAGCAGCAACCCAGACCCC |
| 1875 | SPCC16B2.10_DN | GCGACTGACGGAAACCCCCA | 1977 | SPCC962.02c_DN | TCATTACCCGACCGACGT |
| 1876 | SPCC16A11.02_UP | TGACATCGCTCAGTCGGGAG | 1978 | SPAC56F8.16_UP | GACTAACCGTCGGGGCTCAT |
| 1877 | SPCC16A11.02_DN | TGCGAACAGGTCTCCACGTC | 1979 | SPAC56F8.16_DN | TCGTTAGCGTGGCACCTATG |
| 1878 | SPCC16C4.19_UP | CCAACGGATTTTCCACCGCT | 1980 | SPAC1002.01_UP | GCTTGGTTAGTGGACGCCCC |
| 1879 | SPCC16C4.19_DN | TGGGGGATTTGAGGCATGGA | 1981 | SPAC1002.01_DN | CAGGAAACATTACGCCGCCC |
| 1880 | SPCC1739.01_UP | TGTGCCGCTCCGGTTGCCTTC | 1982 | SPAC1002.02_UP | TGGTTTCACGACATGGCGCA |
| 1881 | SPCC1739.01_DN | ACATAGCCACCGCCACCAG | 1983 | SPAC1002.02_DN | AGGGGGATTGTCGAAGCGGG |
| 1882 | SPCC1739.15_UP | AGGTCGACCCGCGGTAAAGGT | 1984 | SPAC1002.03c_UP | CTAGGCGGCCGGGCTTCAAA |
| 1883 | SPCC1739.15_DN | TTCCGCTCGGACGGATTCTG | 1985 | SPAC1002.03c_DN | CGCGGCGGCATAATTACGTTT |
| 1884 | SPCC1753.01c_UP | GGGGGGTTAGGGTCAACAGAG | 1986 | SPAC1007.04c_UP | AGCACAGGCCGCGATTATGA |
| 1885 | SPCC1753.01c_DN | CAAACGGGACGCCACAATCA | 1987 | SPAC10C2.04c_DN | ACCCGGGACGAAGTCAAGCA |
| 1886 | SPCC1795.02c_UP | ATTCCGCCCGCCTCCCAGTCAG | 1988 | SPAC1002.05c_UP | TTCCCTCAAGACCCGCCTGC |
| 1887 | SPCC1795.02c_DN | CCTCCCCCAGCGGTCCTTTT | 1989 | SPAC1002.05c_DN | AAAAGTGGAGGGGGCACGGG |
| 1888 | SPCC1795.08c_UP | CGGTTATAGTCGACGGGCCA | 1990 | SPAC1002.06c_UP | TGTTTGGCCCCGCACTTTCA |
| 1889 | SPCC1795.08c_DN | ACACGGCTCGCGCATATTGA | 1991 | SPAC1002.06c_DN | GCAGGCGATGGACGAGCAGT |
| 1890 | SPCC1B.04_UP | GAGGTGGGCAGCAGGGTAGG | 1992 | SPAC1002.07c_UP | AACGTTAGCCGTCGGCCCCT |
| 1891 | SPCC1B.04_DN | GCAGGGGGACTTGGTCGGTC | 1993 | SPAC1002.07c_DN | GTGTGCGCTTTAGACGGGC |
| 1892 | SPCC1B.18c_UP | CGAGTGGAAGGGGTGACGCT | 1994 | SPAC1002.09c_UP | CCCCTCACCCACAGGACCCA |
| 1893 | SPCC1B.18c_DN | TGCCGTTAGCGGTCTACGGA | 1995 | SPAC1002.08c_DN | TCGCAGCCCGCCCTTTAGTG |
| 1894 | SPCC1827.06c_UP | CGACGGGACCTAAAATGCGCA | 1996 | SPAC1002.11_UP | CTACGCACGTGCACAATCGC |
| 1895 | SPCC1827.06c_DN | ACCGCGACCAACCAATACCC | 1997 | SPAC1002.11_DN | ACGGGCCGTATAGAGTGTGC |
| 1896 | SPCC1840.12_UP | CGACTCCCGAGGCATAAGGG | 1998 | SPAC1002.12c_UP | CCTCAATCGGCCACAAGCCC |
| 1897 | SPCC1840.12_DN | ACGGCAGCCAGTTGCCCCAAG | 1999 | SPAC1002.12c_DN | AGGGCTGCCGTGAGGCTTCA |
| 1898 | SPCC1B.12_UP | ATGGGGGGCGTGGTTATCGA | 2000 | SPAC1002.13c_UP | TTGCGGGATGCTTCGAGCAC |
| 1899 | SPCC1B.12_DN | GCCCGCCTGTCTTTGCCACA | 2001 | SPAC1002.13c_DN | ATCTCCGCTAGACTCGCCCT |
| 1900 | SPCC1B85.01c_UP | TCGCTAACCTCAACGCACGA | 2002 | SPAC1002.14_UP | TGCATGACACCATACCGCCG |
| 1901 | SPCC1B85.01c_DN | ACACCACCCCAACAGCGAAG | 2003 | SPAC1002.14_DN | CGCTAGGCCATTTCGGCATC |
| 1902 | SPCC1B85.03_UP | TGTCCCCACCGCTAAGCACC | 2004 | SPAC1002.15_UP | CCACGGGTTTACGGCAAGC |
| 1903 | SPCC1B85.03_DN | TACCCCCCGCACTCCTACGC | 2005 | SPAC1002.15c_DN | TATGCCACTATGCCGGCCAG |
| 1904 | SPCC191.02c_UP | TTGACAGCTGTGGTGGGGGC | 2006 | SPAC1002.17c_UP | CAGAGTGGGTGGCTAGGGGC |
| 1905 | SPCC191.02c_DN | TGCATGTCCAAACCCTCCCG | 2007 | SPAC1002.17c_DN | TCTTCGCGCGACCTCTCGTA |
| 1906 | SPCC1919.01_UP | CCTCGCCCACTCACCACCAG | 2008 | SPAC1002.18_UP | GGGTTTCACGGTTCTGGGCC |
| 1907 | SPCC1919.01_DN | CATTGCCTTTGACTTCGCCG | 2009 | SPAC1002.18_DN | ATGATCGAGGCCGCGGCTAA |
| 1908 | SPCC1919.11_UP | TACTGCACGCCCATTGCCGG | 2010 | SPAC1002.19_UP | CAAATCCTCCCGCGTGACCA |
| 1909 | SPCC1919.11_DN | GCCCCCAGCTAATCCGAATG | 2011 | SPAC1002.19_DN | GTTCCTCCTTTGCGCGGTTG |
| 1910 | SPCC1919.15_UP | TCGTTCTGGTGGCGTGCTG | 2012 | SPAC1002.20_UP | CAGCCGTCGCACGCTAAATG |
| 1911 | SPCC1919.15_DN | CACCCTCACTCACGCCCCCA | 2013 | SPAC1002.20_DN | TCGTGCCACGTGTGTGCTTT |
| 1912 | SPCC24B10.18_UP | TGCTTGCGGGGTTTTGCTCG | 2014 | SPAC1006.01_UP | AGGACGGGATGCGGAGAGAG |
| 1913 | SPCC24B10.18_DN | GGCCAGACAAGACCCAACGC | 2015 | SPAC1006.01_DN | TTGATGCTCGTTGCTTGGCG |
| 1914 | SPCC24B10.22_UP | TCGCCAGTTCTCGCCCACAA | 2016 | SPAC1006.02_UP | GGGTGGACTGGACAGGCGAG |
| 1915 | SPCC24B10.22_DN | GATTGCCGTCCGACGGGCTT | 2017 | SPAC1006.02_DN | ACCCCGACACCCAAAACCTG |
| 1916 | SPCC297.06c_UP | AGGGGCGGGTGTCTGCAAGA | 2018 | SPAC1006.03c_UP | CTTGGGGCCTTCCGTGTTGG |
| 1917 | SPCC297.06c_DN | GGATGGGCAGGATGAGCTCG | 2019 | SPAC1006.03c_DN | GAGGCTCACGGTCAGGTT |
| 1918 | SPCC2H8.05c_UP | AACCGCCAATCCCCAGCTTT | 2020 | SPAC1006.04c_UP | TCCGTGCCGCGTTATTGTG |
| 1919 | SPCC2H8.05c_DN | GGACATTGCGGGGGACCTC | 2021 | SPAC1006.04c_DN | GCGCGGGATGTGGTAGAACT |
| 1920 | SPCC306.03c_UP | CCCGGGTTACTCCGTCGCAC | 2022 | SPAC1006.05c_UP | ATATGGGTGCCTGGGGCTCA |
| 1921 | SPCC306.03c_DN | GCACGCCTAAACGCAACCGGT | 2023 | SPAC1006.05c_DN | ACACACACCGAAGCCGGGAG |
| 1922 | SPCC306.07c_UP | TCGGTTGAGTTGGGCGTCGGA | 2024 | SPAC1006.06_UP | CGGGCGGTGGCGAGTATGAC |
| 1923 | SPCC306.07c_DN | CGCGGTCGTGAAGTATGCGC | 2025 | SPAC1006.06_DN | ATTCACCCGCATGTCCGTCG |
| 1924 | SPCC31H12.07_UP | TGCCTTCCCTCACCCATCCG | 2026 | SPAC1006.07_UP | GCCGACCTATCCCGTCGCACC |
| 1925 | SPCC31H12.07_DN | CCCCCCAATTGGTGTGTCG | 2027 | SPAC1006.07_DN | GCCCAATGAGCGNACCCTGC |
| 1926 | SPCC320.11c_UP | TGGGCAACCCAAAAGCACT | 2028 | SPAC1039.01_UP | TCGTTCCCACCGCGCTATCT |
| 1927 | SPCC320.11c_DN | GGGCCAAGGTGAAAGGGGAT | 2029 | SPAC1039.01_DN | GGGCATAGGACGGCGGGATT |
| 1928 | SPCC320.13c_UP | TTCGGTGCGCCCCTTATTCGG | 2030 | SPAC1039.02_UP | GCGGTCTGGAGTTGGGTGGT |
| 1929 | SPCC320.13c_DN | CGCATCCCGCGTCCACCCTCG | 2031 | SPAC1039.02_DN | AGTGACAGAGGGGGCCAGGA |
| 1930 | SPCC330.01c_UP | GACGGGGTGGCAAGGGCATA | 2032 | SPAC1039.03_UP | GCACGGACCAGTCGTGAGAT |
| 1931 | SPCC330.01c_DN | GTGATAGGGCGCGAGAAGG | 2033 | SPAC1039.03_DN | CGGGCGTACAAAGGGCAAAG |
| 1932 | SPCC338.05c_UP | GCCGATTTTCCCACTGCTG | 2034 | SPAC1039.04_UP | AGCACCCGCCAAATCAAAC |
| 1933 | SPCC338.05c_DN | GACCAAAAACGACGGCGCAC | 2035 | SPAC1039.04_DN | AGGGGCTCGGTTTTAGGAGG |
| 1934 | SPCC338.07c_UP | TTGACCCATTAGCCGGAGCG | 2036 | SPAC1039.05c_UP | TGTCGACGCATCGTGGGAGT |
| 1935 | SPCC338.07c_DN | TCGTCGCAGTCAGTTGGGGG | 2037 | SPAC1039.05c_DN | CGGGAAGCTGCAAGATGCGG |
| 1936 | SPCC364.02c_UP | TGACGTTTCGGCGCCTTCTC | 2038 | SPAC1039.06_UP | TTCAGTCCAACGCCCATCG |
| 1937 | SPCC364.02c_DN | GCTTTGGCGGCGTTTGTTGG | 2039 | SPAC1039.06_DN | GCGGGGGACGTAGCAACAC |
| 1938 | SPCC4B3.02c_UP | GCATCAACACGGCCCCAAC | 2040 | SPAC1039.07c_UP | CCCGTGTTTCCTCGAGCCTG |

Figure 19:
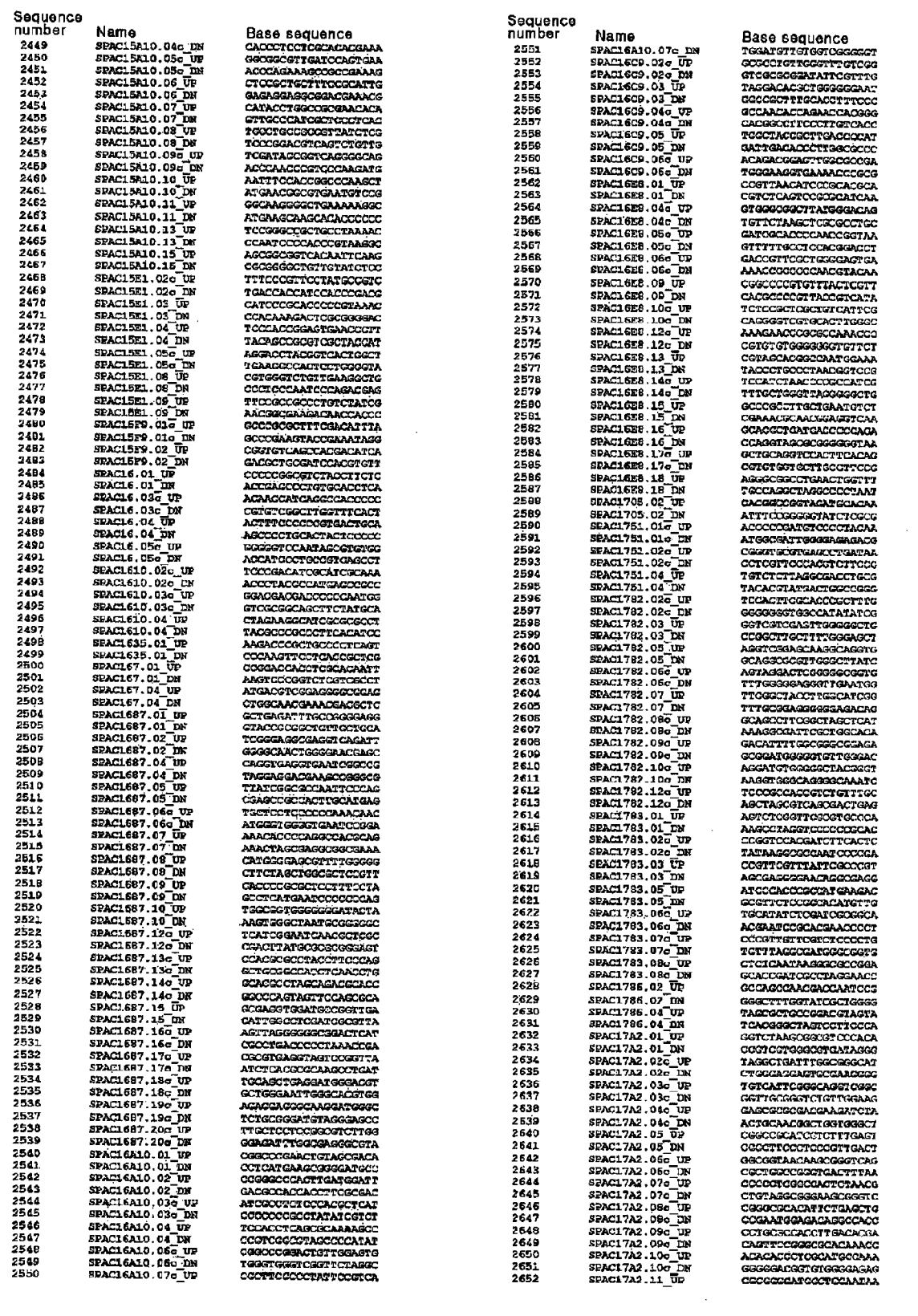

| Sequence number | Name | Base sequence |
|---|---|---|
| 2449 | SPAC15A10.04c_DN | CACCCTCCTCGCACACGAAA |
| 2450 | SPAC15A10.05c_UP | GGCGGCGTTGATCCAGTGAA |
| 2451 | SPAC15A10.05c_DN | ACCCAGAAAGCCGCCGAAAG |
| 2452 | SPAC15A10.06_UP | CTCCGCTGCTTTCCGCATTG |
| 2453 | SPAC15A10.06_DN | GAGAGGAGGCGGACGAAACG |
| 2454 | SPAC15A10.07_UP | CATACCTGGCCGCGAACACA |
| 2455 | SPAC15A10.07_DN | GTTGCCCATCGCTGCCTCAC |
| 2456 | SPAC15A10.08_UP | TGGCTGCCGCCGTTATCTCG |
| 2457 | SPAC15A10.08_DN | TCCCGGACGTCAGTCTGTTG |
| 2458 | SPAC15A10.09c_UP | TCGATAGCGGTCAGGGGCAG |
| 2459 | SPAC15A10.09c_DN | ACCCAACCCGTCCCAAGATG |
| 2460 | SPAC15A10.10_UP | AATTTCCACCGGCCCAAGCT |
| 2461 | SPAC15A10.10_DN | ATGAACGGCGTGAATGTCCG |
| 2462 | SPAC15A10.11_UP | GGCAAGGGGCTGAAAAAGGC |
| 2463 | SPAC15A10.11_DN | ATGAAGCAAGCACACCCCCC |
| 2464 | SPAC15A10.13_UP | TCCGGGCCGCTGCCTAAAAC |
| 2465 | SPAC15A10.13_DN | CCAATCCCCACCCGTAAGGC |
| 2466 | SPAC15A10.15_UP | AGCGGCGGTCACAATTCAAG |
| 2467 | SPAC15A10.15_DN | CGCGGGGCTGTTGTATCTCC |
| 2468 | SPAC15E1.02c_UP | TTTCCCGTTCCTATGCCGTC |
| 2469 | SPAC15E1.02c_DN | TGACCACCATCCACCCGACG |
| 2470 | SPAC15E1.03_UP | CATCCCGCACCCCCGTAAAC |
| 2471 | SPAC15E1.03_DN | CCACAAAGACTCGCGGGGAC |
| 2472 | SPAC15E1.04_UP | TCCCACCGGAGTGAACCCTT |
| 2473 | SPAC15E1.04_DN | TACAGCCGCGTCGCTACCAT |
| 2474 | SPAC15E1.05c_UP | AGGACCTACGGTCACTGGCT |
| 2475 | SPAC15E1.05c_DN | TGAAGGCCACTCCTGGGGTA |
| 2476 | SPAC15E1.08_UP | CGTGGGTCTGTTGAAGGCTG |
| 2477 | SPAC15E1.08_DN | CCCTCCCAATCCCAGACGAG |
| 2478 | SPAC15E1.09_UP | TTCCGCCGCCCTGTCTATCG |
| 2479 | SPAC15E1.09_DN | AACGGCGAAGACAACCACCC |
| 2480 | SPAC15F9.01c_UP | GCCCGCGCTTTCGACATTTA |
| 2481 | SPAC15F9.01c_DN | GCCCGAAGTACCGAAATAGG |
| 2482 | SPAC15F9.02_UP | CGGTGTCAGCCACGACATCA |
| 2483 | SPAC15F9.02_DN | GACGCTGCGATCCACGTGTT |
| 2484 | SPAC16.01_UP | CCCCCGGCGTCTACCTTCTC |
| 2485 | SPAC16.01_DN | ACCGAGCCCTGTGCACCTCA |
| 2486 | SPAC16.03c_UP | ACAAGCCATCAGGCCACCCC |
| 2487 | SPAC16.03c_DN | CGTGTCGGCTTGGTTTCACT |
| 2488 | SPAC16.04_UP | ACTTTCCCCCGGTGACTGCA |
| 2489 | SPAC16.04_DN | AGCCCCTGCACTACTCCCCC |
| 2490 | SPAC16.05c_UP | GGGGGTCCAATAGCGTGTGG |
| 2491 | SPAC16.05c_DN | ACCATGCCTGCCGTGAGCCT |
| 2492 | SPAC1610.02c_UP | TCCCGACATCGCATCGCAAA |
| 2493 | SPAC1610.02c_DN | ACCCTACGCCATGAGCCGCC |
| 2494 | SPAC1610.03c_UP | GGACGACGACCCCCCAATGG |
| 2495 | SPAC1610.03c_DN | GTCGCGGCAGCTTCTATGCA |
| 2496 | SPAC1610.04_UP | CTAGAAGGCATCGCGCGCCT |
| 2497 | SPAC1610.04_DN | TACGCCCGCCCTTCACATCC |
| 2498 | SPAC1635.01_UP | AAGACCCGCTGCCCCTCAGT |
| 2499 | SPAC1635.01_DN | CCCAAGTTCCTCACCGCTCG |
| 2500 | SPAC167.01_UP | CCGGACCACCTCGCACAATT |
| 2501 | SPAC167.01_DN | AAGTCCCGGTCTCGTCGCCT |
| 2502 | SPAC167.04_UP | ATGACGTCGGAGGGGCCGAC |
| 2503 | SPAC167.04_DN | CTGGCAACGAAACGACGCTC |
| 2504 | SPAC1687.01_UP | GCTGAGATTTGCCGGGGAGG |
| 2505 | SPAC1687.01_DN | GTACCGCGGCTGTTGCTGCA |
| 2506 | SPAC1687.02_UP | TCGGGAGGCGAGGTCAGATT |
| 2507 | SPAC1687.02_DN | GGGGCAACTGGGGAACGAGC |
| 2508 | SPAC1687.04_UP | CAGGTGAGGTGAATCGGCCG |
| 2509 | SPAC1687.04_DN | TAGGAGGACGAAGCCGGGCG |
| 2510 | SPAC1687.05_UP | TTATCGGCGCCAATTCCCAG |
| 2511 | SPAC1687.05_DN | CGAGCCGCCACTTGCATGAG |
| 2512 | SPAC1687.06c_UP | TGCTCCTCCCCCCAAACAAC |
| 2513 | SPAC1687.06c_DN | ATGGGTGGGTGAATCCGGA |
| 2514 | SPAC1687.07_UP | AAACACCCCAGGCCACGCAG |
| 2515 | SPAC1687.07_DN | AAACTAGCGAGGCGGCGAAA |
| 2516 | SPAC1687.08_UP | CATGGGGAGCGTTTTGGGGG |
| 2517 | SPAC1687.08_DN | CTTCTAGCTGGCGCTCCGTT |
| 2518 | SPAC1687.09_UP | CACCCCGCGCTCCTTTCCTA |
| 2519 | SPAC1687.09_DN | GCCTCATGAATCCCCCCCAG |
| 2520 | SPAC1687.10_UP | TGGCGGTGGGGGGGATACTA |
| 2521 | SPAC1687.10_DN | AAGTGGGCTAATGCGGCGGC |
| 2522 | SPAC1687.12c_UP | TCATCGGAATCAACGCTCGC |
| 2523 | SPAC1687.12c_DN | CGACTTATGCGCGCGGGAGT |
| 2524 | SPAC1687.13c_UP | CCACGCGCCTACCTTCCCAG |
| 2525 | SPAC1687.13c_DN | GCTGCGGCCATCTCAACCTG |
| 2526 | SPAC1687.14c_UP | GCACGCCTAGCAGACGCACC |
| 2527 | SPAC1687.14c_DN | GGCCCAGTAGTTCCAGCGCA |
| 2528 | SPAC1687.15_UP | GCGAGGTGGATGCCGGTTGA |
| 2529 | SPAC1687.15_DN | CATTGGCCTCGATCGCGTTA |
| 2530 | SPAC1687.16c_UP | AGTTAGGGGGGCGGACTCAT |
| 2531 | SPAC1687.16c_DN | CGCCTGACCCCCTAAACCGA |
| 2532 | SPAC1687.17c_UP | CGCGTGAGGTAGTCCGGTTA |
| 2533 | SPAC1687.17c_DN | ATCTCACGCGCAAGCCTGAT |
| 2534 | SPAC1687.18c_UP | TGCAGCTGAGGATGGGACGT |
| 2535 | SPAC1687.18c_DN | GCTGGGAATTGGGCACGTGG |
| 2536 | SPAC1687.19c_UP | AGAGGAGGGCAAGGATGGGC |
| 2537 | SPAC1687.19c_DN | TCTGCGGGATGTAGGGAGCC |
| 2538 | SPAC1687.20c_UP | TTGCTCCTCCGGGCGTCTTGG |
| 2539 | SPAC1687.20c_DN | GGAGATTTGGCGAGGGCGTA |
| 2540 | SPAC16A10.01_UP | CGGCCCGAACTGTAGCGACA |
| 2541 | SPAC16A10.01_DN | CCTCATGAAGCGGGGATGCC |
| 2542 | SPAC16A10.02_UP | CCGGGCCCACTTGATGGATT |
| 2543 | SPAC16A10.02_DN | GACGCCACCACCTTCGCGAC |
| 2544 | SPAC16A10.03c_UP | ATCGCCTCTCCCACGCTCAT |
| 2545 | SPAC16A10.03c_DN | CCCCCCCGCCTATATCGTCT |
| 2546 | SPAC16A10.04_UP | TCCACCTCAGCGCAAAAGCC |
| 2547 | SPAC16A10.04_DN | CCGTCGGCGTAGCCCCATAT |
| 2548 | SPAC16A10.06c_UP | CGGCCCGGACTGTTGGAGTG |
| 2549 | SPAC16A10.06c_DN | TGGGTGGGTCGGTTCTAGGC |
| 2550 | SPAC16A10.07c_UP | CGCTTCCCCCTATTCCGTCA |
| 2551 | SPAC16A10.07c_DN | TGGATGTTGTGGTCGGGGGT |
| 2552 | SPAC16C9.02c_UP | GCGCCTGTTGGGTTTGTCGG |
| 2553 | SPAC16C9.02c_DN | GTCGCGCGGATATTCGTTTG |
| 2554 | SPAC16C9.03_UP | TAGGACACGCTGGGGGGAAT |
| 2555 | SPAC16C9.03_DN | GGCCGCTTTGCACCTTTCCC |
| 2556 | SPAC16C9.04c_UP | GCCAACACCAGAACCACGGG |
| 2557 | SPAC16C9.04c_DN | CACGGCCTTCCCTTGTCACC |
| 2558 | SPAC16C9.05_UP | TGGCTACCGCTTGACCGCAT |
| 2559 | SPAC16C9.05_DN | GATTGACACCCTTGGCGCCC |
| 2560 | SPAC16C9.06c_UP | ACAGACGGAGTTGGCGCCGA |
| 2561 | SPAC16C9.06c_DN | TGGGAAGGTGAAAACCCGCG |
| 2562 | SPAC16E8.01_UP | CCGTTAACATCCCGCACGCA |
| 2563 | SPAC16E8.01_DN | CGTCTCAGTCCGCGCATCAA |
| 2564 | SPAC16E8.04c_UP | GTGGGCGGCTTATGGGACAG |
| 2565 | SPAC16E8.04c_DN | TGTTCTAAGCTCGCGCCTGC |
| 2566 | SPAC16E8.05c_UP | GATCGCACCCCAACCGGTAA |
| 2567 | SPAC16E8.05c_DN | GTTTTTGCCTCCACGGACCT |
| 2568 | SPAC16E8.06c_UP | GACCGTTCGCTGGGGAGTGA |
| 2569 | SPAC16E8.06c_DN | AAACCCCCCCAACGTACAA |
| 2570 | SPAC16E8.09_UP | CGGCCCCGTGTTTACTCGTT |
| 2571 | SPAC16E8.09_DN | CACGCCCCGTTACCGTCATA |
| 2572 | SPAC16E8.10c_UP | TCTCCGCTCGCTGTCATTCG |
| 2573 | SPAC16E8.10c_DN | CAGGGGTCGTGCACTTGGGC |
| 2574 | SPAC16E8.12c_UP | AAAGAACCCGCGCCAAACCC |
| 2575 | SPAC16E8.12c_DN | CGTGTGTGGGGGGTGTTCT |
| 2576 | SPAC16E8.13_UP | CGTAGCACGGCCAATGGAAA |
| 2577 | SPAC16E8.13_DN | TACCCTGCCCTAACGGTCCG |
| 2578 | SPAC16E8.14c_UP | TCCATCTAACCCCGCCATCG |
| 2579 | SPAC16E8.14c_DN | TTTGCTGGGTTAGGGGGCTG |
| 2580 | SPAC16E8.15_UP | GCCCGCCTTGCTGAATGTCT |
| 2581 | SPAC16E8.15_DN | CGAAACGCAACGGAGGTCAA |
| 2582 | SPAC16E8.16_UP | GCACGCTGATGACCCCCAGA |
| 2583 | SPAC16E8.16_DN | CCAGGTAGCGCGGGGGGTAA |
| 2584 | SPAC16E8.17c_UP | GCTGCAGGTCCACTTCACAG |
| 2585 | SPAC16E8.17c_DN | CGTGTGGTGCTTGCCTTCCG |
| 2586 | SPAC16E8.18_UP | AGGGCGGCCTGAACTGGTTT |
| 2587 | SPAC16E8.18_DN | TGCCAGGCTAGGCCCCTAAT |
| 2588 | SPAC1705.02_UP | CACGGCCGGTAGATGCACAA |
| 2589 | SPAC1705.02_DN | ATTTCGGGGGTATCTCGCG |
| 2590 | SPAC1751.01c_UP | ACCCCCGATGTCCCCTACAA |
| 2591 | SPAC1751.01c_DN | ATGGCGATTGGGGAGAGACG |
| 2592 | SPAC1751.02c_UP | CGGGTGCGTGAGCCTGATAA |
| 2593 | SPAC1751.02c_DN | CCTCGTTCCCACGTCTTCCG |
| 2594 | SPAC1751.04_UP | TGTCTCTTAGGCGACCTGCG |
| 2595 | SPAC1751.04_DN | TACACGTATGACTGGCCGGG |
| 2596 | SPAC1782.02c_UP | TCCACTTCGCACCCGCTTTG |
| 2597 | SPAC1782.02c_DN | GGGGGGTGGCCATATATCG |
| 2598 | SPAC1782.03_UP | GGTCGTCGAGTTGGGGGCTG |
| 2599 | SPAC1782.03_DN | CCGGCTTGCTTTTGGGAGCT |
| 2600 | SPAC1782.05_UP | AGGTCGGAGCAAGGCAGGTG |
| 2601 | SPAC1782.05_DN | GCAGGCGCGTTGGGCTTATC |
| 2602 | SPAC1782.06c_UP | AGTAGGACTCGGGGGCGGTG |
| 2603 | SPAC1782.06c_DN | TTTGGGGGAGGGTTGAATGG |
| 2604 | SPAC1782.07_UP | TTGGGCTACCTTGGCATCGG |
| 2605 | SPAC1782.07_DN | TTTGCGGAGGGGGGAGACAG |
| 2605 | SPAC1782.08c_UP | GCAGCCTTCGGCTAGCTCAT |
| 2607 | SPAC1782.08c_DN | AAAGGCGATTCGCTGGCACA |
| 2608 | SPAC1782.09c_UP | GACATTTTGGCGGGCGGAGA |
| 2609 | SPAC1782.09c_DN | GCGGATGGGGGTGTTGGGAC |
| 2610 | SPAC1782.10c_UP | AGGATGTGGGGGCTACGGGT |
| 2611 | SPAC1782.10c_DN | AAGGTGGGCAGGGGCAAATC |
| 2612 | SPAC1782.12c_UP | TCCCGCCACCGTCTGTTTGC |
| 2613 | SPAC1782.12c_DN | AGCTAGCGTCAGCGACTGAG |
| 2614 | SPAC1783.01_UP | AGTCTCGGTTCGCGTGCCCA |
| 2615 | SPAC1783.01_DN | AAGCCTAGGTCCCCCCGCAC |
| 2616 | SPAC1783.02c_UP | CCGGTCCACGATCTTCACTC |
| 2617 | SPAC1783.02c_DN | TATAAGGCGCCAATCCCCGA |
| 2618 | SPAC1783.03_UP | CCGTTCGTTTATTCGCCCGT |
| 2619 | SPAC1783.03_DN | AGCGAGGCGAACAGGCGAGG |
| 2620 | SPAC1783.05_UP | ATCCCACCCGCCATGAAGAC |
| 2621 | SPAC1783.05_DN | GCGTTCTCCGGCACATGTTG |
| 2622 | SPAC1783.06c_UP | TGCATATCTCGATCGCGGCA |
| 2623 | SPAC1783.06c_DN | ACGAATCCGCACGAACCCCT |
| 2624 | SPAC1783.07c_UP | CCCGTTGTTCGTCTCCCCTG |
| 2625 | SPAC1783.07c_DN | TGTTTAGGCGATGGGCGGTG |
| 2626 | SPAC1783.08c_UP | CTCTCAATAAGGGCGCCGGA |
| 2627 | SPAC1783.08c_DN | GCACCGATCGCCTAGGAACC |
| 2628 | SPAC1786.02_UP | GCCAGCCAACGACCAATCCG |
| 2629 | SPAC1786.07_DN | GGGCTTTGGTATCGCTGGGG |
| 2630 | SPAC1786.04_UP | TAGCGCTGCCGGACGTAGTA |
| 2631 | SPAC1786.04_DN | TCACGGGCTAGTCCTTCCCA |
| 2632 | SPAC17A2.01_UP | GGTCTAAGCGGCGTCCCACA |
| 2633 | SPAC17A2.01_DN | CCGTCGTGGGCGTGATAGGG |
| 2634 | SPAC17A2.02c_UP | TAGGCTGATTTGGCGGGCAT |
| 2635 | SPAC17A2.02c_DN | CTGGGAGGAGTGCCGAACGGC |
| 2636 | SPAC17A2.03c_UP | TGTCATTCGGGCAGGTCGGC |
| 2637 | SPAC17A2.03c_DN | GGTTGCGGGTCTGTTGGAAG |
| 2638 | SPAC17A2.04c_UP | GAGCGCGCGACGAAGATCTA |
| 2639 | SPAC17A2.04c_DN | ACTGCAACGGCTGGTGGGCT |
| 2640 | SPAC17A2.05_UP | CGGCCGCATCCTCTTTGAGT |
| 2641 | SPAC17A2.05_DN | CGGCTTCCCTCCCGTTGACT |
| 2642 | SPAC17A2.06c_UP | GGCGGTAACAAGCGGGTCAG |
| 2643 | SPAC17A2.06c_DN | CGCTGGCCGGCTGACTTTAA |
| 2644 | SPAC17A2.07c_UP | CCCCCTCGGCCACTCTAACG |
| 2645 | SPAC17A2.07c_DN | CTGTAGGCGGGAAGCGGGTC |
| 2646 | SPAC17A2.08c_UP | CGGGCGCACATTCTGAGCTG |
| 2647 | SPAC17A2.08c_DN | CCGAATGGAGACAGGCCACC |
| 2648 | SPAC17A2.09c_UP | CCTGCGCCACCTTGACACGA |
| 2649 | SPAC17A2.09c_DN | CAGTTCCGGGCGCACAAACC |
| 2650 | SPAC17A2.10c_UP | ACACACCCTCGCATGCCAAA |
| 2651 | SPAC17A2.10c_DN | GGGGGACGGTGTGGGGAGAG |
| 2652 | SPAC17A2.11_UP | CGCCGCCCATCGCTCCAATAA |

FIG.20

| Sequence number | Name | Base sequence |
|---|---|---|
| 2653 | SPAC17A2.11_DN | TTTGGGGAAGGTCGTGGGCC |
| 2654 | SPAC17A2.12_UP | CCAGGCCTCTTCAACCCGCC |
| 2655 | SPAC17A2.12_DN | GTGCCTTTGCGGGTGTTGCT |
| 2656 | SPAC17A2.13a_UP | TGTTTGGGCCTCATGGCAGC |
| 2657 | SPAC17A2.13a_DN | CCATCACCCGTTTGAGCGAA |
| 2658 | SPAC17A5.01_UP | CGCCAACATAAGCTCCCCGC |
| 2659 | SPAC17A5.01_DN | ATGGCGGTGGGGCAAGTCAG |
| 2660 | SPAC17A5.02a_UP | AACCCCAGACGCCAAAGCCA |
| 2661 | SPAC17A5.02a_DN | CATCATCCACCCCCACGGCT |
| 2662 | SPAC17A5.03_UP | GACTGGGGAACCTCGGGACG |
| 2663 | SPAC17A5.03_DN | ATTGCCCTCCCACACGAAG |
| 2664 | SPAC17A5.04a_UP | GTGGGCATTTTTCGCTTGGC |
| 2665 | SPAC17A5.04a_DN | TGCTTGCCCGAGACCCTGTC |
| 2666 | SPAC17A5.05a_UP | CCCGCCCAAAGTCTGCCCTC |
| 2667 | SPAC17A5.05a_DN | CGATGCACCACAXXTACXX |
| 2668 | SPAC17A5.06_UP | AGCTTTTGATCGCGCGGAG |
| 2669 | SPAC17A5.06_DN | GGCGCGGCTGTCTTCTTGT |
| 2670 | SPAC17A5.09a_UP | GTGTACATGTCTGCGGCGGG |
| 2671 | SPAC17A5.09a_DN | GTGTGTGATGGAGGCCCGTG |
| 2672 | SPAC17A5.10_UP | TCAGAAACCAGATCGGGGCG |
| 2673 | SPAC17A5.10_DN | TTGATAATTGCCGGTGCCCC |
| 2674 | SPAC17A5.11_UP | GCTTCTAGATCGGGGCGCAC |
| 2675 | SPAC17A5.11_DN | CCAAACATACCCGTGCGCG |
| 2676 | SPAC17A5.12_UP | CCACTTCAATCCCCGCACCG |
| 2677 | SPAC17A5.12_DN | CGCGAACCCACCAAAGCCT |
| 2678 | SPAC17A5.14_UP | CCCTCCGCTTCGCCCTGTAG |
| 2679 | SPAC17A5.14_DN | GGATGAGGGGACCGGGAGCT |
| 2680 | SPAC17A5.16_UP | TCCGGCGGTAGGCGGACAGT |
| 2681 | SPAC17A5.16_DN | CATGTTGGGGCGCGATTTGA |
| 2682 | SPAC17A5.18a_UP | CGCTCTGATCAGTGAGCCCT |
| 2683 | SPAC17A5.18a_DN | CCGTGTTGCAGTGCCGGATA |
| 2684 | SPAC17C9.02a_UP | ACATTTTGGGGGTGGTTCG |
| 2685 | SPAC17C9.02a_DN | CGAGAGGCCAACAGCGGGA |
| 2686 | SPAC17C9.05a_UP | TCCCCGAACGGTAATCTGCA |
| 2687 | SPAC17C9.05a_DN | TTATTGCGGGCGGCGGTTAT |
| 2688 | SPAC17C9.07_UP | ACAGAGCGTGGCCGAGGTGG |
| 2689 | SPAC17C9.07_DN | ACCCCCGACCAACGCACACA |
| 2690 | SPAC17C9.08_UP | GATGAGTGCGGTGAACGGGG |
| 2691 | SPAC17C9.08_DN | CCACTCCGGTTCCCTTTCGT |
| 2692 | SPAC17C9.09a_UP | ATCACACCGTGCGTATCCCG |
| 2693 | SPAC17C9.09a_DN | ACGAGGCCCTAGTGAGGCAA |
| 2694 | SPAC17C9.10_UP | CTACGGAGGAGGGGATGCGA |
| 2695 | SPAC17C9.10_DN | GCCCCGTGACAGCCCAATTT |
| 2696 | SPAC17C9.11a_UP | CTTTGGGAGATGCTGCGCGG |
| 2697 | SPAC17C9.11a_DN | CAGTAACGGCCTCATGCCCA |
| 2698 | SPAC17C9.12_UP | CCGCGCCAGTAGAGGAGAA |
| 2699 | SPAC17C9.12_DN | TGGAAGAGAGCGGATGGGC |
| 2700 | SPAC17C9.13a_UP | GCGGTCGAGGGGAAACGGG |
| 2701 | SPAC17C9.13a_DN | AGCTCCTCCCCCCTCGGTAA |
| 2702 | SPAC17C9.14_UP | CCAAATCGCTAGCACGCCG |
| 2703 | SPAC17C9.14_DN | ACGGGTCATGTTGGGGGTGT |
| 2704 | SPAC17C9.15a_UP | CCAAATTCGCTGCTTGCCAG |
| 2705 | SPAC17C9.15a_DN | TAGCTGCGTGGGGGATTCA |
| 2706 | SPAC17C9.16a_UP | AAGTCTCGTTGACACGTCCC |
| 2707 | SPAC17C9.16a_DN | CACTTACTGGGCACCCGCTT |
| 2708 | SPAC17D4.02_UP | CGGCAGCACCCTTGCCCGAG |
| 2709 | SPAC17D4.02_DN | TCAATGCGGGGGAAACAGCG |
| 2710 | SPAC17D4.03a_UP | GGAAAGGTTGGCTTGAGGGAT |
| 2711 | SPAC17D4.03a_DN | CCACCCACCTCCTGCTCCGCT |
| 2712 | SPAC17G6.02a_UP | CCGGGCAATTTCTCCCTGAT |
| 2713 | SPAC17G6.02a_DN | CGTCAAGTAGTCAGGCCCGT |
| 2714 | SPAC17G6.03_UP | CAACAACGCGCCAGAGAAGG |
| 2715 | SPAC17G6.03_DN | CCCTCGGCCAACGAAACGAT |
| 2716 | SPAC17G6.05a_UP | ATTGAAGGCCCCTACGCCCC |
| 2717 | SPAC17G6.05a_DN | AGTTGCAGGCGGGCATGTGA |
| 2718 | SPAC17G6.06_UP | AGACACGCCTACGCCGAGCC |
| 2719 | SPAC17G6.06_DN | TTTCAAGGGTTTCGTGCCGC |
| 2720 | SPAC17G6.07a_UP | TAGGTTGGACAGTCGAGCG |
| 2721 | SPAC17G6.07a_DN | ACACCCGCTGCGAAAGCCACG |
| 2722 | SPAC17G6.08_UP | GCCCCTCAGTGCCCCTCCAA |
| 2723 | SPAC17G6.08_DN | TGAACTATCCCCATCGCCCC |
| 2724 | SPAC17G6.10_UP | AGGCGACGTGCACGGTAATG |
| 2725 | SPAC17G6.10_DN | GCGAGAGGGCATCATAGCGG |
| 2726 | SPAC17G6.12_UP | CATTTACAAGCCCGCGGAG |
| 2727 | SPAC17G6.12_DN | TTCAGACCCCCACCCAACCC |
| 2728 | SPAC17G6.13_UP | CATCGTGGGCCTTCCGGGTC |
| 2729 | SPAC17G6.13_DN | TATTTGCGCGCTCACTCGTT |
| 2730 | SPAC17G6.14a_UP | TTCTGGCGGCTCTTGCTGGG |
| 2731 | SPAC17G6.14a_DN | TTGTTGCCTGCCGCACCGTC |
| 2732 | SPAC17G6.15a_UP | CGCCAATCCCAACTCGCCCT |
| 2733 | SPAC17G6.15a_DN | CGACGGCTTTTATGGCACGC |
| 2734 | SPAC17G6.16a_UP | ACTGGGCGCCAAGTTCGAAT |
| 2735 | SPAC17G6.16a_DN | ACCGTGGAGCCCTTGCTTG |
| 2736 | SPAC17G6.17_UP | AACCCATCCCCGCAACCTAG |
| 2737 | SPAC17G6.17_DN | CGTGGGATGCGGATATTGC |
| 2738 | SPAC17G8.02_UP | CCCCACCGACGTACCAAGCC |
| 2739 | SPAC17G8.02_DN | GCGGGAGGTGCAACGAGATG |
| 2740 | SPAC17G8.03a_UP | CTGTGGACGTGCTGCGGCTC |
| 2741 | SPAC17G8.03a_DN | GGGCGGCACTAGGGGGAAATC |
| 2742 | SPAC17G8.04a_UP | TGGTCGGCTTGGAATCGGG |
| 2743 | SPAC17G8.04a_DN | TGGACACAGGGGGCCGAGTT |
| 2744 | SPAC17G8.07_UP | TTGCAACACAACCCACACCC |
| 2745 | SPAC17G8.07_DN | GCCGGGCGAAGCTGAACCT |
| 2746 | SPAC17G8.08a_UP | CCGCCACGCCACCTATTCTC |
| 2747 | SPAC17G8.08a_DN | TCTGTCCCCGTGCTGCCATA |
| 2748 | SPAC17G8.11a_UP | AAGCAGGGTAAGCGGGGGAG |
| 2749 | SPAC17G8.11a_DN | CAGCTGCCCAACATTTCCGC |
| 2750 | SPAC17G8.12_UP | CGTAATGCGCTCGCCGAAGT |
| 2751 | SPAC17G8.12_DN | AATTTGCCGCCCTACTCCG |
| 2752 | SPAC17G8.13a_UP | ACAGAGCGGGGACCAGGGAG |
| 2753 | SPAC17G8.13a_DN | CCAGCCAAGCCCGTACATGC |
| 2754 | SPAC17H9.01_UP | CCCCGGATGAGAAAAGGCGT |

| Sequence number | Name | Base sequence |
|---|---|---|
| 2755 | SPAC17H9.01_DN | ACTTGGCAGGCGTCGGGTTG |
| 2756 | SPAC17H9.02_UP | GGGATGCGGAATGGGATGGC |
| 2757 | SPAC17H9.02_DN | AAACGGAAAAGCAGCGGGTG |
| 2758 | SPAC17H9.03a_UP | CGGTATGGGGTGGCTTCGTG |
| 2759 | SPAC17H9.03a_DN | AATCCTGTTGCTCGGGGTGC |
| 2760 | SPAC17H9.04a_UP | TCGGATGCGCCTCACCCTA |
| 2761 | SPAC17H9.04a_DN | TCGCAAGCCGGTCCCCTAAT |
| 2762 | SPAC17H9.06a_UP | GGGCGGGACTTGTCTTGGCT |
| 2763 | SPAC17H9.06a_DN | AGCAAGCAAGCAAAGCCGCC |
| 2764 | SPAC17H9.08_UP | AGGCGCGGCTGACTTACTCA |
| 2765 | SPAC17H9.08_DN | TGCGGCCAGCTGACGTTCAT |
| 2766 | SPAC17H9.09a_UP | TGTATGACCCCGCTCCCGA |
| 2767 | SPAC17H9.09a_DN | GAGAATTGGTGGACGGGGGG |
| 2768 | SPAC17H9.10a_UP | ATTCACTGTCCCCCGGCTG |
| 2769 | SPAC17H9.10a_DN | TGCCTAGLACCCCTCGAGCC |
| 2770 | SPAC17H9.11_UP | AGAACACGGGCAGCCAGAGCG |
| 2771 | SPAC17H9.11_DN | CCGGCCCCTCAAGTGATCGT |
| 2772 | SPAC17H9.12a_UP | TCGTCCCATCCAACCCCTCC |
| 2773 | SPAC17H9.12a_DN | CATCCCGGCTCCTCGTCCGC |
| 2774 | SPAC17H9.13a_UP | AGAACATGCTGGGGTGGGCG |
| 2775 | SPAC17H9.13a_DN | CATCCGGCTTCGGCCATCTT |
| 2776 | SPAC17H9.14a_UP | CGGTCCCGCTCCTCTCACTG |
| 2777 | SPAC17H9.14a_DN | CCCACCCAAGCGCACCTAAC |
| 2778 | SPAC17H9.16_UP | AGCCCCGAAACCACAGCGTA |
| 2779 | SPAC17H9.16_DN | AACAACAGCGAACCAGCGCC |
| 2780 | SPAC17H9.17a_UP | CAACAACTGGGCGCCGGATAA |
| 2781 | SPAC17H9.17a_DN | CGCGCGGGTTTCTCCCCTAAT |
| 2782 | SPAC17H9.18a_UP | CGGTTCGGTCTTCGTGCGTG |
| 2783 | SPAC17H9.18a_DN | CGCGTTTCACATCCTTGGGC |
| 2784 | SPAC17H9.19a_UP | TGAGGGATGGAATGCCGGTG |
| 2785 | SPAC17H9.19a_DN | TTTTGGATACCGTCCCCCGG |
| 2786 | SPAC1805.02a_UP | AGCAGTCGGCGGCATTTTGG |
| 2787 | SPAC1805.02a_DN | ATACCCAGGTCGGTTTCGCG |
| 2788 | SPAC1805.04_UP | TACAGCGTGGCACACTCGTC |
| 2789 | SPAC1805.04_DN | ACCCAGCCGCTAGATCTGCCA |
| 2790 | SPAC1805.05_UP | CGTGCCCATTTTCCCAGCC |
| 2791 | SPAC1805.05_DN | TGTGTCCCGTCCCTTTGGCG |
| 2792 | SPAC1805.06a_UP | GTGGGGCGACTGCTGTTGGT |
| 2793 | SPAC1805.06a_DN | GGGGCGTTTGCAGGGGTAGG |
| 2794 | SPAC1805.07a_UP | TACCTGGGCGTGCACTTTCG |
| 2795 | SPAC1805.07a_DN | TCAGATCGCCCCTCACCAGC |
| 2796 | SPAC1805.09a_UP | CGCCCAACCCCCCTATCCTT |
| 2797 | SPAC1805.09a_DN | AGGCGTGGCGTGTGGTCTCG |
| 2798 | SPAC1805.10_UP | GTCTGTCATCGCGGGCCCTC |
| 2799 | SPAC1805.10_DN | GGGCGCCGGCAAAACCTATA |
| 2800 | SPAC1805.11a_UP | CCGACCCGTTAAGGCCAAAG |
| 2801 | SPAC1805.11a_DN | CCGACCTCCACTTAAGCCCA |
| 2802 | SPAC1805.12a_UP | ACGGCCAGCCTGACTAACGA |
| 2803 | SPAC1805.12a_DN | CGCCCCAACGCACCACTCTT |
| 2804 | SPAC1805.15a_UP | AGGAGGAGAGGGAAGGCGGG |
| 2805 | SPAC1805.15a_DN | CACTTGAACCCACCCCCCCA |
| 2806 | SPAC1805.16a_UP | CAGGCGCCCAGGAAACACCA |
| 2807 | SPAC1805.16a_DN | ACTTGACATGGAGGCCCTGG |
| 2808 | SPAC1834.01_UP | CCATAAAAGGGCTCCCGGCAA |
| 2809 | SPAC1834.01_DN | CCGCCGAGCGAATGTCAAGT |
| 2810 | SPAC1834.03a_UP | GCGGGGGCCTACTCATGAGG |
| 2811 | SPAC1834.03a_DN | TTGCACCCAGCTCGTCGTCG |
| 2812 | SPAC1834.04_UP | CGCACATGGGGGTCICGGATT |
| 2813 | SPAC1834.04_DN | CGCCCGCGATAAAGCGAACA |
| 2814 | SPAC1834.05_UP | CGGCCGATTACGGTCACGT |
| 2815 | SPAC1834.05_DN | CACCCCCGGTACGCAACCACT |
| 2816 | SPAC1834.06a_UP | AATGGACCCACACCCTTCGG |
| 2817 | SPAC1834.06a_DN | CCCGTGTCGGCTCAGGTGTC |
| 2818 | SPAC1834.07_UP | TACGCACCCCTCGCCTTACC |
| 2819 | SPAC1834.07_DN | GGGGGGTGTCAAGGGACGGT |
| 2820 | SPAC1834.08_UP | TGTCTTCCTCCCCCCATGTC |
| 2821 | SPAC1834.08_DN | GCGCGATGAAGGGAGGGAG |
| 2822 | SPAC1834.09_UP | AAATGCCGTAGGGCGAGGGG |
| 2823 | SPAC1834.09_DN | GAGCCTTTGTTCCCCCCGA |
| 2824 | SPAC1834.10a_UP | TGGTGTTGGTCGCGCTTTT |
| 2825 | SPAC1834.10a_DN | ATGCTCGCGTTTTCTCCCA |
| 2826 | SPAC4H3.09_UP | ACCAAACCAAGGCCACCCAA |
| 2827 | SPAC4H3.09_DN | ACGATGAAGGGGCGGGGACCT |
| 2828 | SPAC1851.03_UP | CCAGCCGCCAGCACAAATCC |
| 2829 | SPAC1851.03_DN | CTCCGCACCTCGCCTCAGAA |
| 2830 | SPAC186.01_UP | TACCTGGCGCTTGAATCCG |
| 2831 | SPAC186.01_DN | GACCAACCTTAGCCCGCTAC |
| 2832 | SPAC186.02a_UP | CCGCTCGTCCCTCTTTCCTG |
| 2833 | SPAC186.02a_DN | TGCAGCCACAAACCCAAGCG |
| 2834 | SPAC186.03_UP | ATACAAGATCCGGCCGTGGG |
| 2835 | SPAC186.03_DN | GTGGCGGTTGTTCTTGCGTG |
| 2836 | SPAC186.05a_UP | TCGGATGTAAGCGTTGGCCC |
| 2837 | SPAC186.05a_DN | GCCATTCTGCCGGGACTCAC |
| 2838 | SPAC186.06_UP | TCCCGTCATAGCCCTTCCCG |
| 2839 | SPAC186.06_DN | AATGGGCGGGGAGTAGGGAA |
| 2840 | SPAC186.07a_UP | CCGTTGCCGTGTGTATGCGT |
| 2841 | SPAC186.07a_DN | TGCTTGCGGCGACGGTAGGT |
| 2842 | SPAC186.08a_UP | AAATCCCGCTCCTCCCCCTA |
| 2843 | SPAC186.08a_DN | AGGGGGATTAGCGGTGCAGG |
| 2844 | SPAC186.09_UP | GCGCTGCACCCCGACAAATC |
| 2845 | SPAC186.09_DN | TGCTCTCCGTCCTTACCCGC |
| 2846 | SPAC18B11.02a_UP | AGTTGGGGCAGCGTGGTGAA |
| 2847 | SPAC18B11.02a_DN | TAGGGGATATTCGGACGCGG |
| 2848 | SPAC18B11.03a_UP | CAATCCTCCACCACCACGCA |
| 2849 | SPAC18B11.03a_DN | CGGGGCGGCAATCGATAAAA |
| 2850 | SPAC18B11.04_UP | ACCCCTCTGCACCAATGCCG |
| 2851 | SPAC18B11.04_DN | ATGCCCAAAGACCGCCCCTG |
| 2852 | SPAC18B11.06_UP | TGACCCCGCTTTGTTGAGCC |
| 2853 | SPAC18B11.06_DN | GGCATAACTCAGGGGCAGCG |
| 2854 | SPAC18B11.07a_UP | GCTGCGGGGATTGGAGGAC |
| 2855 | SPAC18B11.07a_DN | TCTGGTGGTTGGTGCGTGCC |
| 2856 | SPAC18B11.10_UP | CGCGATGTTACGGGGCTACG |

FIG.21

| Sequence number | Name | Base sequence |
|---|---|---|
| 2857 | SPAC18B11.10_DN | CCCGCGTGTCTGCTGCAATA |
| 2858 | SPAC18G6.01c_UP | CTGGGCTCGTTGGCTGATCA |
| 2859 | SPAC18G6.01c_DN | ACAACAAGGCGGCGAGAGGT |
| 2860 | SPAC18G6.02c_UP | AAGTGTGGGCTCGTGGGCGG |
| 2861 | SPAC18G6.02c_DN | AAATGAGCGGTTGCGGTCGT |
| 2862 | SPAC18G6.03_UP | TAAATCGGGGCTTCACGGCT |
| 2863 | SPAC18G6.03_DN | ACGCACCAACTCCGCCGAAT |
| 2864 | SPAC18G6.04c_UP | TCACTTCGCCGACTTCGGCT |
| 2865 | SPAC18G6.04c_DN | TACCTGTTCTGTCGCCGCGC |
| 2866 | SPAC18G6.05c_UP | ACGGGCGGTGGTGATTTGCT |
| 2867 | SPAC18G6.05c_DN | AAATGCTGGGGGTCGTGGCT |
| 2868 | SPAC18G6.07c_UP | CAACAGGGGCGTAAGACCAG |
| 2869 | SPAC18G6.07c_DN | GTCTGGGTGGTGCGTGTCGC |
| 2870 | SPAC18G6.10_UP | TTCTTACCGGCCTGTGCCGA |
| 2871 | SPAC18G6.10_DN | CGCTATTGCGTTGGATCCGA |
| 2872 | SPAC18G6.12c_UP | CAGGGGGAGGTCGTATGGCC |
| 2873 | SPAC18G6.12c_DN | ATTGGGTACGGCGCAGGGTT |
| 2874 | SPAC18G6.13_UP | TTTGTTTTCGGGTGCGGATG |
| 2875 | SPAC18G6.13_DN | CACCACCAACCGCGCCATAG |
| 2876 | SPAC18G6.14c_UP | ACTGGGAACGGCAAGGGGGT |
| 2877 | SPAC18G6.14c_DN | ATTCGCTCCCTCTGCCGGGT |
| 2878 | SPAC18G6.15_UP | ATCGCGGCATATACCCCTGC |
| 2879 | SPAC18G6.15_DN | GAAATTGCGACCTGGCGGTG |
| 2880 | SPAC1952.03_UP | ACACGACGCTCCTTCGCAAA |
| 2881 | SPAC1952.03_DN | CGTACAAATGGGGGCGGACA |
| 2882 | SPAC1952.05_UP | CGCGGCACATTCCACCCTTC |
| 2883 | SPAC1952.05_DN | ACTTCATTCCTGCATCGGGG |
| 2884 | SPAC1952.06c_UP | CAGTGCCCTCCGTTGACCGT |
| 2885 | SPAC1952.06c_DN | CGTGGGCAGGACAGAAGCAG |
| 2886 | SPAC1952.07_UP | TTTGTCCGGTCTTTCGCGCG |
| 2887 | SPAC1952.07_DN | GGCTCCCGGTTCGCTTATTG |
| 2888 | SPAC1952.09c_UP | TGGGAAACCTGGTGGGGTGA |
| 2889 | SPAC1952.09c_DN | CCCTTCGCTGTTTCGGTTCC |
| 2890 | SPAC1952.09c_UP | AGACACTTGGCCAAGAGAG |
| 2891 | SPAC1952.09c_DN | GTATGCCGCTAACGCCGAGA |
| 2892 | SPAC1952.10c_UP | AGTTAGGCGTTGGCGTTGGCC |
| 2893 | SPAC1952.10c_DN | ATGCGGCCGGAATTTGTGTG |
| 2894 | SPAC1952.11c_UP | CCAGGGGCAACGATTAACGC |
| 2895 | SPAC1952.11c_DN | CGTTCCGTGCGCTTCCTATG |
| 2896 | SPAC1952.12c_UP | ACTATCACAAAGCGGCGGCA |
| 2897 | SPAC1952.12c_DN | CCGCAGCACCCCAACACTCT |
| 2898 | SPAC1952.13_UP | GTGCCGTCTTTGGCAGGCAG |
| 2899 | SPAC1952.13_DN | AGACGCCCGTTGCGGATTGA |
| 2900 | SPAC1952.14c_UP | CCACCGCGATCAACCCGAGA |
| 2901 | SPAC1952.14c_DN | CGTTCTGCCTCCCACCACCT |
| 2902 | SPAC1952.15c_UP | TGACATGTACCGCGAAGGCCG |
| 2903 | SPAC1952.15c_DN | TCCCTGAGCCCACAAACCCT |
| 2904 | SPAC1952.16_UP | GGTTGCCCAGGCTGATCCGA |
| 2905 | SPAC1952.16_DN | GTGCCGTTGTGGGCCCCTCT |
| 2906 | SPAC19A8.02_UP | CAGCCTCCCGCCTTCACGAC |
| 2907 | SPAC19A8.02_DN | GCTTCAGCGACTCGGATCGT |
| 2908 | SPAC19A8.03_UP | CGGGTCAAAACTGGGGGCAA |
| 2909 | SPAC19A8.03_DN | AAAATCTACCATGGGCCGCG |
| 2910 | SPAC19A8.04_UP | TCCCCGGAAGTTTGGAGCCC |
| 2911 | SPAC19A8.04_DN | ACCGGGAGGGCTTGGGAATC |
| 2912 | SPAC19A8.05c_UP | CCACGGACGTAGTCCGCAAT |
| 2913 | SPAC19A8.05c_DN | GATTTTAGCGCGCGTCCATG |
| 2914 | SPAC19A8.07c_UP | GTAGGCAATTGGGAGGCGAG |
| 2915 | SPAC19A8.07c_DN | ATGACCGCACACCCTGCTCCC |
| 2916 | SPAC19A8.08_UP | TCTCACAAGGGCTCACGCGA |
| 2917 | SPAC19A8.09_UP | GCCTTCCAGCAGTCCGGTCC |
| 2918 | SPAC19A8.09_DN | GCCTGGTGGCGCGTTTTTCA |
| 2919 | SPAC19A8.09_DN | TCAAGGGGTGCGCGGGTAGA |
| 2920 | SPAC19A8.10_UP | CTACACGCGTCACAAGCGCAT |
| 2921 | SPAC19A8.10_DN | TGGCGTGGCTCTCAAATGGA |
| 2922 | SPAC19A8.12_UP | TCAGCCACGGCAAGCCCATC |
| 2923 | SPAC19A8.12_DN | AGGGTGGTGGCGACGAACAA |
| 2924 | SPAC19A8.13_UP | GTGCTGCGCCGGAAGAAAAG |
| 2925 | SPAC19A8.13_DN | TTTCCACGCCGGACCCACAGAC |
| 2926 | SPAC19A8.14_UP | CGTGCCACCCAATGACAACT |
| 2927 | SPAC19A8.14_DN | GCCTGTGTCTTCGGGGATCG |
| 2928 | SPAC19B12.02c_UP | CGGTTGGGAAGTTGGGTGCC |
| 2929 | SPAC19B12.02c_DN | AGATACTCTCTTCGGCCGCG |
| 2930 | SPAC19B12.04_UP | AAATGTCGAGCGGAGGGGTG |
| 2931 | SPAC19B12.04_DN | CAGCCGGACGAATGGAAAC |
| 2932 | SPAC19B12.05c_UP | TTTCCCGCCACCTTCCAGTC |
| 2933 | SPAC19B12.05c_DN | GGGGAGCTTTCCAGTGGGGT |
| 2934 | SPAC19B12.06c_UP | ACCAACACCGCCCCGTAAAC |
| 2935 | SPAC19B12.06c_DN | CCACCCACATCGCCTCTCGT |
| 2936 | SPAC19B12.07c_UP | GCTCCTGACTGTACGCGAGA |
| 2937 | SPAC19B12.07c_DN | GCTGGAAAATCCGTTGTCCG |
| 2938 | SPAC19B12.08_UP | GAACTGCCAATGCCCCTCGG |
| 2939 | SPAC19B12.08_DN | CGAGCTCCTCTCALTGGGCG |
| 2940 | SPAC19B12.09_UP | CCTAGAACCCATGCGCCTCG |
| 2941 | SPAC19B12.09_DN | TGGGGGGATTTGCAACGGTA |
| 2942 | SPAC19B12.10_UP | TTACACGTCCGCGGGGCCAA |
| 2943 | SPAC19B12.10_DN | CTGATGTTGGGAGCACGCGC |
| 2944 | SPAC19B12.11c_UP | AGAAGCGAGGGGGACAGCGG |
| 2945 | SPAC19B12.11c_DN | GGCTAGCCGAAGGGCACGTC |
| 2946 | SPAC19B12.12c_UP | GCTGGCGGTTAAAGGGCTG |
| 2947 | SPAC19B12.12c_DN | TTAACTATGACGGGGGCGGG |
| 2948 | SPAC19B12.13_UP | TGAGCGGCCGGAGGTTATGG |
| 2949 | SPAC19B12.13_DN | GTACGAATCCCAACCCGGCG |
| 2950 | SPAC19D5.01_UP | CTCATCCCGCCCCATTGCTT |
| 2951 | SPAC19D5.01_DN | GCGGGGGGTAATCAAATGG |
| 2952 | SPAC19D5.02c_UP | CACGCGTCCCCACCCTTCTG |
| 2953 | SPAC19D5.02c_DN | TCCGTTCAGGGAGCAGGGTT |
| 2954 | SPAC19D5.03_UP | CGCGAATGACGGGACTACCA |
| 2955 | SPAC19D5.03_DN | TGAACTCTTAGCGTGCCCCG |
| 2956 | SPAC19D5.04_UP | TGGGTCGGTGGGCGAATAAGA |
| 2957 | SPAC19D5.04_DN | CCTCTCTTGCTTCGCCTCCG |
| 2958 | SPAC19D5.05c_UP | GGGGGCCGCGATAGTCACTG |

| Sequence number | Name | Base sequence |
|---|---|---|
| 2959 | SPAC19D5.05c_DN | GTTAACGGCCACTCCGCCCA |
| 2960 | SPAC19D5.06c_UP | AAGGGCGCGGGTGTTTGTAA |
| 2961 | SPAC19D5.06c_DN | GAGCCAACCCCACGACCAAG |
| 2962 | SPAC19D5.07_UP | GGCGGCCGTGAGAGGAAGAG |
| 2963 | SPAC19D5.07_DN | CAGTCGAGGGCGGGGATTTC |
| 2964 | SPAC19D5.09c_UP | CACAGTCCCCGATCCAGCAA |
| 2965 | SPAC19D5.09c_DN | GACAGGTTCAGGCCAGCGGT |
| 2966 | SPAC19D5.10c_UP | TGCGACGCGCGATCTACTGT |
| 2967 | SPAC19D5.10c_DN | ATGCCGCCTACGGACGTACA |
| 2968 | SPAC19D5.11c_UP | GCGCCCTAGTACGTGTCCAT |
| 2969 | SPAC19D5.11c_DN | ACGACTACCAGAGGCCCGAT |
| 2970 | SPAC19E9.01c_UP | GGGCCAGTCCCACGTTTACA |
| 2971 | SPAC19E9.01c_DN | AGCCGAAGGCGCATTTGAGC |
| 2972 | SPAC19E9.02_UP | GGCCCCACCCAACTCGCTGT |
| 2973 | SPAC19E9.02_DN | TGCAGGTCTTGGGGTCGTC |
| 2974 | SPAC19G12.01c_UP | TGGCTGGATTTGGTTCGGGA |
| 2975 | SPAC19G12.01c_DN | CTGTTCCCACTCGGCCCTCG |
| 2976 | SPAC19G12.02c_UP | CATTGCGTAGGCTGCGGACA |
| 2977 | SPAC19G12.02c_DN | CGTGGATGCGGGGAAACGAC |
| 2978 | SPAC19G12.03_UP | GAACCCCACCCCAGCGAAAT |
| 2979 | SPAC19G12.03_DN | CGCTTGAGTGCCCGATGAAG |
| 2980 | SPAC19G12.04_UP | CGCCCAATAGGTCTTCGCCC |
| 2981 | SPAC19G12.04_DN | CCACGCGTCTGTAATGCCCG |
| 2982 | SPAC19G12.05_UP | TGATTCTCGGGCTGGTGTGC |
| 2983 | SPAC19G12.05_DN | TGTCTCGTCATCCTACCCGC |
| 2984 | SPAC19G12.06c_UP | CTGGGGACAACCGAAGGCGA |
| 2985 | SPAC19G12.06c_DN | AGCTGGGGCCTTGTCACGTG |
| 2986 | SPAC19G12.08_UP | CAGCACCCCCATCCCCTTTG |
| 2987 | SPAC19G12.08_DN | TGGATGGCGCTATGGTGTGG |
| 2988 | SPAC19G12.09_UP | ATCGTCGCTCACCCTCTCGG |
| 2989 | SPAC19G12.09_DN | CCTTTCCTTCCATCGCGCAG |
| 2990 | SPAC19G12.10c_UP | ATGACAGAAGCGGCAGGCAA |
| 2991 | SPAC19G12.10c_DN | TGCCCTTCACTTTGTCGCCC |
| 2992 | SPAC19G12.11_UP | TGGCAGTCGGGGGCTAAAAA |
| 2993 | SPAC19G12.11_DN | GGGGGGAGATCGGCATGGAG |
| 2994 | SPAC19G12.12_UP | GCCAATCATACCGCAGACATG |
| 2995 | SPAC19G12.12_DN | CAGCCGCGCTCGGATCATAAA |
| 2996 | SPAC19G12.13c_UP | CGTGGTTCGTCGTGCTCGCC |
| 2997 | SPAC19G12.13c_DN | CTCGTTCGGTGCAGTCGCCG |
| 2998 | SPAC19G12.14_UP | TAAGGTCGAGACGCGGGCTG |
| 2999 | SPAC19G12.14_DN | GGTGCCGATCAGTGCCTGTT |
| 3000 | SPAC19G12.15c_UP | CCCTACTATGCCCGCCATTG |
| 3001 | SPAC19G12.15c_DN | TCGCAATCGGGAAATCGTCC |
| 3002 | SPAC19G12.16c_UP | ACCATCCCGCCTTCACAAAA |
| 3003 | SPAC19G12.16c_DN | CGTCGTTTTGCGCCGTAAGC |
| 3004 | SPAC1A6.04c_UP | AATCAGGTTCCCAGGGCGAC |
| 3005 | SPAC1A6.04c_DN | TGCCTGTCGGATGGTCACTC |
| 3006 | SPAC1A6.05c_UP | CCCGGTACCCCTGCAAATG |
| 3007 | SPAC1A6.05c_DN | ATTGTCCCGCCGTCCAACAA |
| 3008 | SPAC1A6.06c_UP | GTATGGATTGCGGTCGAGCC |
| 3009 | SPAC1A6.06c_DN | CTTTTTCGACCCCACCGCTC |
| 3010 | SPAC1A6.07_UP | GCTGAACAATAACCCCGGTCG |
| 3011 | SPAC1A6.07_DN | GGAGAAGGGATCGGAACCGC |
| 3012 | SPAC1A6.08c_UP | TAGCTCCATCCGCCACTGCA |
| 3013 | SPAC1A6.08c_DN | TGCAGCCACGATAGACCGCC |
| 3014 | SPAC1A6.09c_UP | GCATGGGCCGTAAGCTCGT |
| 3015 | SPAC1A6.09c_DN | ACGAAAGCGCCAGCAACAGG |
| 3016 | SPAC1B1.01_UP | CCACCAGCAGCAGTTCCCCG |
| 3017 | SPAC1B1.01_DN | CCCGCAAACTCACCCCCGT |
| 3018 | SPAC1B1.02c_UP | ACCCTAGGCCGTTAGCGTGGT |
| 3019 | SPAC1B1.02c_DN | CGTGATCGCCGACTAAGGCT |
| 3020 | SPAC1B1.03c_UP | CACACCAGCCGTCCAACCGT |
| 3021 | SPAC1B1.03c_DN | CTTCCGACCCGACAACCCTC |
| 3022 | SPAC1B1.04c_UP | CCGGTGAGGGACTGGCTGAG |
| 3023 | SPAC1B1.04c_DN | ATCCACGCGTCACCAAAGGC |
| 3024 | SPAC1B2.02c_UP | CCCTAAGACCCCACCGCTTT |
| 3025 | SPAC1B2.02c_DN | GCCGAAACCTCCACAACCAG |
| 3026 | SPAC1B2.04_UP | TGGAGGTGCCCGGGAAGGAG |
| 3027 | SPAC1B2.04_DN | TCCGATGAGCGGCGAACAAT |
| 3028 | SPAC1B3.01c_UP | TAATGGTGTTGCCCCGTGCG |
| 3029 | SPAC1B3.01c_DN | ATGCTCGTGCGCGGTTATTG |
| 3030 | SPAC1B3.02c_UP | AGGGGGTGTTGTCGGGATGT |
| 3031 | SPAC1B3.02c_DN | CACCACCTGGCGAACAACCG |
| 3032 | SPAC1B3.03c_UP | GGGGTTTGACGGGCGAAGT |
| 3033 | SPAC1B3.03c_DN | TTCCGCTTTGTCCGCTCCTG |
| 3034 | SPAC1B3.04c_UP | CCACCCCGTCGCTCATCCT |
| 3035 | SPAC1B3.04c_DN | GACGATCCGGAGTGGGCAAA |
| 3036 | SPAC1B3.05_UP | ACGGCGATAGCCATTTCCCC |
| 3037 | SPAC1B3.05_DN | TTCATCAAACTCTCGGCGCG |
| 3038 | SPAC1B3.06c_UP | TCGCGGGGGTGGGTCTTTTA |
| 3039 | SPAC1B3.06c_DN | GTCTTTGGTTCCCCCGCTCG |
| 3040 | SPAC1B3.07c_UP | TCAGCAAGCGCGCAACGTAC |
| 3041 | SPAC1B3.07c_DN | TGTCCTTCCCGGTGTGCCTC |
| 3042 | SPAC1B3.08_UP | GTTGCGGCCAGCGTATGAAA |
| 3043 | SPAC1B3.08_DN | GTTCTCACCCCGGCATTTGG |
| 3044 | SPAC1B3.09c_UP | CACGTGCTATCTCACCGGGA |
| 3045 | SPAC1B3.09c_DN | ACACGTACGAGCCACGAAGC |
| 3046 | SPAC1B3.10c_UP | CGGGTAGGAGCGGATGATGG |
| 3047 | SPAC1B3.10c_DN | ACACTACTCGCCGCGCCCAC |
| 3048 | SPAC1B3.11c_UP | AAAGGCCGCACCGCAAGAAA |
| 3049 | SPAC1B3.11c_DN | CCTGGCTCCTCTCCTGCTTG |
| 3050 | SPAC1B3.12c_UP | GCCCGAAAGCGCAGGATCAC |
| 3051 | SPAC1B3.12c_DN | CCATTGAATTTCCGGCGGGG |
| 3052 | SPAC1B3.15c_UP | TCCAACATCTCCCGCCCAGG |
| 3053 | SPAC1B3.15c_DN | GTGTATGGAGAAGGGCGGTA |
| 3054 | SPAC1B3.16c_UP | GGTGTAGAGGCGGGTGCGGA |
| 3055 | SPAC1B3.16c_DN | GGCGGGCAAGAAGAGGTTG |
| 3056 | SPAC1B3.17_UP | TCAGGGCGGGAGAATCGAAT |
| 3057 | SPAC1B3.17_DN | AATCCGCCCCGCAAACAGAC |
| 3058 | SPAC1B3.18c_UP | TCCGAGCGGTCCACAGAACG |
| 3059 | SPAC1B3.18c_DN | CGAACTCACCACGCTGCCGA |
| 3060 | SPAC1B3.20_UP | GGAAAAGCTCAGTGCCGGGG |

FIG.22

| Sequence number | Name | Base sequence | Sequence number | Name | Base sequence |
|---|---|---|---|---|---|
| 3061 | SPAC1B3.20_DN | CATCGCCTCCCACACCCTTG | 3163 | SPAC1F8.04c_DN | GGGGCGTTACTCCGAGCAGG |
| 3062 | SPAC1B9.02c_UP | AATGTCCCGCCCCCTAAAGC | 3164 | SPAC1F8.05_UP | TTGGACGGGGATTTACGGCG |
| 3063 | SPAC1B9.02c_DN | CGACGCCACAACTTCCACGA | 3165 | SPAC1F8.05_DN | GGTCAGAATGGGTGGCGGAC |
| 3064 | SPAC1D4.02c_UP | GTGTCTACCCCGCTGCCGGT | 3166 | SPAC1F8.06_UP | CGGACGGAGAGGCGGGTACA |
| 3065 | SPAC1D4.02c_DN | GAGCCGGTGTTCGGGGGTAT | 3167 | SPAC1F8.06_DN | TTCCAAGGCGCGGGTATCAA |
| 3066 | SPAC1D4.03c_UP | AATTCCGCTATGGCCCCGT | 3168 | SPAC1F8.07c_UP | CTGACCGCTCGCCCGGAATGT |
| 3067 | SPAC1D4.03c_DN | AGGGCCAGAGCGACGTAGCA | 3169 | SPAC1F8.07c_DN | TCCATTAGTCGTGCGTCGGG |
| 3068 | SPAC1D4.04_UP | CGAGGCGGACTTGGTGGTCT | 3170 | SPAC1F8.08_UP | CGTTGATCAGGCAGGGCAAG |
| 3069 | SPAC1D4.04_DN | CATACAAGCACGCGCCTCGA | 3171 | SPAC1F8.08_DN | CGCGCTTCACGTACGTCGTT |
| 3070 | SPAC1D4.05c_UP | CTTCCAGTCCGCATCACCCC | 3172 | SPAC20G4.01_UP | CGCGCGACCCCAATAAACCC |
| 3071 | SPAC1D4.05c_DN | TACGGATCGCGGGGAACAAA | 3173 | SPAC20G4.01_DN | CGTTTGGAAGGGGTGCGTCA |
| 3072 | SPAC1D4.06c_UP | GGGGCGAGGATTGCATGAGT | 3174 | SPAC20G4.02c_UP | CGAGTTGGGGAGCCCGTGTC |
| 3073 | SPAC1D4.06c_DN | ACATCAACTTGCCGTCGGGG | 3175 | SPAC20G4.02c_DN | CAGGTTCATGGCGCCGTCTC |
| 3074 | SPAC1D4.07c_UP | AGGTCGTGCGGGTATGGGGG | 3176 | SPAC20G4.03c_UP | TTATGCGACGGCGGACGAT |
| 3075 | SPAC1D4.07c_DN | AGTTGCGGCGGTTGATGAGC | 3177 | SPAC20G4.03c_DN | GCATTGATCGGGCAGACGGC |
| 3076 | SPAC1D4.08_UP | TGACAGGATTCGTAGGGCCG | 3178 | SPAC20G4.04c_UP | TAGGGGCGGAGGACGGTAT |
| 3077 | SPAC1D4.08_DN | AATAAGAGCGCGTCGCCACA | 3179 | SPAC20G4.04c_DN | AATCCCCGTCCCATTCCAGC |
| 3078 | SPAC1D4.09c_UP | AGCGGTTGTTTGGAGGTGGG | 3180 | SPAC20G4.05c_UP | GCACAACGGGGAAATGGAGG |
| 3079 | SPAC1D4.09c_DN | CCAAGAGCCCAGACCGAAG | 3181 | SPAC20G4.05c_DN | TCGATTCLTGTCCTCCCGGG |
| 3080 | SPAC1D4.11c_UP | CGCACCCTATTCCACTGCC | 3182 | SPAC20G4.06c_UP | CGCCGTCCGTCTTCGCCTTA |
| 3081 | SPAC1D4.11c_DN | AGCCGACCCAAACGAGCAGA | 3183 | SPAC20G4.06c_DN | TGACGGGCATTGTTGGGGAC |
| 3082 | SPAC1D4.12_UP | CTGGCAATAGCCCCGTCGG | 3184 | SPAC20G4.07c_UP | GCCGCGCTACACCCGTTATT |
| 3083 | SPAC1D4.12_DN | ACGTTGAAGGGGGTTGGACG | 3185 | SPAC20G4.07c_DN | CGCGGTGGGAGAAGTGGGTA |
| 3084 | SPAC1D4.13_UP | ATTCCGGCGTGACCCACCTG | 3186 | SPAC20G8.01_UP | GGGAACCCAGTAGCCCGAT |
| 3085 | SPAC1D4.13_DN | GACGGAGACGTGGGACGCG | 3187 | SPAC20G8.01_DN | GTCGGTTATGGGTGGGTCGC |
| 3086 | SPAC1F12.02c_UP | GCAGGAGGCATTTAGGCCGG | 3188 | SPAC20G8.03_UP | GGGTGTGACTGGCGGGAAA |
| 3087 | SPAC1F12.02c_DN | AGATGTGGCCCCGCTGTGAA | 3189 | SPAC20G8.03_DN | TGGAGCGTATGGAGGGCAGG |
| 3088 | SPAC1F12.03c_UP | GGCCTTAATCGAGCGGGGGA | 3190 | SPAC20G8.04c_UP | TCACCCAGCCGCAGTTACA |
| 3089 | SPAC1F12.03c_DN | TGGCAGCAGACACGGGAT | 3191 | SPAC20G8.04c_DN | CCGGAATGAACGTAGGCGCC |
| 3090 | SPAC1F12.04c_UP | GCGCTAAATCCCCGCTCCCC | 3192 | SPAC20G8.06_UP | AGCCCAACAGCCGACCAGTC |
| 3091 | SPAC1F12.04c_DN | GCTTCGCGGCCATGTACCTCC | 3193 | SPAC20G8.06_DN | GAGTTGGGAAGCACGACGCC |
| 3092 | SPAC1F12.05_UP | CCTGGGTTCGGGGTGCGTTC | 3194 | SPAC20G8.07c_UP | GGCCTGCTGAACGAACCGAT |
| 3093 | SPAC1F12.05_DN | TGGCCTTTGTCGCGTGGGTT | 3195 | SPAC20G8.07c_DN | TCGGGCGAACATGATCCAGC |
| 3094 | SPAC1F12.06c_UP | CCGGGAATACCCCCACAAAA | 3196 | SPAC20G8.08c_UP | ACCGGGTGTGGAGCTGCATG |
| 3095 | SPAC1F12.06c_DN | CTCGAAGCCGTCTTTCCCAC | 3197 | SPAC20G8.08c_DN | AGACGGTAGCGGGAAGGGGT |
| 3096 | SPAC1F12.C7_UP | AGCCTGCAAACATCTCCCCC | 3198 | SPAC20G8.09c_UP | GAGGAGACTGTGGTGGGGGC |
| 3097 | SPAC1F12.07_DN | ACGCGAGCTGGGACGAACAC | 3199 | SPAC20G8.09c_DN | ACGTTACGTACTACGCGGCT |
| 3098 | SPAC1F12.08_UP | ACCATCGATCCCCCGTTCC | 3200 | SPAC20H4.02_UP | CCTCGCGTCCGATTTGTGAG |
| 3099 | SPAC1F12.08_DN | TCAGATGTTGTCCGCGTCCG | 3201 | SPAC20H4.02_DN | CGCGTCAGCTACCCCGATA |
| 3100 | SPAC1F12.09_UP | CACGGGGTCAAATGGCGGTC | 3202 | SPAC20H4.03c_UP | TTCCGCGCAGTTTGGGTCTG |
| 3101 | SPAC1F12.09_DN | CTAGGGCAGGCGTTGGCATC | 3203 | SPAC20H4.03c_DN | ACAAGCGTTCCCGGACTGAG |
| 3102 | SPAC1F12.10c_UP | CGGAGTCGCATGACGAAGC | 3204 | SPAC20H4.04_UP | CCTCTCTTGGCCCCGTC7C |
| 3103 | SPAC1F12.10c_DN | AGACGCACTATCGGCGGAGG | 3205 | SPAC20H4.04_DN | ATTCGGCTTGTTGGCTCCCC |
| 3104 | SPAC1F3.01_UP | GCGGGCGAGAAAAACGTCA | 3206 | SPAC20H4.C5c_UP | CCGGGGGCTGAAGACACAATG |
| 3105 | SPAC1F3.01_DN | CCACCCCGCCTCAGACGTTA | 3207 | SPAC20H4.C5c_DN | CTTGTGGGGCGAACCGCTA |
| 3106 | SPAC1F3.02c_UP | GCTTGCGGGGATACGACGGG | 3208 | SPAC20H4.06c_UP | TAACTGCGCAACGGGAAGG |
| 3107 | SPAC1F3.02c_DN | TAGGGCAGTTTGGACGGCGG | 3209 | SPAC20H4.06c_DN | GCTGTTCTCGTCGTCGGCTG |
| 3108 | SPAC1F3.03_UP | CGCTATTGGCCGGGGTCTTT | 3210 | SPAC20H4.07_UP | TGACTGCAAGCGGCCCGATA |
| 3109 | SPAC1F3.03_DN | CGTGGGCGGAGGTTGAAGAC | 3211 | SPAC20H4.07_DN | AGCTTTGCGGCTACGGGCAG |
| 3110 | SPAC1F3.05_UP | CTCGCAGAAAGGGCCACGTT | 3212 | SPAC20H4.08_UP | ATTGGATTGCGGCCCTTGAG |
| 3111 | SPAC1F3.05_DN | CCCCCCAAAGATAGACGCCA | 3213 | SPAC20H4.08_DN | GCGCTCGGATATGGGTATCG |
| 3112 | SPAC1F3.06c_UP | CCTATAAAGCCGCGGTCCA | 3214 | SPAC20H4.09_UP | AGCCGGTGCCAAGGGTGAAGG |
| 3113 | SPAC1F3.06c_DN | TACACGTCGCCTTGCCCCCT | 3215 | SPAC20H4.09_DN | AACTGGGCGTAGGACAGGGC |
| 3114 | SPAC1F3.07c_UP | GCATGGCCGTGGGTTTTGAA | 3216 | SPAC20H4.10_UP | CACCCCGCCCTGTAATCGCT |
| 3115 | SPAC1F3.07c_DN | TGGCCGCGTGCCGTCTGGTAC | 3217 | SPAC20H4.10_DN | CAGAAACCGCCCAGCAAGCG |
| 3116 | SPAC1F3.08c_UP | CGGGGGTTATCGGGACTTGA | 3218 | SPAC20H4.11c_UP | GGGTCCCGCAAACCCCATTG |
| 3117 | SPAC1F3.08c_DN | CAAACGGTCGCCCAACAATG | 3219 | SPAC20H4.11c_DN | CCCAGCCCTGCATCACACAC |
| 3118 | SPAC1F3.09_UP | CCGCACCAGGACAAACCAGA | 3220 | SPAC212.01c_UP | TGCCCGTGTAACTCTCCCCG |
| 3119 | SPAC1F3.09_DN | CCAGGGGGCAAGGTACGTA | 3221 | SPAC212.01c_DN | TCCCTATTCCCCGTGCCCTG |
| 3120 | SPAC1F3.10c_UP | GAGGGCGGGAGCCGAACAG | 3222 | SPAC212.02_UP | GCAGAACCCTCCCGCCAGTA |
| 3121 | SPAC1F3.10c_DN | GTTGGGTGGGGTTGTCTGGG | 3223 | SPAC212.02_DN | CCGTCCGTCCATCTTCTGCCC |
| 3122 | SPAC1F5.02_UP | GCCCCTTCCAAGTACCCGCT | 3224 | SPAC212.03_UP | ACATTAACCCCGGACCCGC |
| 3123 | SPAC1F5.02_DN | TCCACACATTACCCTCGGCG | 3225 | SPAC212.03_DN | AAGTCGCCCGAGAGTTAGGC |
| 3124 | SPAC1F5.03c_UP | TTAGGGGTGGAGCGGAGCAT | 3226 | SPAC212.04c_UP | ACGGGATTCGGTCTGTCGTT |
| 3125 | SPAC1F5.03c_DN | GTGGCTGCGGGGTCGGATAC | 3227 | SPAC212.04c_DN | CGTTTGGTTGGGTTGCGTCG |
| 3126 | SPAC1F5.04c_UP | TGTAGGGTATGCTGGCGGGG | 3228 | SPAC212.08c_UP | ACAGCGTCCTCCCAGCCGAG |
| 3127 | SPAC1F5.04c_DN | CTGCCGACCCAACCCTCTCA | 3229 | SPAC212.08c_DN | AGGAAAGCAAAACCCCCGA |
| 3128 | SPAC1F5.05c_UP | GCAGGGTTTGATAGGGCGGC | 3230 | SPAC212.11_UP | TGCTTTTAGGTCGTGGCGGG |
| 3129 | SPAC1F5.05c_DN | AGTGCGGAACTCGATTGTGA | 3231 | SPAC212.11_DN | GCGGTTGGCGGGTGTGTAGG |
| 3130 | SPAC1F5.07c_UP | GCGCCGTGTGTATAGCCCAA | 3232 | SPAC21E11.03c_UP | ACGGCAGGCGGCTCTAACAC |
| 3131 | SPAC1F5.07c_DN | TTGTGGGGCGGCTAGTGCTT | 3233 | SPAC21E11.03c_DN | CGCAGTTTGCATGAACGCCG |
| 3132 | SPAC1F5.08c_UP | GCGGAGGCATTGAGGCGAGTC | 3234 | SPAC21E11.04_UP | GGACGTTGATCGGGGCAGA |
| 3133 | SPAC1F5.08c_DN | TGATTGGGGGAGCCTGTGTG | 3235 | SPAC21E11.04_DN | GCGGAGCCGATATGGGGAACA |
| 3134 | SPAC1F5.09c_UP | AGGTGGGGCAGGTAAGCGG | 3236 | SPAC21E11.05c_UP | GTGAGGGACCGTATGGGAGA |
| 3135 | SPAC1F5.09c_DN | AGTGAGGGGCTGGCGAAGG | 3237 | SPAC21E11.05c_DN | CGGGGGGTCTGCCTTGTAT |
| 3136 | SPAC1F5.10_UP | GGGTTGTGGGGGTGGGTGC | 3238 | SPAC21E11.06_UP | CGCCCCTCGTCCTCTGCCTA |
| 3137 | SPAC1F5.10_DN | GGAGGTTGAGGGCGGGGGTA | 3239 | SPAC21E11.06_DN | CATTAACGTCTGGCCCGCC |
| 3138 | SPAC1F5.11c_UP | TGGGAGGTCAAGAGCGGCAA | 3240 | SPAC21E11.07_UP | CCTGTAGCGCCGGGTGTTCG |
| 3139 | SPAC1F5.11c_DN | CGCCGGGTGCTACCTCAGT | 3241 | SPAC21E11.07_DN | TCCCTGGCAGCTCTGACGTA |
| 3140 | SPAC1F7.02c_UP | GAACTCATGAGGGAGGGCGG | 3242 | SPAC222.05c_UP | TGACCGCCACCTCGACGTTG |
| 3141 | SPAC1F7.02c_DN | GCCCCGCCGATCGAGTCTCT | 3243 | SPAC222.05c_DN | CGTATGAGCCCGACGTCCCC |
| 3142 | SPAC1F7.03_UP | AGGTGCGACGGGAATTGTGGC | 3244 | SPAC222.06_UP | CCGTCCATCCGCCTTAFCCA |
| 3143 | SPAC1F7.03_DN | TAGCGCCTCCGGTTCCTTGC | 3245 | SPAC222.06_DN | ATTCGTCGGGTGTCGTCGGG |
| 3144 | SPAC1F7.06_UP | TGCCACCAACGAAGCGAATC | 3246 | SPAC222.07c_UP | TCGCGTCGTTCCGTTTGGTA |
| 3145 | SPAC1F7.06_DN | CCGTAATTCCGGACCCCTAA | 3247 | SPAC222.07c_DN | CTGCCCGTATTTTCTCCCG |
| 3146 | SPAC1F7.07c_UP | AGGCTATTGTTGGGCGGGGG | 3248 | SPAC222.08c_UP | ATCCGTGTTAGCCCCCTGCCC |
| 3147 | SPAC1F7.07c_DN | GGGAAAATGGGTTAGGGGCG | 3249 | SPAC222.08c_DN | AATCTTCCFCTTGCGCGGCT |
| 3148 | SPAC1F7.08_UP | ATACCCAACTCCCCCCCGAC | 3250 | SPAC222.09_UP | TGCCCACCTCGTTTCACCACG |
| 3149 | SPAC1F7.08_DN | GCGGCAAGTTAGGAGCGGAA | 3251 | SPAC222.09_DN | AGCGGTTCGGGTGGAGTGAT |
| 3150 | SPAC1F7.09c_UP | AAAGCCCGCAPACCCACCACG | 3252 | SPAC222.10c_UP | TCAACTCTGCGGGCTCCTCG |
| 3151 | SPAC1F7.09c_DN | CCAGCAACACAGCAGCCAA | 3253 | SPAC222.10c_DN | TGCATGACCGCCCAGTTTGG |
| 3152 | SPAC1F7.10_UP | TGGGGAGCCAGAGAAGCGGC | 3254 | SPAC222.12_UP | AACCACCCGAGCACCAGCCT |
| 3153 | SPAC1F7.10_DN | ACCACGTTACCTCCCGCCCC | 3255 | SPAC222.12c_DN | TTACGGGTGGGCGTGTATGC |
| 3154 | SPAC1F7.11c_UP | TGAGCCTTCCGACAATTGCG | 3256 | SPAC222.13c_UP | TGATTGGAGCGCGTCTGGGA |
| 3155 | SPAC1F7.11c_DN | CCCTGCGCCACACATCAAGC | 3257 | SPAC222.13c_DN | CGGCTTTCGCTTCTGGGGTT |
| 3156 | SPAC1F8.01_UP | CCAGCAAGCCTCAAAACGC | 3258 | SPAC222.14c_UP | GACCCACCCGCATCACAACC |
| 3157 | SPAC1F8.01_DN | TGCTCGCTTCGTTCTGCCTG | 3259 | SPAC222.14c_DN | ACAGTCCTGCCGTCTGCGAA |
| 3158 | SPAC1F8.02c_UP | AGATCGCCGCAAGCCAAGGA | 3260 | SPAC227.03c_UP | GGGGCAAGACCAGGATGGGG |
| 3159 | SPAC1F8.02c_DN | TGTGTTCACTCCGAGGCTGC | 3261 | SPAC227.03c_DN | CTCTGGGGTTGGGCCTGGTA |
| 3160 | SPAC1F8.03c_UP | GAATGGGGGTGGGCTTTCAA | 3262 | SPAC227.04_UP | ACCGTCATCACLAACACCGC |
| 3161 | SPAC1F8.03c_DN | GTCGTGGGGGAGATAGGCG | 3263 | SPAC227.04_DN | TCGAGGGCGCGCTTAACACT |
| 3162 | SPAC1F8.04c_UP | ACATGCCCATCGCGGACCGA | 3264 | SPAC227.05_UP | ATTATGGCGGAGCGGGGGT |

FIG.23

| Sequence number | Name | Base sequence |
|---|---|---|
| 3265 | SPAC227.05_DN | CGAACGAAGCATTCCAGGGC |
| 3266 | SPAC227.06_UP | CCGTTACCGCTTTGGCCTGG |
| 3267 | SPAC227.06_DN | GGGCGAGTCGCGGTGCTTGT |
| 3268 | SPAC227.07c_UP | CCCTGCCCGTCACCTCATCG |
| 3269 | SPAC227.07c_DN | GGCAGGGGCTTACGGTCGGT |
| 3270 | SPAC227.08c_UP | TCGCCCCGTACCCTACCACG |
| 3271 | SPAC227.08c_DN | GATTAAAGCGACGCGAGGCC |
| 3272 | SPAC227.09_UP | TAGGGGCGGGGCTTGTGTCC |
| 3273 | SPAC227.09_DN | CAGAAGGATCCGGGCGCAAC |
| 3274 | SPAC227.10_UP | AACACATGTGGCCAACCCCG |
| 3275 | SPAC227.10_DN | CCCGAACACCGCCATAGATG |
| 3276 | SPAC227.11c_UP | ATTTCCCGAGCACCCCTTCC |
| 3277 | SPAC227.11c_DN | TCCTCCTAGCCCGCAACTGG |
| 3278 | SPAC227.12_UP | TTTGTGGCGGAACTATGCG |
| 3279 | SPAC227.12_DN | TCTCGGTGCGGGGGTGTTTC |
| 3280 | SPAC227.13c_UP | CAGGGGCTGTCATCGTCGGG |
| 3281 | SPAC227.13c_DN | TGCTTGTGGGACCCTGCGCT |
| 3282 | SPAC227.15_UP | GCGGCGAATGAAGTGAGGCT |
| 3283 | SPAC227.15_DN | GGGGACTGGTGATGGCGATG |
| 3284 | SPAC227.17c_UP | CGGCGTCGGTGAGGAAGGAT |
| 3285 | SPAC227.17c_DN | AGTCGTCTAGACCGTCGGGT |
| 3286 | SPAC22A12.02c_UP | CGTTGATCCGCCGCTTATGC |
| 3287 | SPAC22A12.02c_DN | CGCTGCTCCTGCCTTCGATG |
| 3288 | SPAC22A12.03c_UP | CTTTTGGCAGGGGACCGGAG |
| 3289 | SPAC22A12.03c_DN | ATGCTTTGGAGGAACGGCA |
| 3290 | SPAC22A12.04c_UP | CCAAFCGGCGTCAATGCTTG |
| 3291 | SPAC22A12.04c_DN | AGGGGCTGGGACGGGGGACA |
| 3292 | SPAC22A12.05_UP | CGAGAACCAAGCGGGTGGGA |
| 3293 | SPAC22A12.05_DN | GGCGGCTGATATGTCGGGAC |
| 3294 | SPAC22A12.06c_UP | CCCGATGTAGCGCCGAGTTC |
| 3295 | SPAC22A12.06c_DN | AGGGCTGCGGGGAAATATCGT |
| 3296 | SPAC22A12.07c_UP | TGTAGACAACGCCGAGCCC |
| 3297 | SPAC22A12.07c_DN | TTTGGGCGAAAGCCACTTG |
| 3298 | SPAC22A12.09c_UP | CGTGCCCCACTCGTCTCCTG |
| 3299 | SPAC22A12.09c_DN | TGTTCCGTTTCGGTTGGCA |
| 3300 | SPAC22A12.10_UP | AGGCCCTCCAGCGAATTAGCG |
| 3301 | SPAC22A12.10_DN | CTCCCCAGCTGTCGTCCCCG |
| 3302 | SPAC22A12.11_UP | TTCCCCCTATTCGCACACGG |
| 3303 | SPAC22A12.11_DN | TTCGGAGTTGGATGGCCGGT |
| 3304 | SPAC22A12.12c_UP | ATCGGCAAGGTCGGTCAGGC |
| 3305 | SPAC22A12.12c_DN | ACACGCAGCGCCCGGTAACT |
| 3306 | SPAC22A12.13_UP | GCCCCTAAGCCTCCATCCCG |
| 3307 | SPAC22A12.13_DN | TAACCCAGGCTCTCGTCCCA |
| 3308 | SPAC22A12.14c_UP | GGGCGTGGTCGGGATGGTAT |
| 3309 | SPAC22A12.14c_DN | TTAGTTTGGGTTGCGGGGC |
| 3310 | SPAC22A12.15c_UP | CAACTAGCGGGGTGGCTCGA |
| 3311 | SPAC22A12.15c_DN | ACTCGCGGGTACTCACGCTT |
| 3312 | SPAC22A12.16_UP | TGCAAATGAGCCCCACGTCG |
| 3313 | SPAC22A12.16_DN | TGCGTTGATGGGGAGGTTGA |
| 3314 | SPAC22A12.17c_UP | TCACCGTCAGTCCCCGCCAC |
| 3315 | SPAC22A12.17c_DN | GGGGTGTGGCGGACGAAATT |
| 3316 | SPAC22E12.01_UP | ACGGGTCTGGTCTTTGCGG |
| 3317 | SPAC22E12.01_DN | CGCTAACATGGGCTCGGGAT |
| 3318 | SPAC22E12.02_UP | AAGCCAAGGAGGGGGTGCCA |
| 3319 | SPAC22E12.02_DN | GCCCATCGATCACCCCTCCAC |
| 3320 | SPAC22E12.03c_UP | CGAGGGGACATGTGGGGGTA |
| 3321 | SPAC22E12.03c_DN | GGACGAGTAGGGGGAGCGCG |
| 3322 | SPAC22E12.04_UP | GTCATCTTCCGTGGGCCCTC |
| 3323 | SPAC22E12.04_DN | ACCGACCCGCCCCCGTTAAT |
| 3324 | SPAC22E12.05c_UP | GGAACCGCAGAACACGTGAC |
| 3325 | SPAC22E12.05c_DN | TGGAGGGCTAGGAGGCGTGG |
| 3326 | SPAC22E12.06c_UP | CCGTTGCCACCGATTTGGGA |
| 3327 | SPAC22E12.06c_DN | GGCTGAAGTGGATGGCGCAA |
| 3328 | SPAC22E12.07_UP | AGCACGCTATTACCCGCCGA |
| 3329 | SPAC22E12.07_DN | TATCCTAGCACGCGGGGGTT |
| 3330 | SPAC22E12.09c_UP | GCAAGCCCGCCAATCAGTCC |
| 3331 | SPAC22E12.09c_DN | TCGTCGCCGTGCCTCATTTC |
| 3332 | SPAC22E12.10c_UP | CCCGCGAAGCTGTTCCTAACC |
| 3333 | SPAC22E12.10c_DN | CATTCACTACCGCCCCCAGG |
| 3334 | SPAC22E12.11c_UP | GAGCGGCCAACGTGCAAAC |
| 3335 | SPAC22E12.11c_DN | GGACGGTGGGATCTTGCGAT |
| 3336 | SPAC22E12.13c_UP | TGCAATACCGGCCGAAAGGA |
| 3337 | SPAC22E12.13c_DN | CCCGGGGTTGCGAAAGTTGA |
| 3338 | SPAC22E12.14c_UP | CCCGAACTGACAAAGGGCCG |
| 3339 | SPAC22E12.14c_DN | GTACTAGGCCCCCCGTTGCC |
| 3340 | SPAC22E12.16c_UP | AACGCGGAAATTTGGGGCTC |
| 3341 | SPAC22E12.16c_DN | TGTGTGGGGTATCCGAGGCG |
| 3342 | SPAC22E12.17c_UP | TCACGCCGGTAAGCGACAGT |
| 3343 | SPAC22E12.17c_DN | ACGGCTATACCCCCATCGCC |
| 3344 | SPAC22E12.18_UP | TGCGTCCCCTTCAGCTCGTC |
| 3345 | SPAC22E12.18_DN | GTCCAACAGGGCCGAAGCAT |
| 3346 | SPAC22F3.02_UP | TTACGTAGTCCATGCCGGGG |
| 3347 | SPAC22F3.02_DN | TCCACATTCGCAAAGCCACG |
| 3348 | SPAC22F3.03c_UP | AAGAGCGCAGAGCGAGCCAG |
| 3349 | SPAC22F3.03c_DN | TGCCGCGTAAATTCCCATG |
| 3350 | SPAC22F3.04_UP | CAGGCACGAAACCGCAAGGA |
| 3351 | SPAC22F3.04_DN | ACGAAAAGCCCGGCATCGTCA |
| 3352 | SPAC22F3.06c_UP | AGGACGCACCAACCGACGAT |
| 3353 | SPAC22F3.06c_DN | TAGAACCCATCGCAAGCGCA |
| 3354 | SPAC22F3.07c_UP | GCGATGTTTGAGATGGGCGT |
| 3355 | SPAC22F3.07c_DN | GAGAGAGCCGACTGCGGGTGG |
| 3356 | SPAC22F3.08c_UP | CGGCTTCCAGCAAACTCCCA |
| 3357 | SPAC22F3.08c_DN | AAACCTAGGGGGAATGCGGG |
| 3358 | SPAC22F3.09_UP | TTGCGCCTTGACCTACCCGG |
| 3359 | SPAC22F3.09c_DN | TCCTTGGTACGGGGTGGCTC |
| 3360 | SPAC22F3.10c_UP | TGGCAACGCGGCGGATTGTAG |
| 3361 | SPAC22F3.10c_DN | ACACTACCGCACGCAACCC |
| 3362 | SPAC22F3.11c_UP | GCGTGATCAAGGAGGCGGTG |
| 3363 | SPAC22F3.11c_DN | GCCGTGAAGGATTGGGAGGT |
| 3364 | SPAC22F3.12c_UP | GTGGTGGGGGAGATGAGGGG |
| 3365 | SPAC22F3.12c_DN | CCGTCAACAATCACGCAGCA |
| 3366 | SPAC22F3.13_UP | TCGTTCGCCCCCCATCCTAG |
| 3367 | SPAC22F3.13_DN | ACGCCTGCCATTCCCCATTT |
| 3368 | SPAC22F8.02c_UP | CCCGCAAGCAACCAGACACG |
| 3369 | SPAC22F8.02c_DN | ACACACCCACTCCGCAGCAA |
| 3370 | SPAC22F8.03c_UP | CATCCCCGATCAGTTTGGC |
| 3371 | SPAC22F8.03c_DN | ATTCCGACCCCGAGCCGTTA |
| 3372 | SPAC22F8.04_UP | CAAACCGCGGAGACAGGAA |
| 3373 | SPAC22F8.04_DN | TGGGCGGGTACATGGGAGAT |
| 3374 | SPAC22F8.05_UP | TGGAGCGAGCGGAGACGGAG |
| 3375 | SPAC22F8.05_DN | CCGCCCACCGTAAAGCAATC |
| 3376 | SPAC22F8.07c_UP | GCAAGCCAGCCACATCACCA |
| 3377 | SPAC22F8.07c_DN | TCCGTGCTACACCTATGGCG |
| 3378 | SPAC22F8.09_UP | CAGGCGAGGGACGTTGGGGT |
| 3379 | SPAC22F9.09_DN | TCGGTGCGGAGGGCTTTGAG |
| 3380 | SPAC22F9.11_UP | AAGTAAGGCTCCGTCGGGCA |
| 3381 | SPAC22F8.11_DN | CGCGTGGATGGGGTCAAAAG |
| 3382 | SPAC22G7.01c_UP | AGGGATCGGGTGCTACGGCT |
| 3383 | SPAC22G7.01c_DN | GGGCCGTGGTCGTGAGTGTG |
| 3384 | SPAC22G7.02_UP | CACCGGGTCCGTTCGAATCT |
| 3385 | SPAC22G7.02_DN | TAGGAGCCCGGTCACTGCTA |
| 3386 | SPAC22G7.03_UP | CAGGCAAGGCGGGACGATTA |
| 3387 | SPAC22G7.03_DN | GTGTCCCCGACGATAAGACG |
| 3388 | SPAC22G7.04_UP | TGAAATACCGGCAGCCACGC |
| 3389 | SPAC22G7.04_DN | TGTGCGGCTCCCTGTGGCTGG |
| 3390 | SPAC22G7.05_UP | TTTCTTCTTTGGGCGGGCA |
| 3391 | SPAC22G7.05_DN | GGGCTTCGGGTGCTCGTTTA |
| 3392 | SPAC22G7.06c_UP | ACGCGCGATGCCAGATATG |
| 3393 | SPAC22G7.06c_DN | GCAATGGGCACGGGAACAAA |
| 3394 | SPAC22G7.07c_UP | TCCAATGCAGTCCCCGTTT |
| 3395 | SPAC22G7.07c_DN | GATGGAATGCGGGGAATGA |
| 3396 | SPAC22G7.08_UP | ACGCCCAAGGTCAAAGGCCA |
| 3397 | SPAC22G7.08_DN | CGTGCAAGCCAGGTCCAAAA |
| 3398 | SPAC22G7.09c_UP | ACGTGAGCGTACGTGCGAAT |
| 3399 | SPAC22G7.09c_DN | CCTAGCGCATATAGCCGCA |
| 3400 | SPAC22G7.10_UP | TTGACGGCCGGCAGGTATTT |
| 3401 | SPAC22G7.10_DN | TACCACCAGCGCGCACACCT |
| 3402 | SPAC22H10.03c_UP | TGAGCGCGAAGTGTGGGAGT |
| 3403 | SPAC22H10.03c_DN | TCCCCCCTACCGACCGCCTC |
| 3404 | SPAC22H10.04_UP | AGCGCCGTGTGATTTGGACA |
| 3405 | SPAC22H10.04_DN | CCCACTGCATTAGCGCACC |
| 3406 | SPAC22H10.05c_UP | GCGCGTGGGAATAAAAGGCG |
| 3407 | SPAC22H10.05c_DN | CAGGGATCGGCATAACGGCG |
| 3408 | SPAC22H10.06c_UP | CGGGGGGGCTGTCCTAATTT |
| 3409 | SPAC22H10.06c_DN | AAATTAATGGGGGTCGTGCG |
| 3410 | SPAC22H10.07_UP | CCTCCTGGCCGCTGAATCCA |
| 3411 | SPAC22H10.07_DN | TCCCGCCCGGTAATCAGTGG |
| 3412 | SPAC22H10.08_UP | ACAACAAAATGCACCACCCG |
| 3413 | SPAC22H10.08_DN | CGAACGCGGCACCAGAATAG |
| 3414 | SPAC22H10.09_UP | CGCATCCCGCTTCCCCAGAG |
| 3415 | SPAC22H10.09_DN | AAGCCGCCCTACAAACCCCS |
| 3416 | SPAC22H10.10_UP | CTGCCCCGACCGCCCGTCTTA |
| 3417 | SPAC22H10.10_DN | CGAGAAACCTGCCAACCCGC |
| 3418 | SPAC22H10.11c_UP | TACGGCTGGCCGGTTGAGG |
| 3419 | SPAC22H10.11c_DN | GGTTTGGATGGGCCGGTCTG |
| 3420 | SPAC22H10.13_UP | GCGCATGGTTGGGTTGGGAC |
| 3421 | SPAC22H10.13_DN | CGGACCCTTCTTACCCCCGA |
| 3422 | SPAC22H12.02_UP | TAGGTTGGCGCAAAGGGCTC |
| 3423 | SPAC22H12.02_DN | ATGCGTTCTCCAATGCGGTG |
| 3424 | SPAC22H12.03_UP | GCTGACGCGGATTGGACTGG |
| 3425 | SPAC22H12.03_DN | CAGGTTGTCGCGCGGGTCAG |
| 3426 | SPAC22H12.04c_UP | TCTGTGCTACCGGGGGGAA |
| 3427 | SPAC22H12.04c_DN | ACCCTAACAAACGGCCCGG |
| 3428 | SPAC22H12.05c_UP | TGCCACACCCATCTCGCGT |
| 3429 | SPAC22H12.05c_DN | CTTCACCCGCCCGCATCAAA |
| 3430 | SPAC23A1.02c_UP | TTCTCGCTCCTACGCACCAG |
| 3431 | SPAC23A1.02c_DN | CAGCAATGAGCAAGCCCCGT |
| 3432 | SPAC23A1.04c_UP | GAACGCAGGGAGAATGGGCA |
| 3433 | SPAC23A1.04c_DN | CGTAACTAGACGTGCCGGCG |
| 3434 | SPAC23A1.06c_UP | ATTCAGGTGCGGCCCAAGCA |
| 3435 | SPAC23A1.06c_DN | TCTCACCGCGCGGAACATCT |
| 3436 | SPAC23A1.07_UP | TTGCACTCCAGCACCATCCC |
| 3437 | SPAC23A1.07_DN | GCTTGACCGCGATTTCCCG |
| 3438 | SPAC23A1.08c_UP | ACGGCGCTGTTCGTACCATG |
| 3439 | SPAC23A1.08c_DN | GCCAAACGCATCAGGCATCC |
| 3440 | SPAC23A1.09_UP | GTGCGGCTATACCTGGGATG |
| 3441 | SPAC23A1.09_DN | TAGTCGCCACGGTGAGAGGC |
| 3442 | SPAC23A1.12c_UP | TCCAGTACTTCGCTTGCTAC |
| 3443 | SPAC23A1.12c_DN | TGCCGTGCCCCAGATAGTCC |
| 3444 | SPAC23A1.14c_UP | CATGCTCTTGTCGTGGGCCG |
| 3445 | SPAC23A1.14c_DN | TGTTGGCCCTCCCCTGTCAT |
| 3446 | SPAC23A1.15c_UP | CCCCCCCTAGAAIAACCCCG |
| 3447 | SPAC23A1.15c_DN | ACCTTGGTTACGCGGTCGCT |
| 3448 | SPAC23A1.16c_UP | TAGCACATGCGGGGGGTTG |
| 3449 | SPAC23A1.16c_DN | TACCCGGAACGCGACTGCAC |
| 3450 | SPAC23A1.17_UP | TGGTTGGGCGTTCGGGAGTA |
| 3451 | SPAC23A1.17_DN | GCCTGCTTATTCGGGCCAAG |
| 3452 | SPAC23C11.01c_UP | GGGCCTCCGAAAATCTGCTG |
| 3453 | SPAC23C11.01c_DN | CGGGCAACCAGCAGAAGCAG |
| 3454 | SPAC23C11.02c_UP | CCCAATCAGTTTCGTGCCA |
| 3455 | SPAC23C11.02c_DN | CAGGCCGTAGCCCAACCATG |
| 3456 | SPAC23C11.03_UP | CGGGGAACAGCTGAGTTGGA |
| 3457 | SPAC23C11.03_DN | CTGATTCGATACCGGCGGC |
| 3458 | SPAC23C11.04c_UP | AGTGACACGGATGAGGGCGG |
| 3459 | SPAC23C11.04c_DN | GGGACCCACCCATTGTCTG |
| 3460 | SPAC23C11.05_UP | CCCTCCCGCACAAGCAAGGT |
| 3461 | SPAC23C11.05_DN | TCCTCCTTTCGCTTCCCACG |
| 3462 | SPAC23C11.06c_UP | AAATCCCCCACGCCCAGAAC |
| 3463 | SPAC23C11.06c_DN | TGCGTTTGATGACCCCCGA |
| 3464 | SPAC23C11.07_UP | GGTATGGCTTTTCCCGGCGT |
| 3465 | SPAC23C11.07_DN | TTCCATGCTCTTCCGCGCTCC |
| 3466 | SPAC23C11.10_UP | AATGAAACGGGAAGCTGCGG |
| 3467 | SPAC23C11.10_DN | CACGCGGGATGAATAAGGC |
| 3468 | SPAC23C11.11_UP | GCAGGTTGCTACAGAGTGCG |

| Sequence number | Name | Base sequence |
|---|---|---|
| 3673 | SPAC25B8.08_DN | CCCCCAGCGGACTCAAAGA |
| 3674 | SPAC25B8.09_UP | CAATCGTATCCGCCTTCCGC |
| 3675 | SPAC25B8.09_DN | ACCATTGCCACCGCCGTTCCG |
| 3676 | SPAC25B8.10_UP | TGCTTCGTACGCGCTAGCCT |
| 3677 | SPAC25B8.10_DN | GAAGAACCGGTCGTCGCTTG |
| 3678 | SPAC25B8.11_UP | AGGCTCACCCGAACGCGAAT |
| 3679 | SPAC25B8.11_DN | ATTCTACGTAGCGGGGCCGG |
| 3680 | SPAC25B8.12c_UP | CCGCAGCAACAACAGCCATC |
| 3681 | SPAC25B8.12c_DN | CCCCGAAGGCAGCAGGATGA |
| 3682 | SPAC25B8.13c_UP | GTGCCATACACAAGACGGGC |
| 3683 | SPAC25B8.13c_DN | AAGCTAGTGACCGGCCCCCA |
| 3684 | SPAC25B8.14_UP | TCGATGGTCACGCCACTTGT |
| 3685 | SPAC25B8.14_DN | GTAGGTTTCGGCTCCGGGAA |
| 3686 | SPAC25B8.15c_UP | CTGAGAAGTATGCCGCGGGA |
| 3687 | SPAC25B8.15c_DN | ACCGTTTCGCGCATTCTTGC |
| 3688 | SPAC25B8.16_UP | TCAATAAGGTCCCGGCCCCC |
| 3689 | SPAC25B8.16_DN | CCCCCTCCTGCCGAACAATC |
| 3690 | SPAC25B8.17_UP | AGGCAGCGACACATCACCGG |
| 3691 | SPAC25B8.17_DN | TTTTCGTCTCTGGGGGGTGC |
| 3692 | SPAC25B8.18_UP | TATTGACTGCCCGCTGCCGG |
| 3693 | SPAC25B8.18_DN | CCCCGCATCCAGGCCACATA |
| 3694 | SPAC25G10.02_UP | CCATGTTCCACCCCCCTGCG |
| 3695 | SPAC25G10.02_DN | CGATGGGTTGGACGAGCAGT |
| 3696 | SPAC25G10.03_UP | GACCCGGAAAGCGTCTGTGC |
| 3697 | SPAC25G10.03_DN | CGGGTCGCTCTTCAGGTGCA |
| 3698 | SPAC25G10.04c_UP | ACAACGACCTGACCCACGCA |
| 3699 | SPAC25G10.04c_DN | AACACAGGCACCACGGTAGG |
| 3700 | SPAC25G10.05c_UP | GCGTGAGGATGTGGAGCGGA |
| 3701 | SPAC25G10.05c_DN | TCCCGGCGAGCAAACACACA |
| 3702 | SPAC25G10.07c_UP | CTGCAACCACACAAACGCTG |
| 3703 | SPAC25G10.07c_DN | ACAAGGGGTAAATCGGGGGG |
| 3704 | SPAC25G10.08_UP | GCTGACCCGTTCTTTGCCCG |
| 3705 | SPAC25G10.08_DN | CCTCAAGCGCGTGTCCCATA |
| 3706 | SPAC25H1.02_UP | CGTGGGCGGCAGGTACGTTT |
| 3707 | SPAC25H1.02_DN | GCCGCCGCAAATCAGCTCTA |
| 3708 | SPAC25H1.03_UP | CGGGCCGGCTAAGATGGTCAA |
| 3709 | SPAC25H1.03_DN | CACGGCCTGGCCATTCGTTGA |
| 3710 | SPAC25H1.04_UP | CGAACCTGCGGCCCACAATCA |
| 3711 | SPAC25H1.04_DN | GCCCCAAAATGCATAGCCCA |
| 3712 | SPAC25H1.05_UP | CATGCACGTGGCGACTCATC |
| 3713 | SPAC25H1.05_DN | AAATTCCCACCGTATCGCCG |
| 3714 | SPAC25H1.06_UP | TGCGATGACAGGTTGGGGAG |
| 3715 | SPAC25H1.06_DN | AGCATGTACCGCGTTTGGGG |
| 3716 | SPAC25H1.07_UP | TGCTCGTGGGCTGGACTGGA |
| 3717 | SPAC25H1.07_DN | TAACCCAGCGCGCCCTAACCT |
| 3718 | SPAC25H1.08c_UP | CGGGCTCGGACTGCAGGAAG |
| 3719 | SPAC25H1.08c_DN | CGGTGCCCCAGTAAAAAGGC |
| 3720 | SPAC25H1.09_UP | TTCTTTCCCGCCCCACCGAT |
| 3721 | SPAC25H1.09_DN | TCCTTCGCCACCACCACCAA |
| 3722 | SPAC26A3.01_UP | CATCAGTCGAACCGCAGGCGG |
| 3723 | SPAC26A3.01_DN | GACAGGGCACCGATGACACG |
| 3724 | SPAC26A3.02_UP | CACCCAACCAACATCGCAA |
| 3725 | SPAC26A3.02_DN | AGGGCCGGACAGGGTGAGT |
| 3726 | SPAC26A3.03c_UP | CGTAGGGTAAGGATGCCGCC |
| 3727 | SPAC26A3.03c_DN | TTACCCCGCGTGTTGTGCA |
| 3728 | SPAC26A3.04_UP | GCAAAACTCCGGCTGCAGCT |
| 3729 | SPAC26A3.04_DN | GCGACAAAAACCGCCTCGGA |
| 3730 | SPAC26A3.05_UP | GAACCCACCCCCAGCACAAG |
| 3731 | SPAC26A3.05_DN | TCAACCCGACACACTCCCCG |
| 3732 | SPAC26A3.06_UP | CGGGGGGGTTAACTGAGGTG |
| 3733 | SPAC26A3.06_DN | TGCCCGATAACCGCTCCCGT |
| 3734 | SPAC26A3.08_UP | CCACACCTGCCGATTCCTCG |
| 3735 | SPAC26A3.08_DN | CATACACCCGACTTGCCCGA |
| 3736 | SPAC26A3.09c_UP | CATCCGTGCCCGTTGGTTGCT |
| 3737 | SPAC26A3.09c_DN | CGCCGACCGATACACAACGC |
| 3738 | SPAC26A3.10_UP | ACCGAGGGCTTGGGGACACC |
| 3739 | SPAC26A3.10_DN | CCGACCCCACGATGGAAAAT |
| 3740 | SPAC26A3.11_UP | ATTCTTTGGCTGCGAGGCG |
| 3741 | SPAC26A3.11_DN | CGCCACCTCCAGCCGAAACT |
| 3742 | SPAC26A3.12c_UP | GCACTGGCGTGTAAGCAGAC |
| 3743 | SPAC26A3.12c_DN | ACTTGGAGTGCCCCGAAGAG |
| 3744 | SPAC26A3.13c_UP | AAAGCGGGGCAGGACTACGG |
| 3745 | SPAC26A3.13c_DN | CGCAGGGTGAGGGGAGGAGG |
| 3746 | SPAC26A3.14c_UP | CGGCACCCGGGGGATAAGTC |
| 3747 | SPAC26A3.14c_DN | CACTCCGCACCTCCGTTCAC |
| 3748 | SPAC26A3.15c_UP | GAATCGGGAAGGGCGGAAA |
| 3749 | SPAC26A3.15c_DN | TGGGCAGGCGGTAGGGGTTC |
| 3750 | SPAC26A3.16_UP | CAGCCCCTAACGAAGCCACC |
| 3751 | SPAC26A3.16_DN | TCCCCACCCCTCAGTCCAAG |
| 3752 | SPAC26F1.02_UP | CCAGGTGCGCGGGTTGACAT |
| 3753 | SPAC26F1.02_DN | AATACGTTCCGGCGACCCCT |
| 3754 | SPAC26F1.03_UP | CCAAGGGGGCGGATTCAACA |
| 3755 | SPAC26F1.03_DN | TGGGCCTTTTCCGGTCTGGG |
| 3756 | SPAC26F1.04c_UP | GTTGCGGCGTCTTCGTCTCG |
| 3757 | SPAC26F1.04c_DN | CCTACCGCGATTGGCCAGTT |
| 3758 | SPAC26F1.05_UP | CGGGCACCGACTGTAGTGTT |
| 3759 | SPAC26F1.05_DN | GCGCAGGGCCAAAACATTCT |
| 3760 | SPAC26F1.07_UP | AGCGCGCGAGGCAAAAAGTG |
| 3761 | SPAC26F1.07_DN | GTCGTGGAGGTGCCGTGAAG |
| 3762 | SPAC26F1.08c_UP | TGGCATGCGGGGAACTTTC |
| 3763 | SPAC26F1.08c_DN | GCCCTCTTGGCGGGATCAATC |
| 3764 | SPAC26F1.09_UP | CAGCGTGCGGCCTCAATCTA |
| 3765 | SPAC26F1.09_DN | GGCCAAACCGCACTCACATT |
| 3766 | SPAC26F1.10c_UP | TGGGTAGCGTGTGTGGCGTT |
| 3767 | SPAC26F1.10c_DN | CCACCTCCCGCACGACTTCA |
| 3768 | SPAC26F1.11_UP | CAGGGTGTGAGCCTAATCGAA |
| 3769 | SPAC26F1.11_DN | AGGGCGGACTTCTTGGGCTA |
| 3770 | SPAC26H5.02c_UP | CACCACGACCGAACCACGCA |
| 3771 | SPAC26H5.02c_DN | TCCCCTCGTGTTTGCTTGCG |
| 3772 | SPAC26H5.03_UP | TCGGAAAGCGGCGGTGAATA |
| 3773 | SPAC26H5.03_DN | ATCAACCCCGCTCAGGCGAA |
| 3774 | SPAC26H5.04_UP | AACGGAAAGAAACGCGACGG |
| 3775 | SPAC26H5.04_DN | GCTCGCTACTGCCCTCTCGC |
| 3776 | SPAC26H5.05_UP | TTGCCATCCAGTCGATCCGG |
| 3777 | SPAC26H5.05_DN | TCCTCGCCAGCCTCCTGAAC |
| 3778 | SPAC26H5.06_UP | AGGCAACCGGCGAGCATCAC |
| 3779 | SPAC26H5.06_DN | TGCGGACCATAAGCGGGTTG |
| 3780 | SPAC26H5.07c_UP | ATACGGCAGATGCGTACCCG |
| 3781 | SPAC26H5.07c_DN | GGTGCATTGGCGTTAGGGGG |
| 3782 | SPAC26H5.08c_UP | CCCGGCGTCAACTTTTCCTG |
| 3783 | SPAC26H5.08c_DN | CGACCCCTAAGATGACGCG |
| 3784 | SPAC26H5.09c_UP | AAACGCCCCTCACTTCCCG |
| 3785 | SPAC26H5.09c_DN | AGAATTTGAAGCGCGGGACG |
| 3786 | SPAC26H5.10c_UP | CCACTCGCACGAGTCCTCCA |
| 3787 | SPAC26H5.10c_DN | GCAAAGGCGCATCACCTCAG |
| 3788 | SPAC26H5.11_UP | GCCAAGTCAAACCGCCGTCC |
| 3789 | SPAC26H5.11_DN | TTACCTCCGTGACCTGCCCC |
| 3790 | SPAC26H5.13c_UP | AAACCATSCGGCCTCAACCC |
| 3791 | SPAC26H5.13c_DN | CCCCGGACACCTACGAGCCC |
| 3792 | SPAC27D7.02c_UP | TGGACTGAACCGATCGCTCG |
| 3793 | SPAC27D7.02c_DN | AAAGCCGGCGCCTAATGAACG |
| 3794 | SPAC27D7.03_UP | AGGACTGTGCCGGGAGTGGT |
| 3795 | SPAC27D7.03c_DN | CCCTCACCACCGCCGTAATG |
| 3796 | SPAC27D7.04_UP | AGGAGGTGGGGCGAGACATG |
| 3797 | SPAC27D7.04_DN | TGCCCGCACATACCCTCACA |
| 3798 | SPAC27D7.05c_UP | CGTTCGTCCCTTAGCGCTCG |
| 3799 | SPAC27D7.05c_DN | GCCCGGCCTCAGCAACACAC |
| 3800 | SPAC27D7.06_UP | CCGGCAAGCATTGGATGGTG |
| 3801 | SPAC27D7.06_DN | AGAGGGCTCCGGTTGAAGGG |
| 3802 | SPAC27D7.07c_UP | GCGTGGGGGAGTTTGGCATT |
| 3803 | SPAC27D7.07c_DN | CTAAAGCCACCAACCCCCGC |
| 3804 | SPAC27D7.08c_UP | AGCTTATTCGCACCCTCCCC |
| 3805 | SPAC27D7.08c_DN | GCCCATTCGTCCTTGCAATC |
| 3806 | SPAC27D7.09c_UP | CGCACGAACTAACGCCCCCA |
| 3807 | SPAC27D7.09c_DN | CCAGTTCGGGGGCTTATC |
| 3808 | SPAC27D7.10c_UP | GTTAATCGGGCAGACGGGGA |
| 3809 | SPAC27D7.10c_DN | ACCGGTTCTCCGTCTGCCAA |
| 3810 | SPAC27D7.11c_UP | GGAGCCGCACCCCATTAAGG |
| 3811 | SPAC27D7.11c_DN | CGGCCACGAGGGAAAAACGG |
| 3812 | SPAC27D7.12c_UP | GGGGTACCAGGCAGCGATTC |
| 3813 | SPAC27D7.12c_DN | ATGCGGGCAGGGAAAAAGCAG |
| 3814 | SPAC27E2.01_UP | TTCGGCAACTGTCGGAGCAC |
| 3815 | SPAC27E2.01_DN | ATAGCCACGGCTCACTAGGC |
| 3816 | SPAC27E2.02_UP | CCATCTGCGGCCTTCCAACA |
| 3817 | SPAC27E2.02_DN | ACGGCCGCGCTGACAACTAT |
| 3818 | SPAC27E2.03_UP | CACGCAATCCCTGAGTCCGA |
| 3819 | SPAC27E2.03c_DN | CTTCGCGGAGGTGTTAGGTA |
| 3820 | SPAC27E2.04c_UP | TTTAGTCCCGCCAACGTCCG |
| 3821 | SPAC27E2.04c_DN | AATCAGCCGTGACCCGTAGC |
| 3822 | SPAC27E2.05_UP | CAGCGTGGTTTTCGGCGGTC |
| 3823 | SPAC27E2.05_DN | TTGTCTCCCGCCCCCATTT |
| 3824 | SPAC27E2.06c_UP | AACGGGCGGCGAGACACTCA |
| 3825 | SPAC27E2.06c_DN | TGCCGGGTTGGTGCTTGGTC |
| 3826 | SPAC27E2.07_UP | GTGAGTCTGGTGTGTTGCGG |
| 3827 | SPAC27E2.07_DN | TGCCTCTCCTGCCTCACCCC |
| 3828 | SPAC27E2.09_UP | GCGGCCGACGAAACCGTTAGC |
| 3829 | SPAC27E2.09_DN | AGGGCAGGCACGACGAGA2G |
| 3830 | SPAC27F1.03c_UP | GCCCCCGTCTGTCCGATAAA |
| 3831 | SPAC27F1.03c_DN | GGACATCGATGCGGGCGTGG |
| 3832 | SPAC27F1.04c_UP | GTTCGCAGGTGGGCTTCGCT |
| 3833 | SPAC27F1.04c_DN | CCCCATAACAAGGCGAAGCC |
| 3834 | SPAC27F1.05c_UP | AACCGGATACGCTGTCGCGGG |
| 3835 | SPAC27F1.05c_DN | CTGCAAACGCGGGCTAACA |
| 3836 | SPAC27F1.06c_UP | GGCAAAAGATCGCACACAGG |
| 3837 | SPAC27F1.06c_DN | TGCCCTTGCCGTCATCTCTGA |
| 3838 | SPAC27F1.07_UP | GATAGCGGAATTGCGCAGGG |
| 3839 | SPAC27F1.07_DN | ACCCGTTGGCGGAAGAGTCA |
| 3840 | SPAC27F1.08_UP | CGCACGCCCCAGTCAAGAAC |
| 3841 | SPAC27F1.08_DN | GGGGCAAGAGGGGTTAGGGC |
| 3842 | SPAC27F1.09c_UP | TGTGTGAGGGTGGGTGCGGA |
| 3843 | SPAC27F1.09c_DN | ACTTTGCCCCACGACCGAAA |
| 3844 | SPAC27F1.10_UP | GTTCGCCATGTGACAGCTCC |
| 3845 | SPAC27F1.10_DN | CGCGCTCAGCCTAGAGTACA |
| 3846 | SPAC29A4.02c_UP | ATGCGCACCTAGGTCAGTCC |
| 3847 | SPAC29A4.02c_DN | AACGGTCGGTCCCGGGATTTT |
| 3848 | SPAC29A4.03c_UP | GCCATGGGGAGCCGGGAATA |
| 3849 | SPAC29A4.03c_DN | GCCGGTGTTTGCAGGATGGC |
| 3850 | SPAC29A4.04c_UP | CATGCGCCAACCCTCTGTGT |
| 3851 | SPAC29A4.04c_DN | CGCGGGAACAAAGCCTGCAT |
| 3852 | SPAC29A4.05_UP | AACCCACCCACCACAAGGCA |
| 3853 | SPAC29A4.05_DN | AACGAAGTGGCGAGGCGAGA |
| 3854 | SPAC29A4.07_UP | ATCCGTTCGCTGCCCAACTT |
| 3855 | SPAC29A4.07_DN | AAAATGCCGGCAAGACGGTT |
| 3856 | SPAC29A4.08c_UP | GACAATCGCGAGGGAAACGG |
| 3857 | SPAC29A4.08c_DN | TGGTGGGTTGACGTCGAGCG |
| 3858 | SPAC29A4.09_UP | CCTAGGCCGGCGTTCTTGCT |
| 3859 | SPAC29A4.09_DN | TGCCTTGGCGTAGGTGTCGG |
| 3860 | SPAC29A4.10_UP | ACTCTGACCGCCCCCGACTT |
| 3861 | SPAC29A4.10_DN | TCGTCCAGAGTTCACCGCCC |
| 3862 | SPAC29A4.11_UP | TCAGATCGGGGAACGAGGCT |
| 3863 | SPAC29A4.11_DN | TGCTGTGGGGACGTACTCCA |
| 3864 | SPAC29A4.12c_UP | CCGCACCCATACAACGCCCT |
| 3865 | SPAC29A4.12c_DN | TCCCACAATCCGACACGCCC |
| 3866 | SPAC29A4.13_UP | CTACGCGCGCAAGGATGGAT |
| 3867 | SPAC29A4.13_DN | TCGCCGCAAATCGTCCTTGA |
| 3868 | SPAC29A4.15_UP | CCAGTCCACCACCGCAGGAA |
| 3869 | SPAC29A4.16_UP | TGGACAACCTACCGCAGCGC |
| 3870 | SPAC29A4.19_UP | GCCCCTCAAACCACGATCGC |
| 3871 | SPAC29A4.19_DN | TATCCCCGCCCCTCGTCCCAT |
| 3872 | SPAC29A4.19c_UP | GCAGATGGAGGAACGAGGGG |
| 3873 | SPAC29A4.19c_DN | AGCAGGTCTAACCGGTCCGT |
| 3874 | SPAC29A4.20_UP | CCTGTATTGCGCGTTCCGGG |
| 3875 | SPAC29A4.20_DN | AACCACGCGATCCACCAACG |
| 3876 | SPAC29B12.02c_UP | ACGCCTAGACCCTCGCCAC |

FIG.26

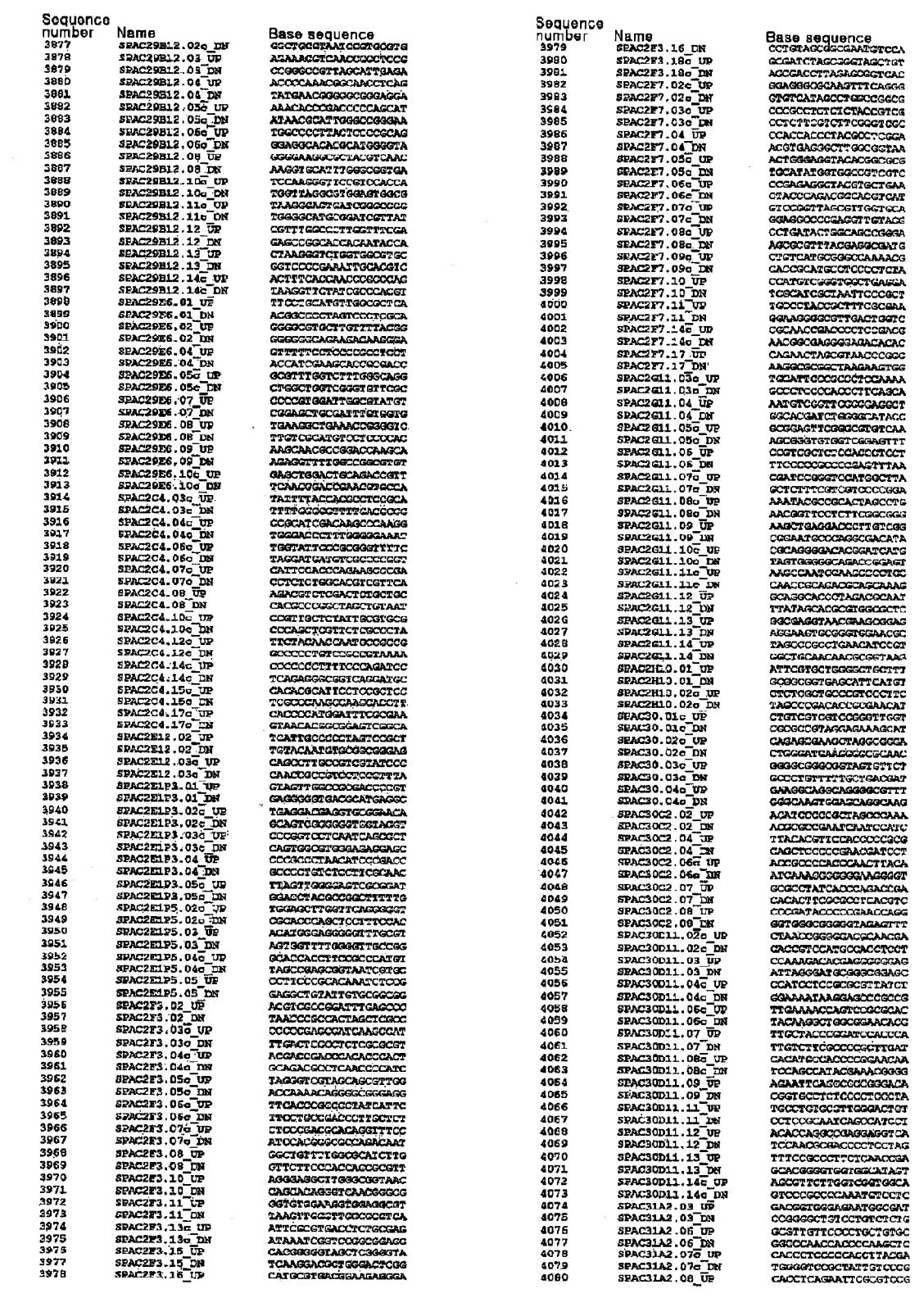

This figure is a large table of DNA sequence data that is too small and low-resolution to transcribe reliably.

FIG.27

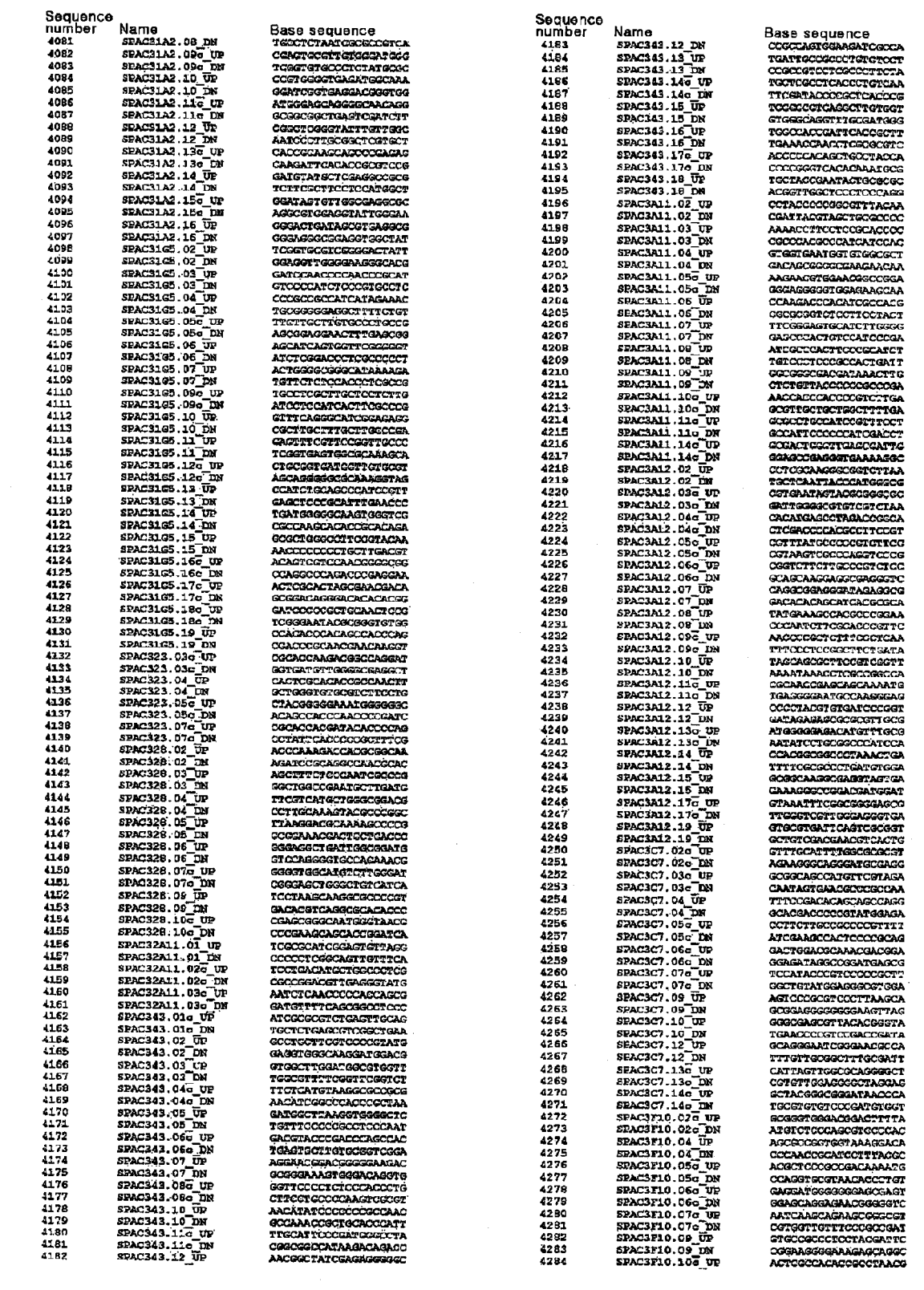

This page consists of a large table of DNA sequence data that is too dense and low-resolution to transcribe reliably.

| Sequence number | Name | Base sequence |
|---|---|---|
| 4489 | SPAC4F8.06_DN | ATCCCACCTTAGCCCCCCGGC |
| 4490 | SPAC4F8.08_UP | ACAACACGACGCCGCCAGAA |
| 4491 | SPAC4F8.08_DN | CTAGCTTGCGCCGGTTTGG |
| 4492 | SPAC4F8.10c_UP | GGCAACGATCCACGAGCCG |
| 4493 | SPAC4F8.10c_DN | GTTTACCGAACCCCCACGGC |
| 4494 | SPAC4F8.11_UP | ATGCAGTTGGTCCTCGGCAG |
| 4495 | SPAC4F8.11_DN | AAGCCGCTCGACGATCACTC |
| 4496 | SPAC4F8.12c_UP | CGTGCGACTTAGTTCCCGGT |
| 4497 | SPAC4F8.12c_DN | TGGAGCTTTCGCCGCTACAA |
| 4498 | SPAC4F8.13c_UP | ATAGTTTCGACCCGCCGCCG |
| 4499 | SPAC4F8.13c_DN | GGGCCCTTTCACTTGCGATA |
| 4500 | SPAC4G8.03c_UP | ATACGGGGGAGTGGGTGCGA |
| 4501 | SPAC4G8.03c_DN | AGCAAAAGCGGAAAGAGGGG |
| 4502 | SPAC4G8.04_UP | ACCCCCATGTAGCCCGCAGT |
| 4503 | SPAC4G8.04_DN | CCACGGGGCTTGCATCACAA |
| 4504 | SPAC4G8.05_UP | GCAACCAATCGGCTACGGCG |
| 4505 | SPAC4G8.05_DN | ACTCCGGTTAGACTCCTGGC |
| 4506 | SPAC4G8.06c_UP | GCCCCTTGTCTGGTCCGGTG |
| 4507 | SPAC4G8.06c_DN | CACCCTCCCTCGTCTGCTCG |
| 4508 | SPAC4G8.07c_UP | ATTCCAGCAGGGGGTGGGTT |
| 4509 | SPAC4G8.07c_DN | CCCCCCCCGAGAAACCACTA |
| 4510 | SPAC4G8.08_UP | CAACTGCCACAACCCCCCA |
| 4511 | SPAC4G8.08_DN | GGGGCCGGAAGGGATATTGT |
| 4512 | SPAC4G8.09_UP | AGCTACCCTCCGGGGCAATA |
| 4513 | SPAC4G8.09_DN | TGGTCTGACGGCGTCGATGA |
| 4514 | SPAC4G8.10_UP | TGGACGTAACGCGGCTACAA |
| 4515 | SPAC4G8.10_DN | ACACTCGCGGCTGAGTACAA |
| 4516 | SPAC4G8.11c_UP | TTATGGCTCCCACGGCGGTG |
| 4517 | SPAC4G8.11c_DN | CGATCAAGGGTCGTACCGGC |
| 4518 | SPAC4G8.12c_UP | GACGATGGTAGCCCGGTCAT |
| 4519 | SPAC4G8.12c_DN | AGCTCCCACCCCTGTCCATG |
| 4520 | SPAC4G8.13c_UP | CTACAAGAGCGGCGACCCGT |
| 4521 | SPAC4G8.13c_DN | TCAAATCGCTCTTCCGCGCA |
| 4522 | SPAC4G9.02_UP | CGCGGCATAAAACGGCCATA |
| 4523 | SPAC4G9.02_DN | TGCATCCGAACAGAAGGATA |
| 4524 | SPAC4G9.04c_UP | CGGTATCGTCCCGCTTCTGG |
| 4525 | SPAC4G9.04c_DN | CGCTCTCCCGAACCCGCATA |
| 4526 | SPAC4G9.05_UP | TCTGGAGGGACGAGGGGTCA |
| 4527 | SPAC4G9.05_DN | TGGCTGAGGGAGGGCGAGT |
| 4528 | SPAC4G9.06c_UP | ATCGCACTCCCCACTGACC |
| 4529 | SPAC4G9.06c_DN | TCCGACAACGGGCTCTCAAA |
| 4530 | SPAC4G9.07_UP | GGAGGGCTGTTGAAGGGACG |
| 4531 | SPAC4G9.07_DN | TGCGTCCCATCCCGTTCTGT |
| 4532 | SPAC4G9.08c_UP | TTTCACCCGCCCCACTCTTT |
| 4533 | SPAC4G9.08c_DN | GTTTCGTATTCGCGACGGCC |
| 4534 | SPAC4G9.09c_UP | CAGATGGCGAGGAGGGGGTG |
| 4535 | SPAC4G9.09c_DN | TGGAGTCATGGGGGTTGCAG |
| 4536 | SPAC4G9.10_UP | CCATAAATCCCTCCGTGCGC |
| 4537 | SPAC4G9.10_DN | GGCTCGTGTTGGATAGGGCG |
| 4538 | SPAC4G9.11c_UP | ATGGCCGGGTGCTTCTGGAA |
| 4539 | SPAC4G9.11c_DN | CACAAGATGAACGCGCCGC |
| 4540 | SPAC4G9.12_UP | TGGATGTGTACGGCCGAGG |
| 4541 | SPAC4G9.12_DN | ATACCGCGCGCCTACATAGC |
| 4542 | SPAC4G9.13c_UP | TGGGAACAAGCGGGGAAGC |
| 4543 | SPAC4G9.13c_DN | TACGTTGCCCCCGAGCTGA |
| 4544 | SPAC4G9.14_UP | TGTGATGCACTGTCCCGCCA |
| 4545 | SPAC4G9.14_DN | CGGCCGAGGTGGGTTGGTCT |
| 4546 | SPAC4G9.15_UP | TCCAGCCAAACAAAGCCCGC |
| 4547 | SPAC4G9.15_DN | CTCTCGCAACCCAACCGCCT |
| 4548 | SPAC4G9.16c_UP | TTCCGCCCTACTCGTTTCCC |
| 4549 | SPAC4G9.16c_DN | CCTCCGGAACAATCGCCTC |
| 4550 | SPAC4G9.17c_UP | CCCAGTCAAACCCCAACGCA |
| 4551 | SPAC4G9.17c_DN | TGTGCTGCCTCCACCATTCG |
| 4552 | SPAC4G9.19_UP | AACTGGCTCCTGATGA |
| 4553 | SPAC4G9.19_DN | CTAACGTGCCGGCTGTACAA |
| 4554 | SPAC4G9.20c_UP | TAGACGCGCAGCGAGAGCC |
| 4555 | SPAC4G9.20c_DN | AGTTGGGTGGTGAAGCGGCG |
| 4556 | SPAC4H3.01_UP | ACCTGCTGCTTGTGCCTCGC |
| 4557 | SPAC4H3.01_DN | ACCCCCCACCTTTGCTCGAG |
| 4558 | SPAC4H3.02c_UP | GAGTTCGCAAGGCGCCCAGT |
| 4559 | SPAC4H3.02c_DN | CCAGCCCCCCTCCACTCTCC |
| 4560 | SPAC4H3.03c_UP | GAGCTTCTGCGTGGGGGGTA |
| 4561 | SPAC4H3.03c_DN | GTACGCCCCATCAAGTCGC |
| 4562 | SPAC4H3.04c_UP | GCGAGCGACTTGGCGGTTTG |
| 4563 | SPAC4H3.04c_DN | ATGATGGGGTTCCGGGATT |
| 4564 | SPAC4H3.05_UP | CCGGTTCTCAGCGTTCCCAT |
| 4565 | SPAC4H3.05_DN | TTTTGAGGTCGTGTCCGGC |
| 4566 | SPAC4H3.07c_UP | CCCCCTGGAACTTCTGCTCG |
| 4567 | SPAC4H3.07c_DN | TAAACAGCCGAGCCCCCACC |
| 4568 | SPAC4H3.08_UP | TACCGGGTCTCGCTGTACAA |
| 4569 | SPAC4H3.08_DN | AGCGAACTCGTACACCCTG |
| 4570 | SPAC4H3.10c_UP | ACGCTGACGGCTCGAGTTACA |
| 4571 | SPAC4H3.10c_DN | TGTACACGGCGTCACGATGA |
| 4572 | SPAC4H3.12c_UP | TTCAAGATCCTCCGCCACCGG |
| 4573 | SPAC4H3.12c_DN | CAGAAAACACCCCGCAAGGCA |
| 4574 | SPAC4H3.13_UP | TGGCGCGTCACAACAGGATGA |
| 4575 | SPAC4H3.13_DN | GCACGTTGACGGCTCGTACAA |
| 4576 | SPAC4H3.14c_UP | GGGGCTCCGGGCATTCAGTC |
| 4577 | SPAC4H3.14c_DN | GCCCACCTTCCGCACGACCT |
| 4578 | SPAC513.02_UP | ATGCTACCGTGTACTGCGAC |
| 4579 | SPAC513.02_DN | AGGCGGGAAGGGCGGTGTTA |
| 4580 | SPAC513.03_UP | GCGGTCGGATTGTTGCTCTC |
| 4581 | SPAC513.03_DN | CCTCTGACATGCCCGCGGTA |
| 4582 | SPAC513.04_UP | ACTGACACACCCCGCCAAA |
| 4583 | SPAC513.04_DN | AAGGAACGGCGGCAGAAAGG |
| 4584 | SPAC513.05_UP | AAGTGTGCCCCCAAACGGTC |
| 4585 | SPAC513.05_DN | CGTCCCTTCTCGCCGTGCCT |
| 4586 | SPAC513.06_UP | ACTGGTTAGGCGTCGATGA |
| 4587 | SPAC513.06c_DN | GGATGCTCACGCGTCCGGC |
| 4588 | SPAC513.07_UP | CCAAAACCCCGGGATGCGCTA |
| 4589 | SPAC513.07_DN | GCCGCTTGTTCGACGTTCAG |
| 4590 | SPAC521.02_UP | CGGCAACACCTCTCCACCCCG |

| Sequence number | Name | Base sequence |
|---|---|---|
| 4591 | SPAC521.02_DN | ATGCCCACCCTGTTCCTGCG |
| 4592 | SPAC521.03_UP | CGCCATCCACGAAGACGACCA |
| 4593 | SPAC521.03_DN | CAGCTTATGATGGGGGCGGC |
| 4594 | SPAC521.04c_UP | GATGGGCTCGTGGGGTGAGA |
| 4595 | SPAC521.04c_DN | GGGTGCGGGAGTGTTGTGGA |
| 4596 | SPAC521.05_UP | CGAACCGGCACGGGGCTATT |
| 4597 | SPAC521.05_DN | CGGGATTCGAGAGCCGTGCAC |
| 4598 | SPAC56E4.02c_UP | AGGTCTGCACGGCTGTACAA |
| 4599 | SPAC56E4.02c_DN | ATAGAGCGCCGGCGTACAA |
| 4600 | SPAC56E4.03_UP | GGAAGGCAATTGTCGGCGTG |
| 4601 | SPAC56E4.03_DN | CGCCCTTGCGAGTTTGGGTG |
| 4602 | SPAC56E4.04c_UP | TCCACATCTCATCGCCCACG |
| 4603 | SPAC56E4.04c_DN | GATACTTGCGGGCGGCTA |
| 4604 | SPAC56E4.05_UP | TTGAGCTTGACTGGCCCCGG |
| 4605 | SPAC56E4.05_DN | CGGGCGTACAAGGGGACACA |
| 4606 | SPAC56E4.06c_UP | GGAGTGCGGGCGGAAAAAG |
| 4607 | SPAC56E4.06c_DN | TTCAGTCACCACCCGCCCAT |
| 4608 | SPAC56E4.07_UP | CATGAGGAGTTCGACGGGCA |
| 4609 | SPAC56E4.07_DN | CGCAGCTCAACCGTCACCCC |
| 4610 | SPAC56F8.02_UP | GACCCGACACACGCCCAGGA |
| 4611 | SPAC56F8.02_DN | ATATAACGTCCCCGCGCCTG |
| 4612 | SPAC56F8.03_UP | CAAAACGGCGAGACGGTAAC |
| 4613 | SPAC56F8.03_DN | TTGGGGTTGGGCTGCTAAGGT |
| 4614 | SPAC56F8.04c_UP | CAACCCGTAAAATGCGCCAA |
| 4615 | SPAC56F8.04c_DN | GGGAAGGGGATAGCGACGAGC |
| 4616 | SPAC56F8.05c_UP | CGACAGACGACGAAACCGCC |
| 4617 | SPAC56F8.05c_DN | GCAGCCACGCGGAACAACCCTA |
| 4618 | SPAC56F8.06c_UP | GTCCCGGCGATTCAGAGCCT |
| 4619 | SPAC56F8.06c_DN | GGCAGCTGTGGGAGGTACCC |
| 4620 | SPAC56F8.08_UP | CTCCAAACACCCTCCCGCGT |
| 4621 | SPAC56F8.08_DN | CCCTGAACCCCCTGCTACGC |
| 4622 | SPAC56F8.09_UP | GGCTTGCTCGGGGGTTCACT |
| 4623 | SPAC56F8.09_DN | AAGGTGGAACAGCGAGCCCC |
| 4624 | SPAC56F8.10_UP | CATGCGGCGTCCGATGATGA |
| 4625 | SPAC56F8.10_DN | TGGGTTCAACGCGGCTACAA |
| 4626 | SPAC56F8.11_UP | AACGCCTCACCTCCCAACCA |
| 4627 | SPAC56F8.11_DN | GCTGGGAAAGCGAGGGTGTC |
| 4628 | SPAC56F8.12_UP | CCAGGATCGGCTGCTACAA |
| 4629 | SPAC56F8.12_DN | GTAGTTCATTGGCGCGAGC |
| 4630 | SPAC56F8.14c_UP | CGGGTTTGAGCGTGCGATTA |
| 4631 | SPAC56F8.14c_DN | GCGCAGAGGTTCAAAAGGGG |
| 4632 | SPAC56F8.15_UP | ACCTCCGCAATCCGCTTTCA |
| 4633 | SPAC56F8.15_DN | TACACAGCCAGAACCGCCGA |
| 4634 | SPAC57A10.02_UP | TGTGTTCGGCCTGTTGCCTG |
| 4635 | SPAC57A10.02_DN | GGTGGGAATGAGGTGAGGCG |
| 4636 | SPAC57A10.03_UP | CAGCAGCCCACTTCCTCCGA |
| 4637 | SPAC57A10.03_DN | GCGCCGGTGATTCGGATCT |
| 4638 | SPAC57A10.04_UP | CCCGATGCTCTCCCGTCCAA |
| 4639 | SPAC57A10.04_DN | GGCGTTATTGGTGCTGCGAA |
| 4640 | SPAC57A10.05c_UP | CCGTTCCCCTCACATACGCC |
| 4641 | SPAC57A10.05c_DN | GATTCGCGGGGTTAGGCGAA |
| 4642 | SPAC57A10.06_UP | ACTCTAGGCGTCGCGGATGA |
| 4643 | SPAC57A10.06_DN | GTCTGGACATCCGGCGATGA |
| 4644 | SPAC57A10.07_UP | TTCGCGGCCTCTTGTCGCTCT |
| 4645 | SPAC57A10.07_DN | AGGCTCATCCACTCGCTGCA |
| 4646 | SPAC57A10.08c_UP | AACAGGGGGTTCGTCAGCA |
| 4647 | SPAC57A10.08c_DN | GGCGGCATAGGGGACTAGGG |
| 4648 | SPAC57A10.09c_UP | CTTTGCCTGCGCGGGTTCTA |
| 4649 | SPAC57A10.09c_DN | TGCATCTGCGCTGAATCCTT |
| 4650 | SPAC57A10.10c_UP | GCTGGGAACGGGACGCAAGA |
| 4651 | SPAC57A10.10c_DN | TGGGGTGCGGGCCTTCTAAAG |
| 4652 | SPAC57A10.12c_UP | CAGAACATGTCGGAGTGCCG |
| 4653 | SPAC57A10.12c_DN | ACTGCAGCCCGCTGCTACAA |
| 4654 | SPAC57A10.14_UP | TCGACATGCCGCACGAGTGT |
| 4655 | SPAC57A10.14_DN | GCTCCAGTCAGGTGATCGCT |
| 4656 | SPAC57A7.04c_UP | GCCCCCACCCGAAGACAAGC |
| 4657 | SPAC57A7.04c_DN | TCGGAGATGAATGGGGCCCT |
| 4658 | SPAC57A7.05_UP | TTGTTGTACGGGGCTGGGGC |
| 4659 | SPAC57A7.05_DN | CTGAAGGTTTTTGGGGGCGG |
| 4660 | SPAC57A7.07c_UP | TTCGTTCTCGGGGATGGTTG |
| 4661 | SPAC57A7.07c_DN | CTGTTTCGCGCCACGTGTCC |
| 4662 | SPAC57A7.08_UP | TGGTGTTGCCGACTGCGCTT |
| 4663 | SPAC57A7.08_DN | CCCATTGGTGCACGTCCGGT |
| 4664 | SPAC57A7.09_UP | TCAACTTCGCTGCTGCCGTG |
| 4665 | SPAC57A7.09_DN | CTACGCTGGGTGCGGACCGT |
| 4666 | SPAC57A7.10c_UP | CATAACGCCAATCGGCGAA |
| 4667 | SPAC57A7.10c_DN | GGGTGGCTTGGATGTTTGGC |
| 4668 | SPAC57A7.12_UP | GCTACCAGACAAGGCCGCCC |
| 4669 | SPAC57A7.12_DN | GCCGGTTCCGACCAACTCTC |
| 4670 | SPAC57A7.13_UP | CGTTCATCCCCTTCACCGCA |
| 4671 | SPAC57A7.13_DN | TACGGGGGGCAAGTTCAGGG |
| 4672 | SPAC589.02c_UP | CCCAGCCCCAGAACAACGGT |
| 4673 | SPAC589.02c_DN | AGCCCFTTCAGTCCCCGGCT |
| 4674 | SPAC589.03c_UP | CGGCGTGTGCGTAGGGTGTG |
| 4675 | SPAC589.03c_DN | CGGCGATAGTGGAGTTTCAA |
| 4676 | SPAC589.05c_UP | ACCACTCAATCACGCCCGGG |
| 4677 | SPAC589.05c_DN | GGACCGGCTTTACCTGCCCC |
| 4678 | SPAC589.06c_UP | AGAGCAGGTTTCGGTGCGGC |
| 4679 | SPAC589.06c_DN | ACAGCGGGCGAAAAGTCC |
| 4680 | SPAC589.07c_UP | GTTCGTGATGCCCGGGTTGA |
| 4681 | SPAC589.07c_DN | AGGCCCCGAAACAAACCGCT |
| 4682 | SPAC589.08c_UP | ACGCGGGTCCATACTGAGGC |
| 4683 | SPAC589.08c_DN | ATAGCGGCGTGGTGGAGGCA |
| 4684 | SPAC589.09_UP | GCGAGTTGGCAGGCGGACAGT |
| 4685 | SPAC589.09_DN | GCAATGGGGCGTCGTTACCT |
| 4686 | SPAC589.10c_UP | GCAGGCGAGGGACTGTTTGT |
| 4687 | SPAC589.10c_DN | CGTGCGTGTTTGTGCTCCC |
| 4688 | SPAC5D6.01_UP | TGCATTTCTCTAGCGCGCG |
| 4689 | SPAC5D6.01_DN | TCCAGGTGCGCGTTTCGTTC |
| 4690 | SPAC5D6.02c_UP | ACTATGCGTTTGAACGGGC |
| 4691 | SPAC5D6.02c_DN | AGAGGTAGGGCGCATGGGGG |
| 4692 | SPAC5D6.04_UP | GCTGGTGGACTCCGTACAA |

FIG.30

| Sequence number | Name | Base sequence |
|---|---|---|
| 4693 | SPAC5D6.04_DN | CATCCTGGGAGGCGTGATGA |
| 4694 | SPAC5D6.05_UP | TTCGTCCCTGTCGTGCCGCG |
| 4695 | SPAC5D6.05_DN | TTCGCGGGCCCACATCTTCA |
| 4696 | SPAC5D6.06c_UP | AACGGCGTGGGAATTCTGCG |
| 4697 | SPAC5D6.06c_DN | CACTGGCTACTTGGGTCGCG |
| 4698 | SPAC5D6.07c_UP | CCAAATATCGCTGCCGGCTG |
| 4699 | SPAC5D6.07c_DN | AGTAACGGGATTGGCGGCTG |
| 4700 | SPAC5D6.09c_UP | GCGGCACCAGAAATCGAACG |
| 4701 | SPAC5D6.09c_DN | ATCGGAAACCCCCAAGCGTG |
| 4702 | SPAC5D6.10c_UP | TCCCGACACGAAAGCACCAG |
| 4703 | SPAC5D6.10c_DN | CGCTATAGGTCCGCCCCGAA |
| 4704 | SPAC5D6.12_UP | AGCTTTGAGTGTCCCCGGTG |
| 4705 | SPAC5D6.12_DN | TGGGGAACGGAGCCACATGT |
| 4706 | SPAC5H10.01_UP | CAGCAGCCGAAAGGCGAAC |
| 4707 | SPAC5H10.01_DN | TGGTGGTGTCGCCGGTCGTCT |
| 4708 | SPAC5H10.02c_UP | CAGGAGGTGGGACGCAAAGC |
| 4709 | SPAC5H10.02c_DN | GCCCAACCCGACATCTTCCC |
| 4710 | SPAC5H10.03_UP | TGATGGATAGCTCGCCGGGT |
| 4711 | SPAC5H10.03_DN | GJAGATTGGCGGGCATCGTGG |
| 4712 | SPAC5H10.04_UP | GSTAAGCATGCGGTGGGCCT |
| 4713 | SPAC5H10.04_DN | TAGCAAGGGGCCGGTCGAAA |
| 4714 | SPAC5H10.05c_UP | AGGGGGCGTGGGATTGAAAG |
| 4715 | SPAC5H10.05c_DN | CACAACGGAAGGGCAGCAAG |
| 4716 | SPAC5H10.06c_UP | CGAAACGAGACGGGCGAGAA |
| 4717 | SPAC5H10.06c_DN | TCGGACGGGCAGGGACTACT |
| 4718 | SPAC5H10.07_UP | ACTTCACGTGCTGCTCCCGA |
| 4719 | SPAC5H10.07_DN | ACTTGTGCAGGGTTCGGCCG |
| 4720 | SPAC5H10.08c_UP | CTGCTTGGGCTGGAGTTGCG |
| 4721 | SPAC5H10.08c_DN | GTCGTCTCCCTTCGCTCCCA |
| 4722 | SPAC5H10.09c_UP | CGGATAGAGGGCGACAGGGT |
| 4723 | SPAC5H10.09c_DN | TAAAGTATGGGACGCGCGGC |
| 4724 | SPAC5H10.10_UP | TCTCCACGCCACCCCCTAAC |
| 4725 | SPAC5H10.10_DN | GCGTGGATTTGCGGGGTGTT |
| 4726 | SPAC5H10.11_UP | AATGTGGCTAGGGTTCGGCG |
| 4727 | SPAC5H10.11_DN | AGCCTGCCGCTCCTGGCTAG |
| 4728 | SPAC5H10.12c_UP | ACAATAACCCCCCCTGCCGA |
| 4729 | SPAC5H10.12c_DN | CCGCCCCGTACAAGCCAGAA |
| 4730 | SPAC5H10.13c_UP | CTCCGGCATTGTAACGCTGC |
| 4731 | SPAC5H10.13c_DN | GGCGAATGTGGGGCGGAAAT |
| 4732 | SPAC607.03c_UP | TGGTGTCTTCTGAGGGGGCG |
| 4733 | SPAC607.03c_DN | AGGCCCAGGAATGCACCAACG |
| 4734 | SPAC607.06c_UP | TTTCACCCCGTCCTCGGTCT |
| 4735 | SPAC607.06c_DN | CCTCGCCCGGCCTCCTGAAA |
| 4736 | SPAC607.07c_UP | ACAGCGGGAGGCACTATCGG |
| 4737 | SPAC607.07c_DN | GCCCCCATCCCTAGTCCCAG |
| 4738 | SPAC607.08c_UP | ATGGGCGTTCCGTGAGTGTG |
| 4739 | SPAC607.08c_DN | CTGGGGACATTGGGAACGGC |
| 4740 | SPAC607.09c_UP | ACCGGCAAAGCAACCACCTC |
| 4741 | SPAC607.09c_DN | TTTATCGAGGGCCAACGCGCA |
| 4742 | SPAC607.10_UP | TGGTAGTCGCCGGCGAAATC |
| 4743 | SPAC607.10_DN | CGGTTGGCGTCGGTGGATTC |
| 4744 | SPAC630.03_UP | ACCCGCAGAAATGCAACCCT |
| 4745 | SPAC630.03_DN | GTCTAACGGGAGCGGGGAGT |
| 4746 | SPAC630.04c_UP | TTGCGGGGGGCCTTCATTGGT |
| 4747 | SPAC630.04c_DN | CGCGTTCAGGCTCAGGGTGC |
| 4748 | SPAC630.05_UP | GAAGGCCCCGTGTGTCGAGC |
| 4749 | SPAC630.05_DN | CCACCAATTGCTGCCCCTTG |
| 4750 | SPAC630.06c_UP | TGGGGGTTCTCACGTGGGCT |
| 4751 | SPAC630.06c_DN | GTGCCCGAATTCAAGCCAGG |
| 4752 | SPAC630.07c_UP | CATACCTCGGCGTCGGATCA |
| 4753 | SPAC630.07c_DN | GATGTGACGGGCGGTCGATG |
| 4754 | SPAC630.08c_UP | CGGAGGAACAGCAATTGACA |
| 4755 | SPAC630.08c_DN | CCGACAACCGCACCAACCGT |
| 4756 | SPAC630.09c_UP | AGTGGCGTGGAAGGGGAGCA |
| 4757 | SPAC630.09c_DN | TCTTTCGTGGTTCTCCCGCC |
| 4758 | SPAC630.10_UP | GGAAGGTGGGATGAAAGTCG |
| 4759 | SPAC630.10_DN | TGAAGGAGTCGCAAAATCGA |
| 4760 | SPAC630.12_UP | CGCTCACCCTTGCTTTGCCG |
| 4761 | SPAC630.12_DN | GTGGGGGCAAGCGGATAAAG |
| 4762 | SPAC630.13c_UP | CTGCGCCTTTTGGGGGAACG |
| 4763 | SPAC630.13c_DN | ACCGGAACAGCACCCTCCAA |
| 4764 | SPAC630.14c_UP | GCGGGCGGTAGAAAGACGGG |
| 4765 | SPAC630.14c_DN | GGGGAGGAATCGGTGAAGCC |
| 4766 | SPAC630.15_UP | TCACGTACGGACCCGGCAAT |
| 4767 | SPAC630.15_DN | ATTGCCTAACGGTGCCCGAA |
| 4768 | SPAC631.01c_UP | GGACGCCTTTACGGACCCAGG |
| 4769 | SPAC631.01c_DN | GCATCGGTGCCCTAACAGGC |
| 4770 | SPAC637.03_UP | GCCCCTCATTGTCACGCCAT |
| 4771 | SPAC637.03_DN | ACGGTGGGAGTGGAGACGGG |
| 4772 | SPAC637.04_UP | CCCACAACCCCCCCCAAGAG |
| 4773 | SPAC637.04_DN | GAATAACGGGGCTTGGGGCA |
| 4774 | SPAC637.05c_UP | CCCGCATTACCGCCACTCTC |
| 4775 | SPAC637.05c_DN | GCCGGTGTCTTTCGCTGTGT |
| 4776 | SPAC637.06_UP | TGCGTGGGCTAAAGTGTACGG |
| 4777 | SPAC637.06_DN | GGATGTGCTCGCCGGTGAGTC |
| 4778 | SPAC637.07_UP | GACCTCCCCGGTCAGCTGC |
| 4779 | SPAC637.07_DN | CAGTACCGCCTTCTCCGCCT |
| 4780 | SPAC637.08_UP | TCAACTAGCCCCACCGACCC |
| 4781 | SPAC637.08_DN | GTTCCCCCGTGATCGACAA |
| 4782 | SPAC637.09_UP | CATCCCACGCACAGAAACAA |
| 4783 | SPAC637.09_DN | ATTTCGTCTTGCGGGGCTTC |
| 4784 | SPAC637.10c_UP | GTGGTGCTGCTGCTCGGCAA |
| 4785 | SPAC637.10c_DN | GTCCCCATCATCACCGCGTT |
| 4786 | SPAC637.11_UP | CGCCCGCATGCTTATTCTCA |
| 4787 | SPAC637.11_DN | TGTCGCCTAGGCCCCAAAGA |
| 4788 | SPAC637.12c_UP | ATACTCGCCGAGGGAACGCC |
| 4789 | SPAC637.12c_DN | TGGGTTACCGAGACGGCGG |
| 4790 | SPAC637.13c_UP | AAATTTTGCGGCAAGGGGG |
| 4791 | SPAC637.13c_DN | GTACCCGCCTTCACCCACCG |
| 4792 | SPAC644.04_UP | CTTGAAGTCGTCCGCCGTGC |
| 4793 | SPAC644.04_DN | GCCTTGGCGCCGTTCTCTT |
| 4794 | SPAC644.05c_UP | TGCGCTGTGCCTCGTGATTG |

| Sequence number | Name | Base sequence |
|---|---|---|
| 4795 | SPAC644.05c_DN | CCTAGAAACCACGGTCAGAG |
| 4796 | SPAC644.06c_UP | GAGCTGCTGCACACCCCCAG |
| 4797 | SPAC644.06c_DN | TTATCGGAAATCGGCCACGC |
| 4798 | SPAC644.07_UP | CCCACCCTCTCACGCTCGCT |
| 4799 | SPAC644.07_DN | TGCGGAATCGGTCGTTCGGT |
| 4800 | SPAC644.08_UP | GTGGCGGTCGGGCGTTTAGA |
| 4801 | SPAC644.08_DN | GAACAAATGAGGGCGGGCA |
| 4802 | SPAC644.09_UP | CTAGCCAACGACCCCCTCCG |
| 4803 | SPAC644.09_DN | GAGTCGCCGGGTTAAGTGGG |
| 4804 | SPAC644.11c_UP | GTTCAATGCTCCGCCGACGCA |
| 4805 | SPAC644.11c_DN | ACCCCGCCCCGTATCCTATC |
| 4806 | SPAC644.12_UP | AAAGGGACGACGGCAGGGAT |
| 4807 | SPAC644.12_DN | AACACAATCATCGCCCCCCA |
| 4808 | SPAC644.13c_UP | TCCCTTGTCGCGCCACTGT |
| 4809 | SPAC644.13c_DN | ACGGATCAGCACCCAGAAGG |
| 4810 | SPAC644.14c_UP | TCTTGTTCCTGTCGCGTGTG |
| 4811 | SPAC644.14c_DN | CGCCACGCCTCACACCATGT |
| 4812 | SPAC644.16_UP | TGGACCCCGCCGCAATCTGAG |
| 4813 | SPAC644.16_DN | ACTTGCGTCTGGCGGGCTAC |
| 4814 | SPAC644.17c_UP | CGCTGACAAAAGCCTCGGCC |
| 4815 | SPAC644.17c_DN | GAGCAGTCGCAACCCACCGG |
| 4816 | SPAC664.02c_UP | CAGAGTGGCGCAACGACGGT |
| 4817 | SPAC664.02c_DN | CGCAGGCCGCTACGTCATTC |
| 4818 | SPAC664.03_UP | ACGCTCGCACACCCACTCA |
| 4819 | SPAC664.03_DN | TCCTGTTTGGCCTGGCTGGA |
| 4820 | SPAC664.04c_UP | ATGGGAAGGCGTGCACTGCCG |
| 4821 | SPAC664.04c_DN | GGGCCTCGACGGAACTAGCA |
| 4822 | SPAC664.05_UP | CGGTCAAGAATCGGCATGGG |
| 4823 | SPAC664.05_DN | CAAAAAGCGGGCAGAGCGGC |
| 4824 | SPAC664.07c_UP | CCGCAATACCGCGTTACCCT |
| 4825 | SPAC664.07c_DN | TTCGGAAGGGAGAAGCCGCC |
| 4826 | SPAC664.09_UP | GACTCGGGGCTTGGGTGAAG |
| 4827 | SPAC664.09_DN | ATCTGTCGGTCGGCTCCTGG |
| 4828 | SPAC664.10_UP | TGTGTCACGCAGGTGCACTA |
| 4829 | SPAC664.10_DN | ACCATCCGACGGCTCTTTG |
| 4830 | SPAC664.11_UP | GCGGGACCTTTGCTGCACGT |
| 4831 | SPAC664.11_DN | CGACATCTCGGCAAAGCGGC |
| 4832 | SPAC664.12c_UP | TAGGCTTCGAGTCCCGGGTT |
| 4833 | SPAC664.12c_DN | TGCTCCTCCCGTGCCTGCTCA |
| 4834 | SPAC664.13_UP | ACCCACTCCGCACCCTGTCA |
| 4835 | SPAC664.13_DN | GATGTCCTGTCTCCCGGCGCC |
| 4836 | SPAC664.14_UP | CGTTGTTCCCTGGTCCCGCA |
| 4837 | SPAC664.14_DN | CCGCAGCCCTAACCCAATGT |
| 4838 | SPAC683.03_UP | ATGCGCCCACTACTAACCCG |
| 4839 | SPAC683.03_DN | AGACGGAACCGGACGTACA |
| 4840 | SPAC688.02c_UP | GGTCGTTTCGTTTCGCGGTT |
| 4841 | SPAC688.02c_DN | TCCCCAGCACAAGACCGCAA |
| 4842 | SPAC688.03c_UP | TCGTCCCGTGCGCCTTTATGA |
| 4843 | SPAC688.03c_DN | TGCCTGCGCGTACGTTTTC |
| 4844 | SPAC688.04c_UP | AGGGGGCGCGGTTGCATATA |
| 4845 | SPAC688.04c_DN | GGACGTTATAGCGGCGAGGC |
| 4846 | SPAC688.06c_UP | CGCGACCCTCACCGATTCCT |
| 4847 | SPAC688.06c_DN | CAAGTGCATCATCGGCCCGT |
| 4848 | SPAC688.06c_DN | CAACAGACCCCGCGATCCGT |
| 4849 | SPAC688.07c_UP | GAACAGACCCCCGCGATCCCT |
| 4850 | SPAC688.07c_DN | TCCTGCAACCCTCTCGAATT |
| 4851 | SPAC688.09_UP | GCGAGGCTCACACATACCCGA |
| 4852 | SPAC688.09_DN | GATTTCCTTCCGCGGCAGCT |
| 4853 | SPAC688.10_UP | TGCCCTCACCACGCACTCAA |
| 4854 | SPAC688.10_DN | ATCGGTCAGGGGTTAGCGGG |
| 4855 | SPAC688.11_UP | GCGAGCCGAAGGTAGTCGGGA |
| 4856 | SPAC688.11_DN | CCCGCAGCGATCAGTTGCCC |
| 4857 | SPAC688.12c_UP | GGCAACAAGCAGCAAAGCGG |
| 4858 | SPAC688.12c_DN | TGGTGTAGGCATCGGGGGCC |
| 4859 | SPAC688.13_UP | CTGGCACCCCGGCTTTTTA |
| 4860 | SPAC688.13_DN | TGGGAACATTTGGGGCACG |
| 4861 | SPAC688.14_UP | CTGTCTAGCGGCGGCCATCT |
| 4862 | SPAC688.14_DN | CCTAACGGGAAGGGTCCCGC |
| 4863 | SPAC694.02_UP | GCGGCAAGGAGGTGTGGCTA |
| 4864 | SPAC694.02_DN | GGCACAAAGCGAGGGGAACA |
| 4865 | SPAC694.05c_UP | TCCGTCGGGCTCAAAAACCT |
| 4866 | SPAC694.05c_DN | TCCGCCCGCCATCTTTCTC |
| 4867 | SPAC694.05c_UP | CACTTGGATCGCCCCCTGT |
| 4868 | SPAC694.05c_DN | GGCGGTTGGGAGAAGGCGAG |
| 4869 | SPAC5B12.02c_UP | CCTACGCCCATTTACCCCCC |
| 4870 | SPAC5B12.02c_DN | TCGTTTCTCTGCGGCTCCCC |
| 4871 | SPAC5B12.03c_UP | GAGTCCCCCACAAGAAGCCG |
| 4872 | SPAC5B12.03c_DN | CAAACCCCCGACTCCAACGC |
| 4873 | SPAC5B12.04c_UP | ACCAGCTAGCCCGCGAAAGA |
| 4874 | SPAC5B12.04c_DN | GGGCTTAATTGGCGACTGTT |
| 4875 | SPAC5B12.05c_UP | AAGAGAGGGCACCGGCCAAA |
| 4876 | SPAC5B12.05c_DN | CTGGTGAGCGGAAAAGCGGC |
| 4877 | SPAC5B12.07c_UP | GTCTTCTCCGCCGCGATTTC |
| 4878 | SPAC5B12.07c_DN | TAGCGAGCCTCAACACGCGG |
| 4879 | SPAC5B12.08_UP | GTTACAGCCCCCGTGCCCTC |
| 4880 | SPAC5B12.08_DN | CAAGCAAAACCTACGCGCGAA |
| 4881 | SPAC5B12.09_UP | CTCCTAGAATGTCCGCGCGC |
| 4882 | SPAC5B12.09_DN | TCTTTTCGGAGGGCGTGGCT |
| 4883 | SPAC5B12.10c_UP | GTGGTCAGGCCGTGTGGCT |
| 4884 | SPAC5B12.10c_DN | CGCTACCCACCCCCGCATTTA |
| 4885 | SPAC5B12.12_UP | TTGGCACGCCTGGAAGCGACG |
| 4886 | SPAC5B12.12_DN | GTGCAGAGGTGTGGTCGGGA |
| 4887 | SPAC5B12.14c_UP | CTACACCCAGCCACATGCCG |
| 4888 | SPAC5B12.14c_DN | GGCGGCTCCCAATCACGAAT |
| 4889 | SPAC5B12.15_UP | GCCAAGCAACTCGGCGGTTG |
| 4890 | SPAC5B12.15_DN | AGCCCGTAGGGCAAAGTGCG |
| 4891 | SPAC5B12.16_UP | CATCTTCCGCGTGCTTGTGC |
| 4892 | SPAC5B12.16_DN | GACTGGTAAGGGAGCGCGGG |
| 4893 | SPAC6C3.02c_UP | CCTTGGGCTGCGGTGGCTTA |
| 4894 | SPAC6C3.02c_DN | CCCATCGTGTCGCCCAGCCT |
| 4895 | SPAC6C3.03c_UP | TCCCCTGCGCTCTCCAAATT |
| 4896 | SPAC6C3.03c_DN | GGGGGCCGATTGATGAAAAA |
| 4897 | SPAC6C3.04_UP | TTGGGTGAGCGGATAGGGCA |

FIG.31

| Sequence number | Name | Base sequence |
|---|---|---|
| 4897 | SPAC6C3.04_DN | GTTGGGGCGGATTCGGAGTA |
| 4898 | SPAC6C3.05_UP | TTACCCCATTATCCGCCCCA |
| 4899 | SPAC6C3.05_DN | AACTTCCAACATGCGGGGGG |
| 4900 | SPAC6C3.06a_UP | ACCAGGGAAGGCGGAAGGT |
| 4901 | SPAC6C3.06a_DN | CACCATATCCCCCAAGTCCC |
| 4902 | SPAC6C3.07_UP | GTGGAAATCGGCTGCGAGGC |
| 4903 | SPAC6C3.07_DN | AGCGCCCGGTAGAGCACTTT |
| 4904 | SPAC6C3.08_UP | GGGCTCCGCGCTTCATAGTC |
| 4905 | SPAC6C3.08_DN | ATCGAATAATGGGCGGCAC |
| 4906 | SEAC6C3.09_UP | TCGCGGGGCCTAAGCATTT |
| 4907 | SPAC6C3.09_DN | GTGGTCCGCGTTCGGAGTAT |
| 4908 | SPAC6F12.02_UP | TTTCCTGGGCCCGTCCTGTA |
| 4909 | SPAC6F12.02_DN | ACCATCCATCTCACGGGCCA |
| 4910 | SPAC6F12.03c_UP | AGAAGCCCTGCGCGATACCC |
| 4911 | SPAC6F12.03c_DN | TGATTTTAGGCCCCGGGATGG |
| 4912 | SPAC6F12.04_UP | ACCTGGGATCGCGTTGGGTA |
| 4913 | SPAC6F12.04_DN | GTTGCGATCGAGTTCCCCGG |
| 4914 | SPAC6F12.06_UP | CCGCCCAATTTAAAAGCTGCC |
| 4915 | SPAC6F12.06_DN | TCACTTTCGGCCGGGGCTTTA |
| 4916 | SPAC6F12.07_UP | TTGGACGGTGGGACAGTGGA |
| 4917 | SPAC6F12.07_DN | GCAGGAGTGTCAGACGTCGG |
| 4918 | SPAC6F12.08c_UP | CCTAAGCAACATCCCCCCGA |
| 4919 | SPAC6F12.08c_DN | AACGCTCCCCATTTCGCTCC |
| 4920 | SPAC6F12.09_UP | CCAATTGAGAACCGCCAGCG |
| 4921 | SPAC6F12.09_DN | CACGGGGGGGGACACTATC |
| 4922 | SPAC6F12.10a_UP | TCAGCTCGGCCACGTTCATT |
| 4923 | SPAC6F12.10c_DN | CCTTGCCCTGTCCATCTCGC |
| 4924 | SPAC6F12.11c_UP | TGCCCCCGATTTACCGATTC |
| 4925 | SPAC6F12.11c_DN | GCCGTGGAGCGTTATGGAGG |
| 4926 | SPAC6F12.12_UP | TTAGGTCAGTGTGGCCGGCA |
| 4927 | SPAC6F12.12_DN | TGACACACCCGTTTTTGCCG |
| 4928 | SPAC6F12.13c_UP | GCCAATATGCGTCACAGGC |
| 4929 | SPAC6F12.13c_DN | TGGCGAGTGCCGTGCATATC |
| 4930 | SPAC6F12.14_UP | GGGGCTGCAAAAGGACGAGG |
| 4931 | SPAC6F12.14_DN | CATAAGGGCACCGTGGGGCT |
| 4932 | SPAC6F12.16a_UP | GCGGGTGAGGAGAGGTGGGT |
| 4933 | SPAC6F12.16c_DN | TCGTCCGCCTCAGTCTTCCG |
| 4934 | SPAC6F12.17_UP | CTGCCCCTAGTTCCGGTCGA |
| 4935 | SPAC6F12.17_DN | TGTTCCCATCTCGCGCTCGT |
| 4936 | SPAC6F6.01_UP | CGGCACCCCGTCGTTCTCTG |
| 4937 | SPAC6F6.01_DN | TGTTTACCGTTCCCCCAGCC |
| 4938 | SPAC6F6.02c_UP | ATTTTGGGGCTGGCTCGGCT |
| 4939 | SPAC6F6.02c_DN | GGGTGGTTCGGGACTGGTGT |
| 4940 | SPAC6F6.03a_UP | ATGGATTCCGCCTCTGTCGC |
| 4941 | SPAC6F6.03c_DN | GCCAGAAAGGGGCTACAAG |
| 4942 | SPAC6F6.04c_UP | CACCTCGGCTGCTTTCCATA |
| 4943 | SPAC6F6.04c_DN | TTCGGCGTTGGAGACAGTTGC |
| 4944 | SPAC6F6.05_UP | ACCGACGCTTTGCCCGATTT |
| 4945 | SPAC6F6.05_DN | ACTCGAAAAGGCCGCCGGATA |
| 4946 | SPAC6F6.06c_UP | AAATCATGCCCCAACCCCC |
| 4947 | SPAC6F6.06c_DN | CCCGTCTTGGTCCATCCACC |
| 4948 | SPAC6F6.07c_UP | TTTGAGCTACCGGTTCGGCA |
| 4949 | SPAC6F6.07c_DN | CCGAGTCGCGAACCTCACAT |
| 4950 | SPAC6F6.08c_UP | GCGCCACAAGGGGACAG |
| 4951 | SPAC6F6.08c_DN | CCAATTGCCCGCTGCTACCC |
| 4952 | SPAC6F6.10c_UP | GGAACCGGGACATAGGCACA |
| 4953 | SPAC6F6.10c_DN | GGCTGTCGGTCGGGGCTACA |
| 4954 | SPAC6F6.11c_UP | TGATTATGTCGCAGGGGCG |
| 4955 | SPAC6F6.11c_DN | AGTGTTTCTGCGGGACGGGA |
| 4956 | SPAC6F6.12_UP | GTGTCCCGCGTCTCCATT |
| 4957 | SPAC6F6.12_DN | CCGGGGGCAATTGGAGGGTA |
| 4958 | SPAC6F6.13c_UP | CAGGCGCCAAAGCAGATT |
| 4959 | SPAC6F6.13c_DN | GTCATCACGGGCACAGGGG |
| 4960 | SPAC6F6.15_UP | TCGGGAGGGGGTAAAGGGTG |
| 4961 | SPAC6F6.15_DN | TACAAATGGGGAGGACGGAC |
| 4962 | SPAC6F6.16a_UP | GCGAAGTAGCGGAGGGGACC |
| 4963 | SPAC6F6.16c_DN | GCCTGTCTCGGGTCTGCTCG |
| 4964 | SPAC6F6.18c_UP | TTCCGAGAAGTCCGTGACGC |
| 4965 | SPAC6F6.18c_DN | ACTGCGTCGTCAGGAGCGT |
| 4966 | SPAC6G10.02c_UP | CGGATACGTCCCCCAACAGG |
| 4967 | SPAC6G10.02c_DN | ACCCACCCACATCGTTCACCG |
| 4968 | SPAC6G10.03c_UP | ACTAAGGGCGGGGAGAACG |
| 4969 | SPAC6G10.03c_DN | TGAGCGCAGGGTGAATCCAA |
| 4970 | SPAC6G10.05c_UP | CACGGACCCACATTCCCCCC |
| 4971 | SPAC6G10.05c_DN | TGAACAGTGGGCAGACCCGT |
| 4972 | SPAC6G10.06_UP | TTCACCCGTTCCGGACTCCGT |
| 4973 | SPAC6G10.06_DN | TCCGGGGCGCCTAATCCATA |
| 4974 | SPAC6G10.07_UP | AGTGGCAAGATGAGCGGCCG |
| 4975 | SPAC6G10.07_DN | GCGGKGCGACGTATTAATGA |
| 4976 | SPAC6G10.08_UP | AGAGGAGGGAAAAGCACCG |
| 4977 | SPAC6G10.08_DN | CCATGCTGTTCGCGCCCATA |
| 4978 | SPAC6G10.09_UP | CGGCCCCCTATAAACGTCG |
| 4979 | SPAC6G10.09_DN | CCGCCTATTGTCGCCCTTGT |
| 4980 | SPAC6G10.10c_UP | CTCCCACACTTGCCGCTACG |
| 4981 | SPAC6G10.10c_DN | GGGACTGGGCTACCAACGGA |
| 4982 | SPAC6G10.11c_UP | GAGGGAGAGTAGGCAGCGGCA |
| 4983 | SPAC6G10.11c_DN | AACACGCTCCCCAATCCAC |
| 4984 | SPAC6G10.12c_UP | AGCGGCCTATCGGCTGTGTC |
| 4985 | SPAC6G10.12c_DN | GCCGATTGGCAGGAGCGCTA |
| 4986 | SPAC6G9.01c_UP | GACCCTCATGCAAGACCGCC |
| 4987 | SPAC6G9.01c_DN | TTGGCGCAAAACAGAACCGC |
| 4988 | SPAC6G9.02c_UP | AGGACACGCGATCCCAGGTT |
| 4989 | SPAC6G9.02c_DN | CCTAGTGGGCAGTGCAGCAA |
| 4990 | SPAC6G9.03c_UP | CAAGGAAAAGACCGGCCATC |
| 4991 | SPAC6G9.03c_DN | GTCACCTACAACCGCGCACG |
| 4992 | SPAC6G9.04_UP | GCCGCCACCACAGGAACAAG |
| 4993 | SPAC6G9.04_DN | TTAACTCCAGCCACGTGCCG |
| 4994 | SPAC6G9.05_UP | TCACCACCGCCCATCGAGAA |
| 4995 | SPAC6G9.05_DN | TGCCTAGGGGTCCAATGCCG |
| 4996 | SPAC6G9.06c_UP | AGCGGGGATTTTGCGCATGCA |
| 4997 | SPAC6G9.06c_DN | GGCCGGCACCCTTACCAACA |
| 4998 | SPAC6G9.07c_UP | AACCCGTCCAAGCCATCATG |
| 4999 | SPAC6G9.07c_DN | CAGGACAGAGCTCGAGGGGG |
| 5000 | SPAC6G9.08_UP | TCGGGGATTTTGGCGGTCAC |
| 5001 | SPAC6G9.08_DN | AAGTGGGTCATCGGCGCAAC |
| 5002 | SPAC6G9.09c_UP | ATGTTGATGTGCGGACGGGG |
| 5003 | SPAC6G9.09c_DN | ACGAGCCCCGCAAACAACTG |
| 5004 | SPAC6G9.10c_UP | TCGGTTTCCGGGCGTCTTAT |
| 5005 | SPAC6G9.10c_DN | GGCAAAAGCAAGGGGCGTTC |
| 5006 | SPAC6G9.12_UP | CGGGGGTGGCCATAGCAAAA |
| 5007 | SPAC6G9.12_DN | TGCCGGCTTCGCTCCCTGTA |
| 5008 | SPAC6G9.13c_UP | CCGGTGGTGCTCGTCTGGGT |
| 5009 | SPAC6G9.13c_DN | GTGGTTGGGCGGCTGTGGAG |
| 5010 | SPAC6G9.14_UP | TCTTTGTCGGGACCGCACTG |
| 5011 | SPAC6G9.14_DN | ATCCTCCCGGCCGGTTACAT |
| 5012 | SPAC6G9.15c_UP | CATCGCAAGGCCGTCAAAAG |
| 5013 | SPAC6G9.15c_DN | AGCTGCGATCGGGACCTTCC |
| 5014 | SPAC6G9.16c_UP | ATATGCTTCGCGAGCGGGTC |
| 5015 | SPAC6G9.16c_DN | TCTCAGCGTGTGCTGACGGA |
| 5016 | SPAC732.01_UP | TCATCCTTGCCATCGCTTTGC |
| 5017 | SPAC732.01_DN | CGTCCCGCCCAGTCAAAACA |
| 5018 | SPAC732.02c_UP | ACCATGACCTGAGCGAGCTG |
| 5019 | SPAC732.02c_DN | CTGTCCTCGTCCCAAGTCTC |
| 5020 | SPAC750.02c_UP | CCGTCCGTTGGTCTTTGCGT |
| 5021 | SPAC750.02c_DN | GGGGGCTGAGTTGCGATTTG |
| 5022 | SPAC750.03c_UP | TCAGAAACAACGCGCGGGAC |
| 5023 | SPAC750.03c_DN | TCAACAAAAGCCGCGGATCCG |
| 5024 | SPAC750.04c_UP | CAAGCCAGCCGCCGTACGAC |
| 5025 | SPAC750.04c_DN | AACAGCACACCACGGCGCAG |
| 5026 | SPAC750.05c_UP | GACAGGCTCGGCACTACCTT |
| 5027 | SPAC750.05c_DN | GTCGCAAACACCACCCCCTT |
| 5028 | SPAC750.06c_UP | CACGCCGACCCATGCTACTG |
| 5029 | SPAC750.06c_DN | GATTGGATGCGGGTACGGGA |
| 5030 | SPAC750.07c_UP | AATATGCGCGCACCAACCA |
| 5031 | SPAC750.07c_DN | AGACGCGGCCCACATAGCAA |
| 5032 | SPAC7D4.02c_UP | GCGGCACTCGGTTTAGGCG |
| 5033 | SPAC7D4.02c_DN | TGCTTTGGACCCGTATGGC |
| 5034 | SPAC7D4.03c_UP | GGGAGGTTGACGGTGGGCAT |
| 5035 | SPAC7D4.03c_DN | ACCCAATGGCGAACGGCTAG |
| 5036 | SPAC7D4.04_UP | TCGGCCGCAAAGTACCCAAA |
| 5037 | SPAC7D4.04_DN | TTCCCGGTCACCTGCAGTCA |
| 5038 | SPAC7D4.05_UP | TGGGGCTCGTGTCCGTTTCT |
| 5039 | SPAC7D4.05_DN | CCACACCCAACGCTACGCAA |
| 5040 | SPAC7D4.06c_UP | CCATGTTGAGGGGTCGAGGT |
| 5041 | SPAC7D4.06c_DN | TTGAGGGTTAAGCGGAGGCG |
| 5042 | SPAC7D4.37c_UP | ACCTGTTCCTCGTGCGCCCT |
| 5043 | SPAC7D4.07c_DN | GCGAGCCAAATCATGACGGG |
| 5044 | SPAC7D4.08_UP | CCCCAGAGCGTGATGCAACA |
| 5045 | SPAC7D4.08_DN | ACTTTGGGTCTGGGGTGCAC |
| 5046 | SPAC7D4.09c_UP | GGCGGGATGGTTAGGGGCAC |
| 5047 | SPAC7D4.09c_DN | CGAACCTCGGCTCCGCCTTCC |
| 5048 | SPAC7D4.10_UP | AGAATCCACGGCTCCCCACA |
| 5049 | SPAC7D4.10_DN | CCTCAGACTCCCGCTTGCCA |
| 5050 | SPAC7D4.12c_UP | CAGACACGCTTCCGGCAGCC |
| 5051 | SPAC7D4.12c_DN | CTCGACGCCGCCTCTTACGG |
| 5052 | SPAC7D4.13c_UP | GGGGGCGATGAAATGGTGT |
| 5053 | SPAC7D4.13c_DN | AGCAGCAAACGCACCCAAGA |
| 5054 | SPAC7D4.14c_UP | CATTCCCCCGTCAGTCCAT |
| 5055 | SPAC7D4.14c_DN | TCTCTTCAGTTTGGCCGGCA |
| 5056 | SPAC7D4.15c_UP | ACTGCCGACGAGCCGATACA |
| 5057 | SPAC7D4.15c_DN | GCGGTACCCGGATTCCGTT |
| 5058 | SPAC906.02c_UP | TTGACAGGCGCACGGGAGTA |
| 5059 | SPAC906.02c_DN | CTTAACGATTGGACCGCGCG |
| 5060 | SPAC906.03c_UP | TGGGGGTGAGAGTTGGCCGA |
| 5061 | SPAC906.03c_DN | CCGCCTGCCCTTTGTTTCAC |
| 5062 | SPAC906.04c_UP | AATTGCCACCCCATCGAACG |
| 5063 | SPAC906.04c_DN | GCTCCCTCCAACGTCCGAAC |
| 5064 | SPAC906.05_UP | GGGGGGTAGGAATTGCCGGG |
| 5065 | SPAC906.05_DN | CGAAGAAGATGACCCCCCGC |
| 5066 | SPAC906.07_UP | ACCCGCCGAACGCTACCCTC |
| 5067 | SPAC906.07_DN | GCCCCCGCAAATTCCATACG |
| 5068 | SPAC906.08c_UP | CCCCGGAGAACACTGCATCA |
| 5069 | SPAC906.08c_DN | GGGGCTGGTGACCTAGCTCG |
| 5070 | SPAC821.03c_UP | GCTTGATCGGCCCACGTTA |
| 5071 | SPAC821.03c_DN | GAAGCGTTGTCCCGGGGTCTG |
| 5072 | SPAC821.04c_UP | ACCCCTGCCCAAGTCAAACG |
| 5073 | SPAC821.04c_DN | GTGATTCGTCGCCGTGCTTC |
| 5074 | SPAC821.05_UP | TTATGTCGGGTGGCGAGGC |
| 5075 | SPAC821.05_DN | ATGGCTGGGGTTACGATGGG |
| 5076 | SPAC821.06_UP | AATCCACAGCCCCGATGAGC |
| 5077 | SPAC821.06_DN | TGGCCGATAGAAAGTCCCGC |
| 5078 | SPAC821.07c_UP | GTCGACATGACCGGGTGCCT |
| 5079 | SPAC821.07c_DN | AATCGTCAAATGGTCCCGGC |
| 5080 | SPAC821.08c_UP | ATGATCCCGGCCTTTCCGAC |
| 5081 | SPAC821.08c_DN | TGCTCGGGGTGCGTATCAGG |
| 5082 | SPAC821.09_UP | TAGCCCCATTCCCACCCCGA |
| 5083 | SPAC821.09_DN | TCCACATACACCTGCGGGTC |
| 5084 | SPAC821.10c_UP | CTCTTGCGTTGGTCCCCTGG |
| 5085 | SPAC821.10c_DN | AAGCGCGGCAAACTAGGGAC |
| 5086 | SPAC821.11_UP | GACCCGGACGCTCAACCATG |
| 5087 | SPAC821.11_DN | TTGAATTCGCGTGGTGGGGC |
| 5088 | SPAC821.12_UP | GTCGCAAATGGGCCGCTGAC |
| 5089 | SPAC821.12_DN | GACCAAGGCCTCGGGGAAAG |
| 5090 | SPAC828.02_UP | CTAAACCGCCGACTCACCGA |
| 5091 | SPAC828.02_DN | CTCCCAAAAGCCCCAGGTCG |
| 5092 | SPAC823.03_UP | ACCACGCCTCCCCCTTTTTG |
| 5093 | SPAC823.03_DN | GTGTGTACTGGATGCGCGGA |
| 5094 | SPAC823.04_UP | GCGGGACGAACAACGGCCAA |
| 5095 | SPAC823.04_DN | CAACAAGGCCGGAGGCAGCAA |
| 5096 | SPAC823.05c_UP | TTCCAAGCCAATCGATCCGG |
| 5097 | SPAC823.05c_DN | GTAGTGGCGGGGAGGGTGC |
| 5098 | SPAC823.06_UP | CAGCACCCCACCGTTTAGGC |
| 5099 | SPAC823.06_DN | TTGGTGATGAAACGGCGCGA |
| 5100 | SPAC823.07_UP | GAAGGGGGGCCAATCAGGT |

FIG.32

| Sequence number | Name | Base sequence | Sequence number | Name | Base sequence |
|---|---|---|---|---|---|
| 5101 | SPAC823.07_DN | GCGCGAATTGGGGTCGTAATG | 5203 | SPAC8E11.10_DN | CGGCTCAACAATTCACCGCA |
| 5102 | SPAC823.08c_UP | TCGTCTGCTTTTACCCCGCC | 5204 | SPAC8F11.02c_UP | GGGGCAGGCGCATGAAATAC |
| 5103 | SPAC823.08c_DN | GCAATGGGCAACACCCGTACG | 5205 | SPAC8F11.02c_DN | GCGGCAAGGCAGTACGTCAA |
| 5104 | SPAC823.09c_UP | AAAGCATTCAGCAGCGGGCG | 5206 | SPAC8F11.03_UP | AAGACCACACCCCGAGCAA |
| 5105 | SPAC823.09c_DN | CCCTGTCCCCTGTTTCTGCG | 5207 | SPAC8F11.03_DN | ACGGAAAGCGGGCAAAGACA |
| 5106 | SPAC823.10c_UP | GTCCGGGCCTGTTTTGGGT | 5208 | SPAC8F11.04_UP | TAGCAGCAGGTAGGCGGGGG |
| 5107 | SPAC823.10c_DN | CTATTTTTGGCACCGGCGCC | 5209 | SPAC8F11.04_DN | ACTGATGCGTGGTGGTTGCG |
| 5108 | SPAC823.11_UP | ACCTTCGCGGGCGTTTCTT | 5210 | SPAC8F11.05c_UP | TTTCGCACGTGCGTACCGTT |
| 5109 | SPAC823.11_DN | TTGCCGCGCCCTAAAATGCA | 5211 | SPAC8F11.05c_DN | CAGTGAGGGACCGAGCCGTT |
| 5110 | SPAC823.13c_UP | CTCACTCCAGCCGCAATCGG | 5212 | SPAC8F11.07c_UP | CGGCGCCATCAGAACCCATT |
| 5111 | SPAC823.13c_DN | TCGGGCGCATTTGGAACAGA | 5213 | SPAC8F11.07c_DN | CCTTTAACGCACGCGCCCAG |
| 5112 | SPAC823.14_UP | GGCATACCCCGTCCGCCTAG | 5214 | SPAC8F11.08c_UP | CGGACCTATCCGAGCCACAA |
| 5113 | SPAC823.14_DN | TCGATGGTCGGCTGAGGTGG | 5215 | SPAC8F11.08c_DN | AAACTCACGTGGTCGCCAGC |
| 5114 | SPAC823.15_UP | CCCATTCGAAAAACAGCCCG | 5216 | SPAC8F11.09c_UP | CCTTTCTGCTTTGGGGCCCC |
| 5115 | SPAC823.15_DN | CGTCCCCATAAAGCCACAA | 5217 | SPAC8F11.09c_DN | TCTTGGAGGCCCGATGCTGT |
| 5116 | SPAC823.16c_UP | TACGCGCCACGTGCGTAAA | 5218 | SPAC9.02c_UP | GGGTGCGGTTTGCTATTTGC |
| 5117 | SPAC823.16c_DN | AACATGTACGGGCGTGGGT | 5219 | SPAC9.02c_DN | GCCTCCAAGCTACTCCCGGG |
| 5118 | SPAC824.02_UP | ACATCCCGCCTACGTTTGCG | 5220 | SPAC9.03c_UP | TTTGGGAAGCGTTGGCAGGA |
| 5119 | SPAC824.02_DN | GTCGGCGATTGGCGGATTT | 5221 | SPAC9.03c_DN | GCAGCGGAGGTCAAAGAGGC |
| 5120 | SPAC824.03c_UP | TGCGTGGGGAGGCCTGTACT | 5222 | SPAC9.04_UP | AGCGAGAACGAATAGGCGGG |
| 5121 | SPAC824.03c_DN | GGACACCACGGCACTCGAGC | 5223 | SPAC9.04_DN | CATATGCAGAGCGGACGCCC |
| 5122 | SPAC824.04_UP | CAGCCCACATATCGCGGAAA | 5224 | SPAC9.05_UP | CCATTGTTTTGGCCGGCCTCC |
| 5123 | SPAC824.04_DN | GCATAAGCCGCAAATCCCCA | 5225 | SPAC9.05_DN | CAGCGGGAAGCGAGTGGACT |
| 5124 | SPAC824.05_UP | CCCGGCGCAATCAAAGACT | 5226 | SPAC9.06c_UP | CCTCGGGCGGAAGAATTGAA |
| 5125 | SPAC824.05_DN | ACCAAAAGCGCAACGCAACG | 5227 | SPAC9.06c_DN | GGTCTTTTTGCCAATCCGCG |
| 5126 | SPAC824.06_UP | TCCCGCCTTAGGCGTTGCCAC | 5228 | SPAC9.07c_UP | GTTGCATGTGCCTGTCGGCA |
| 5127 | SPAC824.08_DN | CTTGACCGACGCTCCGCCTA | 5229 | SPAC9.07c_DN | TGGTGGTCAGGCCGCAGTAA |
| 5128 | SPAC824.09c_UP | CATGTCGCGGCAACTTGGAA | 5230 | SPAC9.08c_UP | AGCCGCCACTAGTCCACGCA |
| 5129 | SPAC824.09c_DN | AAAACATGTCGCACTCGCCG | 5231 | SPAC9.08c_DN | TCGGGGCAGGACATGTGGAG |
| 5130 | SPAC869.01_UP | TTATGACGGCGGAAGGGCAG | 5232 | SPAC9.10_UP | CCCGACCCACAACACGACAA |
| 5131 | SPAC869.01_DN | CGCCACCACCGACACAAATG | 5233 | SPAC9.10_DN | GAAGCCAGCAAAGCAGCCGT |
| 5132 | SPAC869.02c_UP | CAGGACGGGCCAAAGAAGGG | 5234 | SPAC9.11_UP | GGCGTGTTTGAGGGGTTCGA |
| 5133 | SPAC869.02c_DN | CAAAATCTCTATGCGCCGCG | 5235 | SPAC9.11_DN | TGCTGCCCCGAATCCTTCT |
| 5134 | SPAC869.03c_UP | AAAGCCCCTACCCCCGCTAC | 5236 | SPAC9.12c_UP | AGCTGTTTCGCCCGCATCTC |
| 5135 | SPAC869.03c_DN | GCGTGAGGGATGTGGTCGGA | 5237 | SPAC9.12c_DN | GGGGGCCATGACGGTACGGT |
| 5136 | SPAC869.04_UP | TTGGTGTCGCGCGGAATTGA | 5238 | SPAC922.03_UP | CGCCCGTTGCCGGGTTCATTT |
| 5137 | SPAC869.04_DN | AAAAGGCTTGTCAGGGGTGC | 5239 | SPAC922.03_DN | CTCGGGCCTCACAAATTGCC |
| 5138 | SPAC869.05c_UP | GGAGGGTGCCGTGGTGGTTC | 5240 | SPAC922.04_UP | TCGATGAGAGGGAGCGTGGA |
| 5139 | SPAC869.05c_DN | CTGGAGTCGACGTGCCATGA | 5241 | SPAC922.04_DN | CATGCCCAACCGCCCCTTA |
| 5140 | SPAC869.06c_UP | CCCTGCGTCTCTCCCCCTGC | 5242 | SPAC922.05c_UP | TTCACTATACCGGCAGCAGC |
| 5141 | SPAC869.06c_DN | TCGAATCCCAAACCCGCTGT | 5243 | SPAC922.05c_DN | CCAGGGCGAAACGATGACGG |
| 5142 | SPAC869.07c_UP | ACTCGCGTGAGTGCGCTAAC | 5244 | SPAC922.06_UP | AGTGTAAGAGTGGCCCCTTCG |
| 5143 | SPAC869.07c_DN | TTCAATTGTGTGGCCCGTGC | 5245 | SPAC922.06_DN | GCGACTGTCATGTGGCAGGA |
| 5144 | SPAC869.08_UP | TTTTGACGGGGGGCTTTTG | 5246 | SPAC922.07c_UP | GCGCCCGACCCTTAAGAACC |
| 5145 | SPAC869.08_DN | TCGGTCATCGTGGCTGGAGGG | 5247 | SPAC922.07c_DN | GTGTGCTGAGTGGCGGGTCG |
| 5146 | SPAC869.09_UP | CGGCGCTGGGTGTACGACGG | 5248 | SPAC926.02_UP | AGCCACACCGCGTCCCTATTT |
| 5147 | SPAC869.09_DN | TGGAGAAGAGGGCGCGAAGA | 5249 | SPAC926.02_DN | TGAGTGCGGGTGTAACTGCGG |
| 5148 | SPAC869.10c_UP | GGTAGCGGGGATGGAGGTT | 5250 | SPAC926.03_UP | GATGGGGAACGAGGGAGGCG |
| 5149 | SPAC869.10c_DN | ATGTGCCCCCGCCCCAAAAA | 5251 | SPAC926.03_DN | ACGGCACCTTCTCTCACCGC |
| 5150 | SPAC890.02c_UP | CTCATCACGCCTCCGCCTA | 5252 | SPAC926.04c_UP | GCAACAGGGGAGCCAAGAA |
| 5151 | SPAC890.02c_DN | TCTTCGTTGCCGCGCCTGCTT | 5253 | SPAC926.04c_DN | GTCTGGCGGCTTGCTTTGC |
| 5152 | SPAC890.03_UP | TAGTGCAAAAATCGCGGCG | 5254 | SPAC926.05c_UP | CCACAAAGATGCAGCCCGAA |
| 5153 | SPAC890.03_DN | AATCGTCACAGCGTGGGCAA | 5255 | SPAC926.05c_DN | TGTCGGTGCGTATTGGGGGA |
| 5154 | SPAC890.04c_UP | GCGTTCTTAGGCCCCGGTGT | 5256 | SPAC926.06c_UP | CCCTCGCCACCTGCTTCATT |
| 5155 | SPAC890.04c_DN | TCGATTTTTCCCGGCCCATG | 5257 | SPAC926.06c_DN | TGGTTTGTGACCATTCGGCC |
| 5156 | SPAC890.05_UP | ACCGCACCAGCATTCACACA | 5258 | SPAC926.07c_UP | TGCGGGCAGAAGTTATGGGG |
| 5157 | SPAC890.05_DN | GCCTCGGCTCGACAATGCCAA | 5259 | SPAC926.07c_DN | GGGGCTAATTCGTCACGGGG |
| 5158 | SPAC890.06_UP | ATTGCGGAGGGGAGGCTTA | 5260 | SPAC926.08c_UP | ACTGAGCCGGTCGCAACATA |
| 5159 | SPAC890.06_DN | TCGTCGCGCTCAAATGCCAC | 5261 | SPAC926.08c_DN | CCCGGGAACCAAAGCACCTA |
| 5160 | SPAC890.07c_UP | TCGCGGACTATAGCGCTCGT | 5262 | SPAC926.09c_UP | ACCCCATGGTACGCAGACCT |
| 5161 | SPAC890.07c_DN | ATGGGCCGGATAGCGTAAC | 5263 | SPAC926.09c_DN | GGTAACTACGGGCGCTGAGA |
| 5162 | SPAC890.08_UP | ACGGACGTCACGTTAGGCAT | 5264 | SPAC959.03c_UP | ACCAACACGGGGAGAGGGT |
| 5163 | SPAC890.08_DN | CAACGTCTCACGCTGCATGG | 5265 | SPAC959.03c_DN | CTCGCCCGTGATGGAATTCG |
| 5164 | SPAC8C9.04_UP | GCGAGCTGGGACGGTTGGTT | 5266 | SPAC959.04c_UP | TGTTGGCCGTGTTGTGCAGG |
| 5165 | SPAC8C9.04_DN | ACGCAAGAGAACGGGACGCC | 5267 | SPAC959.04c_DN | TACACGCCACCGACCCCATC |
| 5166 | SPAC8C9.05_UP | GGCTTTGACGTCCTTTGCCG | 5268 | SPAC959.05c_UP | TCAGCGAGGACCGGCATCAA |
| 5167 | SPAC8C9.05_DN | TGGCTTTACACGCGTGGAG | 5269 | SPAC959.05c_DN | ACACGGTGACCAGCGAAGAC |
| 5168 | SPAC8C9.06c_UP | TGTGACGCAAAATCCGGACG | 5270 | SPAC959.06c_UP | AGCAGGCAGTCAGCGCAGTC |
| 5169 | SPAC8C9.06c_DN | AGGGGGTGTGGGGCTGTCAT | 5271 | SPAC959.06c_DN | CGTCGGGCTTCTTACTGGTG |
| 5170 | SPAC8C9.07_UP | TGCCCTGATTACCCAACCCG | 5272 | SPAC959.07_UP | AGGTGGGAAATCGGGCCAAC |
| 5171 | SPAC8C9.07_DN | CCCGCTGTCCGTTTCTTGG | 5273 | SPAC959.07_DN | GGGGCAAAGGAGTGAGGGGG |
| 5172 | SPAC8C9.08_UP | CGGGGGCAGGAGACCAAC | 5274 | SPAC959.08_UP | GGCGTGAGCGTCGTGATGAA |
| 5173 | SPAC8C9.08_DN | AAGAACCCTGCAAAGCCCGC | 5275 | SPAC959.08_DN | TCCCAGCCATTCCCGCTTC |
| 5174 | SPAC8C9.09c_UP | CGGTGTCATAATCGGGGCGT | 5276 | SPAC959.10_UP | TTGAGGTCCCGAGAGGTGCT |
| 5175 | SPAC8C9.09c_DN | TCCACTCTACCCGCGTCCCCG | 5277 | SPAC959.10_DN | TGACCGGCGTTAGTCGCTCA |
| 5176 | SPAC8C9.10c_UP | GGTCGGCCGTGATTGAGGTG | 5278 | SPAC977.01_UP | CTAGCTTGCCCCCCCGAAA |
| 5177 | SPAC8C9.10c_DN | GGCCTCTTGACGTCCTTTGTGC | 5279 | SPAC977.01_DN | GACTGATCCTGCCCAGCGAT |
| 5178 | SPAC8C9.11_UP | ACGAGTAGGCGCCCAGCAAT | 5280 | SPAC977.02_UP | CCAACCACAGGCACCCAAGC |
| 5179 | SPAC8C9.11_DN | GACGTGTATGGGCAGCCCGA | 5281 | SPAC977.02_DN | GCTTCGCTCCTCACTCGG |
| 5180 | SPAC8C9.12c_UP | TTCTCCCATTGCTGTGCCCC | 5282 | SPAC977.03_UP | GGCTGCGGCTTGGGAGTACA |
| 5181 | SPAC8C9.12c_DN | TCTGGGCGGAGATGCAATTG | 5283 | SPAC977.03_DN | ACCGCCGTCCACCTCATCGA |
| 5182 | SPAC8C9.14_UP | TGAGGACGGGCAGGAGCGAG | 5284 | SPAC977.06_UP | AAGGGCGCGCATATTCTGAG |
| 5183 | SPAC8C9.14_DN | GGGCCGGGTATACTGGGTCA | 5285 | SPAC977.06_DN | GGCCAACAACCGTCGGCTAT |
| 5184 | SPAC8C9.15c_UP | CACGACGCAGCCAAAGAACC | 5286 | SPAC977.08_UP | AGCGGGCCGTTGCAAAATACA |
| 5185 | SPAC8C9.15c_DN | TCGGAGGGCGAATTCCGTAC | 5287 | SPAC977.08_DN | TAAACCCCCCGGCCACGAGTA |
| 5186 | SPAC8C9.16c_UP | GGAAGTGCGGTCAGCAAC | 5288 | SPAC977.09c_UP | ATCCATTAACTCCCCGCCGT |
| 5187 | SPAC8C9.16c_DN | CGCCGAAAGCCACGTATGCC | 5289 | SPAC977.09c_DN | AGCGTGTGAGGGGTGCGTGG |
| 5188 | SPAC8C9.17c_UP | AGGGCGATCCTCCCGCGTTC | 5290 | SPAC977.10_UP | TCACCGATCCCCTGCCACTC |
| 5189 | SPAC8C9.17c_DN | TGCTGGCCGGGTTGTAGGTG | 5291 | SPAC977.10_DN | AAGGATTGAAACGGGTGGCG |
| 5190 | SPAC8C9.19_UP | ACTTCCGCTACACCAGGGA | 5292 | SPAC977.11_UP | ACCGCCATGCCCTTCCGTAG |
| 5191 | SPAC8C9.19_DN | TTCCTCGGTCACTCGGCACA | 5293 | SPAC977.11_DN | CGCTGCTCCCGTTGTTCTCA |
| 5192 | SPAC8E11.02c_UP | GAAGGCCGGGAGATGCATA | 5294 | SPAC977.12_UP | CTTCACCCACCGCCCTGTTT |
| 5193 | SPAC8E11.02c_DN | TCTTTTCCGGTCGTCAGGCG | 5295 | SPAC977.12_DN | AAGGTCGCCCGTCTCAACGAT |
| 5194 | SPAC8E11.03c_UP | TGCCAATCCCTTCCCCAGCG | 5296 | SPAC977.13c_UP | GACAGCGGCACACAAGGGT |
| 5195 | SPAC8E11.03c_DN | TGCTGGTAATGGAAGACGCGG | 5297 | SPAC977.13c_DN | TGATGTGCCCGTGGTTTGG |
| 5196 | SPAC8E11.05c_UP | GAATGGCTAAACGGTCGGG | 5298 | SPAC977.14c_UP | GCGCCACAACCACCTTGCAC |
| 5197 | SPAC8E11.05c_DN | TCGCTACCCGAACCCTTGCCA | 5299 | SPAC977.14c_DN | GATCCAGTCGCACGCAAAGC |
| 5198 | SPAC8E11.06_UP | GTTGCGGCGTTGCGTAGTTC | 5300 | SPAC977.15_UP | TGGTGGAGATTGAGGCCGGC |
| 5199 | SPAC8E11.06_DN | TTGAAAACTCCGCCCATCCC | 5301 | SPAC977.15_DN | GTAGCCAGGCATGGCAGGT |
| 5200 | SPAC8E11.07c_UP | CCCGAGCCGCGCCTCTGATGA | 5302 | SPAC977.16c_UP | TGGATGGGCGGAGAGTCGGT |
| 5201 | SPAC8E11.07c_DN | ACTTGGCCGCCTCTCTCTCC | 5303 | SPAC977.16c_DN | GAACACGGCCCTGCAAATT |
| 5202 | SPAC8E11.10_UP | AGCTTCGATGGCGGTGGTTG | 5304 | SPAC977.17_UP | CTCGCACCCCATCACCCAGC |

FIG.33

| Sequence number | Name | Base sequence |
|---|---|---|
| 5305 | SPAC977.17_DN | AGGGGAGGGAGCGGCGGTAT |
| 5306 | SPAC9E9.03_UP | GTAGACATCGCGCCCAACG |
| 5307 | SPAC9E9.03_DN | GAGGGATAGCGAAACCCCCC |
| 5308 | SPAC9E9.04_UP | GTGGGGCTCCGGTTTCAAGA |
| 5309 | SPAC9E9.04_DN | AGCAGAACAACGGGGAACGT |
| 5310 | SPAC9E9.05_UP | TCGGCCTCATGTCGCTTTTT |
| 5311 | SPAC9E9.06_DN | GGCTCTTCGCTGCACTCCCG |
| 5312 | SPAC9E9.08_UP | CGCCCTGTGCAGACGCTAAC |
| 5313 | SPAC9E9.08_DN | CATGCGAGCAGGGGTCAAGA |
| 5314 | SPAC9E9.09c_UP | TTGCGCATTGTTCGGACGCG |
| 5315 | SPAC9E9.09c_DN | ATTCGCATGGACGTAGGGG |
| 5316 | SPAC9E9.10c_UP | GGGGTTCGCTCGCGGTGTAC |
| 5317 | SPAC9E9.10c_DN | GGTGCGGGTTGGGAATGGTC |
| 5318 | SPAC9E9.12c_UP | CGCCGACCTTCGCIACCCACG |
| 5319 | SPAC9E9.12c_DN | TGCGGGAGATGGGGTCAGAG |
| 5320 | SPAC9E9.13_UP | CCTCGTTCTTCCCAAGGCCG |
| 5321 | SPAC9E9.13_DN | CTAAAGTCGGCTCTCGCGCG |
| 5322 | SPAC9E9.14_UP | GCGAGCAACAAGCCGACCAA |
| 5323 | SPAC9E9.14_DN | TGAACGTCGATAGCGGGCGG |
| 5324 | SPAC9E9.15_UP | AGAAACACCCGCGCCACCTC |
| 5325 | SPAC9E9.15_DN | CAGGGTAGCGAGGAGAGCGG |
| 5326 | SPAC9E9.17c_UP | GCCCCTCGGTGCCAAGTAC |
| 5327 | SPAC9E9.17c_DN | CCACCACAATTTTCCGCCGT |
| 5328 | SPAC9G1.02_UP | TGAGGTCTATGGCGGGGCAG |
| 5329 | SPAC9G1.02_DN | TACTCCTCGCTCACCCCCGA |
| 5330 | SPAC9G1.03c_UP | TCCACCCAGTCTCCCGCCCT |
| 5331 | SPAC9G1.03c_DN | TACCCGCCCACGCGACAITA |
| 5332 | SPAC9G1.04_UP | ATTCGTTGAGCTTCGCCGGG |
| 5333 | SPAC9G1.04_DN | TAGGGCGGGAGTCGTCAAAG |
| 5334 | SPAC9G1.05_UP | ATAGTTGCGGGGACCTCGGA |
| 5335 | SPAC9G1.05_DN | ATCGTTGTCTTCCCGCCCTC |
| 5336 | SPAC9G1.06c_UP | TTGCATTTCCGCCCTGGTGA |
| 5337 | SPAC9G1.06c_DN | GTTCGCGACTTGATGAGCC |
| 5338 | SPAC9G1.07_UP | AAGCGTCCGTCCCCTGGTTA |
| 5339 | SPAC9G1.07_DN | AACTCATCCCCTCCCCCAC |
| 5340 | SPAC9G1.08c_UP | AGGGAAGCAGCCCCAGGTTTA |
| 5341 | SPAC9G1.08c_DN | CGGTTGCGCGGTTAATGAAA |
| 5342 | SPAC9G1.09_UP | CGGGTGGCTATTTCTGGCGC |
| 5343 | SPAC9G1.09_DN | TTCCGACGCTAATGGCCCCC |
| 5344 | SPAC9G1.10c_UP | AGGCGTCTCCGTTCGTGCA |
| 5345 | SPAC9G1.10c_DN | GCTTTAATCGCTGCCGCCTC |
| 5346 | SPAC9G1.11c_UP | GTGAGGGATAACGCCGGAA |
| 5347 | SPAC9G1.11c_DN | GAAATTTGCTTCGCGGGCCT |
| 5348 | SPAC9G1.12_UP | TTTCGGTTCGAGGTGCTGGC |
| 5349 | SPAC9G1.12_DN | GCGCACTCGCTCCATAACGA |
| 5350 | SPAC9G1.13c_UP | AGGCGGTTAGGGGGTGAGGA |
| 5351 | SPAC9G1.13c_DN | TCGCCCACGACTGACTGCAT |
| 5352 | SPACUNK12.02c_UP | TCCCCGGCTTTACCTCGCAA |
| 5353 | SPACUNK12.02c_DN | AGGGCCGGAACTGGTAGGGGC |
| 5354 | SPACUNK4.08_UP | GAAGCAACGGGAACAGCACG |
| 5355 | SPACUNK4.08_DN | TGGTCGCTTCGCTTCCCTTG |
| 5356 | SPACUNK4.09_UP | TTGGGCGGGAACAAGGAAGA |
| 5357 | SPACUNK4.09_DN | CCACCTTGTTTTGCGGACC |
| 5358 | SPACUNK4.10_UP | CGCCCTCCCAGCATGTCGTA |
| 5359 | SPACUNK4.10_DN | TCACAAGCCCGAAACCCTCCA |
| 5360 | SPACUNK4.11c_UP | ATGACGGCGAGAGGGGGAA |
| 5361 | SPACUNK4.11c_DN | TTGCACGGAGTCGACGCGCC |
| 5362 | SPACUNK4.12c_UP | CCTCGCCCTGGTTGTGTCCT |
| 5363 | SPACUNK4.12c_DN | GAGTTATGGGCGTCGGGTGC |
| 5364 | SPACUNK4.13c_UP | ACATCTTTGTCGTCCCTGCCG |
| 5365 | SPACUNK4.13c_DN | CCGCCAACCCGTGTACACC |
| 5366 | SPACUNK4.14_UP | GCACGGGATGGGGAAAATT |
| 5367 | SPACUNK4.14_DN | CGAGGGCACGAGGTTACGCA |
| 5368 | SPACUNK4.15_UP | GTGGGTGAGTCGGAAGGGG |
| 5369 | SPACUNK4.15_DN | TTTCCTAAGCTTCCGGGCCC |
| 5370 | SPACUNK4.16c_UP | GGGGCGGGGTCCTTGATACT |
| 5371 | SPACUNK4.16c_DN | CCGTCCTGCACCTGTTTCCG |
| 5372 | SPACUNK4.17_UP | TCACCACGCTCAACCGAAG |
| 5373 | SPACUNK4.17_DN | AGCGGTATTGCCTTGGGTGC |
| 5374 | SPAP11E10.02c_UP | TAAGTCCTCTCCCCCGCC |
| 5375 | SPAP11E10.02c_DN | GCAAACCGAACGCCCAGAAA |
| 5376 | SPAP14E8.02_UP | AGATCCGGCAACCCCGCTGT |
| 5377 | SPAP14E8.02_DN | CCCCACCGAGTACCATGTCA |
| 5378 | SPAP14E8.04_UP | CGCAAAGCCCCACGGTAAGA |
| 5379 | SPAP14E8.04_DN | TGCCGTGACGCTCGTGACTC |
| 5380 | SPAP14E8.05c_UP | GCCTTCAGCCGTCCCCATGC |
| 5381 | SPAP14E8.05c_DN | TACGGCTGGGGTTTGCAGG |
| 5382 | SPAP19A11.05c_UP | GTGGGGCATATTGCAGGCGA |
| 5383 | SPAP19A11.05c_DN | CGCGCCACCCTAACAACTGA |
| 5384 | SPAP27G11.02_UP | AGCGGCCCTGAGCAAGAAAA |
| 5385 | SPAP27G11.02_DN | TTTCGGAGGTGAGTGCGTGC |
| 5386 | SPAP27G11.06c_UP | GTGGGAGCGCGCGGATAATG |
| 5387 | SPAP27G11.06c_DN | CCTCGCACCTTCCGTCGTCC |
| 5388 | SPAP27G11.10c_UP | CCGGTTACGCCAGGACAAGT |
| 5389 | SPAP27G11.10c_DN | GAACGCGACCGTCCTCTCTT |
| 5390 | SPAP27G11.11c_UP | CGCGGGGTTTGCCTAGTGAC |
| 5391 | SPAP27G11.11c_DN | TCAGAACTCAGGCCCACCTC |
| 5392 | SPAP27G11.12_UP | CTTTCCGCCAAGCCATGTA |
| 5393 | SPAP27G11.12_DN | CAGGCGGATGGAGCGTTACC |
| 5394 | SPAP27G11.13c_UP | CCACGGGGAAAAAAAACCGG |
| 5395 | SPAP27G11.13c_DN | GGCGTTCAATCGTCGTCAT |
| 5396 | SPAP27G11.14c_UP | GAACCAATTGCCCATTCGCC |
| 5397 | SPAP27G11.14c_DN | TGGTCACGTGAATCGCGGCA |
| 5398 | SPAP27G11.15_UP | CCGTGCCAGTTCGTTCGTCG |
| 5399 | SPAP27G11.15_DN | CTTATCGCCCCTCAGACCCG |
| 5400 | SPAP27G11.16_UP | TCCTAGCTAGCGACCTGGCA |
| 5401 | SPAP27G11.16_DN | CGACACGCGGTCCGGAGAGAT |
| 5402 | SPAP32A8.02_UP | CTGGGGCCTGTGCGTACGTT |
| 5403 | SPAP32A8.02_DN | CCTCTCCCATTCCTCGCACG |
| 5404 | SPAP32A8.03c_UP | AATGGTAGGAGAGGGGCGCC |
| 5405 | SPAP32A8.03c_DN | TTTGTCCGGAGTGCGCATGC |
| 5406 | SPAP7G5.03_UP | ATCATGGGGTCCGGGCTTTG |
| 5407 | SPAP7G5.03_DN | TGTAATCCGCGCAAACGTCG |
| 5408 | SPAP7G5.04c_UP | CACGCCCCCCCTGAGATGT |
| 5409 | SPAP7G5.04c_DN | TGACCCCCGCACGAATGACC |
| 5410 | SPAP7G5.05_UP | CACGCGGATTCTGTCCACC |
| 5411 | SPAP7G5.05_DN | TCACTGACGCCGCCTTTCT |
| 5412 | SPAPBA3.02c_UP | CCCCCGCTTTCTTGCATCAC |
| 5413 | SPAPBA3.02c_DN | CCAAGCCACCCCTACGCCAG |
| 5414 | SPAPBA3.03_UP | CGTGTAAAAGGCGCGAACCA |
| 5415 | SPAPBA3.03_DN | GAGCGGTGGGGRCGAGGRAC |
| 5416 | SPAPBA3.04c_UP | CAAAACCGGAAGGCAACGC |
| 5417 | SPAPBA3.04c_DN | CGCCGGACCCATACCACAGT |
| 5418 | SPAPBA3.05_UP | TTTTTCCAACCGAASCCCGT |
| 5419 | SPAPBA3.05_DN | GCGGTCTTGGCICGCGTTGC |
| 5420 | SPAPBA3.07c_UP | CGGTTCACATGGGCGTTTC |
| 5421 | SPAPBA3.07c_DN | ACGTGCTCATGGCCTTTTT |
| 5422 | SPAPBA3.08_UP | GGATCGCCCCAGATGAGAC |
| 5423 | SPAPBA3.08_DN | TTATGTCAGAACAACCSCGG |
| 5424 | SPAPBA3.09c_UP | TTGTCCCGATAGCTCTGCCG |
| 5425 | SPAPBA3.09c_DN | ATGGGGCCTCTCGGATGTTG |
| 5426 | SPAPBA3.10_UP | GGTACCCCCTCTGCACAGCG |
| 5427 | SPAPBA3.10_DN | CCGCTTGATGTCCGCCTTTC |
| 5428 | SPAPBA3.11c_UP | GGCCTCAAACGCGCAGCATA |
| 5429 | SPAPBA3.11c_DN | GCCTGCCGATGCCCGTATAC |
| 5430 | SPAPBA3.12c_UP | CGGGTCATCAAAAGGGTGGC |
| 5431 | SPAPBA3.12c_DN | TCCGAAGTACCCCAAGCGGC |
| 5432 | SPAPBA3.13c_UP | CACAAACTCCCGATCTCCCG |
| 5433 | SPAPBA3.13c_DN | ASGGAAGCAGGATCGGGGAG |
| 5434 | SPAPBA3.14c_UP | GCGTAGGTGCGCGGACAGAG |
| 5435 | SPAPBA3.14c_DN | GCGCCCTCTTCGTGCTTGTT |
| 5436 | SPAPB15E9.03c_UP | CAGTTAGCTCCGTGCGAGGT |
| 5437 | SPAPB15E9.03c_DN | AACGCGTACTGACGGAGCGG |
| 5438 | SPAPB17E12.02_UP | AGGCTCACGTGCTCGTCACA |
| 5439 | SPAPB17E12.02_DN | CGATCGCCGCGTTATTCGCT |
| 5440 | SPAPB17E12.04c_UP | ATACCCTTACGCTGCACCG |
| 5441 | SPAPB17E12.04c_DN | TCAAGGACTGCTACCGTCGG |
| 5442 | SPAPB17E12.05_UP | ATCCGTGCGACGCTAAGCAG |
| 5443 | SPAPB17E12.05_DN | ATGGACGTCCGTGTGTTCCC |
| 5444 | SPAPB17E12.07c_UP | CGGGTCCTTACGTCGCATCT |
| 5445 | SPAPB17E12.07c_DN | CGACCGGAGTTACTCACGCA |
| 5446 | SPAPB17E12.08_UP | GGAGGTCACTATGCGGCCAA |
| 5447 | SPAPB17E12.08_DN | CATGCGAGGTTGACCGCTCT |
| 5448 | SPAPB17E12.09_UP | CACTTGTGGTACGGGCGGTT |
| 5449 | SPAPB17E12.09_DN | TAGGCGTGGCCTTAGCGAGA |
| 5450 | SPAPB17E12.10c_UP | ACTTCCGGCAATCACGTGGA |
| 5451 | SPAPB17E12.10c_DN | CGACGCCCTGCGCATACACA |
| 5452 | SPAPB17E12.11_UP | GAGCATCGTCCAGCCGATAT |
| 5453 | SPAPB17E12.11_DN | TTCATCCCGGACACGTCGCT |
| 5454 | SPAPB17E12.12c_UP | TTCACTCGACCGTGGCGACT |
| 5455 | SPAPB17E12.12c_DN | AACCGGTCGACTCCGGATGT |
| 5456 | SPAPB17E12.14c_UP | TCGAAAGCGACCCTAGGCGA |
| 5457 | SPAPB17E12.14c_DN | ATCTCTCTGCGCGACCACAA |
| 5458 | SPAPB18E9.01_UP | TGGACGGACAGATCAAGCC |
| 5459 | SPAPB18E9.01_DN | TACTCACCTGGGCGGACCAA |
| 5460 | SPAPB18E9.04c_UP | CTGTGAGCGCCAGTGTGAGT |
| 5461 | SPAPB18E9.04c_DN | TGTCGCGACCGCTAGCGAAA |
| 5462 | SPAPB1A10.02_UP | CGCCCACCAATTCGAGCTCT |
| 5463 | SPAPB1A10.02_DN | AAAGCGGGTGCTCAATCGGG |
| 5464 | SPAPB1A10.03_UP | CCCCAGGGTGCTACCCAGCC |
| 5465 | SPAPB1A10.03_DN | GCTACACGCGACATCACGCC |
| 5466 | SPAPB1A10.04c_UP | TGTGCGGGCTGCAGGATCTT |
| 5467 | SPAPB1A10.04c_DN | ACGGCAGCCGTAGAACGGTT |
| 5468 | SPAPB1A10.05_UP | ACCAASCTATCAGCCCCGCS |
| 5469 | SPAPB1A10.05_DN | GTTCCCCGTCTTTTGCCAGC |
| 5470 | SPAPB1A10.06c_UP | TACCCGTTCCTGGCTTCTGGC |
| 5471 | SPAPB1A10.06c_DN | CAACGGCCGGGACATCAAGA |
| 5472 | SPAPB1A10.07c_UP | GTGAACTGGGGGCGACTTGG |
| 5473 | SPAPB1A10.07c_DN | AAGCGATTACCCCTGCACGG |
| 5474 | SPAPB1A10.08_UP | CGGGCCAGCTGAAAAGAGGT |
| 5475 | SPAPB1A10.08_DN | CACTAAAATTTCCGCGCCCC |
| 5476 | SPAPB1A10.09_UP | TTTCGGTCACCCGAGTTGGT |
| 5477 | SPAPB1A10.09_DN | TGTGCCGCAGTACCTGGATT |
| 5478 | SPAPB1A10.10c_UP | ATCTCCAACGGGCGAACCTG |
| 5479 | SPAPB1A10.10c_DN | GCGGGCATGGTTCGATACAA |
| 5480 | SPAPB1A10.11c_UP | CGGATTCAGTCCACATGCGG |
| 5481 | SPAPB1A10.11c_DN | CTGCCGACGCTTCATGGACC |
| 5482 | SPAPB1A10.12c_UP | GGACCTCCCCGCTGGCATT |
| 5483 | SPAPB1A10.12c_DN | GGGACGAGCCATGACCGGGT |
| 5484 | SPAPB1A10.13_UP | TCCGAAAGGCCTGAAAGCCA |
| 5485 | SPAPB1A10.13_DN | ATTTTTGCCCGACACCTCCG |
| 5486 | SPAPB1A10.14_UP | CTCCCCTTGAAAATACGCCCG |
| 5487 | SPAPB1A10.14_DN | TCTGCGTTTCGGAGTGGCTT |
| 5488 | SPAPB1A10.15_UP | ACAAACACGCGGCAACATCG |
| 5489 | SPAPB1A10.15_DN | CTGTTTTTTGGCCGGGACGA |
| 5490 | SPAPB1A11.02_UP | ACGCGCAGACTCTCCCCCTC |
| 5491 | SPAPB1A11.02_DN | CATGAAAGGGGGCAGTCCA |
| 5492 | SPAPB1A11.03_UP | GGGGCACTGACTCCGGGATG |
| 5493 | SPAPB1A11.03_DN | TAGGGCGTGCGAAGGGAAAT |
| 5494 | SPAPB1A11.04c_UP | CCTGGCGCATGCTCCCAATA |
| 5495 | SPAPB1A11.04c_DN | GGGGCTGAGATGTAGGGCCA |
| 5496 | SPAPB1E7.01c_UP | ACCGCGATGCCACACCCCA |
| 5497 | SPAPB1E7.01c_DN | CGAACCCGCCACRACCCAGA |
| 5498 | SPAPB1E7.02c_UP | CTCGTGTGTTTGCGGCTGGC |
| 5499 | SPAPB1E7.02c_DN | TTGAGGACTTGGCACCGCGT |
| 5500 | SPAPB1E7.03_UP | CGCCCAGTACTCCCAACGCC |
| 5501 | SPAPB1E7.03_DN | TGACTTTGGCGCTGAGGGGG |
| 5502 | SPAPB1E7.04c_UP | TCGGGTCGTCGCGTTCTAGC |
| 5503 | SPAPB1E7.04c_DN | AGCGTTTCTGCGATGCGGTC |
| 5504 | SPAPB1E7.05_UP | TTCAAACGCGCGGGGACTG |
| 5505 | SPAPB1E7.05_DN | ACCCCGCCTCCTTCCTATGG |
| 5506 | SPAPB1E7.06c_UP | AAACCGCGAATTCGGCAGCCT |
| 5507 | SPAPB1E7.06c_DN | GCAGGGCACGGTTAGGGAAG |
| 5508 | SPAPB1E7.09c_UP | GCCTGAATCGACGTGCCTCA |

FIG. 34

| Sequence number | Name | Base sequence | Sequence number | Name | Base sequence |
|---|---|---|---|---|---|
| 5509 | SPAFB1E7.08c_DN | TCGAACTCCGCTGGGCGAGA | 5611 | SPBC1105.02c_DN | CCTCAACAATATGCCCCCCG |
| 5510 | SPAFB1E7.10_UP | TCCATCCAACCGCCGTCATA | 5612 | SPBC1105.03c_UP | AAGCCGCGGGATAAGAAGTG |
| 5511 | SPAFB1E7.10_DN | CACCTCCGAAAATCCCGCCT | 5613 | SPBC1105.03c_DN | GCAGCCGCCCAATAACCTCG |
| 5512 | SPAFB1E7.11c_UP | AAAATGGCGCGGACAATGCA | 5614 | SPBC1105.04c_UP | CGCGCCCGTTCATCGATGAT |
| 5513 | SPAFB1E7.11c_DN | AGATGGAGGGGCAGCAAGCA | 5615 | SPBC1105.04c_DN | CGGTGGTGCTCCTGTTCGTG |
| 5514 | SPAFB1E7.12_UP | ACCCTGCACAACGAGCCCCT | 5616 | SPBC1105.05_UP | TCAGCCCCGCCAGTGTTGTC |
| 5515 | SPAFB1E7.12_DN | CCCGAATCCGCGCATAAAGTT | 5617 | SPBC1105.05_DN | CGCCTTGAGTCACCACCCGT |
| 5516 | SPAFB21F2.02_UP | GACGGCGCGGAGCTGAGAAA | 5618 | SPBC1105.06_UP | TGATTCTTCTCCGCACCGAG |
| 5517 | SPAFB21F2.02_DN | GTCCGTTGGGCTGCGTGTCC | 5619 | SPBC1105.06_DN | ACCCAGTAGGCTAGAGCGGT |
| 5518 | SPAFB24D3.02c_UP | ACGACCTTACCCGCACCCAA | 5620 | SPBC1105.07c_UP | CCTTACGCCACCGCTCCCTA |
| 5519 | SPAFB24D3.02c_DN | ACTGGCTTCCCCGACTCCCG | 5621 | SPBC1105.07c_DN | TTATGTGGTTCGCGCCCGTC |
| 5520 | SPAFB24D3.03_UP | AGTGCTGGAAATGCGTGTCG | 5622 | SPBC1105.09_UP | AAGCACAGGGAAGACCCCGA |
| 5521 | SPAFB24D3.03_DN | TAGACCGGCACAAGGAGCCCG | 5623 | SPBC1105.09_DN | TTCGGAGGATTGGGCTGGAC |
| 5522 | SPAFB24D3.04c_UP | CTTCGGCGCACGCGATTGA | 5624 | SPBC1105.10_UP | TCAAGAGGCGCGGGATCACT |
| 5523 | SPAFB24D3.04c_DN | TTGGGGCCGACGATGATGAG | 5625 | SPBC1105.10_DN | CCCATTGGCCGGGTCGTTAA |
| 5524 | SPAFB24D3.06c_UP | GGGAGACCCCGCGAATGTA | 5626 | SPBC1105.11c_UP | CAGTCGGCAGGTGGTAGGCC |
| 5525 | SPAFB24D3.06c_DN | CTATGGTGGAACTCGGCGGG | 5627 | SPBC1105.11c_DN | TCGTTGCTGCATCCCTCGCG |
| 5526 | SPAFB24D3.07c_UP | CCAAACACGCTACCGACCCA | 5628 | SPBC1105.12_UP | CCGAATGAGCCCAAGGCCAC |
| 5527 | SPAFB24D3.07c_DN | GTGAAGGGTTAGGGGCGGCG | 5629 | SPBC1105.12_DN | GGGCCGGACAAAAAAGGCAG |
| 5528 | SPAFB24D3.08c_UP | CTTCTCAACTCGCCTGCCCG | 5630 | SPBC1105.13c_UP | TGCTGGTTGACTCCGTGGGG |
| 5529 | SPAFB24D3.08c_DN | GTGCGGGAGTTAGCGTCG | 5631 | SPBC1105.13c_DN | GCCGCCCAATACCGAAGACG |
| 5530 | SPAFB24D3.09c_UP | ATTATGGAGCTAGCGGCCGG | 5632 | SPBC1105.14_UP | CGCTGCCGCATTTGAGAAAG |
| 5531 | SPAFB24D3.09c_DN | ATAAATGGCGATCGGGGCT | 5633 | SPBC1105.14_DN | CCGTTTCACTCGCATCGCAT |
| 5532 | SPAFB24D3.10c_UP | ATCTCCCGTTCGCGCTCTCC | 5634 | SPBC1105.15c_UP | GACGCACACTCCTCCCCCAT |
| 5533 | SPAFB24D3.10c_DN | CCAAATGAGGCAAGCGGGTG | 5635 | SPBC1105.15c_DN | CGCACCACACTAGCCCCCAC |
| 5534 | SPAFB2B4.01c_UP | GTAGGTAGCGCGCTGTACAA | 5636 | SPBC1105.16c_UP | TGTTCTCCCGCCCAGCCAGC |
| 5535 | SPAFB2B4.01c_DN | TGTAGCGATCGGGGAAGTC | 5637 | SPBC1105.16c_DN | AATGGACGGGGCAACACAGG |
| 5536 | SPAFB2B4.03_UP | GCTTGGACTGGGGGAAGGTTG | 5638 | SPBC1105.18c_UP | TCGGGGATAGCGGTTTGGA |
| 5537 | SPAFB2B4.03_DN | TACATACAGCGGGGAGGCGG | 5639 | SPBC1105.18c_DN | TCTGGTGCCGGGAATGAACA |
| 5538 | SPAFB2B4.04c_UP | CCGGCGATGTCGAGATGGAC | 5640 | SPBC115.01c_UP | CCGATGGGGCCAACCTGTTT |
| 5539 | SPAFB2B4.04c_DN | TGCTTACGACCGCGCCGATC | 5641 | SPBC115.01c_DN | TCCCGCATTCAGAGCCCATT |
| 5540 | SPAFB2B4.05_UP | GTCTTGGGTGCGAATGGCG | 5642 | SPBC115.02c_UP | AGAAACATCCGGGCGCACAA |
| 5541 | SPAFB2B4.05_DN | AGTCGCAGCGTGACTACCAG | 5643 | SPBC115.02c_DN | TTCGGAGACTTCGGGGGGTC |
| 5542 | SPAFB2B4.07_UP | CTGGGCTGAGGGAGGGACTG | 5644 | SPBC119.01_UP | CCCCTTCCACGTGCTTGCG |
| 5543 | SPAFB2B4.07_DN | ACATTGACCGCTTGGCCCTG | 5645 | SPBC119.01_DN | CGCGATTGGGCCTGTTTGCT |
| 5544 | SPAFB2C8.01_UP | TTGGGGTCATGGCGGGTCTA | 5646 | SPBC119.02_UP | TGACGTTCTTTTTGGCGGCG |
| 5545 | SPAFB2C8.03_DN | CGTGAGTTGCGAGGATGGCG | 5647 | SPBC119.02_DN | ATCGTCAACCGCCAAAACG |
| 5546 | SPAFB9E5.02c_UP | CCTATGACGGAACGGCCCAA | 5648 | SPBC119.03_UP | TTCAGCCCCGATCCAGAGCC |
| 5547 | SPAFB9E5.02c_DN | ACGAACCGCGTGGACGAAAC | 5649 | SPBC119.03_DN | CGACAAAGGAACGGCCGATG |
| 5548 | SPAFB9E5.03_UP | TGATTTGTCGGTTGGGCGTC | 5650 | SPBC119.04_UP | CTGCTTCTGCCGTTATCGACC |
| 5549 | SPAFB9E5.03_DN | ATCCTGTCCCCTCTTGGCA | 5651 | SPBC119.04_DN | CTGAAGACCCTGCGCGTGGG |
| 5550 | SPAFB9E5.04c_UP | GCCGACACCTGCCTGAAACC | 5652 | SPBC119.05c_UP | GCTTTCAGGGACGGGACCGG |
| 5551 | SPAFB9E5.04c_DN | GAAAGGAACGGGGCATCGA | 5653 | SPBC119.05c_DN | ATATCGGCCACCCCCTGCTC |
| 5552 | SPAFB9E5.05_UP | TACGCGGGTCGTCTGGCCTC | 5654 | SPBC119.06_UP | GGGTAAATGGGACCGTGCGG |
| 5553 | SPAFB9E5.05_DN | TAGGCGCCCACGCGTTTAGT | 5655 | SPBC119.06_DN | TACCTCTCCGCCCCACCTCC |
| 5554 | SPAFB9E5.06_UP | CGCCGCTTCACTATACCCCG | 5656 | SPBC119.07_UP | AGCCCTGCCAACCTACGTCG |
| 5555 | SPAFB9E5.06c_DN | GAACATCCCACAGGGGCGC | 5657 | SPBC119.07_DN | GTAGTGCGGGAAAAGGGGGC |
| 5556 | SPAFB9E5.07c_UP | GACAGGCAACTCAACCGCCA | 5658 | SPBC119.08_UP | CCTTACAACAACCGCCCCCC |
| 5557 | SPAFB9E5.07c_DN | AGGGCCGGATGTGCAGGTATG | 5659 | SPBC119.09_DN | AACCCCGTCCCGTCTTCGCT |
| 5558 | SPAFB9E5.08_UP | TTCCGCCGCACTGATTACGA | 5660 | SPBC119.12_UP | CCGTTATTGTGGTGCGCGGG |
| 5559 | SPAFB9E5.08_DN | TAGCGCCGGATGTTTCCAA | 5661 | SPBC119.12_DN | ACCACCCCTTAAACGGCCGC |
| 5560 | SPAPJ691.02_UP | TGCCTGGAGTGGGGGAGAT | 5662 | SPBC119.14_UP | CTACCCATCCCCTGCCGTCG |
| 5561 | SPAPJ691.02_DN | ATCAGCTCCAGGCCGGTCCA | 5663 | SPBC119.14_DN | CCGGAAGGGCGCACGGATTAT |
| 5562 | SPAPJ695.01c_UP | AGAAGCTTGGGCGTGGTA | 5664 | SPBC119.15_UP | CTCGGGAAACGGGGGCTTGAT |
| 5563 | SPAPJ695.01c_DN | TCCGGGTGCCTTACATTTGG | 5665 | SPBC119.15_DN | CGTAGGAACAGTGGCGCGAG |
| 5564 | SPAPJ596.01c_UP | TTGATCTGCCTTGGACCCCC | 5666 | SPBC119.15c_UP | AGTCAAAAGGCGCGAGTCC |
| 5565 | SPAPJ596.01c_DN | ACCACACCACAAAGCCGGCC | 5667 | SPBC119.15c_DN | CGCCAATGTCAACCCCGGAG |
| 5566 | SPAPJ596.02_UP | ACAAAAAGGGCGTCCTCGGG | 5668 | SPBC119.18_UP | AAGTGACCCGCAGTCGCACA |
| 5567 | SPAPJ596.02_DN | TGAGATTTGCGTCTTGCCGG | 5669 | SPBC119.18_DN | ACACAGGGCTAGTCCGCAGT |
| 5568 | SPAPJ598.03c_UP | GCGTATTGGTCGGTGGGCGA | 5670 | SPBC1198.01_UP | AAAAAAACTGGTCGGGGCG |
| 5569 | SPAPJ598.03c_DN | TCGCAGTTCCAGTCGTTCGCC | 5671 | SPBC1198.01_DN | GCCCACGCGACCATGCATCT |
| 5570 | SPAPJ760.02c_UP | CGGCGTTCACGACAGTGGTT | 5672 | SPBC1198.02_UP | GATGCGTTTTTGGGGCGAAG |
| 5571 | SPAPJ760.02c_DN | CAAGTGCCTGACGTTCGCCT | 5673 | SPBC1198.02_DN | CCCCCTTTTCTGTGGTCGCA |
| 5572 | SPAPJ760.03c_UP | TTAACGGGGCTGCGTGTGGC | 5674 | SPBC1198.03c_UP | CCCACACTTAAGCCGCAGC |
| 5573 | SPAPJ760.03c_DN | CTCACCGCGCCAGACGTTTT | 5675 | SPBC1198.03c_DN | CATGCCAATCCAGCCCCACG |
| 5574 | SPAPYUG7.03c_UP | CTTCCTGGCGGGCGTGTTT | 5676 | SPBC1198.05_UP | GCGTCTTTGTCGCCATGGGC |
| 5575 | SPAPYUG7.03c_DN | GGCTTGCGTTGGGAATTGG | 5677 | SPBC1198.05_DN | GCAAAGGGACAGGACCCGT |
| 5576 | SPAPYUG7.04c_UP | TGCAAAGGCGTCGTCAGGTT | 5678 | SPBC1198.06_UP | GCTTCTTGGGTGGCATTCGG |
| 5577 | SPAPYUG7.04c_DN | AGGACTCAATCCACCACCAC | 5679 | SPBC1198.06c_DN | CTCCCGAACAGGCAAACCGC |
| 5578 | SPAPYUG7.06_UP | CGACACCGAAGCAGGCAAC | 5680 | SPBC1198.07c_UP | TGCTGCTTTCGGTTCCCTCA |
| 5579 | SPAPYUG7.06_DN | GTCAACGGCACCCGTGTCCA | 5681 | SPBC1198.07c_DN | AAGGCACCCCACCCAGCATC |
| 5580 | SPAPYUK71.03c_UP | GCGCGGGGCATCTAGGTGT | 5682 | SPBC1198.08_UP | CAGCCAAGCCCTCCCTCCAC |
| 5581 | SPAPYUK71.03c_DN | CCCGCCTAGGATGCAAGTC | 5683 | SPBC1198.08_DN | CATAGCGCGCGGGAATCTCA |
| 5582 | SPBC106.02c_UP | GGAGTTTGGCCTGTACGCCC | 5684 | SPBC1198.09_UP | GCAAGGAGCGGAAGGCTGGG |
| 5583 | SPBC106.02c_DN | GCCGCAGAAAAGACCCGCTA | 5685 | SPBC1198.09_DN | GGGAGGGTTTCTGGCGGAG |
| 5584 | SPBC106.03_UP | TGCTCAACACACCGCCGACC | 5686 | SPBC1198.10c_UP | TGACGAATTTGAACCCGCG |
| 5585 | SPBC106.03_DN | CGTCGCGCGTGTCTCTGTCT | 5687 | SPBC1198.10c_DN | CCGAGGTTGTATGGGAGCGC |
| 5586 | SPBC106.04_UP | GGTCCCCAATTCCTCACGCCG | 5688 | SPBC11B10.01_UP | TGACGCGCCAGCCTTACTTG |
| 5587 | SPBC106.04_DN | GGTTAAGGAGCGAGGGGGCG | 5689 | SPBC11B10.01_DN | TTTTGGGGTTGGCGGTGGAC |
| 5588 | SPBC106.05c_UP | ACCCATCCCACGCAATCGAA | 5690 | SPBC11B10.02c_UP | TGGGTTCTAGCCGAGCGAC |
| 5589 | SPBC106.05c_DN | CGCACATATCGGTCCCCAGG | 5691 | SPBC11B10.02c_DN | ATCCCTGACAGGCCCTTGTG |
| 5590 | SPBC106.06_UP | CCGGGAATATCTAGGCGCCA | 5692 | SPBC11B10.03_UP | AGAGCGGCGACGAGGAGAGG |
| 5591 | SPBC106.06_DN | AGAAGCCGCGATCCCACGTC | 5693 | SPBC11B10.03_DN | TCGCCCTGACGCCTACCATT |
| 5592 | SPBC106.08c_UP | CCGTTCTCCCCCGATCCTCT | 5694 | SPBC11B10.04c_UP | GGCCGATGCCTAATGCTTGC |
| 5593 | SPBC106.08c_DN | CCGCCGGAGCACGAATAAAC | 5695 | SPBC11B10.04c_DN | CGTTCCAGGGTGGGCGCTTA |
| 5594 | SPBC106.09_UP | ATCGCAGTCTAGCCTTGCGG | 5696 | SPBC11B10.05c_UP | CACGCGCATCACCCACCGTCT |
| 5595 | SPBC106.09_DN | TGGGGTCCCACGCGTATCCAA | 5697 | SPBC11B10.05c_DN | CAAPTGCATCCACACAGGCCGT |
| 5596 | SPBC106.10_UP | CAGCCCCCAAAAGAGGCAGA | 5698 | SPBC11B10.06_UP | TGGGTGCGGATTCTAGGGCC |
| 5597 | SPBC106.10_DN | GGATAGGGAACTCGGGCGCG | 5699 | SPBC11B10.06_DN | AGACGGGGAGTAGGCGGTT |
| 5598 | SPBC106.11c_UP | CGGAACTGCTGCCCCACCTA | 5700 | SPBC11B10.07c_UP | TCTTGTTGTGGTGCGGGGCA |
| 5599 | SPBC106.11c_DN | CACGAGCGGAGGGAGGAATC | 5701 | SPBC11B10.07c_DN | ATGGGGGCTCAGGGAGAGG |
| 5600 | SPBC106.12c_UP | CAGTATGGCGACCAGCCTGT | 5702 | SPBC11B10.08_UP | ACCCGCGACCTTCACCACCGA |
| 5601 | SPBC106.12c_DN | TAACTAAACGGCGCGCCA | 5703 | SPBC11B10.08_DN | CAACCGCGCAAGGAGCATCA |
| 5602 | SPBC106.13_UP | CTCGCGGCCACAAAAGCTCA | 5704 | SPBC11B10.09_UP | CCTGTGTCTGGCACCTGCG |
| 5603 | SPBC106.13_DN | GTTTGAGCGACGGCAGGTGA | 5705 | SPBC11B10.09_DN | GGGGCTTGGGGTACGTGAGG |
| 5604 | SPBC106.14c_UP | GTGATTTTCGGTGCGACGCC | 5706 | SPBC11B10.10c_UP | CCCCCTGTGGATGTTTGGCC |
| 5605 | SPBC106.14c_DN | TACTTGGTCTGCCCGCCTGGC | 5707 | SPBC11B10.10c_DN | TGGCGGGTAGGTCGAGGAAC |
| 5606 | SPBC106.16_UP | ACTCCCATCCAACCGACCCA | 5708 | SPBC11C11.02_UP | GCCTTGGGTGGTGCCGTTAT |
| 5607 | SPBC106.16_DN | ATGATGTACCCGCGGCCTTC | 5709 | SPBC11C11.02_DN | CAGGGGTACGGGACGGGAAT |
| 5608 | SPBC106.17c_UP | CGCCGGCCTTTTCATTGGTA | 5710 | SPBC11C11.03_UP | CCCAAGGTTCGCACTCGGTC |
| 5609 | SPBC106.17c_DN | TGAACCGGACCACCCAGCTA | 5711 | SPBC11C11.03_DN | TTGGGCCGCGGTGTAAATC |
| 5610 | SPBC1105.02c_UP | CGAAAGGTCAACGGCAGGGC | 5712 | SPBC11C11.05_UP | TTGCTTGCGCGGACTTTTCG |

FIG.35

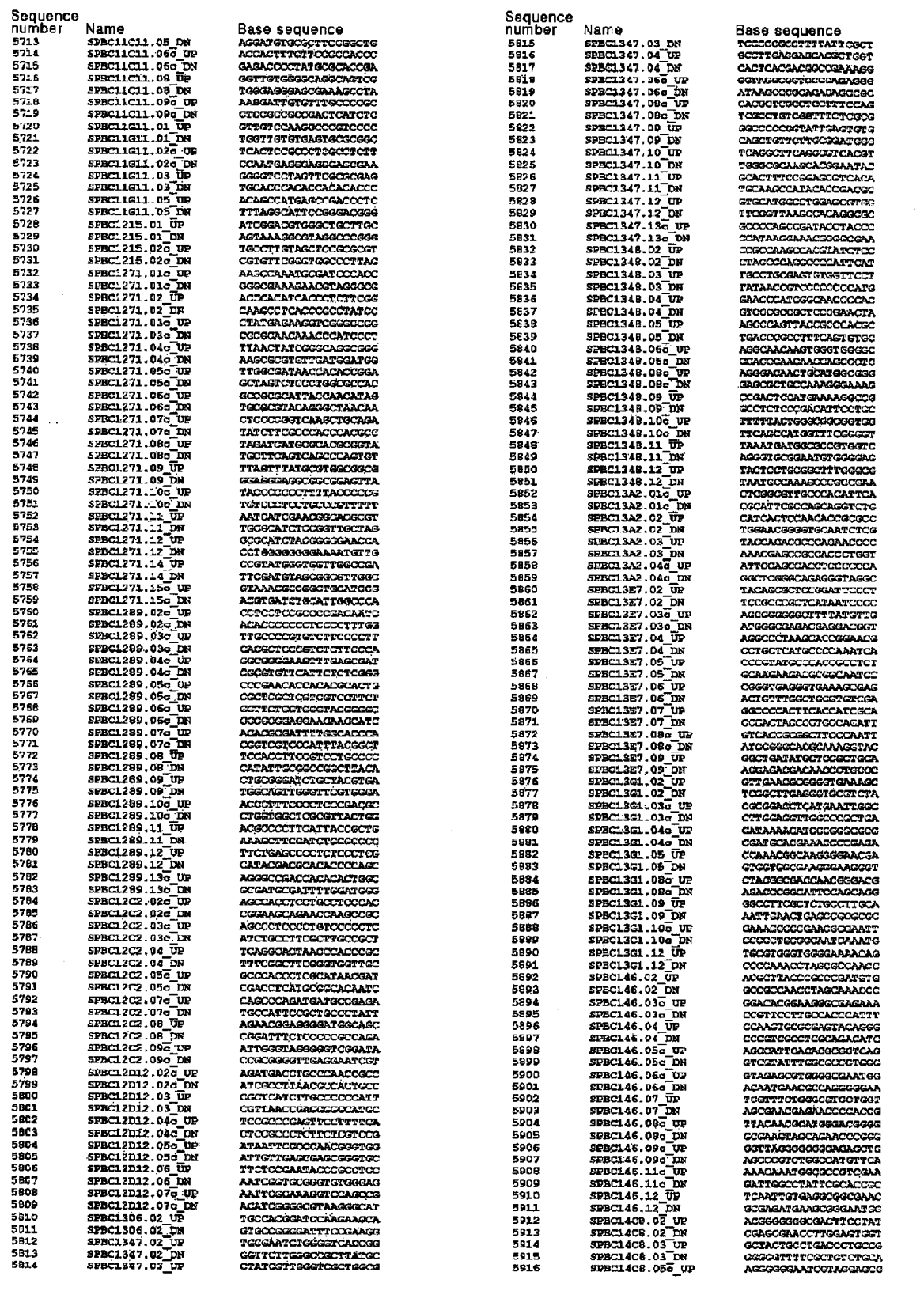

| Sequence number | Name | Base sequence |
|---|---|---|
| 5713 | SPBC11C11.05_DN | AGGATGTGCGCTTCCGGCTG |
| 5714 | SPBC11C11.06c_UP | ACCACTTTGTTCCGCCACCC |
| 5715 | SPBC11C11.06c_DN | GAGACCCCTATGCGCACCGA |
| 5716 | SPBC11C11.08_UP | GGTTGTGGGGCAGGCAGTCG |
| 5717 | SPBC11C11.08_DN | TGGGAGGGAGCGAAAGCCTA |
| 5718 | SPBC11C11.09c_UP | AAGGATTGTGTTTGCCCCGC |
| 5719 | SPBC11C11.09c_DN | CTCCGCCGCCGACTCATCTC |
| 5720 | SPBC11G11.01_UP | GTTGTCCAAGGCCCGTCCCC |
| 5721 | SPBC11G11.01_DN | TGGTTGTGTGAGTGCGCGGC |
| 5722 | SPBC11G11.02c_UP | TCACTCCGCCCTCGCCTCTT |
| 5723 | SPBC11G11.02c_DN | CCAATGAGGGAGGGAGCGAA |
| 5724 | SPBC11G11.03_UP | GGGGTCCTAGTTCGCGCGAG |
| 5725 | SPBC11G11.03_DN | TGCACCCACACCACACACCC |
| 5726 | SPBC11G11.05_UP | ACAGCCATGAGCCGACCCTC |
| 5727 | SPBC11G11.05_DN | TTTAGGCATTCCGGGACGGG |
| 5728 | SPBC1215.01_UP | ATCGGACGTGGGCTGCTTGC |
| 5729 | SPBC1215.01_DN | AGTAAAGGCGTAGGCCCGGG |
| 5730 | SPBC1215.02c_UP | TGCCTTGTAGCTCCGCGCGT |
| 5731 | SPBC1215.02c_DN | CGTGTTCGGGTGGCCCTTAG |
| 5732 | SPBC1271.01c_UP | AAGCCAAATGCGATCCCACC |
| 5733 | SPBC1271.01c_DN | GGGCGAAAGAACGTAGGGCC |
| 5734 | SPBC1271.02_UP | ACCCACATCACCCTCTTCGG |
| 5735 | SPBC1271.02_DN | CAAGCCTCACCCGCCTATCC |
| 5736 | SPBC1271.03c_UP | CTATGAGAAGGTCGGGGCGG |
| 5737 | SPBC1271.03c_DN | CGCGCAACAAACCCATCCCT |
| 5738 | SPBC1271.04c_UP | TTAACTATCGGGCAGGCGGG |
| 5739 | SPBC1271.04c_DN | AAGCGCGTGTTGATGGATGG |
| 5740 | SPBC1271.05c_UP | TTGGCGATAACCACACCGGA |
| 5741 | SPBC1271.05c_DN | GCTAGTCTCCCTGGCGCCAC |
| 5742 | SPBC1271.06c_UP | GCCGCGCATTACCAACATAG |
| 5743 | SPBC1271.06c_DN | TGCGCGTACAGGGCTAACAA |
| 5744 | SPBC1271.07c_UP | CTCCCCGGTCAAGCTGCAGA |
| 5745 | SPBC1271.07c_DN | TATCTTCGCCCACCCACGCC |
| 5746 | SPBC1271.08c_UP | TAGATCATGCGCACGCGGTA |
| 5747 | SPBC1271.08c_DN | TGCTTCAGTCAGCCCAGTGT |
| 5748 | SPBC1271.09_UP | TTAGTTTATGCGTGGCGGCG |
| 5749 | SPBC1271.09_DN | GGAGGGAGGCGGCGGAGTTA |
| 5750 | SPBC1271.10c_UP | TACCCCCCCTTTTACCCCCG |
| 5751 | SPBC1271.10c_DN | TGTCCCTCCTGCCCGTTTTT |
| 5752 | SPBC1271.11_UP | AATCATCGAACGGCACGCGT |
| 5753 | SPBC1271.11_DN | TGCGCATCTCCGGTTGCTAG |
| 5754 | SPBC1271.12_UP | GCGCATCTACGGGGGAACCA |
| 5755 | SPBC1271.12_DN | CCTGGGGGGGAAAATGTTG |
| 5756 | SPBC1271.14_UP | CCGTATGGGTGGTTGGCCGA |
| 5757 | SPBC1271.14_DN | TTCGATGTAGCGGCGTTGGC |
| 5758 | SPBC1271.15c_UP | GTAAACGCCGGCTGCATCCG |
| 5759 | SPBC1271.15c_DN | ACGTGATCTGCATTGGCCCA |
| 5760 | SPBC1289.02c_UP | CCTCCTCCGCCCCGACAATC |
| 5761 | SPBC1289.02c_DN | ACACCCCCCCTCCCCTTTGG |
| 5762 | SPBC1289.03c_UP | TTGCCCCGTGTCTTCCCCTT |
| 5763 | SPBC1289.03c_DN | CACGCTCCCGTCTCTTCCCA |
| 5764 | SPBC1289.04c_UP | GGCGGGGAAGTTTGAGCGAT |
| 5765 | SPBC1289.04c_DN | CGCGTGTTCATTCTCTCGGG |
| 5766 | SPBC1289.05c_UP | CCCGAACACCACACGCACTG |
| 5767 | SPBC1289.05c_DN | CGCTCGCTCGTCGTCCTTCT |
| 5768 | SPBC1289.06c_UP | GCTTCTGGTGGGTACGGGGC |
| 5769 | SPBC1289.06c_DN | GCCGCGGAGGAAGAAGCATC |
| 5770 | SPBC1289.07c_UP | ACACGCGATTTTGGCACCCA |
| 5771 | SPBC1289.07c_DN | CGGTCGTCCCATTTACGGCT |
| 5772 | SPBC1289.08_UP | TCCACCTTCCGTCCTGCCCC |
| 5773 | SPBC1289.08_DN | CATATTCCGGCCGGCTTACA |
| 5774 | SPBC1289.09_UP | CTGCGGGATCTGCTACGTGA |
| 5775 | SPBC1289.09_DN | TGGCAGTTGGGTTCGTGGGA |
| 5776 | SPBC1289.10c_UP | ACCCTTTCCCCTCCCGACGC |
| 5777 | SPBC1289.10c_DN | CTGGTGGCTCGCGTTACTGC |
| 5778 | SPBC1289.11_UP | ACGCCCCTTCATTACCGCTG |
| 5779 | SPBC1289.11_DN | AAAGCTTCGATCTGCGCCCC |
| 5780 | SPBC1289.12_UP | TTCTGAGCCCCTCTCCCTCG |
| 5781 | SPBC1289.12_DN | CATACGACGCACACCCCAGC |
| 5782 | SPBC1289.13c_UP | AGGGCCGACCACACACTGGC |
| 5783 | SPBC1289.13c_DN | GCGATGCGATTTTGGATGGG |
| 5784 | SPBC12C2.02c_UP | AGCCACCTCCTGCCTCCCAC |
| 5785 | SPBC12C2.02c_DN | CGGAAGCAGAACCAAGCCGC |
| 5786 | SPBC12C2.03c_UP | AGCCCTCCCCTGTCCCCCTC |
| 5787 | SPBC12C2.03c_DN | ATCTGCCTTCGCTTGCCGCT |
| 5788 | SPBC12C2.04_UP | TCAGGCACTAACCCACCCGC |
| 5789 | SPBC12C2.04_DN | TTTCGGCTTCGGGTGGTTGC |
| 5790 | SPBC12C2.05c_UP | GCCCACCCTCGCATAACGAT |
| 5791 | SPBC12C2.05c_DN | CGACCTCATGCGGCACAATC |
| 5792 | SPBC12C2.07c_UP | CAGCCCAGATGATGCCGAGA |
| 5793 | SPBC12C2.07c_DN | TGCCATTCCGCTGCCCTATT |
| 5794 | SPBC12C2.08_UP | AGAACGGAGGGGATGGCAGC |
| 5795 | SPBC12C2.08_DN | CGGATTTCTCCCCCGCCAGA |
| 5796 | SPBC12C2.09c_UP | ATTGGGTAGGGGGTCGGATA |
| 5797 | SPBC12C2.09c_DN | CCGCGGGGTTGAGGAATCGT |
| 5798 | SPBC12D12.02c_UP | AGATGACCTGCCCAACCGCC |
| 5799 | SPBC12D12.02c_DN | ATCGCCTTAACGCCACTGCC |
| 5800 | SPBC12D12.03_UP | CGCTCATCTTGCCCCCCATT |
| 5801 | SPBC12D12.03_DN | CGTTAACCGAGGGGGCATGC |
| 5802 | SPBC12D12.04c_UP | TCCGCCCGAGTTCCTTTTCA |
| 5803 | SPBC12D12.04c_DN | CTCCGCCCTCTTCTCGTCCG |
| 5804 | SPBC12D12.05c_UP | ATAATTCGCCCAACGGGTGG |
| 5805 | SPBC12D12.05c_DN | ATTGTTGAGCGAGCGGGTGC |
| 5806 | SPBC12D12.06_UP | TTCTCCGAATACCCGCCTCC |
| 5807 | SPBC12D12.06_DN | AATCGGTGCGGGTGTGGGAG |
| 5808 | SPBC12D12.07c_UP | AATTCGCAAAGGTCCAGCCG |
| 5809 | SPBC12D12.07c_DN | ACATCGGGGCGTAAGGGCAT |
| 5810 | SPBC1306.02_UP | TGCCACGGATCCAAGAAGCA |
| 5811 | SPBC1306.02_DN | GTGCCGGGGATTTCCGAAGG |
| 5812 | SPBC1347.02_UP | TGCGAATCTGGGGTCACCGG |
| 5813 | SPBC1347.02_DN | GGTTCTTGGGCCGCTTATGC |
| 5814 | SPBC1347.03_UP | CTATCGTTGGGTCGCTGGCG |
| 5815 | SPBC1347.03_DN | TCCCCCGCCTTTTATTCGCT |
| 5816 | SPBC1347.04_UP | GCCTTGAGGAGCACGCTGGT |
| 5817 | SPBC1347.04_DN | CACTCACGACGGCCGAAAGG |
| 5818 | SPBC1347.06c_UP | GGTAGGCGGTGCGGAGAGGG |
| 5819 | SPBC1347.06c_DN | ATAAGCCCGCACACAGCCGC |
| 5820 | SPBC1347.08c_UP | CACGCTCGCCTCCTTTCCAG |
| 5821 | SPBC1347.08c_DN | TCGCCTGTCGGTTTCTCGCG |
| 5822 | SPBC1347.09_UP | GGCCCCCGGTATTGAGTGTG |
| 5823 | SPBC1347.09_DN | CAGCTGTTCTTGCGGATGGG |
| 5824 | SPBC1347.10_UP | TCAGGCTTCAGCCGTCACGT |
| 5825 | SPBC1347.10_DN | TGGGCGCAAGCACGGAATAC |
| 5826 | SPBC1347.11_UP | GCACTTTCCGGAGCGTCACA |
| 5827 | SPBC1347.11_DN | TGCAAGCCATACACCGACGC |
| 5828 | SPBC1347.12_UP | GTGCATGGCCTGGAGCGTGG |
| 5829 | SPBC1347.12_DN | TTCGGTTAAGCCACAGGCGC |
| 5830 | SPBC1347.13c_UP | GCCCCAGCCGATACCTACCC |
| 5831 | SPBC1347.13c_DN | CCATAAGGAAACGGGGCGAA |
| 5832 | SPBC1348.02_UP | CCGCCAAGCCACGTATCTCC |
| 5833 | SPBC1348.02_DN | CTAGCCCAGGCCCCATTCAT |
| 5834 | SPBC1348.03_UP | TGCCTGCGAGTGTGGTTCCT |
| 5835 | SPBC1348.03_DN | TATAACCGTCCCCCCCCATG |
| 5836 | SPBC1348.04_UP | GAACCCATCGGCAACCCCAC |
| 5837 | SPBC1348.04_DN | GTCCCGCCGCTCCCGAACTA |
| 5838 | SPBC1348.05_UP | AGCCCAGTTACCGCCCACGC |
| 5839 | SPBC1348.05_DN | TGACCGGCCTTTCAGTGTGC |
| 5840 | SPBC1348.06c_UP | AGGCAACAAGTGGGTGGGGC |
| 5841 | SPBC1348.06c_DN | GCAGCCAACAACCAGCCCTC |
| 5842 | SPBC1348.08c_UP | AGGGACAACTGCATGGCGGG |
| 5843 | SPBC1348.08c_DN | GAGCGCTGCCAAAGGGAAAG |
| 5844 | SPBC1348.09_UP | CCGACTCCATGAAAAGGCCG |
| 5845 | SPBC1348.09_DN | GCCTCTCCCGACATTCCTGC |
| 5846 | SPBC1348.10c_UP | TTTTTACTGGGCGGCGGTGG |
| 5847 | SPBC1348.10c_DN | TTCAGCCATGGTTTCGGGGT |
| 5848 | SPBC1348.11_UP | TAAATGATGGCGCCGTGGTC |
| 5849 | SPBC1348.11_DN | AGGGTGCGGAATGTGGGGAG |
| 5850 | SPBC1348.12_UP | TACTCCTGCGGCTTTGGGCG |
| 5851 | SPBC1348.12_DN | TAATGCCAAAGCCCGCCGAA |
| 5852 | SPBC13A2.01c_UP | CTCGGCGTTGCCCACATTCA |
| 5853 | SPBC13A2.01c_DN | CGCATTCGCCAGCAGGTCTG |
| 5854 | SPBC13A2.02_UP | CATCACTCCAACACCGCGCC |
| 5855 | SPBC13A2.02_DN | TGGAACGGGGTGCAATCTCG |
| 5856 | SPBC13A2.03_UP | TAGCAGACGCCCAGAACCCC |
| 5857 | SPBC13A2.03_DN | AAACGAGCCGCCACCCTGGT |
| 5858 | SPBC13A2.04c_UP | ATTCCAGCCACCTCCCCCCA |
| 5859 | SPBC13A2.04c_DN | GGCTCGGGCAGAGGGTAGGC |
| 5860 | SPBC13E7.02_UP | TACAGCGCTCCGGATTCCCT |
| 5861 | SPBC13E7.02_DN | TCCGCCCGCTCATAATCCCC |
| 5862 | SPBC13E7.03c_UP | AGCCGGGGGCTTTTATGTTG |
| 5863 | SPBC13E7.03c_DN | ATGGGCGAGACGAGGACGGT |
| 5864 | SPBC13E7.04_UP | AGGCCCTAAGCACCGGAACG |
| 5865 | SPBC13E7.04_DN | CCTGCTCATGCCCCAAATCA |
| 5866 | SPBC13E7.05_UP | CCCGTATGCCCACCGCCTCT |
| 5867 | SPBC13E7.05_DN | GCAAGAAGACGCGGCAATCC |
| 5868 | SPBC13E7.06_UP | CGGGTGAGGGTGAAAGCGAG |
| 5869 | SPBC13E7.06_DN | ACTGTTTGGCTGCGTGTCGA |
| 5870 | SPBC13E7.07_UP | GGCCCCACTTCACCATCGCA |
| 5871 | SPBC13E7.07_DN | CCGACTACCCCTGCCAGATT |
| 5872 | SPBC13E7.08c_UP | GTCACCGCGGCTTCCCAATT |
| 5873 | SPBC13E7.08c_DN | ATCCGGGCACGCAAAGGTAC |
| 5874 | SPBC13E7.09_UP | GGCTGATATGCTCGGCTGCA |
| 5875 | SPBC13E7.09_DN | ACGAGACGACAACCCTGCCC |
| 5876 | SPBC13G1.02_UP | GTTGAACGCGGGGTGAAAGC |
| 5877 | SPBC13G1.02_DN | TCGGCTTGAGCGTGCGTCTA |
| 5878 | SPBC13G1.03c_UP | CGCGGAGCTCATGAATTGGC |
| 5879 | SPBC13G1.03c_DN | CTTGCAGGTTGGCCCGCTCA |
| 5880 | SPBC13G1.04c_UP | CATAAAACATCCCGGGCGCG |
| 5881 | SPBC13G1.04c_DN | CGATGCACGAAACCCCGAGA |
| 5882 | SPBC13G1.05_UP | CCAAACGGCAAGGGGAACGA |
| 5883 | SPBC13G1.05_DN | GTGGTGGCGAAGGGAAGGGT |
| 5884 | SPBC13G1.08c_UP | CTACGGCGACCAACGGGACG |
| 5885 | SPBC13G1.08c_DN | AGACCCGGCATTCCAGCAGG |
| 5886 | SPBC13G1.09_UP | GGCCTTCGCTCTGCCTTGCA |
| 5887 | SPBC13G1.09_DN | AATTGAACTGAGCCGCGCGC |
| 5888 | SPBC13G1.10c_UP | GAAAGGCCCGAACGCGAATT |
| 5889 | SPBC13G1.10c_DN | CCCCCTGCGGCAATCAAATG |
| 5890 | SPBC13G1.12_UP | TGCGTGGGTGGGGAAAACAG |
| 5891 | SPBC13G1.12_DN | CCCCAAACCTAGCGCCAACC |
| 5892 | SPBC146.02_UP | ACGCTTACCCGCCCGATGTG |
| 5893 | SPBC146.02_DN | GCCGCCAACCTAGCAAACCC |
| 5894 | SPBC146.03c_UP | GGACACGGAAGGGCGAGAAA |
| 5895 | SPBC146.03c_DN | CCGTTCCTTGCCACCCATTT |
| 5896 | SPBC146.04_UP | CCAAGTGCGCGAGTACAGGG |
| 5897 | SPBC146.04_DN | CCCGTCGCCTCGCAGACATC |
| 5898 | SPBC146.05c_UP | AGCCATTCACACGCGGTCAG |
| 5899 | SPBC146.05c_DN | GTCGTATTTGGCGCCCTGGG |
| 5900 | SPBC146.06c_UP | GTAGAGCGTGGGGCGAATGG |
| 5901 | SPBC146.06c_DN | ACAATGAACGCCAGGGGGAA |
| 5902 | SPBC146.07_UP | TCGTTTCTGGGCGTGCTGGT |
| 5903 | SPBC146.07_DN | AGCGAACGAGAACCCCACCG |
| 5904 | SPBC146.09c_UP | TTACAACGCATGGGACGGGG |
| 5905 | SPBC146.09c_DN | GCGAAGTAGCAGAACCCGGG |
| 5906 | SPBC146.09c_UP | GGTTAGGGGGGGGAGAGCTG |
| 5907 | SPBC146.09c_DN | AGCCCGTCTGGCCATGTTCA |
| 5908 | SPBC146.11c_UP | AAACAAATGGCGCCGTCGAA |
| 5909 | SPBC146.11c_DN | GATTGGCCTATTCGCACCGC |
| 5910 | SPBC146.12_UP | TCAATTGTGAGGCGGCGAAC |
| 5911 | SPBC146.12_DN | GCGAGATGAAGCGGGAATGG |
| 5912 | SPBC14C8.02_UP | ACGGGGGGCGACTTCCTAT |
| 5913 | SPBC14C8.02_DN | CGAGCGAACCTTGGAGTGGT |
| 5914 | SPBC14C8.03_UP | GCTACTGCCTGACCCTGCCG |
| 5915 | SPBC14C8.03_DN | GGGGGTTTTCGCTGTCTGCA |
| 5916 | SPBC14C8.05c_UP | AGGGGGGAATCGTAGGAGCG |

FIG.36

| Sequence number | Name | Base sequence | Sequence number | Name | Base sequence |
|---|---|---|---|---|---|
| 5917 | SPBC14C8.05q_DN | GTTCCCCTGCCTCTTGCTGC | 6019 | SPBC1604.13c_DN | AATGAATGGTCAGCACGGGA |
| 5918 | SPBC14C8.06_UP | AGTAGCCACTCCACGCGCGC | 6020 | SPBC1604.14c_UP | AATGCCGTTCCCTGTCCTG |
| 5919 | SPBC14C8.06_DN | TACCGCTTCCCGGGTTCCTC | 6021 | SPBC1604.14c_DN | GCCGTACTACAGGGTCGCAA |
| 5920 | SPBC14C8.08c_UP | CCCTTCGATACCACCGCCAC | 6022 | SPBC1604.16c_UP | TAACCGAACCGCCTCACGCT |
| 5921 | SPBC14C8.08c_DN | CCGCCGATGTGAGTGATTGC | 6023 | SPBC1604.16c_DN | ACCTCGTTAGGGCCGATCCA |
| 5922 | SPBC14C8.09c_UP | CAGGGCGCAAGTGGGGTGTC | 6024 | SPBC1604.17c_UP | GCCCCCAGGCATCCGTCATT |
| 5923 | SPBC14C8.09c_DN | ACCCCACCGCGTTCATGCAG | 6025 | SPBC1604.17c_DN | ATGGAAGCGGCGAGCAAAGC |
| 5924 | SPBC14C8.10_UP | CGGGCCGCAACCCTTGATCT | 6026 | SPBC1604.18c_UP | GGGCGGCT7AACTTGGGGCA |
| 5925 | SPBC14C8.10_DN | TGTTATGCGGCACGACGGAC | 6027 | SPBC1604.18c_DN | GATCGGGGCCTGGGTGTGGT |
| 5926 | SPBC14C8.11c_UP | GGCTGTGGGCGAGGAGGGAG | 6028 | SPBC1604.19c_UP | CCCGAGCCGCCATAGACCTT |
| 5927 | SPBC14C8.11c_DN | AGAATCCGGCGCCATACAG | 6029 | SPBC1604.19c_DN | AATCCCCGTGTCCTCTCCCC |
| 5928 | SPBC14C8.12_UP | CCGTCGTTTCCCTAACCCCA | 6030 | SPBC1604.20c_UP | CAGCCCGTCGAACAGGCCAG |
| 5929 | SPBC14C8.12_DN | TTTCCGGACTTCCTGCCCAA | 6031 | SPBC1604.20c_DN | TCAGCCGAGCGCACATAAG |
| 5930 | SPBC14C8.13_UP | GATGATGTTCGGCCGGTTGGT | 6032 | SPBC1652.01_UP | AAGTGGGGTCGCCTATGGGA |
| 5931 | SPBC14C8.13_DN | TTGTGTTTTGAAGGCGCCGA | 6033 | SPBC1652.01_DN | GAGAATTGGGGGTCCCAGCC |
| 5932 | SPBC14C8.14c_UP | CATCTACGCCCAACCCGCTG | 6034 | SPBC1652.02_UP | GCGGCAGAGAGGCGGAAGAG |
| 5933 | SPBC14C8.14c_DN | GCGAAGACGAGAGGCTGGG | 6035 | SPBC1652.02_DN | AGACCGCCCAAACCCCAACG |
| 5934 | SPBC14C8.15_UP | GGTCTCCGCCGCCTCCTTAC | 6036 | SPBC1677.02_UP | CCTTGCAAAAACCCGGGGAA |
| 5935 | SPBC14C8.15_DN | CCGAGACGAAATGACGCGCA | 6037 | SPBC1677.02_DN | CGGGGGCAAGTGACGGGCTC |
| 5936 | SPBC14C8.16c_UP | ACCAAGGCCGCACCGATGAT | 6038 | SPBC1683.01_UP | TACAGACCGGCCTTCCGTG |
| 5937 | SPBC14C8.16c_DN | GCTGCCTTACGCGGGATTGG | 6039 | SPBC1683.01_DN | TGGGAGGTGTTGGCGTGAG |
| 5938 | SPBC14C8.17c_UP | TAATGGTCTTGGAGGTGGCG | 6040 | SPBC1683.02_UP | GCAGCAAAGCCGACTACCCG |
| 5939 | SPBC14C8.17c_DN | ACAGGGACCGATGAGAGGCG | 6041 | SPBC1683.02_DN | TCGCCTCGGTATCTTTCGGC |
| 5940 | SPBC14F5.01_UP | CGGATCCGGACTCGCTCATT | 6042 | SPBC1683.03c_UP | CGTTCCCCATCCCCATCCAC |
| 5941 | SPBC14F5.01_DN | TGAGCTCGACCGCACTAGGT | 6043 | SPBC1683.03c_DN | TCCTGCCCGACCTTTTGTGC |
| 5942 | SPBC14F5.02_UP | GCAGCAGTACGGGCCAACAA | 6044 | SPBC1683.04_UP | CGCCCAGCAGAGTTTCACCC |
| 5943 | SPBC14F5.02_DN | TCGCGGTGGTGCAAAGGAAA | 6045 | SPBC1683.04_DN | AGGCCGGCTCCCAACAAGAC |
| 5944 | SPBC14F5.04c_UP | CTTTCTCCGCTTGCCCGTTC | 6046 | SPBC1683.05_UP | TACTCGCCACCACCCCCATT |
| 5945 | SPBC14F5.04c_DN | GGACGGGCAGGGGAAAGACA | 6047 | SPBC1683.05_DN | CCACCCCGTCACACGCAATA |
| 5946 | SPBC14F5.06_UP | GCACGCCACGAAAAGGAAA | 6048 | SPBC1683.06c_UP | GAGCAGGGAATTTGACGGCG |
| 5947 | SPBC14F5.06_DN | AGGCACTGGCGGGTATTTGG | 6049 | SPBC1683.06c_DN | AACGGCAATAGCCACCCTGC |
| 5948 | SPBC14F5.07_UP | GTGCGTTTGGACCCTGTGGC | 6050 | SPBC1683.07_UP | TCATGTCCACCCTGTCCCAC |
| 5949 | SPBC14F5.07_DN | TCGTTCCGGCGGTTACTCC | 6051 | SPBC1683.07_DN | CACCCTCACCCTCGCCTCCAT |
| 5950 | SPBC14F5.08_UP | GCGGTTGCTGCTTTGATGA | 6052 | SPBC1683.08_UP | AGCAGGGCAACAGCTAAGGA |
| 5951 | SPBC14F5.08_DN | CCCGCCGTCTTGCTGCTATT | 6053 | SPBC1683.08_DN | TCGGCTCGGTCCTCCCCTCT |
| 5952 | SPBC14F5.09c_UP | ACACCCAGTCCAGGCCCAGC | 6054 | SPBC1683.09c_UD | TCACAAGCGGCAACCTACGG |
| 5953 | SPBC14F5.09c_DN | TGCGGTCGGGTAATGCCTCT | 6055 | SPBC1683.09c_DN | ACCGGACAGCCCAACAACGT |
| 5954 | SPBC14F5.10c_UP | ACGGCACACGACGATACGGAA | 6056 | SPBC1683.10c_UP | CCGGCTGCGCTCCCTTTCTT |
| 5955 | SPBC14F5.10c_DN | AATGATGTGTCGGCCGCGAT | 6057 | SPBC1683.10c_DN | CCTCCCATCCCTCCCCACGT |
| 5956 | SPBC14F5.11c_UP | CATTCCTCGTGCTTTCCCCG | 6058 | SPBC1683.11c_UP | ACCGCCCCCCAGCAATAAGC |
| 5957 | SPBC14F5.11c_DN | CATGGCAAAGTCGGGAAGCG | 6059 | SPBC1683.11c_DN | TGGGACAGGGCGGAGTAGCA |
| 5958 | SPBC14F5.12c_UP | GGGCGTAGGCACTTCTTGGC | 6060 | SPBC1683.12_UP | ACCGTGGGCGGGTGAACATT |
| 5959 | SPBC14F5.12c_DN | TTGTTTCGGGGATCGCTACC | 6061 | SPBC1683.12_DN | TCACACCTCACCCCGTTCGC |
| 5960 | SPBC14F5.13c_UP | TCATGACACGTCGCGGGGTA | 6062 | SPBC1683.13c_UP | ACAGGAAGGACCGCGTGCAG |
| 5961 | SPBC14F5.13c_DN | TGCGTGCCACGTCATCGAAT | 6063 | SPBC1683.13c_DN | CCGCTGCCTAATTAAGCCCG |
| 5962 | SPBC1539.02_UP | GGACCACGCCAAGGACCTGA | 6064 | SPBC1685.01_UP | TGCGGAAAACTACGGGGCAG |
| 5963 | SPBC1539.02_DN | CATGGGTTTCAGGTGCGCT | 6065 | SPBC1685.01_DN | TTTCGGCTCTTGCGTCCCTC |
| 5964 | SPBC1539.03c_UD | CCCACCGCAACGCCATTCCAC | 6066 | SPBC1685.02c_UP | CTGTCTATGCGGAGGTGGCG |
| 5965 | SPBC1539.03c_DN | GTGCGTTACTGTTGCCGGCG | 6067 | SPBC1685.02c_DN | CTCCGTCGCTCGTGCTTGTG |
| 5966 | SPBC1539.04_UP | CGGGGACACAGGGGATGAGG | 6068 | SPBC1685.03_UP | GGGGGTTCACTAGTCGGGGGG |
| 5967 | SPBC1539.04_DN | TTCACCCCCAGACCCGTTCT | 6069 | SPBC1685.03_DN | CGCTCCCCGCCTTTACCCTA |
| 5968 | SPBC1539.05_UP | TTCCGTAAGGTCGAGCCGGG | 6070 | SPBC1685.04_UP | GACGGTGTGCGGGATATCGG |
| 5969 | SPBC1539.05_DN | CGCGGGAAGCTGTAGTGGGG | 6071 | SPBC1685.04_DN | AAACCAACGCGGAGGAAGCC |
| 5970 | SPBC1539.07c_UP | AGTGCTCTGCCGCGTTGGTC | 6072 | SPBC1685.05_UP | CCTAGCATCCCAAACGCGCA |
| 5971 | SPBC1539.07c_DN | TGATAATGCGCAGGACGGGG | 6073 | SPBC1685.05_DN | ATTAAACCCGGCCGCGACCA |
| 5972 | SPBC1539.09_UP | AGAATGGAAACGTGCGCCCC | 6074 | SPBC1685.06_UP | AATAATGCGCCAACCCCCAC |
| 5973 | SPBC1539.09_DN | TCCACCCCGCCTCAATCTA | 6075 | SPBC1685.06_DN | TACTTCCCCTGCTTCGCCCA |
| 5974 | SPBC15C4.02_UP | TTGCCCGCTGTCCTCCTTGC | 6076 | SPBC1685.07c_UP | TAGCCCCGCCTCCGACAAT |
| 5975 | SPBC15C4.02_DN | CGGTGGTCGCGGTGAAFCTT | 6077 | SPBC1685.07c_DN | AGGTTGAGAGCAAGGGGGGG |
| 5976 | SPBC15C4.04c_UP | CGACGCCCACATACCTGAAA | 6078 | SPBC1685.08_UP | ACCAACGGACAAGCCCCACT |
| 5977 | SPBC15C4.04c_DN | ATACCCGCCTACCGACCGCA | 6079 | SPBC1685.08_DN | CCAATATTGTGCGCGGTGCC |
| 5978 | SPBC15C4.05_UP | CCGGAGCCACAGGGACAGCT | 6080 | SPBC1685.09_UP | GTCTGGGGCCTCGGCTTTTG |
| 5979 | SPBC15C4.05_DN | CATGCAGTCCGTGGGAGGGC | 6081 | SPBC1685.09_DN | TATGACCCTGACTCCGCCGC |
| 5980 | SPBC15D4.02_UP | ATTCATAACCGCGGGACAGCT | 6082 | SPBC1685.11_UP | TGACAGCCAACTCCAGCGCC |
| 5981 | SPBC15D4.02_DN | ACGCCTGCTTTGTGACCGAC | 6083 | SPBC1685.11_DN | CTTGTCCACTGACTGGCGCG |
| 5982 | SPBC15D4.03_UP | TTCCCTGCCAACGACACTGC | 6084 | SPBC1685.12c_UP | TGGTTGTGGTGCGAAGAGGG |
| 5983 | SPBC15D4.03_DN | CCCCCAGGCATCACATCACC | 6085 | SPBC1685.12c_DN | CGCCTCAGCCCCTTTCCTCG |
| 5984 | SPBC15D4.04_UP | ACCATGCGAAACGGCCAACT | 6086 | SPBC1685.13_UP | TCAATGTGGGGCGCGGATAG |
| 5985 | SPBC15D4.04_DN | GTCATAGAAGGGCCTGCGCC | 6087 | SPBC1685.13_DN | ACCTGCCGCAATGAAACGC |
| 5986 | SPBC15D4.05_UP | GTTCAAAAGAGGGCGGGGGC | 6088 | SPBC1685.14c_UP | TCCCGCATCGCCCTTACACA |
| 5987 | SPBC15D4.05_DN | TTTGAGGCGCGGATGGTTCA | 6089 | SPBC1685.14c_DN | TGCGGGTTGGCTTATGTGGC |
| 5988 | SPBC15D4.06_UP | CCAATACCGTTCCGCCTCGT | 6090 | SPBC1685.16_UP | ACTCGTACAGTCGACGCTCG |
| 5989 | SPBC15D4.06_DN | TGACGGGAGCAAGGCGATGA | 6091 | SPBC1685.16_DN | AAACCGCAGTGAGACGCGRA |
| 5990 | SPBC15D4.07c_UP | TCAGAAATCGCGAGGGGGGT | 6092 | SPBC16A3.03c_UP | GCGGGCCAAACGACCAAAACG |
| 5991 | SPBC15D4.07c_DN | AGAATTCGCAGACGCCCGGG | 6093 | SPBC16A3.03c_DN | GACTGGCGAGGCGAAGACGG |
| 5992 | SPBC15D4.09c_UP | AGAGCGGTGCGCGTATTCGA | 6094 | SPBC16A3.04_UP | AGGACACGGCCGACAGACAG |
| 5993 | SPBC15D4.09c_DN | CATGCGTTGCCGTTCCTTTG | 6095 | SPBC16A3.04_DN | TCCTTGGCTTGTGTGGCGTGC |
| 5994 | SPBC15D4.10c_UP | GGTAGTTTGTCCCGCCCGTC | 6096 | SPBC16A3.05c_UP | ACACAACGCCCCGAACCTCT |
| 5995 | SPBC15D4.10c_DN | TGGTGTTGGACGGATGGCTG | 6097 | SPBC16A3.05c_DN | CGCTCCCACTCCGCCCAAAT |
| 5996 | SPBC15D4.12c_UP | AGGCGCCTCGACTGAATTGC | 6098 | SPBC16A3.06_UP | CCGGTGTCTGTGCATGCT |
| 5997 | SPBC15D4.12c_DN | GGTCCGGAATACGCAAAAGC | 6099 | SPBC16A3.06_DN | CGGGGCTAATTGGTTGGTTG |
| 5998 | SPBC15D4.13c_UP | CGACCATACTCCCCGCTCCC | 6100 | SPBC16A3.07c_UP | AGACAGTTGACCGAGGGCGC |
| 5999 | SPBC15D4.13c_DN | GCCCCAAAACGTTCCAGCAC | 6101 | SPBC16A3.07c_DN | GACGAGGGGACGAGGGGATT |
| 6000 | SPBC15D4.15_UP | GGGGAGTCGGCATCACAGGGA | 6102 | SPBC16A3.08c_UP | CGACCGTACGGGACTTTCGC |
| 6001 | SPBC15D4.15_DN | TAACGTAGCGGCGAGAGCCA | 6103 | SPBC16A3.08c_DN | GGCCGTGGGATTACGCAAAA |
| 6002 | SPBC1604.02c_UP | TGTGGGCTGCTGGGGTCAAA | 6104 | SPBC16A3.09c_UP | TAAGGGGAGACTTGGTGCGA |
| 6003 | SPBC1604.02c_DN | CCCGCCGAGATTAGGTTGGC | 6105 | SPBC16A3.09c_DN | GCTGGCGGGAAGAGGAAAGC |
| 6004 | SPBC1604.03c_UP | ACACCCTGCCCCCTCTTCAA | 6106 | SPBC16A3.10_UP | CTTCTTCCGTTCGCCTCCGG |
| 6005 | SPBC1604.03c_DN | GCTCCGCCTCCCCCACCCTA | 6107 | SPBC16A3.10_DN | AGGGTCCGGTATGGCAGGGC |
| 6006 | SPBC1604.04_UP | GCCTATGATCGCGCGCTTTG | 6108 | SPBC16A3.11_UP | GGGGACGGACGACTGGGGAG |
| 6007 | SPBC1604.04_DN | GAAGTATGCGGCGACGCCTCG | 6109 | SPBC16A3.11_DN | ATCAGCAATCGGCCAACCCC |
| 6008 | SPBC1604.05_UP | GCGCCGTTCCGAAGTACCATG | 6110 | SPBC16A3.12c_UP | ACACAGGCCTCCTGAGCCGAA |
| 6009 | SPBC1604.05_DN | GCGCCTCCCTCTTCGTTGGAA | 6111 | SPBC16A3.12c_DN | AAGCGCCGCAATGTTAGTGTG |
| 6010 | SPBC1604.07_UP | CAAGGGTTTTGTCGGGGCA | 6112 | SPBC16A3.13_UP | CAACGCCTGCCCGACAGTTC |
| 6011 | SPBC1604.07_DN | GTGAGCGGAGGGGGCACTGT | 6113 | SPBC16A3.13_DN | AAAAAGAGGCAGGCGGGACG |
| 6012 | SPBC1604.10_UP | CGACAATCGAACTCCGCGGC | 6114 | SPBC16A3.14_UP | AATGCCTGAGCTCACCGACG |
| 6013 | SPBC1604.10_DN | CGGGGACGATCGTAGGCTGC | 6115 | SPBC16A3.14_DN | GTCACTGGTTGCGGCGTTG |
| 6014 | SPBC1604.11_UP | GGCAGGGGCTACATTCGGI | 6116 | SPBC16A3.15c_UP | GCCAAGGAGGGGGACTGGCT |
| 6015 | SPBC1604.11_DN | CGGTTGCTCGCTGTTTCGCT | 6117 | SPBC16A3.15c_DN | TGACAGTTTGACGGCGGGAG |
| 6016 | SPBC1604.12_UP | GAGCCGCGTGACAGGTATTG | 6118 | SPBC16A3.16_UP | TGACCCATAAGCCCCGGGAT |
| 6017 | SPBC1604.12_DN | AGGGGAGGGAGAGCTGCGGA | 6119 | SPBC16A3.16_DN | AGCGGCGAGGTTGCATATGC |
| 6018 | SPBC1604.13c_UP | GATATTCCGCCGGCCGACC | 6120 | SPBC16A3.17c_UP | TGCCGTGTTCTCCGCTTCCA |

FIG.37

| Sequence number | Name | Base sequence | Sequence number | Name | Base sequence |
|---|---|---|---|---|---|
| 6121 | SPBC16A3.17c_DN | TGAACGACCAAGCACCGCCC | 6223 | SPBC16G5.17_DN | GTGGTGACAGACGGCCAGGC |
| 6122 | SPBC16A3.18_UP | GTGGGTCGGACTTCGATCCT | 6224 | SPBC16G5.19_UP | ACTCTTAGGGCGCCCGTTAC |
| 6123 | SPBC16A3.18_DN | ACCCTCGTCGAGCTGGGAAT | 6225 | SPBC16G5.18_DN | GAGTGCGATTCGGGACGTA |
| 6124 | SPBC16C6.01c_UP | AGAATAGCAGGCCGCGGAAA | 6226 | SPBC16H5.C2_UP | ATCGCGGAGGGGCTAACACA |
| 6125 | SPBC16C6.01c_DN | TTTGGCGAGGTGGACAGGG | 6227 | SPBC16H5.02_DN | TGCTTGTCCGGCTCTTCGCT |
| 6126 | SPBC16C6.02c_UP | TTTGGCGCGCATTTTCACAT | 6228 | SPBC16H5.03c_UP | ACACCGCCCCACTCCAAAAA |
| 6127 | SPBC16C6.02c_DN | GCGCCAGATCTTTCCCCAC | 6229 | SPBC16H5.03c_DN | ATTGCGGGGGTCCAGTTGA |
| 6128 | SPBC16C6.03c_UP | AGCTAACCCGCCGCAACTGT | 6230 | SPBC16H5.04_UP | TTACCCCTTCGCCCGCACTT |
| 6129 | SPBC16C6.03c_DN | CCCCCGCTCTTGTACCCTCC | 6231 | SPBC16H5.04_DN | CGATGATTTGGGGTCGTGG |
| 6130 | SPBC16C6.04_UP | CCCCTGTCCCATCCCCGTCG | 6232 | SPBC16H5.05c_UP | CGTCCGCAGAACATGGCTCC |
| 6131 | SPBC16C6.04_DN | CGGGTGGGCAGCAGATTGGT | 6233 | SPBC16H5.05c_DN | TCCCGAGGCGTAGCACAGGA |
| 6132 | SPBC16C6.05_UP | GTAGGGAATCAGGGCGGGCG | 6234 | SPBC16H5.06_UP | CGGCCATAGTCGTCGGTTCT |
| 6133 | SPBC16C6.05_DN | GTCCTATCGAAACCCCGCGG | 6235 | SPBC16H5.06_DN | ACACCTGATCACCCCGCTC |
| 6134 | SPBC16C6.06_UP | AGGTCCAGATTCTCCGCGCC | 6236 | SPBC16H5.07c_UP | TGATTGCCTTGGGGGTGTGA |
| 6135 | SPBC16C6.06_DN | ACTGCAACCCCCGCTCATTA | 6237 | SPBC16H5.07c_DN | CCTTCATCCCTGCTGCCCGA |
| 6136 | SPBC16C6.07c_UP | ATTGGTTTTGGGCGCTCGGA | 6238 | SPBC16H5.08c_UP | TAGGGACCGACTGCCGGAAC |
| 6137 | SPBC16C6.07c_DN | AAAAGCGACGTGGGGCAAAC | 6239 | SPBC16H5.08c_DN | AATGACCCACGGGAGACGGT |
| 6138 | SPBC16C6.08c_UP | ATCCACCCCGCATAATCCCA | 6240 | SPBC16H5.09c_UP | CTCGCCGTCTTCTCTCGCT |
| 6139 | SPBC16C6.08c_DN | TGGGCTTTTGTTCGGATGCA | 6241 | SPBC16H5.09c_DN | GTTCGGCGTCCATTGCAGGT |
| 6140 | SPBC16C6.09_UP | ACGGGCATGGTCGACGGCTA | 6242 | SPBC16H5.11c_UP | TGCTCCAATCCCGACCCCAG |
| 6141 | SPBC16C6.09_DN | TTTCCAAGGGCGGGCGAGTT | 6243 | SPBC16H5.11c_DN | CTCCTCCGCCCTCGGCTAAC |
| 6142 | SPBC16C6.10_UP | GCCCGCATACTCGTCGTCT | 6244 | SPBC16H5.13_UP | TCTCAACGCCGTCTCCGCAC |
| 6143 | SPBC16C6.10_DN | CACATTCGGTGGTTCAGCGC | 6245 | SPBC16H5.13_DN | TTAGGCATTCTGGGACCGGG |
| 6144 | SPBC16C6.11_UP | TCGTTGGTTTCAGGGCGCAC | 6246 | SPBC16H5.14c_UP | ATGTAGGCGACTCTCCCGT |
| 6145 | SPBC16C6.11_DN | CCTTGGACCGCACCCTGGAC | 6247 | SPBC16H5.14c_DN | AACGCGGCTCTGTTCTACCG |
| 6146 | SPBC16D10.02_UP | TGGTCTGTTCGTGGGCATGG | 6248 | SPBC16H5.15_UP | TGCTTTCTGCGTCCGGCTGT |
| 6147 | SPBC16D10.02_DN | TCAGAAGGGGGTGCACAGGG | 6249 | SPBC16H5.15_DN | CGGAGTGGACACGACACTGA |
| 6148 | SPBC16D10.03_UP | CGCGACCCCACCGAGACCTA | 6250 | SPBC1703.01c_UP | GCGAATGGGAGCGAAAATCG |
| 6149 | SPBC16D10.03_DN | CTGTTCACTGCGCGCCCTCC | 6251 | SPBC1703.01c_DN | GGGGCGATGTGAGAGGCAAA |
| 6150 | SPBC16D10.04c_UP | TACGGGCTGCCACAGGTTAG | 6252 | SPBC1703.02_UP | TGTAACGACGGGGCGAAGC |
| 6151 | SPBC16D10.04c_DN | GGTGCAGGGGTACGAACTCT | 6253 | SPBC1703.02_DN | GACCCATCGAACCCGCCACA |
| 6152 | SPBC16D10.05_UP | CAAGGGGATCCCACAAGGCT | 6254 | SPBC1703.03c_UP | ATTGTCCCGTGCTTGGCCCC |
| 6153 | SPBC16D10.05_DN | GCCTACACGAGAACCGGCGT | 6255 | SPBC1703.03c_DN | GGCGGTTGTGGCTGATCGAC |
| 6154 | SPBC16D10.06_UP | GACGAAGAGGCGGGGGCAAGT | 6256 | SPBC1703.04_UP | ATAACCCACTGCCCGGACCA |
| 6155 | SPBC16D10.06_DN | CAAAACCCCCCAATCCCTGT | 6257 | SPBC1703.04_DN | CATCTCCTCGGCGACTCACG |
| 6156 | SPBC16D10.07c_UP | GGACAATCGGTGGGAGGGTG | 6258 | SPBC1703.05_UP | ATTGCGGGAAAGTGCGACCT |
| 6157 | SPBC16D10.07c_DN | AGCGACCACGAAGAACGGCG | 6259 | SPBC1703.05_DN | AGGTAAGCATGAACGTCGC |
| 6158 | SPBC16D10.08c_UP | AAAACAGTTGCCCGCCGAGCG | 6260 | SPBC1703.06_UP | CAAAAATTCCGCAAACGGCG |
| 6159 | SPBC16D10.08c_DN | GGGAGAAACGGGCAGGCCTA | 6261 | SPBC1703.06_DN | AGCCTTGCTGTCCGCCCTAG |
| 6160 | SPBC16D10.10_UP | AACCCGGACGAGCCCAAAGC | 6262 | SPBC1703.07_UP | CGGCGGAGAGGCAAAAGGCAA |
| 6161 | SPBC16D10.10_DN | GGAGAGGCCATGCAACACGC | 6263 | SPBC1703.07_DN | TTACCCGCCAGCATCCCAGG |
| 6162 | SPBC16D10.11c_UP | CCAAACGCCGACCGACAATC | 6264 | SPBC1703.08c_UP | CTCGCGTAGCCGTCGATCTA |
| 6163 | SPBC16D10.11c_DN | CCTTTTGTGTACCCTTCCCG | 6265 | SPBC1703.08c_DN | TCGCTGCGCAGGTCTTTAGG |
| 6164 | SPBC16E9.02c_UP | ATCGTGGAAGCTGCGCGGTC | 6266 | SPBC1703.09_UP | ACCCCTCGTGCTGGTTTGTC |
| 6165 | SPBC16E9.02c_DN | TGTGACTTGGAGGGCCGGTG | 6267 | SPBC1703.09_DN | CTGCCCTTCCCTAACCGCCT |
| 6166 | SPBC16E9.03c_UP | TGGGGTGTCGGGCAGGTAGC | 6268 | SPBC1703.12_UP | CCAGAAAGCGGTAGGGGTCG |
| 6167 | SPBC16E9.03c_DN | AACAGGGAAGGCCGACCAGG | 6269 | SPBC1703.12_DN | TGACAATCCCTGCGCCATCG |
| 6168 | SPBC16E9.05_UP | GGCTTGTCTCAGGGCGATCT | 6270 | SPBC1703.13c_UP | GGGGATGGGTTGTGGGACAG |
| 6169 | SPBC16E9.05_DN | GCTTACTAGGGTGCCAGCGT | 6271 | SPBC1703.13c_DN | AAGGTATGCGGTGCGGGTG |
| 6170 | SPBC16E9.06c_UP | CCGTTCGTCCCACCTTGCCA | 6272 | SPBC1703.14c_UP | AGGACCCGAGCACAACCCG |
| 6171 | SPBC16E9.06c_DN | AACAACCGAAGGGGCTGACG | 6273 | SPBC1703.14c_DN | GCGGGAACCGAAAGGAAGG |
| 6172 | SPBC16E9.07_UP | CGGCAGCGGACAAGAGAGGT | 6274 | SPBC1706.01_UP | CACTAAAAGCCTGCACCGCG |
| 6173 | SPBC16E9.07_DN | GGCTCACTTTCGCATTCCCC | 6275 | SPBC1706.01_DN | ACAAGCCGGGGTCAGTCCC |
| 6174 | SPBC16E9.08_UP | CGTAGATCCGCCAGAAGCCG | 6276 | SPBC1709.03_UP | TTCCGACCGGCCACTACACCC |
| 6175 | SPBC16E9.08_DN | GCCCCCTCCGTCACACACGA | 6277 | SPBC1709.03_DN | AGGGGTTGTCGTTATGGCGG |
| 6176 | SPBC16E9.10c_UP | GTTGTGGGTGGAGGGGGGCAG | 6278 | SPBC1709.04c_UP | GCAGTGGGGAGGAACGGAAC |
| 6177 | SPBC16E9.10c_DN | GCCCGTCCGTCCGAACCTT | 6279 | SPBC1709.04c_DN | TCCGACCCGACCACGCTTG |
| 6178 | SPBC16E9.11c_UP | GGTGTTGATGGCGGGGCTGT | 6280 | SPBC1709.05_UP | CAGAACGAATTCCCGATGCGGCC |
| 6179 | SPBC16E9.11c_DN | CATCTGGTCGGCGTTGTGGC | 6281 | SPBC1709.05_DN | AGTTAGGGGTTCCATCGCCG |
| 6180 | SPBC16E9.12c_UP | ACCCCCGGCCACCATCGATA | 6282 | SPBC1709.06_UP | GCGGAGGGGTGTCGGATAGC |
| 6181 | SPBC16E9.12c_DN | TGCGGAGATAGGGTCGGGGC | 6283 | SPBC1709.06_DN | ATGCTTCTCGGGGGGCTGCT |
| 6182 | SPBC16E9.13_UP | GGCGTCCCGAAGCATCAGCT | 6284 | SPBC1709.07_UP | ATACTCAGCCCTGGACCGGA |
| 6183 | SPBC16E9.13_DN | CGTCCTATCGGGTTCCCTTG | 6285 | SPBC1709.07_DN | ATCCGGTCAGTCTGTGCCAG |
| 6184 | SPBC16E9.14c_UP | CTGGCCATTCGCGACGTTG | 6286 | SPBC1709.09_UP | GTTTCCTGGGGTGAGGTCGC |
| 6185 | SPBC16E9.14c_DN | CGCACTCCTCGACCACGCTC | 6287 | SPBC1709.09_DN | ACCCCCCTCCCCCAACATAG |
| 6186 | SPBC16E9.15_UP | GGGATAGTCGGGCGGTTGGTC | 6288 | SPBC1709.10c_UP | GCCTTTTCCTCGCCGCTCTC |
| 6187 | SPBC16E9.15_DN | TTAACCCAGCCCGCCCCACT | 6289 | SPBC1709.10c_DN | ACCCGCGGCCGTCCTACTTTG |
| 6188 | SPBC16E9.17c_UP | ATACCATCCGCGGCCCTGAA | 6290 | SPBC1709.11c_UP | AACGTCGCCGAAACAGCACC |
| 6189 | SPBC16E9.17c_DN | AAGGGGGGGGGCAAGGACTAG | 6291 | SPBC1709.11c_DN | CACACGGGTGCATTCGCAAT |
| 6190 | SPBC16E9.19_UP | AGTCGCGTCACCATGTAGG | 6292 | SPBC1709.12_UP | CAAAGCCTCTCCACCCCCCT |
| 6191 | SPBC16E9.19_DN | CCTGCGTCACGAGCGTATGA | 6293 | SPBC1709.12_DN | GCGCGCACGTGAGGTACAAG |
| 6192 | SPBC16G5.02c_UP | CGCCTCGTCGCGCTTTGTTA | 6294 | SPBC1709.13c_UP | GAGGATATTTGGCGCTGGG |
| 6193 | SPBC16G5.02c_DN | ATGGCCCTCGATCACGTCAG | 6295 | SPBC1709.13c_DN | GCCCAGGTACCAATGCACAG |
| 6194 | SPBC16G5.03_UP | TCGCGGATTGATAACGTGGC | 6296 | SPBC1709.14_UP | GCCCCGGGTTATGGAAGCTT |
| 6195 | SPBC16G5.03_DN | GATAGCCACCCATTGCGCCC | 6297 | SPBC1709.14_DN | GCTGCCGCGCTGGGTAACAAC |
| 6196 | SPBC16G5.04_UP | TTTGCGCACCGGTATGCACC | 6298 | SPBC1709.15c_UP | CTGACACATCGCCGCAACG |
| 6197 | SPBC16G5.04_DN | CTAGGAGGGGACGAAGGGCA | 6299 | SPBC1709.15c_DN | CCTTGGCTTCGCCCGTCTCT |
| 6198 | SPBC16G5.05c_UP | AAGATCAAACCGCCACCCGA | 6300 | SPBC1709.16c_UP | GCCCCAGCGCCCACTATGTT |
| 6199 | SPBC16G5.05c_DN | TAGACCCCTCCGCGTTTGCG | 6301 | SPBC1709.16c_DN | TCTCGACACCACCAAAGCGC |
| 6200 | SPBC16G5.06_UP | CACGGTTCAGCATGGGTCGG | 6302 | SPBC1709.18_UP | TCGTTGACATGACTCCCCGG |
| 6201 | SPBC16G5.06_DN | CGCCCCCTTGTCGATGGTT | 6303 | SPBC1709.18_DN | GAAGGGTAGGCGGGTGTCC |
| 6202 | SPBC16G5.07c_UP | TTTGGCTTGGGAATGGGCGA | 6304 | SPBC1709.20_UP | ATACGCGGCCGAGTTGTACT |
| 6203 | SPBC16G5.07c_DN | CGTGGCGGAGCGGAGAAGAT | 6305 | SPBC1709.20_DN | GCTCAGTGCACCGGCTAGTT |
| 6204 | SPBC16G5.08_UP | AGACCGGAGCGAGGCGATTA | 6306 | SPBC1711.01c_UP | TAAATACCCGGGTGCCGCTG |
| 6205 | SPBC16G5.08_DN | ACCCAGTCCACCTGTCAAGG | 6307 | SPBC1711.01c_DN | TCGAGTGCACCCGTAGACAC |
| 6206 | SPBC16G5.09_UP | GACCCCTCCCGGCATTCGTT | 6308 | SPBC1711.03_UP | AGGCAAGCGGCATAGGGCAG |
| 6207 | SPBC16G5.09_DN | AGTGGGGCAGACGCGTGAAG | 6309 | SPBC1711.03_DN | TGTTGGAGCTCTTTGGCGGC |
| 6208 | SPBC16G5.10_UP | TTTCAGTTGGGCTGGACGGC | 6310 | SPBC1711.04_UP | CTAGGGATGGGAGCGGGCAG |
| 6209 | SPBC16G5.10_DN | CATCCGTCCCGCTCCGCACC | 6311 | SPBC1711.04_DN | AGGTGCGGGGAAGTGTTGG |
| 6210 | SPBC16G5.11c_UP | GGATCGAGTTTGCGGGGTTG | 6312 | SPBC1711.05_UP | GCCACCCTGCTTTGACCGCT |
| 6211 | SPBC16G5.11c_DN | ACCGGTAGCACGGAACGGCA | 6313 | SPBC1711.05_DN | AAAAATGCGAGGACGGGGGG |
| 6212 | SPBC16G5.12c_UP | ACCGCGGAAACGCCGTAGAGT | 6314 | SPBC1711.06_UP | CGCTTTCCCGGTCAGGTCCAA |
| 6213 | SPBC16G5.12c_DN | GCCCGGATCTCGCATAGCCTT | 6315 | SPBC1711.06_DN | CCAAGAGCAAGCGCATAACG |
| 6214 | SPBC16G5.13_UP | GGTGCCCCTTTAAATCGCC | 6316 | SPBC1711.07_UP | AACTTCTCGAATCCGGCACC |
| 6215 | SPBC16G5.13_DN | AAGGCCTGCGTAGCGACTGA | 6317 | SPBC1711.07_DN | ATAAACTCGCACGGACGCCG |
| 6216 | SPBC16G5.14c_UP | CGGGATCAAGAGAGGGGGCT | 6318 | SPBC1711.08_UP | CACCATTCACGTTCCGCCCT |
| 6217 | SPBC16G5.14c_DN | TTGCCCCGCCACTTGATCTT | 6319 | SPBC1711.08_DN | AACGGGGACAGGAACCATC |
| 6218 | SPBC16G5.15c_UP | GCACGAAAGATGCGCGCAC | 6320 | SPBC1711.09c_UP | CACCTAGGCGCGCTAAGGTT |
| 6219 | SPBC16G5.15c_DN | GGCGGGTCCAGTTTGGGGAT | 6321 | SPBC1711.09c_DN | AATCTTTTGTCGTGGGGCCG |
| 6220 | SPBC16G5.16_UP | ATCGTTGACAGAGGCGGGA | 6322 | SPBC1711.10c_UP | GGACCCAGGGCGTCGTGAAAG |
| 6221 | SPBC16G5.16_DN | GGCGGCCGAACGAAAAGTAC | 6323 | SPBC1711.10c_DN | GCTGGCTTAGGGGCGTGAGT |
| 6222 | SPBC16G5.17_UP | ATTCACTTCCGTGGGCGGCC | 6324 | SPBC1711.11_UP | ACTACCCGATCCGACCACCC |

FIG.38

| Sequence number | Name | Base sequence | Sequence number | Name | Base sequence |
|---|---|---|---|---|---|
| 6325 | SPBC1711.11_DN | AAGGTACACCGCCAGCCTC | 6427 | SPBC17D11.02c_DN | ACGTTTTGGGTTGGTTGGCC |
| 6326 | SPBC1711.12_UP | TTGTGGCCGTCCTTTCGTTG | 6428 | SPBC17D11.03c_UP | TACCAATTGAGGCGCCGCAA |
| 6327 | SPBC1711.12_DN | GGACGCGGGTGGGCTTAATT | 6429 | SPBC17D11.03c_DN | TGGGCACGCGAGGGTAACTG |
| 6328 | SPBC1711.13_UP | CGACCCTGCAAAGCCAAACA | 6430 | SPBC17D11.04c_UP | ACGGCCAATTTTCCCTGCAC |
| 6329 | SPBC1711.13_DN | GAGGGGCTAGTGCGGGTCTG | 6431 | SPBC17D11.04c_DN | AAACGCGCCAGCCACTCTTG |
| 6330 | SPBC1718.01_UP | GGGGCGCGATTTTTGTGACT | 6432 | SPBC17D11.05_UP | CCATAACTTGGCCCATGCCG |
| 6331 | SPBC1718.01_DN | ATAGGGCTGGCGAGGCGGAG | 6433 | SPBC17D11.05_DN | GGGCTCCGGCTCACGACTTAT |
| 6332 | SPBC1718.02_UP | CCCGCCACGGATCCATTCAG | 6434 | SPBC17D11.06_UP | GAGTCTTGGCTGGGTGGCTG |
| 6333 | SPBC1718.02_DN | CCACCGATGACCTGCGTTCC | 6435 | SPBC17D11.06_DN | CGCCCAACTCCCGCACTCTA |
| 6334 | SPBC1718.03_UP | GAGGTGCGGGGAGTTCAAG | 6436 | SPBC17D11.08_UP | CGTGGGCGTAACAATCCGGA |
| 6335 | SPBC1718.03_DN | GGGGGCGAGGGACGAGCTAT | 6437 | SPBC17D11.08_DN | TGAAACTTACCCCGGCGACG |
| 6336 | SPBC1718.06_UP | CTTGCGGATCCATTTGCCCG | 6438 | SPBC17F3.02_UP | TCACATCGCTGTAGAGGCCA |
| 6337 | SPBC1718.06_DN | CCAGATCTCGAGCAGCCACG | 6439 | SPBC17F3.02_DN | GCCAATCTAGCGCGGACCCA |
| 6338 | SPBC1718.07c_UP | GCGGGAAAGAGGGGCAGGAT | 6440 | SPBC17G9.02c_UP | TCGGGGCATTCTGGTGGGTG |
| 6339 | SPBC1718.07c_DN | CGGCTTCCCACCGACCTCCT | 6441 | SPBC17G9.02c_DN | CCAAAAAGCCCCTTCCCACC |
| 6340 | SPBC1734.05c_UP | TGCCCCTGCTGATTTTGTTC | 6442 | SPBC17G9.03c_UP | TACCCCGTGGTTTCTGCGGA |
| 6341 | SPBC1734.05c_DN | CAAGCGGGGGTACTCGGGCA | 6443 | SPBC17G9.03c_DN | AGGCGGCGGAACATACGTCA |
| 6342 | SPBC1734.06_UP | GCCAGCCGATATGTTCCCGT | 6444 | SPBC17G9.04c_UP | ATGTAACCGCGTACCGTGC |
| 6343 | SPBC1734.06_DN | TTGGGGCACGGCGGGTAAAT | 6445 | SPBC17G9.04c_DN | ACTACACGGGGCGCGTAAAT |
| 6344 | SPBC1734.07c_UP | TTTGGGGGCTGTGAGGCGAA | 6446 | SPBC17G9.05_UP | GACAAGACCCACACGCGGGA |
| 6345 | SPBC1734.07c_DN | CGAGCCCGCTATCACCACAA | 6447 | SPBC17G9.05_DN | TACGTGTGCCGCGTGGCTTT |
| 6346 | SPBC1734.08_UP | AAGGGGGCTTCGCGTGTCTT | 6448 | SPBC17G9.06c_UP | TCCATCTCGCTCACCATCCG |
| 6347 | SPBC1734.08_DN | GTTGGGGCACTTGAGCGAGC | 6449 | SPBC17G9.08c_DN | GCGGGAAGCGAACTGCGAAG |
| 6348 | SPBC1734.09_UP | GCCCCCTGGGACATTGTTGGA | 6450 | SPBC17G9.09_UP | CGCTGGGGATCCGATATGAA |
| 6349 | SPBC1734.09_DN | TGCCTCCGCTAGCGGCTCAAC | 6451 | SPBC17G9.09_DN | AATTGGAGTTTGGTGCGCGC |
| 6350 | SPBC1734.12c_UP | AAAAAGTGAAGCGCTCGGGG | 6452 | SPBC17G9.10_UP | CGGTCTGCCCGCCAGAAAGG |
| 6351 | SPBC1734.12c_DN | GCTCTGGTTGCGGTTGCCATA | 6453 | SPBC17G9.10_DN | CCCGCCATCACCCAGAATCC |
| 6352 | SPBC1734.13_UP | AGTCTCGTGCGCGGTTTCCC | 6454 | SPBC17G9.11c_UP | AAGCCCATCCGCAACCATGC |
| 6353 | SPBC1734.13_DN | GTAGCGGCCGCAGGGGAAAA | 6455 | SPBC17G9.11c_DN | CTGCTGCGGGGGCGCAAAATG |
| 6354 | SPBC1734.14c_UP | CGCCCAACCGCCCAAATGAAG | 6456 | SPBC17G9.12c_UP | GTCTCGGCACGCAAATCAGC |
| 6355 | SPBC1734.14c_DN | CCAACGCACAAACAAACCGC | 6457 | SPBC17G9.12c_DN | TACGGGGCGCACAATCTACG |
| 6356 | SPBC1734.15_UP | GAGTCAGGGATGGCGGTGGA | 6458 | SPBC1861.02_UP | GACCTCCGCCTGCTCCCACT |
| 6357 | SPBC1734.15_DN | ACCCGACCCTACGCTACCGC | 6459 | SPBC1861.02_DN | TCCCCTACCTGCCGGTTTTG |
| 6358 | SPBC1773.01_UP | GGACCCCGCAAGTTACGAAT | 6460 | SPBC1861.03_UP | ATCACCCTGCCACGCTCCAT |
| 6359 | SPBC1773.01_DN | GTCACTACGAAGGCCGGCCC | 6461 | SPBC1861.03_DN | ACCACCTCATGCCACGTCCG |
| 6360 | SPBC1773.02c_UP | TCCAGCCCGGTCATTATCCG | 6462 | SPBC1861.04c_UP | ATGAAGCGTGCCTGTAGCGC |
| 6361 | SPBC1773.02c_DN | CAATGTAATGACCGCGGCCG | 6463 | SPBC1861.04c_DN | TCCGACGCGTGTGATCAGGA |
| 6362 | SPBC1773.03c_UP | CGTCAGCTCCTATGCGGTCT | 6464 | SPBC1861.05_UP | AGAATGCGGCCGTACTGCGGA |
| 6363 | SPBC1773.03c_DN | CTGCCCGCTATGACCCGCAC | 6465 | SPBC1861.05_DN | AGACGCTCATTCCCCGCAG |
| 6364 | SPBC1773.04_UP | GGATCTACGTGGGTCGGGCC | 6466 | SPBC1861.06c_UP | TTCGGCGTCTCATGGGTTCC |
| 6365 | SPBC1773.04_DN | CACGGCGGAGGAATAGGAA | 6467 | SPBC1861.06c_DN | CCACCGCGCCTATTGAACCA |
| 6366 | SPBC1773.05c_UP | ATCCACCCCCAAACCCTGCC | 6468 | SPBC1861.07_UP | CGCTCCATCCAAACCGTCAA |
| 6367 | SPBC1773.05c_DN | TTCGGTTCGGTTCAATGGGC | 6469 | SPBC1861.07_DN | AGAAGCTGCATGTGGGCGCA |
| 6368 | SPBC1773.06c_UP | CGGGTTGGGAAAGTTGAGCG | 6470 | SPBC1861.08c_UP | ATGTTAGGGGGGCGTGGGT |
| 6369 | SPBC1773.06c_DN | TCTTCAGTCCCCCAGGCCGT | 6471 | SPBC1861.08c_DN | CAGCCCCAACGTCACTGCT |
| 6370 | SPBC1773.07c_UP | TGCTTCCCCCCGTCGCTAAC | 6472 | SPBC1861.09_UP | CTGCAATGGGGGTACTACC |
| 6371 | SPBC1773.07c_DN | CGGTCGTTTTCGTGCCCATT | 6473 | SPBC1861.09_DN | CTCAAATCCAACTCCCACCG |
| 6372 | SPBC1773.08c_UP | CAAGCAGATTACAGCGCGGC | 6474 | SPBC18A7.02c_UP | CTCGGCAGCACACGCCCTTCA |
| 6373 | SPBC1773.08c_DN | GCGAAAAACGACCGGGGGAG | 6475 | SPBC18A7.02c_DN | ATAAGAGTCGTCGCCGGGGG |
| 6374 | SPBC1773.09c_UP | AAATGGTGCGATGGCGTGCT | 6476 | SPBC18E5.04_UP | CTTCGGGAGGCAATAGGGGG |
| 6375 | SPBC1773.09c_DN | TTTATCGCCTGCCCAATCCC | 6477 | SPBC18E5.04_DN | CTCTGGGGGGCATATGTCCC |
| 6376 | SPBC1773.10c_UP | ACATCCGTGGGCCCTTTGGC | 6478 | SPBC18E5.05c_UP | ATAGCTGATCTGCGGGCGG |
| 6377 | SPBC1773.10c_DN | TTTCGGCGCTCCATGAGTCA | 6479 | SPBC18E5.05c_DN | ATGGGCGCACAACTCGAAGC |
| 6378 | SPBC1773.12_UP | CAAAAGTGTGCCCGGCTGCA | 6480 | SPBC18E5.06_UP | AAACCCGGCCCTGAACCATG |
| 6379 | SPBC1773.12_DN | CGAGCCGTCCGTGATGTCCCA | 6481 | SPBC18E5.06_DN | TTGGCGGTTGCTCTTTGGGA |
| 6380 | SPBC1773.13_UP | TCCAAACGGGCCATCACGAT | 6482 | SPBC18E5.07_UP | GCGCGTGTTTGCTTTGGGG |
| 6381 | SPBC1773.13_DN | AAGTGGTGCGTGCGCGTCTC | 6483 | SPBC18E5.07_DN | CGGGGAATAGGAAGGAGCGG |
| 6382 | SPBC1773.14_UP | TCCAATACCTGCTCGGGCCT | 6484 | SPBC18E5.08_UP | AGCCTGCGTGGGAATAAGCCG |
| 6383 | SPBC1773.14_DN | CATCAATTCCCGGCCAGAA | 6485 | SPBC18E5.08_DN | GATCTGGAGGCGCTGGTTGC |
| 6384 | SPBC1773.15_UP | TGCCAGGTGATGTCGGATCC | 6486 | SPBC18E5.09c_UP | CGGGCCCACGCCCTTGATCAT |
| 6385 | SPBC1773.15_DN | GTCGGCTCTGCTGCTTTTGG | 6487 | SPBC18E5.09c_DN | CGGCTTCGGTCGGGTTGATG |
| 6386 | SPBC1773.16c_UP | CCGGGAGCTGTATGGATGGC | 6488 | SPBC18E5.10_UP | TGAAGGCTGATGGGCGGTCC |
| 6387 | SPBC1773.16c_DN | GCGCCGTCTTAAGCGCCATGT | 6489 | SPBC18E5.10_DN | GGGTTCTTGTTGTCCGGGGG |
| 6388 | SPBC1778.02_UP | TCCTCGACTCACATTGCGCC | 6490 | SPBC18E5.14c_UP | ACACCACCAGGCTGAACCGA |
| 6389 | SPBC1778.02_DN | GCCCTGCGTCCCCTAACACC | 6491 | SPBC18E5.14c_DN | AGGTCGGACTCATGTCACGC |
| 6390 | SPBC1778.03c_UP | TGCTGTGTAGTGGGCGACGG | 6492 | SPBC18H10.03_UP | TTGCCCTGCCAGCTAGTCTGG |
| 6391 | SPBC1778.03c_DN | TCGACCCTGCCCAACCAAGA | 6493 | SPBC18H10.03_DN | CACGCGATCTAGGGTGAGCA |
| 6392 | SPBC1778.04_UP | CGAAGTGCGGGCAGCCAGGC | 6494 | SPBC18H10.04c_UP | CCGCAACCCCATGAATGATG |
| 6393 | SPBC1778.04_DN | TTTCCGGCTGCAAAAGCTCT | 6495 | SPBC18H10.04c_DN | GCCCTGGGGTTGGGGTTAAG |
| 6394 | SPBC1778.05c_UP | CTCCACCAGAAACGCGCAGC | 6496 | SPBC18H10.05_UP | CCACTCCCACGTCTGCCCAT |
| 6395 | SPBC1778.05c_DN | TACTCTCGCCGCGCTGATCC | 6497 | SPBC18H10.05_DN | TGCGCCTCGGTTCTTCTCC |
| 6396 | SPBC1778.06_UP | GGGTCTGGTTCCGGGGTCGA | 6498 | SPBC18H10.06c_UP | TGGTGAAGAGGGTACGCCCG |
| 6397 | SPBC1778.06c_DN | CCGCGCTGGGCCAATTCTTC | 6499 | SPBC18H10.06c_DN | GAGCAAATGAACGCGAGGCG |
| 6398 | SPBC1778.07_UP | TTCCGGTGCTCGGACCATAG | 6500 | SPBC18H10.07_UP | CCAAAGACTCTGCTCCCGAC |
| 6399 | SPBC1778.07_DN | AACGTAGGAGAGGGCCGGC | 6501 | SPBC18H10.07_DN | ACGCACAATCCGAAACCCCC |
| 6400 | SPBC1778.08c_UP | AACCGTTCGCTCCCATCCTG | 6502 | SPBC18H10.08_UP | GCGTTGTTCCGGAGGCGTAG |
| 6401 | SPBC1778.08c_DN | CCCCTCCGCGGATAGCTCCAC | 6503 | SPBC18H10.08c_DN | GCGGGGAGGACCAAGAATGA |
| 6402 | SPBC1778.09_UP | CCGAGTCACGCCCACGAGTC | 6504 | SPBC18H10.09_UP | TGGTAGGAGCGTGGGGGTGA |
| 6403 | SPBC1778.09_DN | TCGATTAGCTGGCCGGTCG | 6505 | SPBC18H10.09_DN | TGGGCAGATTTGGGCGAGCT |
| 6404 | SPBC17A3.02_UP | TAACACCCTCTGGCGCCTGG | 6506 | SPBC18H10.10c_UP | CCTGTTCGCCCCTTGCCTCC |
| 6405 | SPBC17A3.02_DN | TGAGGATAACCGGTGGGCGT | 6507 | SPBC18H10.10c_DN | CGGCGGGATGATGGGATGAC |
| 6406 | SPBC17A3.03c_UP | CAAGCAGGCTGTGTGCGGGGC | 6508 | SPBC18H10.11c_UP | TCCGCGCGTTGGCCCTATTA |
| 6407 | SPBC17A3.03c_DN | CGGGCAGGAAGGGAAGGTCG | 6509 | SPBC18H10.11c_DN | GCGGGGGCTTGGATTGGTGT |
| 6408 | SPBC17A3.06_UP | TCCAGGGCGGATAGCTCCAC | 6510 | SPBC18H10.13_UP | CGCGACGTTTACCCAGTTCT |
| 6409 | SPBC17A3.06_DN | TAGCGCAAGCGCCCTCAAAAA | 6511 | SPBC18H10.13_DN | AGAACGCGACAGGAACGCA |
| 6410 | SPBC17A3.07_UP | AGCGGACACGTAGTGCTGGAT | 6512 | SPBC18H10.15_UP | ACTGGGGCCGGAGGATTACG |
| 6411 | SPBC17A3.07_DN | TACGCCCGTGCCGCTATCAACA | 6513 | SPBC18H10.15_DN | CTCCAAAGCACTGCCGCCGG |
| 6412 | SPBC17A3.08_UP | AGCAGCGCGACAGCGTTGGT | 6514 | SPBC18H10.16_UP | TGTCCTACGCCCTTTCGCCT |
| 6413 | SPBC17A3.08_DN | GTAAGCGGGCAGCAAGGTCG | 6515 | SPBC18H10.16_DN | TTTTTTTCGGCTTGCGGCT |
| 6414 | SPBC17A3.10_UP | GCAGCGTGCCCCTATCTCT | 6516 | SPBC18H10.18c_UP | GAGCGTGGGCGGAGTGGATA |
| 6415 | SPBC17A3.10_DN | CTTTCCCCTATCGGCGGTGC | 6517 | SPBC18H10.18c_DN | TAGCCCCAATCGCGAACACG |
| 6416 | SPBC17D1.02_UP | ACTAAACCCGCCGCACTCGA | 6518 | SPBC18H10.19_UP | GGGCATGCGATCGAAGGGAG |
| 6417 | SPBC17D1.02_DN | GACTTTCGCCTCGGCGGGTT | 6519 | SPBC18H10.19_DN | ACAATGGGCGCGCAGACAGC |
| 6418 | SPBC17D1.03c_UP | GGCAGATGTGGCGGTGACGT | 6520 | SPBC18H10.20c_UP | TAGCTTGTCGGGAGGGGCGT |
| 6419 | SPBC17D1.03c_DN | ACAAATCCGCTCCGTGCGT | 6521 | SPBC18H10.20c_DN | ACGTGGCGGGGTTTTCCTC |
| 6420 | SPBC17D1.05_UP | TTTCCCGGTGCCGGTTTGA | 6522 | SPBC1921.03c_UP | CCTTGGCTCCCATCGCTTTG |
| 6421 | SPBC17D1.05_DN | TTGGTGGCGTTTGGGCATCG | 6523 | SPBC1921.03c_DN | GAGGGTCGTGGGGGTGCTCT |
| 6422 | SPBC17D1.06_UP | GTCGGGCGTGCCTGGGTAAT | 6524 | SPBC1921.04c_UP | CCAGCAACCGCCCAAATAG |
| 6423 | SPBC17D1.06_DN | CCCTTTCTTGCCATGCCCCC | 6525 | SPBC1921.04c_DN | CAATGACGGCTGGGCAAGAA |
| 6424 | SPBC17D1.07c_UP | ACATCAAGGCCCCAACAGGG | 6526 | SPBC1921.05_UP | ACCCGTTTGCATCCCTCCCT |
| 6425 | SPBC17D1.07c_DN | TCACCTTGACCTCGCTCCC | 6527 | SPBC1921.05_DN | TGCTCGCCAATTGATCGTCC |
| 6426 | SPBC17D11.02c_UP | AGGTCTCGAAAGCGCGCGT | 6528 | SPBC1921.06c_UP | CTCCGGCACGCAGAACGTCC |

FIG. 39

| Sequence number | Name | Base sequence |
|---|---|---|
| 6529 | SPBC1921.06c_DN | TACAAGTCGTGGTCGGGGCC |
| 6530 | SPBC19C2.02_UP | GGGCAGCGGGAGCAATTAA |
| 6531 | SPBC19C2.02_DN | GGCATGACCCTAACTCGGCG |
| 6532 | SPBC19C2.03_UP | CCTAAGGGGCGAGACCGGTC |
| 6533 | SPBC19C2.03_DN | AGCGCGGCCATCCTAGACAT |
| 6534 | SPBC19C2.04c_UP | CCTCCACCCCACACTCCGTT |
| 6535 | SPBC19C2.04c_DN | GGTAATTGATGGCGGGCTGG |
| 6536 | SPBC19C2.05_UP | GACTTATGGACGGCACCGCG |
| 6537 | SPBC19C2.05_DN | CCTTGGTGGGGGGTCTGTCA |
| 6538 | SPBC19C2.06c_UP | TGCCGCATAGCAACGCGAACA |
| 6539 | SPBC19C2.06c_DN | GCTTTGCTTGGCGGGGTTTA |
| 6540 | SPBC19C2.08_UP | CAGCCACAGTAAAGCGCCGA |
| 6541 | SPBC19C2.08_DN | CACACTCGGGCGCCTTTAA |
| 6542 | SPBC19C2.09_UP | ACCCCGCTTTCAATCCGTCG |
| 6543 | SPBC19C2.09_DN | AACTCCTCCCGGTCTCGCAA |
| 6544 | SPBC19C2.10_UP | AGCCCAAAGGTAGCACCCGC |
| 6545 | SPBC19C2.10_DN | TTCTGATAGGGGAGGCGCA |
| 6546 | SPBC19C2.13c_UP | GTTCATGCCCGTTTCGCCCA |
| 6547 | SPBC19C2.13c_DN | ACCTCCCCTCAAGTTCCGCC |
| 6548 | SPBC19C2.14_UP | TCCACGCAAAACCTCGCCTT |
| 6549 | SPBC19C2.14_DN | CGGAATACGCTGGGAGTGCA |
| 6550 | SPBC19C7.03_UP | AGTGTTGCGAGGCGGAGGAA |
| 6551 | SPBC19C7.03_DN | TCACCTTTTGTGGGGCGGT |
| 6552 | SPBC19C7.04c_UP | TTACCGCCGGCCACTCTCA |
| 6553 | SPBC19C7.04c_DN | TTTGTCCATTGCCCGAGCCT |
| 6554 | SPBC19C7.05_UP | GCGAGTAAAGCCCGATTGG |
| 6555 | SPBC19C7.05_DN | GGAGCTATGGCGACTTGGGG |
| 6556 | SPBC19C7.06_UP | CCAGCCACGTTTTCCCCCTT |
| 6557 | SPBC19C7.06_DN | CACGCGCACCTTTCCACACT |
| 6558 | SPBC19C7.07c_UP | TTCTCGCTGCTCGCTTCCGT |
| 6559 | SPBC19C7.07c_DN | CTCGGCTCCCTCCCGTGTTA |
| 6560 | SPBC19C7.08c_UP | ACGGTGATAGAGACGGGCGC |
| 6561 | SPBC19C7.08c_DN | TGCCCGGACGAGGTAATGGA |
| 6562 | SPBC19C7.09c_UP | CTGCCTGCCCCACTCTCGGT |
| 6563 | SPBC19C7.09c_DN | GCTGCGTGGAGGGGGGTAGT |
| 6564 | SPBC19C7.10_UP | GTGTGCGTGCTGGGGATGTG |
| 6565 | SPBC19C7.10_DN | GAGGCAACGGACGCGAAGAA |
| 6566 | SPBC19C7.11_UP | GAAGCGGCGAGACGACAGGC |
| 6567 | SPBC19C7.11_DN | AAGTCGAACTGGAACGAGGC |
| 6568 | SPBC19C7.12c_UP | CCCGATACCCCCCCACGTCT |
| 6569 | SPBC19C7.12c_DN | TCCGCCCCCAAACCCTACTC |
| 6570 | SPBC19F5.02c_UP | ATGATGAAGGCCCACCCGCC |
| 6571 | SPBC19F5.02c_DN | ACCTGTCACCCGCTGCCCTC |
| 6572 | SPBC19F5.03_UP | GCCAATATGTCCCCTCCCCC |
| 6573 | SPBC19F5.03_DN | GGACCGCGAGTATGCATGCG |
| 6574 | SPBC19F5.04_UP | CGTTCCGCTGCTCGTGGCTG |
| 6575 | SPBC19F5.04_DN | ACTGATATGCCCCCGTCCCC |
| 6576 | SPBC19F8.02_UP | GGCAACAAACGCGACATGGC |
| 6577 | SPBC19F8.02_DN | CCTGCTGTTCCGTCCCACA |
| 6578 | SPBC19F8.03c_UP | CGGCTAAGCCGTTTGGCGAA |
| 6579 | SPBC19F8.03c_DN | CGATTAATGCCCCGTTGCCA |
| 6580 | SPBC19F8.04c_UP | AATTGAACAGACCCCCGCC |
| 6581 | SPBC19F8.04c_DN | TTTCCCGACACAGACCCGAG |
| 6582 | SPBC19F8.06c_UP | TCCACCGCCACTCCAGCAAT |
| 6583 | SPBC19F8.06c_DN | GGGGGTTGTGGCTTTGCTGC |
| 6584 | SPBC19F8.07_UP | CCGCAAACAAGGACCAGGGG |
| 6585 | SPBC19F8.07_DN | GCCATCTCGTGCCGCGTTAA |
| 6586 | SPBC19G7.02_UP | CGTTAGGACTGCGTGGGCTG |
| 6587 | SPBC19G7.02_DN | TGGGAGCGGCATGTTGGAAG |
| 6588 | SPBC19G7.03c_UP | CCAAAGCAGCAAAGGGCAC |
| 6589 | SPBC19G7.03c_DN | ATGGGCAGTTGCTGAGCGC |
| 6590 | SPBC19G7.04_UP | TCACTCATCCCAGCACGCCG |
| 6591 | SPBC19G7.04_DN | CAAGACCAGGGGCCGTTCAC |
| 6592 | SPBC19G7.05c_UP | GTGTTTTGCGGCTCCAGGGT |
| 6593 | SPBC19G7.05c_DN | CCCATACGCACCTCCGACGG |
| 6594 | SPBC19G7.06_UP | GACGACGGTGTACGGGTAGA |
| 6595 | SPBC19G7.06_DN | AGAAGGTGGGCAACGGCAAA |
| 6596 | SPBC19G7.07c_UP | CGACGCAACAGGGGAACAG |
| 6597 | SPBC19G7.07c_DN | CCCGTGGTCTTGGCGTGCTA |
| 6598 | SPBC19G7.08c_UP | ATCACGCTCCCAAGATCCCG |
| 6599 | SPBC19G7.08c_DN | CCCCAAATCGACGCTCCTG |
| 6600 | SPBC19G7.09_UP | AACTTGGTGCGTGCCGGGAC |
| 6601 | SPBC19G7.09_DN | CGGCAAATCGGCTCCAGTGT |
| 6602 | SPBC19G7.10c_UP | AAGGTCCCAGCTCCCCGAAG |
| 6603 | SPBC19G7.10c_DN | CAGGAAACCCGACACGATG |
| 6604 | SPBC19G7.13_UP | TCCAGCCCCTGTTGCCTCCC |
| 6605 | SPBC19G7.13_DN | GCCGCGAAGTGGACGCTTAT |
| 6606 | SPBC19G7.15_UP | GCAAGTCATCGGGCATTACG |
| 6607 | SPBC19G7.16_UP | CATGCACACTAGGCCACGGA |
| 6608 | SPBC19G7.17_UP | ATGAGACCTAACCGCCCCCG |
| 6609 | SPBC19G7.17_DN | CCTTCCAGCCCCTGACGATG |
| 6610 | SPBC1A4.03c_UP | AACCGAAAGGAAGCCGGAG |
| 6611 | SPBC1A4.03c_DN | TGCCCTAGGTGCTAGATGCG |
| 6612 | SPBC1A4.04_UP | TCCGGGCCTTTTCGATCTTG |
| 6613 | SPBC1A4.04_DN | AGGTGCGCGGTTTCCATGAT |
| 6614 | SPBC1A4.05_UP | TTTTTGCAGGAGGGCGCTTT |
| 6615 | SPBC1A4.05_DN | CGGGTCTTAGGCGTGGGGA |
| 6616 | SPBC1A4.06c_UP | GATTGAGTGGGGGTGGCGAC |
| 6617 | SPBC1A4.06c_DN | TGCAAAGGGATCCCGGGAGG |
| 6618 | SPBC1A4.07c_UP | CAGTTCACGATGGGCGAGCA |
| 6619 | SPBC1A4.07c_DN | TCCCGCATCCCCTTGCACAT |
| 6620 | SPBC1A4.08c_UP | CGCGTGGTGGAGTTCTTTGT |
| 6621 | SPBC1A4.08c_DN | GTCGGGGATGTTCGGGATTG |
| 6622 | SPBC1A4.11c_UP | AGACGGCCTTTGTTGCTGA |
| 6623 | SPBC1A4.11c_DN | AACATTCGAAAGCGCCCCCG |
| 6624 | SPBC1D7.01_UP | CGTGATCCGGAAGCAATCCG |
| 6625 | SPBC1D7.01_DN | GCCCTGTCTTGACTTCCGCG |
| 6626 | SPBC1D7.03_UP | CATCGGGTAGAAGGCGGCTG |
| 6627 | SPBC1D7.03_DN | GCCGTTCCTGCCCAATCCATC |
| 6628 | SPBC1D7.04_UP | GACGCCCCCCAAAGATAGG |
| 6629 | SPBC1D7.04_DN | GAAAGCCCAAAGCTCACCCG |
| 6630 | SPBC1E8.02_UP | ATTGCCCCCATAGTCCGCCC |
| 6631 | SPBC1E8.02_DN | TTAGGCGGGATTGGCGGAAA |
| 6632 | SPBC1E8.03c_UP | GTCGCTCGTGGGGGTCAAT |
| 6633 | SPBC1E8.03c_DN | GCAAGGAAGGAGGGGGGGTG |
| 6634 | SPBC20F10.02c_UP | AACATCCCGCCCCACTGAAG |
| 6635 | SPBC20F10.02c_DN | ACCTTCGCGGCCCCTTGTTG |
| 6636 | SPBC20F10.03_UP | TAAACCGCCGCAAAACCGCA |
| 6637 | SPBC20F10.03_DN | TTGTTGTTCTGGTCGGGCCC |
| 6638 | SPBC20F10.05_UP | CTGTTGCCCGATTAGCCCGA |
| 6639 | SPBC20F10.05_DN | CACGTCGAGGCCAATACCGC |
| 6640 | SPBC20F10.06_UP | TGGCGACCGGGATGAACTCA |
| 6641 | SPBC20F10.06_DN | ATGCGAAACCGATGAACGC |
| 6642 | SPBC20F10.07_UP | ACGGGCGAGGAACGAACGAC |
| 6643 | SPBC20F10.07_DN | CTGCGGGTGAACTTTTGGCG |
| 6644 | SPBC20F10.08c_UP | GCAGGTCGACGACATCGCGT |
| 6645 | SPBC20F10.08c_DN | GGGCTGTTGGGGCGACTGAT |
| 6646 | SPBC20F10.10_UP | GATGCGGGGTGCCAAGGAGA |
| 6647 | SPBC20F10.10_DN | CCCATCCGCCCACCCAAAGT |
| 6648 | SPBC21.01_UP | CGAGATCAGGCGCCCACAAC |
| 6649 | SPBC21.01_DN | AGCCATACACCCGACGACCG |
| 6650 | SPBC21.02_UP | CCTCGAATCCGCAAAGACA |
| 6651 | SPBC21.02_DN | TGCGATGCCGTTTCAGGTTG |
| 6652 | SPBC21.03c_UP | TCCGCTCCCCCATCCTTAAG |
| 6653 | SPBC21.03c_DN | TTGGGAAGCCGACGACGAAG |
| 6654 | SPBC21.04_UP | CGGCAGAGGTACAGCGGAGG |
| 6655 | SPBC21.04_DN | AGACTTCCCCATGCCCGCG |
| 6656 | SPBC21.05c_UP | CCGCGCCACGACTAAAGGCT |
| 6657 | SPBC21.05c_DN | CCACAATCGGACGGAGCAT |
| 6658 | SPBC21.06c_UP | ACACTGGCGGAGGAGCATT |
| 6659 | SPBC21.06c_DN | GCCGGGACTGAAGGGTGCAT |
| 6660 | SPBC21.07c_UP | CCCGGTCGTAAGTGGCATGC |
| 6661 | SPBC21.07c_DN | CGACGCTAGAAGGATAGCGA |
| 6662 | SPBC211.02c_UP | CGGCGGCAATTAATACGACA |
| 6663 | SPBC211.02c_DN | CAAGCGCACAAAAGGGAACG |
| 6664 | SPBC211.03c_UP | AGGGAGTATGGCCACGCGAC |
| 6665 | SPBC211.03c_DN | GCCCCGCATTTTCATTCTCG |
| 6666 | SPBC211.04c_UP | AGCTCCCCGTGCTTAACCCT |
| 6667 | SPBC211.04c_DN | TTCACCCCGGCCACCTGCAG |
| 6668 | SPBC211.06_UP | GTTGGCAGGGAGCGCGTTCT |
| 6669 | SPBC211.06_DN | TGGTGCCCTTTCGGTTCGCT |
| 6670 | SPBC211.07c_UP | ACCCCCGACAGAGCAACACC |
| 6671 | SPBC211.07c_DN | TGCCCACACATCGTCCCAAT |
| 6672 | SPBC211.08c_UP | GGCTCTTGCGGCTTTTGCCT |
| 6673 | SPBC211.08c_DN | CAAAAGGACACGGAGCCCCA |
| 6674 | SPBC215.02_UP | AACCCAGCCCAAAGTCACCC |
| 6675 | SPBC215.02_DN | GGGGGCGTGGAGGACTATG |
| 6676 | SPBC215.03c_UP | GAGACGCACATTCGAGCAAA |
| 6677 | SPBC215.03c_DN | TGAGGGCTGGTGATTTGGCA |
| 6678 | SPBC215.04_UP | GTCGTAACCGTCCACCACT |
| 6679 | SPBC215.04_DN | ATCGTTGTCGGCAGTGCCTG |
| 6680 | SPBC215.05_UP | AAGAGGAGGCGGAGCGAGGC |
| 6681 | SPBC215.05_DN | TCCCCCGTTATTCATCCGCC |
| 6682 | SPBC215.06_UP | TGAATCGTGAGCTGCGCGAA |
| 6683 | SPBC215.06c_DN | CGGATAAGCCCGCGAGAGCA |
| 6684 | SPBC215.07c_UP | GTGCTGCTTGCGGCTGCTGT |
| 6685 | SPBC215.07c_DN | GAGGAGCGCCCCCACGAGAT |
| 6686 | SPBC215.08c_UP | TGCCGGCGAGAGGGAGTAAT |
| 6687 | SPBC215.08c_DN | CAGACGCACCCATATCCCGG |
| 6688 | SPBC215.09c_UP | TTGGGCGCACCCGTAGGATA |
| 6689 | SPBC215.09c_DN | TGTGGTGCCCCGTAAGTGGA |
| 6690 | SPBC215.10_UP | CCTCAGTGCCATTCCCCCCA |
| 6691 | SPBC215.10_DN | AACCGTGGGTCGATGCGTTC |
| 6692 | SPBC215.11c_UP | TCCACACATGCAAGCCCACG |
| 6693 | SPBC215.11c_DN | CACGACCCCAGCCGCAAGAT |
| 6694 | SPBC215.13_UP | GAACGTTGGGCGCGGTAAAA |
| 6695 | SPBC215.13_DN | AACACCCTTCCAGCCACCGC |
| 6696 | SPBC215.14c_UP | AGCCATACAGGGGGGGGAAG |
| 6697 | SPBC215.14c_DN | TCCCCTTTCACCCGAGCCAG |
| 6698 | SPBC216.02_UP | CGGGAGGGCTGGGATCGAAG |
| 6699 | SPBC216.02_DN | AGTCCCGTCTGCATAGCGCG |
| 6700 | SPBC216.03_UP | TCGGGATATTTGGCAGCGTG |
| 6701 | SPBC216.03_DN | ACAAGAGCACCCCGGAACGA |
| 6702 | SPBC216.04c_UP | CGGCGTCGCGTATAGGCAGA |
| 6703 | SPBC216.04c_DN | GCGACGCTACAACATCGGGA |
| 6704 | SPBC216.05_UP | CAGAGAGATGTGCCCCCCG |
| 6705 | SPBC216.05_DN | GGTACGTCCGCTCTCGCCGT |
| 6706 | SPBC216.06c_UP | TTTGCTCCGCCACCGTCCAC |
| 6707 | SPBC216.06c_DN | AAGCAAACGAGAGCCGAGCG |
| 6708 | SPBC21B10.02_UP | CAGCCCCACCCGAGAAGAAC |
| 6709 | SPBC21B10.02_DN | GCGGGGAACGGAATAGACGG |
| 6710 | SPBC21B10.03c_UP | GTCGTGTAGGATCCGGCCGA |
| 6711 | SPBC21B10.03c_DN | TTCTCTGGACGGGCCGTGAT |
| 6712 | SPBC21B10.04c_UP | CCCGAACCGCCAAACCTGGG |
| 6713 | SPBC21B10.04c_DN | CCGCACGCCGACACTCTCAC |
| 6714 | SPBC21B10.05c_UP | AGAGGCCGTGGCGGATGAGTC |
| 6715 | SPBC21B10.05c_DN | CTTGCTCGCTGCACGGTTCC |
| 6716 | SPBC21B10.06c_UP | CGGGATCATTTGGGCCTTTG |
| 6717 | SPBC21B10.06c_DN | ACCTGTACGCCCCACCTCGA |
| 6718 | SPBC21B10.07_UP | CGCGAGAACGAGCCAACAGC |
| 6719 | SPBC21B10.07_DN | TCAGGCAGGCACACGGACAT |
| 6720 | SPBC21B10.09_UP | TCTGCCTCGCCTCAGCCACC |
| 6721 | SPBC21B10.09_DN | GCAAGCGGAGACGGGAACGA |
| 6722 | SPBC21B10.10_UP | CACCCAATCCCAGCAGCAG |
| 6723 | SPBC21B10.10_DN | AACGCCGAAAGGACGGGACA |
| 6724 | SPBC21B10.11_UP | CAACTAATAGGGCCCGTGCCA |
| 6725 | SPBC21B10.11_DN | TCCGGGCTGCGTACTCACTG |
| 6726 | SPBC21B10.12_UP | CCCCGAACGAATTAGACCGC |
| 6727 | SPBC21B10.12_DN | ACGCCCCTCGAGCACATGTG |
| 6728 | SPBC21B10.13c_UP | TCCCAGGTCATCCCCGTTGA |
| 6729 | SPBC21B10.13c_DN | CGGCGCGTAGCGTAAACGAT |
| 6730 | SPBC21C3.02c_UP | CTTTCGGTTGCGGAATTCGG |
| 6731 | SPBC21C3.02c_DN | TGGCGTTTTGGGTCGGTTCA |
| 6732 | SPBC21C3.03_UP | CCGTGCCCCCATCAGCTTA |

FIG.40

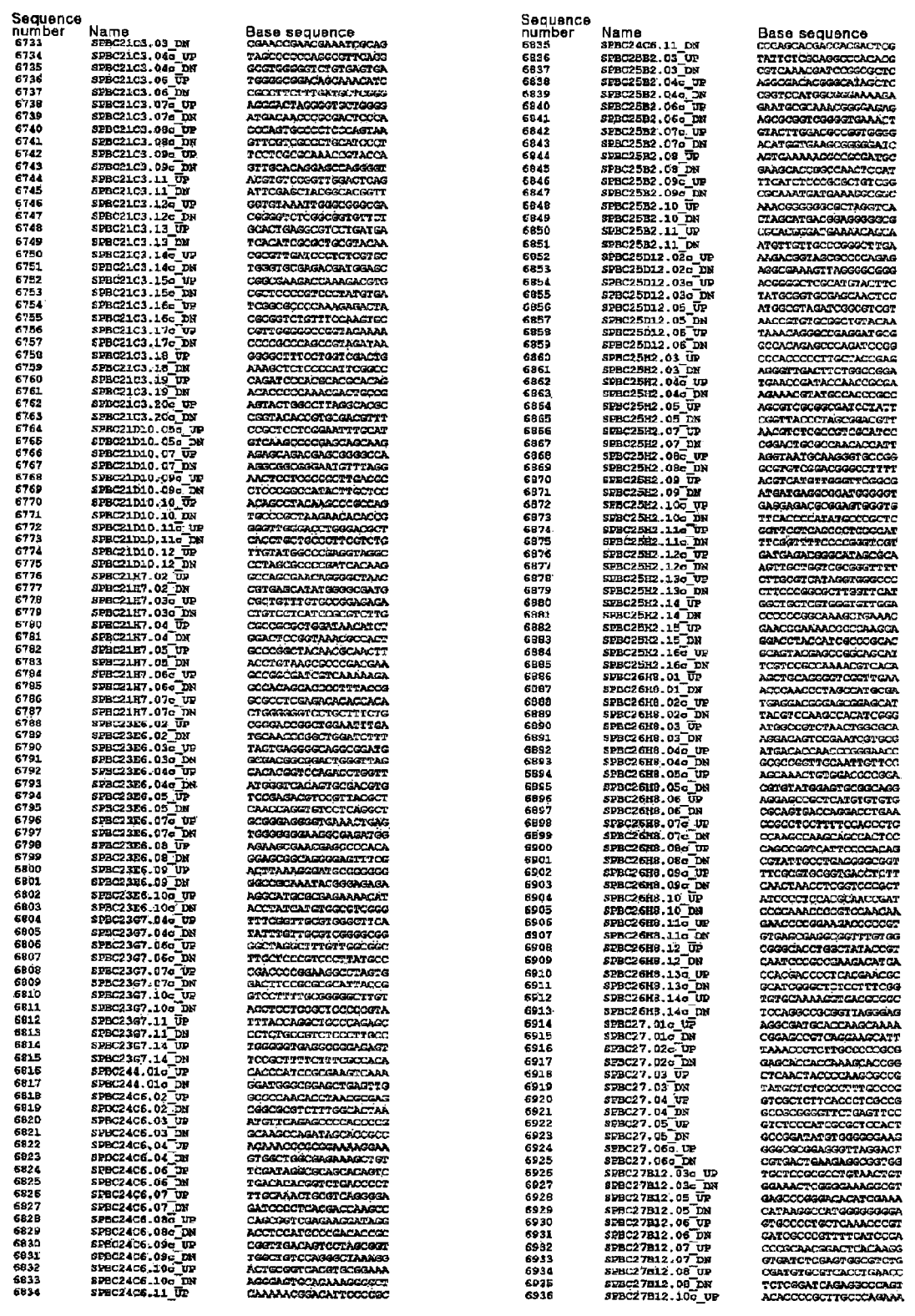

| Sequence number | Name | Base sequence |
|---|---|---|
| 6733 | SPBC21C3.03_DN | CGAACCGAACGAAATCGCAG |
| 6734 | SPBC21C3.04c_UP | TAGCCCCCCAGGCGTTCAGG |
| 6735 | SPBC21C3.04c_DN | GCGTGGGGTCTGTGAGTGA |
| 6736 | SPBC21C3.05_UP | TGGGGCGGACAGCAAACATC |
| 6737 | SPBC21C3.06_DN | CGCCTTCTTTGATGCTCGGG |
| 6738 | SPBC21C3.07c_UP | AGGGACTAGGGGTGCTGGGG |
| 6739 | SPBC21C3.07c_DN | ATGACAACCCGCGACTCCCA |
| 6740 | SPBC21C3.08c_UP | CCCAGTGCCCCTCCCAGTAA |
| 6741 | SPBC21C3.08c_DN | GTTCGTCGCCCTGCATCCCT |
| 6742 | SPBC21C3.09c_UP | TCCTCGCGCAAACCGTACCA |
| 6743 | SPBC21C3.09c_DN | GTTGCACAGGAGCCAGGGGT |
| 6744 | SPBC21C3.11_UP | ACGTGTCCGGTTGGACTCAG |
| 6745 | SPBC21C3.11_DN | ATTCGAGCTACGGCACGGTT |
| 6746 | SPBC21C3.12c_UP | GGTGTAAATTGGGCGGGCGA |
| 6747 | SPBC21C3.12c_DN | CGGGGTCTCGGCGGTGTTCT |
| 6748 | SPBC21C3.13_UP | GCACTGAGGCGTCCTGATGA |
| 6749 | SPBC21C3.13_DN | TCACATCGCGCTGCGTACAA |
| 6750 | SPBC21C3.14c_UP | CGCGTTGATCCCTCTCGTGC |
| 6751 | SPBC21C3.14c_DN | TGGGTGCGAGACGATGGAGC |
| 6752 | SPBC21C3.15c_UP | CGGCGAAGACCAAAGACGTG |
| 6753 | SPBC21C3.15c_DN | CGCTCCCCGTCCCTATGTGA |
| 6754 | SPBC21C3.16c_UP | TCGGCGCCCCAAAGAGACTA |
| 6755 | SPBC21C3.16c_DN | CGCGGTCTGTTTCCAAGTGC |
| 6756 | SPBC21C3.17c_UP | CGTTGGGGGCCCGTAGAAAA |
| 6757 | SPBC21C3.17c_DN | CCCCGCCCAGCCGTAGATAA |
| 6758 | SPBC21C3.18_UP | GGGGCTTTCCTGGTCGACTG |
| 6759 | SPBC21C3.18_DN | AAAGCTCTCCCCATTCGGCC |
| 6760 | SPBC21C3.19_UP | CAGATCCCACGCACGCACAG |
| 6761 | SPBC21C3.19_DN | ACACCCCCAAACGACTGCCC |
| 6762 | SPBC21C3.20c_UP | AGTACTGGCCTTAGGCACGC |
| 6763 | SPBC21C3.20c_DN | CGGTACACCGTGCGACGTTT |
| 6764 | SPBC21D10.05c_UP | CCGCTCCTCGGAATTTGCAT |
| 6765 | SPBC21D10.05c_DN | GTCAAGCCCCGAGCAGCAAG |
| 6766 | SPBC21D10.07_UP | AGAGCAGACGAGCGGGGCCA |
| 6767 | SPBC21D10.07_DN | AGGCGGCGGGAATGTTTAGG |
| 6768 | SPBC21D10.09c_UP | AACTCCTCCCCCCTTGACCC |
| 6769 | SPBC21D10.09c_DN | CTCCCGGCCATACTTGCTCC |
| 6770 | SPBC21D10.10_UP | ACAGCCTACAAGCCCGCCAG |
| 6771 | SPBC21D10.10_DN | TGCCCGCTAAGAACACACCG |
| 6772 | SPBC21D10.11c_UP | GGGTTGGGACCTGGGACGCT |
| 6773 | SPBC21D10.11c_DN | CACCTGCTGCCCTTCGTCTG |
| 6774 | SPBC21D10.12_UP | TTGTATGGCCCGAGGTAGGC |
| 6775 | SPBC21D10.12_DN | CCTAGCGCCCCGATCACAAG |
| 6776 | SPBC21H7.02_UP | GCCAGCGAACAGGGGCTAAC |
| 6777 | SPBC21H7.02_DN | CGTGAGCATATGGGGCGATG |
| 6778 | SPBC21H7.03c_UP | CGCTGTTTGTGCCGGAGAGA |
| 6779 | SPBC21H7.03c_DN | CTGTCCTCATCCGCGTCTTG |
| 6780 | SPBC21H7.04_UP | CGCCGCGCTGGATAACATCT |
| 6781 | SPBC21H7.04_DN | GGACTCCGGTAAACGCCACT |
| 6782 | SPBC21H7.05_UP | GCCCGGCTACAACGCAACTT |
| 6783 | SPBC21H7.05_DN | ACCTGTAAGCGCCCGACGAA |
| 6784 | SPBC21H7.06c_UP | GCCGGCGATCGTCAAAAAGA |
| 6785 | SPBC21H7.06c_DN | GCCACAGCACCCCTTTACCG |
| 6786 | SPBC21H7.07c_UP | GCGCCTCGAGACACACCACA |
| 6787 | SPBC21H7.07c_DN | CTGGGGGGTCCTGCTTTCTG |
| 6788 | SPBC23E6.02_UP | CGGGACCGGCTGGAATTTGA |
| 6789 | SPBC23E6.02_DN | TGCAACCCGGCTGGATCTTT |
| 6790 | SPBC23E6.03c_UP | TAGTGAGGGGCAGGCGGATG |
| 6791 | SPBC23E6.03c_DN | GCGACGGCGGACTGGGTTAG |
| 6792 | SPBC23E6.04c_UP | CACACGGTCCAGACCTGGTT |
| 6793 | SPBC23E6.04c_DN | ATGGGTCACAGTGCGACGTG |
| 6794 | SPBC23E6.05_UP | TCCGAGACGTCCGTTACGCT |
| 6795 | SPBC23E6.05_DN | CAACCAGGTGTCCTCAGGCT |
| 6796 | SPBC23E6.07c_UP | GCGGGAGGGGTGAAACTGAG |
| 6797 | SPBC23E6.07c_DN | TGGGGGGGAAGGCGAGATGG |
| 6798 | SPBC23E6.08_UP | AGAAGCGAACGAGCCCCACA |
| 6799 | SPBC23E6.08_DN | GGAGCGGCAGGGGAGTTTCG |
| 6800 | SPBC23E6.09_UP | ACTTAAAGGGATGCGGGGGG |
| 6801 | SPBC23E6.09_DN | GGCCGCAAATACGGGAGAGA |
| 6802 | SPBC23E6.10c_UP | AGGCATGCGCGAGAAAACAT |
| 6803 | SPBC23E6.10c_DN | ACCTATCATGTGGCGTCGGG |
| 6804 | SPBC23G7.04c_UP | TTTCGGTTGCGTGGGCTTCA |
| 6805 | SPBC23G7.04c_DN | TATTTGTTGCGTCGGGGCGG |
| 6806 | SPBC23G7.06c_UP | GGCTAGGCTTTGTTGGCGGC |
| 6807 | SPBC23G7.06c_DN | TTGCTCCCGTCCCTTATGCC |
| 6808 | SPBC23G7.07c_UP | CGACCCCGGAAGGCCTAGTG |
| 6809 | SPBC23G7.07c_DN | GACTTCCGCGCGCATTACCG |
| 6810 | SPBC23G7.10c_UP | GTCCTTTTGCGGGGGCTTGT |
| 6811 | SPBC23G7.10c_DN | AGCTCCTCCGCTCCCCGGTA |
| 6812 | SPBC23G7.11_UP | TTTACCAGGCTGCCCAGAGC |
| 6813 | SPBC23G7.11_DN | CCTCTGCCGTCTCCCTTGCC |
| 6814 | SPBC23G7.14_UP | TGGGGGTGAGGCGGGAGAGT |
| 6815 | SPBC23G7.14_DN | TCCGCTTTTCTTTCGCCACA |
| 6816 | SPBC244.01c_UP | CACCCATCCGCGAAGTCAAA |
| 6817 | SPBC244.01c_DN | GGATGGGCGGAGCTGAGTTG |
| 6818 | SPBC24C6.02_UP | GCGCCAACACCTAACGCGAG |
| 6819 | SPBC24C6.02_DN | CGGCGCGTCTTTGGCACTAA |
| 6820 | SPBC24C6.03_UP | ATGTTCAGAGCCCCACCCCG |
| 6821 | SPBC24C6.03_DN | GCAAGCCAGATAGCACCGCC |
| 6822 | SPBC24C6.04_UP | AGAAACCGCGCGAAAAGGAA |
| 6823 | SPBC24C6.04_DN | GTGGCTGGCGAGAAAGCTGT |
| 6824 | SPBC24C6.06_UP | TCGATAGGCGCAGCACAGTC |
| 6825 | SPBC24C6.06_DN | TGACACACGGTCTGACCCCT |
| 6826 | SPBC24C6.07_UP | TTGCAAACTGCGTCAGGGGA |
| 6827 | SPBC24C6.07_DN | GATCCCCTCACGACCAAGCC |
| 6828 | SPBC24C6.08c_UP | CAGCGGTCGAGAAGGATAGG |
| 6829 | SPBC24C6.08c_DN | ACCTCCATCCCCGACACCGC |
| 6830 | SPBC24C6.09c_UP | CGGTTGACAGTCCTAGCGGT |
| 6831 | SPBC24C6.09c_DN | TGGCTGTCCAGGGCTAAAGG |
| 6832 | SPBC24C6.10c_UP | ACTGCGGTCACGTGCGGAAA |
| 6833 | SPBC24C6.10c_DN | AGGGAGTGCAGAAAGCCGCT |
| 6834 | SPBC24C6.11_UP | CAAAAACGGACATTCCCCGC |
| 6835 | SPBC24C6.11_DN | CCCAGCACGACCACGACTCG |
| 6836 | SPBC25B2.03_UP | TATTCTCGCAGGCCCACACG |
| 6837 | SPBC25B2.03_DN | CGTCAAACGATCCGGCGCTC |
| 6838 | SPBC25B2.04c_UP | AGGCGACACGGGCATAGCTC |
| 6839 | SPBC25B2.04c_DN | CGGTCCATGGCGGGAAAAGA |
| 6840 | SPBC25B2.06c_UP | GAATGCGCAAACGGGGAGAG |
| 6841 | SPBC25B2.06c_DN | AGCGCGGTCGGGGTGAAACT |
| 6842 | SPBC25B2.07c_UP | GTACTTGGACGCCGGTGGGG |
| 6843 | SPBC25B2.07c_DN | ACATGGTGAAGCGGGGGATC |
| 6844 | SPBC25B2.08_UP | AGTGAAAAAGCCCGCGATGC |
| 6845 | SPBC25B2.08_DN | GAAGCACCGGCCAACTCCAT |
| 6846 | SPBC25B2.09c_UP | TTCATCTCCCGCGCTGTCGG |
| 6847 | SPBC25B2.09c_DN | CGCAAATGATGAAAGGCGGC |
| 6848 | SPBC25B2.10_UP | AAACGGGGGGCGCTAGGTCA |
| 6849 | SPBC25B2.10_DN | CTAGCATGACGGAGGGGGCG |
| 6850 | SPBC25B2.11_UP | CGCACGGGATGAAAACAGCA |
| 6851 | SPBC25B2.11_DN | ATGTTGTTGCCCGGGCTTGA |
| 6852 | SPBC25D12.02c_UP | AAGACGGTAGCGCCCCAGAG |
| 6853 | SPBC25D12.02c_DN | AGGCGAAAGTTAGGGGCGGG |
| 6854 | SPBC25D12.03c_UP | ACGGGGCTCGCATGTACTTC |
| 6855 | SPBC25D12.03c_DN | TATGCGGTGCGAGCAACTCC |
| 6856 | SPBC25D12.05_UP | ATGGCGTAGATCGGCGTCGT |
| 6857 | SPBC25D12.05_DN | AACCGTGTGCGGCTGTACAA |
| 6858 | SPBC25D12.06_UP | TAAACAGGGCCGAGGATGCG |
| 6859 | SPBC25D12.06_DN | GCCACAGAGCCCAGATCCGG |
| 6860 | SPBC25H2.03_UP | CCCACCCCCTTGCTACCGAG |
| 6861 | SPBC25H2.03_DN | AGGGTTGACTTCTGGCCGGA |
| 6862 | SPBC25H2.04c_UP | TGAACCGATACCAACCGCCA |
| 6863 | SPBC25H2.04c_DN | AGAAACGTATGCCACCCGCC |
| 6864 | SPBC25H2.05_UP | AGCGTCGCGGCGATCCTATT |
| 6865 | SPBC25H2.05_DN | CGGTTACCCTAGCGGACGTT |
| 6866 | SPBC25H2.07_UP | AACGTCTCGCCGTCGCATCC |
| 6867 | SPBC25H2.07_DN | CGGACTGCGCCAACACCATT |
| 6868 | SPBC25H2.08c_UP | AGGTAATGCAAGGGTGCCGG |
| 6869 | SPBC25H2.08c_DN | GCGTGTCGGACGGGCCTTTT |
| 6870 | SPBC25H2.09_UP | ACGTCATGTTGGGTTCGGCG |
| 6871 | SPBC25H2.09_DN | ATGATGAGGCGGATGGGGGT |
| 6872 | SPBC25H2.10c_UP | GAGGAGACGCGGAGTGGGTG |
| 6873 | SPBC25H2.10c_DN | TTCACCCCATATGCCCGCTC |
| 6874 | SPBC25H2.11c_UP | GGTTCGTCAGCCCTCGGCAT |
| 6875 | SPBC25H2.11c_DN | TTCGGTTTTCCCCGGGTCGT |
| 6876 | SPBC25H2.12c_UP | GATGAGACGGGCATAGCGCA |
| 6877 | SPBC25H2.12c_DN | AGTTGCTGGTCGCGGGTTTT |
| 6878 | SPBC25H2.13c_UP | CTTGCGTCATAGGTGGGCCC |
| 6879 | SPBC25H2.13c_DN | CTTCCCGGCGCTTGGTTCAT |
| 6880 | SPBC25H2.14_UP | GGCTGCTCGTGGGTGTTGGA |
| 6881 | SPBC25H2.14_DN | CCCCCCGGCAAAGCTGAAAC |
| 6882 | SPBC25H2.15_UP | GAACCGAAAACCCCCAAGCA |
| 6883 | SPBC25H2.15_DN | GGACCTACCATCGCCCGCAC |
| 6884 | SPBC25H2.16c_UP | GCAGTACGAGCCGGCAGCAT |
| 6885 | SPBC25H2.16c_DN | TCGTCCGCCAAAACGTCACA |
| 6886 | SPBC26H8.01_UP | AGCTGCAGGGGTCGGTTGAA |
| 6887 | SPBC26H8.01_DN | ACCCAACCCTAGCCATGCGA |
| 6888 | SPBC26H8.02c_UP | TGAGGACGGGAGCGGAGCAT |
| 6889 | SPBC26H8.02c_DN | TACGTCCAAGCCACATCGGG |
| 6890 | SPBC26H8.03_UP | ATGGCCGTCTAACTGGCGCA |
| 6891 | SPBC26H8.03_DN | AGGACAGTCCGAATCGTGCG |
| 6892 | SPBC26H8.04c_UP | ATGACACCAACCCGGGAACC |
| 6893 | SPBC26H8.04c_DN | GCGCCGGTTGCAATTGTTCC |
| 6894 | SPBC26H8.05c_UP | AGCAAACTGTGGACCCCGGA |
| 6895 | SPBC26H8.05c_DN | CGTGTATGGAGTGCGGCAGG |
| 6896 | SPBC26H8.06_UP | AGGAGCCGCTCATGTGTGTG |
| 6897 | SPBC26H8.06_DN | CGCAGTGACCAGGACCTGAA |
| 6898 | SPBC26H8.07c_UP | CCGCCTCCTTTTCCACCCTC |
| 6899 | SPBC26H8.07c_DN | CCAAGCCAAGCAGCCACTCC |
| 6900 | SPBC26H8.08c_UP | CAGCCGGTCATTCCCCACAG |
| 6901 | SPBC26H8.08c_DN | CGTATTGCCTGAGGGGCGGT |
| 6902 | SPBC26H8.09c_UP | TTCGCGTGCGGTGACCTCTT |
| 6903 | SPBC26H8.09c_DN | CAACTAACCTCGGTCCCGCT |
| 6904 | SPBC26H8.10_UP | ATCCCCTCCACGCAACCGAT |
| 6905 | SPBC26H8.10_DN | CCGCAAACCCCGTCCAACAA |
| 6906 | SPBC26H8.11c_UP | GAACCCCGGAAGACCCCCGT |
| 6907 | SPBC26H8.11c_DN | GTGAGCGAGGCGGTTTGTGG |
| 6908 | SPBC26H8.12_UP | CGGGCACCTGGCTATACCGT |
| 6909 | SPBC26H8.12_DN | CAATCCCGCCGAAGACATGA |
| 6910 | SPBC26H8.13c_UP | CCACGACCCCTCACGAACGC |
| 6911 | SPBC26H8.13c_DN | GCATCGGGCTCTCCTTTCGG |
| 6912 | SPBC26H8.14c_UP | TGTGCAAAACGTGACGCGGC |
| 6913 | SPBC26H8.14c_DN | TCCAGGCCGCGGTTAGGGAG |
| 6914 | SPBC27.01c_UP | AGGCGATGCACCAAGCAAAA |
| 6915 | SPBC27.01c_DN | CGGAGCCGTCAGGAAGCATT |
| 6916 | SPBC27.02c_UP | TAAACCCTCTTGCCCCCGCG |
| 6917 | SPBC27.02c_DN | GAGCACCACCAAAGCACCGG |
| 6918 | SPBC27.03_UP | CTCAACTACCCCAAGCGCCG |
| 6919 | SPBC27.03_DN | TATGCTCTCGCCTTTGCCCG |
| 6920 | SPBC27.04_UP | GTCGCTCTTCACCCTCGCCG |
| 6921 | SPBC27.04_DN | GCCGCGGGGTTCTGAGTTCC |
| 6922 | SPBC27.05_UP | GTCTCCCATCGCGCTCCACT |
| 6923 | SPBC27.05_DN | GCCGGATATGTGGGGGGAAG |
| 6924 | SPBC27.06c_UP | GGGCGCGGAGGGTTAGGACT |
| 6925 | SPBC27.06c_DN | CGTGACTGAAGAGGCGGTGG |
| 6926 | SPBC27B12.03c_UP | TGCTCCGCGCCTGTAACTGT |
| 6927 | SPBC27B12.03c_DN | GGAAACTCGGGGAAAGGCGT |
| 6928 | SPBC27B12.05_UP | GAGCCCGGGACACATCGAAA |
| 6929 | SPBC27B12.05_DN | CATAAGGCCATGGGGGGGGA |
| 6930 | SPBC27B12.06_UP | GTGCCCCTGCTCAAACCCGT |
| 6931 | SPBC27B12.06_DN | GATCGCCCGTTTTCATCCCA |
| 6932 | SPBC27B12.07_UP | CCCGCAACGGACTCACAAGG |
| 6933 | SPBC27B12.07_DN | GTGATCTCGAGTGGCGTCTG |
| 6934 | SPBC27B12.08_UP | CGATGTGCGTCACCTGAACC |
| 6935 | SPBC27B12.08_DN | TCTCGGATCAGAGGCCCAGT |
| 6936 | SPBC27B12.10c_UP | ACACCCCGCTTGCCCAGAAA |

FIG.41

| Sequence number | Name | Base sequence | Sequence number | Name | Base sequence |
|---|---|---|---|---|---|
| 6937 | SPBC27B12.10c_DN | GGACCTCCGCCCTTCTTCGA | 7039 | SPBC2A9.05c_DN | ACCCCCGCGACTAGACTTG |
| 6938 | SPBC27B12.11c_UP | AAACCGGTCGACTTGCTCCA | 7040 | SPBC2A9.06c_UP | CGTCACCGAGACCCTAGCCG |
| 6939 | SPBC27B12.11c_DN | TGCAGGGAGTGGTGACGGGT | 7041 | SPBC2A9.06c_DN | GCGCAATTCCACCTCAGCAG |
| 6940 | SPBC27B12.14_UP | CTGAGRAGGGGAGTGCGGGT | 7042 | SPBC2A9.07c_UP | TAAAACCAATGCCGCGGACC |
| 6941 | SPBC27B12.14_DN | ACAAGCGCCGAACAGCCACA | 7043 | SPBC2A9.07c_DN | GACCCCCGGCACGTATTCCT |
| 6942 | SPBC28E12.03_UP | TTTTACGAACCGGCTCGGGG | 7044 | SPBC2A9.08c_UP | TAGGCGGACTCGGGCAGAAT |
| 6943 | SPBC28E12.03_DN | ACGTCTTACCCGGCGCACAA | 7045 | SPBC2A9.08c_DN | TTCGCGCCTCCACCCTCAGT |
| 6944 | SPBC28E12.04_UP | TGGGCTCGGCACGTATCCGG | 7046 | SPBC2A9.13_UP | GCACGGTGATGCGTCGATGA |
| 6945 | SPBC28E12.04_DN | CCTAGGTGTTTCGGGGTCGC | 7047 | SPBC2A9.13_DN | TCATCCGTCGGAGCAGAGCA |
| 6946 | SPBC28F2.02_UP | CGCCGCCAGAAACCGATTAC | 7048 | SPBC2D10.03c_UP | TCCCTGGCTCTTCTGCCACG |
| 6947 | SPBC28F2.02_DN | CCCTTCCAGACCCAGCCAACC | 7049 | SPBC2D10.03c_DN | GGACCTGCCGCGCTTTACAT |
| 6948 | SPBC28F2.03_UP | GGTCCAAAGGGCCAGATGCG | 7050 | SPBC2D10.04_UP | TGTGCTCTTGCGTCCCGATT |
| 6949 | SPBC28F2.03_DN | TTGCGAGCACTACCGGGCTA | 7051 | SPBC2D10.04_DN | GCGGGCTTCTCTTGCTGGGT |
| 6950 | SPBC28F2.05c_UP | TTACATGGTGCGCGTCGGGT | 7052 | SPBC2D10.05_UP | ACCACCAGACACGCTCCGCT |
| 6951 | SPBC28F2.05c_DN | CTCGGCCTTCGCTCTCCCTC | 7053 | SPBC2D10.05_DN | GGGCGGGTGGCTAAAATCGG |
| 6952 | SPBC28F2.06c_UP | CCGGGGTTTAGGATCGAGGC | 7054 | SPBC2D10.06_UP | GCGGGGGGATAGGTGTAGGC |
| 6953 | SPBC28F2.06c_DN | CCCCATGATGTTTACGCGGC | 7055 | SPBC2D10.06_DN | GTGTCGGTCTTCGGGAGGGC |
| 6954 | SPBC28F2.07_UP | TGGGAGACTTTGGCTGGCGT | 7056 | SPBC2D10.07c_UP | ATTCGGTCGTGGGGGTCCTC |
| 6955 | SPBC28F2.07_DN | TGTCCGCCCCGTCCTTCTGA | 7057 | SPBC2D10.07c_DN | CCGCTGCCCCTTTTATTTCG |
| 6956 | SPBC28F2.08c_UP | CAGCGTCGACCGGGAAAAAC | 7058 | SPBC2D10.08c_UP | GCAACGGAAATACCCCGCAT |
| 6957 | SPBC28F2.08c_DN | GCGGTGGGGTGGCGAATACG | 7059 | SPBC2D10.08c_DN | GAATAGCGGCGTTGGCCAAA |
| 6958 | SPBC28F2.10c_UP | CCTCCAGACAATCGCCCTCC | 7060 | SPBC2D10.09_UP | CTGCGAGGGGGGAACTTTGA |
| 6959 | SPBC28F2.10c_DN | ACCAGACCTTGACCCGCTCG | 7061 | SPBC2D10.09_DN | ATGAGCGACGGTTCGCGAGA |
| 6960 | SPBC28F2.11_UP | CCCGATGCGGCTTGTTCCTG | 7062 | SPBC2D10.10c_UP | GCCCAGCACAGCGTAAACCG |
| 6961 | SPBC28F2.11_DN | ATCCTTTTGGCGCGCGTGTA | 7063 | SPBC2D10.10c_DN | CACCCCGCACCACGATCAGTC |
| 6962 | SPBC28F2.12_UP | TGCTCGTACCTTGCCCCTGG | 7064 | SPBC2D10.11c_UP | AAGTTGGATGGGGGTCGGCC |
| 6963 | SPBC28F2.12_DN | CCGGGGAAATCGCAGTGTCT | 7065 | SPBC2D10.11c_DN | CGTTTCTCTGCGAATGCCG |
| 6964 | SPBC29A10.04_UP | AACCGCCCCAAGAAATCCGA | 7066 | SPBC2D10.12_UP | CGGTTGCCCACTTTCGTCCC |
| 6965 | SPBC29A10.04_DN | GTCAAACTTAAATCGCGGCC | 7067 | SPBC2D10.12_DN | CTCCTCCTGATGCCCAACCG |
| 6966 | SPBC29A10.05_UP | CACCATTTCTCGGCGTCCC | 7068 | SPBC2D10.13_UP | TCGGAAGGGGGCTAGGGGAG |
| 6967 | SPBC29A10.05_DN | TTTGTCGGGGCTGTGCAC | 7069 | SPBC2D10.13_DN | ACCCGCACTTGACCCATTCC |
| 6968 | SPBC29A10.06c_UP | TTCGGGTGTGGTCGGTGTG | 7070 | SPBC2D10.14c_UP | GAAGAAATCCCACCCATCGG |
| 6969 | SPBC29A10.06c_DN | GCTCGCCTCCCGGTTGCCT | 7071 | SPBC2D10.14c_DN | GGAAGGGTTTTTTGGCGCG |
| 6970 | SPBC29A10.07_UP | CCCCAGAACCAGCCGCACACA | 7072 | SPBC2D10.15c_UP | CCCAATGAACCGTAACCACC |
| 6971 | SPBC29A10.07_DN | GGAGGGGACGGTCTTTTGT | 7073 | SPBC2D10.15c_DN | ACTTGTAACCTCCCGCCGGA |
| 6972 | SPBC29A10.09_UP | CCCACTGCCCGAATTGTCAA | 7074 | SPBC2D10.17_UP | TCACCTTAGTGCGACGGGGC |
| 6973 | SPBC29A10.09_DN | GCGCCCCTCCGTATCTAGC | 7075 | SPBC2D10.17_DN | GCCTGTTGGGCTTCGCGTAT |
| 6974 | SPBC29A10.09c_UP | TATTGTAAGCGGCACGGGCG | 7076 | SPBC2D10.18_UP | CGGGAAGGAAGGGTGCCAATA |
| 6975 | SPBC29A10.09c_DN | CAAGTTGCAAGAGGCAGCGC | 7077 | SPBC2D10.18_DN | TCTTCGCCGCGTCTTTCTCG |
| 6976 | SPBC29A10.10c_UP | AAGTGAGGGTACCGAGGGAA | 7078 | SPBC2D10.19c_UP | CCCCACGATCATTTCCGCCT |
| 6977 | SPBC29A10.10c_DN | TTCCCACTCAAACCCCGCCT | 7079 | SPBC2D10.19c_DN | GCCGGCACAACGAATGGAGA |
| 6978 | SPBC29A10.11c_UP | GGCCCGCACCATCGTCATTA | 7080 | SPBC2F12.02c_UP | GCCCTAAATAACGCCTAGCCS |
| 6979 | SPBC29A10.11c_DN | TGGCGTTAACCTAGTCGCCC | 7081 | SPBC2F12.02c_DN | CCGCCTGCAATTCGTCAAAG |
| 6980 | SPBC29A10.13_UP | TGGGAGCAGCAACGGGAGAC | 7082 | SPBC2E12.03c_UP | GATTTGCTAACGAGGGCGGG |
| 6981 | SPBC29A10.13_DN | TGCCTGCCAACACTTGCTCA | 7083 | SPBC2E12.03c_DN | GCGTTGCCCCTCTCCTGCTG |
| 6982 | SPBC29A10.14_UP | GGTAATTCCCCGCGAGCCTT | 7084 | SPBC2E12.04_UP | GCGGGCGGGTACTGTAACGG |
| 6983 | SPBC29A10.14_DN | GCGGCGCATCGAATTAAAT | 7085 | SPBC2E12.04_DN | CAGGGTTCCACCGTCCGCAT |
| 6984 | SPBC29A10.15_UP | CCCCTCGCCAAGCAAAGCAA | 7086 | SPBC2E12.05c_UP | AGGCATCAGGTTCGGGGAGG |
| 6985 | SPBC29A10.15_DN | TGTGGCAACGTGATGGAGCT | 7087 | SPBC2E12.05c_DN | AAGATTACCACAGCCGCGCC |
| 6986 | SPBC29A10.16c_UP | CCAACAAAAGGGAGGTTGGG | 7088 | SPBC2E12.07c_UP | GGCGGGGGTTAAACTCAGCTG |
| 6987 | SPBC29A10.16c_DN | GCCTTCGCTGCCCCGATTAA | 7089 | SPBC2E12.07c_DN | CCCCCAAATCACTCCCGCTG |
| 6988 | SPBC2A3.01_UP | CCACCGCTTTTCACCCCGA | 7090 | SPBC2E12.08c_UP | GTCGGCCTAGCACACACCGA |
| 6989 | SPBC2A3.01_DN | GCCAAGGGCGGCCTAACTCT | 7091 | SPBC2E12.08c_DN | TCGCCTTCCATGGGCTTAGC |
| 6990 | SPBC2A3.02c_UP | TTCCCCAGCCCCGCCCTATT | 7092 | SPBC2E12.09c_UP | AGATCCACTGCCCCCCTACC |
| 6991 | SPBC2A3.02c_DN | CACGGGAAAGCATGCGACCA | 7093 | SPBC2E12.09c_DN | TGGGTCCTTGGGGGCTAGTG |
| 6992 | SPBC2A3.03c_UP | CCGCGATACCAGGAGCATGA | 7094 | SPBC2E12.10_UP | GAAAGGGCGATGTTGCGAAC |
| 6993 | SPBC2A3.03c_DN | CGCTTCCAGGTCGTTGATC | 7095 | SPBC2E12.10_DN | AGCGCCGACAGCCCAGACAA |
| 6994 | SPBC2A3.04_UP | AACGCCCGGCCCGTATTAAA | 7096 | SPBC2E12.11c_UP | GATTTGGCGATGGGTCGGTC |
| 6995 | SPBC2A3.04_DN | ACGCGGGACCGGTTCGAATA | 7097 | SPBC2E12.11c_DN | CGCATTTTGCTCGTTCCACG |
| 6996 | SPBC2A3.05_UP | GTTCTTGGATGGAGCGCCGA | 7098 | SPBC2E12.12c_UP | TGCTAATGCTTTGCTCGCGG |
| 6997 | SPBC2A3.05_DN | GGCTGCGGTGCTGTGGTAGA | 7099 | SPBC2E12.12c_DN | AATTCGCAAACCGCGCGAT |
| 6998 | SPBC2A3.06_UP | CGGGGGGGCTCGACTAGCTGAA | 7100 | SPBC2E12.13_UP | CGTTATTTCGTGTGCGCGG |
| 6999 | SPBC2A3.06_DN | TGCCCCCTCTTACATACCG | 7101 | SPBC2E12.13_DN | CGGCAGACGGTGAAGACAGA |
| 7000 | SPBC2A3.07c_UP | CAGCGGTATCACGGTCGGACT | 7102 | SPBC2F12.14c_UP | GCCAATCACGGGGCACTAGT |
| 7001 | SPBC2A3.07c_DN | AACAGTGGCTCAGCTCTCCC | 7103 | SPBC2F12.14c_DN | CCTAAGGCGCGACTTCGCTA |
| 7002 | SPBC2A3.08_UP | CCCACGGATCCGGGCAAACC | 7104 | SPBC2F12.15c_UP | TCATCCGGGCCCGTAGTTTT |
| 7003 | SPBC2A3.08_DN | GCCCGCTTTTCCTTACGGCCA | 7105 | SPBC2F12.15c_DN | GCCGGGGACAAAAATGACGC |
| 7004 | SPBC2A3.09_UP | CCGAGGCTGCATTGGAGCGT | 7106 | SPBC2G2.02_UP | GGCTTACGCGGGGCATTCGG |
| 7005 | SPBC2A3.09_DN | TGTACGATCTGTGCGGCCGG | 7107 | SPBC2G2.02_DN | CGGTGAAGATTGCGCAGTGG |
| 7006 | SPBC2A3.10c_UP | GGTCCCGCTTGGAGTTCCCC | 7108 | SPBC2G2.03c_UP | TCACTCCCGCCGATTGTCCC |
| 7007 | SPBC2A3.10c_DN | TAGCAAACAGCAGACGGCCG | 7109 | SPBC2G2.03c_DN | TGATCCCCTCCCTCCGCACT |
| 7008 | SPBC2A3.11c_UP | AAAAGGTCTATCCGGGGTCG | 7110 | SPBC2G2.04c_UP | GGGATGCGGGCGAGACAGAA |
| 7009 | SPBC2A3.11c_DN | GCGCGTTGTTACGATTGGGA | 7111 | SPBC2G2.04c_DN | CAGTACCCGCTCCCGGCCAAA |
| 7010 | SPBC2A3.12_UP | CGCCGGGGAAAAAAATGTGAG | 7112 | SPBC2G2.06c_UP | TTTTTTGGGGACGGGTTCGGG |
| 7011 | SPBC2A3.12_DN | TTGGCAACCTACCTCCCGCT | 7113 | SPBC2G2.06c_DN | AGGGAGCCCGTAACCGATGGG |
| 7012 | SPBC2A3.13_UP | TGAACGCAGACGGACCCAGG | 7114 | SPBC2G2.07c_UP | TCAACCGGATGGACTGGGGC |
| 7013 | SPBC2A3.13_DN | GGGGGCCAATAACTCGTCCA | 7115 | SPBC2G2.07c_DN | GCGGCCCATGGAATCTCCA |
| 7014 | SPBC2A3.14c_UP | GGTGTGATGGAGTCGGGAGC | 7116 | SPBC2G2.08_UP | CGCGCGACATAGGAACAGCA |
| 7015 | SPBC2A3.14c_DN | CAGTTCCGCCACCAAGCCGT | 7117 | SPBC2G2.08_DN | GAGCCCTGTTCATTCCCCGC |
| 7016 | SPBC2A3.15c_UP | CTGAGTTCCCACAACCCGCA | 7118 | SPBC2G2.09c_UP | GGCCGGCTACGAGGTTTCC |
| 7017 | SPBC2A3.15c_DN | GTACTGCTCGGCTGGCCCTT | 7119 | SPBC2G2.09c_DN | CACTTTCCGCGTTCCTTGGG |
| 7018 | SPBC2A3.16_UP | CCCGGCTCGCATATGGTTCG | 7120 | SPBC2G2.10c_UP | GGTCAGGCCTCGGGTTCATC |
| 7019 | SPBC2A3.16_DN | CTCGCACCCGACACCAAACC | 7121 | SPBC2G2.10c_DN | AGCGCATCCTCGAACCACT |
| 7020 | SPBC2A3.17_UP | TCGCAGGCGGTGAGTGAC | 7122 | SPBC2G2.11_UP | TTTGCGGTTGTCGAGATCGG |
| 7021 | SPBC2A3.17_DN | TCCCCCACCCTTGAGCAAAA | 7123 | SPBC2G2.11_DN | CTTTCTGAGGCGCGCCCTGT |
| 7022 | SPBC2A3.18_UP | ACTCGTTCGGGCTGGCTGGA | 7124 | SPBC2G2.12_UP | CGCGCTTTCCAGTTACCCCG |
| 7023 | SPBC2A3.18_DN | CTGCTCTGCCCTCGAATGCC | 7125 | SPBC2G2.12_DN | CTGGGCCGCGCTCCTAGCCT |
| 7024 | SPBC2A3.21_UP | ACGCGGAGACCGTGTACTTT | 7126 | SPBC2G2.13c_UP | CCCCGTAGCCGGAGCACCAG |
| 7025 | SPBC2A3.21_DN | TCGTCTCAGAGGTCCCACGC | 7127 | SPBC2G2.13c_DN | ACGCCGCACCACATCACAAA |
| 7026 | SPBC2B5.01_UP | CCCCAGTAAACCCAGCCCA | 7128 | SPBC2G2.14_UP | TGCAGAATGGGCGAGACCGA |
| 7027 | SPBC2B5.01_DN | AGCCCACCCTTCACCCGATT | 7129 | SPBC2G2.14_DN | CCCACGCCACTCACTCAGCA |
| 7028 | SPBC2B5.02_UP | AGTGGAGAGGCACCAAGCGC | 7130 | SPBC2G2.15c_UP | ACCACCGCCCCTTCATTGCT |
| 7029 | SPBC2B5.02c_DN | ATGTGCCGTGTGGCGTTCCC | 7131 | SPBC2G2.15c_DN | TGGAGGCGTGGTGGGAATGT |
| 7030 | SPBC2B5.04c_UP | AGCGACAACGACCCAACCCT | 7132 | SPBC2G2.16_UP | AGCGGACGAGCAGCGAGAC |
| 7031 | SPBC2B5.04c_DN | GATGGGGCGTATTGCAGAGCG | 7133 | SPBC2G2.16_DN | GCGTGTAGAGGCGTTGTGGGG |
| 7032 | SPBC2A9.02_UP | AGCCGCCCAATTTCTCCCGA | 7134 | SPBC2G2.17_UP | GGGTCTCGGTTGTGCTGCTG |
| 7033 | SPBC2A9.02_DN | GGCGTCCCTGCGTTCGTTAT | 7135 | SPBC2G2.17c_DN | GGCAATAGGGACGGATGGCA |
| 7034 | SPBC2A9.05_UP | TGGTATCGCGGGCAAGCTTG | 7136 | SPBC2G5.01_UP | CGGGGAACCAAATACGGCGG |
| 7035 | SPBC2A9.05_DN | TTTGCCCCGGTGTGTTCGTTG | 7137 | SPBC2G5.01_DN | GCCAGTCACGAATCGACTGC |
| 7036 | SPBC2A9.04c_UP | CACCGTTACCAGCGGCCCAGG | 7138 | SPBC2G5.02c_UP | ACTTATTTTGCCGGGGGATG |
| 7037 | SPBC2A9.04c_DN | CAGGTCGGGCACATATGCGC | 7139 | SPBC2G5.02c_DN | GAAAAAGCCCGCCCACCAC |
| 7038 | SPBC2A9.05c_UP | CCCCTGAATTGAGCTCCGCC | 7140 | SPBC2G5.03_UP | CGTAAGATTGTGTCCGCGCG |

FIG.42

| Sequence number | Name | Base sequence | Sequence number | Name | Base sequence |
|---|---|---|---|---|---|
| 7141 | SPBC2G5.03_DN | GAGACGGAGATGTGGCGCGA | 7243 | SPBC32H8.02c_DN | TAAGCGCCAGGGGGGAGAG |
| 7142 | SPBC2G5.04c_UP | GCCCCGACCATCCAGAGACA | 7244 | SPBC32H8.03_UP | CATTGGGGAGCGGGTTCAGG |
| 7143 | SPBC2G5.04c_DN | CGGATGGTGCGAATTGATGG | 7245 | SPBC32H8.03_DN | AGCAGCCCATCGAGCCCAGT |
| 7144 | SPBC2G5.05_UP | CTATTTCATGGGAGCGCCG | 7246 | SPBC32H8.04c_UP | GCTTCTCGACCCTCCCTGCA |
| 7145 | SPBC2G5.05_DN | GTTTCGTGCCCGGTGTATCA | 7247 | SPBC32H8.04c_DN | GTGTCCGCCCCTCCAAAGTG |
| 7146 | SPBC2G5.06c_UP | CCCCCGGCAACCAACCTATG | 7248 | SPBC32H8.05_UP | GACCCTACACGTCAAGCGGA |
| 7147 | SPBC2G5.06c_DN | GCACGGAATCATGGAGGCAA | 7249 | SPBC32H8.05_DN | GTCGTGTATGAGCGTCGGGA |
| 7148 | SPBC2G5.07c_UP | ATGAAAGGCAGCGCCAACGT | 7250 | SPBC32H8.06_UP | CGCGCGCACAAACTTCGTAA |
| 7149 | SPBC2G5.07c_DN | ACCTTCCAATGACCCGGCCG | 7251 | SPBC32H8.06_DN | GAGGGGGTGCTGCCTACGGC |
| 7150 | SPBC30B4.02c_UP | GCCGTTTGGGTCTGGTGCTG | 7252 | SPBC32H8.07_UP | TTTTGGCGGCTGTGTTCCGT |
| 7151 | SPBC30B4.02c_DN | GACCGCGCAGCCCCTATAAC | 7253 | SPBC32H8.07_DN | ATGTGAACTGCCCCCCACCG |
| 7152 | SPBC30B4.03c_UP | GAAAGCCCAGCGACCAACCA | 7254 | SPBC32H8.08c_UP | AGCAAAAACAGCCGCGGCAA |
| 7153 | SPBC30B4.03c_DN | TCGCCACCATCGTAACGGC | 7255 | SPBC32H8.08c_DN | AACGTTGCACACGGCTCCAC |
| 7154 | SPBC30B4.04c_UP | TGGGGTGCTACGGCAGGAAC | 7256 | SPBC32H8.09_UP | GCGCCGGAGAGAAGTGGGAA |
| 7155 | SPBC30B4.04c_DN | TAGCTACGTCGGGGGGGGTC | 7257 | SPBC32H8.09_DN | CCGCATTCTCCTCCGCACCT |
| 7156 | SPBC30B4.05_UP | ATCGGTAGACGGGGCTCAGA | 7258 | SPBC32H8.10_UP | CCATTCCAGACGCTTCCCC |
| 7157 | SPBC30B4.05_DN | CCGACGCCGGGTAGGATCAG | 7259 | SPBC32H8.10_DN | CCGCCGCATACAAACGCCAT |
| 7158 | SPBC30B4.06c_UP | TACATTCGGTACCGCGGCCT | 7260 | SPBC32H8.12c_UP | AAAGGGGCGCGGTGTAACGG |
| 7159 | SPBC30B4.06c_DN | TGGCCGAAAAGGGGGTTGGA | 7261 | SPBC32H8.12c_DN | CGTCCCCTTCCCTCAAATCCC |
| 7160 | SPBC30B4.07c_UP | CGGCGGGCACCAGAGATTTT | 7262 | SPBC32H8.13c_UP | GCAAAGCTGTGGGCGGAAGA |
| 7161 | SPBC30B4.07c_DN | CCCATTCGGGCCCACTCTAG | 7263 | SPBC32H8.13c_DN | TTGAATTCGGTCACGGGGGA |
| 7162 | SPBC30B4.08_UP | GTGTGGGCCTGCCTTTGATG | 7264 | SPBC336.01_UP | GGCCGTGGGAAGGATGTCTC |
| 7163 | SPBC30B4.08_DN | ATCTCGCCCCGCTTTTGCAC | 7265 | SPBC336.01_DN | TCACGCGTTTTGTTGGCCCC |
| 7164 | SPBC30D10.02_UP | CCCGACTCTCGCAACGCTCAA | 7266 | SPBC336.03_UP | CCAGGGCGGCTGTCTTGAAT |
| 7165 | SPBC30D10.02_DN | AAGGCGCCCACCTGCTGAAT | 7267 | SPBC336.03_DN | GCCCGGTACACGTAACCGTA |
| 7166 | SPBC30D10.03c_UP | GGCAATACCCACCCCTCACG | 7268 | SPBC336.04_UP | GTGCAGCTCGCCATTCAGGT |
| 7167 | SPBC30D10.03c_DN | TTCCACACAACCGTCCCAGC | 7269 | SPBC336.04_DN | AACAGGAGGCCCAAAGCACC |
| 7168 | SPBC30D10.04_UP | AAGGGGAGGCAGGAAACGGT | 7270 | SPBC336.05c_UP | ACCCTAGCCCGTCTCCGTCG |
| 7169 | SPBC30D10.04_DN | CGCGCCTGTGGTGATGAAAT | 7271 | SPBC336.05c_DN | TACCATTCGTGCCTGCCCCC |
| 7170 | SPBC30D10.05c_UP | TGCTGTGGCGGCTGATAAGC | 7272 | SPBC336.06c_UP | GTGCTTCGAGACGTGGGCGG |
| 7171 | SPBC30D10.05c_DN | GTGCTCCCGTTAAGATGCGA | 7273 | SPBC336.06c_DN | CAAACTGCATATCGCGGGGG |
| 7172 | SPBC30D10.07c_UP | GCTGTGCTGGATCCGGGGTA | 7274 | SPBC336.07_UP | GTGGATGTGTGGGACGGCC |
| 7173 | SPBC30D10.07c_DN | CCCAGCATACTCCCGGTCCC | 7275 | SPBC336.07_DN | TGAAGTGGTGGTCGTGCCCG |
| 7174 | SPBC30D10.08_UP | TCCGAACCACACGTAGCCGA | 7276 | SPBC336.10c_UP | CCCACGGGTCGATCCTACCA |
| 7175 | SPBC30D10.08_DN | AAGCACGGGATGGCGAGACA | 7277 | SPBC336.10c_DN | GACTAACACCCGCCCGCACT |
| 7176 | SPBC30D10.10c_UP | AACGGCCTGAGGCGTAGTTC | 7278 | SPBC336.12c_UP | GGGGGGGAAGCTGGGGCAATA |
| 7177 | SPBC30D10.10c_DN | AAGATGGTCGGAGCACGGCT | 7279 | SPBC336.12c_DN | CAGAGGGGTTAGCGGTGGCC |
| 7178 | SPBC30D10.12c_UP | CTCCCCGTACAAGTCCGCCCC | 7280 | SPBC336.13c_UP | GAATCTCCCGCCGCGCTCCACGT |
| 7179 | SPBC30D10.12c_DN | GGAGGACGCCAGGGAGAGGG | 7281 | SPBC336.13c_DN | TGCGTGGAGGGCTTGGCGATA |
| 7180 | SPBC30D10.13c_UP | TGGAAGCAGGGACCGGGAAT | 7282 | SPBC336.14c_UP | GGAACGGCAGGAACATCCG |
| 7181 | SPBC30D10.15c_DN | CCGCGGCCTCCTTCGTTCTAT | 7283 | SPBC336.14c_DN | CAGATGGATATGCGCGTGCG |
| 7182 | SPBC30D10.14_UP | TTTCCGCGGCTTTTGTGCG | 7284 | SPBC337.03_UP | CCGATGAAGAAACCGGCAA |
| 7183 | SPBC30D10.14_DN | GCGTCTCGGTGTGCTGCCTA | 7285 | SPBC337.03_DN | TAGCGGAGGGATGACCGGGA |
| 7184 | SPBC30D10.16_UP | TTGGGGCTCTTGCAGTGGGT | 7286 | SPBC337.04_UP | GATGCAACAGCAAGGGCGAC |
| 7185 | SPBC30D10.16_DN | CCGTTCCGTTGCCAGGGGTA | 7287 | SPBC337.04_DN | TTGCCGTGTGGGGTGAGTCA |
| 7186 | SPBC30D10.18a_UP | GGTGGTGAGGGAGCTCGTCG | 7288 | SPBC337.05c_UP | ACCGCCAGGCCACAGTATCC |
| 7187 | SPBC30D10.18a_DN | AGGAACCCGCGCAAGCAGAT | 7289 | SPBC337.05c_DN | GATCTGGCTGTGAGGGGCA |
| 7188 | SPBC317.01_UP | CAATATGCCTGGAACCGCCG | 7290 | SPBC337.06c_UP | CGGGCCTCCAGTACAGGGTT |
| 7189 | SPBC317.01_DN | CCACATGCCCGTCCCAACGA | 7291 | SPBC337.06c_DN | CAATGTTAGAGCACGCCCGC |
| 7190 | SPBC31E1.02c_UP | TCGGACCCACAAAAGACGGG | 7292 | SPBC337.07c_UP | CGCGAATTTACGCACCCGAC |
| 7191 | SPBC31E1.02c_DN | TCATGCCTGTGGCTTTCGCA | 7293 | SPBC337.07c_DN | AGGCCGGCTGTGTGCTTTCCC |
| 7192 | SPBC31E1.05_UP | GGTCGGGCACGAAGGATTCC | 7294 | SPBC337.08c_UP | CACCAACCACCCGAGCCCAA |
| 7193 | SPBC31E1.05_DN | ACCGAACTCTCGACGGTCCT | 7295 | SPBC337.08c_DN | CGCCTCTCTTCCGTTGGCAT |
| 7194 | SPBC31F10.02_UP | CTCTTGCGATCGGGGCTCCT | 7296 | SPBC337.11_UP | TGAGCGCCCGAATAGAGCAA |
| 7195 | SPBC31F10.02_DN | AGGTCAGGCGGGAGGGTCA | 7297 | SPBC337.11_DN | CTTGGCGCTGTACCCCTTTC |
| 7196 | SPBC31F10.03_UP | ACGTCCACGACCCCAGTCCC | 7298 | SPBC337.12_UP | TGCCCGGATCCCTAGCTCCC |
| 7197 | SPBC31F10.03_DN | AGCTAGCGCAACCGATCCCG | 7299 | SPBC337.12_DN | GAAAAGGTGGGCGCCAAAGA |
| 7198 | SPBC31F10.04c_UP | TCAAGGACGTTCAGCGCGGT | 7300 | SPBC337.14_UP | CAGTATCTCTCCGGGCCGCC |
| 7199 | SPBC31F10.04c_DN | GCTTTTAACGGGTTGGGCGG | 7301 | SPBC337.14_DN | AGGGCGCATCACTCGGGGTT |
| 7200 | SPBC31F10.06c_UP | TACTGCACGACCCGCCGACAA | 7302 | SPBC337.15c_UP | AATCAGCCCCGACACCGATC |
| 7201 | SPBC31F10.06c_DN | TCCGGAAATCAAGCACGCAA | 7303 | SPBC337.15c_DN | TAACCGGCCATCAACGGGAT |
| 7202 | SPBC31F10.07_UP | CCGAACCTCCGGATCAATGC | 7304 | SPBC342.02_UP | CTGCGTACCTGCATCCGTCG |
| 7203 | SPBC31F10.07_DN | GATGGTCCGGTTCGGAGCG | 7305 | SPBC342.02_DN | CCTGACGCGCCCCTTACGAC |
| 7204 | SPBC31F10.08_UP | GGGGAACACAGGACCAGGGA | 7306 | SPBC342.03_UP | CCCGAATACGCCACCCAATG |
| 7205 | SPBC31F10.08_DN | ACAAGGGCCCGAAATGAGC | 7307 | SPBC342.03_DN | GTTTCGCGTTCGGGGTCTGT |
| 7206 | SPBC31F10.09c_UP | ACCGTTAGCCCGTTTTTCGA | 7308 | SPBC342.04_UP | CCACTCCCATCATCCCGCTGC |
| 7207 | SPBC31F10.09c_DN | TTTGACGAGCCTCGCGACG | 7309 | SPBC342.04_DN | GCACCACCGGCCTACAATGA |
| 7208 | SPBC31F10.10c_UP | TGCGTGGTGAAATGGGGCAT | 7310 | SPBC342.05_UP | GGGGCAACAACGACCTGGAG |
| 7209 | SPBC31F10.10c_DN | GGCTGGCTTGGGTTAGGTGC | 7311 | SPBC342.05_DN | GAAGCAGGGAGCGGGGTGAG |
| 7210 | SPBC31F10.12_UP | ACGCAGTTGGTTGCGAGGCGA | 7312 | SPBC342.06c_UP | GCTTGGCAGGCCGGATTACA |
| 7211 | SPBC31F10.12_DN | TCGCTCCCCTCGCACAGATA | 7313 | SPBC342.06c_DN | GGGGGCTTGAACCGGGATGA |
| 7212 | SPBC31F10.13c_UP | AGCAAGCTGGTCACGTCACG | 7314 | SPBC354.02c_UP | GGCAAAAAGTGGGCAGGGT |
| 7213 | SPBC31F10.13c_DN | CCCATGCGGGCTACAAGTCG | 7315 | SPBC354.02c_DN | ACCCAGGAACTACCAAGCGA |
| 7214 | SPBC31F10.14c_UP | AAGGGGAGCAGACGGAGGAG | 7316 | SPBC354.03_UP | TACCAAACGCACGGAAACCC |
| 7215 | SPBC31F10.14c_DN | CGCCACTAGCGCTCATTCCC | 7317 | SPBC354.03_DN | TCCTGTTTATGCCGAGCCGG |
| 7216 | SPBC31F10.15c_UP | CCCTTGCCGGGGTGTTGGAAT | 7318 | SPBC354.04_UP | CAAAATGCTAACAGGCGCGGC |
| 7217 | SPBC31F10.15c_DN | TACGGGCTCTTTTTTGGCGG | 7319 | SPBC354.04_DN | ACCAAGCACAGCGCAACTCG |
| 7218 | SPBC31F10.16_UP | ATAGGTTTTGCATCGCCGCG | 7320 | SPBC354.05c_UP | CACCGACGAGCAGGCGATAA |
| 7219 | SPBC31F10.16_DN | AACTTTGGTCCGCGCTCGAG | 7321 | SPBC354.05c_DN | TAGGTGTTGGGGCTTTGCGG |
| 7220 | SPBC31F10.17c_UP | TCCGCGTCGCAAAACTCTTC | 7322 | SPBC354.06_UP | CGTTTGATTCGGGATGGCCA |
| 7221 | SPBC31F10.17c_DN | CCAGCAAGACACGCGGCTCCG | 7323 | SPBC354.06_DN | CGGTTGGGCTGCTCGTGATC |
| 7222 | SPBC32C12.02_UP | ACCTCGCAATCCCCAGCAAG | 7324 | SPBC354.07c_UP | GTTCCCTTCCCGGCTTGTGG |
| 7223 | SPBC32C12.02_DN | CATTTACCCGCTGCCCCACT | 7325 | SPBC354.07c_DN | CACAGCACCGAGCACCATGA |
| 7224 | SPBC32C12.03c_UP | TGAGGGTTCGAGCGGGGAGT | 7326 | SPBC354.08c_UP | AACTTGTGGACGGGGGGGCT |
| 7225 | SPBC32C12.03c_DN | GCCTTCCCCCAAGTCAA | 7327 | SPBC354.08c_DN | TGTGCCAGTGTCCTGGATCG |
| 7226 | SPBC32F12.02_UP | CAAGCCAAGGCGAGCCCCTG | 7328 | SPBC354.09c_UP | GTAGGGGGGTGCGGTTAGGG |
| 7227 | SPBC32F12.02_DN | TTTCATTCGCAGCGTCCAAG | 7329 | SPBC354.09c_DN | CCCCAATCGCTCTGCCACAA |
| 7228 | SPBC32F12.03c_UP | GACATTAAGAGGACCGCGGG | 7330 | SPBC354.10_UP | GGGCGGGCGAAAGGTTACTC |
| 7229 | SPBC32F12.03c_DN | CAGCAGGCGGGGAATATCG | 7331 | SPBC354.10_DN | TTTGAGCGCTCGACCCGA |
| 7230 | SPBC32F12.04_UP | TCTTCGTGGCGGTTCTGTGC | 7332 | SPBC354.11c_UP | ACGGGGGGTGTTGTTGGTGG |
| 7231 | SPBC32F12.04_DN | AGGACGCCAGGCAGGAAT | 7333 | SPBC354.11c_DN | AACTTGGTTGTGCCACGTTA |
| 7232 | SPBC32F12.06_UP | CAAGCCCTGGCTAAGACCCA | 7334 | SPBC354.12_UP | AGTCCCCGGCAGTCGATAAG |
| 7233 | SPBC32F12.06_DN | TGATCGTGCGACGTCAAGGA | 7335 | SPBC354.12_DN | TAATCGGTGCTGGGAACGGC |
| 7234 | SPBC32F12.07_UP | GCGGTGCTTCTGATGCTTGC | 7336 | SPBC354.13_UP | CGGGTACGCTAAGAAGGTGCT |
| 7235 | SPBC32F12.07c_DN | ATGCGCCGATGTTCGTTGGT | 7337 | SPBC354.13_DN | GAGGGGGCTTTCGGCCAACT |
| 7236 | SPBC32F12.08c_UP | GCCGGGTTCCGTCACGTCTTA | 7338 | SPBC354.14c_UP | ACTCCGCTCCCTTCCCCCAC |
| 7237 | SPBC32F12.08c_DN | TTCCGTACGGCTACCCCAGT | 7339 | SPBC354.14c_DN | TGTACATCACGGCCCGAGTG |
| 7238 | SPBC32F12.09_UP | CTGCCGCAGGCTGCTAAT | 7340 | SPBC354.15_UP | AACACGCGTTGCCGATCTCA |
| 7239 | SPBC32F12.09_DN | GCAGCGAGGTTAACGGGGAG | 7341 | SPBC354.15_DN | TCCGAGCGGGTCATGAAAGG |
| 7240 | SPBC32F12.12c_UP | GGGGGAAGTCAGGTGTGCGC | 7342 | SPBC359.02_UP | AGACCCCGACGCTACCGCTT |
| 7241 | SPBC32F12.12c_DN | GATACCCTCCGCATTGGCC | 7343 | SPBC359.02_DN | AATCTTGGGTGCGTCGGGAG |
| 7242 | SPBC32H8.02c_UP | TGGTCGTGGTTCGCTGGATG | 7344 | SPBC359.03c_UP | CCATCACGCAACCACTCGCC |

FIG.43

| Sequence number | Name | Base sequence | Sequence number | Name | Base sequence |
|---|---|---|---|---|---|
| 7345 | SPBC3B9.03q_DN | CCTCCACCCCGTCAGCCTCA | 7447 | SPBC3B9.19_DN | CGTTTCCCGGTGCGTATCTG |
| 7346 | SPBC359.04c_UP | GAGGGGCCGGGTGGAGTAGA | 7448 | SPBC3D6.02_UP | ATGCTTAGGCTTGGTTGCGG |
| 7347 | SPBC359.04c_DN | CTGCTGCTCCGGTCCGCCAT | 7449 | SPBC3D6.02_DN | CCCACCCGGCGACAGAAATT |
| 7348 | SPBC359.05_UP | GGGGACACAGGCAAAACGGG | 7450 | SPBC3D6.03c_UP | CGGTTACTCGCGCTGTACAA |
| 7349 | SPBC359.05_DN | CCGCACAGGACAAACACGCA | 7451 | SPBC3D6.03c_DN | CCCGGTACGGCTGGATACAA |
| 7350 | SPBC359.06_UP | ACTGAAGGACCAAGCGCGGA | 7452 | SPBC3D6.04c_UP | GGTGCCAAAGACAGGCGGAA |
| 7351 | SPBC359.06_DN | GAGACCCATTTCCGGATGAT | 7453 | SPBC3D6.04c_DN | GCTTTGGTGCCTTGGGCTGC |
| 7352 | SPBC36.01c_UP | TGGCGGGCTGAGGGACTTTG | 7454 | SPBC3D6.05_UP | ACGCAGACTCGCGTTGACGA |
| 7353 | SPBC36.01c_DN | TTTTGTCCGTTTTCCCGCCG | 7455 | SPBC3D6.05_DN | TCTGGCTCACGGCTGTACAA |
| 7354 | SPBC36.02c_UP | CCAATCCACTCCTGCTGCGA | 7456 | SPBC3D6.06c_UP | CCTAACCGCCGCTGAACGAA |
| 7355 | SPBC36.02c_DN | CACACCCGCACAACCCCAAT | 7457 | SPBC3D6.06c_DN | TGATGACGCCGGTGGAAGA |
| 7356 | SPBC36.03c_UP | CGAAAACCTCACGCCCGCAG | 7458 | SPBC3D6.07_UP | TGCCCAACATTACCCACGGA |
| 7357 | SPBC36.03c_DN | TCACCGATACCCAGCCAACG | 7459 | SPBC3D6.07_DN | TCGTACTGGTCTGGGGTTTG |
| 7358 | SPBC36.04_UP | CCCGAACAGGGCATGGTAGA | 7460 | SPBC3D6.08c_UP | CGAGGTACGCGTAGCCAACA |
| 7359 | SPBC36.04_DN | TCTCGCGCGGTCCATCCATA | 7461 | SPBC3D6.08c_DN | ACCGCACGGGACTCTCACGTA |
| 7360 | SPBC36.05c_UP | TTAGTGATTTCGCGCUCGGT | 7462 | SPBC3D6.09_UP | CTCAGCTGCGTGTAGCCCAT |
| 7361 | SPBC36.05c_DN | CTGGGTTCTGGAAATTAGCGGC | 7463 | SPBC3D6.09_DN | GTGGGGCTCCGCGTGATTAA |
| 7362 | SPBC36.07_UP | GGAGCCCCGAAAGGCGATA | 7464 | SPBC3D6.10_UP | TCCCAAAAACGGCCGCACATA |
| 7363 | SPBC36.07_DN | GCCCGATCACGTACAGCCGC | 7465 | SPBC3D6.10_DN | GTGGGGTTTGGACGGACGGT |
| 7364 | SPBC36.10_UP | AAATGAACGTGCAGGTCACC | 7466 | SPBC3D6.11c_UP | GATCGGGAGACGCCCTTTT |
| 7365 | SPBC36.10_DN | CTGCCCACCCTCCGAAACAG | 7467 | SPBC3D6.11c_DN | CAAAAGCTGCCCCAACACGG |
| 7366 | SPBC36.11_UP | CCTCCTTCCCACCCTCGCAG | 7468 | SPBC3D6.12_UP | AAGCATTCCCAACGCGAGGC |
| 7367 | SPBC36.11_DN | CCGTTATCCTCAGCCCGTGC | 7469 | SPBC3D6.12_DN | TGGGCCTCACTCTGCGGGAT |
| 7368 | SPBC365.01_UP | GGGCCCATCGTCGGTCAGTC | 7470 | SPBC3D6.13c_UP | GCCCGACGGAAACCGATCAC |
| 7369 | SPBC365.01_DN | CGCCAGCGGGGGGAGTAAGT | 7471 | SPBC3D6.13c_DN | CCAAGTAGCCCACACCGCAA |
| 7370 | SPBC365.02c_UP | TAGCGGCGGTGCAGATCAAG | 7472 | SPBC3E7.02c_UP | GCCGTTGGAGTGCAGTTCCG |
| 7371 | SPBC365.02c_DN | AGCAGGAGGTTGTGGGCCGA | 7473 | SPBC3E7.02c_DN | TTGCAGTTGGCTTTGCCCTG |
| 7372 | SPBC365.04c_UP | GGGCCGACGTATGCGGGTAA | 7474 | SPBC3E7.05c_UP | GGCTCTGCGGGACCAATCAG |
| 7373 | SPBC365.04c_DN | TGACTAGCGTCCAGGTCACC | 7475 | SPBC3E7.05c_DN | GCGCCTAAATTGCCGATTGG |
| 7374 | SPBC365.07c_UP | GGGTAGGCAGGGGAGTGGGC | 7476 | SPBC3E7.06c_UP | ATCTACACGACTGCGTCGCI |
| 7375 | SPBC365.07c_DN | ATCTTTTGGCTCGGCGGTCG | 7477 | SPBC3E7.06c_DN | CCCCCCGAACTGACCCCTTT |
| 7376 | SPBC365.08c_UP | AGGGCGCGGGCGACTTGTAT | 7478 | SPBC3E7.07c_UP | CCTCGAAGAACACCGCTGGC |
| 7377 | SPBC365.08c_DN | TTGGGGGTATCGTGGCATGC | 7479 | SPBC3E7.07c_DN | TTCCGCTTCACGCATTCCGC |
| 7378 | SPBC365.09c_UP | ACTAACCATCGCACCGGCCA | 7480 | SPBC3E7.08c_UP | TCCTAGCCCCGCACGAACGT |
| 7379 | SPBC365.09c_DN | GTGGCCAACCTCCCCGCTCT | 7481 | SPBC3E7.08c_DN | TTTGGCCCGAACCATCGCTA |
| 7380 | SPBC365.10_UP | CTTGCCAGCCCTTTGCCGTG | 7482 | SPBC3E7.09_UP | TGTTGGGCTTCCTTCGCTGG |
| 7381 | SPBC365.10_DN | GCCCGGGAGAGGACTCGACA | 7483 | SPBC3E7.09_DN | AAAAGCCCGCCAAGAGACCA |
| 7382 | SPBC365.11_UP | GTTGCGCGATGGTTGAGGTG | 7484 | SPBC3E7.10_UP | GCTGGAAGACGTGCGAGGATA |
| 7383 | SPBC365.11_DN | AGTTTCGGCGGGGGTCAGAG | 7485 | SPBC3E7.10_DN | CAGGGGTGTTGGGGAAAGGC |
| 7384 | SPBC365.12c_UP | TGCATATCGCACGACGGGGA | 7486 | SPBC3E7.11c_UP | GCGGGCCATTGCTTTTGTCA |
| 7385 | SPBC365.12c_DN | AGGGTTTGGGCGTTTGCGGT | 7487 | SPBC3E7.11c_DN | ACACGTTTTCCCCACCCCCC |
| 7386 | SPBC365.14c_UP | AATTTTGGAACGCGCCCTCA | 7488 | SPBC3E7.12c_UP | CCGGCCTATAGCACCCAAA |
| 7387 | SPBC365.14c_DN | AGGGGTGTGCAAAGGTCCGG | 7489 | SPBC3E7.12c_DN | GGCACGGCATTGGGGGACTA |
| 7388 | SPBC365.16_UP | TTGGCGGGGAGAGAACCTTG | 7490 | SPBC3F6.01c_UP | GGGTTGCTGGGGCCTTCTCT |
| 7389 | SPBC365.16_DN | TAGCCGAGACGCCCACGACC | 7491 | SPBC3F6.01c_DN | TAATCGGAAGGCAGGCTGG |
| 7390 | SPBC365.20c_UP | TATCTTCGTGCCCCGTCCTG | 7492 | SPBC3F6.04c_UP | AAGGATGCAAGTGTGGCGGG |
| 7391 | SPBC365.20c_DN | GGGACGATCGGCAAGCAGGA | 7493 | SPBC3F6.04c_DN | CGCCCCAAGTACAGCTCCCC |
| 7392 | SPBC36B7.02_UP | GCGCCGGCCACAGTATGATC | 7494 | SPBC3H7.01_UP | CTCCCCTCGTTCCCAACCAC |
| 7393 | SPBC36B7.02_DN | GGGGCCTTCGTTCGCGGACTT | 7495 | SPBC3H7.01_DN | CCAGGGATGAACGGGAGCCA |
| 7394 | SPBC36B7.03_UP | TGCGAAACCGTGATTCGGCT | 7496 | SPBC3H7.02_UP | CCCCTACATCCCGCCAACCG |
| 7395 | SPBC36B7.03_DN | AGCAAATGCGGACTGCCTGT | 7497 | SPBC3H7.02_DN | CCCGCCGAAATCAGTGCCAA |
| 7396 | SPBC36B7.04_UP | AATTAGCCCCCGTGCACTCG | 7498 | SPBC3H7.03c_UP | GCGTTTGACGGACCACCAGT |
| 7397 | SPBC36B7.04_DN | GGTTAGGGCGCGCTTTCGAG | 7499 | SPBC3H7.03c_DN | GCTGCGAAGCCGRAAGTAGG |
| 7398 | SPBC36B7.05c_UP | ACAACCATCCTGCACGCCCA | 7500 | SPBC3H7.04_UP | GGGGCGGCGGAATCTTTGAG |
| 7399 | SPBC36B7.05c_DN | CCGTGGTCGTATGTGCGCTT | 7501 | SPBC3H7.04_DN | TACCAAGCCCCGCATTCTGCC |
| 7400 | SPBC36B7.06c_UP | CGCGGTTACAGATTGGCACAG | 7502 | SPBC3H7.05c_UP | ACAAGGACATCGCGGCCACA |
| 7401 | SPBC36B7.06c_DN | TGTCGGGGGCTGTGATGCA | 7503 | SPBC3H7.05c_DN | GCCCGGCGGACTCTCTACT |
| 7402 | SPBC36B7.08c_UP | GAGACGGCAGGCTATGGGG | 7504 | SPBC3H7.06c_UP | TGGTTATTCGCGCGCAGCCT |
| 7403 | SPBC36B7.08c_DN | GAACTTGCTTGTCGCGCGGC | 7505 | SPBC3H7.06c_DN | AATAGCCGCCAGCCGTCCAG |
| 7404 | SPBC3B8.02_UP | TAACGTCGGCTCGAGGCACC | 7506 | SPBC3H7.07c_UP | CTTCAGGGGCGGCTTGGACT |
| 7405 | SPBC3B8.02_DN | CGCCTGTCGGTTGGGGACTA | 7507 | SPBC3H7.07c_DN | TTTCAGCACAGGATCCCGCA |
| 7406 | SPBC3B8.03_UP | TACTGGTGTGCCTTTGCCGG | 7508 | SPBC3H7.09c_UP | CAACAAAGCACTCGCCGGGG |
| 7407 | SPBC3B8.03_DN | GACGGGCTTTAGGGCACAGG | 7509 | SPBC3H7.08c_DN | CTGACGGGAGGATTGGCAT |
| 7408 | SPBC3B8.04c_UP | CACCTAACCGACCCACGCCG | 7510 | SPBC3H7.09_UP | GGGATGACTGGTTGAGGCCG |
| 7409 | SPBC3B8.04c_DN | GAGGGCGCGTGACGCAGGTTCG | 7511 | SPBC3H7.09_DN | GCGGAAGCACGGAGAGCACC |
| 7410 | SPBC3B8.05_UP | TAAAAGGGGGGCCGAAAGCG | 7512 | SPBC3H7.10_UP | TGTACAAGACGCGACGGGGA |
| 7411 | SPBC3B8.05_DN | GACTCCTGCCGCCACCTCC | 7513 | SPBC3H7.10_DN | GGCTTGGCTCGGTTCCGATTC |
| 7412 | SPBC3B8.06_UP | TGCGGGATCTGTCATCCTGG | 7514 | SPBC3H7.12_UP | GGCCCAGCGGCAGTAGTTCGA |
| 7413 | SPBC3B8.06_DN | AAGCCATGTCCGCTCGGAAG | 7515 | SPBC3H7.12_DN | CGCTTCGTCATTGGCCATCC |
| 7414 | SPBC3B8.08_UP | GACAACCCCACTCGCAGGCC | 7516 | SPBC3H7.13_UP | TGGAAACGGGACGATAGCGG |
| 7415 | SPBC3B8.08_DN | AACAAGGAAACCCCGCCAT | 7517 | SPBC3H7.13_DN | ATACGTCCCCCTCCCCCGAG |
| 7416 | SPBC3B8.10c_UP | GCCCGGCTTATTTCGCCATG | 7518 | SPBC3H7.14_UP | ACTAAATCGGTGGGCGCTCG |
| 7417 | SPBC3B8.10c_DN | GTTGGGGGACGGAGCGCTTT | 7519 | SPBC3H7.14_DN | GACCTGCCCTCTTCACCCGA |
| 7418 | SPBC3B8.11_UP | CCCATGCTCTGCCCACTCCT | 7520 | SPBC3H7.15_UP | CGCAGCACTACCACGGACCC |
| 7419 | SPBC3B8.11_DN | CGGCGGRGGAATTGGTGCAG | 7521 | SPBC3H7.15_DN | TCCGTCATCCCCATCCGICG |
| 7420 | SPBC3B9.01_UP | CAGTCAGCACTCAGGCTAGCA | 7522 | SPBC4.01_UP | ATCTTACACCGAGCGCCCCT |
| 7421 | SPBC3B9.01_DN | TGCCCGGTCCCTTCAACTGG | 7523 | SPBC4.01_DN | TAGTATGTCGGCGGGCGGTC |
| 7422 | SPBC3B9.02c_UP | GCCGGGGCTCAAGATGGGCTA | 7524 | SPBC4.02c_UP | ACCGAATACTGGCCGTGGGA |
| 7423 | SPBC3B9.02c_DN | CCACTGCTGAAGCGGCGGAG | 7525 | SPBC4.02c_DN | TCCTGCCGGTCCACTCCTCA |
| 7424 | SPBC3B9.04_UP | CTATCGCTTACACCGCCGCC | 7526 | SPBC4.03c_UP | GGAGGCATGACTGGGTGGGA |
| 7425 | SPBC3B9.04_DN | CCCAGCGCTACTTCGTTCCC | 7527 | SPBC4.03c_DN | GCTCAAGCCGGTGCAGGACG |
| 7426 | SPBC3B9.05_UP | GTCGTAGATCTTCGCCGCGC | 7528 | SPBC4.04c_UP | GAAGGCCGGCCAATCGACTT |
| 7427 | SPBC3B9.05_DN | CTCGGTGTTGTTGGCGCCC | 7529 | SPBC4.04c_DN | CTCGGGCCTATCACGCGCTC |
| 7428 | SPBC3B9.06c_UP | TGCGGGTATCGAACGGGAGT | 7530 | SPBC4.05_UP | AGGTCGGGGGGGGTTGGAAT |
| 7429 | SPBC3B9.06c_DN | TGCCCCGCACCAATACTACG | 7531 | SPBC4.05_DN | GGGGACTGGGTGGAGTGAGC |
| 7430 | SPBC3B9.07c_UP | ATGGGACTTTGGAGGGCGCA | 7532 | SPBC4.06_UP | CAAAATTACGTCGCCCCCCC |
| 7431 | SPBC3B9.07c_DN | TGAGCTTGCACCGCGATTGC | 7533 | SPBC4.06_DN | CCCACAGACCAAACCGCAAA |
| 7432 | SPBC3B9.08c_UP | CCCCTGTTTTGGTCCCTCTGC | 7534 | SPBC4.07c_UP | TCCGTTAAGCGGTCCTGCAT |
| 7433 | SPBC3B9.08c_DN | TCAACCAGACGATTCCCAGG | 7535 | SPBC4.07c_DN | GTTTTAGGGTCGTCCCACCGT |
| 7434 | SPBC3B9.09_UP | GGCGCACTACGGACAACCCC | 7536 | SPBC405.03c_UP | CCCGCCCACATTTCCACTGC |
| 7435 | SPBC3B9.09_DN | CTGCGTCCCTGGTCCCTCAT | 7537 | SPBC405.03c_DN | CGGATGGGTATTGCGAAGGG |
| 7436 | SPBC3B9.11c_UP | AGCTGCCTATGAGGTCGCAC | 7538 | SPBC405.04c_UP | TTCGGTCTTTCATGGCGCAG |
| 7437 | SPBC3B9.11c_DN | ACAGGCTAGCACCCTCCAT | 7539 | SPBC405.04c_DN | ACCACGCCGCATTCCACATA |
| 7438 | SPBC3B9.14c_UP | ACGATCCGTCCCGCTAGCCT | 7540 | SPBC405.05_UP | GCCGGCCTTTGGTGTACTGG |
| 7439 | SPBC3B9.14c_DN | GGGGTGAGAGCGACGGGTTAGG | 7541 | SPBC405.05_DN | AGGAGCTGGGCCGGGTAGTG |
| 7440 | SPBC3B9.15c_UP | GTTTTTGACTCGGCGCCTGG | 7542 | SPBC405.06_UP | TGATCTGGGGAAGCGAAGSG |
| 7441 | SPBC3B9.15c_DN | TGTGCCTACACACAGTGGGG | 7543 | SPBC405.06_DN | GGGGGATGAAGCAAACCTGG |
| 7442 | SPBC3B9.17_UP | CAAGCCTGCCGACCACCCAA | 7544 | SPBC405.07_UP | TTGAGCCCACGAAACGCCTG |
| 7443 | SPBC3B9.17_DN | AAGGGTGCGGATGAAGGACG | 7545 | SPBC405.07_DN | TTAGGACGCGCCCACTTTCA |
| 7444 | SPBC3B9.18c_UP | TCAAACACCGCTACGAACCA | 7546 | SPBC409.03_UP | CTGACGGGTCCGACGTACAA |
| 7445 | SPBC3B9.18c_DN | GGGGCAGGTAGATGGGCAGG | 7547 | SPBC409.03_DN | GCGTGAACCTGGGGAGAACC |
| 7446 | SPBC3B9.19_UP | GTTTTACGACCGCTGCCGCA | 7548 | SPBC409.05_UP | TCAGTTGCACGGCATTCCCG |

FIG.44

| Sequence number | Name | Base sequence | Sequence number | Name | Base sequence |
|---|---|---|---|---|---|
| 7549 | SPBC409.05_DN | CCGATATCTTTGGGGGCG | 7651 | SPBC4F6.07c_DN | GGCCACCGGACTTATCGCCC |
| 7550 | SPBC409.06_UP | CCTTTACCGCGGCCCAATTA | 7652 | SPBC4F6.08c_UP | TCCGCCCTCCCGAGCATCTA |
| 7551 | SPBC409.06_DN | GCCCCCCTCTGTCTGATGC | 7653 | SPBC4F6.08c_DN | ACCTCAGCCGTCGTCTCCCG |
| 7552 | SPBC409.07c_UP | TGGGCGGTTTCGGGGAGTAT | 7654 | SPBC4F6.09_UP | GGGTGCTGTGGTGGGAGAG |
| 7553 | SPBC409.07c_DN | GCGGTTCCTTTGGATSGGTA | 7655 | SPBC4F6.09_DN | CAATACCCGCACATCCGCAA |
| 7554 | SPBC409.08_UP | TGACCCCATCCGCCTCTTCC | 7656 | SPBC4F6.10_UP | GCCTGCGGAATTGGGGCTC |
| 7555 | SPBC409.08_DN | CCCGAGTCCCCTCGGTTCAC | 7657 | SPBC4F6.10_DN | ACGTAAGGCGGCGGGGAAAA |
| 7556 | SPBC409.09c_UP | TATTGGGCGCCGGTGGGATT | 7658 | SPBC4F6.11c_UP | TTGTCGGTCCTCTGCCGGTGT |
| 7557 | SPBC409.09c_DN | AAGTTACAGAGGGGGGGCGG | 7659 | SPBC4F6.11c_DN | GTGGAAAAGGCGGGGATGC |
| 7558 | SPBC409.10_UP | CAAAGACGTCCCGCAGCAAG | 7660 | SPBC4F6.12_UP | AACGGTCCGTAGGCTAAGCG |
| 7559 | SPBC409.10_DN | CCATCAGGGCGGTTACTGGG | 7661 | SPBC4F6.12_DN | ACCGATGAGTCCCCCCGATC |
| 7560 | SPBC409.11_UP | CTCCTCCCCCGCCGTCTAAA | 7662 | SPBC4F6.13c_UP | TCCGCCACGTTGCACCTATG |
| 7561 | SPBC409.11_DN | AGGCGGCAGGGTTCGATTGG | 7663 | SPBC4F6.13c_DN | CCTGGGGGGTATTTTCCGCT |
| 7562 | SPBC409.14c_UP | GGCTGAAAACGCATGCCCGGGT | 7664 | SPBC4F6.14_UP | ACGTCACGGTCCCCCACTTA |
| 7563 | SPBC409.14c_DN | CCCGCTTGATCATGTCCGCG | 7665 | SPBC4F6.14_DN | AGTTTGCACGGACTTGACCT |
| 7564 | SPBC409.15c_UP | CCCCTCACAATCTCGCTCCC | 7666 | SPBC4F6.15c_UP | GCGTCGCGTTACCTAAGCAC |
| 7565 | SPBC409.15c_DN | GGGGGCAAAAGAACCAGGC | 7667 | SPBC4F6.15c_DN | TGAGTCTAGTCCCGCCTCCGA |
| 7566 | SPBC409.17c_UP | CGGGGACCCAAAAACGAT | 7668 | SPBC4F6.16c_UP | GCTTAGCCGGCCAAACGATG |
| 7567 | SPBC409.17c_DN | ACACCCCTCACGTGTTCGCC | 7669 | SPBC4F6.16c_DN | TGTIGGGAGTGCGCCTGCTG |
| 7568 | SPBC409.18_UP | CAAACCACACATCCCGGCAC | 7670 | SPBC4F6.17c_UP | TGCTATGGACCGATCGGCGT |
| 7569 | SPBC409.18_DN | GCCCGCGCTGCCATACTTTA | 7671 | SPBC4F6.17c_DN | CCAGCGGAGCACCACGAATG |
| 7570 | SPBC409.19c_UP | TGCAGCAGTGGCCCAAGAAA | 7672 | SPBC4F6.18c_UP | GAGAGAGGGGCGGAACAT |
| 7571 | SPBC409.19c_DN | CGCAGGCGAATAGAAAGACG | 7673 | SPBC4F6.18c_DN | ACAGGCGTGGCAAGGTAGGC |
| 7572 | SPBC409.20c_UP | CCCCCTGCGCCATAAACGAC | 7674 | SPBC530.01_UP | GCCCCCAGGACCAGAAATGA |
| 7573 | SPBC409.20c_DN | CCCGAACCGCGATCCACTTT | 7675 | SPBC530.01_DN | CATCAGACCCCCTTGCCGTT |
| 7574 | SPBC409.21_UP | TTGGGGGGGAGGGTACTGT | 7676 | SPBC530.02_UP | TCCCCACCCACCCCTCTCAA |
| 7575 | SPBC409.21_DN | ACGTTTGGGTTGCGAGCGG | 7677 | SPBC530.02_DN | CATCCGACAAAAGCCCCACG |
| 7576 | SPBC418.02_UP | TCCCGCTCGRACGCCTGTAC | 7678 | SPBC530.03c_UP | TAGCAAAGCGGGAGCATCGG |
| 7577 | SPBC418.02_DN | AAAGCACAACGGAGCAGCGG | 7679 | SPBC530.03c_DN | GCAGCGCTGGAAACATGAAG |
| 7578 | SPBC428.03c_UP | ACCAAAAGCGCCCGAAGAAA | 7680 | SPBC530.04_UP | AAGCAGGACAGGAGCGGGGA |
| 7579 | SPBC428.03c_DN | CGTGGTGACGGCCGAATTGT | 7681 | SPBC530.04_DN | TCGCTGCTAATCCCCCTTG |
| 7580 | SPBC428.03c_UP | TCAGCTGTTGCCCTATCGAG | 7682 | SPBC530.05_UP | GAGCAAAGGCGGAAAGGCGG |
| 7581 | SPBC428.03c_DN | TGGTGCACGGAGCGACTTGT | 7683 | SPBC530.05_DN | AAAACGCCAACACTCGCCCA |
| 7582 | SPBC428.04_UP | ACGCAACGAGCCGAGTACCG | 7684 | SPBC530.06c_UP | ATGTGAACCCGCCTTTGCGC |
| 7583 | SPBC428.04_DN | TCCGGCGCTCCTTCAGTCA | 7685 | SPBC530.06c_DN | GGCTAGGCGCAGGAGGGCTT |
| 7584 | SPBC428.05c_UP | TTCGTCCCCGTTCTGCGGTT | 7686 | SPBC530.07c_UP | CGGCGTAGTGGGTGAGGCTG |
| 7585 | SPBC428.05c_DN | TGATCCCTTGACGGCTACCG | 7687 | SPBC530.07c_DN | CGGGCTGAAAGACATGGGG |
| 7586 | SPBC428.06c_UP | GCGGAATCGGGTGAAATGCG | 7688 | SPBC530.08_UP | CCTCAGGAACCCCACACGAAT |
| 7587 | SPBC428.06c_DN | GAGCTACACGGCGCGGGAAA | 7689 | SPBC530.08_DN | GCAGCAGGCGGATAGGAGA |
| 7588 | SPBC428.07_UP | ACGGACGGGCAACTCCAAAAT | 7690 | SPBC530.09c_UP | TTGCGGGGCTCTTGGATCGA |
| 7589 | SPBC428.07_DN | GGTCTCCTCCGCGGTTTGTC | 7691 | SPBC530.09c_DN | TCAAGACCCACGGCCTAGGA |
| 7590 | SPBC428.08c_UP | CCCAAGCCCCACCTCATCA | 7692 | SPBC530.10c_UP | CAEAACCGTCCGTCCCCGGCT |
| 7591 | SPBC428.08c_DN | GCGTTGGAATTGGCGTTTGGT | 7693 | SPBC530.10c_DN | GCGGCAGGTGATCGTGGTTC |
| 7592 | SPBC428.10_UP | GGTTAGCCGGGGTGATGAT | 7694 | SPBC530.11c_UP | ACACGAGACGCACCCATCCC |
| 7593 | SPBC428.10_DN | CGAAGGAGGCGTAGACCGA | 7695 | SPBC530.11c_DN | TCACACGAACCCGAAGCAGG |
| 7594 | SPBC428.11_UP | ATGCGGCGGGGGTTGTAGCT | 7696 | SPBC530.13_UP | CTCGTCCCTGCCTTGTGCCG |
| 7595 | SPBC428.11_DN | GTCGATCCAACACCGTCGCGA | 7697 | SPBC530.13_DN | TCTGCTCTGGGGCTGCTGTG |
| 7596 | SPBC428.12c_UP | AGCGGTACTCGACTGATCTT | 7698 | SPBC530.14c_UP | CAATCCACGCACAAATCCCG |
| 7597 | SPBC428.12c_DN | ATTGAGCCCAGGTGCGAAAC | 7699 | SPBC530.14c_DN | TCTCGACCCAGGTCGGTCGA |
| 7598 | SPBC428.13c_UP | ACCACGTGGGTAGCCTAACG | 7700 | SPBC543.02c_UP | CATGCCGCCACTCCGTGTAG |
| 7599 | SPBC428.13c_DN | GTGCCACCGGTACAACGTGT | 7701 | SPBC543.02c_DN | GCTGGGCGGATTCGGACGTT |
| 7600 | SPBC428.14_UP | AGGCAATAGGGCAAAGGCGG | 7702 | SPBC543.03c_UP | TTCATTTCGCTCACCGCCCG |
| 7601 | SPBC428.14_DN | TCTGTCTGGTGGCCCTGGT | 7703 | SPBC543.03c_DN | GGGGGCGGAAATGGAAACTC |
| 7602 | SPBC428.15_UP | ACACCATGCGCAAAGGGGCT | 7704 | SPBC543.04_UP | ACCGGCACCCCTCATGTTCA |
| 7603 | SPBC428.15_DN | TGCGTTGGTGCGTCGGTAAC | 7705 | SPBC543.04_DN | TGATGATGGGAACAGGGGGG |
| 7604 | SPBC428.17c_UP | TCCCTGCCCTTATACGTCAG | 7706 | SPBC543.05c_UP | CCAACCCCATCCCTTTTCCG |
| 7605 | SPBC428.17c_DN | ACGTTGATCTCCCTTTGTGC | 7707 | SPBC543.05c_DN | ACCAAGAATCCCCGTGTCCC |
| 7606 | SPBC428.18_UP | TTCGTTTAGTCCCACCGGGT | 7708 | SPBC543.06c_UP | AACATACGGTCGTGGCGGCT |
| 7607 | SPBC428.18_DN | AAGCTAGCGCGAGCGCTTAG | 7709 | SPBC543.06c_DN | CAACACGGCTACTCGCGCAG |
| 7608 | SPBC4B4.01c_UP | TCTGATTGGGTGGGGGCTGT | 7710 | SPBC543.07_UP | CATCGCAAATAACCCCCCGT |
| 7609 | SPBC4B4.01c_DN | TTGGATGGATTGGTACGGGG | 7711 | SPBC543.07_DN | GGGGACTGATGGGCAACGGAC |
| 7610 | SPBC4B4.02_UP | TGGATCTCAAGGCCTGCCGT | 7712 | SPBC543.08_UP | TGCTAAAACCACCGCCACGC |
| 7611 | SPBC4B4.02c_DN | CAGACGGGATGGCGTGATTG | 7713 | SPBC543.08_DN | ACGCCATGCCCCCACCAGAT |
| 7612 | SPBC4B4.03_UP | GCCGACGACTGCATGACCCA | 7714 | SPBC543.09_UP | GCGPACAGTAGAGGGGCGCA |
| 7613 | SPBC4B4.03_DN | TCACAAAGAGAGCCGGGCGA | 7715 | SPBC543.09_DN | AAGACGGACACACCCGCCCTG |
| 7614 | SPBC4B4.04_UP | CCCGCAGACCCTTTCCCAGT | 7716 | SPBC543.10_UP | GGCGCCCCCATCCTGGATCTT |
| 7615 | SPBC4B4.04_DN | GTTCGTCAGTGAACACCTCG | 7717 | SPBC543.10_DN | CGCGGCCCCTTATACGTCAG |
| 7616 | SPBC4B4.06_UP | GGGGGGAAGGGTCAGTTGGA | 7718 | SPBC557.02c_UP | TCAGTCATCGGCGGGCAATT |
| 7617 | SPBC4B4.06_DN | GAAAGCGGGTTGGGAGGGAC | 7719 | SPBC557.02c_DN | GTGGGTCGCCGTTGATTCGG |
| 7618 | SPBC4B4.07c_UP | TGAIAAGTCGACGCGCGGTT | 7720 | SPBC557.04_UP | GGCGACGGAGCAGCTAGGAG |
| 7619 | SPBC4B4.07c_DN | GCAGTGAGTCATTCGCGCTT | 7721 | SPBC557.04_DN | CCATAAGGATCGCGAACGGC |
| 7620 | SPBC4B4.08_UP | ACGTCATCCGTGAGGGGCTA | 7722 | SPBC557.05_UP | TCTGAGGGGGTCCGGTGTCG |
| 7621 | SPBC4B4.08_DN | TCTGTGCAGTGAGCACCTCG | 7723 | SPBC557.05_DN | AGCAGTATCGGCCGGCATTC |
| 7622 | SPBC4B4.09_UP | GGATTTCTTGCGAGGCCCG | 7724 | SPBC56F2.01_UP | CTGTTCGATCTCCCGCTCCG |
| 7623 | SPBC4B4.09_DN | CGGTTTGCATCGCCTCCCAA | 7725 | SPBC56F2.01_DN | TCCGGTTGGGGCTTGAGAAT |
| 7624 | SPBC4B4.10_UP | CGGCATTGGCGTGGTTTCCTA | 7726 | SPBC56F2.02_UP | ACTCGTGCCGGGTTGACTCG |
| 7625 | SPBC4B4.10c_DN | GCTATGGGGCTACTCGCGGA | 7727 | SPBC56F2.02_DN | CCCACTTATTCGGCCGAGCG |
| 7626 | SPBC4B4.12c_UP | ATCGAAACTGGGGGGCAAT | 7728 | SPBC56F2.03_UP | CCCTGTCTAGCTCCGCCCAT |
| 7627 | SPBC4B4.12c_DN | ACCTACGCGCGCTTGACACA | 7729 | SPBC56F2.03_DN | ATCGGGTGTATCGCACCGACA |
| 7628 | SPBC4C3.03_UP | TGGAGGTGGTCGGCGGCTA | 7730 | SPBC56F2.04_UP | ACATTACACCACCGGCGCCC |
| 7629 | SPBC4C3.03_DN | TTTGACGGGTTTCGGCAGCA | 7731 | SPBC56F2.04_DN | AACCCCGGAGCGTCAGGATA |
| 7630 | SPBC4C3.04_UP | TGTACACCCGCACAGCCCGT | 7732 | SPBC56F2.05c_UP | CTTCGCCCGCCACCTACCCT |
| 7631 | SPBC4C3.04c_DN | ATCCCAGCCCGCGTTGAAAG | 7733 | SPBC56F2.05c_DN | CGCACACCACCATCAACGGC |
| 7632 | SPBC4C3.05c_UP | TGCGTCCAATAGCTCCGCGG | 7734 | SPBC56F2.06_UP | GGGAAAGCCGAGACACAGGC |
| 7633 | SPBC4C3.05c_DN | GACTGGACCCGCCCAAACGA | 7735 | SPBC56F2.06_DN | GGCCCACGTAAATCGCGACA |
| 7634 | SPBC4C3.06_UP | GGCAACGGCAACTCCAATCG | 7736 | SPBC56F2.08c_UP | ACCACACTATGTCGTGGCCC |
| 7635 | SPBC4C3.06_DN | CGGAGGGTGGGTCGTGGATC | 7737 | SPBC56F2.08c_DN | AATCGGTGGTCGATTCTGG |
| 7636 | SPBC4C3.07_UP | CCCTCCGACTGCCTGCCTTT | 7738 | SPBC56F2.09c_UP | GGGACCAAGCGGGGAAGAAA |
| 7637 | SPBC4C3.07_DN | AGTCTCCCGTCCCCGCTCAAA | 7739 | SPBC56F2.09c_DN | CCAAGCCGGCAGCGAATCAG |
| 7638 | SPBC4C3.08_UP | CGCCATTTCTCACCCAACGC | 7740 | SPBC56F2.10c_UP | TCCCTCCGGCTCCATCCTTT |
| 7639 | SPBC4C3.09_DN | CGATCCCGTTTGCCTTGTGA | 7741 | SPBC56F2.10c_DN | CCGTGCTCTGCCTCGTTTCG |
| 7640 | SPBC4C3.09_UP | CGGATTGGCATTGGGTCGG | 7742 | SPBC56F2.11_UP | GTGGCGCCGGTTTCTTGTCA |
| 7641 | SPBC4C3.09_DN | GGACGGGAGCTTTGTGGGC | 7743 | SPBC56F2.11_DN | AACCGGCGCCCTCCTACTGC |
| 7642 | SPBC4C3.12_UP | AGTTCCGCGAGCGCAGTCA | 7744 | SPBC56F2.12_UP | ATGGGCGTTGTCGGATGTTG |
| 7643 | SPBC4C3.12_DN | IACCCGCGAGGACCAGGAAT | 7745 | SPBC56F2.12_DN | TGAGTTATTGGCGGCGGTT |
| 7644 | SPBC4F6.04_UP | GGGGCGGGAGGACTC | 7746 | SPBC56F2.14_UP | TGGTACTAGGTGGAACGGCG |
| 7645 | SPBC4F6.04_DN | CCCGGGAAGAAAGCGCATGT | 7747 | SPBC56F2.14_DN | TTGAGCGCATAGACTGCCGA |
| 7646 | SPBC4F6.05c_UP | TTCCTGGGTTTGGCCCTCTCG | 7748 | SPBC577.03c_UP | CTGGCCGCAACCGCAAATAC |
| 7647 | SPBC4F6.05c_DN | CGGCGCACAGTTTCGTTTGG | 7749 | SPBC577.03c_DN | CACGTCTGCGCGGTCTCACA |
| 7648 | SPBC4F6.06_UP | CCCGGCTAATCGCGCTAGGG | 7750 | SPBC577.05c_UP | CAGCCAGCCTCCATCACGTG |
| 7649 | SPBC4F6.06_DN | ACTGGCTAGGCAAGACGGGC | 7751 | SPBC577.05c_DN | TGCTTTCATTGCTGCGGGTT |
| 7650 | SPBC4F6.07c_UP | TTTATTGCTCGCCTCCGCGT | 7752 | SPBC577.06c_UP | CTATTCCTGCCCCCCCCTT |

| Sequence number | Name | Base sequence |
|---|---|---|
| 7957 | SPBC776.03_DN | TCGTCCCGCTCTTGCCTCTG |
| 7958 | SPBC776.04_UP | TGGGGGCGTGGAGTTAGGC |
| 7959 | SPBC776.04_DN | CCAGCCGATGTGCACTTTG |
| 7960 | SPBC776.05_UP | GTTCCGGGTGCGCTCCTTTA |
| 7961 | SPBC776.05_DN | CCCGAGATCACCAGACGCCC |
| 7962 | SPBC776.06c_UP | CCTGGTGCCTTTCCTTGCCG |
| 7963 | SPBC776.06c_DN | TCCTTCGCAGCGGTCTTTT |
| 7964 | SPBC776.07_UP | GCAGCCCGTCAGCTTCGTTG |
| 7965 | SPBC776.07_DN | CTTGAACGCCCTAGCCCCGA |
| 7966 | SPBC776.08c_UP | TTGGTCGAGGGCGGAGGGTA |
| 7967 | SPBC776.08c_DN | CCATGAGCGACGGCTTTTGA |
| 7968 | SPBC776.09_UP | CACGAAATGCCCCAACCCAT |
| 7969 | SPBC776.09_DN | TAGCCGATTTGTGGGGGACC |
| 7970 | SPBC776.11_UP | GGGTGCCACGGCTTGAAGAT |
| 7971 | SPBC776.11_DN | GCCGCCCTACGTCAAATGCT |
| 7972 | SPBC776.13_UP | AAGTAACCGCACGCCAATG |
| 7973 | SPBC776.13_DN | GACCCCGTTAGTTGGCCGA |
| 7974 | SPBC776.14_UP | TGGGGAATGCGCGGAACTCT |
| 7975 | SPBC776.14_DN | CACCTTTGTCGGCCGTCTCA |
| 7976 | SPBC776.15c_UP | CAATGGAAAGCACACCGCGG |
| 7977 | SPBC776.15c_DN | TCGGGCGCATGGATTACTG |
| 7978 | SPBC776.16_UP | GTCCGCTTCGCTCCTGTCCG |
| 7979 | SPBC776.16_DN | GACTCTCCGCGCACCAACAG |
| 7980 | SPBC776.17_UP | CATTGACCCAACACCACGCC |
| 7981 | SPBC776.17_DN | GGGGCTTCGGTGCGTTCGTA |
| 7982 | SPBC776.18c_UP | GGCTGCGAGCTGAAAGGGT |
| 7983 | SPBC776.18c_DN | CATAGCGCCCTCCCGAGTC |
| 7984 | SPBC800.02_UP | ACCGTCCACGAATCCGCACC |
| 7985 | SPBC800.02_DN | TCGGGAGAGCACACCGCGC |
| 7986 | SPBC800.03_UP | CGGCCAGATCGGGGGGTATA |
| 7987 | SPBC800.03_DN | CCGAAACGCCCCTGAAGTGCAT |
| 7988 | SPBC800.04c_UP | CTCCTCCGCCGCACGAAAAG |
| 7989 | SPBC800.04c_DN | GATTAAAGCGCGCCCGAGT |
| 7990 | SPBC800.05c_UP | GATGGGACGGATGCCTGGAT |
| 7991 | SPBC800.05c_DN | CAAGAGACTGCACGGCGCCC |
| 7992 | SPBC800.06_UP | AGGTTGAATAGCGCCACGGG |
| 7993 | SPBC800.06_DN | CAGAATGAGAGTCAGCGCGG |
| 7994 | SPBC800.07c_UP | TTGCGTGGGGGGACGAGGT |
| 7995 | SPBC800.07c_DN | CTGGCACAGCTTTGGACGGC |
| 7996 | SPBC800.08_UP | CCCCGGCCCAAGCCATTAAT |
| 7997 | SPBC800.08_DN | CGTGCGGCCTACCAAATTCC |
| 7998 | SPBC800.09_UP | CCTTGGGGGTATGCGTTTGG |
| 7999 | SPBC800.09_DN | CGGGAAGATCGACCACGACGG |
| 8000 | SPBC800.11_UP | TCTTTAATCCCAGCGCCGGT |
| 8001 | SPBC800.11_DN | TCTTTGTGCCGCTTCCGCC |
| 8002 | SPBC800.12c_UP | AACATTTGACGCGACGGGCT |
| 8003 | SPBC800.12c_DN | TCGGAGAGGCCGCAGAAACA |
| 8004 | SPBC800.13_UP | CGGCGCCCATGAAAAGAGTG |
| 8005 | SPBC800.13_DN | GGGGGAATAGCCGTTCGAATA |
| 8006 | SPBC83.01_UP | TATGGGGACGTGTTGGGGT |
| 8007 | SPBC83.01_DN | CATCAAACGGCGGAAGGGA |
| 8008 | SPBC83.02c_UP | TCACTAGCGCCGGCCCAAAA |
| 8009 | SPBC83.02c_DN | ATGATTCCCGACCCCCCTCG |
| 8010 | SPBC83.03c_UP | CAGCCGAGCGCCGAATTAGA |
| 8011 | SPBC83.03c_DN | CACCACTCCACGCATTCCGC |
| 8012 | SPBC83.05_UP | AAGCCCGCCTGTCTTACCCC |
| 8013 | SPBC83.05_DN | AAGGGCAACGGGACGGACA |
| 8014 | SPBC83.06_UP | ATTGGCGACGGGTCTTCAGG |
| 8015 | SPBC83.06_DN | TCCGCCCGTCGCAAAGAATG |
| 8016 | SPBC83.07_UP | AGAGATCCCGCCTGCCAACA |
| 8017 | SPBC83.07_DN | TCCGCCACGTCCACTTGAGA |
| 8018 | SPBC83.08_UP | CTGGGTGAAACGGCTGCTCC |
| 8019 | SPBC83.08_DN | GGGTAAATGCGCCGGTACGG |
| 8020 | SPBC83.09c_UP | TGGCGTCTCCCCTGTTGTGG |
| 8021 | SPBC83.09c_DN | TGGCAGATGGGGGCGTGGTA |
| 8022 | SPBC83.10_UP | GCCTCCACTGTCTCGGCGAT |
| 8023 | SPBC83.10_DN | TAGTACGGGCCTTTATCGCG |
| 8024 | SPBC83.12_UP | AATGGATGTTGACGCGGCG |
| 8025 | SPBC83.12_DN | GTGGACGGCGAGGTGTGGCT |
| 8026 | SPBC83.13_UP | TGATGTCTACAGGGCGGCGC |
| 8027 | SPBC83.13_DN | ACGGCGCTAAGCGAGTACC |
| 8028 | SPBC83.15_UP | CGGTGCGGGCGTCTCATACA |
| 8029 | SPBC83.15_DN | AAACCCCGGTAAGGCAAGCA |
| 8030 | SPBC83.16c_UP | GGGCCGCAGGATCAAGAATG |
| 8031 | SPBC83.16c_DN | AAGTGCCGGGGGTTGAGAG |
| 8032 | SPBC83.17_UP | GTGGGCCAAGGGGCGATGTA |
| 8033 | SPBC83.17_DN | AGTTCCGCTCACGCTCCCTG |
| 8034 | SPBC83.18c_UP | GCCTTGTCACTGCCCGAACC |
| 8035 | SPBC83.18c_DN | GGTCGATGTTGGGTCAAGCA |
| 8036 | SPBC83.19c_UP | TTGCCCGGATAATAGGCAGCG |
| 8037 | SPBC83.19c_DN | ATTATGCGGACCACGGGACC |
| 8038 | SPBC839.02_UP | TCAACGGCAGGAAAGGGCGA |
| 8039 | SPBC839.02_DN | CCGGTTATTGGCGTGCTCGA |
| 8040 | SPBC839.03c_UP | GATTTCGGCCGCGGGATACT |
| 8041 | SPBC839.03c_DN | AAGGTCCGGCACAGAGGGAAC |
| 8042 | SPBC839.04_UP | CATGCGGCGTGCGAGGAATC |
| 8043 | SPBC839.04_DN | CCACACGGCCTCGGACTTCA |
| 8044 | SPBC839.05c_UP | GAGAGAGGGAAATCGGGCCG |
| 8045 | SPBC839.05c_DN | GGCTCATTGCTTGTGCGACG |
| 8046 | SPBC839.06_UP | TTCATTATTCGGGGGGCA |
| 8047 | SPBC839.06_DN | AGGAAACAACAAGGGCGGG |
| 8048 | SPBC839.07_UP | ACGGAATGAAAGGGCCACGG |
| 8049 | SPBC839.07_DN | ATACTTATCGGACGCGCGGG |
| 8050 | SPBC839.08c_UP | ATTTGGTGCAGGACGGTGGC |
| 8051 | SPBC839.08c_DN | GTTACAGAGCGGGAACCCCA |
| 8052 | SPBC839.09c_UP | TTCAGTGCGTTCGGGGCTTA |
| 8053 | SPBC839.09c_DN | AAAAAGAGTGGCCGCGAAGCC |
| 8054 | SPBC839.11c_UP | GGGGCGGTTCTTTGAGTTGC |
| 8055 | SPBC839.11c_DN | TGCCCCGCGTGTCTCTCGTTG |
| 8056 | SPBC839.13c_UP | AGGACATCACGGACTACGCGG |
| 8057 | SPBC839.13c_DN | CGAGCCCGAGATTGCCTGCAC |
| 8058 | SPBC839.15c_UP | GCAGCCACTCCCTATCCCCG |
| 8059 | SPBC839.15c_DN | TCGGGATCAGCCAGTCGTTG |
| 8060 | SPBC839.16_UP | TGACCTCCGCGACTGCAATT |
| 8061 | SPBC839.16_DN | CGAACGAATTGGGCCGAGGT |
| 8062 | SPBC839.17c_UP | CGGCACCGCGGATAATTGTC |
| 8063 | SPBC839.17c_DN | GCGGGCCTTGCCATGACTTT |
| 8064 | SPBC887.01_UP | TGTTTATCGGCGGGGGGCCT |
| 8065 | SPBC887.01_DN | ATAGCGCGAGGTCACAGGGC |
| 8066 | SPBC887.02_UP | AGGGCGGGCTGGAGGATGAG |
| 8067 | SPBC887.02_DN | TTCTGCCCTTTACCCAGCCG |
| 8068 | SPBC887.05c_UP | ACTCTTGGCCGATCTGCGTG |
| 8069 | SPBC887.05c_DN | ATCTCTCGGGATAGACGGCCA |
| 8070 | SPBC887.06c_UP | GGCCCTCTTCACGCAATCCG |
| 8071 | SPBC887.06c_DN | TACAGGAGGGGACCGGCGAG |
| 8072 | SPBC887.07_UP | CTGGGCTAGTCGGCAAGGG |
| 8073 | SPBC887.07_DN | ATGATCCGCCAACCAGCACG |
| 8074 | SPBC887.10_UP | CCTATTCGGTTCCTCTGCCC |
| 8075 | SPBC887.10_DN | GTTTGCCGCTTTCGCCTGTG |
| 8076 | SPBC887.11_UP | GCCTGACGGCCTACGCCAAA |
| 8077 | SPBC887.11_DN | GGCGGGGTGAGGGGAGAATT |
| 8078 | SPBC887.12_UP | GCGAAAGGCGAAATAGCGGT |
| 8079 | SPBC887.12_DN | AGTGGGGGACGGACGGCAAC |
| 8080 | SPBC887.15c_UP | AATACCACACGGAAGCGCCCG |
| 8081 | SPBC887.15c_DN | TCTCCCCGCAGCCACACCTT |
| 8082 | SPBC887.16_UP | TGTGGTATGAAGCGCGGGAG |
| 8083 | SPBC887.16_DN | GCAGGCTTATTTTTCGCGGC |
| 8084 | SPBC887.17_UP | CGCCCTGCAACGCTCACTCC |
| 8085 | SPBC887.17_DN | TGGATCGCCGTCAACAGGGA |
| 8086 | SPBC887.18c_UP | TGCGGCAACAGGAACTTGCA |
| 8087 | SPBC887.18c_DN | TCCGTTGGGAATCACGGTGG |
| 8088 | SPBC887.19_UP | CCCGAACCCCCGATGAGATGG |
| 8089 | SPBC887.19_DN | CAACAAGCCCTTCCCCGTGAT |
| 8090 | SPBCD2.09c_UP | CCGGCAATCGGGTTCCACTA |
| 8091 | SPBCD2.09c_DN | GCCGACAGTTCACGCGACTA |
| 8092 | SPBCD2.10c_UP | GCTCACGAACTCGCCAAAAA |
| 8093 | SPBCD2.10c_DN | GAAGTGATGGACGGCAGGCA |
| 8094 | SPBCD2.16c_UP | TCTAATCGGAATCGCCACGCC |
| 8095 | SPBCD2.16c_DN | CAAAAGCGACTGCCCCCGAA |
| 8096 | SPBCD2.17_UP | CGACAGGAGGCCGGAAAAGC |
| 8097 | SPBCD2.17_DN | AAGCAACTTCCGGCCTCGCA |
| 8098 | SPBCD2.18c_UP | GGTGGAGGCCGTGAATTGCA |
| 8099 | SPBCD2.18c_DN | AGCTTTTTGATCCATGCGGG |
| 8100 | SPBCD2.19_UP | CACCTCTATGCGATCCGGCC |
| 8101 | SPBCD2.19_DN | CGCCGCGTTTTGTTCAGCTC |
| 8102 | SPBCD2.20c_UP | GCGAAGAAAATGGCAGGGCG |
| 8103 | SPBCD2.20c_DN | CTTCCTCACCCCTCCCAACG |
| 8104 | SPBCE4.02c_UP | GCCCCGTAGCTGCGAAAGAG |
| 8105 | SPBCE4.02c_DN | GCGCGGGTAGGTGCGTGTGA |
| 8106 | SPBCE4.03_UP | CCCCCGTTTCCCTGGCACTA |
| 8107 | SPBCE4.03_DN | AGCGGGGTGAGGTACGAAAG |
| 8108 | SPBCE4.04_UP | GCGGATGCTACGAATTGGCG |
| 8109 | SPBCE4.04_DN | GCTTGGCCGGAGGGGTACAC |
| 8110 | SPBCE4.05c_UP | AACGCTTCCGGCCCTAGACG |
| 8111 | SPBCE4.05c_DN | CGACTTCCGCATCTCCCCAC |
| 8112 | SPBC902.02c_UP | GACTCTGCGCGCTCCAICGG |
| 8113 | SPBC902.02c_DN | TGGGATCTACGGCCCTTGGG |
| 8114 | SPBC902.03_UP | CTCCCGCAACCGATCAGCTG |
| 8115 | SPBC902.03_DN | TTGTTCCATTACAGGCGTGCT |
| 8116 | SPBC902.04_UP | TTAGGGCAGCAGGCGGAGGG |
| 8117 | SPBC902.04_DN | GTTCGGGTTCCTTGCCTTGC |
| 8118 | SPBC902.05c_UP | AACACACCGCCCAGCCATCG |
| 8119 | SPBC902.05c_DN | AGGTTGGGGTCGACTGTGGC |
| 8120 | SPBC902.06_UP | GGTTTCGGCCGCTAGGTGTC |
| 8121 | SPBC902.06_DN | TCGACCCGCATATCCCCCAG |
| 8122 | SPBC947.01_UP | GGCCAAAACAAGCACCGCAA |
| 8123 | SPBC947.01_DN | GAAACGCAGGCGTGGGCGAT |
| 8124 | SPBC947.02_UP | CCAATCTGTGCTCTCCGCGA |
| 8125 | SPBC947.02_DN | CGTCGGCCAGGTTGCAAGG |
| 8126 | SPBC947.03c_UP | GGCGGTAAGATTGGCGAAGC |
| 8127 | SPBC947.03c_DN | GTGGGGCAATCGGCAAAAAG |
| 8128 | SPBC947.04_UP | ACACCCGGCATTCACCCACG |
| 8129 | SPBC947.04_DN | GTTTGGGTTGGAGTGCGTCT |
| 8130 | SPBC947.05c_UP | GCGCCCTCGHTTGGTACCCC |
| 8131 | SPBC947.05c_DN | TGATCGTATTTGCAGGGCGC |
| 8132 | SPBC947.06c_UP | GCGGAGGGAAGGGTTGTGTC |
| 8133 | SPBC947.06c_DN | CACGAACTAAGCCAACGGCG |
| 8134 | SPBC947.07_UP | GGGGGGGCTGCTCTAGTTTG |
| 8135 | SPBC947.07_DN | AAAACTGCATGCGCCGTCGA |
| 8136 | SPBC947.08c_UP | TGGGCGGTTCGGGTGTTGAC |
| 8137 | SPBC947.08c_DN | CCGCTTTCCCGCCTTGACTA |
| 8138 | SPBC947.09_UP | GGACAAATGCGGGAAGGGAA |
| 8139 | SPBC947.09_DN | GCTCAATCGCCCCCATTCT |
| 8140 | SPBC947.10_UP | TATCCCGCCTTGAGCCGTTT |
| 8141 | SPBC947.10_DN | GTGGGGGAGGGGACTGTGAA |
| 8142 | SPBC947.11c_UP | ACCGATTACCTTGCGCCTGG |
| 8143 | SPBC947.11c_DN | TAGCGCATCAACCCACACGG |
| 8144 | SPBC947.12_UP | CCCGCACAGATCGCACGAAA |
| 8145 | SPBC947.12_DN | CGCCCTAAGCACAACACAAA |
| 8146 | SPBC947.13_UP | GACCGACCCCTCCCAGCCTC |
| 8147 | SPBC947.13_DN | GGACACCCCGGAAAGAGCAG |
| 8148 | SPBC947.15c_UP | CAAAGTGCGGCTAATCCCC |
| 8149 | SPBC947.15c_DN | GACATGCAAATACGCCGCCC |
| 8150 | SPBC9B6.02c_UP | GTGGAGGGCAGGCAGGAAG |
| 8151 | SPBC9B6.02c_DN | AGGGGACGAAGGCACCAGGG |
| 8152 | SPBC9B6.03_UP | AAACACCCACGCCAAACCCT |
| 8153 | SPBC9B6.03_DN | TGTTGGGTCTGGTGCGAAGG |
| 8154 | SPBC9B6.04c_UP | GCTTGTCGGCATGTACCCGG |
| 8155 | SPBC9B6.04c_DN | TCTAACGGTCTGCCCCGCGC |
| 8156 | SPBC9B6.06_UP | ACGGAGGCACAGCGGGGATCA |
| 8157 | SPBC9B6.06_DN | CCTACCCCTGCGTGCCGTTC |
| 8158 | SPBC9B6.07_UP | GCAGCGAGAGGAGGGCAACT |
| 8159 | SPBC9B6.07_DN | CACCGAAGCGAGCACCCGTT |
| 8160 | SPBC9B6.09c_UP | GTCGCGGCTGGCATCTTGTT |

FIG.47

| Sequence number | Name | Base sequence |
|---|---|---|
| 8161 | SPBC9B6.09c_DN | TGCTAGCAGCCCCTCCCGAC |
| 8162 | SPBC9B6.10_UP | CCTTCCGCATGCCCAGGTAC |
| 8163 | SPBC9B6.10_DN | GTGGAACCCAGTGGCTGCAA |
| 8164 | SPBC9B6.11c_UP | GGGCGCTTGTCTCGGTTGTG |
| 8165 | SPBC9B6.11c_DN | GGGGTACGCCTGGTGCAATT |
| 8166 | SPBCPT2R1.01c_UP | GCCTACGTCGCTCCCCTGCC |
| 8167 | SPBCPT2R1.01c_DN | ATGGAGAGATGGCGACGGCG |
| 8168 | SPBCPT2R1.02_UP | CAGCACCGTGATCCGACACT |
| 8169 | SPBCPT2R1.02_DN | CTACATGCGTCGCACTGGCA |
| 8170 | SPBCPT2R1.08c_UP | TCACGTCGGTCGAAGCAGTC |
| 8171 | SPBCPT2R1.08c_DN | ACACTGCAGGTAGGGCGCAA |
| 8172 | SPBP16F5.03c_UP | CCATCCGGGTCCAAATCGAA |
| 8173 | SPBP16F5.03c_DN | GGGTGCTTGTGGGCGGATTT |
| 8174 | SPBP16F5.04_UP | TTGCCTCTCTGCCTCGCACC |
| 8175 | SPBP16F5.04_DN | CTGGAACAGCCCCCCTTGGA |
| 8176 | SPBP16F5.05c_UP | AGCACGTCCCATCAGCACCG |
| 8177 | SPBP16F5.05c_DN | CAAACCCAAGAAAGCGCCCA |
| 8178 | SPBP16F5.06_UP | TACCAAAGGGCGACATGGGC |
| 8179 | SPBP16F5.06_DN | TGCCATTGCCGATAAAGCGG |
| 8180 | SPBP16F5.08c_UP | CCCGAGGGGGTGGTAGGTGT |
| 8181 | SPBP16F5.09c_DN | CCTTCGGTAGGAGCCCTGGC |
| 8182 | SPBP18G5.03_UP | ACGCAACACCCAATCATCCG |
| 8183 | SPBP18G5.03_DN | TACTTGCTTTGCGGGCCTCG |
| 8184 | SPBP19A11.01_UP | ATGTTCCATTGAGCGCCCCG |
| 8185 | SPBP19A11.01_DN | GTTTTCCCCGGCTGACCTGC |
| 8186 | SPBP19A11.02c_UP | GCCAGTGGCTGGTTCCTGCAA |
| 8187 | SPBP19A11.02c_DN | GGGCCCACAAAAAAAAGCGCA |
| 8188 | SPBP19A11.04c_UP | GTCATTTCGGGGTCGGCAAG |
| 8189 | SPBP19A11.04c_DN | GGTCGGGGGAAAGGGAATGT |
| 8190 | SPBP22H7.02c_UP | GCGCTAGTGGATGGGCAGAG |
| 8191 | SPBP22H7.02c_DN | CGGCGAACGAACGACTGGAC |
| 8192 | SPBP22H7.04_UP | TCCACGTCCCCCCGCTACC |
| 8193 | SPBP22H7.04_DN | GCCGCGCCGTCAAGTGTTCAG |
| 8194 | SPBP22H7.05c_UP | GACCTCCACACACCCTGCC |
| 8195 | SPBP22H7.05c_DN | CGGGGGGTCAGTAGACGTG |
| 8196 | SPBP22H7.06_UP | CAGACACTCGCGGCCAAAAT |
| 8197 | SPBP22H7.06_DN | TCGCCGGCTTCGTCATCTTT |
| 8198 | SPBP22H7.09c_UP | ACAGCCATGCGTACGTGGGT |
| 8199 | SPBP22H7.09c_DN | ACGCGGCCGATCTAAGGGTA |
| 8200 | SPBP23A10.02_UP | CCGTAACGCCCATGCAACGC |
| 8201 | SPBP23A10.02_DN | TCCCAGCCCCAGCTACCAGA |
| 8202 | SPBP23A10.03c_UP | GCAGAGTGACCCCGCCAAG |
| 8203 | SPBP23A10.03c_DN | AGCAAATGGTGTCCGCGCAG |
| 8204 | SPBP23A10.05_UP | TGTGGAGAAGCGTGATGCGG |
| 8205 | SPBP23A10.05_DN | ACTGATGAAAGCACCGCGGC |
| 8206 | SPBP23A10.06_UP | TCTGGATCAGCGCAGGGCTT |
| 8207 | SPBP23A10.06_DN | TTGGCACAATGGGGGTTCCG |
| 8208 | SPBP23A10.07_UP | ATGATCCACCAAACCGGCCG |
| 8209 | SPBP23A10.07_DN | GCCTGCCACGATTCGACCCA |
| 8210 | SPBP23A10.08_UP | GGGAGTCGATGCGCGCTTTGC |
| 8211 | SPBP23A10.08_DN | TCATAGGAACGGGGCTGCGT |
| 8212 | SPBP23A10.10_UP | CCGCTCTCGCGTTTTCACAG |
| 8213 | SPBP23A10.10_DN | CGGACCACTCCACACACCCG |
| 8214 | SPBP23A10.12_UP | TGAAGGGGGGGCTACGCTGA |
| 8215 | SPBP23A10.12_DN | TGATGATGGGTCTTGCGGGA |
| 8216 | SPBP23A10.13_UP | TCGGAAGACACACCATCGGG |
| 8217 | SPBP23A10.13_DN | GTGTGTGGTCGGTGCGTCGG |
| 8218 | SPBP23A10.14c_UP | CAACCGGCCACACATTTCCC |
| 8219 | SPBP23A10.14c_DN | TTGCCCGCGGAGGTATCGTA |
| 8220 | SPBP23A10.15c_UP | ACTCGAACTGCATGGGGACA |
| 8221 | SPBP23A10.15c_DN | GTAGACGGTTGGGGGAGGCG |
| 8222 | SPBP23A10.16_UP | CGGGGGTTGTCATTCGGTCG |
| 8223 | SPBP23A10.16_DN | CCCCCGACGCGTTTATCCTT |
| 8224 | SPBP26C9.02c_UP | CGATGGGAGGGCGGTAGCTA |
| 8225 | SPBP26C9.02c_DN | CATTCGAAGAGCCAACCGGC |
| 8226 | SPBP26C9.03c_UP | TGTGGGCGGAGTGTGTGCTC |
| 8227 | SPBP26C9.03c_DN | TGGAGTGTATTGGGGGGGA |
| 8228 | SPBP35G2.02_UP | GCCCTCCTACACCTGCCGTC |
| 8229 | SPBP35G2.02_DN | AGCACACGAAACACAGGCGG |
| 8230 | SPBP35G2.03c_UP | AATTCCCGACCTGCCCACCC |
| 8231 | SPBP35G2.03c_DN | AGACCGGGGCACTTAGGCAG |
| 8232 | SPBP35G2.04c_UP | CCAGTTGCCCTCAGCCGTCT |
| 8233 | SPBP35G2.04c_DN | AGAAAAGGGAGAGGGCGGA |
| 8234 | SPBP35G2.05c_UP | ACGGACCACACCCCTCGTC |
| 8235 | SPBP35G2.05c_DN | GGCAAGGACATCGGGTGGAA |
| 8236 | SPBP35G2.06c_UP | ACATCCGCGTACTGCTCCCA |
| 8237 | SPBP35G2.06c_DN | TCGCTACGGGTCTGACTTCG |
| 8238 | SPBP35G2.07_UP | ACACAGGGGTTGGGCGGGAC |
| 8239 | SPBP35G2.07_DN | GGTTGAAGTGGAGTGGGGCT |
| 8240 | SPBP35G2.08_UP | TCCCCAATCCGCATCACGA |
| 8241 | SPBP35G2.08c_DN | AAGCCACCCGCCTGCCAAAT |
| 8242 | SPBP35G2.10_UP | CGCGGGATTGCATTGTGTGA |
| 8243 | SPBP35G2.10_DN | CGAGGGAGTGGAGTGGGGGC |
| 8244 | SPBP35G2.11c_UP | GCGGGTAACTTGGCGGTCGT |
| 8245 | SPBP35G2.11c_DN | CCGGTGCGAGAACCCTTTA |
| 8246 | SPBP35G2.12_UP | GGCGTTGGGGGGGACTACA |
| 8247 | SPBP35G2.12_DN | GGCAGGACCGCAACCACCCT |
| 8248 | SPBP35G2.13c_UP | CCTGCCCCTAAAACCCGTGC |
| 8249 | SPBP35G2.13c_DN | TTTCCCCCGGTTCGTTCAA |
| 8250 | SPBP35G2.14_UP | TCGCCGTGTCTGAAGCGCTAT |
| 8251 | SPBP35G2.14_DN | GCGAGGCTTATGTCCGGTGA |
| 8252 | SPBP4G3.02_UP | TCATGACCTCGCGTCTCGCG |
| 8253 | SPBP4G3.02_DN | GGGTTGAGGGTACGGTTGCG |
| 8254 | SPBP4G3.03_UP | GCCGAGAACGGCGAACACCT |
| 8255 | SPBP4G3.03_DN | CGCGCGAGATACGAATGAGG |
| 8256 | SPBP4H10.03_UP | TGATGGGGTCCAGGGAAACC |
| 8257 | SPBP4H10.03_DN | GCAACCCACCGTACGAAGGC |
| 8258 | SPBP4H10.04_UP | GCGATTTGCATGGACGCGTA |
| 8259 | SPBP4H10.04_DN | TAGGCAAACCGGGCACACAC |
| 8260 | SPBP4H10.05c_UP | GCCAGGGGAGGAGCAACAA |
| 8261 | SPBP4H10.05c_DN | AGAGGATCCATAGCCGGCCA |
| 8262 | SPBP4H10.07_UP | CGGCGCCACACTCCCTAATC |
| 8263 | SPBP4H10.07_DN | TTGCTGCGCGGTTAAAGTGG |
| 8264 | SPBP4H10.09_UP | ACTCCCGTCCGCGTTCAATG |
| 8265 | SPBP4H10.09_DN | CACGGGCTGGATGACGGAGG |
| 8266 | SPBP4H10.10_UP | TAGACGGGATCCCAAGGGCG |
| 8267 | SPBP4H10.10_DN | TCAGGGCGTCAGGGTCACAA |
| 8268 | SPBP4H10.11c_UP | GGATTAACCCGGGCCCTGAC |
| 8269 | SPBP4H10.11c_DN | CGGCCCCTGGAACTTTTGGT |
| 8270 | SPBP4H10.13_UP | GCGGCAATGAGGGGGAGTT |
| 8271 | SPBP4H10.13_DN | AACCGGTGTCCCCCATGAAG |
| 8272 | SPBP4H10.14c_UP | CCTAGACCCTCCAATCGCGG |
| 8273 | SPBP4H10.14c_DN | ACGGGGCTTTCGTGCTTGTT |
| 8274 | SPBP4H10.16c_UP | CTACCCGCCGCCCCTTAGTT |
| 8275 | SPBP4H10.16c_DN | AAGGCGATAGGGGTGAGCA |
| 8276 | SPBP4H10.17c_UP | CCGCAATACGTCACAGCAGC |
| 8277 | SPBP4H10.17c_DN | CCTTTCGACTTCCCATCCCGC |
| 8278 | SPBP4H10.18c_UP | CATCCCGCCCTGAGACCTTG |
| 8279 | SPBP4H10.18c_DN | ACCGCCCTGCCACTGTTAGC |
| 8280 | SPBP4H10.19c_UP | TGTTACAGCGGGCCGTACAA |
| 8281 | SPBP4H10.19c_DN | CACTCGTTCCGACACGGACT |
| 8282 | SPBP4H10.20_UP | TACCTGGGAACTGCGGCCTT |
| 8283 | SPBP4H10.20_DN | GCCGAGCGCAGAGTACCCGC |
| 8284 | SPBP4H10.21c_UP | GGTGCGGGATGGTACGGTG |
| 8285 | SPBP4H10.21c_DN | AAGTACTGCTGCGCCCCGG |
| 8286 | SPBP8B7.02_UP | CGGTTCGAGGTGTGAGGCGC |
| 8287 | SPBP8B7.02_DN | AATGGGGAACTTTGGCGTG |
| 8288 | SPBP8B7.04_UP | CAGCTCCGTGACGGCGAATTA |
| 8289 | SPBP8B7.04_DN | ATGGTTCCCCCTGTTTGCCC |
| 8290 | SPBP8B7.05c_UP | AACGGTCAGGGGTCGGCGTC |
| 8291 | SPBP8B7.05c_DN | CTCAAGGATCGGGGCGCTA |
| 8292 | SPBP8B7.06_UP | CCCCCTCCGGGTTTTTGAGT |
| 8293 | SPBP8B7.06_DN | GGCAAACGGGGCAGAGGGTA |
| 8294 | SPBP8B7.07c_UP | TTTACGGGGTGCGCTTTCCA |
| 8295 | SPBP8B7.07c_DN | TTCACAAGCGAGCCGTCACC |
| 8296 | SPBP8B7.08c_UP | TTCTCTGTCGCCCCCACCGT |
| 8297 | SPBP8B7.08c_DN | TGTACGTCATCCTCCGGCCC |
| 8298 | SPBP8B7.09c_UP | ACCGCAAGAGGTGGCCAATC |
| 8299 | SPBP8B7.09c_DN | TCTCCACCCGCGGTAGATCA |
| 8300 | SPBP8B7.10c_UP | ACGTCACCCAACCAGCCTCC |
| 8301 | SPBP8B7.10c_DN | TACCGGCCGAAGAAGCAAGG |
| 8302 | SPBP8B7.11_UP | GCGCACTCCAGTGCAGGAGA |
| 8303 | SPBP8B7.11_DN | GTCGACTCGGCATGTGCCAT |
| 8304 | SPBP8B7.13_UP | CGCATTTCAACCCCCTCGCT |
| 8305 | SPBP8B7.13_DN | CAGCGCCTTCATTCCCCGTG |
| 8306 | SPBP8B7.14c_UP | TGGCGATATGCACGTAGCGT |
| 8307 | SPBP8B7.14c_DN | GGGCTCGGGGTTTAGCGTT |
| 8308 | SPBP8B7.15c_UP | AGAGGCTTGGGGATGGTCG |
| 8309 | SPBP8B7.15c_DN | AGGGGAATGGTTCTGGGCGT |
| 8310 | SPBP8B7.16c_UP | GGGTAAGCAGGCAAGCGGGT |
| 8311 | SPBP8B7.16c_DN | TGCCCGAACCCCCATTTTAG |
| 8312 | SPBP8B7.17c_UP | AACCTGGGCTTCCGTAGGGT |
| 8313 | SPBP8B7.17c_DN | ATGGGGCTGGGGTCGGAAAC |
| 8314 | SPBP8B7.18c_UP | TGATCACGGAGCCCAACGCC |
| 8315 | SPBP8B7.18c_DN | TTAGCTGCGTGGGCCCTTGT |
| 8316 | SPBP8B7.19_UP | TAAGGGCGGTGGCTGGAAGC |
| 8317 | SPBP8B7.19_DN | TTCGGTCGCTGGGTCGTCTT |
| 8318 | SPBP8B7.20c_UP | CGCCGGGCCCTTACGACAAC |
| 8319 | SPBP8B7.20c_DN | CCCTCCCCAAGGCCCATCAG |
| 8320 | SPBP8B7.21_UP | TCAGCCCGTCATCACGCGTT |
| 8321 | SPBP8B7.21_DN | CTACGCGCCCTTTCCACCAA |
| 8322 | SPBP8B7.23_UP | CCCCAGCCAGTAAAAGCCAG |
| 8323 | SPBP8B7.23_DN | ATGAGGGTGGGGGTCCGTTG |
| 8324 | SPBP8B7.24c_UP | ACTGGGCAAGGCAATGGGAA |
| 8325 | SPBP8B7.24c_DN | AGGTCCCCCACCCGTACCAA |
| 8326 | SPBP8B7.25_UP | CGGCTGCTCCACGAAGCTAG |
| 8327 | SPBP8B7.25_DN | TCCGACACCCCCACCGTAAG |
| 8328 | SPBP8B7.27_UP | CTCTTGGGGTTGGATGGCCG |
| 8329 | SPBP8B7.27_DN | AGACGCGGGGGATTTTTGTG |
| 8330 | SPBP8B7.28c_UP | CCTATCGGCCCCTTCGTTCA |
| 8331 | SPBP8B7.28c_DN | CAAAGCAAGTCCCCCGTCCC |
| 8332 | SPBP8B7.30c_UP | GAAGGTGGCGACAAACGGA |
| 8333 | SPBP8B7.30c_DN | GTGCTTCTTCGTGGTGGCGG |
| 8334 | SPBPB10D8.01_UP | GGGGGAAGGCGAAAAGCAGA |
| 8335 | SPBPB10D8.01_DN | GGCAGAGGTGACGGCAAGCG |
| 8336 | SPBPB10D8.02c_UP | GCCGGCCACCACACAGTCAA |
| 8337 | SPBPB10D8.02c_DN | ACGCCAGCCCTCACATTTG |
| 8338 | SPBPB10D8.04c_UP | TTTCCCCATCCCTCGCCCTG |
| 8339 | SPBPB10D8.04c_DN | AGGAGGGGCAATGTGAGGC |
| 8340 | SPBPB10D8.05c_UP | TGCGGGAGGGACAGGGGTAA |
| 8341 | SPBPB10D8.05c_DN | TAGGAGTGTGCGGGGACGGG |
| 8342 | SPBPB10D8.06c_UP | AAGCGGGGGTTAGGAGGCTG |
| 8343 | SPBPB10D8.06c_DN | ACGTTCTTTGCGGCCGGGTC |
| 8344 | SPBPB10D8.07c_UP | TACGACGTAGTCACCGCGTG |
| 8345 | SPBPB10D8.07c_DN | TTCACGCCCCCCTATACCGC |
| 8346 | SPBPB21E7.01c_UP | CCGTGCGATCGCCTGAGTAA |
| 8347 | SPBPB21E7.01c_DN | AGTAATGCACGCTGCGCAAG |
| 8348 | SPBPB21E7.05_UP | CCCAGTGCCGATTGACCTCT |
| 8349 | SPBPB21E7.05_DN | ATCCCGACCTCTAGGCGGTA |
| 8350 | SPBPB21E7.09_UP | TCAGCCGCTGTGAGGTCCAA |
| 8351 | SPBPB21E7.09_DN | TAGAGAGCGGCTGTCACGCA |
| 8352 | SPBPB2B2.01_UP | CCCTCCACCCTGTCCACCG |
| 8353 | SPBPB2B2.01_DN | TGGTTGCCGACTTTCGTCCCG |
| 8354 | SPBPB2B2.02_UP | TGCTGCTCTGTGACGGTACG |
| 8355 | SPBPB2B2.02_DN | GTCATGACGAAGCTCGGTCCA |
| 8356 | SPBPB2B2.05_UP | CTCACGTGCGCGGCATTTAA |
| 8357 | SPBPB2B2.05_DN | CTTCTGCCCTGCTCGTCCCG |
| 8358 | SPBPB2B2.06c_UP | TGTGGCGAGCGCTGTTTTA |
| 8359 | SPBPB2B2.06c_DN | CGGAGCTCGCCTTTGGTCAT |
| 8360 | SPBPB2B2.07c_UP | CGAGGGAGAGTTTGGCGGCAG |
| 8361 | SPBPB2B2.07c_DN | TCTGCGCCAAAATCTCCCGG |
| 8362 | SPBPB2B2.08_UP | CGAATCGGCCGAGGGTAAGCT |
| 8363 | SPBPB2B2.08_DN | GGGCGGCGGTTGTGTTGTT |
| 8364 | SPBPB2B2.09c_UP | TCCACCTTAATCCCGCGGCC |

FIG.48

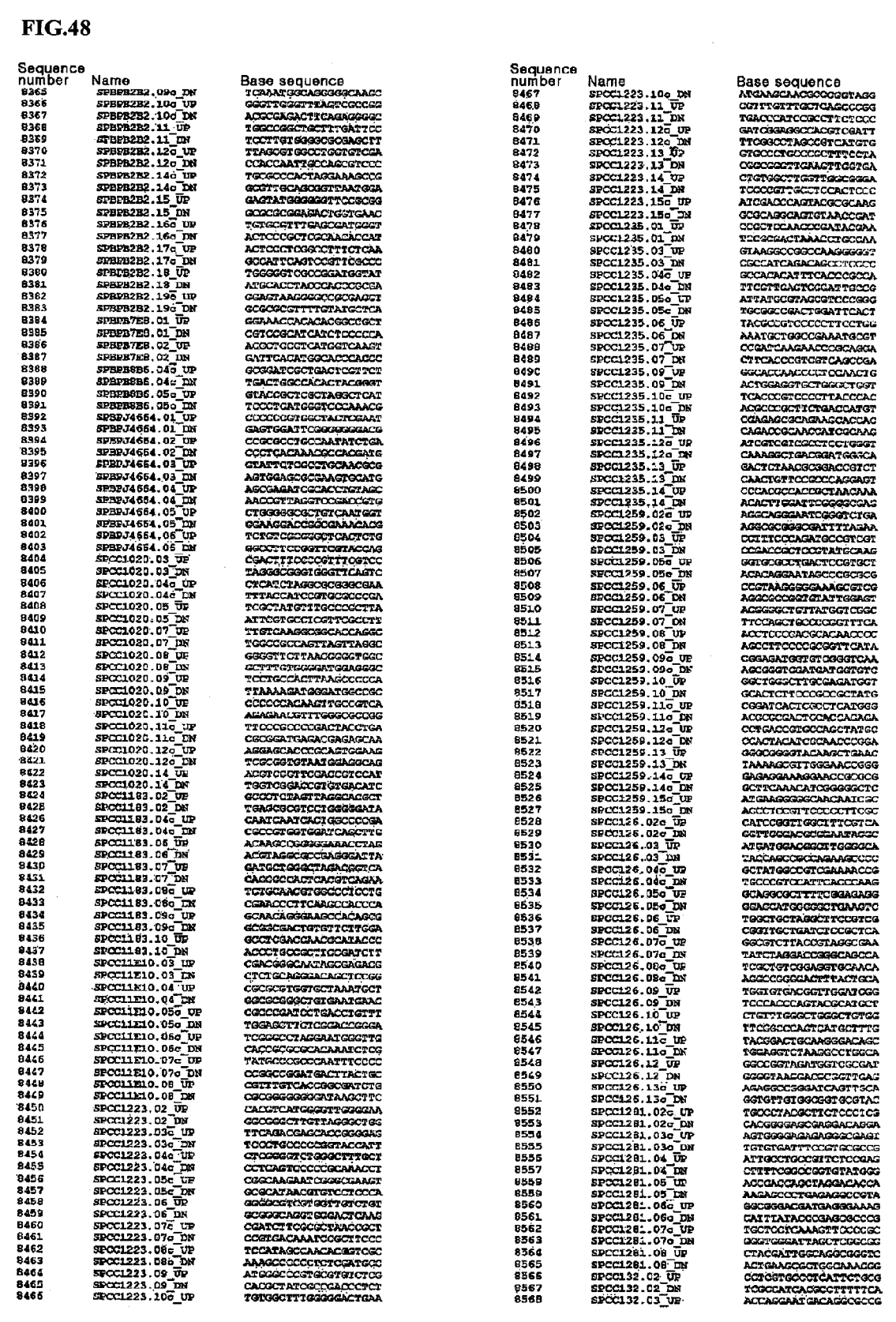

| Sequence number | Name | Base sequence |
|---|---|---|
| 8365 | SPBPB2B2.09c_DN | TCAAATGGCAGGGGGCAAGC |
| 8366 | SPBPB2B2.10c_UP | GGGTTGGGTTAAGTCGCCGG |
| 8367 | SPBPB2B2.10c_DN | ACGCGAGACTTCAGAGGGGC |
| 8368 | SPBPB2B2.11_UP | TGGCCGGCTGCTTTGATTCC |
| 8369 | SPBPB2B2.11_DN | TCCTTGTGGGGCGGGAGCTT |
| 8370 | SPBPB2B2.12c_UP | TTAGCGTGGCCTGGTGTCGA |
| 8371 | SPBPB2B2.12c_DN | CCACCAATTGCCAGCGTCCC |
| 8372 | SPBPB2B2.14c_UP | TGCGCCCACTAGGAAAGCCG |
| 8373 | SPBPB2B2.14c_DN | GCGTTGCAGCGGTTAATGGA |
| 8374 | SPBPB2B2.15_UP | GAGTATGGGGGTTCCGCGG |
| 8375 | SPBPB2B2.15_DN | GCGCGCGGAGACTGGTGAAC |
| 8376 | SPBPB2B2.16c_UP | TGTGCGTTTGAGCGATGGGT |
| 8377 | SPBPB2B2.16c_DN | ACTCCCGCTCGCAACACCAT |
| 8378 | SPBPB2B2.17c_UP | ACTCCCTCGGCCTTTCTCAA |
| 8379 | SPBPB2B2.17c_DN | GCCATTCAGTCCGTTCGCCC |
| 8380 | SPBPB2B2.18_UP | TGGGGGTCGCCGGATGGTAT |
| 8381 | SPBPB2B2.18_DN | ATGCACCTACCCACCCGCGA |
| 8382 | SPBPB2B2.19c_UP | GGAGTAAGGGGCCGCGAGCT |
| 8383 | SPBPB2B2.19c_DN | GCGCGCGTTTTGTATGCTCA |
| 8384 | SPBPB7E8.01_UP | GGAAACCACACACGGCCGCT |
| 8385 | SPBPB7E8.01_DN | CGTCCGCATCATCTCCCCCA |
| 8386 | SPBPB7E8.02_UP | ACGCTGCCTCATGGTCAAGT |
| 8387 | SPBPB7E8.02_DN | GATTCACATGGCACCCACCC |
| 8388 | SPBPB8B6.04c_UP | GCGGATCGCTGACTCGTTCT |
| 8389 | SPBPB8B6.04c_DN | TGACTGGCCACACTACGGGT |
| 8390 | SPBPB8B6.05c_UP | GTACCGCTCGCTAGGCTCAT |
| 8391 | SPBPB8B6.05c_DN | TCCCTGATGGGTCCCAAACG |
| 8392 | SPBPJ4664.01_UP | CCCCCCGTGGCTACTCGAAT |
| 8393 | SPBPJ4664.01_DN | GAGTGGATTCGGGGGGGACG |
| 8394 | SPBPJ4664.02_UP | CCGCGCCTGCCAATATCTGA |
| 8395 | SPBPJ4664.02_DN | CCCTCACAAACGCCACGATG |
| 8396 | SPBPJ4664.03_UP | GTATTCTCGCCTGCAACGCG |
| 8397 | SPBPJ4664.03_DN | AGTGGAGCGCGAAGTGCATG |
| 8398 | SPBPJ4664.04_UP | AGCGAGATCGCACCTGTAGC |
| 8399 | SPBPJ4664.04_DN | AACCGTTAGGTCCGACCGTG |
| 8400 | SPBPJ4664.05_UP | CTGGGGGCGCTGTCAATGGT |
| 8401 | SPBPJ4664.05_DN | GGAAGGACCGGCGAAACACG |
| 8402 | SPBPJ4664.06_UP | TCTGTCGGGGGTCACTCTG |
| 8403 | SPBPJ4664.06_DN | GGCCTTCCGGTTCGTACCAG |
| 8404 | SPCC1020.03_UP | CGACTTTCCCCGTTTCGTCC |
| 8405 | SPCC1020.03_DN | TAGGGCGGGTGGGTTCAGTC |
| 8406 | SPCC1020.04c_UP | CTCATCTAGGCGCGGGCGAA |
| 8407 | SPCC1020.04c_DN | TTTACCATCCGTGCGCCCGA |
| 8408 | SPCC1020.05_UP | TCGCTATGTTTGCCCCCTTA |
| 8409 | SPCC1020.05_DN | ATTCGTGCCTCGTTCGCCTT |
| 8410 | SPCC1020.07_UP | TTGTCAAGGCGGCACCAGGC |
| 8411 | SPCC1020.07_DN | TGGCCGCCAGTTAGTTAGGC |
| 8412 | SPCC1020.08_UP | GGGGTTCTTAACGGGGTGGC |
| 8413 | SPCC1020.08_DN | GCTTTGTGGGGATGGAGGGC |
| 8414 | SPCC1020.09_UP | TCCTGCCACTTAAGCCCCCA |
| 8415 | SPCC1020.09_DN | TTAAAAGATGGGATGGCCGC |
| 8416 | SPCC1020.10_UP | CCCCCCACAAGTTGCCGTCA |
| 8417 | SPCC1020.10_DN | AGAGAAUGTTTGGGCGCCGG |
| 8418 | SPCC1020.11c_UP | TTCCCGCCCCGACTACCTGA |
| 8419 | SPCC1020.11c_DN | CGCGGATGAGACGAGAGCAA |
| 8420 | SPCC1020.12c_UP | AGGAGCACCCGCAGTGGAAG |
| 8421 | SPCC1020.12c_DN | TCGCGGTGTAATGGAGGCAG |
| 8422 | SPCC1020.14_UP | ACGTCGGTTCGACCGTCCAT |
| 8423 | SPCC1020.14_DN | TGGTCGGACCGTGTGACATC |
| 8424 | SPCC1183.02_UP | GCCCTCTAGTTAGGCACGCT |
| 8425 | SPCC1183.02_DN | TGAGCGCGTCCTGGGGGATA |
| 8426 | SPCC1183.04c_UP | CAATCAATCACTGGCCCCGA |
| 8427 | SPCC1183.04c_DN | CGCCGTGGTGGATCAGCTTC |
| 8428 | SPCC1183.06_UP | ACAAGCCGGGGGAAACCTAG |
| 8429 | SPCC1183.06_DN | ACGTAGGCGCCGAGGGATTA |
| 8430 | SPCC1183.07_UP | GATGCTGGGCTAGACGGTCA |
| 8431 | SPCC1183.07_DN | CAGGGCCACTCACGTCAGAA |
| 8432 | SPCC1183.08c_UP | TGTGCAACGTGGCCCTCCTG |
| 8433 | SPCC1183.08c_DN | CGAACCCTTCAAGCCACCCA |
| 8434 | SPCC1183.09c_UP | GCAACAGGGAAGCCACAGCG |
| 8435 | SPCC1183.09c_DN | GCGGCGACTGTGTTCTTGGA |
| 8436 | SPCC1183.10_UP | GCCTCGACCAACGCATACCC |
| 8437 | SPCC1183.10_DN | ACCCTGCCGCTTCCGATCTT |
| 8438 | SPCC11E10.03_UP | CGACGGGCAATAGCGAGACG |
| 8439 | SPCC11E10.03_DN | CTCTGCAGGGACAGCTCCGG |
| 8440 | SPCC11E10.04_UP | CGCGCGTGGTGCTAAATGCT |
| 8441 | SPCC11E10.04_DN | GGCGCGGGCTGTGAATGAAC |
| 8442 | SPCC11E10.05c_UP | CGCCCGATCCTGACCTGTTT |
| 8443 | SPCC11E10.05c_DN | TGGAGCTTGTCGGACCGGGA |
| 8444 | SPCC11E10.06c_UP | TCGGCCCTAGGAATGGGTTG |
| 8445 | SPCC11E10.06c_DN | CACCGCGCGCACAAATCTCG |
| 8446 | SPCC11E10.07c_UP | TATGCCCGGCCAATTTCCCC |
| 8447 | SPCC11E10.07c_DN | CCGGCCGGATGACTTACTGC |
| 8448 | SPCC11E10.08_UP | CGTTTGTCACCGGCGATCTG |
| 8449 | SPCC11E10.08_DN | CGCGGGGGGGATAAGCTTC |
| 8450 | SPCC1223.02_UP | CACGTCATGGGGTTGGGGAA |
| 8451 | SPCC1223.02_DN | GGCGGGCTTGTTAGGGCTGG |
| 8452 | SPCC1223.03c_UP | TTCAGACGAGCACCGGGGAG |
| 8453 | SPCC1223.03c_DN | TCCCTGCCCCCGGTACCATT |
| 8454 | SPCC1223.04c_UP | CTCGGGGTCTGGGCTTTGCT |
| 8455 | SPCC1223.04c_DN | CCTCAGTCCCCCGCAAACCT |
| 8456 | SPCC1223.05c_UP | CGGCAAGAATCGGGCGAAGT |
| 8457 | SPCC1223.05c_DN | GCGCATAACGTGTCCTCCCA |
| 8458 | SPCC1223.06_UP | GGGGCGTCGTGGTTGTCTGT |
| 8459 | SPCC1223.06_DN | GCGGGCAGGTGGGACTCAAG |
| 8460 | SPCC1223.07c_UP | CGATCTTCGCGCTAACCGCT |
| 8461 | SPCC1223.07c_DN | CCGTGACAAATCCGCTTCCC |
| 8462 | SPCC1223.08c_UP | TCCATAGCCAACACGGTCGC |
| 8463 | SPCC1223.08c_DN | AAAGCCCCCCTCTCGATGCC |
| 8464 | SPCC1223.09_UP | ATGGGCCCGTGCGTGTCTCG |
| 8465 | SPCC1223.09_DN | CACGCTATCGCCGACCCTCT |
| 8466 | SPCC1223.10c_UP | TGTGGCTTTGGGGGACTGAA |

| Sequence number | Name | Base sequence |
|---|---|---|
| 8467 | SPCC1223.10c_DN | ATGAAGCAACGCCCGGTAGG |
| 8468 | SPCC1223.11_UP | CGTTTGTTTGCTCAGCCCGG |
| 8469 | SPCC1223.11_DN | TGACCCATCCGCCTTCTCCC |
| 8470 | SPCC1223.12c_UP | GATCGGAGGCCACGTCGATT |
| 8471 | SPCC1223.12c_DN | TTCGGCCTAGCCGTCATGTG |
| 8472 | SPCC1223.13_UP | GTGCCCTGCCCGCTTTCCTA |
| 8473 | SPCC1223.13_DN | CGGCGGGTTGAAGTTGGTGA |
| 8474 | SPCC1223.14_UP | CTGTGGCTTGGTTGGCGGGA |
| 8475 | SPCC1223.14_DN | TCCCCGTTGCCTCCACTCCC |
| 8476 | SPCC1223.15c_UP | ATCGACCCAGTACGCGCAAG |
| 8477 | SPCC1223.15c_DN | GCGCAGGCAGTGTAACCGAT |
| 8478 | SPCC1235.01_UP | CCGCTCCAACCCGATACGAA |
| 8479 | SPCC1235.01_DN | TCCGCGACTAAACCTGCCAA |
| 8480 | SPCC1235.03_UP | GTAAGGCCGGCCAAGGGGGT |
| 8481 | SPCC1235.03_DN | CGCCATCAGACAGCCCTCCCC |
| 8482 | SPCC1235.04c_UP | GCCACACATTTCACCCGCCA |
| 8483 | SPCC1235.04c_DN | TTCGTTGACTCGCATTGCCG |
| 8484 | SPCC1235.05c_UP | ATTATGCGTAGCGTCCCGGG |
| 8485 | SPCC1235.05c_DN | TGCGGCCGACTGGATTCACT |
| 8486 | SPCC1235.06_UP | TACGCCGTCCCCCTTCCTGG |
| 8487 | SPCC1235.06_DN | AAATGCTGGCCGAAATGCGT |
| 8488 | SPCC1235.07_UP | CCGATCAAGAACCCGCAGGA |
| 8489 | SPCC1235.07_DN | CTTCACCCGTCGTCAGCCGA |
| 8490 | SPCC1235.09_UP | GGCACCAACCCCTCCAACTG |
| 8491 | SPCC1235.09_DN | ACTGGAGGTGCTGGGCTGGT |
| 8492 | SPCC1235.10c_UP | TCACCCGTCCCCTTACCCAC |
| 8493 | SPCC1235.10c_DN | ACGCCCGCTTCTGACCATGT |
| 8494 | SPCC1235.11_UP | CGAGAGCGCAGAAGCACCAC |
| 8495 | SPCC1235.11_DN | CAGACCGCAACCATCGCAAG |
| 8496 | SPCC1235.12c_UP | ATCGTCGTCGCCTCCTGGGT |
| 8497 | SPCC1235.12c_DN | CAAAGGCTGACGGATGGGCA |
| 8498 | SPCC1235.13_UP | GACTCTAACGCGGACCGTCT |
| 8499 | SPCC1235.13_DN | CAACTGTTCCGCCCAGGAGT |
| 8500 | SPCC1235.14_UP | CCCACGCCACCGCTAACAAA |
| 8501 | SPCC1235.14_DN | ACACTTGGATTCGGGGCGAG |
| 8502 | SPCC1259.02c_UP | AGGCAGGGAATCGGGTCTGA |
| 8503 | SPCC1259.02c_DN | AGGCGCGGGCGATTTTAGAA |
| 8504 | SPCC1259.03_UP | CGTTTCCCAGATGCCGTCGT |
| 8505 | SPCC1259.03_DN | CCGACCGCTCCGTATGCAAG |
| 8506 | SPCC1259.05c_UP | GGTGCGCCTGACTCCGTGCT |
| 8507 | SPCC1259.05c_DN | ACACAGGAATAGCCCGCGCG |
| 8508 | SPCC1259.06_UP | CCGTAAGGGGAAAGCGTCG |
| 8509 | SPCC1259.06_DN | AGGCGCCGGTGTATTGGAGT |
| 8510 | SPCC1259.07_UP | ACGGGGCTGTTATGGTCGGC |
| 8511 | SPCC1259.07_DN | TTCCAGCTGCCCCGGTTTCA |
| 8512 | SPCC1259.08_UP | ACCTCCCCACGCACAACCCC |
| 8513 | SPCC1259.08_DN | AGCCTTCCCCGCGGTTCATA |
| 8514 | SPCC1259.09c_UP | CGGAGATGGTGTCGGGTCAA |
| 8515 | SPCC1259.09c_DN | AGCGGGTCGATGATGGTGTC |
| 8516 | SPCC1259.10_UP | GGCTGGGCTTGCGAGATGGT |
| 8517 | SPCC1259.10_DN | GCACTCTTCCCGCCGCTATG |
| 8518 | SPCC1259.11c_UP | CGGATCACTCGCCTCATGGG |
| 8519 | SPCC1259.11c_DN | ACGCGCGACTGCACCAGAGA |
| 8520 | SPCC1259.12c_UP | CCTGACCGTGCCAGCTATGC |
| 8521 | SPCC1259.12c_DN | CCACTACATCGCAACCCGGA |
| 8522 | SPCC1259.13_UP | GGGCGGGGTACAAGCTGAAC |
| 8523 | SPCC1259.13_DN | TAAAAGCGTTGGGAACCGGG |
| 8524 | SPCC1259.14c_UP | GAGAGGAAAGGAACCGCGCG |
| 8525 | SPCC1259.14c_DN | GCTTCAAACATCGGGGGCTC |
| 8526 | SPCC1259.15c_UP | ATGAAGGGGGCAACAATCGC |
| 8527 | SPCC1259.15c_DN | AGCCTCCGTTCCCCCTTCGC |
| 8528 | SPCC126.02c_UP | CATCCGGTTGGCTTTCGTCA |
| 8529 | SPCC126.02c_DN | GGTTGCGACGCCGAATAGGC |
| 8530 | SPCC126.03_UP | ATGATGGACGGCTTGGGGCA |
| 8531 | SPCC126.03_DN | TACCAGCCGCCAGAAGCCCC |
| 8532 | SPCC126.04c_UP | GCTATGGCCGTCGAAAACCG |
| 8533 | SPCC126.04c_DN | TGCCCGTCCATTCACCCAAG |
| 8534 | SPCC126.05c_UP | GCAGGCGCTTTTCGGAGAGG |
| 8535 | SPCC126.05c_DN | GGAGCATGGGGGCTGAAGTC |
| 8536 | SPCC126.06_UP | TGGCTGCTAGGCTTCCGTCG |
| 8537 | SPCC126.06_DN | CGGTTGCTGATCTCCGCTCA |
| 8538 | SPCC126.07c_UP | GGCGTCTTACCGTAGGCGAA |
| 8539 | SPCC126.07c_DN | TATCTAGGACCGGGCAGCCA |
| 8540 | SPCC126.08c_UP | TCGCTGTCGGAGGTGCAACA |
| 8541 | SPCC126.08c_DN | AGGCCGGGCACTTTACTGCA |
| 8542 | SPCC126.09_UP | TGGTGTGACGGTTGGATCGG |
| 8543 | SPCC126.09_DN | TCCCACCCAGTACGCATGCT |
| 8544 | SPCC126.10_UP | CTGTTTGGGCTGGGCTGTGG |
| 8545 | SPCC126.10_DN | TTCGGCCCAGTCATGCTTTG |
| 8546 | SPCC126.11c_UP | TACGGACTGCAAGGGACAGC |
| 8547 | SPCC126.11c_DN | TGGAGGTCTAAGGCCTGGCA |
| 8548 | SPCC126.12_UP | GGCCGGTAGATGGTCGCGAT |
| 8549 | SPCC126.12_DN | GGGGTAACGACCCGCTTGAG |
| 8550 | SPCC126.13c_UP | AGAGGCCGGGATCAGTTGCA |
| 8551 | SPCC126.13c_DN | GGTGTTGTGGCGGTGCGTAC |
| 8552 | SPCC1281.02c_UP | TGCCCTACGCTTCTCCCTCG |
| 8553 | SPCC1281.02c_DN | CACGGGGAGCGAGGACAGGA |
| 8554 | SPCC1281.03c_UP | AGTGGGGAGAGAGGGCGAGT |
| 8555 | SPCC1281.03c_DN | TGTGTGATTTCCGTGCGCCG |
| 8556 | SPCC1281.04_UP | ATTGCCTGCCGTTCTCCGAG |
| 8557 | SPCC1281.04_DN | CTTTTCGGCCGGTGTATGGG |
| 8558 | SPCC1281.05_UP | ACCGACCAGCTAGGACACCA |
| 8559 | SPCC1281.05_DN | AAGAGCCCTGAGAGGCCGTA |
| 8560 | SPCC1281.06c_UP | GGCGGGACGATGAGGGAAAG |
| 8561 | SPCC1281.06c_DN | CATTTATACCCGAGCGCCCG |
| 8562 | SPCC1281.07c_UP | TGCTCCTCAAAGTTCCCCGC |
| 8563 | SPCC1281.07c_DN | GGGTGGGATTAGCTCGGCGG |
| 8564 | SPCC1281.08_UP | CTACGATTGGCAGGCGGGTC |
| 8565 | SPCC1281.08_DN | ACTGAAGCGCTGGCAAACGG |
| 8566 | SPCC132.02_UP | CCTCGTGCCCTCATTCTGCG |
| 8567 | SPCC132.02_DN | TCGCCATCACGCCTTTTTCA |
| 8568 | SPCC132.03_UP | ACCAGGAATGACAGGCGCCG |

| Sequence number | Name | Base sequence |
|---|---|---|
| 8773 | SPCC16A11.04_DN | GGCAACTTCCCGTAGGACGA |
| 8774 | SPCC16A11.06c_UP | CGCGCACGGGTAAGCAACCG |
| 8775 | SPCC16A11.06c_DN | CAGAAAGCACAGGGGACGG |
| 8776 | SPCC16A11.07_UP | CGGCCTCGGTTTGGTGGTGT |
| 8777 | SPCC16A11.07_DN | GCGGTAATAAGGCGGGGGT |
| 8778 | SPCC16A11.08_UP | ATAGGCTCGGGGGTCGATGA |
| 8779 | SPCC16A11.08_DN | GTGGTCCAAGCGGTCGATCA |
| 8780 | SPCC16A11.10c_UP | GAAATCCTCACGGGGTGCCTG |
| 8781 | SPCC16A11.10c_DN | GGGGAAAGGTGTCGCATGCG |
| 8782 | SPCC16A11.11_UP | GCGCTCGTTAATGCTCACGA |
| 8783 | SPCC16A11.11_DN | ADGCAGAGAGGGCGCAGAAGC |
| 8784 | SPCC16A11.12c_UP | TGCTCGTATTGCCTTGGTCC |
| 8785 | SPCC16A11.12c_DN | GGCGTGGGCAGAGAGAGGTG |
| 8786 | SPCC16A11.14_UP | CCAAAAGGGCATGGTCCACG |
| 8787 | SPCC16A11.14_DN | CGGGACGGAGAGGGCTGACT |
| 8788 | SPCC16A11.15c_UP | TGAGCCTCCGAGTGGTGTGT |
| 8789 | SPCC16A11.15c_DN | ACGTGACTCTAGCGCAGCGA |
| 8790 | SPCC16A11.16c_UP | CATTACCTAGCGACGCCTTC |
| 8791 | SPCC16A11.16c_DN | ACATAGTGCAGGTCCGTCGC |
| 8792 | SPCC16C4.01_UP | CTCCACCTCCCGCCTTCTCC |
| 8793 | SPCC16C4.01_DN | GGACGTCACCTGACCGTCTT |
| 8794 | SPCC16C4.02c_UP | AGTTGTAGGGTCGGGGGGAG |
| 8795 | SPCC16C4.02c_DN | ATGAGGGGTTGGCGGTGGG |
| 8796 | SPCC16C4.03_UP | CCCCGGCTCTCGTCTTCTCC |
| 8797 | SPCC16C4.03_DN | GGCCGCACCAACATCTTCCG |
| 8798 | SPCC16C4.05_UP | CGCCGTATTTCCCCAGTTCG |
| 8799 | SPCC16C4.05_DN | CGTCCGGGCTGACGTAACTT |
| 8800 | SPCC16C4.06c_UP | GAGTCGGCGGGCTTTCAGGT |
| 8801 | SPCC16C4.06c_DN | AGGTGTGGGTGTTCTGGCGC |
| 8802 | SPCC16C4.07_UP | CGCCCCCTCGTCAACACCCT |
| 8803 | SPCC16C4.07_DN | CTCCCCTGTTCTCGCCCACC |
| 8804 | SPCC16C4.08c_UP | GGAAGTGGGCCGTAAAGCGA |
| 8805 | SPCC16C4.08c_DN | GCTTGTGCAAGCCGATACGC |
| 8806 | SPCC16C4.09_UP | ATCACGCCCTCCCACTTCGT |
| 8807 | SPCC16C4.09_DN | TTTGCGTGGTTCGCTGCGTA |
| 8808 | SPCC16C4.10_UP | TCAAGTCGCCTTAGACCCGT |
| 8809 | SPCC16C4.10_DN | AGCCTATGCCCGCTTCACCG |
| 8810 | SPCC16C4.11_UP | CCAGACCGCGAGCCGAAGAA |
| 8811 | SPCC16C4.11_DN | TGGATCCCGTGGGCCGTATT |
| 8812 | SPCC16C4.12_UP | GGCCGGATTAGTGCCACCTA |
| 8813 | SPCC16C4.12_DN | CGGTGTACGTCGAACCGTTG |
| 8814 | SPCC16C4.13c_UP | ACGGTACTCGCGAGAGTGGA |
| 8815 | SPCC16C4.13c_DN | TGCCGTGACTTTATGCTGGT |
| 8816 | SPCC16C4.14c_UP | AACTGGCCCACTACCCGTCG |
| 8817 | SPCC16C4.14c_DN | GCTGACCTAAAGACGGCGGG |
| 8818 | SPCC16C4.15_UP | GACGTTAAATGGCGAGCGCG |
| 8819 | SPCC16C4.15_DN | GCGCGGGGTTATCGTGCTT |
| 8820 | SPCC16C4.16c_UP | ATAGGCCCGGAACTCGCACT |
| 8821 | SPCC16C4.16c_DN | TCATCGGGAACTCCACTGCG |
| 8822 | SPCC16C4.17_UP | TGGAGCCCGGACAGGACTAA |
| 8823 | SPCC16C4.17_DN | ACTACACGGACCACGGGAAA |
| 8824 | SPCC16C4.18c_UP | TTGCCCCTCATTCCCCGCCA |
| 8825 | SPCC16C4.18c_DN | CCAGCGGCGTTGCGTTTCAGA |
| 8826 | SPCC16C4.20c_UP | GAGCACGGGGTATCCAATGC |
| 8827 | SPCC16C4.20c_DN | TCGTTGCGCCCTTGTTCACC |
| 8828 | SPCC1739.02c_UP | GGTCATGGTAGGGTGGCGGG |
| 8829 | SPCC1739.02c_DN | GTTCCACTCTACTCGGCGGC |
| 8830 | SPCC1739.03_UP | GTCTTCTGGAGGTGCGGGGA |
| 8831 | SPCC1739.03_DN | CGAGGAAACGGTGATCGGGT |
| 8832 | SPCC1739.04c_UP | TGAAGCCCGGGTGATACCGA |
| 8833 | SPCC1739.04c_DN | TGCTGCCTGGACGGCTGTTA |
| 8834 | SPCC1739.05_UP | AGAGTGCCGAGCACTGAGAC |
| 8835 | SPCC1739.05_DN | AGTCCCTAGCTACAGGCGGA |
| 8836 | SPCC1739.06c_UP | CCAGCGTGTCGTGCAGAGAT |
| 8837 | SPCC1739.06c_DN | ACTCTGCGATCCGTGAAGC |
| 8838 | SPCC1739.07_UP | GCCAAGGGTGGGCGGAAATC |
| 8839 | SPCC1739.07_DN | GGGGGGGAGTCAATAGGCA |
| 8840 | SPCC1739.08c_UP | ACTTCCGGCACGACCGGATAG |
| 8841 | SPCC1739.08c_DN | ACCCGGTTAGCCTCGCATAC |
| 8842 | SPCC1739.09c_UP | CATCAAGCAGGGCGAGGCCA |
| 8843 | SPCC1739.09c_DN | CCACGTGTCCCAACCAGCCA |
| 8844 | SPCC1739.10_UP | TGGTAGCCTCGTACAGGCGA |
| 8845 | SPCC1739.10_DN | TAGGACAAGGCCGCGGGAC |
| 8846 | SPCC1739.11c_UP | GTGTTGAGGGAAGCGAGGCG |
| 8847 | SPCC1739.11c_DN | ACTGACGGGAGGGCATACGG |
| 8848 | SPCC1739.12_UP | CCGGCAAGAAAATGTGCCCT |
| 8849 | SPCC1739.12_DN | ACCACACCCCGTTGCCTCGT |
| 8850 | SPCC1739.13_UP | AGGACTCCGCTAGTGCCCTT |
| 8851 | SPCC1739.13_DN | AACACAGCTCGGAGCCTCAC |
| 8852 | SPCC1739.14_UP | TGACCTCGTGGGACGACTGT |
| 8853 | SPCC1739.14_DN | CGCTCGACGCTCTGTGACAA |
| 8854 | SPCC1742.01_UP | TGTTAAAGTCGCAACGGTGCT |
| 8855 | SPCC1742.01_DN | AGGTCGGACACCCTCACGTA |
| 8856 | SPCC1753.02c_UP | TTTGGGGCGACTTCGCCATG |
| 8857 | SPCC1753.02c_DN | CCCCCCTGAGAACGCACCAA |
| 8858 | SPCC1753.03c_UP | TGGTTAAGCCGCTCGGGGGT |
| 8859 | SPCC1753.03c_DN | GCGCCCAATGAAAGGGTTTG |
| 8860 | SPCC1753.04_UP | TTGGATGCCGTGTGACGAGA |
| 8861 | SPCC1753.04_DN | AGGGCCACGCCTTAGTACACC |
| 8862 | SPCC1753.05_UP | ATCCACCGGTCCGGGTTAGT |
| 8863 | SPCC1753.05_DN | GGGCGGTATCGTAACTGCGG |
| 8864 | SPCC1795.03_UP | GTCCGGCGGGTAGAGTGGCA |
| 8865 | SPCC1795.03_DN | CGTTGGTGATACCGGAGGGG |
| 8866 | SPCC1795.04c_UP | TGGCTTGCCACGGGGATCTT |
| 8867 | SPCC1795.04c_DN | TTTCGGGCGTAAGTGCCCC |
| 8868 | SPCC1795.05c_UP | TAATACCTTTCGCCGCCCCA |
| 8869 | SPCC1795.05c_DN | GCATGCTGTCGGTGGCCT |
| 8870 | SPCC1795.06_UP | CTGCTGCGGATGGGGTTCTG |
| 8871 | SPCC1795.06_DN | TGGCGATGGCTTTGCAGGTA |
| 8872 | SPCC1795.07_UP | AGTGGGCAGTTGCCGCATCAT |
| 8873 | SPCC1795.07_DN | AAGCCTCAAGCCCAACGCAC |
| 8874 | SPCC1795.09_UP | AATCCGTGTCCCCCCACGAC |
| 8875 | SPCC1795.09_DN | ATGGACGGGTTTGAGGGGGC |
| 8876 | SPCC1795.10c_UP | GACAAGTCGCACTTGCACCC |
| 8877 | SPCC1795.10c_DN | ATCTGCGACCCTACGGAACC |
| 8878 | SPCC1795.11_UP | TGGGTGCCCAGTACGGTCGT |
| 8879 | SPCC1795.11_DN | TGGAGGTCGACGGAAACTCG |
| 8880 | SPCC1795.12c_UP | GTGGCACCGACCGGTTACAA |
| 8881 | SPCC1795.12c_DN | TAACGGATGAGATCCGCCCG |
| 8882 | SPCC18.02_UP | CGCCGTAAACCCCCACTTTC |
| 8883 | SPCC18.02_DN | AGCAACCCCTGCCCACAGA |
| 8884 | SPCC18.03_UP | AGGGCGACGGGTAGGATGGT |
| 8885 | SPCC18.03_DN | GGGGATTCGGTGTCGTTGGA |
| 8886 | SPCC18.05c_UP | AGTGTGCATGGGCACTGTCT |
| 8887 | SPCC18.05c_DN | AACCCTCTTCGCGTCCGGCT |
| 8888 | SPCC18.06c_UP | ACCAAAAGCCCCTAGCGCC |
| 8889 | SPCC18.06c_DN | AGTCGCGACACGCGACTCT |
| 8890 | SPCC18.07_UP | TGTCAAAACCGGGTCAACCT |
| 8891 | SPCC18.07_DN | GCAATCCGCCCGACCACTAT |
| 8892 | SPCC18.08_UP | CTACGCGGGCATTTGCACGA |
| 8893 | SPCC18.08_DN | GCAACTTCGGGAAAGCGGAC |
| 8894 | SPCC18.09c_UP | TGAGAGCGCACGGTGCATTA |
| 8895 | SPCC18.09c_DN | CGCCGTGGGTGATCCGAAAG |
| 8896 | SPCC18.10_UP | GCCGGCAGCAGAAAAGGTAGG |
| 8897 | SPCC18.10_DN | TGGACGTGCGCCGGAAGTTG |
| 8898 | SPCC18.11c_UP | AGTGCACCCTACGGCGATTC |
| 8899 | SPCC18.11c_DN | TGTCACAGGGACCCAGGCAT |
| 8900 | SPCC18.12c_UP | TTTCTGCCCACTAAGGCCGC |
| 8901 | SPCC18.12c_DN | GTCGGAGCGGATCGCAGTTC |
| 8902 | SPCC18.14c_UP | AGTAGCCCCTGACTTGACGC |
| 8903 | SPCC18.14c_DN | GACACAGTCGGCTCCGCAAT |
| 8904 | SPCC18.16c_UP | CGCGGGCCGTTAACCGAGATC |
| 8905 | SPCC18.16c_DN | ACTTGCCCGTTCCACCCAGC |
| 8906 | SPCC18.17c_UP | GTCCCTAAGAAACCCCGCGA |
| 8907 | SPCC18.17c_DN | CGATAGGGCAACGGGGGATG |
| 8908 | SPCC1827.02c_UP | AGGGAGGTGGCGCTTAGGGA |
| 8909 | SPCC1827.02c_DN | CAAACGTGGGTGCAGGCTCG |
| 8910 | SPCC1827.03c_UP | CAACGGCACAGCAAACCCCA |
| 8911 | SPCC1827.03c_DN | TGCCTGTCCCTCGCCTGATT |
| 8912 | SPCC1827.04_UP | TGTGGATGGCGCAGTTGAGGT |
| 8913 | SPCC1827.04_DN | CCGCGTTCTCGCTGCTTGTC |
| 8914 | SPCC1827.05c_UP | AAGGGCCAACGTCGCACACT |
| 8915 | SPCC1827.05c_DN | CGAGGTCACGTTAAGCCCCT |
| 8916 | SPCC1827.08c_UP | GGAGCAAGATCGGGTACGGT |
| 8917 | SPCC1827.08c_DN | GCTGATCTCACGCGACTCCA |
| 8918 | SPCC1840.02c_UP | GTACAACTGCCGGCCTGCCA |
| 8919 | SPCC1840.02c_DN | GCCGGTAAAGCCATCGCCAC |
| 8920 | SPCC1840.04_UP | GGGGGGCGAGTGAGGTGTTG |
| 8921 | SPCC1840.04_DN | TTCCAAGCTACTCGCGCCCC |
| 8922 | SPCC1840.05c_UP | GTAGCGGCCCTTTTCGGTGA |
| 8923 | SPCC1840.05c_DN | CTGGCGGGTGTTGGTGGAC |
| 8924 | SPCC1840.06_UP | CGTTTCGCCGTTTTCAGCAG |
| 8925 | SPCC1840.06_DN | GGCGATTTCCTTTCCTTGCG |
| 8926 | SPCC1840.07c_UP | AAACTTTTCGGAACGCCGGG |
| 8927 | SPCC1840.07c_DN | CTTTATGGGGCCGGGGTTGC |
| 8928 | SPCC1840.08c_UP | TTAAACCCTCGCGCACACCA |
| 8929 | SPCC1840.08c_DN | CGTCGCTACTTGTTCCCCCC |
| 8930 | SPCC1840.09_UP | TCATCGGGGAAGCACAGGC |
| 8931 | SPCC1840.09_DN | ACGTCGCGGTTATATCGGGC |
| 8932 | SPCC1840.10_UP | GGCTCTTTGCGGTTGTCGC |
| 8933 | SPCC1840.10_DN | TTCCCCACCCCAACCCGAAT |
| 8934 | SPCC188.02_UP | AACCCCGTTCGCAGACGATC |
| 8935 | SPCC188.02_DN | GGAGCGGTGTCAACAGGGGA |
| 8936 | SPCC188.03_UP | GGCCCCTTGCGTGTTAGTG |
| 8937 | SPCC188.03_DN | CTCAATGCAATGCGGCGTGCC |
| 8938 | SPCC188.06c_UP | CTGCGTGGCAGTCCCAAATG |
| 8939 | SPCC188.06c_DN | AGATCTACGCGGTGACGCGA |
| 8940 | SPCC188.07_UP | CACGAGCCCCGCACATACAA |
| 8941 | SPCC188.07_DN | CAGATCGCGGTTTGCCTTCA |
| 8942 | SPCC188.08c_UP | TAACCCCCGCCACCAAGACA |
| 8943 | SPCC188.08c_DN | ACACACGAACCCGCACAACC |
| 8944 | SPCC188.09c_UP | AACCTTTCTGTGACGGCGGG |
| 8945 | SPCC188.09c_DN | ACCGGATACGGCTTCCCTCA |
| 8946 | SPCC18B5.04_UP | ATCCAAGGGTCTCAATCCGA |
| 8947 | SPCC18B5.04_DN | TCACCCTTCTTTGGCTCGCA |
| 8948 | SPCC18B5.05c_UP | CTACGGCCCGTTGGATTGGG |
| 8949 | SPCC18B5.05c_DN | CCGGCAAACCCCACGACAAC |
| 8950 | SPCC18B5.06_UP | CGCGTCTCATCGATGCCCTT |
| 8951 | SPCC18B5.06_DN | CGGATCAGGGGCGAGGGTTT |
| 8952 | SPCC18B5.07c_UP | CGAGACGCACCCAACATCCC |
| 8953 | SPCC18B5.07c_DN | TCTTTGATGGGGGCAAGCG |
| 8954 | SPCC18B5.08c_UP | CAGACCTGTTGAACGCCCCA |
| 8955 | SPCC18B5.08c_DN | GGGCCATCTCGAACTTGCAC |
| 8956 | SPCC18B5.09c_UP | TCTGTTAAGGGCGGCATGGG |
| 8957 | SPCC18B5.09c_DN | GGAAAGAGAGCGGCACGGGT |
| 8958 | SPCC18B5.10c_UP | AACGGGCGGGATGAGGTGGT |
| 8959 | SPCC18B5.10c_DN | CTTCATTCCCCCTTCCCGCG |
| 8960 | SPCC18B5.11c_UP | TTCAATACGGCGGGACACGA |
| 8961 | SPCC18B5.11c_DN | CGGGCAAGGTACCCCCAACT |
| 8962 | SPCC1902.02_UP | ACAAGCCGCCAGAGCCTCAA |
| 8963 | SPCC1902.02_DN | AATGGAAGGTGCCTGCGTGA |
| 8964 | SPCC1906.01_UP | CTCACAGTTCGGGGTTGTCC |
| 8965 | SPCC1906.01_DN | ACCGGCCAATTCCTTCCTCC |
| 8966 | SPCC1906.02c_UP | GCGGGTGGGTTAGTGTGCGG |
| 8967 | SPCC1906.02c_DN | AGCCCCGGCCACCCAGTCTA |
| 8968 | SPCC1906.03_UP | CCTTATCGACGTTCCGCCA |
| 8969 | SPCC1906.03_DN | CCCTCGCTCCTGTCGTCGGCT |
| 8970 | SPCC1906.04_UP | TAAGGGCCGGGGATCGTCTC |
| 8971 | SPCC1906.04_DN | TATCCGGCGGGCATTTCTTG |
| 8972 | SPCC191.01_UP | AGCGCAACCCAGCAAAATC |
| 8973 | SPCC191.01_DN | ACTAGGAGCACATGGGCGG |
| 8974 | SPCC191.03c_UP | CGCCGGCGCGCTAGGTTACAA |
| 8975 | SPCC191.03c_DN | CCGATCATAGCACAAGCCGA |
| 8976 | SPCC191.04c_UP | TCCTCGCCTCCACCACCATA |

FIG.51

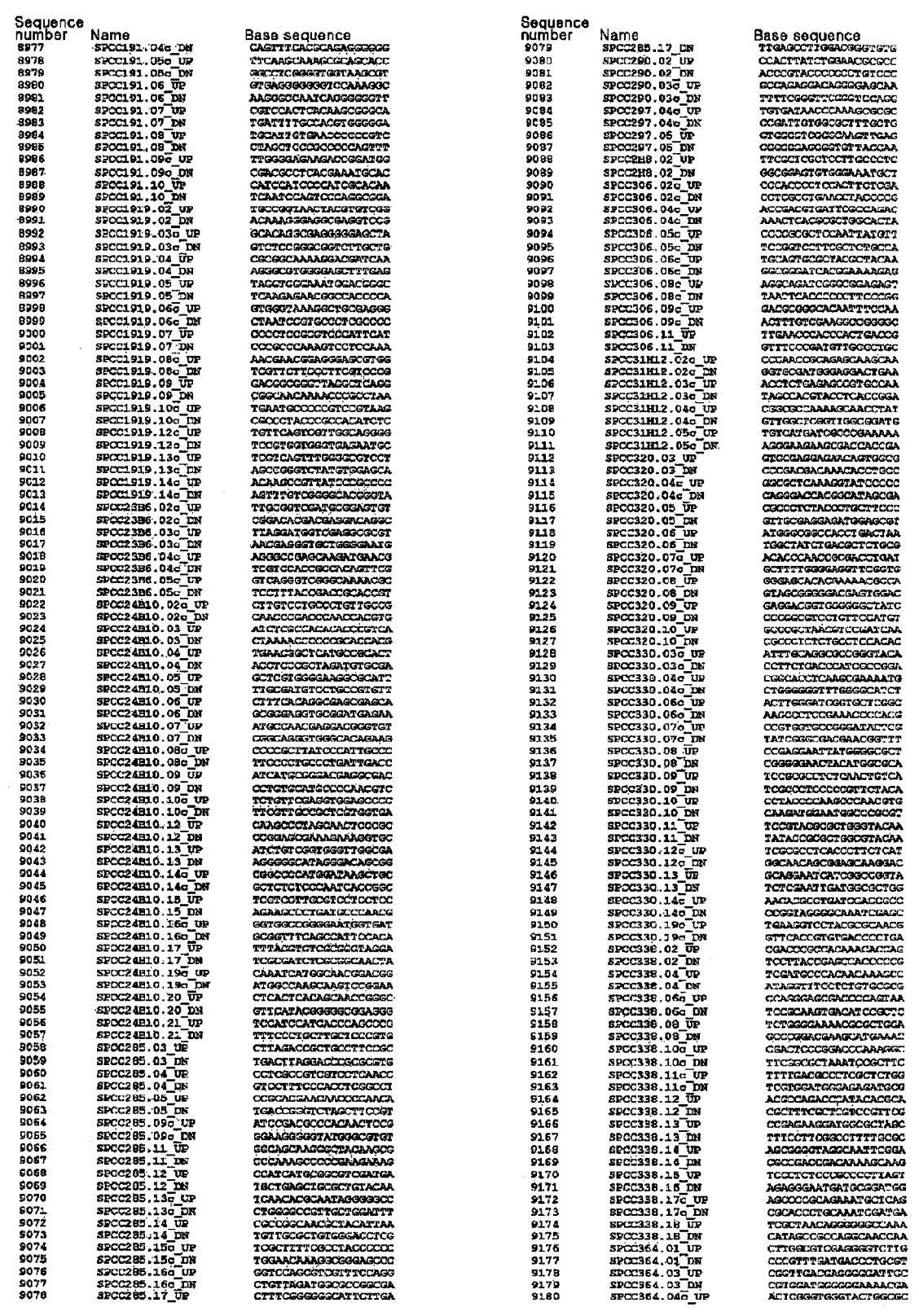

| Sequence number | Name | Base sequence |
|---|---|---|
| 8977 | SPCC191.04c_DN | CAGTTTCACGCAGAGGGGGG |
| 8978 | SPCC191.05c_UP | TTCAAGCAAAGCGCAGCACC |
| 8979 | SPCC191.05c_DN | GGCCTCGGGGTGGTAAGCGT |
| 8980 | SPCC191.06_UP | GTGAGGGGGGGTCCAAAGGC |
| 8981 | SPCC191.06_DN | AAGGGCCAATCAGGGGGGTT |
| 8982 | SPCC191.07_UP | CGTCCACTCACAAGCGGGCA |
| 8983 | SPCC191.07_DN | TGATTTTGCCACGTGGGGGA |
| 8984 | SPCC191.08_UP | TGCATTGTGAACCCCCCGTC |
| 8985 | SPCC191.08_DN | CTAGCTCCCGCCCCCAGTTT |
| 8986 | SPCC191.09c_UP | TTGGGGAGAAGACCGGATGG |
| 8987 | SPCC191.09c_DN | CGACGCCTCACGAAATGCAC |
| 8988 | SPCC191.10_UP | CATCCATCCCCATCGCACAA |
| 8989 | SPCC191.10_DN | TCAATCCAGTCCCAGGCGGA |
| 8990 | SPCC1919.02_UP | TGCCGGTAACTACGTGTCGG |
| 8991 | SPCC1919.02_DN | ACAAAGGGAGGCGAGGTCCG |
| 8992 | SPCC1919.03c_UP | GCACAGGCGAGGGGGAGCTA |
| 8993 | SPCC1919.03c_DN | GTCTCCGGGCGGTCTTGCTG |
| 8994 | SPCC1919.04_UP | CGCGGCAAAAGGACGATCAA |
| 8995 | SPCC1919.04_DN | AGGGCGTGGGGAGCTTTGAG |
| 8996 | SPCC1919.05_UP | TAGGTGGCAAATGGACGGGC |
| 8997 | SPCC1919.05_DN | TCAAGAGAACGGCCACCCCA |
| 8998 | SPCC1919.06c_UP | GTGGGTAAAGGCTGCGAGGG |
| 8999 | SPCC1919.06c_DN | CTAATCCGTGCCCTCGCCCC |
| 9000 | SPCC1919.07_UP | CCCCTCCGCGTCCCATTCAT |
| 9001 | SPCC1919.07_DN | CCCGCCCAAAGTCCTCCAAA |
| 9002 | SPCC1919.08c_UP | AACGAACGGAGGGAGCGTGG |
| 9003 | SPCC1919.08c_DN | TCGTTCTTCCCTTCGTCCCG |
| 9004 | SPCC1919.09_UP | GACGGCGGGTTAGGCTCAGG |
| 9005 | SPCC1919.09_DN | CGGCAACAAAACCCGCCTAA |
| 9006 | SPCC1919.10c_UP | TGAATGCCCCCGTCCGTAAG |
| 9007 | SPCC1919.10c_DN | CGCCCTACCCGCCACATCTC |
| 9008 | SPCC1919.12c_UP | TGTTCAGTCGTTGGCAGGGG |
| 9009 | SPCC1919.12c_DN | TCCGTGGTGGGTGAGAATGC |
| 9010 | SPCC1919.13c_UP | TCGTCAGTTTGGGGCGTCCT |
| 9011 | SPCC1919.13c_DN | AGCCGGGTCTATGTGGAGCA |
| 9012 | SPCC1919.14c_UP | ACAAGCCGTTATCCCGCCCC |
| 9013 | SPCC1919.14c_DN | AGTTTGTCGGGGCACGGGTA |
| 9014 | SPCC23B6.02c_UP | TTGCGGTCGATGCGGAGTGT |
| 9015 | SPCC23B6.02c_DN | CGGACACGACGAGGACAGGC |
| 9016 | SPCC23B6.03c_UP | TTAGGATGGTCGAGGCGCGT |
| 9017 | SPCC23B6.03c_DN | AACGAGGGTGCTGGGGAATG |
| 9018 | SPCC23B6.04c_UP | AGGGCCGAGCAAGATGAACG |
| 9019 | SPCC23B6.04c_DN | TCGTCCACCGCCACAGTTCG |
| 9020 | SPCC23B6.05c_UP | GTCAGGGTCGGGCAAAACGC |
| 9021 | SPCC23B6.05c_DN | TCCTTTACCGACCGCACCGT |
| 9022 | SPCC24B10.02c_UP | CTTGTCCTGCCCTGTTGCCG |
| 9023 | SPCC24B10.02c_DN | CAACCCGACCCAACCACGTG |
| 9024 | SPCC24B10.03_UP | ATCTCGCCACACACCCGTCA |
| 9025 | SPCC24B10.03_DN | CTAAAACCCCCCGCACCACG |
| 9026 | SPCC24B10.04_UP | TGAACGGCTCATGCCGCACT |
| 9027 | SPCC24B10.04_DN | ACCTCCCGCTAGATGTGCGA |
| 9028 | SPCC24B10.05_UP | GCTCGTGGGGAAGGCGCATT |
| 9029 | SPCC24B10.05_DN | TTGCGATGTCCTGCCGTGTT |
| 9030 | SPCC24B10.06_UP | CTTTCACAGGCGAGCGAGCA |
| 9031 | SPCC24B10.06_DN | GCGGGAGGTGCGGATGAGAA |
| 9032 | SPCC24B10.07_UP | ATGCCAACGAGGACGGGTGT |
| 9033 | SPCC24B10.07_DN | CGGCAGGGTGGGCACAGAAG |
| 9034 | SPCC24B10.08c_UP | CCCCGCTTATCCCATTGCCC |
| 9035 | SPCC24B10.08c_DN | TTCCCCTGCCCTGATTGACC |
| 9036 | SPCC24B10.09_UP | ATCATGCGGGACGAGGCGAC |
| 9037 | SPCC24B10.09_DN | CCTGTGCATGCCCCAACGTC |
| 9038 | SPCC24B10.10c_UP | TCTGTTCGAGGTGGAGCCCC |
| 9039 | SPCC24B10.10c_DN | TTCGTTGCCGCTCGTGGTGA |
| 9040 | SPCC24B10.12_UP | CAAGCCCTAGCAACTCCCGC |
| 9041 | SPCC24B10.12_DN | CCGGAGCGAAAGAAAGGTGC |
| 9042 | SPCC24B10.13_UP | ATCTGTCGGTGGGTTGGCGA |
| 9043 | SPCC24B10.13_DN | AGGGGGCATAGGGACAGCGG |
| 9044 | SPCC24B10.14c_UP | CGGCCCCATGGATAAGCTGC |
| 9045 | SPCC24B10.14c_DN | GCTCTCTCCCAATCACCGGC |
| 9046 | SPCC24B10.15_UP | TCGTCGTTGCGTCCTCCTCC |
| 9047 | SPCC24B10.15_DN | AGAAGCCCTGATGCCCAACG |
| 9048 | SPCC24B10.16c_UP | GGTGGCCGGGGAATGGTGAT |
| 9049 | SPCC24B10.16c_DN | GCGGTTTCAGCCATTCCACA |
| 9050 | SPCC24B10.17_UP | TTTACGTCTCGCCGGTAGGA |
| 9051 | SPCC24B10.17_DN | TCGCGATCTCGCGGCAACTA |
| 9052 | SPCC24B10.19c_UP | CAAATCATGGCAACGGACGG |
| 9053 | SPCC24B10.19c_DN | ATGGCCAAGCAAGTCCGGAA |
| 9054 | SPCC24B10.20_UP | CTCACTCACAGCAACCGGGC |
| 9055 | SPCC24B10.20_DN | GTTCATACGGGGGCGGAGGG |
| 9056 | SPCC24B10.21_UP | TCCATCCATCACCCAGCCCG |
| 9057 | SPCC24B10.21_DN | TTTCCCTGCTTGCTCCCGTG |
| 9058 | SPCC285.03_UP | CTTAGACCGCTGCCTTCCGC |
| 9059 | SPCC285.03_DN | TGACTTAGGACCCGCGCGTG |
| 9060 | SPCC285.04_UP | CCTCGCCGTCGTCCTCAACC |
| 9061 | SPCC285.04_DN | GTCCTTTCCCACCTCGGCCT |
| 9062 | SPCC285.05_UP | CCGCACGAACAACCCCAACA |
| 9063 | SPCC285.05_DN | TGACCGGGTCTAGCTTCCGT |
| 9064 | SPCC285.09c_UP | ATCCGACGCCCACAACTCCG |
| 9065 | SPCC285.09c_DN | GGAAGGGGGTATGGGCGTGT |
| 9066 | SPCC285.11_UP | GGCAGCAAGGGCTACAAGCG |
| 9067 | SPCC285.11_DN | GCCAAAGCCCCCGAAGAAAG |
| 9068 | SPCC285.12_UP | CCATCATGCGGCGTCGATGA |
| 9069 | SPCC285.12_DN | TGCTGAGCTGCGCTGTACAA |
| 9070 | SPCC285.13c_UP | TCAACACGCAATAGGGGGCC |
| 9071 | SPCC285.13c_DN | CTGGGGCCGTTGCTGGATTT |
| 9072 | SPCC285.14_UP | CGCCGGCAACGCTACATTAA |
| 9073 | SPCC285.14_DN | TGTTGCGCTGTGGGACCTCG |
| 9074 | SPCC285.15c_UP | TCGCTTTTCGCCTACCCCCC |
| 9075 | SPCC285.15c_DN | TGGAACAAAGGCGGGAGCCC |
| 9076 | SPCC285.16c_UP | GGTCCAGCGTCGTTTCCAGG |
| 9077 | SPCC285.16c_DN | CTGTTAGATGGCGCCGGCGA |
| 9078 | SPCC285.17_UP | CTTTCGGGGGGCATTCTTGA |
| 9079 | SPCC285.17_DN | TTGAGCCTTGGACGGGTGTG |
| 9080 | SPCC290.02_UP | CCACTTATCTGGAACGCGCC |
| 9081 | SPCC290.02_DN | ACCCGTACCCCCCCTGTCCC |
| 9082 | SPCC290.03c_UP | GCCAGAGGACAGGGGAGCAA |
| 9083 | SPCC290.03c_DN | TTTTCGGGTTCGGGTCCAGG |
| 9084 | SPCC297.04c_UP | TGTGATAACCCAAAGCGCGC |
| 9085 | SPCC297.04c_DN | CCGATTGTGGCGCTTTGCTG |
| 9086 | SPCC297.05_UP | GTGGCGTCGGCCAAGTTGAG |
| 9087 | SPCC297.05_DN | CGGCGGAGCGGTGTTACCAA |
| 9088 | SPCC2H8.02_UP | TTCGCTCGCTCCTTGCCCTC |
| 9089 | SPCC2H8.02_DN | GGCGGAGTGTGGGAAATGCT |
| 9090 | SPCC306.02c_UP | CCCACCCCTCCACTTCTCGA |
| 9091 | SPCC306.02c_DN | CCTCGCCTGAACCTACCCCG |
| 9092 | SPCC306.04c_UP | ACCGACGTGATTCGCCAGAC |
| 9093 | SPCC306.04c_DN | AAACTCACGCGCTGGCACTA |
| 9094 | SPCC306.05c_UP | CCCCGCGCTCCAATTATGTT |
| 9095 | SPCC306.05c_DN | TCCGGTCCTTCGCTCTGCCA |
| 9096 | SPCC306.06c_UP | TGCAGTGCGCTACGCTACAA |
| 9097 | SPCC306.06c_DN | GGCGGGATCACGGAAAAGAG |
| 9098 | SPCC306.08c_UP | AGGCAGATCGGGCGGAGAGT |
| 9099 | SPCC306.08c_DN | TAATTCACCCCCCTTCCCGG |
| 9100 | SPCC306.09c_UP | GACGCGGGCACAATTTCCAA |
| 9101 | SPCC306.09c_DN | ACTTTGTCGAAGGCCGGGGC |
| 9102 | SPCC306.11_UP | TTGAACCCACCCACTGACCG |
| 9103 | SPCC306.11_DN | GTTTCCCGATGTTGGCCTGC |
| 9104 | SPCC31H12.02c_UP | CCCAACCGCAGAGCAAGCAA |
| 9105 | SPCC31H12.02c_DN | GGTGCGATGGGAGGACTGAA |
| 9106 | SPCC31H12.03c_UP | ACCTCTGAGAGCCGTGCCAA |
| 9107 | SPCC31H12.03c_DN | TAGCCACGTACCTCACCGGA |
| 9108 | SPCC31H12.04c_UP | CGGCGCCAAAAGCAACCTAT |
| 9109 | SPCC31H12.04c_DN | GTTGGCTCGGTTGGCGGATG |
| 9110 | SPCC31H12.05c_UP | TGTCATGATCGCCCGAAAAA |
| 9111 | SPCC31H12.05c_DN | AGGGAAGAAGCGACCACCGA |
| 9112 | SPCC320.03_UP | GTGCCGAGGAGAACAGTGGCG |
| 9113 | SPCC320.03_DN | CCCGACGACAAACACCTGCC |
| 9114 | SPCC320.04c_UP | GGCGCTCAAAGGTATCCCCC |
| 9115 | SPCC320.04c_DN | CAGGGACCACGGCATAGCGA |
| 9116 | SPCC320.05_UP | CGCCCTCTACCCTGCTTCCC |
| 9117 | SPCC320.05_DN | GTTGCGAGGAGATGGAGCGT |
| 9118 | SPCC320.06_UP | ATGGGCGGCCACCTGACTAA |
| 9119 | SPCC320.06_DN | TGGCTATCTGACGCTCTGCG |
| 9120 | SPCC320.07c_UP | ACACCCAACCGCGACCTGAT |
| 9121 | SPCC320.07c_DN | GCTTTTGGGGAGGTTCGGTG |
| 9122 | SPCC320.08_UP | GGGAGCACACGAAAACGCCA |
| 9123 | SPCC320.08_DN | GTAGCGGGGGACGAGTGGAC |
| 9124 | SPCC320.09_UP | GAGGACGGTGGGGGGCTATC |
| 9125 | SPCC320.09_DN | CCCGGCGTCCTGTTCCATGT |
| 9126 | SPCC320.10_UP | GCCCGCTAACGTCCGATCAA |
| 9127 | SPCC320.10_DN | CGCCCTCTCTGCCTCCACAC |
| 9128 | SPCC330.03c_UP | ATTTGCAGGCGCCGGGTACA |
| 9129 | SPCC330.03c_DN | CCTTCTGACCCATCGCCGGA |
| 9130 | SPCC330.04c_UP | CGGCACCTCAAGCGAAAATG |
| 9131 | SPCC330.04c_DN | CTGGGGGGTTTGGGGCATCT |
| 9132 | SPCC330.06c_UP | ACTTGGGATCGGTGCTCGGC |
| 9133 | SPCC330.06c_DN | AAGCCCTCCGAAACCCCACG |
| 9134 | SPCC330.07c_UP | CCGTGGTGCCGGGATACTCG |
| 9135 | SPCC330.07c_DN | TATCGGGCGACGAACGGTTT |
| 9136 | SPCC330.08_UP | CCGAGGAATTATGGGGCGCT |
| 9137 | SPCC330.08_DN | CGGGGGAACTACATGGCGCA |
| 9138 | SPCC330.09_UP | TCCGCGCCTCTCAACTGTCA |
| 9139 | SPCC330.09_DN | TCGCCCTCCCCCGTTCTACA |
| 9140 | SPCC330.10_UP | CCTACCCCAAGCCCAACGTG |
| 9141 | SPCC330.10_DN | CAAGATGGAATGGCCCGCGT |
| 9142 | SPCC330.11_UP | TCCGTACGCGCTGGGTACAA |
| 9143 | SPCC330.11_DN | TATACCGCGCTGGCGTACAA |
| 9144 | SPCC330.12c_UP | TCGCGCCTCACCCTTCTCAT |
| 9145 | SPCC330.12c_DN | GGCAACAGCGGAGCAAGGAC |
| 9146 | SPCC330.13_UP | GCAGGAATCATCGGCGGGTA |
| 9147 | SPCC330.13_DN | TCTCGAATTGATGGCGCTGG |
| 9148 | SPCC330.14c_UP | AACACGCCTGATCCACCGCC |
| 9149 | SPCC330.14c_DN | CCGGTAGGGGCAAATCGAGC |
| 9150 | SPCC330.19c_UP | TGAAGGTCCTACGCGCAACG |
| 9151 | SPCC330.19c_DN | GTTCACCGTGTGACCCCTGA |
| 9152 | SPCC338.02_UP | CGACCCGCCACAAACACCAG |
| 9153 | SPCC338.02_DN | TCCTTACCGAGCCACCCCCG |
| 9154 | SPCC338.04_UP | TCGATGCCCACAACAAAGCC |
| 9155 | SPCC338.04_DN | ATAGGTTTCCTCTGTGCGCG |
| 9156 | SPCC338.06c_UP | CCAGGGAGCGACCCCAGTAA |
| 9157 | SPCC338.06c_DN | TCCGCAAGTGACATCCGCTC |
| 9158 | SPCC338.08_UP | TCTGGGGAAAACGCGCTGGA |
| 9159 | SPCC338.08_DN | GCCCGGACGAAGCATGAAAC |
| 9160 | SPCC338.10c_UP | CGACTCCCGGACCCAAAGGC |
| 9161 | SPCC338.10c_DN | TTCGGCGCTAAATCCGCTTC |
| 9162 | SPCC338.11c_UP | TTTTGACGCCCTCGCTCTGG |
| 9163 | SPCC338.11c_DN | TCGTGGATGGGAGAGATGCG |
| 9164 | SPCC338.12_UP | ACGCCAGACCCATACACGCA |
| 9165 | SPCC338.12_DN | CGCTTTCGCTCGTCCGTTCG |
| 9166 | SPCC338.13_UP | CCGAGAAGGATGGCGCTAGC |
| 9167 | SPCC338.13_DN | TTTCCTTCGGCCTTTTGCGC |
| 9168 | SPCC338.14_UP | AGCGGGGTAGGCAATTCGGA |
| 9169 | SPCC338.14_DN | CGCCGACCGACAAAAGCAAG |
| 9170 | SPCC338.15_UP | TCCCTCTCCCGCCCCTTAGT |
| 9171 | SPCC338.15_DN | AGAGGGAATGATGCGGATGG |
| 9172 | SPCC338.17c_UP | AGCCCCGCAGAAATGCTCAG |
| 9173 | SPCC338.17c_DN | CGCACCCTGCAAATCGATGA |
| 9174 | SPCC338.18_UP | TCGCTAACAGGGGGGCCAAA |
| 9175 | SPCC338.18_DN | CATAGCCGCCAGGCAACCAA |
| 9176 | SPCC364.01_UP | CTTGGCGTCGAGGGGTCTTG |
| 9177 | SPCC364.01_DN | CCCGTTTGATGACCCTGCGT |
| 9178 | SPCC364.03_UP | CGGTTGACGAGGGGGATTGC |
| 9179 | SPCC364.03_DN | CGTGGATGGGGGAAAACGA |
| 9180 | SPCC364.04c_UP | ACTCGGGTGGGTACTGGCGC |

FIG.52

| Sequence number | Name | Base sequence | Sequence number | Name | Base sequence |
|---|---|---|---|---|---|
| 9181 | SPCC364.04c_DN | CTGCTTGTGCCCCTCTCCCG | 9283 | SPCC548.07c_DN | GGAAGACGGGGGGTGCGAAT |
| 9182 | SPCC364.05_UP | CCAAGCAAAGGGCGCAACAC | 9284 | SPCC550.01c_UP | CGAAGCACCCAGCCCAATCA |
| 9183 | SPCC364.05_DN | ACCGAGCATAGGACCTGACG | 9285 | SPCC550.01c_DN | CAACGATTCATGAGCGCGGC |
| 9184 | SPCC364.06_UP | CCTCCTAGCCGCAACACCCA | 9286 | SPCC550.02c_UP | TGGGGGCGTAGGTGACGAGA |
| 9185 | SPCC364.06_DN | CGCCTAAACCCGCACAGCAC | 9287 | SPCC550.02c_DN | CAAGGCTAGGCGCTCACGAT |
| 9186 | SPCC364.07_UP | AATATGCGGGCGGTGGAAA | 9288 | SPCC550.03c_UP | CCCGGAGTACGGCTGCTACAA |
| 9187 | SPCC364.07_DN | CCGCGCTTGGTCTTCTTCGA | 9289 | SPCC550.03c_DN | AAGGCCAGTCGGCTGTTACA |
| 9188 | SPCC417.02_UP | GGCGAGGTGCAATGGGTGAG | 9290 | SPCC550.04c_UP | TGTCGCGATGGCCGATAACA |
| 9189 | SPCC417.02_DN | CCGCCAGTATGACCGACCCT | 9291 | SPCC550.04c_DN | TGTCGGCTACCGGGTCAACA |
| 9190 | SPCC417.03_UP | CTGCGTGGCTGAATGGATGC | 9292 | SPCC550.05_UP | CTCGCCCCACCTACCCCGAC |
| 9191 | SPCC417.03_DN | GAGAACCGCGCTGCACAAAC | 9293 | SPCC550.05_DN | CCATTTCATTAGCGGGGGGC |
| 9192 | SPCC417.04_UP | TGCGGCGTAGGGTTAAGGGC | 9294 | SPCC550.06c_UP | GCGTAAAAGGTGCGAGCCGT |
| 9193 | SPCC417.04_DN | CCGCCCCACATCCTGCCAA | 9295 | SPCC550.06c_DN | AAGACCCGCGCGGATAACAG |
| 9194 | SPCC417.05a_UP | AGGATACGCTAGTCGCCTGC | 9296 | SPCC550.07_UP | AGCAAGCCAAAGCCGGCAGA |
| 9195 | SPCC417.05a_DN | AGCACGACTCCTAGGTCGCA | 9297 | SPCC550.07_DN | GACGGGAAGGAGCGAGGAGG |
| 9196 | SPCC417.06c_UP | ATGGTCACGGCCCAAAACGG | 9298 | SPCC550.08_UP | GAATTCCGGTCCCTTGCCCT |
| 9197 | SPCC417.06c_DN | TCAGGCGAGGTGATGCGGAT | 9299 | SPCC550.08_DN | GAGGGATAAGCGCGAGCAG |
| 9198 | SPCC417.07c_UP | GCAGACGGCCTAAGTGGGGG | 9300 | SPCC550.09_UP | CTTGGAACATGTCGGCGCAA |
| 9199 | SPCC417.07c_DN | GAAAACGTCAAGCCCCCACC | 9301 | SPCC550.09_DN | ATGCACGGCTGCGCATACAA |
| 9200 | SPCC417.08_UP | TGCCCAAATTCCCCCCGTGA | 9302 | SPCC550.10_UP | GGATTGGGAGCTGGGAGGAG |
| 9201 | SPCC417.08_DN | CTTCGCCGTGGTGGGCTCTG | 9303 | SPCC550.10_DN | AGTGTTGACGTAGAGCGGCG |
| 9202 | SPCC417.09c_UP | CGCAGTCAAACCACCACGCT | 9304 | SPCC550.11_UP | TGAATGTGGGCTGCGGGGT |
| 9203 | SPCC417.09c_DN | TTTGGGTCTGTGTGCGGGG | 9305 | SPCC550.11_DN | CCACCTCTTTGGTCCCTCGC |
| 9204 | SPCC417.10_UP | ACCAGACGTTGTAACGCCGA | 9306 | SPCC550.12_UP | TTCGGGGTCGTAGGGTTCCA |
| 9205 | SPCC417.10_DN | TGACGCCACAGGTGATCGAG | 9307 | SPCC550.12_DN | TATGATGACACCGGCCTGCG |
| 9206 | SPCC417.12_UP | AGCGCGCGGGGTGTATGTAT | 9308 | SPCC550.13_UP | CCGATGTGTGAGGCGCACTT |
| 9207 | SPCC417.12_DN | CGATCATGGTAGCGGGGAGG | 9309 | SPCC550.13_DN | GCCACGAGGGACTCCGAAGC |
| 9208 | SPCC4B3.01_UP | TGTGATGCGCGCTGCAATGA | 9310 | SPCC550.14_UP | TGCCGCGTAGGTACGCACTA |
| 9209 | SPCC4B3.01_DN | GATTCCCGCATAGGCACGGA | 9311 | SPCC550.14_DN | CCTGCCATGACGTACCGACA |
| 9210 | SPCC4B3.04c_UP | ATGGATTGCGCAGAAGGCGT | 9312 | SPCC550.15c_UP | AGTCTCCCACTCCCCCGAAT |
| 9211 | SPCC4B3.04c_DN | CCCTTTGACCCGTTCCCGTC | 9313 | SPCC550.15c_DN | AGAAAGACGCAACCAACCCG |
| 9212 | SPCC4B3.05c_UP | GCAACGATGACCGAAGCCT | 9314 | SPCC553.02_UP | CCTCCAATCCTCACCTCGGC |
| 9213 | SPCC4B3.05c_DN | GCCCCTACCCATTCGACCTT | 9315 | SPCC553.02_DN | TGGGAAACAACGTCGGAGGA |
| 9214 | SPCC4B3.06c_UP | ACCCGAAACAACTGGCUACT | 9316 | SPCC553.03_UP | TTGCTGTGGCGGAATGTGGA |
| 9215 | SPCC4B3.06c_DN | AGGCACTAACGCAGACCGGC | 9317 | SPCC553.03_DN | ACGACGACCCACGGACATC |
| 9216 | SPCC4B3.07_UP | ACCGTGCTCCTGCTTTGCCC | 9318 | SPCC553.04_UP | CCGTGCCACAAGCGTAGCGA |
| 9217 | SPCC4B3.07_DN | TTGTCCCGGAACACGCTGTA | 9319 | SPCC553.04_DN | AACCGATGGAAGGGCGCTTT |
| 9218 | SPCC4B3.08_UP | AGGGCCCGGTGGTATTAGGG | 9320 | SPCC553.06_UP | AGGGCGGTACCGGGATTTTG |
| 9219 | SPCC4B3.08_DN | GATGTGCTTCAGAGGGCGCC | 9321 | SPCC553.06_DN | TCAGTCCATCCGCTATCGCC |
| 9220 | SPCC4B3.09_UP | TGCGGTGCTAGGGTGATTCG | 9322 | SPCC553.07c_UP | GTCGCCATCCCCTAGCTCCA |
| 9221 | SPCC4B3.09c_DN | AIGGCGCTCCGGTACGACTA | 9323 | SPCC553.07c_DN | GCACGAATGAGACAGGGCGC |
| 9222 | SPCC4B3.10c_UP | TTACAATGCGGGGGTCGCTT | 9324 | SPCC553.08c_UP | AGCCTAATTGCGAGCGGTCG |
| 9223 | SPCC4B3.10c_DN | GCACGCAATGCCCTACGTCAA | 9325 | SPCC553.08c_DN | CGGTCTTGGATATCGCCCCA |
| 9224 | SPCC4B3.11c_UP | TCCCAAAAGGCACCCCAAAC | 9326 | SPCC553.09c_UP | TGTGCACGGTGTCGCCATTA |
| 9225 | SPCC4B3.11c_DN | TATCGCCGTATTCGGGCAGG | 9327 | SPCC553.09c_DN | ACACGATCTGACGCGTGTGG |
| 9226 | SPCC4B3.12_UP | AGGGCACGGGTAGAAGGCGT | 9328 | SPCC553.11c_UP | CACTGGATAACGAGGGCCGG |
| 9227 | SPCC4H3.12_DN | AGGTGAACGAAGGGCGGTT | 9329 | SPCC553.11c_DN | CCTGAACCCCCCGACAGACG |
| 9228 | SPCC4H3.13_UP | CTGCTCCCGTCGCGGGCTTA | 9330 | SPCC569.02c_UP | AAACAACAACCGCAACCGCC |
| 9229 | SPCC4B3.13_DN | GCGTCCGCACCTGCTGCTAA | 9331 | SPCC569.02c_DN | GCAGGGCGCCGAAACGATAC |
| 9230 | SPCC4B3.14_UP | CGGGGGCAGGTTCAGGGTAG | 9332 | SPCC569.03_UP | CGGATGGCCCTATTGCACAC |
| 9231 | SPCC4B3.14_DN | CCCATTCAACGGCCCAAGC | 9333 | SPCC569.03_DN | TTGTTGCGGCTATGTCGGGG |
| 9232 | SPCC4B3.15_UP | AAAATACCCCGTGCGTCGC | 9334 | SPCC569.04_UP | CGAAGGCGGCGATTAATGGA |
| 9233 | SPCC4B3.15_DN | TTCTTCATGCCTGCCCACCA | 9335 | SPCC569.04_DN | GTGGCTACTCGGACGGGGGG |
| 9234 | SPCC4B3.16_UP | GGGTGGTAAGGTGGGAGGGC | 9336 | SPCC569.05c_UP | CAAGGGCGTATCCACGCGAA |
| 9235 | SPCC4B3.16_DN | CCCGCGCAAAGAAAGTACCC | 9337 | SPCC569.05c_DN | TGCCATAAGGCTTAGCGCCC |
| 9236 | SPCC4B3.17_UP | ACGGACCGAAATGAACCGCC | 9338 | SPCC569.06_UP | TTCCCCGCTCTCCGCTCTTC |
| 9237 | SPCC4B3.17_DN | CCGGGGTTTAGCTGGCGAG | 9339 | SPCC569.06_DN | GTCCCACCGTACAGGTCACA |
| 9238 | SPCC4F11.02_UP | AACGCTGGGGGATTTGTGGC | 9340 | SPCC569.07_UP | GCGCCGAAGGAGGGCATAGC |
| 9239 | SPCC4F11.02_DN | CGGAGGGGTCACGAAAGACG | 9341 | SPCC569.07_DN | CTTGAGATTTCGGGCGAGGA |
| 9240 | SPCC4F11.03c_UP | TCCGGGTGGGGTGCTATGAT | 9342 | SPCC576.02_UP | TGCCAGAGTCGGCTGTACAA |
| 9241 | SPCC4F11.03c_DN | TTTCCGATAGCCGAGTGCCC | 9343 | SPCC576.02_DN | TCCGTGTTCCCGGGTTAAGG |
| 9242 | SPCC4F11.04c_UP | AATACCAAACATGCGCCCCG | 9344 | SPCC576.03c_UP | CCCCCACAGAATGAGCCCCA |
| 9243 | SPCC4F11.04c_DN | GCAGGGAGGGGCGAAGGTTG | 9345 | SPCC576.03c_DN | CCGTGGTGCTGCCTCGTTGAC |
| 9244 | SPCC4G3.02_UP | TCAGTCGGGGGATTTGGGTC | 9346 | SPCC576.04_UP | CCCCTCTGGCCCCTCGTTAC |
| 9245 | SPCC4G3.02_DN | TATGCATCACACCGCCGTGC | 9347 | SPCC576.04_DN | CACCACCCCGCGTTCCCTCCC |
| 9246 | SPCC4G3.03_UP | GGCTGGTCAAAAGTGGGGGG | 9348 | SPCC576.05_UP | AGTGTGGTGGGGGGGGACA |
| 9247 | SPCC4G3.03_DN | ACTCCGCCCCATCTGACCG | 9349 | SPCC576.05_DN | TCCCGACTCCACCGTTTGCC |
| 9248 | SPCC4G3.04c_UP | TGTACCGACCCTTGACCCCC | 9350 | SPCC576.07_UP | TCGGTTAAGCGCAGGGCAGG |
| 9249 | SPCC4G3.04c_DN | GGGAGGCGTAACATGGGCAA | 9351 | SPCC576.07_DN | GATGGCGCATAGCTAGCCCA |
| 9250 | SPCC4G3.05c_UP | TGCCTCCTCCTGCCGGAATG | 9352 | SPCC576.08c_UP | CGCCAACCCGCTTTACTCGC |
| 9251 | SPCC4G3.05c_DN | TGCCTATTCGCCGCTCACTG | 9353 | SPCC576.08c_DN | ACCCCCGTCCCCTGTCCAAG |
| 9252 | SPCC4G3.06c_UP | AACAGGCGGACGGGCATAAG | 9354 | SPCC576.09_UP | TCTCGCCCCGGAATCATCCG |
| 9253 | SPCC4G3.06c_DN | GTGGGGGCAGGGCGTTGTCT | 9355 | SPCC576.09_DN | GGGTGACGTATCGGCGATGT |
| 9254 | SPCC4G3.07c_UP | AGCAGAAACCACGCCAACGA | 9356 | SPCC576.10c_UP | TCTGACCGCGCAACTGAG |
| 9255 | SPCC4G3.07c_DN | ATGGAGGAGGGTGGACTGCG | 9357 | SPCC576.10c_DN | GTGTAACTGCCCCCCTCGGA |
| 9256 | SPCC4G3.08_UP | CACCACCTCCGGACGACCT | 9358 | SPCC576.11_UP | CAAAGACCCGCCCCGACTGT |
| 9257 | SPCC4G3.08_DN | CCAACGCCTGCTCCATTCTG | 9359 | SPCC576.11_DN | TTGGGCTTGGTTTTTGCCGC |
| 9258 | SPCC4G3.09c_UP | CACGGAGATGCGAAACCAGC | 9360 | SPCC576.12c_UP | CGAGTTACGGCTCCTCGGCAT |
| 9259 | SPCC4G3.09c_DN | GTGCCCCTGACGCTCATTCAGA | 9361 | SPCC576.12c_DN | CCATTTACGCAACTCCCGCA |
| 9260 | SPCC4G3.11_UP | CGCACAAACAGACCGGCTAC | 9362 | SPCC576.13_UP | GCTAGGGAGGTTGGCGCATG |
| 9261 | SPCC4G3.11_DN | ATGGCGTCGTTTGGCTTGTG | 9363 | SPCC576.13_DN | GGTGCTCCCCGCCTGAAATT |
| 9262 | SPCC4G3.13_UP | TAGGTGCTTTGGCGGAGGGT | 9364 | SPCC576.14_UP | ACCCAACGAACGATCACCGC |
| 9263 | SPCC4G3.13c_DN | GACTGGGGCGGTGCTTTGTC | 9365 | SPCC576.14_DN | ATTTGGTTGGGGGATGGGGG |
| 9264 | SPCC4G3.14_UP | TGCTTTGCCGTTGTCCCCAG | 9366 | SPCC576.15c_UP | AACAGCCAAAACCAGGGGC |
| 9265 | SPCC4G3.14_DN | TGCGAGAAGCGAGGGCGGTA | 9367 | SPCC576.15c_DN | TTTCTGTCTTCCCCGGCCGA |
| 9266 | SPCC4G3.15c_UP | CCACTCTTTTCCCACCCCGC | 9368 | SPCC576.17_UP | AGTACGCGCACGGTACATCT |
| 9267 | SPCC4G3.15c_DN | CAAGCAGCTCGGAGACCGTT | 9369 | SPCC576.17c_DN | GAACAGGCTCTTCACGGGGA |
| 9268 | SPCC4G3.16_UP | GCGCCCCCTCCCTGACACAT | 9370 | SPCC584.01c_UP | GAGCCTGCGAAAATGGCCTA |
| 9269 | SPCC4G3.16_DN | TTCGTTTAGTCGCCCGCCT | 9371 | SPCC584.01c_DN | CTGGTGTCATGGTGGGCCGG |
| 9270 | SPCC4G3.17_UP | TGTGGGTACGGTGCGGAAGG | 9372 | SPCC584.02_UP | CGCTACACCCGACCGACTCA |
| 9271 | SPCC4G3.17_DN | GTGATACGGCAGCGGGGAAT | 9373 | SPCC584.02_DN | GCAACCCGCAAGGTATTCA |
| 9272 | SPCC4G3.18_UP | CCCCCTGCCAATGCCTTAAA | 9374 | SPCC584.03_UP | TGGGGCGCGCATTCTTGTAC |
| 9273 | SPCC4G3.18_DN | GTTTTCCCCGCGTTTAAGGCC | 9375 | SPCC584.03_DN | CATCGCCCACATTAGCACCG |
| 9274 | SPCC4G3.19_UP | ATTCTCTCGGGCTGGCGGTGG | 9376 | SPCC584.04_UP | GGGGATTTCAGGGCCAGAGG |
| 9275 | SPCC4G3.19_DN | CGGAACGGCAGACAGGACGG | 9377 | SPCC584.04_DN | ATTCGTGGGGGGGGTTGAACA |
| 9276 | SPCC548.04_UP | ACAACGACCCCTGCCTTCCG | 9378 | SPCC584.11q_UP | TCGAACCAACCATAGGCCCC |
| 9277 | SPCC548.04_DN | GAAGGCAGGGGTGGAAGGCAC | 9379 | SPCC584.11c_DN | TTTTGGCGGCTGCGTTCTTG |
| 9278 | SPCC548.05c_UP | TGTCCCCGTAACCACGCCTA | 9380 | SPCC584.12_UP | CGCGGACTACAAGCACCACGG |
| 9279 | SPCC548.05c_DN | CCGTCCACCTCCGTTCCGCT | 9381 | SPCC584.12_DN | CGATGGGTGGTTTTTGGAGA |
| 9280 | SPCC548.06c_UP | AGGGAGGGAACCAAACGGGA | 9382 | SPCC584.13_UP | TGCTCGGTCGCTCTCGCTG |
| 9281 | SPCC548.06c_DN | GCAATGGGGGGGTCGTGAGG | 9383 | SPCC584.13_DN | TGCGGGGGATTCAGGCGGTTA |
| 9282 | SPCC548.07c_UP | CAACCCCACCGAAAATCCGC | 9384 | SPCC584.14_UP | GACGACACCCAGCACCAGCA |

FIG.53

| Sequence number | Name | Base sequence |
|---|---|---|
| 9385 | SPCC594.14_DN | CAACCACCCAACGGCAATCG |
| 9386 | SPCC594.15c_UP | ACAAACAATGGTGCGCGGC |
| 9387 | SPCC594.15c_DN | TCCCCTGATAATTGGCCCCG |
| 9388 | SPCC594.02c_UP | ACAAGCGTCAGGGGGTCGTC |
| 9389 | SPCC594.02c_DN | GCTAGCCCAACCATTCGCCC |
| 9390 | SPCC594.03_UP | GGCAAAACGCGGATCGAGC |
| 9391 | SPCC594.03_DN | TGTATTTGCCGCCTTTCCC |
| 9392 | SPCC594.04c_UP | TCGCCGTTTAGTGAGCCCGC |
| 9393 | SPCC594.04c_DN | ATGGATGGGACTTCGCGGAC |
| 9394 | SPCC594.05c_UP | TGGAATCGGGGGAGTTGGAC |
| 9395 | SPCC594.05c_DN | CCGTGAAACACCCCGCCTTT |
| 9396 | SPCC594.06c_UP | TCGCCGTGGTCATCCCTCCT |
| 9397 | SPCC594.06c_DN | CTCAAGGAATGGGGAACCGC |
| 9398 | SPCC594.07c_UP | ACGGACGATTGCGGGGTTAC |
| 9399 | SPCC594.07c_DN | TTAGTGCGCGAGACACTCC |
| 9400 | SPCC5E4.03c_UP | TGCCGGCTAGTCGGTGGTGA |
| 9401 | SPCC5E4.03c_DN | ACTCGAGCCAGCACCCGGAC |
| 9402 | SPCC5E4.05c_UP | CTGTGGGCGGATAACGTCGA |
| 9403 | SPCC5E4.05c_DN | ATCACCTTCGCGGCCTTACG |
| 9404 | SPCC5E4.06_UP | CCGCTGCCGAACCCATAGAC |
| 9405 | SPCC5E4.06_DN | CCAGAGGGGTGGTGCGATGA |
| 9406 | SPCC5E4.07_UP | GGCAGGCGAATGCGAAATGC |
| 9407 | SPCC5E4.07_DN | GGCTAAAAGTGCCCACGGGAT |
| 9408 | SPCC5E4.10c_UP | AACCCATTTCCACCGCTCGT |
| 9409 | SPCC5E4.10c_DN | GCAAATGAAGGAAGCCGGCT |
| 9410 | SPCC61.01c_UP | CCCCGCTTGTCGTCCCCATA |
| 9411 | SPCC61.01c_DN | TGACTGAGAGGGCGTTCGGCC |
| 9412 | SPCC61.02_UP | ACCCGTGTCGGGTAACCTTC |
| 9413 | SPCC61.02_DN | TCTCGATAGGCATCGCACCC |
| 9414 | SPCC61.03_UP | ATCCCGTGTCCCGTTCTCCC |
| 9415 | SPCC61.03_DN | CGGGACAATGGGGCTGGCTT |
| 9416 | SPCC61.05_UP | TCGAGCGCTACGTTCCAGAC |
| 9417 | SPCC61.05_DN | ACGGCTCCCTAGAGCAGAGA |
| 9418 | SPCC613.02_UP | TCCGGCCGACGCTGTGTATG |
| 9419 | SPCC613.02_DN | ACGCGGCAAGGTCATGAATG |
| 9420 | SPCC613.03_UP | CCAAGGGCATCAGGCGGTGT |
| 9421 | SPCC613.03_DN | TCCGCCAATCCAAACGTCG |
| 9422 | SPCC613.05c_UP | GAGCGCGCGGAATTGTGATG |
| 9423 | SPCC613.05c_DN | AAGCCCTCCGCAAACGTGTG |
| 9424 | SPCC613.06_UP | AGCGAATCGGGGCGTGAGTC |
| 9425 | SPCC613.06_DN | GATTTGCTTCGAAGGGGCC |
| 9426 | SPCC613.07_UP | GGTGTCGGGTTCCTTCTCCG |
| 9427 | SPCC613.07_DN | CCGTGTCCCCTGCCCTTACC |
| 9428 | SPCC613.08_UP | CGGAGGCGAAGAGGGGTAAG |
| 9429 | SPCC613.08_DN | CGAGCGAAAACACCGGGAAT |
| 9430 | SPCC613.09_UP | CCCTCATCTGCCCCAAAATG |
| 9431 | SPCC613.09_DN | TTGACGGGGCGTAGGTGAT |
| 9432 | SPCC613.10_UP | GGTGGTCATCGGGAACGACT |
| 9433 | SPCC613.10_DN | CCGTACTCCGTAGTCGGACA |
| 9434 | SPCC613.11c_UP | CACATACCCCCCAACGGCA |
| 9435 | SPCC613.11c_DN | TCTTGCCCCCATGAGACCGG |
| 9436 | SPCC613.12c_UP | GAGGGCGTCGCTGAAGATGA |
| 9437 | SPCC613.12c_DN | CGATTGGCGTCGCTCGATGA |
| 9438 | SPCC622.01c_UP | CCCCACGGCATTCATTACC |
| 9439 | SPCC622.01c_DN | CGAACCGATCACTGCCGAAA |
| 9440 | SPCC622.02_UP | TGGCTGGTCTCGGGGCTCTC |
| 9441 | SPCC622.02_DN | ACGTTTGTGCCCGTGAACCG |
| 9442 | SPCC622.03c_UP | CCCGGATCAACAACCCACGT |
| 9443 | SPCC622.03c_DN | GCTFCCCCGTCATCCTTTGC |
| 9444 | SPCC622.04_UP | TGCGGATATTCTGGCGCACG |
| 9445 | SPCC622.04_DN | TGGTTCGGCGCGGGCTAGTA |
| 9446 | SPCC622.06_UP | GGGGCGTGTGATGTCGATGG |
| 9447 | SPCC622.05_DN | CTCGGCCCCCCTACTTCGCA |
| 9448 | SPCC622.07_UP | AGTGCAGGAGAGGGGCGAATC |
| 9449 | SPCC622.07_DN | AAACAAAACACGGTGCCTGC |
| 9450 | SPCC622.08c_UP | CCGAGGGTTATCGACGAGGG |
| 9451 | SPCC622.08c_DN | TGCGGACGGGTAGGAATTGG |
| 9452 | SPCC622.09_UP | ATTGCGGGGCTCTAAGGGCT |
| 9453 | SPCC622.09_DN | TAAGCGATGGCCGGAAGAGG |
| 9454 | SPCC622.10c_UP | GGAATGGCGAGAATGCGGAG |
| 9455 | SPCC622.10c_DN | CGTGTAGGGCGCTGCTTGGA |
| 9456 | SPCC622.11c_UP | CTCGACTCCCGCAACAAGCC |
| 9457 | SPCC622.11c_DN | TTTGCTGCCAAGGTGCGTGC |
| 9458 | SPCC622.12c_UP | TAAAGCGCCGCGCGAGCAGG |
| 9459 | SPCC622.12c_DN | TTCGTCTCGGGGTGGCTGCT |
| 9460 | SPCC622.13c_UP | TCGTTCTGTCGCTGTGCAT |
| 9461 | SPCC622.13c_DN | CCCGAACCACAGCGACACCC |
| 9462 | SPCC622.14_UP | CCGCCTCCCCGCCTAAAAAC |
| 9463 | SPCC622.14_DN | ACCGCCGAACCCTGACCTCC |
| 9464 | SPCC622.15c_UP | TGATGGCGTCCGAGGTGAAG |
| 9465 | SPCC622.15c_DN | AGCCGATTATGGCGGCAAG |
| 9466 | SPCC622.16c_UP | GACCTGCGAACCCCCTCCTC |
| 9467 | SPCC622.16c_DN | AACAGCTTGGTCGGGCAGGA |
| 9468 | SPCC622.17_UP | GGTGGGCGGTTGGGGTCACT |
| 9469 | SPCC622.17_DN | TCACGGGGTTCGTTCAGCAC |
| 9470 | SPCC622.18_UP | TTGGACAGGCGGACTGCTCG |
| 9471 | SPCC622.18_DN | TGCCCATCATCCGCAGTAC |
| 9472 | SPCC63.02c_UP | ACGGTGCCCTCATTTTCGGA |
| 9473 | SPCC63.02c_DN | ACGGCATGGTCGCCGTTCAC |
| 9474 | SPCC63.03_UP | CACCGCCAAGAATCCACGCA |
| 9475 | SPCC63.03_DN | AGTGATCGGCACGGTTGCAT |
| 9476 | SPCC63.04_UP | ACCGGCGCTGTGCCAATAAA |
| 9477 | SPCC63.04_DN | GGGTCTACGGCCACATGCT |
| 9478 | SPCC63.05_UP | CGACGCACCCGGACTCATTTG |
| 9479 | SPCC63.05_DN | AAAAGGCACCAGGCCCAGC |
| 9480 | SPCC63.06_UP | CGGTGACAAGAGGGGCGAGT |
| 9481 | SPCC63.06_DN | GCAGCCGTCCACACCACCCT |
| 9482 | SPCC63.07_UP | ACCTATCCCCGTCCCGGCTTG |
| 9483 | SPCC63.07_DN | CAGGTTAAGATGGCGGGGGG |
| 9484 | SPCC63.08c_UP | TCCGTTGGTAGCCCTCGCTT |
| 9485 | SPCC63.08c_DN | CGTTGGATTCACGCACCCG |
| 9486 | SPCC63.10c_UP | AGGGGAGGCGCTGAATGCAAT |
| 9487 | SPCC63.10c_DN | CGGGTGGGCGGATCGTGATA |
| 9488 | SPCC63.11_UP | CTGACCCTAGAGACCGCGCC |
| 9489 | SPCC63.11_DN | CGTTTACCGTCCCGCCACAG |
| 9490 | SPCC63.12c_UP | ACGGTGTCTGACGTGTCTC |
| 9491 | SPCC63.12c_DN | TCTGTGTGCCGGGTGGAAGG |
| 9492 | SPCC63.13_UP | TACCCGTTCCTGCATTCCGC |
| 9493 | SPCC63.13_DN | CACGCCAGTCTCCCCCTCAT |
| 9494 | SPCC63.14_UP | GGACGGGCAAGCAGGTTTCA |
| 9495 | SPCC63.14_DN | CGTGGCGCGGGGAATAGTA |
| 9496 | SPCC645.02_UP | ACACGGCGGGACGGACATA |
| 9497 | SPCC645.02_DN | CTCTTGATCCGACCGGCCAG |
| 9498 | SPCC645.04_UP | GACGAAACGCAGACCCCGAA |
| 9499 | SPCC645.04_DN | AATGCACCGACCCACGAGCC |
| 9500 | SPCC645.05c_UP | AGTGGGGCAACGTTAGGGCA |
| 9501 | SPCC645.05c_DN | GAAAACGGAGAAGGGCTGCG |
| 9502 | SPCC645.07_UP | AATCATCACCGCGCACACGT |
| 9503 | SPCC645.07_DN | CCAGAGGGATTTCCCCGATC |
| 9504 | SPCC645.08c_UP | GGGACATCCGTACGGCACAT |
| 9505 | SPCC645.09c_DN | GGTTGTGCCGCGGAAATAGGG |
| 9506 | SPCC645.09_UP | TCGCCCACAAGCATCCATCG |
| 9507 | SPCC645.09_DN | AGTCCAGGCCCCCCCAACTA |
| 9508 | SPCC645.10_UP | TTAGCGGGTCGTTGTTGGCG |
| 9509 | SPCC645.10_DN | TTCACTCGTTACCCCCCCA |
| 9510 | SPCC645.11c_UP | AAACGGGGTGACGGTGGCTG |
| 9511 | SPCC645.11c_DN | CGGCAGGTCCCCTAAGTAGA |
| 9512 | SPCC645.12c_UP | CGGGATGGGGACGGATTTTC |
| 9513 | SPCC645.12c_DN | CGGGGTTGGGGAGGCTAGAA |
| 9514 | SPCC645.13_UP | ACTAACTACCCCCCCGAGC |
| 9515 | SPCC645.13_DN | GTCGGTGTGGAAGGCCGAAG |
| 9516 | SPCC645.14c_UP | AGGGACAGCGGACCTTGGTG |
| 9517 | SPCC645.14c_DN | AGTTGGGCGCATGGTGACA |
| 9518 | SPCC663.02_UP | CCTTAACAGCCATCGCGCCC |
| 9519 | SPCC663.02_DN | CCCAACATCTCCCCAAGGCA |
| 9520 | SPCC663.03_UP | CTGTCCCACCCCGCAAAATC |
| 9521 | SPCC663.03_DN | CGATGAAGAACGCCGCCCGT |
| 9522 | SPCC663.04_UP | GGGGCACGGCTGTAATCGAG |
| 9523 | SPCC663.04_DN | ACGCCGCCACTGACGAAATG |
| 9524 | SPCC663.05c_UP | TTGTCGTGCACCCAGGTCAA |
| 9525 | SPCC663.05c_DN | ATTGGGCTGCCTGCAAGCGT |
| 9526 | SPCC663.06c_UP | TCCATAACACAGTCGCGGGG |
| 9527 | SPCC663.06c_DN | GGGTGTCTCCGATCTTGGCG |
| 9528 | SPCC663.08c_UP | AACGACGGAACAAAGCGCAA |
| 9529 | SPCC663.08c_DN | GGCGTGGTCGGTTCTGTCA |
| 9530 | SPCC663.09c_UP | AACGAAGGGGAGTAACCGA |
| 9531 | SPCC663.09c_DN | TCCTCCATTCGGCCGTTCAG |
| 9532 | SPCC663.10_UP | GGATCGGCGCTAGGGGGTTGC |
| 9533 | SPCC663.10_DN | CCCCTCTCGCATCGGTTTCA |
| 9534 | SPCC663.11_UP | TAGGGCGTAGGGGTCGGGA |
| 9535 | SPCC663.11_DN | CGCCACAAAATCAGCACGAG |
| 9536 | SPCC663.12_UP | ACCACCATCCAATTCCCGCA |
| 9537 | SPCC663.12_DN | CCGCGACCGATTTTACCCCC |
| 9538 | SPCC663.14c_UP | ATCTTCGCGCTCCCGTTTCG |
| 9539 | SPCC663.14c_DN | ATCGCCCACCGCCTCACAAA |
| 9540 | SPCC663.15c_UP | CGTTTAAGGGCGGATGCTCC |
| 9541 | SPCC663.15c_DN | CTTTGACCGATTGGGCGTG |
| 9542 | SPCC70.02c_UP | TCGGAGAGGTCGGTTCTGGG |
| 9543 | SPCC70.02c_DN | GGATTGTGGCAGGGGGTT |
| 9544 | SPCC70.03c_UP | TGTGGTGCTGGAGGTGGGAG |
| 9545 | SPCC70.03c_DN | CCCATGCACCGATCCCCCT |
| 9546 | SPCC70.04c_UP | TGCTTCCCACACCCTACTGCC |
| 9547 | SPCC70.04c_DN | TCCGTGCTGTCGTCTTTCCG |
| 9548 | SPCC70.05c_UP | CCGGAAGGCCGTAATTGCAGC |
| 9549 | SPCC70.05c_DN | CCGCCGCCGTTAAAGCTACC |
| 9550 | SPCC70.08c_UP | CGTTACCGTTGCCGCTTCG |
| 9551 | SPCC70.08c_DN | ACATGGGGTCGTGCTCGCT |
| 9552 | SPCC70.10_UP | GGACATCTTGCGGGACCAT |
| 9553 | SPCC70.10_DN | GATTTCCACCCCCCTCTGCG |
| 9554 | SPCC736.02_UP | AACCAGAGGGGGCACAGCT |
| 9555 | SPCC736.02_DN | AGTGGGGTTGGGGGGATGGA |
| 9556 | SPCC736.03c_UP | TCGTGCCTCCTTTCGTTGGG |
| 9557 | SPCC736.03c_DN | CTTCAACTCGGCGCGCAAAC |
| 9558 | SPCC736.04c_UP | GAGCGGAAGCGCCATGCACTT |
| 9559 | SPCC736.04c_DN | CCAACGGAAGCGCCTCGAAGC |
| 9560 | SPCC736.05_UP | CATAGTTTCGCGCCCGTGCT |
| 9561 | SPCC736.05_DN | ACGTCGGGCAAGCGGCATGT |
| 9562 | SPCC736.06_UP | CAGCGAAAGGGCGGGAAGAGG |
| 9563 | SPCC736.06_DN | GGCTACCTGACCGGCCTGGA |
| 9564 | SPCC736.07c_UP | ACGAAAACGCACCCCACTC |
| 9565 | SPCC736.07c_DN | CGGTGGTTCGGATGGTTCTG |
| 9566 | SPCC736.08_UP | CACACTGCCCGTTTTTGAT |
| 9567 | SPCC736.08_DN | AGGCCGGCGTTGCAAGTTTA |
| 9568 | SPCC736.09c_UP | CTAGCCGGCCGTCACCAAAA |
| 9569 | SPCC736.09c_DN | AACAAGCGGTGCCGCACGATG |
| 9570 | SPCC736.10c_UP | TGCTGGTCCTTGGGGATGTG |
| 9571 | SPCC736.10c_DN | GGTGGGCAAAGTGGGTCGT |
| 9572 | SPCC736.11_UP | ACCCATATACCTCCCGGGCA |
| 9573 | SPCC736.11_DN | TGGGCAATCATAGCCGGGCA |
| 9574 | SPCC736.12c_UP | AATGGGCAACAACGAACCGG |
| 9575 | SPCC736.12c_DN | ATCCTGCCTGCTCCTACCGC |
| 9576 | SPCC736.13_UP | GCCGGGGTGTCAGTCGAGAT |
| 9577 | SPCC736.13_DN | GCCCACCCACCGTAACCGAA |
| 9578 | SPCC736.14_UP | TACGGGGTGGCGAGTGGTTC |
| 9579 | SPCC736.14_DN | TAGGCCGGTCGCATTATTC |
| 9580 | SPCC737.02c_UP | CGGGGTAGGAGGGTAGTGCG |
| 9581 | SPCC737.02c_DN | TCTTGCTATCCATCCGCGGC |
| 9582 | SPCC737.03c_UP | TGGCGAAGGAAAGGCGATCA |
| 9583 | SPCC737.03c_DN | GACCGGATTGGGCCTTACG |
| 9584 | SPCC737.04_UP | ACTGTCCCGCTGTGCTCGTT |
| 9585 | SPCC737.04_DN | CATACAACTCCGTCCGCGCC |
| 9586 | SPCC737.05_UP | GAGCTAGATCGGGGCGGTG |
| 9587 | SPCC737.05_DN | CCTCGGGTGTTGGGAGTA |
| 9588 | SPCC737.06c_UP | ATTAFCACCGGGACAGCGCG |

FIG.54

| Sequence number | Name | Base sequence |
|---|---|---|
| 9589 | SPCC737.06c_DN | CCCAAGGTCAAGGCGTCCAC |
| 9590 | SPCC737.07c_UP | CGTGGCCCTGCGGTTTGTTT |
| 9591 | SPCC737.07c_DN | ATTCCGTCCTCATTGCCCCG |
| 9592 | SPCC737.08_UP | CAAACGACAGCGGCATTGCA |
| 9593 | SPCC737.08_DN | ATTGTGGTGCCGACCGGGTT |
| 9594 | SPCC74.01_UP | CTAACCCGCCGTCGTCACCC |
| 9595 | SPCC74.01_DN | CTAGCCGCCCCACCATTTCA |
| 9596 | SPCC74.02c_UP | ACAAACGGCGGAGTGCAGGC |
| 9597 | SPCC74.02c_DN | TCACTCCTCGCCCCAAACGG |
| 9598 | SPCC74.03c_UP | TAATGCCAAGGGACGGCAGG |
| 9599 | SPCC74.03c_DN | TTTTCCTGACCAACGCCGAG |
| 9600 | SPCC74.04_UP | GCTGGTGTCGTTGGCGAGGT |
| 9601 | SPCC74.04_DN | GGCGGGTAAGCGTCGGAAAT |
| 9602 | SPCC74.05_UP | AAAAGAGTCCAACGCCCGCA |
| 9603 | SPCC74.05_DN | CTCGTTCGCCCAATGCTCAA |
| 9604 | SPCC74.09_UP | TGCAGGTTATGACGTGCCCT |
| 9605 | SPCC74.09_DN | GAGCAAGTGAGGTGCCTCGT |
| 9606 | SPCC757.02c_UP | TAAGGGGGGTCGGAAAGGT |
| 9607 | SPCC757.02c_DN | CTTAACGCCCTACGCCCGGA |
| 9608 | SPCC757.03c_UP | GTAATGCAAATCCGGGGCCG |
| 9609 | SPCC757.03c_DN | CGCTGTACCGGTCCCTGCTT |
| 9610 | SPCC757.04_UP | CGCCAACCATCCGCACTTCC |
| 9611 | SPCC757.04_DN | TGGGGGGAGAACGGGTGAGC |
| 9612 | SPCC757.05c_UP | GCTCGTTTCTTGCCCGCCTA |
| 9613 | SPCC757.05c_DN | CGCTCCCACTTACCCCATGC |
| 9614 | SPCC757.07c_UP | ACCCGAGGCGACTCGCTTTT |
| 9615 | SPCC757.07c_DN | ACCCTGCCTAGGGACACCTT |
| 9616 | SPCC757.08_UP | GCGATGGAGGGTAGGGGCAA |
| 9617 | SPCC757.08_DN | GATGGAAGAAGGCGGCGGAT |
| 9618 | SPCC757.09c_UP | ATACGCTAGGCAGACCACGC |
| 9619 | SPCC757.09c_DN | GCGTGGATACCTGAGTGCCA |
| 9620 | SPCC757.11c_UP | CTCGTTCTCGATGCGGACCGG |
| 9621 | SPCC757.11c_DN | ACAACACGAGCCCCACCCTC |
| 9622 | SPCC757.12_UP | CTCAATGCGCGCGACCCTAC |
| 9623 | SPCC737.12_DN | GGGTGGACATGAGGTGAGCG |
| 9624 | SPCC757.13_UP | TCGCACCCTAGGGGTATCCA |
| 9625 | SPCC757.13_DN | TACACCGGACTCCGTGAGCA |
| 9626 | SPCC777.02_UP | CCCGCCGCTATTCTTCTCGC |
| 9627 | SPCC777.02_DN | GGGACGGTGGAACATCAGGG |
| 9628 | SPCC777.03c_UP | CCCACGCTAGCCCACAACCG |
| 9629 | SPCC777.03c_DN | CCCGTTCCGCGTAGCTGTTG |
| 9630 | SPCC777.04_UP | ATGGGATGCGTTGGGTTCCG |
| 9631 | SPCC777.04_DN | GCGTGGTCTTCGAGCGGGTG |
| 9632 | SPCC777.05_UP | CAAGATTGGGGCGGGGAGT |
| 9633 | SPCC777.05_DN | GGATGGGGGGGTCTAATGGG |
| 9634 | SPCC777.06c_UP | TCGTTAACGATGGGGCGAGC |
| 9635 | SPCC777.06c_DN | TGCCTCCGCTAAATTTCCCC |
| 9636 | SPCC777.07_UP | ATGGGGGGACGTTAACGGCA |
| 9637 | SPCC777.07_DN | GCGGGTCGTGCCTGGAAGTT |
| 9638 | SPCC777.08c_UP | TGGTAAAAACGCGTGCCTGC |
| 9639 | SPCC777.08c_DN | CCACTGCATGCTTGACCCGC |
| 9640 | SPCC777.09c_UP | CACCTCGAAGAACCCAGCCC |
| 9641 | SPCC777.09c_DN | AAACCACCACCACCCCCAGT |
| 9642 | SPCC777.10c_UP | CCACACCCCGCCATCAAGTC |
| 9643 | SPCC777.10c_DN | CGCGGGCTCTTCATCGTGTG |
| 9644 | SPCC777.11_UP | GTTCGTGTGGGCATGGGGTC |
| 9645 | SPCC777.11_DN | AACAGAGACGACACGGGAGG |
| 9646 | SPCC777.12c_UP | GAGGTAGACGGTGCGCGGGG |
| 9647 | SPCC777.12c_DN | CACTTACCACAGGCCCACACT |
| 9648 | SPCC777.13_UP | TCATTCTGCAACCAACGCCC |
| 9649 | SPCC777.13_DN | CCGCGCCATCACTTCCATCA |
| 9650 | SPCC777.14_UP | ACCTTGTGTATGGGGGCGGC |
| 9651 | SPCC777.14_DN | CACCAGGAAGAAGAAGGCCAC |
| 9652 | SPCC777.15_UP | ACCTCGCCTCTCGTCTCCA |
| 9653 | SPCC777.15_DN | CCGCCCCTTCCTGCCTTCAC |
| 9654 | SPCC777.17c_UP | GACTGGACTAGCCGGGCTTGC |
| 9655 | SPCC777.17c_DN | GTGGTCGTCGGGAGTTGGGT |
| 9656 | SPCC780.02_DN | ATTCGTAGCCTGCGTTGCCCC |
| 9657 | SPCC790.02_DN | GCGCGGCCGAAACTCTATGA |
| 9658 | SPCC790.03_UP | AAGGTTCGCCGGTGTTTCGG |
| 9659 | SPCC790.03_DN | GAGGCGGCGGTCGGATAAAC |
| 9660 | SPCC794.01c_UP | AAAACACCCAGATCGCCCA |
| 9661 | SPCC794.01c_DN | GCAGGGTACAGCCGGGATTG |
| 9662 | SPCC794.02_UP | TAGAAGGGCCGCGGATTGGTA |
| 9663 | SPCC794.02_DN | GCTCCCCGCCTCACCTTACT |
| 9664 | SPCC794.03_UP | CTTGGTTCGTCCCGCTTCGG |
| 9665 | SPCC794.03_DN | CATCCCAGTTTCCCGCCCAA |
| 9666 | SPCC794.04c_UP | CCATAATCCAGCCGCAACGC |
| 9667 | SPCC794.04c_DN | ACCTTGCTGGGAAAAGCCGA |
| 9668 | SPCC794.06_UP | GTGTTGCGGCGTGGTTTTGC |
| 9669 | SPCC794.06_DN | GCAACGACGGAGGGGGAGTGC |
| 9670 | SPCC794.07_UP | CGGGGTAAATCGGTTGCGGC |
| 9671 | SPCC794.07_DN | CAGGCTCCAGCAACTGACCA |
| 9672 | SPCC794.08_UP | CGGGCAGAACACATCCACCC |
| 9673 | SPCC794.08_DN | CTTTGGAGAGTTGCGCGCGG |
| 9674 | SPCC794.09c_UP | TCTCAGCCGCCCGATAAACC |
| 9675 | SPCC794.09c_DN | GAAGCGGCAGACGAAACCC |
| 9676 | SPCC794.10_UP | GGGGCGTAGGGATCGGGTCT |
| 9677 | SPCC794.10_DN | CGGTGGGTGCGCTCTTTTTT |
| 9678 | SPCC794.11c_UP | GGACCAACCCGATGCGAACA |
| 9679 | SPCC794.11c_DN | CAACATGGGGTCGCTTCCTG |
| 9680 | SPCC794.12c_UP | AAGCGGGGCACTGGGTAACA |
| 9681 | SPCC794.12c_DN | GCCGTGTCCCCGTTCGTAAA |
| 9682 | SPCC825.01_UP | GAGATGCATCGCGAGACCGCG |
| 9683 | SPCC825.01_DN | GGTACCATGCTTCGGGGCCA |
| 9684 | SPCC825.02_UP | TGCAGTTATTCAGGGGCCGC |
| 9685 | SPCC825.02_DN | CGCCCTCCTACGTTGCACCG |
| 9686 | SPCC825.04c_UP | CCCCAAGCCGTCATCGAAC |
| 9687 | SPCC825.04c_DN | TACCAGGGGGAGCCCGTCTA |
| 9688 | SPCC825.05c_UP | CCTTGCCTTGCGTTCCCTTG |
| 9689 | SPCC825.05c_DN | ACAGGTGCTATGCAGGGGCC |
| 9690 | SPCC830.03_UP | GTCTGGTTCGCCTACCTTGC |
| 9691 | SPCC830.03_DN | AGCCTCGCCGTTTTTACCCC |
| 9692 | SPCC830.04c_UP | TGGGGGAAGTCACAGCCGTCG |
| 9693 | SPCC830.04c_DN | GCCCAGCACTTTCAACCGCG |
| 9694 | SPCC830.05c_UP | GGTCACTCAATCCCGCACGA |
| 9695 | SPCC830.05c_DN | CGGAAGAACATGCGCAAGAAA |
| 9696 | SPCC830.06_UP | CGGTAGGGCGTCAAAACGGT |
| 9697 | SPCC830.06_DN | ACCCGCCAGTCCGCGATAGA |
| 9698 | SPCC830.07c_UP | CCGACAACCAAACCAGCCCC |
| 9699 | SPCC830.07c_DN | TGACCCTCCCGCACAGCGAA |
| 9700 | SPCC830.08c_UP | GCGCCGTCCAAACTCCAAAC |
| 9701 | SPCC830.08c_DN | CATTCTTTTTGGGCCCGCAG |
| 9702 | SPCC830.09c_UP | AAGAGGCGTGCGGGAAAGG |
| 9703 | SPCC830.09c_DN | TCGCCAACCACAGATTCCA |
| 9704 | SPCC830.10_UP | CGCTCGCCCCTTTGTGTCTC |
| 9705 | SPCC830.10_DN | AGAACAGGGGATGCGGAGGG |
| 9706 | SPCC830.11c_UP | AACACGTCCCCTCCCCATCC |
| 9707 | SPCC830.11c_DN | CAGGTACGCGCAGGAATGGC |
| 9708 | SPCC895.03c_UP | AAGTCTGCGGGGGGAATGGA |
| 9709 | SPCC895.03c_DN | AAGCCCAACCCCGCGATGTA |
| 9710 | SPCC895.04c_UP | TCGCCAGCAAGGACAAGAGC |
| 9711 | SPCC895.04c_DN | CTGAGGGGCATGTCGCTGTG |
| 9712 | SPCC895.05_UP | CGGTGGACGAGTGGCGAAGC |
| 9713 | SPCC895.05_DN | TCGTGTGGCTCGTCGTGAAA |
| 9714 | SPCC895.06_UP | GGGAAATAAGGCGACGACCAG |
| 9715 | SPCC895.06_DN | CTCCCCCGATTCTGCCTTGC |
| 9716 | SPCC895.07_UP | TGGAGGCTGTGGGACACTTT |
| 9717 | SPCC895.07_DN | TACCCGTCCGCTTCCTCGGT |
| 9718 | SPCC895.08c_UP | TACCGCAAGCCTCCACGTCC |
| 9719 | SPCC895.08c_DN | AGCAAGCACGGGGCAAGGAC |
| 9720 | SPCC895.09c_UP | AATGCCAACCCGAAAACCCG |
| 9721 | SPCC895.09c_DN | CGGTTCCCACCTCCCTTGAA |
| 9722 | SPCC962.03c_UP | GATCCACAGTTAGGCGGGCT |
| 9723 | SPCC962.03c_DN | AGTACAGCGCGTAGTGTGCC |
| 9724 | SPCC962.04_UP | TGCGCACGTTCTTCCATCCA |
| 9725 | SPCC962.04_DN | TGGCATTTTCTTCGCCGACG |
| 9726 | SPCC962.05_UP | CCCAACAAAAACCACGCGAA |
| 9727 | SPCC962.05_DN | GCGCAGCAAACAGAGCAGGG |
| 9728 | SPCC962.06c_UP | GGGGACAAAAGCGCGACGA |
| 9729 | SPCC962.06c_DN | GAGGTTGTTTCCGCAGGCG |
| 9730 | SPCC965.04c_UP | ACATCCGCCTATTCCCCCGC |
| 9731 | SPCC965.04c_DN | TGTCCTTGCCCCGACCTTTT |
| 9732 | SPCC965.05c_UP | TCGCTCCCATCCCAATCCCC |
| 9733 | SPCC965.05c_DN | GCCATTCGGGGGGGGTACTC |
| 9734 | SPCC965.06_UP | CCACCTCCTCGTTGCTCCGC |
| 9735 | SPCC965.06_DN | CGTGCAATCCTACCCCCGGA |
| 9736 | SPCC965.07c_UP | CGCTGTGCTCGTGGCCTGTT |
| 9737 | SPCC965.07c_DN | TTGAGGCTTGTTCGGGGGTG |
| 9738 | SPCC965.08c_UP | TATGACACCCTGAACCGGCC |
| 9739 | SPCC965.08c_DN | ATGATCGCGCGCCCTCCTTT |
| 9740 | SPCC965.09_UP | TCCCGAAACAAGCCTCCCAC |
| 9741 | SPCC965.09_DN | CTGCGCCCTCCTCATTGTTG |
| 9742 | SPCC965.10_UP | CGACACGTGTTCTCAAGCCG |
| 9743 | SPCC965.10_DN | AGTTGGACGCCTAAGCGAC |
| 9744 | SPCC965.11c_UP | GGTGTAGGCGGGGGTAAGGC |
| 9745 | SPCC965.11c_DN | TCGTGGGGCATTTCAGCATC |
| 9746 | SPCC965.12_UP | GGCCTGCCCCCCATTGCCTA |
| 9747 | SPCC965.12_DN | AGCGAGGTGGAGAGTGGGGG |
| 9748 | SPCC965.13_UP | GGCTGAGAGGGGCGAGACGG |
| 9749 | SPCC965.13_DN | CATCAGCCCGCCCACCATAG |
| 9750 | SPCC965.14_UP | AACATTAACCCGCCTCCCGC |
| 9751 | SPCC965.14_DN | GCAAGGAAGGGCGTCGGATC |
| 9752 | SPCC970.01_UP | CAGGGGGATGGGTTTAGGCG |
| 9753 | SPCC970.01_DN | TATTGAGCTTCGGCGCGGAC |
| 9754 | SPCC970.02_UP | TGGGATCGCAACAAAACCGG |
| 9755 | SPCC970.02_DN | CGGGCGGGGGGTTCAAATATC |
| 9756 | SPCC970.03_UP | TCATTACCCCTCACGGCGCG |
| 9757 | SPCC970.03_DN | TGAAGCATCGTCCCAACCGG |
| 9758 | SPCC970.04c_UP | GTGCCCTTGCGCTTGATTGA |
| 9759 | SPCC970.04c_DN | TGGACCGCACCCCTCTACGC |
| 9760 | SPCC970.05_UP | TTTGGTCCCTGGCCTCTGC |
| 9761 | SPCC970.05_DN | CGGGCGCTTCTAGCTTCGAT |
| 9762 | SPCC970.06_UP | CCCCAGGTCCAGAAACAGGC |
| 9763 | SPCC970.06_DN | ATTGGCTTTTTGGCGGCTGC |
| 9764 | SPCC970.07c_UP | AACGGGGAGGCGGGGTATTA |
| 9765 | SPCC970.07c_DN | GGTCGTGCTTCGTCGTCTCGG |
| 9766 | SPCC970.08_UP | TGCGTGCGATGGTGCTTTCC |
| 9767 | SPCC970.08_DN | ATGGCGGACTCTTGGCGTTG |
| 9768 | SPCC970.09_UP | CCTTTGAGTTGTGTGCGCCG |
| 9769 | SPCC970.09_DN | GCTTGCTCGGTCGGGGCTTA |
| 9770 | SPCC970.10c_UP | CCTGTAATCGGACTGCCGTGT |
| 9771 | SPCC970.10c_DN | ATGAACGGGCCCCTACAGGA |
| 9772 | SPCC970.11c_UP | AGGAGGTGAGCGCGGATTGT |
| 9773 | SPCC970.11c_DN | CCTTCTCCCTTGGCGCCTCG |
| 9774 | SPCC970.12_UP | GCATTCTGTCCGCACTCCCG |
| 9775 | SPCC970.12_DN | TCTGCATTTGGGGACGCCTT |
| 9776 | SPCP1E11.02_UP | CGTCCTGTACCCCCTACTGC |
| 9777 | SPCP1E11.02_DN | CTGTGGTCGTAGTCGGGGCG |
| 9778 | SPCP1E11.03_UP | TCAATGCCCTTCCCAATTAC |
| 9779 | SPCP1E11.03_DN | TACAAAGGGCGGGAACGGGG |
| 9780 | SPCP1E11.04c_UP | CGTCGTTGCCGGGATCTCAG |
| 9781 | SPCP1E11.04c_DN | CCGAGCCCAAGACGGTTCCA |
| 9782 | SPCP1E11.05c_UP | GCTGCTGGGGTGTGGTCGTT |
| 9783 | SPCP1E11.05c_DN | GGGATCAGCGGGGAGGAATT |
| 9784 | SPCP1E11.06_UP | CGTGAAGGGCGAGTAGGCGT |
| 9785 | SPCP1E11.06_DN | AGCACGCAACAGACGGCACT |
| 9786 | SPCP1E11.07c_UP | CGGGGTGGCGGGTAGTATGT |
| 9787 | SPCP1E11.07c_DN | ATAGGCCAACACGGGGGG |
| 9788 | SPCP1E11.08_UP | CTCGGCCACCTCAAACCCCC |
| 9789 | SPCP1E11.08_DN | TGTAGGTGCGCGCTTCGGGT |
| 9790 | SPCP1E11.09c_UP | CTGCCTCGATTGCGCGTGCC |
| 9791 | SPCP1E11.09c_DN | AAGTACGGCCCCACCTCGCC |
| 9792 | SPCP1E11.10_UP | GCTGCATGCCGGCACTATCGG |

FIG.55

| Sequence number | Name | Base sequence | Sequence number | Name | Base sequence |
|---|---|---|---|---|---|
| 9793 | SPCP1E11.10_DN | GAACAGGCCATGACGCGAAA | 9895 | SPCC576.19c_DN | AAGGCGCATGACGGTCCCTA |
| 9794 | SPCP1E11.11_UP | CTGATTTCCGCGTGCTTGCC | 9896 | SPAC3G5.16c_UP | ATGTGCACTCGCAACCGCCT |
| 9795 | SPCP1E11.11_DN | TCGGCAGGAACAGCAGCACT | 9897 | SPAC3G5.16c_DN | GTTCCGGGGCTCGAATACT |
| 9796 | SPCP20C8.01c_UP | CGCTCACACGCAACCAAGGG | 9898 | SPAC1F3.04c_UP | ACGGCTAGCGCTTACTCCAC |
| 9797 | SPCP20C8.01c_DN | CCGCCGCACCCGTTATATCA | 9899 | SPAC1F3.04c_DN | ATGGTGCCCGAGGGAGCATT |
| 9798 | SPCP20C8.02c_UP | AGCAGAGCGAGTGACGGCAG | 9900 | SPAC23D3.14c_UP | GGTCGAGAGGCGCTAAGTGA |
| 9799 | SPCP20C8.02c_DN | AATTCATCCTAGGGGGCGGC | 9901 | SPAC23D3.14c_DN | TACCACCCGTGACGGTCTCT |
| 9800 | SPCP25A2.02c_UP | GACCGTAGCGCTTTTGCGGG | 9902 | SPAC2F7.16c_UP | GGCAGCGTACGACGTCTCAA |
| 9801 | SPCP25A2.02c_DN | CTTGGCTGCATGCGGTTGGA | 9903 | SPAC2F7.16c_DN | AACGAGAGTGCCCGGAGTGT |
| 9802 | SPCP25A2.03_UP | AGTATTGGGGTTGGCGCTCA | 9904 | SPAC4D7.08c_UP | TGCTCGATCCGGTAGGCAGA |
| 9803 | SPCP25A2.03_DN | CCAAGCGGAGCGAGGGTATC | 9905 | SPAC4D7.08c_DN | AACGTCTGCCGACAGGAGCA |
| 9804 | SPCP31B10.02_UP | GAGCGGAACAAAGGGCGTGG | 9906 | SPAC6B8.08_UP | TTCGTACCGACCGGGCAATC |
| 9805 | SPCP31B10.02_DN | TTGCGGCCCTTCCTCTTGGT | 9907 | SPAC6B8.08_DN | AGGCGGTTCATGTCAGGGTG |
| 9806 | SPCP31B10.03c_UP | AGATCAAACCCCCGCGAAC | 9908 | SPAC9.09_UP | AGCGCTTACCCGTCAGGAAA |
| 9807 | SPCP31B10.03c_DN | TGAAACGCAGCTCGCCAGGA | 9909 | SPAC9.09_DN | GCGGTGCACATAGGACAACC |
| 9808 | SPCP31B10.04_UP | GAGCGGCGTTGTCTGTGTGG | 9910 | SPAP7G5.06_UP | ACGTCGAGTAACCCGTGCAT |
| 9809 | SPCP31B10.04_DN | TAGCCCCTTCTCTCGCCTGG | 9911 | SPAP7G5.06_DN | AACAGTCTGGCCTGTGGCGA |
| 9810 | SPCP31B10.05_UP | CCTCCAGCTTGCCGTCCTC | 9912 | SPAPB15E9.01c_UP | TTGTCCGTACGCACTCTGGC |
| 9811 | SPCP31B10.05_DN | GGCCGCACCGTCTCAGCCTTC | 9913 | SPAPB15E9.01c_DN | CATCCCACCGTCGGAGACAT |
| 9812 | SPCP31B10.06_UP | GGGTGGGCGACAACGAGAAG | 9914 | SPAPB17E12.13_UP | CGCCAGACTAGGTGTGAGCA |
| 9813 | SPCP31B10.06_DN | GACGCTTTGTTGGGCCCTGT | 9915 | SPAPB17E12.13_DN | AGGATACCGCTGAATGCACG |
| 9814 | SPCP31B10.07_UP | TCAGGTGCCCTGGACCACAT | 9916 | SPAPB18E9.02c_UP | TGACGGTCCTAACCTGCGGA |
| 9815 | SPCP31B10.07_DN | AGCGGGGAAGGGACAAGGAC | 9917 | SPAPB18E9.02c_DN | TATGACCGCAGTCGCCGTGA |
| 9816 | SPCP31B10.08c_UP | AGACCGCTCACGTCGAACCT | 9918 | SPBC119.10_UP | TCGTCCACGCTAGAACCTT |
| 9817 | SPCP31B10.08c_DN | ATTAGGTCCAGCTGCGGTCC | 9919 | SPBC119.10_DN | CGACCTCGCAGGTTACGACA |
| 9818 | SPCPB16A4.02c_UP | TAGGCGCATGCACGAAAAGG | 9920 | SPBC16G5.19_UP | ATACGGTGTCGCTCGGATGC |
| 9819 | SPCPB16A4.02c_DN | ATGCCGGACGTTGGTGAGGA | 9921 | SPBC16G5.19_DN | GGGACTGCCCGTTGCTAGTT |
| 9820 | SPCPB16A4.03c_UP | TCGAACCGGGGATAGCTGCC | 9922 | SPBC1711.02_UP | CTTGGACTGCGGTTCCGCTA |
| 9821 | SPCPB16A4.03c_DN | GGGGAGCTTTGGGGCATGAC | 9923 | SPBC1711.02_DN | TGCACCTGGGTCTCGCGTTA |
| 9822 | SPCPB16A4.04c_UP | GGCTGCGGTGGGTCGTGTAA | 9924 | SPBC17G9.06c_UP | TTTGAGACACCTGGGCTCTC |
| 9823 | SPCPB16A4.04c_DN | GCCCGACCCGCTTTTGTACTC | 9925 | SPBC17G9.06c_DN | ACCGCCTGCACGTATGGCTA |
| 9824 | SPCPB16A4.05c_UP | CCCGGTTGCTTGATCGCTTG | 9926 | SPBC1D7.02c_UP | TTGCACCTACGTGACTGCCT |
| 9825 | SPCPB16A4.05c_DN | CGGGGGCCAGAGGGGTAGAG | 9927 | SPBC1D7.02c_DN | CGTTAGTCGAGGCTCGCAGT |
| 9826 | SPCPB16A4.06c_UP | GGCACGCAACCAACCAGACG | 9928 | SPBC1E8.05_UP | GACTGTGCGCACTGCGGTTA |
| 9827 | SPCPB16A4.06c_DN | TCAAAACGGCCGACAAGAGG | 9929 | SPBC1E8.05_DN | TGCCGCGACCTAACATGAG |
| 9828 | SPCPB1C11.01_UP | GGGCCGGAACGAAAGGTGTT | 9930 | SPBC211.05_UP | GGATATGCGATCGGCCCAGA |
| 9829 | SPCPB1C11.01_DN | AACAGCTATTGGGGTGGCGG | 9931 | SPBC211.05_DN | CCTAAACTCGGGTTCGCCAGT |
| 9830 | SPCPB1C11.02_UP | CCTTCTGAGGACCGCGGATTT | 9932 | SPBC215.15_UP | AGACGCGTAACGGCCGGTCTT |
| 9831 | SPCPB1C11.02_DN | CGCGAACGGGACAACTCTGA | 9933 | SPBC215.15_DN | GCGTCACTACGCGTCAGTCT |
| 9832 | SPCPB1C11.03_UP | CAGGACAGGCCAACACCGA | 9934 | SPBC21D10.06c_UP | AAGAGTCCGTGCCAACGTCT |
| 9833 | SPCPB1C11.03_DN | CAAGGAGAGACGCCCCAACG | 9935 | SPBC21D10.06c_DN | TGTAAGTCGCGACCGGTACG |
| 9834 | SPCPJ732.01_UP | TGTCCGGAAGCTCGTAGGGC | 9936 | SPBC23G7.09_UP | GGACATGACACGCGGACCTA |
| 9835 | SPCPJ732.01_DN | ATGCCGGTTCTCTGGTCCCC | 9937 | SPBC23G7.09_DN | CCGTTCGGGTCTAAGGGCAA |
| 9836 | SPCPJ732.02c_UP | CGCGCTAACGGTAGCCCTTTT | 9938 | SPBC23G7.17c_UP | AACGAGTTCGCGTTAGAACCA |
| 9837 | SPCPJ732.02c_DN | GCTGCTCAGCCCTGTAAGATCG | 9939 | SPBC23G7.17c_DN | TCTTGACGTGGACCCAGTGC |
| 9838 | SPCPJ732.03_UP | CAGGGGCAAAGTGGGCARGG | 9940 | SPBC32F12.15_UP | TTGCACGTGAGTCGGCCTAT |
| 9839 | SPCPJ732.03_DN | TGCGAGGGAAGTTAAGCCGG | 9941 | SPBC32F12.15_DN | ATCACCCGGTGGGCTGTATC |
| 9840 | SPAC23A1.10_UP | ACACCCGTGGACCTCACTTG | 9942 | SPBC365.05c_UP | ACCACTAGACGGGCACATCG |
| 9841 | SPAC23A1.10_DN | ATAGCGGGACTCCGGTGGTA | 9943 | SPBC3G5.05c_DN | ATCGTAGCGTGCCCAAAGGT |
| 9842 | SPAC30D11.05_UP | ACGGGGAGCGGAACCTATCA | 9944 | SPBC3B9.22c_UP | GCTGGTCCCTGAGCGTATCA |
| 9843 | SPAC30D11.05_DN | ATCCAGGGGCGCAATCCAAT | 9945 | SPBC3B9.22c_DN | CGCCCTACTTGCGTCGACAT |
| 9844 | SPBC1A4.08_UP | TATCTTTGGGCGTGGCGAGCG | 9946 | SPBC3D6.16_UP | CCCAGATTACCCCACACGCT |
| 9845 | SPBC1A4.09_DN | GGGGTGCGACGTGTTGGCGTC | 9947 | SPBC3D6.16_DN | GAASGCCACCTGTGACAGCA |
| 9846 | SPBC1289.17_UP | AGTCTGCTCAGGGTACACCGA | 9948 | SPBC3F6.03_UP | TTTTGCCCGGACAGCTCTGG |
| 9847 | SPBC1289.17_DN | TAGGGTCCGACCCTGTGGGAA | 9949 | SPBC3F6.03_DN | CCGGCGCTTAAGGGTGGTAT |
| 9848 | SPAC27E2.08_UP | TCTATGTGGTGCCAGAGCCG | 9950 | SPBC6B5.09_UP | TGTAAGTATGCGGGCCGGTT |
| 9849 | SPAC27E2.08_DN | TCACACGTCAGCAGCGGGTGG | 9951 | SPBC6B5.08_DN | CCGTGTCAGTCCGGTTCAGA |
| 9850 | SPCC285.07c_UP | TCTCGCTCGCACTACGACAC | 9952 | SPBC6B1.12c_UP | TGACGACGCAGTAGGGAACC |
| 9851 | SPCC285.07c_DN | ACGGTCGCGGTCACCAGAAT | 9953 | SPBC6B1.12c_DN | ACTCTCAGGGCACAGTGACC |
| 9852 | SPCC622.21_UP | TGCTGTACGCAGAAGGTCGC | 9954 | SPBC800.14c_UP | TGGCGTCGACACGGAGGTTT |
| 9853 | SPCC622.21_DN | ATCGGTGTTAGGCACTCGCC | 9955 | SPBC800.14c_DN | TGCCCAGTCTAGACCCTGACA |
| 9854 | SPAC1250.07_UP | ATCAGCCCCTCGGTGGTAAC | 9956 | SPBCPT2R1.04c_UP | ATCGTTAGACCCGGCACTGCA |
| 9855 | SPAC1250.07_DN | CGAAGCTGGCGCGATAATGC | 9957 | SPBCPT2R1.04c_DN | GCAGTCGACACTGCGTCCAA |
| 9856 | SPAC1142.09_UP | CGTTTGGTATGAGGCGCCGA | 9958 | SPBP23A10.11c_UP | GGCGTTCTCACACGGATCT |
| 9857 | SPAC1142.09_DN | GCGGAAGCGGTCAAAGAGA | 9959 | SPBP23A10.11c_DN | ACCCGCGCCGGCTTATAGTAG |
| 9858 | SPAC17A2.15_UP | CACATGACGGACGGGATCCA | 9960 | SPBPB21E7.04c_UP | CCGTGGCACTCCCGTGAGATT |
| 9859 | SPAC17A2.15_DN | GTTATGCAGCCGCTCGCCAA | 9961 | SPBPB21E7.04c_DN | TCACTCCGGTAGGGTAGCCA |
| 9860 | SPAC1A6.11_UP | TTGCCACTGGTCAGCACAGT | 9962 | SPBPB21E7.07_UP | TGCTCCCCCAGCGTTCATAA |
| 9861 | SPAC1A6.11_DN | ACTGGTGTACGTCCGAGGGA | 9963 | SPBPB21E7.07_DN | CGCCGTCAATCGTGGGACTT |
| 9862 | SPAC27E2.13_UP | CGTTGTCGTTCCGACCCACT | 9964 | SPBPB8B6.02c_UP | TCTCTAACGTGCACGAGGCG |
| 9863 | SPAC27E2.13_DN | CACCACGCGGACGCTCAAAT | 9965 | SPBPB8B6.02c_DN | GTGTGCCACTACCTAGCCCGT |
| 9864 | SPAC56F8.13_UP | CTCAGGCGAAGGACTCGCCAA | 9966 | SPBPB8B6.03_UP | TGCTCTGGGACTACGCCGAA |
| 9865 | SPAC56F8.13_DN | TGTGGCTCTGCTCCAGACGTG | 9967 | SPBPB8B6.03_DN | TGGGCCAGACAGCTAGGCTT |
| 9866 | SPAC6B12.18_UP | TTGGGTCTCCAGGTCCCTCA | 9968 | SPBPB8B6.06c_UP | TGCGTCTGATCCGGGACTGT |
| 9867 | SPAC6B12.18_DN | AAATCCCGCGAGCTACTGGC | 9969 | SPBPB8B6.06c_DN | CAAAGCAGTCCCGTCCAGCA |
| 9868 | SPAC806.11_UP | GACCGGGCCGTGTAACATCA | 9970 | SPCC1322.13_UP | CCACTAGCCGTGCGCATACT |
| 9869 | SPAC806.11_DN | CTGCGTGTACGTCTCGGGAA | 9971 | SPCC1322.13_DN | GGGTCGGCACTACGTTCTCA |
| 9870 | SPAC8E11.08c_UP | TTACGGACTGGCGCTCAAC | 9972 | SPCC1682.05c_UP | TTCCAGTCCGCTCGTACAGC |
| 9871 | SPAC8E11.08c_DN | CAAGCGCCCTGAGCAGACCAA | 9973 | SPCC1682.05c_DN | TTGCACGGCCATTGTGCTCG |
| 9872 | SPAC9E9.02_UP | GTTCGCGCACAGTTACGGCA | 9974 | SPCC290.04_UP | TGGTCATACCCGGAGACGCA |
| 9873 | SPAC9E9.02_DN | CCTAGCGACGGTGCCCATTA | 9975 | SPCC290.04_DN | GGGAGGTTGCACTCTGGTCA |
| 9874 | SPAPB15E9.02c_UP | TTAGGCTCACACCTGGCTGG | 9976 | SPCC330.05c_UP | ATGGGCGCGCGCAGATTACC |
| 9875 | SPAPB15E9.02c_DN | AGATAGCTCGGAGCGGCCAT | 9977 | SPCC330.05c_DN | AGGGTGCAGTCCTGGCTAGA |
| 9876 | SPAPB18E9.05c_UP | GCTCCCACGCTTATACGGCCT | 9978 | SPCCBB3.10_UP | TGTGCCGTGAGTGCCCAGAA |
| 9877 | SPAPB19E9.05c_DN | TCACGCGTGTCGCTAGTTGC | 9979 | SPCCBB3.10_DN | ATGACATGGGGTACGCGGCA |
| 9878 | SPBC12C2.14c_UP | CTGACGGACCATTGACCGA | 9980 | SPCC569.01c_UP | TAGTCGGCCTTATGGGCACG |
| 9879 | SPBC12C2.14c_DN | CTGTTGCGGCACGTCCATCT | 9981 | SPCC569.01c_DN | GTGACGAACTCGCGGAACGA |
| 9880 | SPBC1347.14c_UP | ACGCCCACGGGCTACACTAT | 9982 | SPCC736.15_UP | GTTACGTCGGAACTGCCCA |
| 9881 | SPBC1347.14c_DN | TGTACGCGGACTTGAGTGGC | 9983 | SPCC736.15_DN | TTTCGGATCCGGAGTGTCG |
| 9882 | SPBC13G1.15c_UP | GATGGCCTACTGCCTCCAGA | 9984 | SPAC23C4.04c_UP | AGGGAGTTCGAGGCCCAAA |
| 9883 | SPBC13G1.15c_DN | TCGGTTCGCCACTAGGCTTC | 9985 | SPAC23C4.04c_DN | TTTCGTAGCGTGACGAGGGC |
| 9884 | SPCC16C4.21_UP | ATACGGTGGTACCGTGCCTG | 9986 | SPAC27E2.12_UP | ATCGCGCCAGGGTGTAGAAC |
| 9885 | SPCC16C4.21_DN | ATCACCGGCAGTGTGGGATG | 9987 | SPAC27E2.12_DN | GCGCAGTCGTAGACGGCAAT |
| 9886 | SPCC198.05_UP | AGACGAATCGCTCGGCAGGT | 9988 | SPAC56F8.07_UP | CAAGTGCAGTGGGACTGCCT |
| 9887 | SPCC198.05_DN | TTCTGCACGTCCGGACGAC | 9989 | SPAC56F8.07_DN | GGGGTTAGCCGTCGGAATGA |
| 9888 | SPCC338.03c_UP | AGCCCATGGGACCTACCTCA | 9990 | SPAPB1A10.16_UP | GGGTATGGTCACCGGTCGAA |
| 9889 | SPCC338.03c_DN | ATGTCGGCCAGGTTAGTCGC | 9991 | SPAPB1A10.16_DN | GATCGATCCAGCACCGTGA |
| 9890 | SPCC417.15_UP | TGTCTTGTCGTAGGTGCCCG | 9992 | SPCC1393.14_UP | GCGCTCTAGTCGGCTCGTAT |
| 9891 | SPCC417.15_DN | ATGACGTCACGGAACTGGCA | 9993 | SPCC1393.14_DN | TCCCGTAACGTGGCAGCACT |
| 9892 | SPCC4F11.05_UP | TTTCAGGACCGACACGGCTC | | | |
| 9893 | SPCC4F11.05_DN | GTTCTGCACGTGCTAGGGGT | | | |
| 9894 | SPCC576.19c_UP | AAATCCCAGGTGCACGTGAA | | | |

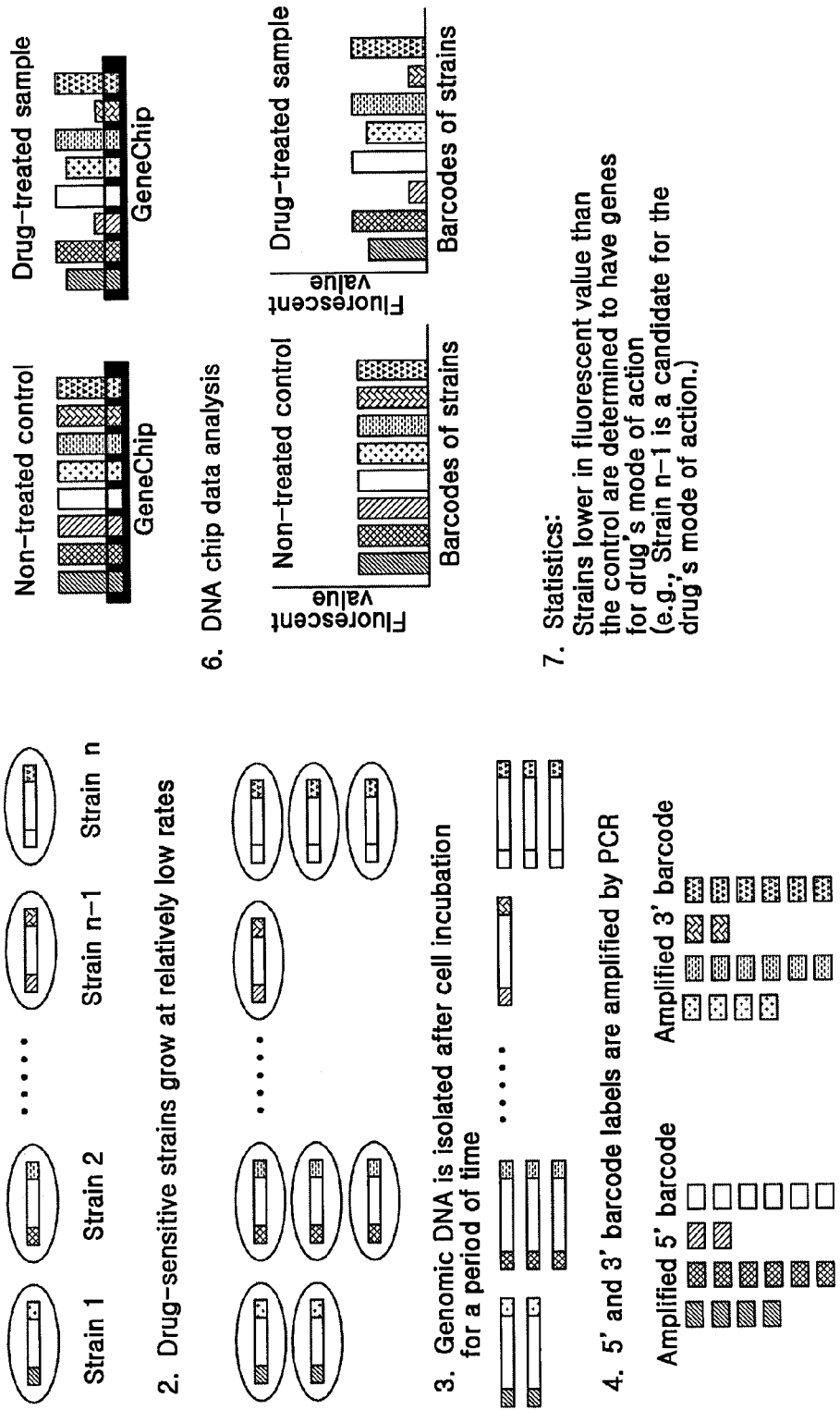
FIG. 56 Process of screening drug's modes of action on the basis of haploinsufficiency FIG. 57 process of constructing a library of gene-targeted deletion mutants
(1) aliquoting of strain mutant mixture
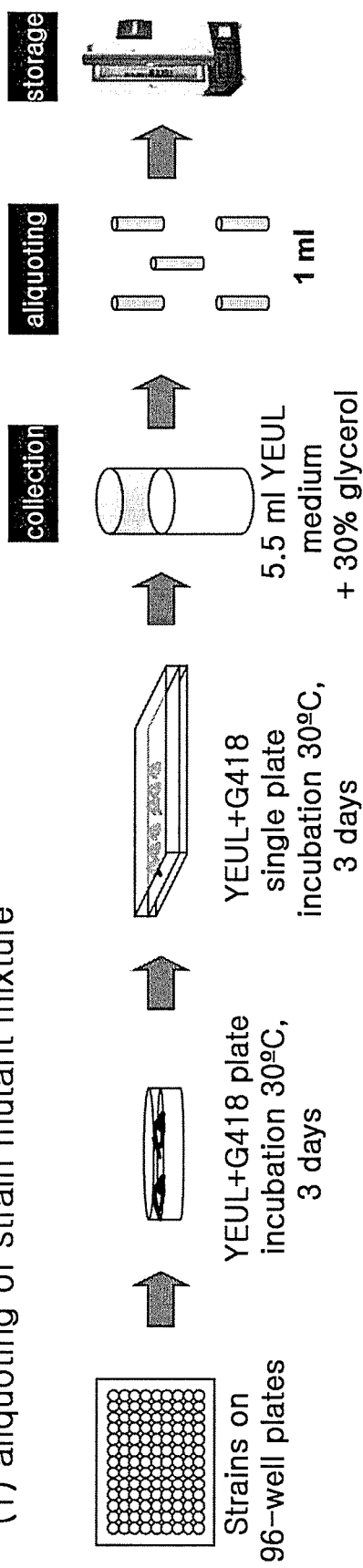
(2) construction of total libraries by pooling aliquots
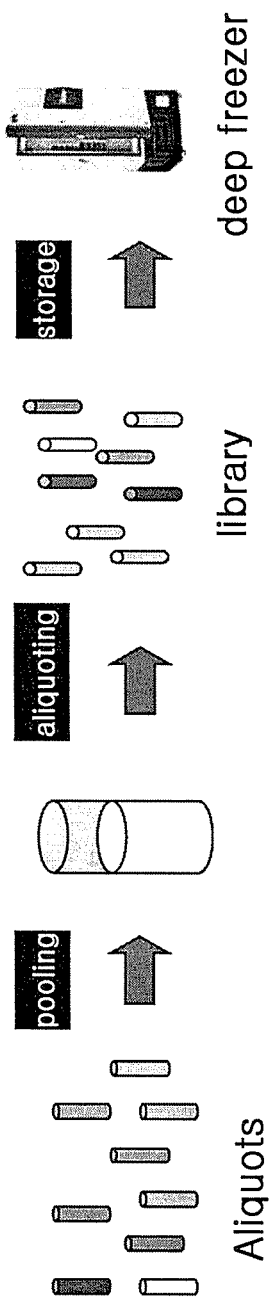

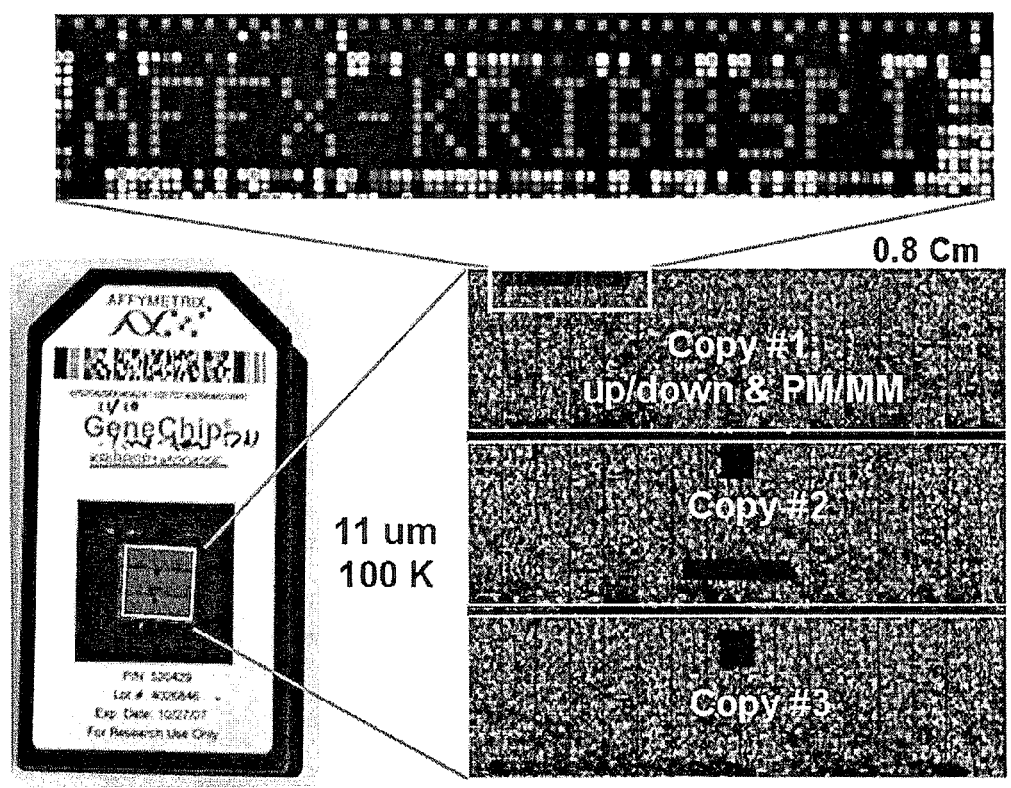
FIG. 58 Made-to-order GeneChip from Affymetrix

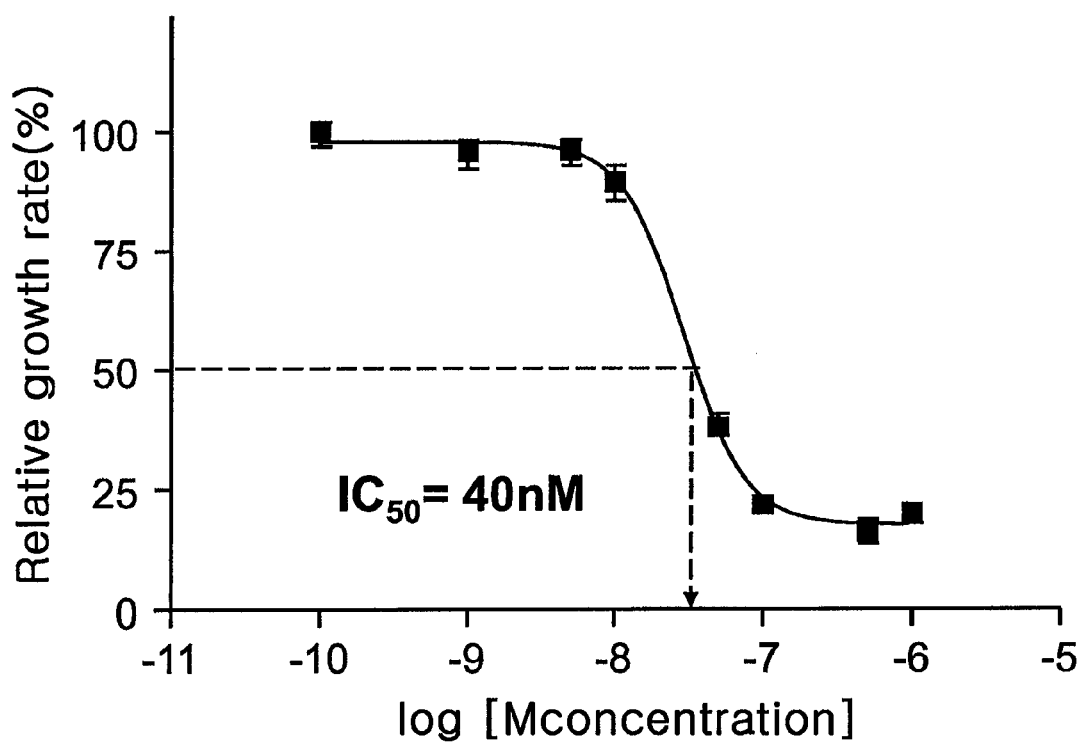
FIG. 59 IC$_{50}$ determination of Terbinafine

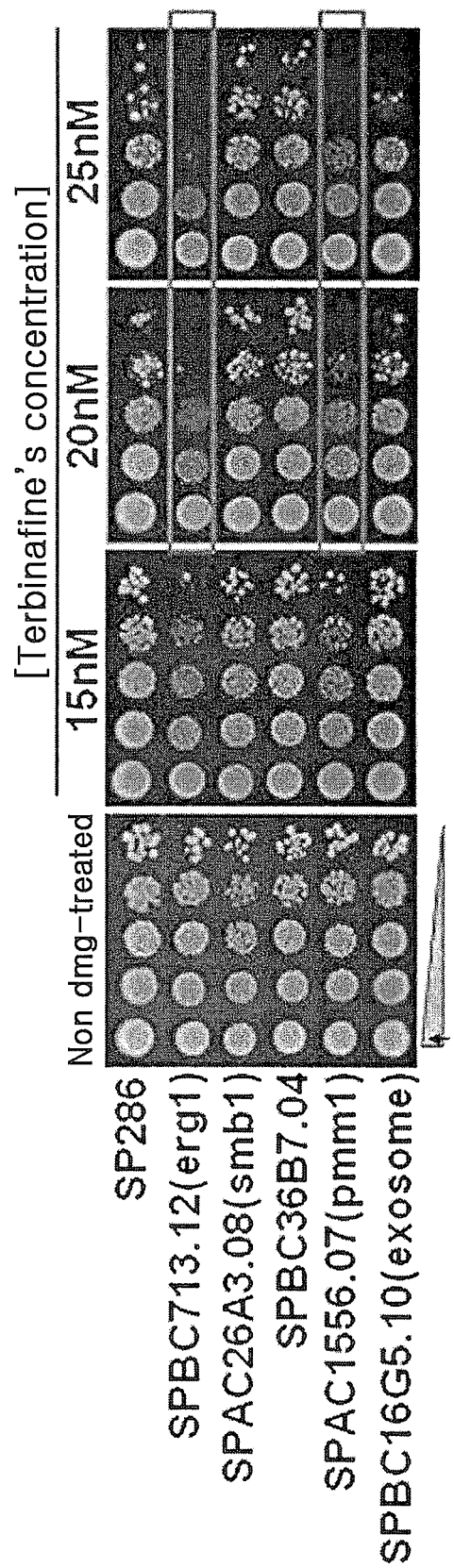
FIG. 60 Confirmation of Terbinafine's Modes of Action erg1 and pmm1

GENOME-WIDE CONSTRUCTION OF *SCHIZOSACCHAROMYCES POMBE* HETEROZYGOUS DELETION MUTANTS CONTAINING GENE-SPECIFIC BARCODES BY THE METHODS OF 4-ROUND SERIAL OR BLOCK PCR, OR TOTAL GENE SYNTHESIS THEREOF

REFERENCE TO SEQUENCE LISTING SUBMITTED ELECTRONICALLY VIA EFS-WEB

The content of the electronically submitted sequence listing (Name: 2472_0070000_updated_sequence_listing_ascii.txt; Size: 1,918,016 bytes; and Date of Creation: Nov. 4, 2013) is incorporated by reference in its entirety.

TECHNICAL FIELD

The present invention relates to a method for systemically preparing gene-targeted heterozygous deletion mutant strains of *Schizosaccharomyces pombe*. More particularly, the present invention relates to a method for the preparation of gene-targeted heterozygous deletion *Schizosaccharomyces pombe* by transforming *Schizosaccharomyces pombe* with a deletion cassette, constructed by four-round serial PCR, block PCR or total gene synthesis, containing a homologous recombination site. Also, the present invention relates to gene-targeted heterozygous deletion *Schizosaccharomyces pombe* mutants prepared by the method, and a library of gene-targeted heterozygous deletion *Schizosaccharomyces pombe* mutants. Further, the present invention is concerned with a method and a kit for screening drug modes of action over the library.

BACKGROUND ART

In 2006, the worldwide drug market was reported to be worth 643 billion dollars and Korean drug products had an 11,472.8 billion won share of the total. The global drug market is expected to increase to 735~745 billion dollars in 2007. It was reported that an average cost of 100~600 million dollars is required to bring a new drug to market, with a developmental period of from 10 to 15 years. In spite of such huge expenses of time and money, the success rate of new drug development is reported to be as low as one in ten thousand. It is accordingly necessary for the successful development of new drugs that highly putative "drug's modes of action" which play critical roles in the occurrence or treatment of diseases, from among a number of possible modes of action, should be defined; this is generally achieved through intelligent bioinformatical tools extracting biological relevance from complex experimental data. Thereby, it is very important to systemically screen specific modes of action directly involved in lots of diseases.

As such, screening technologies are useful in identifying the targets against which drugs exert their therapeutic effects, thus greatly contributing to reducing the time period required for drug development. Also, screening technologies allow the identification of the modes of action which are associated with side effects of the drug. Therefore, there is an imperative need for a novel method for screening a drug's modes of action.

*Schizosaccharomyces pombe*, a fission yeast useful in the preferable embodiment of the present invention, does not have an evolutionarily high correlation with the budding yeast *Saccharomyces cerevisiae* although both belong to ascomycetes. *S. pombe* (Wood V. et al., Nature. 45:871-880, 2002) marked the sixth model eukaryotic organism whose genome has been fully sequenced since *S. cerevisiae* (Goffeau A. et al., Science, 274:546-567, 1996). According to the analysis, *S. pombe* has an effective genomic structure which has the lowest functional repetition of genes among the eukaryotic cells whose genomes have been determined thus far. It was also reported that *S. pombe* contains 4,824 protein-coding genes, which is the smallest number yet identified for a eukaryote, but some 43% of the genes contain introns. Also, *S. pombe* is found to have highly conserved genes important for eukaryotic cell organization including those required for cell-cycle control, proteolysis, protein phosphorylation and RNA splicing. Further, 31% of the genes of *S. pombe* were identified to differ from that of *S. cerevisiae* and to rather share homology with humans. Thus, the comparison of genetic functions between *S. pombe* and *S. cerevisiae* is emerging as an effective methodology to study the functions of human genes.

The term "gene targeting", as used herein to transform yeast strains in the screening of a drug's modes of action, is intended to refer to a genetic technique that uses homologous recombination to change an endogenous gene such as by destroying a gene (knock-out) or by introducing a gene. A transgenic mouse which has had a gene implicated in a specific disease removed therefrom or introduced thereinto has its pathology observed, thus allowing the knock-out gene to be functionally identified.

Since the creation of a transgenic mouse in 1989, gene targeting has made great technical advances. For example, target genes can be introduced at specific developmental stages or into already grown adults. Also, it is possible to design a mutant gene which is expressed at a specific time during development. Martin J. Evans, Oliver Smithies and Mario R. Capecchi were declared laureates of the 2007 Nobel Prize in Physiology and Medicine for their work on gene targeting.

PCR (polymerase chain reaction) is a molecular biological technique for replicating and amplifying DNA (U.S. Pat. Nos. 4,683,195, 4,683,202, and 4,800,159; European Pat. Nos. 0200362, 0201184 and 0229701; Methods in Enzymology, Volume 155, 1987, pp. 335-350, Murakawa et al., DNA 7; 287-295 (1988)). This technique consists typically of from 30 to 40 cycles of denaturation, annealing and extension, and allows a gene segment of interest to be selectively amplified even from trace amounts in the DNA pools. Now variations on the basic PCR technique have been developed, including multiplex-PCR, nested PCR, quantitative PCR, real-time PCR, reverse transcription (RT-PCR), touchdown PCR, etc.

Real-time PCR is an established tool for DNA quantification that measures the accumulation of DNA product after each round of PCR amplification, based on the detection of a fluorescent signal produced proportionally during amplification of a PCR product, because a fluorescent probe is used together with primers. Real-time PCR can obtain PCR results rapidly and conveniently because it does not need electrophoretic determination. Also, real-time PCR enjoys the advantage of a low risk of contamination. For these reasons, real-time PCR enjoys widespread use as a substitute for typical PCR.

Transformation is the genetic alteration of a cell resulting from the uptake, genomic incorporation, and expression of foreign DNA. In practice, the foreign DNA is labeled with a selectable marker to easily select the cells to which the foreign DNA has been successfully introduced. Typical examples of the selectable markers include ampicillin-, tetracycline- and kanamycin-resistance genes. After transformation, culturing in the presence of related antibiotics allows the selection of successfully transformed bacteria. In the present invention, a specific gene is knocked out in the fission yeast by transformation with the introduction of an antibiotic-resistance gene into the corresponding homologous recombination site.

Gene synthesis is a well-known technique on which about 200 articles have published since the development of oligo-ligation based on PCR in the early 1990s (Edge et al., Nature. 292:756-62, Rouillard et al., NAR. 32:176-80, Smith et al., NAR. 10:4467-82, Dillon et al., Biotechniques. 9:298-300, Ciccarelli et al., Nucleic Acid Research. 21:6007-13, Prodromou et al., Protein Engineering. 5:827-29, Stemmer et al., Gene. 164:49-53, Lin et al., Gene. 288:85-94, Venter et al., Proceedings National Academy of Science. 100:15440-45). In principle, oligonucleotides from 20 bp to 60 bp long are annealed and ligated to each other to give a double-stranded DNA fragment which is then used as a template for the amplification of a desired DNA through PCR. The DNA fragment which can be obtained by gene synthesis is generally shorter than 1,000 bp. For a longer gene, the obtained DNA fragments less than 1000 bp are ligated by PCR. In 2003, Dr. Craig Venter succeeded in building the entire 5,386-bp genome of ΦX174 bacteriophage (phiX174 bacteriophage) in such a manner.

With regard to the screening of a drug's mode of action, most widely used are in vitro methods. For example, a mixture of cellular proteins are passed through an affinity column with a drug attached on a resin, and the proteins thus bound to the drug are purified and analyzed by MALDI-TOF (Schreiber et al., Bioorg. Med. Chem. 6:1127-1152). An alternative is to pass a human protein-phage library in which human proteins are expressed on the membrane through an affinity column containing drug-attached resin, followed by selection and analysis of phages bound to the drug to infer the target proteins of the drug (Sche et al., Chem. Biol. 6:707-716).

Recently, attempts have been made on an in vivo screening method which is quite different from the above two methods (Lum et al Cell. 116:121-37). This method, although disadvantageous in that it screens yeast proteins in contrast to the in vitro methods of screening human proteins, has the advantage of being rapid (100 drugs/week), convenient and having a high success rate. In 2004, Drs. Shoemaker and Lum's research team at Merck screened modes of action against 80 pre-existing drugs with an increase in success rate of from 25% to 70%. The screening strategy, referred to as drug-induced haploinsufficiency, is based on the fact that lowering the gene dosage of a drug target increases the susceptibility to the drug. In most cases, one allele is sufficient to permit the cell to function normally, but when the normal phenotype requires the protein product of both alleles, and restitution of 50% of the gene function results in an abnormal phenotype, this is referred to as haploinsufficiency. It was reported that 180 genes, corresponding to 3% of about 6,000 genes, of budding yeast, were implicated in haploinsufficiency such that the mutants grew poorly even in sufficient nutrient media compared to the wild-type (Deutschbauer et al., Genetics. 169:1915-25). This haploinsufficiency is a basis for screening a drug's modes of action in heterozygous mutant yeast strains. For example, assuming that a drug 'a' targets a protein 'A', treatment with the drug 'a' at a dose of $IC_{50}$, a concentration to inhibit the protein 'A' by half, leads to 100% inhibition (knock-down) of the protein 'A' in the gene-targeted heterozygous strain. Accordingly, the drug-treated strain grows at a lower rate than does the non-treated strain. In accordance with the present invention, a method for screening a drug's modes of action on the basis of haploinsufficiency is provided.

Success in constructing gene targeted strains is dependent on the properties of the strains because it is determined by homologous recombination efficiency which differs from one strain to another. However, the homologous recombination efficiency in the same strain is proportional to the length of genomic homologous sites. Thus, a longer DNA fragment corresponding to a genomic homologous site permits the construction of a gene-targeted strain at a more efficient rate. The trials summarized in Table 1 below have been performed on budding yeast, but there are no precedents on fission yeast at such a high success rate (Palaniyandi et al., Nucl Acid Res. 3:2799-2800; Michael et al., Gene. 158:113-17; Kaur et al., Nucl Acid Res. 25:1080-81).

TABLE 1

| Construction of Deletion Cassettes | | Yeasts | Homologous Length (bp) | Success rate(%) |
|---|---|---|---|---|
| PCR with gene-specific Oligo | Serial PCR | Budding | 45~60 | 81 |
| | Single Oligo | Budding | 38~50 | 10 |
| | Single Oligo | Fission | 40 | 1~3 |

Typically, a gene specific linker-mediated PCR method has been used to lengthen homologous recombination sites for use in the construction of gene-targeted fission yeast strains. Using this method, Giaever et al. constructed about 6000 deletion cassettes of the total genome of the budding yeast such that each cassette was flanked by two 40-60 bp homologous regions of yeast DNA sequence (Giaever et al., Nature Genetics 14:450-56; Wach et al., Yeast 10:1793-1808). In the case of the budding yeast, 45~60 bp genomic homologous regions at both termini of each cassette guaranteed a success rate of as high as 81% in the genome-wide construction of mutant strains (Table 1). In fission yeast however, even when the homologous length is extended to 40 bp, the success rate is increased to at most 1~3%. Such a low success rate for the fission yeast indicates that strain preparation is very difficult due to the inferiority of the fission yeast in homologous recombination rate to that of the budding yeast. In full consideration of this background, the present invention provides a method for constructing fission yeast mutants at high efficiency through homologous recombination.

DISCLOSURE

Technical Problem

Reportedly, it is technically more difficult to construct gene-targeted mutants from fission yeasts than from budding yeasts (Decottignies et al., Genome Research. 13:399-406). In the present invention, a deletion cassette is constructed by flanking a selectable marker gene with a pair of 20-mer gene-specific barcodes and assigning a pair of homologous recombination regions 250~350 bp in length to the sides of respective barcodes, and is transformed into the fission yeast to make gene-targeted heterozygous deletion mutants of the fission yeast. Based on a library of the heterozygous deletion mutants, a Genechip allows the high throughput screening of a drug's modes of action.

Technical Solution

It is therefore an object of the present invention to provide a method for preparing a gene-targeted, heterozygous deletion mutant strain of *Schizosaccharomyces pombe*, using a gene targeting deletion cassette comprising a selectable marker gene, barcode base sequences for microarrays, and homologous recombination regions.

It is another object of the present invention to provide a gene-targeted, heterozygous deletion mutant strain of *Schizosaccharomyces pombe*, prepared using the method.

It is a further object of the present invention to provide a library of gene-targeted, heterozygous deletion mutant strains of *Schizosaccharomyces pombe*, prepared using the method.

It is still a further object of the present invention to provide a method of screening a drug's modes of action on the basis of the library of gene-targeted, heterozygous deletion mutant strain of *Schizosaccharomyces pombe*.

It is still another object of the present invention to provide a kit for screening novel drugs, comprising the library of gene-targeted, heterozygous deletion mutant strain of *Schizosaccharomyces pombe*.

Advantageous Effects

A system of preparing gene-targeted, heterozygous deletion mutants of *Schizosaccharomyces pombe* was first established in the world by the present inventors. Also, the present invention increased a success rate in constructing a strain of fission yeast, which is generally recognized as being lower than that for budding yeast, to 95%~99%, which is similar to the success rate for budding yeast. Out of approximately 6,000 genes of *Saccharomyces cerevisiae*, only 5,700 genes (95%) were successfully used in constructing heterozygous deletion mutants of the budding yeast (refer to "*Saccharomyces* Genome Deletion Project" disclosed in the Website sequence.stanford.edu/group/yeast_deletion_project/not_made.html).

In the present invention, 4,945 gene-targeted, heterozygous deletion mutants of *Schizosaccharomyces pombe* which corresponds to 99% of the approximately 5,000 genes (4,989~5,014 genes estimated) obtained, on Jun. 20, 2007, from the public fission yeast database at the Wellcome Trust Sanger Institute genedb.org/genedb/pombe/index.jsp) were successfully constructed.

The 55 genes excluded from the construction, which corresponds to 1% of the total genes and consists of 18 wtf genes, 11 Tf2 genes and 26 dubious genes, are theoretically impossible to use in constructing gene-targeted deletion mutants. A library of the heterozygous mutant strains prepared according to the present invention can be also applied to the system of screening a drug's modes of action on a gene level, thus effectively developing novel drugs.

DESCRIPTION OF DRAWINGS

FIG. 1 is a schematic view showing a structure of a typical deletion cassette for gene targeting, FIG. 2 shows a process of constructing a Kan$^r$-barcode module for use in a deletion cassette, FIG. 3 shows a process of constructing a deletion cassette through four-round serial PCR, FIG. 4 shows a process of constructing a deletion cassette through block PCR, FIG. 5 shows a process of constructing a deletion cassette through gene synthesis, FIG. 6 shows the identification of a desired mutant strain by colony PCR, FIGS. 7 to 55 show base sequences of gene-specific barcodes to be inserted into deletion cassettes for the construction of gene-targeted mutant strains FIG. 56 schematically shows a process of screening a drug's modes of action using GeneChip on the basis of haploinsufficiency, FIG. 57 is a process of preparing a library of gene-targeted mutants for screening a drug's modes of action by use of GeneChip, FIG. 58 shows an order-made GeneChip from Affymetrix, FIG. 59 shows the measurement of the antifungal agent terbinafine for $IC_{50}$ applied to the screening of a drug's modes of action on Genechip, and FIG. 60 shows the reconfirmation of the Genechip-based terbinafine's modes of action on plates.

BEST MODE

In the present invention, four-round serial PCR, block PCR or gene synthesis is employed to amplify deletion cassette modules with which transformed gene-targeted mutants are then constructed. In turn, the mutants are used to construct a library of DNA of which advantage is taken to search for a drug's modes of action.

In an embodiment of the present invention, provided is a method for constructing gene-targeted heterozygous deletion mutants of fission yeast using a deletion cassette which comprises (a) a selectable marker, (2) a pair of gene-specific barcode base sequences, positioned respectively at both flanks of the selectable marker gene, for a microarray, and (3) a pair of at least 150 bp homologous recombination regions, respectively assigned to sides of the barcode base sequences at positions upstream and downstream of the selectable marker gene. A detailed description will be given of each component, below.

Selectable Marker

A selectable marker is used to discriminate successfully transformed yeasts from unsuccessful ones. Examples of the selectable marker useful in the present invention include auxotrophic markers, neomycin resistance ($neo^R$), kanamycin resistance ($kan^R$), hygromycin resistance (hyg), histidinol dehydrogenase (hisD), guanine phosphoribosyltransferase (gpt), tetracycline ($tet^R$), hypoxanthine phosphoribosyltransferase (hprt), ura3, ble and sacB, with preference for kanMX, which is derived from kanamycin resistance gene. The deletion cassette comprising a selectable marker may be integrated into the genome by homologous recombination.

An autographic marker that requires a specific amino acid or nucleic acid for survival, such as ura4, leu1, his3, is currently used for targeted gene integration and disruption in fission yeasts. However, a strain with one or more auxotrophic mutations is requisite for the use of such a marker. Also, a gene conversion may occur in the auxotroph due to the introduction of DNA. Further, auxototrophic mutation itself; together with other mutations, may result in phenotypes which are difficult even to guess, such as somosensitivity, nitrogen-starvation regulated cellular differentiation, sporulation, pseudohyphae, etc. In addition, many auxotrophic mutations may make it difficult for the yeast to grow in a typical medium.

In order to overcome these limitations of auxotrophic markers, the Philippsen group developed the KanMX module as a dominant drug resistance marker. This marker was used for the deletion project of *Saccharomyces cerevisiae*. Resistant to Geneticin® (G418), the kanMX module was designed to serve as a selectable marker. Over auxotrophic markers, the G418 marker has the advantage of giving a high rate of deletion even upon the use of PCR-DNA fragments. Now, additional dominant drug resistance markers have been developed, including those resistant to hygromycin B, nourseothricin, and bialaphos/phosphinothricin.

Used in a preferred embodiment of the present invention is the selection maker KanMX4 which is 810 bp in length and contains Kan transposon Tn903 ORF from *E. coli*. With aminoglycoside phosphotransferase activity, KanMX4 is reported to inhibit kanamycin or its derivative G418 (Lang-Hinrichs et al., Current Genetics. 18:511-6, Oka et al., J. Mol. Biol. 147:217-26). This kanMX module, one of the dominant drug resistance markers, contains the known kan$^r$ open reading-frame (ORF) of the *E. coli* transposon Tn903 fused to transcriptional and translational control sequences of the TEF gene of the filamentous fungus *Ashbya gossypii*. This heterogonous module permits efficient selection of transformants resistant against geneticin (G418).

A high false rate of integration to the target region may generally occur if PCR products are used, or if a marker has low sequence homology to the target region. In contrast, the KanMX module (G418 marker) serving as a heterologous selectable marker guarantees a high rate of deletion thanks to its dominant resistance even if PCR-DNA fragments are used.

Barcode Sequences for Microarrays

In order to efficiently measure growth rates of a library of (6,000) gene-targeted fission yeast mutants, a practical and systematic strategy is necessary for the growth measurement through a gene chip technique. In this regard, barcode sequences for microarrays are introduced into the deletion cassettes (FIG. 3). These barcode sequences make it easy to detect the strains whose growth is inhibited by a drug in such a manner that a chromosome pool isolated from 6,000 strains is used as a template for PCR amplification of barcodes regions, followed by analysis on a gene chip. The barcode sequences must be specifically designated to each strain, thus requiring a population two or more times greater than that of the genomic 1 DNAs of the strains (each one assigned upstream and downstream of genomic DNA, one genomic DNA flanked by at least two barcode sequences). As long as it satisfies this condition, there is no limitation imparted to the length of the barcode sequences.

In a preferred embodiment of the present invention, the KanMX4 of the deletion cassette is flanked by two copies of a 20-mer gene-specific barcode. The theoretically possible number of 20-mer barcodes is $4^{20}$ because the four bases G, A, T and C are used in the barcode sequences. Barcode sequences used in the present invention are those shown in FIGS. 7 to 55.

Homologous Recombination Regions

A success rate in constructing gene-targeted strains is dependent on properties of strains because it is determined by homologous recombination efficiency which differs from one strain to another. However, the homologous recombination efficiency in the same strain is highly proportional to the length of genomic homologous regions (Michael et al., Gene. 158:113-17; Palaniyandi et al., Nucl Acid Res. 3:2799-2800). Thus, the DNA fragments corresponding to genomic homologous regions must have their lengths optimized in order to construct gene-targeted strains with efficiency.

According to an embodiment of the present invention, this homologous recombination region is 150 bp or greater in length and is positioned at each of 5' and 3' sides in the deletion cassette. Preferably, the homologous recombination region ranges in length from 150 bp to 450 bp. A more preferable embodiment of the present invention provides a deletion cassette in which the homologous recombination region with a length of from 150 to 450 bp is positioned at each of 5' and 3' sides.

TABLE 2

| Construction of Deletion Cassettes | | Yeasts | Homologous Length(bp) | Success rate(%) | Note |
|---|---|---|---|---|---|
| PCR with gene-specific Oligo | Serial PCR | Budding | 45~60 | 81 | |
| | Single Oligo | Budding | 38~50 | 10 | |
| | Single Oligo | Fission | 40 | 1~3 | |
| | 4-Round Serial PCR | Fission | 80 | 50 | Present invention |
| | Block PCR | Fission | 350~450 | 80 | |
| Gene Synthesis | | Fission | 150 | 80~98 | |

Construction of Deletion Cassette for Gene Targeting

The deletion cassette of the present invention plays an essential role in targeting about ~5000 yeast genes in such a manner that a marker gene of the deletion cassette transformed into the yeast is substituted for a target gene. As a prerequisite to the construction of gene-targeted, heterozygous fission yeast mutants, the deletion cassette preferably has a gene structure in which the selectable marker is flanked by the gene-specific barcodes which are in turn respectively inserted to chromosome-homologous recombination regions of suitable lengths (FIG. 1).

In a preferred embodiment of the present invention, the KanMX4 module is designed to express the kanamycin resistant gene of Tn903 in the fission yeast, having the structure in which the resistance gene is preceded by the 381 bp TEF promoter sequence of *Ashbya gossypii* just before the initiation codon ATG thereof and followed by the 242 bp TEF terminator of *Ashbya gossypii* just after the stop codon thereof. When used, the promoter or terminator of the budding yeast (*Saccharomyces cerevisiae*) or the fission yeast itself also acts as an additional chromosome-homologous region, resulting in a false homologous recombination. For this reason, the promoter used in the deletion cassette is preferably from a heterogeneous yeast. The KanMX4 module thus constructed becomes 1,433 bp in length. After the deletion cassette is introduced into the fission yeast through transformation, the marker gene undergoes homologous recombination with a chromosomal target gene, so that the marker gene is inserted into the chromosome while the target gene is deleted.

In an example of the present invention, a primary PCR was performed in the presence of a pair of 70 bp-long 5' and 3' barcode primers, each containing a 20 bp barcode, with the kanamycin resistance gene (Kan$^R$) serving as a template, to afford a Kan$^R$-barcode module (FIG. 2) which was in turn used as a template for secondary PCR with a pair of 60~80 bp primers, each consisting of a 40~60 bp chromosome-homologous recombination sequence and a 20 bp-long 5' or 3' terminal region of the Kan$^R$-barcode module, to produce a deletion cassette, useful as a component of the present invention.

Four-Round Serial PCR, Block PCR and Gene Synthesis for Construction of Deletion Cassette The construction of the deletion cassette for gene targeting in accordance with the present invention is accomplished by (1) four-round serial PCR; (2) block PCR; or (3) gene synthesis, preferably as follows.

(1) The term "four-round serial PCR", as used herein, is intended to refer to PCR which is performed four times in series. A primary PCR is performed with a pair of about 70 bp-long 5' and 3' barcode primers to afford a barcode module which is in turn used as a template in three successive PCRs with a pair of 50-mer primers for the first two and with a pair of 40-mer primers for the final one, so as to give a gene-specific barcode and a 80 bp-long gene-homologous recombination region.

(2) The term "block PCR", as used herein, is intended to refer to a block PCR which is performed with 5' and 3' DNA fragments for homologous recombination on the chromosome, which are separately produced to a length of 350~500-bp in length by PCR, in admixture with the produced $Kan^r$-barcode module, to afford a deletion cassette.

(3) The term "gene synthesis" is quite different from PCR and enjoys the following advantages: first, the gene synthesis method can be conducted by one round of phosphorylation and ligation and two rounds of PCR while the four-round PCR is accomplished by four rounds of PCR and four rounds of purification. Thanks to the simplicity thereof, the gene synthesis achieved the genome-wide construction of heterozygous deletion mutants at a success rate of 90% or higher whereas a success rate of 80% was obtained with the block PCR (Table 2); secondly, the gene synthesis can be conducted in series on 96-well plates, thus improving workability. For example, one experienced worker can construct ten strains a week through conventional PCR. In contrast, gene synthesis enables a worker to construct 100 or more strains a week, increasing the efficiency at least 10 times. Finally, only two rounds of PCR are needed whereas the conventional PCR is conducted four times in series, which decreases the possibility of point mutations by two or more times. For instance, 20 strains randomly selected from each group of the mutants constructed according to the methods were subjected to PCR for the amplification of an approximately 2.1-kb target gene, followed by DNA sequencing to find mutations at a rate of 0.2 bases/1 kb, which is two or more times lower than 0.5 bases/1 kb in the conventional PCR.

FIG. 1 is a gene map illustrating a deletion cassette constructed by gene synthesis according to the present invention. The methods (1) and (2) are common in that deletion cassettes are constructed on the basis of PCR, but the method (3) is different in that the construction of deletion cassettes is based on the ligation of synthetic oligonucleotides, but not on PCR. Particularly, the method (3) permitted successful construction of about 200 heterozygous gene-targeted mutants which are difficult to make by conventional PCR methods, showing a success rate as high as 97% from a total 4,988 genes of the fission yeast.

In accordance with an aspect thereof, the present invention provides a high-throughput screening system of in vivo drug's modes of action in which a library of the heterozygous deletion mutants of fission yeast is prepared with the deletion cassettes constructed as described above and is applied to order-made gene chips. In a preferred example of the present invention, the performance of the system was demonstrated by use of the antifungal agent terbinafine.

Heterozygous Fission Yeast

Among the fission yeast group are *Schizosaccharomyces octosporus* and *Schizosaccharomyces pombe*. Any fission yeast may be used in the present invention. The mutant strains transformed with the deletion cassettes are heterozygous deletion mutants in which the gene-specific sequences of the deletion cassettes are exchanged with the chromosomal target genes of the fission yeast by homologous recombination to delete the target genes from the chromosome of the fission yeast.

In a preferable embodiment, the fission yeast may be *Schizosaccharomyces pombe*, but is not limited thereto. The fission yeast *Schizosaccharomyces pombe*, useful in a preferable embodiment of the present invention, was first isolated from African millet beer and is widely used as a model eukaryote for cell and molecular studies as well as in the production of foods such as beer, breads, etc. *S. pombe* is particularly useful in investigating the cell cycle of cells which proliferate through equal division. Introns are distributed among 43% of *S. pombe* genes, showing the feature of higher eukaryotic organisms. Found to have a compact genomic structure with about 5,000 ORFs (open reading frames), the fission yeast is in addition used as a material suitable for gene analysis. Further, *S. pombe* is recognized for making broad contributions to the life sciences, particularly with applications involved with the development of new drugs.

In accordance with a further aspect thereof, the present invention pertains to a gene-targeted, heterozygous deletion mutant of fission yeast which is prepared with a gene-target deletion cassette comprising a selectable marker gene, barcode gene sequences for microarray analysis, and homologous recombination regions.

In accordance with still a further aspect thereof, the present invention pertains to a library of gene-targeted heterozygous fission yeast mutants prepared by the method of the present invention.

In accordance with still another aspect thereof the present invention pertains to a method for screening a drug's modes of action by chemically treating a library of heterozygous fission yeast mutants, culturing the chemically treated library, isolating total genomic DNA from the culture, and applying the isolated genomic DNA to microarray GeneChip or to real-time PCR.

As a tool for identifying a drug's modes of action, a library of heterozygous fission yeast mutants is provided. To identify "a drug's mode of action" is essential to the improvement of preexisting drugs in medicinal efficiency and the development of a new drug free of or with few side effects. The method for screening a drug's mode of action in accordance with the present invention comprises the steps of:

1) treating a library of heterozygous fission yeast mutants with a chemical;

2) culturing the library of the chemically treated, heterozygous fission yeast mutants;

3) isolating genomic DNA from the cultured library; and 4) measuring and analyzing growth rates of the mutants with the isolated genomic DNA applied on microarray gene chips to detect strains which are relatively inhibited from growing.

As long as it inhibits the growth of the mutants, any chemical may be used in the present invention. In a preferred example of the present invention the antifungal agent terbinafine, which targets the gene erg1, was used to examine whether the screening system of a drug's modes of action worked well or not.

As long as it is known in the art, any technique may be used to isolate genomic DNA from the fission yeast. In a preferred example of the present invention, the fungal/bacterial DNA kit (Zymo Research, catalog #D6005) was employed to obtain genomic DNA.

The term "gene chip" or "GeneChip", as used herein, refers to a tool for analyzing the expression of genetic information, which is typically composed of an arrayed series of hundreds to tens of thousands of microscopic spots of DNA oligonucleotides on a solid support of about 1 $cm^2$.

The DNA oligonucleotides of known, specific genetic information are arranged on the surface of the chip and are used as probes to hybridize a target under high-stringency conditions. Probe-target hybridization is usually detected and quantified by fluorescence-based detection of fluorophore-labeled targets to determine a relative abundance of nucleic acid sequences in the target. These gene chips are not only useful for gene studies, but also can detect gene-related diseases quickly. Further, these new analysis systems find a wide spectrum of applications in, for example, selecting or designing optimal customized drugs.

As long as it recognizes the gene-specific barcode sequence inserted to the deletion cassette, any gene chip may be used in the present invention. A preferable embodiment of the present invention employed deletion cassettes with 20-mer barcodes inserted thereinto, and an order-made GeneChip with a serial number of KRIBBSP1-a520429 from Affymetrix to detect the barcodes.

In an alternative embodiment of the present invention, real-time PCR, instead of GeneChip, was performed with inter-chelating dye or flourophore-labeled probe to screen a drug's modes of action. A detailed description will be given of detection with probes, below.

TaqMan probes and cycling probes have been developed for use as fluorescent probes in real-time PCR. The former is a technology utilizing the 5'→3' exonuclease activity of the Taq DNA polymerase for measuring the amount of target sequences in the samples while the cycling probe technology is a method utilizing a combination of chimera probe, composed of RNA and DNA, and RNase H. In this method, one end of the probe is labeled with a fluorescent substance and the other end is labeled with a quencher, which quenches the fluorescence emitted from the fluorescent substance. When this probe forms a hybrid with the complementary sequence of amplified product, RNase H specifically cuts the RNA region of this probe, resulting in emissions of strong fluorescence. Below, a detailed description will be given of the TaqMan probe technology for screening a drug's modes of action.

In a preferable embodiment of the present invention, real-time PCR is conducted with a Taqman probe in addition to common primers. A Taqman probe is an oligonucleotide which is labeled with a reporter fluorophore at the 5' end and with a quencher at the 3' end. During PCR, the probe anneals specifically between the forward and reverse primers to an internal region of the PCR product at the annealing step, with the fluorescence quenched by the quencher. While the polymerase then carries out the extension of the primers and replicates the template to which the TaqMar™ probe is bound, the 5' exonuclease activity of the polymerase cleaves the probe, releasing the reporter molecule away from the close vicinity of the quencher. As a result, the fluorescence intensity of the reporter dye increases and can be detected to determine the expression of the target gene. In the present invention, a Taqman™ probe may be constructed to have a barcode sequence as the oligonucleotide sequence. In this case, real-time PCR with each Taqman probe gives quantitative data on the real time expression of corresponding barcodes, on the basis of which significantly increased or decreased regions can be regarded as a drug's modes of action.

In accordance with still another aspect thereof, the present invention pertains to a novel drug-screening kit, comprising the library of heterozygous fission yeast mutants.

The drug-screening kit of the present invention is used in the method for screening a drug's modes of action. In greater detail, the screening kit is utilized in screening novel drugs as well as a drug's modes of action by 1) culturing the library of heterozygous fission yeast mutants of the screening kit in media containing respective drug candidates and 2) comparatively analyzing the growth of the fission yeast mutants to detect growth-inhibited fission yeast mutants.

MODE FOR INVENTION

A better understanding of the present invention may be obtained through the following examples which are set forth to illustrate, but are not to be construed as limiting the present invention.

Example 1

Construction of Deletion Cassette by Four-Round Serial PCR or Block PCR

Deletion cassettes can be constructed in two different PCR techniques: four-round serial PCR and block PCR. These two PCR-based methods are common in preparing a Kan$^r$-barcode module in advance. The base sequence of KanMX4 is well known in the art and is not described specifically. Primary PCR was performed with a pair of 70-mer 5'- and 3'-barcode primers, each containing a gene-specific barcode while KanMX4 served as a template to prepare a Kan$^r$-barcode module (FIG. 2). After electrophoresis on agarose gel stained with ethidium bromide (EtBR), the Kan$^r$-barcode module thus prepared was extracted from the gel by excising under a UV lamp.

The four-round serial PCR for constructing deletion cassettes is similar to the conventional one used for constructing gene-targeted budding yeast or fission yeast mutants, but different thereto in that 80-bp homologous recombination region is added to either ends of the deletion cassette (Giaever et al., Nature Genetics 14:450-56). Dr. Giaever et al. succeeded in targeting 90% or more of the total 6000 genes of the budding yeast by providing a 45-bp recombination region in one PCR, with Kan$^r$-barcode module serving as a template. As for the fission yeast, however, the 45-bp homologous recombination region is too short to effectively induce homologous recombination on the genome. Thus, the method used for the construction of gene-targeted fission yeast mutants was modified such that PCR was performed three times in series with a pair of 50-mer primers for first two rounds and with a pair of 40-mer primers for the last round, to give a 80-bp homologous recombination region together with a gene-specific barcode (FIG. 3).

This four-round serial PCR was successfully applied only to a quarter of the total 4,988 genes of the fission yeast, with a success rate of 50% or higher in the construction of mutant strains, but failed for the remaining three fourths. Thus, the homologous recombination region was extended using block PCR (FIG. 4). In the block PCR, 5' and 3' DNA fragments for chromosome-homologous recombination, each 350~500 bp long, are separately synthesized by PCR and then subjected, together with the purified Kan$^r$-barcode module, to block PCR to prepare a deletion cassette in which the 5' and 3' 350~500 bp DNA fragments are fused to 5' and 3' ends of the Kan$^r$-barcode module, respectively. As a result, the chromosome-homologous recombination regions in the deletion cassette are extended to 350~500 bp from the 80 bp of the four-round serial PCR, remarkably increasing the construction efficiency of deletion mutants to 90% from 50%.

Example 2

Construction of Deletion Cassette by Gene Synthesis

Even the PCR technology described above failed to prepare gene-targeted mutants for as many as 4% of the total genes. The reason is because the high contents of both adenine (A) and thymine (T) in the promoter and the terminator of the gene do not allow for primer sites of conventional PCR. In consideration of this problem, the gene synthesis method was employed. The present invention is the first to use gene synthesis in constructing deletion cassettes and preparing deletion fission yeast mutants.

A deletion cassette was designed to consist of three fragments: 1) 5' chromosome-homologous region bearing 5' common liker sequence and 5' barcode, 2) kanamycin resistance gene (Kan$^r$), and 3) 3' barcode and 3' chromosome-homologous region bearing 3' common liker sequence. To connect these three fragments into a one line, overlapping link oligo-sequences are arranged between the fragments to be connected with each other (FIG. 5). A length of 250 bp was given as the length of the chromosome-homologous region, which is the most important factor to determine the construction efficiency of mutants. The 5' chromosome-homologous region was identical to the chromosomal nucleotide sequence stretching in the direction toward the promoter from the initiation codon ATG by 250 bp while the 3' chromosome-homologous region was identical to the chromosomal nucleotide sequence stretching in the direction toward poly-A from the stop codon TGA, TAG or TAA, by 250 bp.

The 5' and the 3' chromosome-homologous region, each 250 bp long, are different from one gene to another and the description of their nucleotide sequences is omitted because anyone skilled in the art can infer them.

The link oligo-sequences in the fragments to be linked to each other are designed to overlap with each other, with no gaps between the fragments, so that a double-stranded deletion cassette DNA fragment, albeit having nicks thereon between the fragments, can be obtained only by overlapping the oligo-sequences. On the basis of the Santa Lucia Calculations, all of the oligo-sequences were designed to have a Tm value of 60±3° C. (Santa Lucia PNAS. 95:1460-5). Two relatively short oligo-sequences, 12~16 bp long, were respectively arranged at the opposite terminal regions of the deletion cassette, producing blunt ends. Then, treatment with ligase sealed the nicks to give an intact deletion cassette DNA template.

Example 3

Transformation of Deletion Cassette and Identification of Gene-Targeted Mutants Using the lithium acetate method, the deletion cassette prepared through Examples 1 and 2 was transformed into diploid fission yeast SP286 strains (ade6-M210/ade6-M216, ura4-D18/ura4-D18, leu1-32/leu1-32) (Moreno et al., Methods Enzymol. 194:795-823). The transformed strains were spread over YES agar plates and cultured at 30° C. for 3~4 days to form colonies. Colony PCR was performed to examine whether desired genes were targeted. A small amount of cells were picked from edges of grown colonies on agar plates and suspended in deionized water. A portion of the suspension was subjected to PCR with a pair of primers. As shown in FIG. 6, colony PCR was performed with a pair of CP5 and CPN1 or CPN10 for the 5' side of the deletion cassette inserted into the chromosome and with a pair of CP3 and CPC1 or CPC3 for the 3' side of the deletion cassette. CP5 and CP3 were located 100~200 bp upstream and downstream of corresponding chromosome homologous regions, respectively. CPN1 and CPC1 were located within the KanMX4 gene, with a distance of 200 bp from 5' and 3' ends thereof, respectively, while CPN10 and CPC3 were also located within the KanMX4 gene, with a distance of 300 bp from 5' and 3' ends thereof, respectively. Accordingly the colony PCR products thus obtained had a length of 300~400 bp plus the length of the chromosome homologous region, that is, 80~450 bp, amounting to 500~1,000 bp in total. Reference may be made to Korean Patent No. 10-0475645 for reaction conditions of colony PCR.

The base sequences of CP5 and CP3 which are different depending on the genes are not described in detail because they are readily apparent to those skilled in the art. Base sequences of CPN1, CPN10, CPC1 and CPC3 are given, along with their sequence identification numbers, in Table 3, below.

TABLE 3

| Oligo Names | Base Sequences | SEQ ID NOS. |
|---|---|---|
| CPN1 | 5'-CGTCTGTGAGGGGAGCGTTT-3' | 1 |
| CPN10 | 5'-GATGTGAGAACTGTATCCTAGCAAG-3' | 2 |
| CPC1 | 5'-TGATTTTGATGACGAGCGTAAT-3' | 3 |
| CPC3 | 5'-GGCTGGCCTGTTGAACAAGTCTGGA-3' | 4 |

Example 4

Determination of Base Sequences of Gene-Specific Barcodes and their PCR Amplification Gene-specific barcodes must be needed in order to systemically identify strains using a microarray GeneChip as will be described in Example 5, below. In this regard, two gene-specific barcodes, each 20 bp, were given to 5' and 3' sides of the deletion cassette, respectively (FIG. 1). According to the gene database of the Sanger Institute, 4,988 genes are present in the fission yeast. Hence, as shown in FIGS. 7 to 55, a total of 9,976 barcodes were assigned to the 4,988 genes, with two per gene. The barcodes were named in such a manner that the systematic names of corresponding genes were followed by the extension _UP or _DN. For example, barcodes specific for the gene SPAC1002.09c were named SPAC1002.09c_UP for 5' up-tag, identified by SEQ ID NO. 18, and SPAC1002.09c_DN for 3' down-tag, identified by SEQ ID NO. 19 (FIG. 7). Barcodes were thus artificial DNA sequences which were not present on the chromosome of the fission yeast and were designed to have a Tm value of 60±1° C. according to a computer algorithm.

Example 5

Screening of A Drug's Mode of Action Using a Library of Gene-Targeted Diploid Fission Yeast Mutants A modification of the Giaever's method for screening drug's modes of action in the budding yeast on the basis of haploinsufficiency was applied to the fission yeast in accordance with the present invention (FIG. 56) (Giaever et al., Nature Genetics 14:450-56, Pierce et al., Nature Protocols 11:2958-2974, Pierce et al., Nat Methods: 601-3).

The analysis of a drug's modes of action by use of a GeneChip comprises the following seven steps: 1) pooling of strain libraries, 2) activation, chemical treatment and sampling of a frozen strain pool, 3) isolation of chromosomal DNA and PCR amplification of barcode labels, 4) Order of GeneChip from Affymetrix, 5) hybridization, 6) staining, washing and colorimetry, and 7) result analysis.

1) Pooling of Strain Libraries

A pool in which the mutants were equally mixed was prepared in the manner illustrated in FIG. 57. Because it was not easy to handle a library of 4,884 gene-targeted heterozygous mutants at the same time, they were divided into unit packages of 96 mutants. In detail, 96 mutants were cultured at 30° C. for 3 days on YES agar plates containing G418 at a concentration of 200 mg/ml, followed by incubation at 30° C. for 3 days on 96-well type plates. The strains cultured on the 51 plates were scraped, and suspended in 5.5 ml of respective 2× YES broths. After the addition of glycerol to the concentration of 30%, the 51 cultures were aliquoted at a volume of 1 ml and stored at −80° C. All of the 51 1 ml-aliquots in cryogenic storage were pooled together to afford a library of the mutants which was then aliquoted at a volume of 1 ml and stored at −80° C. A total of $5 \times 10^7$ cells were used so that at least 10,000 cells were assigned to one mutant strain per one round of screening a drug's modes of action.

2) Activation, Chemical Treatment and Sampling of Frozen Strain Pool

Prior to chemical treatment, the strain pool stored at −80° C. was activated. After being thawed, an aliquot of the strain pool was initially inoculated into a YES broth at $O.D_{600}=0.2$ and grown at 25° C. to $O.D_{600}=2.0$. These activated strains were diluted to a density of $O.D_{600}=0.2$ and treated with a chemical at a suitable concentration, followed by sampling therefrom once every three sub-cultures over a total of 20~30 subcultures (typically 4 hours are required for one sub-culture of the fission yeast). Since it was easy to determine the inhibitory activity of the chemical on the growth of cells when the strains must grow at a constant rate without the influence of nutrients, the sampled strains were diluted again at a density of $O.D_{600}=0.2$ in fresh broth containing the chemical. A sample taken from chemical-free broth was used as a control. The samples were centrifuged to give cell pellets which were then stored at −80° C. Genomic DNA was isolated from all of the samples at the same time and subjected to GeneChip analysis.

In order to determine the concentration of the chemical for the treatment, 50% inhibitory concentration ($IC_{50}$) was first measured. Wild-type SP286 strain was grown to $O.D_{600}=2.0$ in YES broth and inoculated with from 5- to 10-fold serial dilutions of the chemical to $O.D_{600}=0.1$, followed by incubation at 30° C. for 24 hours. At each concentration of the chemical, the cultures were measured for final $O.D_{600}$ values which were then plotted against Log [Chemical Concentration]. On the basis of these plots, $IC_{50}$ values were automatically calculated using Prism Software (version 3.0, GraphPad Software Inc., San Diego, Calif.). Scientific experience made it possible to determine the concentrations of the chemical at around the appropriate $IC_{50}$ values.

3) Isolation of chromosomal DNA and PCR Amplification of Barcode Label

Using a Fungal/Bacterial DNA kit (Zymo Research, catalog # D6005), 2-4 µg of genomic DNA was isolated from 200 mg of the cell sample. A 20-~50-fold dilution of the isolated genomic DNA was mixed with a 200-fold dilution of Pico Green dye (Pico Green® dsDNA Assay Kit (Invitrogen Inc. cat # P11495) at a volume ratio of 1:1, followed by quantification with NanoDrop (ND-1000, NanoDrop Inc.). 200 ng of each sample was used for labeling PCR.

For use as probes in GeneChip, only the barcodes present in the isolated genomic DNAs were amplified by PCR using biotin-labeled primers. To this end, first, base sequences of common primers for the amplification of the 20-bp barcodes were determined. It was important to design the common primers which did not form non-specific bonds with the genome of the fission yeast. The base sequences determined through algorithm and serial experiments are given in Table 4, below. Biotin, serving as a label in the PCR amplification of the barcodes, was conjugated to the 5'-ends of the primers which are directed towards the kanamycin resistance gene. The PCR products of the 5' and the 3' barcode were 70 bp and 73 bp in length. Solutions and conditions for PCR amplification are summarized in Table 5, below. After completion of PCR, PCR products were analyzed for length and amount by the electrophoresis of 5 µl of the PCR reaction in 3% agarose gel and stored at 4° C. in a refrigerator until hybridization. About 30 µl of the PCR product was used for each hybridization.

TABLE 4

| Oligo Names | Positions | Directions | Base Sequences | SEQ ID NOS. |
|---|---|---|---|---|
| U1 | 5' Up-tag | Sense | 5'-GCTCCCGCCTTACTTCGCAT-3' | 5 |
| U2 | | Anti-sense | 5'-Biotin-CGGGGACGAGGCAAGC TAA-3' | 6 |
| D1 | 3' Down-tag | Sense | 5'-Biotin-GCCGCCATCCAGTGTC G-3' | 7 |
| D2 | | Anti-sense | 5'-TTGCGTTGCGTAGGGGGG-3' | 8 |

TABLE 5

| Sol'n | Stock | Final Conc./Amount | Volumes (µl) |
|---|---|---|---|
| Water (H$_2$O) | | | 75-x |
| PCR Buffer | 10X | 1X | 10 |
| MgCl$_2$ | 20 mM | 2.5 mM | 10 |
| dNTP | 10 mM | 0.2 mM | 2 |
| Primer Mix | 50 uM | 1 µM | 2 |
| Taq Polymerase | 5 U/µl | 5 U | 1 |
| Genomic DNA | | ~200 ng | x |
| Final Vol. | | | 100 |
| PCR Conditions | 94° C., 2 min, 1 cycle - (94° C., 30 s; 58° C., 30 s; 72° C., 30 s) 29 cycles - 72° C., 3 min, 1 cycle | | |

4) Order of GeneChip from Affymetrix

A made-to-order GeneChip with serial number KRIBBSP1-a520429 from Affymetrix was used to recognize the 20-bp barcodes specifically inserted into the mutant strains (FIG. 58). On this DNA chip with a size of 0.8×0.8 cm were planted 100,000 probes which each have a feature of 11×11 µm. The probes consisted of 1) perfect match (PM) and mismatch (due to mismatch bases assigned to middle sites of barcodes) with 5' and 3' barcodes (each 10,000) in triplicate (60,000 in total); 2) 10,000 control probes for minimizing false positive signals induced by non-specific hybridization; 3) 20,000 spare probes for barcodes; and 4) 10,000 basic structure probes necessary for indicating the manufacturer Affymetrix and Oligo texts and compartmenting.

5) Hybridization

Hybridization between the GeneChip from Affymetrix and the probes obtained by PCR in 3) was conducted as follows. As shown in Table 6, first, the hybridization solution comprising a biotin-labeled text oligo-mix and a blocking oligo-mix in addition to the biotin-labeled barcode probes was mixed in a 1.5 ml tube. The biotin-labeled text oligo-mix gave a standard to the optical recognition system upon analysis on the GeneChip. The blocking oligo-mix composed of 8 oligonucleotides served to block the common primers within the barcode and the gap between the primers and the barcode to expose only the 20-bp barcodes in single strands, thereby allowing the sense single strands to hybridize with the antisense probe oligonucleotides of the GeneChip. Each of the 8 oligonucleotides was used as a 300 pM stock. In the blocking oligo-mix, 5U-Block, K5U-Block, 5U-Block (rev comp) and K5U-Block (rev comp) were each present at a concentration of 37.5 pmole/µl while 3U-Block, K3U-Block, 3U-Block (rev comp) and K3U-Block (rev comp) were each present at a concentration of 12.5 pmole/µl. Immediately after being boiled at 98° C. for 5 min, the hybridization solution was quenched in ice water to expose the 20-bp sense barcode sequences in single strands. To the GeneChip which was pre-treated for 5 min with 140 µl of hybridization buffer was injected 140 µl of the hybridization solution, followed by hybridization at 42° C. for 16 hours.

6) Staining and Washing and Colorimetry

After completion of the hybridization, the GeneChip was stained with phycoerythrin-conjugated streptavidin using a fluidics station (Affymetrix). Streptavidin was strongly bound to the biotin to give fluorescence, affording the quantification of the biotin-labeled barcodes hybridized with the probes on the GeneChip.

The Fluidics station was used according to the protocol recommended by the manufacturer using staining solution (600 µl: 20×SSPE 180.57 µl+50×Denhart's solution 11.94 µl+10% Tween20 0.597 µl+phycoerythrin-conjugated streptavidin 1.019 µl+deionized water 405.874 µl) and a washing solution (Wash A: 20×SSPE 300 ml, 10% Tween 1 ml, distilled water 699 ml in 1 liter; Wash B: 20×SSPE 150 ml, 10% Tween 1 ml, distilled water 849 ml in 1 liter). Thereafter, the GeneChip was scanned with GeneChip® Scanner 3000 G7 (Affymetrix) to detect fluorescence.

TABLE 7

| Conditions | No. of Round | Notes |
| --- | --- | --- |
| Wash A1 Recovery Mixes | 0 | |
| Wash A1 Temperature (° C.) | 25 | |
| Number of Wash A1 Cycle | 2 | |
| Mixes per Wash A1 Cycle | 4 | |
| Wash B Recovery Mixes | 0 | |
| Wash B Temperature (° C.) | 42 | |
| Number of Wash B Cycle | 6 | |
| Mixes per Wash B Cycle | 4 | |
| Stain Temperature (° C.) | 25 | |
| First Stain Time (seconds) | 0 | (dummy step) |
| Wash A2 Recovery Mixes | 0 | (dummy step) |
| Wash A2 Temperature (° C.) | 25 | |
| Number of Wash A2 Cycle | 1 | |
| Mixes per Wash A2 Cycle | 2 | |

TABLE 6

| Solutions | | Compositions and Base Sequences | Vol (µl) | SEQ ID NOS. |
| --- | --- | --- | --- | --- |
| 5' Up- and 3' Down-tag | | 4,884 Gene-specific Up and Down barcodes | 60 (each 30) | |
| 2× Hybridization Buffer | | 200 mM MES, 2M Na+, 40 mM EDTA 0.02% Tween20 | 75 | |
| Text Oligo (20 fmole/µl) | | 5'-biotin-GTCGTCAAGATGCTACCGTTCAGGA-3' | 0.5 | 9 |
| Blocking Oligo-Mix | 5U-Block | 5'-CGCTCCCGCCTTACTTCGCATTTAAA-3' | 12 | 10 |
| | K5U-Block | 5'-GGGGACGAGGCAAGCTAAGATATC-3' | | 11 |
| | 3U-Block | 5'-TTGCGTTGCGTAGGGGGGATTTTAAA-3' | 12 | 12 |
| | K3U-Block | 5'-CGCCATCCAGTGTCGAAAAGTATC-3' | | 13 |
| | 5U-Block (rev comp) | 5'-TTTAAATGCGAAGTAAGGCGGGAGCG-3' | | 14 |
| | K5U-Block (rev comp) | 5'-GATATCTTAGCTTGCCTCGTCCCC-3' | | 15 |
| | 3U-Block (rev comp) | 5'-TTTAAAATCCCCCCTACGCAACGCAA-3' | | 16 |
| | K3U-Block (rev comp) | 5'-GATACTTTTCGACACTGGATGGCG-3' | | 17 |
| 50× Denhardt's Sol'n | | 1% Ficoll 400, 1% PVP, 1% BSA | 3 | |
| | | Total volume | 150.5 | |

TABLE 7-continued

| Conditions | No. of Round | Notes |
|---|---|---|
| Second Stain Time (seconds) | 600 | |
| Third Stain Time (seconds) | 0 | (dummy step) |
| Wash A3 Recovery Mixes | 0 | (dummy step) |
| Wash A3 Temperature (° C.) | 25 | |
| Number of Wash A3 Cycles | 6 | |
| Mixes per Wash A3 Cycle | 4 | |
| Holding Temperature (° C.) | 25 | |

7) Result Analysis

The binding between the PCR-amplified gene-specific sense barcodes and the antisense oligonucleotide probes planted on the GeneChip could be quantified by the fluorescent intensity detected. The fluorescence values measured were stored in files with the extension name cel. Strong fluorescent intensity means that cells with corresponding genes are predominantly growing. On the other hand, weak fluorescent intensity means the inhibition of cell growth. Based on the ANOVA/ANCOVA model, fluorescent data from the GeneChip were analyzed for the heterozygous gene-targeted mutants which were inhibited from growing.

According to the ANCOVA model, the drug-induced inhibition of cell growth is expressed as the reduced passage number which can be obtained according to the following formula.

Reduced passage No. by drug in unit time (12 hrs)=
Changed passage No. upon drug treatment in
unit time (12 hrs)−Changed passage No. in the
absence of drug in unit time (12 hrs)

Passage No. is calculated according to the following formula:

Passage No.=$\log_2$(Fluorescent Intensity of Gene $X$
at a predetermined time)−$\log_2$(Fluorescent
Intensity of Gene $X$ at the previous time)

Example 6

Screening of Terbinafine's Modes of Action Using GeneChip and Verification

In order to screen terbinafine's modes of action with the GeneChip, first, the treatment concentrations of drug were determined by the measurements of $IC_{50}$ obtained in the above-mentioned method. In this regard, relative rates of drug-induced inhibition against cell growth were obtained by treating the cells with terbinafine at doses of 0.1 nM, 1 nM, 5 nM, 10 nM, 50 nM, 100 nM, 500 nM and 1 nM. Analysis with Prism software determined $IC_{50}$=40 nM (FIG. 11).

After the treatment of a strain pool with 40 nM of terbinafine, as shown in Table 8, samples were taken every three passages (approximately 12 hours) till 30~35 passages, GeneChip analysis was performed with 13 controls and 12 drug-treated samples.

TABLE 8

| Chip Nos. | Specimen Group | Specimen Names | Accumulated Passages (Round) | Passage Time(h) |
|---|---|---|---|---|
| 1 | Chip control: | Strain mix in Glycerol | | |
| 2 | Cell activation | Activation Stage 1 | | 6.9 |
| 3 | | Activation Stage 2 | | 6.7 |
| 4 | | Activation Stage 3 | | 4.2 |
| 5 | Drug control: | Control Data Point 1 | 3.1 | 3.6 |
| 6 | YES media | Control Data Point 2 | 6.6 | 3.9 |
| 7 | | Control Data Point 3 | 9.4 | 3.6 |
| 8 | | Control Data Point 4 | 12.8 | 3.8 |
| 9 | | Control Data Point 5 | 16.7 | 3.7 |
| 10 | | Control Data Point 6 | 21.2 | 3.6 |
| 11 | | Control Data Point 7 | 25.6 | 3.5 |
| 12 | | Control Data Point 8 | 32.7 | 3.4 |
| 13 | | Control Data Point 9 | 35.9 | 3.8 |
| 14 | Drug-Treated: | Drug Data Point 1 | 3.1 | 3.6 |
| 15 | YES + 40 nM | Drug Data Point 2 | 6.3 | 4.3 |
| 16 | Terbinafine | Drug Data Point 3 | 8.6 | 4.3 |
| 17 | | Drug Data Point 4 | 10.9 | 5.6 |
| 18 | | Drug Data Point 5 | 13.7 | 5.2 |
| 19 | | Drug Data Point 6 | 17.1 | 4.7 |
| 20 | | Drug Data Point 7 | 20.9 | 4.0 |
| 21 | | Drug Data Point 8 | 23.8 | 4.0 |
| 22 | | Drug Data Point 9 | 26.7 | 4.5 |
| 23 | | Drug Data Point 10 | 29.5 | 4.1 |
| 24 | | Drug Data Point 11 | 32.3 | 4.3 |
| 25 | | Drug Data Point 12 | 34.9 | 4.4 |

The gene candidates which were ranked as the top 10 (or top 20) by ANCOVA analysis, defined as cell growth over time after treatment with terbinafine, are summarized in Table 9, below. The erg1 gene, known as a terbinafine's mode of action, codes for squalene monooxygenase, which plays an important role in the biosynthesis of the membrane component ergosterol. The screening of terbinafine's modes of action with the conventional budding yeast also resulted in a first ranking for the erg1 gene. This coincidence demonstrates that the system of screening drug's modes of action with a library of the gene-targeted fission yeast mutants in accordance with the present invention works properly.

Since the drug's modes of action detected with the GeneChip might include the false positive signals resulting experiment errors and false chip analysis, all the top 10 drug's modes of action, except non-specific ribosome-related genes, were cultured again on YES agar plates containing terbinafine. As shown in FIG. 60, the same results as in the chip were obtained for the genes erg1 and pmm1 whereas there was a difference from the chip result on the smb1 gene. Therefore, the genes erg1 and pmm1 within the red boxes were verified as being targets of terbinafine.

Taken together, the data obtained in the examples demonstrate that the present invention is very useful in accurately searching for novel drug's modes of action as well as already known target proteins.

TABLE 9

| Nos. | Systematic Gene Names | Target Genes | Description of Genes |
|---|---|---|---|
| 1 | SPBC713.12 | erg1 | squalene monooxygenase Erg1 (predicted); similar to S. cerevisiae YGR175C |
| 2 | SPCC622.06c | | dubious; similar to S. pombe SPCC622.03c; tandem duplication; ORF in compositionally biased region |
| 3 | SPAC24H6.07 | rps901 | 40S ribosomal protein S9; similar to S. cerevisiae YPL081W and YBR189W; similar to S. pombe rps902 |

TABLE 9-continued

| Nos. | Systematic Gene Names | Target Genes | Description of Genes |
|---|---|---|---|
| 4 | SPBP23A10.07 | rpa2 | DNA-directed RNA polymerase I complex subunit Rpa2; similar to *S. cerevisiae* YPR010C |
| 5 | SPAC26A3.08 | smb1 | small nuclear ribonucleoprotein (snRNP) (subunit B); complexed with Cdc5p (PMID 11884590); similar to *S. cerevisiae* YER029C |
| 6 | SPBC17G9.07 | rps2402 | 40S ribosomal protein S24; similar to *S. cerevisiae* YER074W and YIL069C |
| 7 | SPAC1F7.13c | rpl801 | 60S ribosomal protein L2A; similar to *S. cerevisiae* YFR031C-A and YIL018W |
| 8 | SPBC12D12.03 | cct1 | chaperonin-containing T-complex alpha subunit Cct1; similar to *S. cerevisiae* YDR212W |
| 9 | SPCC1223.05c | rpl3702 | 60S ribosomal protein L37; similar to *S. cerevisiae* YLR185W and YDR500C |
| 10 | SPAC1556.07 | pmm1 | phosphomannomutase; similar to *S. cerevisiae* YFL045C |

INDUSTRIAL APPLICABILITY

As described hitherto, the present invention provides a deletion cassette with two 20-mer gene-specific barcodes and two 250-~350-bp homologous regions at both ends thereof, which is very useful in constructing gene-targeted yeast mutants. A library of the heterozygous gene-targeted yeast mutants can be used to systematically screen a drug's modes of action on a genomic level, thus affording the effective development of new drugs.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09670480B2). An electronic copy of the "Sequence Listing" will also be available from the USPTO upon request and payment of the fee set forth in 37 CFR 1.19(b)(3).

The invention claimed is:

1. A method for constructing gene-targeted heterozygous *Schizosaccharomyces pombe* mutants, comprising:
   1) constructing a deletion cassette for gene targeting by block PCR or gene synthesis;
   2) introducing the deletion cassette into a *Schizosaccharomyces pombe* strain; and
   3) identifying gene-targeted *Schizosaccharomyces pombe* mutants in which a target gene is replaced by a selectable marker gene of the deletion cassette, wherein the deletion cassette comprises a selectable marker gene; a pair of gene-specific barcode sequences, positioned respectively at both flanks of the selectable marker gene, and a pair of homologous recombination regions, assigned respectively to both sides of the barcode sequences positioned upstream and downstream of the selectable marker gene,
   wherein the homologous recombination regions for block PCR range from 350 bp to 450 bp, and those for gene synthesis ranges from 150 bp to 250 bp, and wherein the barcode sequences are selected from the group consisting of the base sequences of SEQ ID NOs: 18 to 9993,
   wherein for the block PCR, the deletion cassette is constructed by fusing 5' and 3' DNA fragments for the homologous recombination regions separately synthesized by PCR to 5' and 3' ends of a DNA fragment comprising the selectable marker gene and gene-specific barcode sequence through block PCR, and
   wherein for the gene synthesis, the deletion cassette is constructed by designing three DNA fragments of a) the 5' homologous recombination region bearing the 5' barcode, b) the selectable marker, and c) the 3' homologous recombination region bearing the 3' barcode, and connecting these three DNA fragments using 5'- and 3'-link oligos.

2. The method according to claim 1, wherein each of the barcode sequences ranges from 20 bp to 30 bp.

3. The method according to claim 1, wherein the barcode sequences are selected from the group consisting of the sequences of SEQ ID NOs: 18 to 9993 and two of the barcode sequences are respectively assigned upstream and downstream of the selectable marker gene.

4. The method according to claim 1, wherein the selectable marker gene is selected from the group consisting of a kanamycin resistance gene, a neomycin resistance gene, a hygromycin resistance gene, a tetracycline resistance gene, auxotrophic markers, histidinol dehydrogenase (hisD), guanine phosphoribosyltransferase (gpt), hypoxanthine phosphoribosyltransferase (hprt), ura3, ble and sacB.

5. The method according to claim 4, wherein the selectable marker gene is a kanamycin resistance gene.

6. The method of claim 1, wherein the deletion cassette further comprises a pair of universal primers for amplifying the barcode sequences positioned at the 5' side of the selectable marker gene and a pair of universal primers for amplifying the barcode sequences positioned at the 3' side thereof.

7. The method of claim 1, wherein the target gene is selected from the group consisting of erg1, rps901, rpa2, smb1, rps2402, rpl1801, cct1, rpp13702 and pmm1.

8. A library of gene-targeted heterozygous fission yeast mutants prepared by the method according to any one of claims 1, 2-4, 5, 6, and 7.

9. A method of screening a drug's mode of action, comprising:
   1) treating the library of gene-targeted heterozygous fission yeast mutants according to claim 8 with a chemical;
   2) culturing the chemically treated fission yeast mutants;
   3) isolating genomic DNA from the cultured mutants; and
   4) measuring and analyzing growth rates of the mutants with the isolated genomic DNA to detect strains whose relative growth is inhibited.

10. A screening kit for a drug's mode of action, comprising the library of gene-targeted heterozygous fission yeast mutants according to claim 8.

11. The method of screening a drug's mode of action according to claim 9, wherein the growth rate of the mutant is measured by applying the isolated genomic DNA to microarray gene chip or to quantitative real-time PCR.

\* \* \* \* \*